(12) United States Patent
Bates et al.

(10) Patent No.: US 10,975,087 B2
(45) Date of Patent: Apr. 13, 2021

(54) SOLID FORMS OF TETRAHYDROPYRANYL AMINO-PYRROLOPYRIMIDINONE COMPOUNDS

(71) Applicant: ArQule, Inc., Burlington, MA (US)

(72) Inventors: Craig Bates, Pelham, NH (US); Erika Volckova, Concord, MA (US)

(73) Assignee: ArQule Inc., Burlington, MA (US)

( * ) Notice: Subject to any disclaimer, the term of this patent is extended or adjusted under 35 U.S.C. 154(b) by 0 days.

(21) Appl. No.: 16/538,957

(22) Filed: Aug. 13, 2019

(65) Prior Publication Data

US 2020/0140442 A1 May 7, 2020

Related U.S. Application Data

(60) Provisional application No. 62/718,318, filed on Aug. 13, 2018.

(51) Int. Cl.
| | | |
|---|---|---|
| *C07D 487/04* | (2006.01) | |
| *A61P 35/02* | (2006.01) | |
| *A61P 29/00* | (2006.01) | |
| *A61P 9/00* | (2006.01) | |
| *A61P 31/00* | (2006.01) | |
| *A61P 25/00* | (2006.01) | |
| *A61P 19/10* | (2006.01) | |
| *A61P 35/04* | (2006.01) | |

(52) U.S. Cl.
CPC ........ *C07D 487/04* (2013.01); *C07B 2200/13* (2013.01)

(58) Field of Classification Search
CPC .......................... C07B 2200/13; C07D 487/04
See application file for complete search history.

(56) References Cited

U.S. PATENT DOCUMENTS

| 4,522,811 A | 6/1985 | Eppstein et al. |
| 9,630,968 B1 | 4/2017 | Lapierre et al. |

FOREIGN PATENT DOCUMENTS

WO  WO 2018/039310 A1  3/2018

OTHER PUBLICATIONS

Bhattacharya et al. (Brittain, ed. Polymorphism in Pharmaceutical Solids, 2009, p. 334.*
USP (https://www.usp.org/sites/default/files/usp/document/harmonization/gen-chapter/g14_pf_35_3_2009.pdf, downloaded Nov. 23, 2016, pp. 1-11).*
Dipaolo, et al. "Specific Btk inhibition suppresses B cell- and myeloid cell-mediated arthritis." Nat Chem Biol. (2011) 7(1):41-50. doi: 10.1038/nchembio.481.
Hunter, T. "A thousand and one protein kinases." Cell. (1987) 50(6):823-9.
Liu, et al. "Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy." J Pharmacol Exp Ther. (2011) 338(1):154-63. doi: 10.1124/jpet.111.181545.

* cited by examiner

*Primary Examiner* — Susanna Moore
(74) *Attorney, Agent, or Firm* — Dianne Pecoraro; John C. Todaro

(57) ABSTRACT

The present application provides solid forms of (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone free base, and methods of preparing and using the same.

9 Claims, 286 Drawing Sheets

FIG. 99

 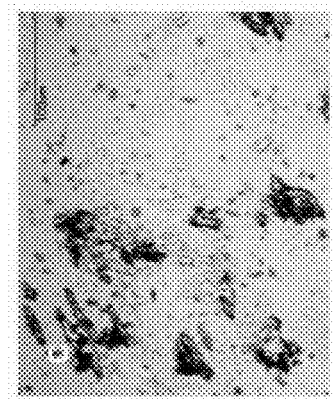 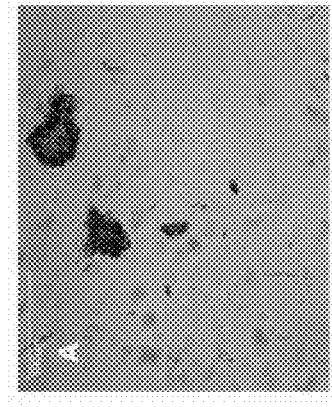
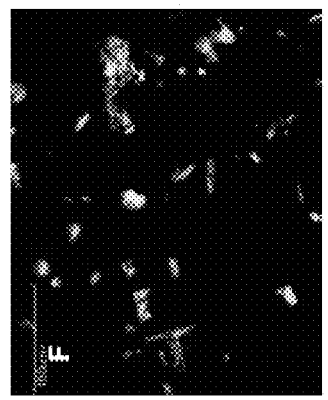 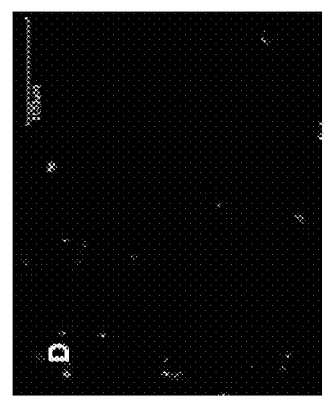 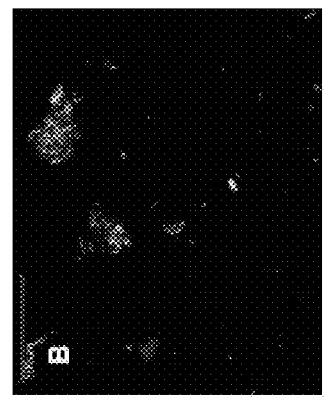
FIG. 197A  FIG. 197C  FIG. 197E
FIG. 197B  FIG. 197D  FIG. 197F

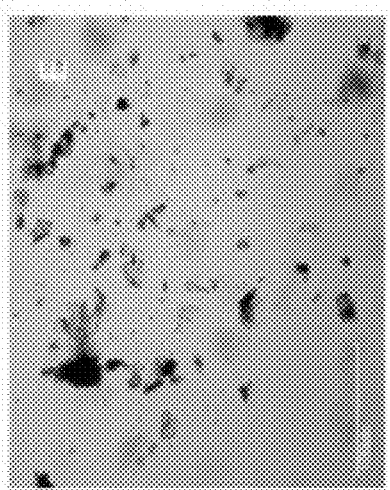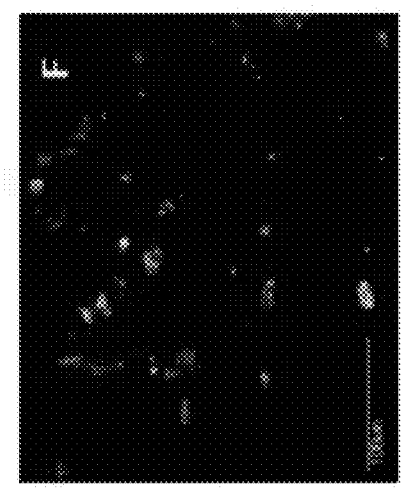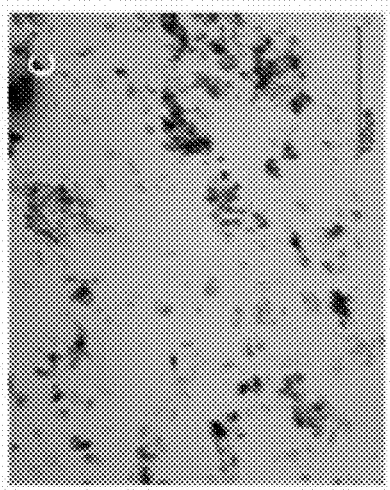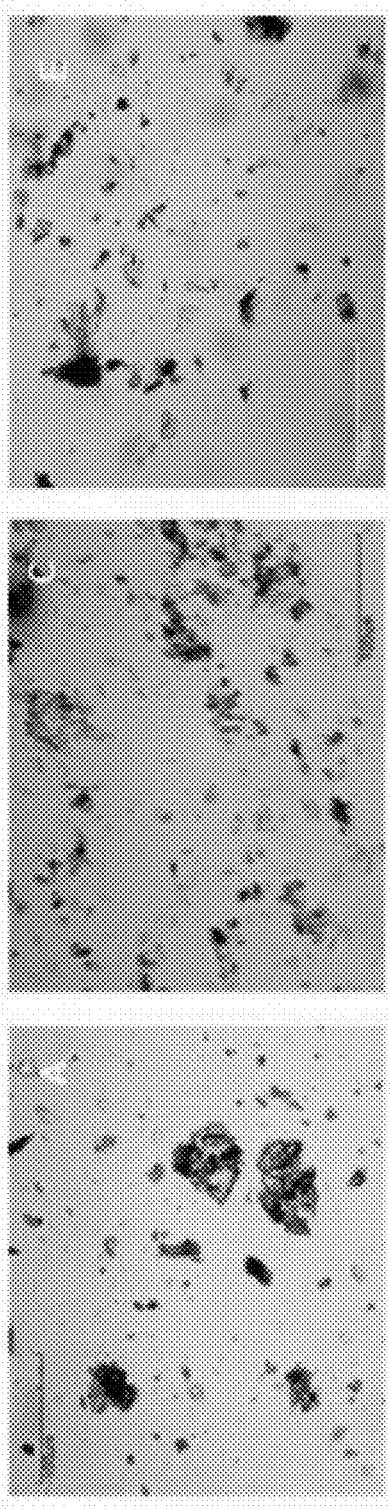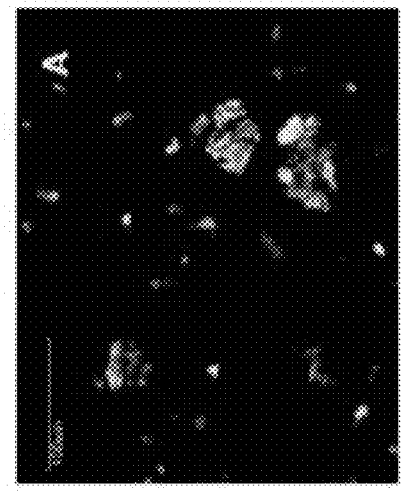

SOLID FORMS OF TETRAHYDROPYRANYL AMINO-PYRROLOPYRIMIDINONE COMPOUNDS

RELATED APPLICATION

This application claims priority to and the benefit of U.S. Application No. 62/718,318, filed on Aug. 13, 2018, the contents of which are incorporated by reference in their entirety.

BACKGROUND

BTK is a member of the Tec family of tyrosine kinases and plays an important role in the regulation of early B-cell development and mature B-cell activation and survival. (Hunter, Cell, 1987 50, 823-829). Functioning downstream of multiple receptors, such as growth factors, B-cell antigen, chemokine, and innate immune receptors, BTK initiates a number of cellular processes including cell proliferation, survival, differentiation, motility, angiogenesis, cytokine production, and antigen presentation.

BTK-deficient mouse models have shown the role BTK plays in allergic disorders and/or autoimmune disease and/or inflammatory disease. For instance, BTK deficiency in standard murine preclinical models for systemic lupus erythematosus (SLE) has been shown to result in a marked amelioration of disease progression. Furthermore, BTK-deficient mice can be resistant to developing collagen-induced arthritis and less susceptible to *Staphylococcus*-induced arthritis. Due to BTK's role in B-cell activation, BTK inhibitors can also be useful as inhibitors of B-cell mediated pathogenic activity (such as autoantibody production). Expression of BTK in osteoclasts, mast cells and monocytes has been shown to be important for the function of these cells. For example, impaired IgE-mediated mast cell activation and reduced TNF-alpha production by activated monocytes has been associated with BTK deficiency in mice and humans. Thus, BTK inhibition can be useful for the treatment of allergic disorders and/or autoimmune and/or inflammatory disease such as: SLE, rheumatoid arthritis, multiple vasculitides, idiopathic thrombocytopenic purpura (ITP), myasthenia gravis, allergic rhinitis, and asthma (Di-Paolo et. al., *Nature Chem. Biol.* 2011, 7(1):41-50; Liu et. al., *Jour. Pharmacol. Exp. Ther.* 2011, 338(1):154-163).

Moreover, BTK's role in apoptosis demonstrates the utility of inhibition of BTK activity for the treatment of cancers, B-cell lymphoma, leukemia, and other hematological malignancies. In addition, given the role of BTK in osteoclast function, inhibition of BTK activity can be useful for the treatment of bone disorders such as osteoporosis.

Inhibition of BTK with small molecule inhibitors therefore has the potential to be a treatment for immune disorders, cancer, cardiovascular disease, viral infections, inflammation, metabolism/endocrine function disorders, and neurological disorders. Thus, there remains a considerable need for potent small molecule inhibitors of BTK.

SUMMARY

The present application provides solid forms of (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone free base (Compound A) of the following structure:

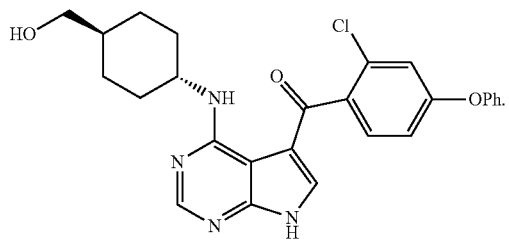 [SMILES: O=C(c1ccc(Oc2ccccc2)cc1Cl)c1c[nH]c2ncnc(N[C@H]3CC[C@H](CO)CC3)c12]

In one embodiment, the present application provides an amorphous form of Compound A. In one embodiment, the amorphous form is characterized by an X-ray powder diffraction (XRPD) pattern substantially similar to that set forth in FIG. 1. In one embodiment, the amorphous form is characterized by an exothermic event with onset at approximately 181° C. as measured by differential thermal analysis (DTA). In one embodiment, the amorphous form is characterized by an endothermic event with onset at approximately 226° C. as measured by DTA. In one embodiment, the amorphous form is characterized by a DTA thermogram substantially similar to that set forth in FIG. 3 or a TG thermogram substantially similar to that set forth in FIG. 3. In one embodiment, the amorphous form is characterized by an exothermic event with onset at approximately 179° C. as measured by differential scanning calorimetry (DSC). In one embodiment, the amorphous form is characterized by an endothermic event with onset at approximately 226° C. as measured by DSC. In one embodiment, the amorphous form is characterized by a DSC thermogram substantially similar to that set forth in FIG. 4.

In one embodiment, the present application provides crystalline forms of Compound A. In one embodiment, the present application provides polymorphs of Compound A.

In one embodiment, the present application provides a Form 1 polymorph of Compound A characterized by an XRPD pattern comprising peaks at approximately 8.0, 22.9, and 25.0° 2θ using Cu Kα radiation. In one embodiment, the Form 1 polymorph is characterized by an XRPD pattern substantially similar to that set forth in FIG. 57.

In one embodiment, the present application provides a Form 1 polymorph of Compound A characterized by endothermic events with onset between approximately 208° C. and approximately 230° C., and an exothermic event with onset at approximately 217° C., as measured by DTA or DSC. In one embodiment, the Form 1 polymorph is characterized by endothermic events with onset between approximately 208° C. and approximately 210° C., between approximately 213° C. and approximately 215° C., and between approximately 227° C. and approximately 230° C., and an exothermic event with onset at approximately 217° C., as measured by DTA or DSC. In one embodiment, the Form 1 polymorph is characterized by a DTA thermogram substantially similar to that set forth in FIG. 11 or FIG. 22 or a DSC thermogram substantially similar to that set forth in FIG. 23.

In one embodiment, the present application provides a Form 2 polymorph of Compound A characterized by an XRPD pattern comprising peaks at approximately 16.4, 16.6, and 22.6° 2θ using Cu Kα radiation. In one embodiment, the Form 2 polymorph is characterized by an XRPD pattern substantially similar to that set forth in FIG. 58.

In one embodiment, the present application provides a Form 2 polymorph of Compound A characterized by endothermic events with onset at approximately 116° C., approximately 207° C., approximately 215° C., and approximately 228° C. as measured by DTA. In one embodiment, the Form 2 polymorph is characterized by a DTA thermogram substantially similar to that set forth in FIG. 12.

In one embodiment, the present application provides a Form 3 polymorph of Compound A characterized by an XRPD pattern comprising peaks at approximately 16.0, 16.4, and 22.2° 2θ using Cu Kα radiation. In one embodiment, the Form 3 polymorph is characterized by an XRPD pattern substantially similar to that set forth in FIG. 59.

In one embodiment, the present application provides a Form 4 polymorph of Compound A characterized by an XRPD pattern comprising peaks at approximately 5.5, 8.4, and 25.1° 2θ using Cu Kα radiation. In one embodiment, the Form 4 polymorph is characterized by an XRPD pattern substantially similar to that set forth in FIG. 60.

In one embodiment, the present application provides a Form 4 polymorph of Compound A characterized by endothermic events with onset between approximately 194° C. and approximately 209° C., and at approximately 226° C., and an exothermic event with onset between approximately 213° C. and approximately 215° C., as measured by DTA or DSC. In one embodiment, the Form 4 polymorph is characterized by a DTA thermogram substantially similar to that set forth in FIG. 13 or FIG. 32 or a DSC thermogram substantially similar to that set forth in FIG. 33.

In one embodiment, the present application provides a Form 5 polymorph of Compound A characterized by an XRPD pattern comprising peaks at approximately 4.5, 4.7, and 20.8° 2θ using Cu Kα radiation. In one embodiment, the Form 5 polymorph is characterized by an XRPD pattern substantially similar to that set forth in FIG. 61.

In one embodiment, the present application provides a Form 5 polymorph of Compound A characterized by endothermic events with onset between approximately 94° C. and approximately 104° C., and between approximately 225° C. and approximately 226° C. as measured by DTA. In one embodiment, the Form 5 polymorph is characterized by a DTA thermogram substantially similar to that set forth in FIG. 14, FIG. 15, or FIG. 16.

In one embodiment, the present application provides a Form 7 polymorph of Compound A characterized by an XRPD pattern comprising peaks at approximately 5.5, 19.0, and 20.6° 2θ using Cu Kα radiation. In one embodiment, the Form 7 polymorph is characterized by an XRPD pattern substantially similar to that set forth in FIG. 62.

In one embodiment, the present application provides a Form 7 polymorph of Compound A characterized by an endothermic event with onset at approximately 225° C. as measured by DTA. In one embodiment, the Form 7 polymorph is characterized by a DTA thermogram substantially similar to that set forth in FIG. 19.

In one embodiment, the present application provides a Form 8 polymorph of Compound A characterized by an XRPD pattern comprising peaks at approximately 5.2, 8.0, and 23.4° 2θ using Cu Kα radiation. In one embodiment, the Form 8 polymorph is characterized by an XRPD pattern substantially similar to that set forth in FIG. 63.

In one embodiment, the present application provides a Form 8 polymorph of Compound A characterized by an endothermic event with onset between approximately 224° C. and approximately 225° C. as measured by DTA or DSC. In one embodiment, the Form 8 polymorph is characterized by a DTA thermogram substantially similar to that set forth in FIG. 17 or FIG. 42 or a DSC thermogram substantially similar to that set forth in FIG. 43.

In one embodiment, the present application provides a Form 9 polymorph of Compound A characterized by an XRPD pattern comprising peaks at approximately 4.9, 16.4, and 16.6° 2θ using Cu Kα radiation. In one embodiment, the Form 9 polymorph is characterized by an XRPD pattern substantially similar to that set forth in FIG. 65.

In one embodiment, the present application provides a Form 9 polymorph of Compound A characterized by endothermic events with onsets at approximately 69° C. and approximately 218° C. as measured by DSC. In one embodiment, the Form 9 polymorph is characterized by a DSC thermogram substantially similar to that set forth in FIG. 66.

In one embodiment, the present application provides a Form 10 polymorph of Compound A characterized by an XRPD pattern comprising peaks at approximately 7.2, 7.4, and 11.9° 2θ using Cu Kα radiation. In one embodiment, the Form 10 polymorph is characterized by an XRPD pattern substantially similar to that set forth in FIG. 68.

In one embodiment, the present application provides a Form 10 polymorph of Compound A characterized by endothermic events with onsets at approximately 106° C., approximately 206° C., and approximately 213° C. as measured by DSC. In one embodiment, the Form 10 polymorph is characterized by a DSC thermogram substantially similar to that set forth in FIG. 71.

In one embodiment, the present application provides a Form 10 polymorph of Compound A characterized by endothermic events with onsets at approximately 195° C. and approximately 230° C. as measured by DSC. In one embodiment, the Form 10 polymorph is characterized by a DSC thermogram substantially similar to that set forth in FIG. 75.

In one embodiment, the present application provides a Form 11 polymorph of Compound A characterized by an XRPD pattern comprising peaks at approximately 16.1, 16.6, and 21.7° 2θ using Cu Kα radiation. In one embodiment, the Form 11 polymorph is characterized by an XRPD pattern substantially similar to that set forth in FIG. 87.

In one embodiment, the present application provides a Form 11 polymorph of Compound A characterized by endothermic events with onsets at approximately 112° C., approximately 197° C., and approximately 221° C. as measured by DTA. In one embodiment, the Form 11 polymorph is characterized by a DTA thermogram substantially similar to that set forth in FIG. 89.

In one embodiment, the present application provides a Form 11 polymorph of Compound A characterized by an XRPD pattern comprising peaks at approximately 16.1, 16.5, and 22.6° 2θ using Cu Kα radiation. In one embodiment, the Form 11 polymorph is characterized by an XRPD pattern substantially similar to that set forth in FIG. 92.

In one embodiment, the present application provides a Form 11 polymorph of Compound A characterized by endothermic events with onsets at approximately 119° C., approximately 195° C., approximately 210° C., and approximately 224° C. as measured by DTA. In one embodiment, the Form 11 polymorph is characterized by a DTA thermogram substantially similar to that set forth in FIG. 93.

In one embodiment, the present application provides a Form 12 polymorph of Compound A characterized by an XRPD pattern comprising peaks at approximately 19.6, 20.2, and 22.6° 2θ using Cu Kα radiation. In one embodiment, the Form 12 polymorph is characterized by an XRPD pattern substantially similar to that set forth in FIG. 95.

In one embodiment, the present application provides crystalline forms of salts of Compound A. In one embodiment, the present application provides polymorphs of salts of Compound A.

In one embodiment, the present application provides an edisylate Form 1 polymorph of Compound A characterized by an XRPD pattern comprising peaks at approximately 4.3, 19.0, and 22.9° 2θ using Cu Kα radiation. In one embodiment, the edisylate Form 1 polymorph is characterized by an XRPD pattern substantially similar to that set forth in FIG. 97.

In one embodiment, the present application provides an edisylate Form 1 polymorph of Compound A characterized by an endothermic event onset at approximately 229° C. or approximately 230° C. as measured by DTA. In one embodiment, the edisylate Form 1 polymorph is characterized by a DTA thermogram substantially similar to that set forth in FIG. 98.

In one embodiment, the present application provides a cyclamate Form 1 polymorph of Compound A characterized by an XRPD pattern comprising peaks at approximately 5.3, 6.4, and 18.5° 2θ using Cu Kα radiation. In one embodiment, the cyclamate Form 1 polymorph is characterized by an XRPD pattern substantially similar to that set forth in FIG. 102.

In one embodiment, the present application provides a cyclamate Form 1 polymorph of Compound A characterized by an endothermic event onset at approximately 220° C. as measured by DTA. In one embodiment, the cyclamate Form 1 polymorph is characterized by a DTA thermogram substantially similar to that set forth in FIG. 103.

In one embodiment, the present application provides a cyclamate Form 2 polymorph of Compound A characterized by an XRPD pattern comprising peaks at approximately 7.1, 18.5, and 21.6° 2θ using Cu Kα radiation. In one embodiment, the cyclamate Form 2 polymorph is characterized by an XRPD pattern substantially similar to that set forth in FIG. 107.

In one embodiment, the present application provides a cyclamate Form 2 polymorph of Compound A characterized by no clear thermal events, with potential events noted at approximately 145° C. and approximately 177° C. as measured by DTA. In one embodiment, the cyclamate Form 2 polymorph is characterized by a DTA thermogram substantially similar to that set forth in FIG. 108.

In one embodiment, the present application provides a naphthalene-2-sulfonic acid salt polymorph of Compound A characterized by an XRPD pattern comprising peaks at approximately 17.5, 22.8, and 25.5° 2θ using Cu Kα radiation. In one embodiment, the naphthalene-2-sulfonic acid salt polymorph is characterized by an XRPD pattern substantially similar to that set forth in FIG. 112.

In one embodiment, the present application provides a naphthalene-2-sulfonic acid salt polymorph of Compound A characterized by endothermic events with onsets at approximately 108° C., approximately 139° C., approximately 173° C., and approximately 244° C. as measured by DTA. In one embodiment, the naphthalene-2-sulfonic acid salt polymorph is characterized by a DTA thermogram substantially similar to that set forth in FIG. 113.

In one embodiment, the present application provides a hydrobromide Form 1 polymorph of Compound A characterized by an XRPD pattern comprising peaks at approximately 4.5, 22.6, and 26.8° 2θ using Cu Kα radiation. In one embodiment, the hydrobromide Form 1 polymorph is characterized by an XRPD pattern substantially similar to that set forth in FIG. 117, FIG. 237, or FIG. 257.

In one embodiment, the present application provides a hydrobromide Form 1 polymorph of Compound A characterized by endothermic events with onsets at approximately 35° C. and approximately 172° C. as measured by DTA. In one embodiment, the hydrobromide Form 1 polymorph is characterized by a DTA thermogram substantially similar to that set forth in FIG. 118.

In one embodiment, the present application provides a hydrobromide Form 1 polymorph of Compound A characterized by an endothermic event with an onset at approximately 46° C. as measured by DTA. In one embodiment, the hydrobromide Form 1 polymorph is characterized by a DTA thermogram substantially similar to that set forth in FIG. 238.

In one embodiment, the present application provides a hydrobromide Form 1 polymorph of Compound A characterized by endothermic events with onsets at approximately 63° C. and approximately 150° C. as measured by DSC. In one embodiment, the hydrobromide Form 1 polymorph is characterized by a DSC thermogram substantially similar to that set forth in FIG. 260.

In one embodiment, the present application provides a hydrobromide Form 2 polymorph of Compound A characterized by an XRPD pattern comprising peaks at approximately 4.5, 21.7, and 26.8° 2θ using Cu Kα radiation. In one embodiment, the hydrobromide Form 2 polymorph is characterized by an XRPD pattern substantially similar to that set forth in FIG. 122.

In one embodiment, the present application provides a hydrobromide Form 2 polymorph of Compound A characterized by an endothermic event with an onset at approximately 202° C. as measured by DTA. In one embodiment, the hydrobromide Form 2 polymorph is characterized by a DTA thermogram substantially similar to that set forth in FIG. 123.

In one embodiment, the present application provides a besylate Form 1 polymorph of Compound A characterized by an XRPD pattern comprising peaks at approximately 5.8, 6.0, and 18.9° 2θ using Cu Kα radiation. In one embodiment, the besylate Form 1 polymorph is characterized by an XRPD pattern substantially similar to that set forth in FIG. 127, FIG. 186, or FIG. 270.

In one embodiment, the present application provides a besylate Form 1 polymorph of Compound A characterized by an endothermic event with an onset at approximately 179° C. or approximately 180° C. as measured by DTA. In one embodiment, the besylate Form 1 polymorph is characterized by a DTA thermogram substantially similar to that set forth in FIG. 128 or FIG. 272.

In one embodiment, the present application provides a besylate Form 1 polymorph of Compound A characterized by an endothermic event with an onset at approximately 184° C. as measured by DTA. In one embodiment, the besylate Form 1 polymorph is characterized by a DTA thermogram substantially similar to that set forth in FIG. 187.

In one embodiment, the present application provides a besylate Form 1 polymorph of Compound A characterized by endothermic events with onsets at approximately 172° C. as measured by DSC. In one embodiment, the besylate Form 1 polymorph is characterized by a DSC thermogram substantially similar to that set forth in FIG. 273.

In one embodiment, the present application provides a hydrochloride Form 1 polymorph of Compound A characterized by an XRPD pattern comprising peaks at approximately 4.6, 19.8, and 22.7° 2θ using Cu Kα radiation. In one embodiment, the hydrochloride Form 1 polymorph is characterized by an XRPD pattern substantially similar to that set forth in FIG. 181.

In one embodiment, the present application provides a hydrochloride Form 2 polymorph of Compound A characterized by an XRPD pattern comprising peaks at approximately 16.0, 16.4, and 21.6° 2θ using Cu Kα radiation. In one embodiment, the hydrochloride Form 2 polymorph is characterized by an XRPD pattern substantially similar to that set forth in FIG. 181 or FIG. 185.

In one embodiment, the present application provides a hydrochloride Form 2 polymorph of Compound A characterized by an endothermic event with an onset at approximately 129° C. as measured by DTA. In one embodiment, the hydrochloride Form 2 polymorph is characterized by a DTA thermogram substantially similar to that set forth in FIG. 182.

In one embodiment, the present application provides an oxalate Form 1 polymorph of Compound A characterized by an XRPD pattern comprising peaks at approximately 4.1, 19.3, and 19.7° 2θ using Cu Kα radiation. In one embodiment, the oxalate Form 1 polymorph is characterized by an XRPD pattern substantially similar to that set forth in FIG. 191.

In one embodiment, the present application provides an oxalate Form 1 polymorph of Compound A characterized by an endothermic event with an onset at approximately 157° C. as measured by DTA. In one embodiment, the oxalate Form 1 polymorph is characterized by a DTA thermogram substantially similar to that set forth in FIG. 192.

In one embodiment, the present application provides an oxalate Form 3 polymorph of Compound A characterized by an XRPD pattern comprising peaks at approximately 8.5, 17.6, and 21.6° 2θ using Cu Kα radiation. In one embodiment, the oxalate Form 3 polymorph is characterized by an XRPD pattern substantially similar to that set forth in FIG. 194.

In one embodiment, the present application provides an oxalate Form 3 polymorph of Compound A characterized by an endothermic event with onset at approximately 148° C. or approximately 156° C. as measured by DTA. In one embodiment, the oxalate Form 3 polymorph is characterized by a DTA thermogram substantially similar to that set forth in FIG. 195 or FIG. 196.

In one embodiment, the present application provides an oxalate Form 5 polymorph of Compound A characterized by an XRPD pattern comprising peaks at approximately 4.0, 19.5, and 19.8° 2θ using Cu Kα radiation. In one embodiment, the oxalate Form 5 polymorph is characterized by an XRPD pattern substantially similar to that set forth in FIG. 191.

In one embodiment, the present application provides an oxalate Form 5 polymorph of Compound A characterized by an endothermic event with an onset at approximately 159° C. as measured by DTA. In one embodiment, the oxalate Form 5 polymorph is characterized by a DTA thermogram substantially similar to that set forth in FIG. 200.

In one embodiment, the present application provides a maleate Form 1 polymorph of Compound A characterized by an XRPD pattern comprising peaks at approximately 6.0, 6.3, and 19.1° 2θ using Cu Kα radiation. In one embodiment, the maleate Form 1 polymorph is characterized by an XRPD pattern substantially similar to that set forth in FIG. 204.

In one embodiment, the present application provides a maleate Form 1 polymorph of Compound A characterized by endothermic events with onsets at approximately 159° C. or approximately 166° C. as measured by DTA. In one embodiment, the maleate Form 1 polymorph is characterized by a DTA thermogram substantially similar to that set forth in FIG. 205 or FIG. 206.

In one embodiment, the present application provides a 1,5-naphthalene disulfonate Form 1 polymorph of Compound A characterized by an XRPD pattern comprising peaks at approximately 5.2, 18.1, and 19.0° 2θ using Cu Kα radiation. In one embodiment, the 1,5-naphthalene disulfonate Form 1 polymorph is characterized by an XRPD pattern substantially similar to that set forth in FIG. 210.

In one embodiment, the present application provides a 1,5-naphthalene disulfonate Form 1 polymorph of Compound A characterized by decomposition. In one embodiment, the 1,5-naphthalene disulfonate Form 1 polymorph is characterized by a DTA thermogram substantially similar to that set forth in FIG. 212.

In one embodiment, the present application provides a 1,5-naphthalene disulfonate mixture of Form 1 and Form 3 polymorphs of Compound A characterized by an XRPD pattern comprising peaks at approximately 4.7, 18.0, and 18.3° 2θ using Cu Kα radiation. In one embodiment, the 1,5-naphthalene disulfonate mixture of Form 1 and Form 3 polymorphs is characterized by an XRPD pattern substantially similar to that set forth in FIG. 210.

In one embodiment, the present application provides a 1,5-naphthalene disulfonate mixture of Form 1 and Form 3 polymorphs of Compound A characterized by an endothermic event with an onset at approximately 111° C. as measured by DTA. In one embodiment, the 1,5-naphthalene disulfonate mixture of Form 1 and Form 3 polymorphs is characterized by a DTA thermogram substantially similar to that set forth in FIG. 211.

In one embodiment, the present application provides a 1,5-naphthalene disulfonate Form 2 polymorph of Compound A characterized by an XRPD pattern comprising peaks at approximately 7.2, 18.1, and 26.0° 2θ using Cu Kα radiation. In one embodiment, the 1,5-naphthalene disulfonate Form 2 polymorph is characterized by an XRPD pattern substantially similar to that set forth in FIG. 216.

In one embodiment, 1,5-naphthalene disulfonate Form 2 and Form 5 is characterized by an endothermic event with an onset at approximately 219° C. as measured by DTA. In one embodiment, 1,5-naphthalene disulfonate Form 2 and Form 5 is characterized by a DTA thermogram substantially similar to that set forth in FIG. 217.

In one embodiment, the present application provides a 1,5-naphthalene disulfonate mixture of Form 2 and Form 5 polymorphs of Compound A characterized by an XRPD pattern comprising peaks at approximately 6.1, 15.9, and 18.1° 2θ using Cu Kα radiation. In one embodiment, the 1,5-naphthalene disulfonate mixture of Form 2 and Form 5 polymorphs is characterized by an XRPD pattern substantially similar to that set forth in FIG. 216.

In one embodiment, the present application provides a 1,5-naphthalene disulfonate Form 4 polymorph of Compound A characterized by an XRPD pattern comprising peaks at approximately 6.1, 8.8, and 16.0° 2θ using Cu Kα radiation. In one embodiment, the 1,5-naphthalene disulfonate Form 4 polymorph is characterized by an XRPD pattern substantially similar to that set forth in FIG. 219

In one embodiment, the present application provides a 1,5-naphthalene disulfonate Form 4 polymorph of Compound A characterized by an endothermic event with an onset at approximately 215° C. as measured by DTA. In one embodiment, the 1,5-naphthalene disulfonate Form 4 polymorph is characterized by a DTA thermogram substantially similar to that set forth in FIG. 220.

In one embodiment, the present application provides a phosphate Form 1 polymorph of Compound A characterized by an XRPD pattern comprising peaks at approximately 3.7, 19.9, and 22.0° 2θ using Cu Kα radiation. In one embodiment, the phosphate Form 1 polymorph is characterized by an XRPD pattern substantially similar to that set forth in FIG. 224 or FIG. 244.

In one embodiment, the present application provides a phosphate Form 1 polymorph of Compound A characterized by an endothermic event with an onset at approximately 157° C. or approximately 158° C. as measured by DTA. In one embodiment, the phosphate Form 1 polymorph is characterized by a DTA thermogram substantially similar to that set forth in FIG. 225, FIG. 226, FIG. 227, or FIG. 246.

In one embodiment, the present application provides a phosphate Form 1 polymorph of Compound A characterized by endothermic events with onsets at approximately 157° C. as measured by DSC. In one embodiment, the phosphate Form 1 polymorph is characterized by a DSC thermogram substantially similar to that set forth in FIG. 247.

In one embodiment, the present application provides a phosphate Form 2 polymorph of Compound A characterized by an XRPD pattern comprising peaks at approximately 4.9, 21.4, and 22.2° 2θ using Cu Kα radiation. In one embodiment, the phosphate Form 2 polymorph is characterized by an XRPD pattern substantially similar to that set forth in FIG. 231.

In one embodiment, the present application provides a phosphate Form 2 polymorph of Compound A characterized by an endothermic event with an onset at approximately 128° C. as measured by DTA. In one embodiment, the phosphate Form 2 polymorph is characterized by a DTA thermogram substantially similar to that set forth in FIG. 232 or FIG. 233.

In one embodiment, the present application provides a mixture of phosphate Form 2 and Form 3 polymorphs of Compound A characterized by an XRPD pattern comprising peaks at approximately 5.0, 16.2, and 24.9° 2θ using Cu Kα radiation. In one embodiment, the mixture of phosphate Form 2 and Form 3 is characterized by an XRPD pattern substantially similar to that set forth in FIG. 231.

The present application also provides a pharmaceutical composition comprising any one of the solid forms of Compound A (e.g., any of Forms 1-12, the amorphous form, and any solid forms of the salts of Compound A) as described herein, and a pharmaceutically acceptable carrier or excipient.

The present application also provides a method of treating a cell proliferative disorder, comprising administering, to a subject in need thereof, a therapeutically effective amount of a composition comprising any one of the solid forms of Compound A as described herein.

The present application also provides a solid form of Compound A as described herein for use in the manufacture of a medicament for treating a cell proliferative disorder in a subject in need thereof.

The present application also provides use of a solid form of Compound A as described herein in treating a cell proliferative disorder in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the disclosure will be apparent from the following detailed description and claims.

BRIEF DESCRIPTION OF THE FIGURES

Figure 99:
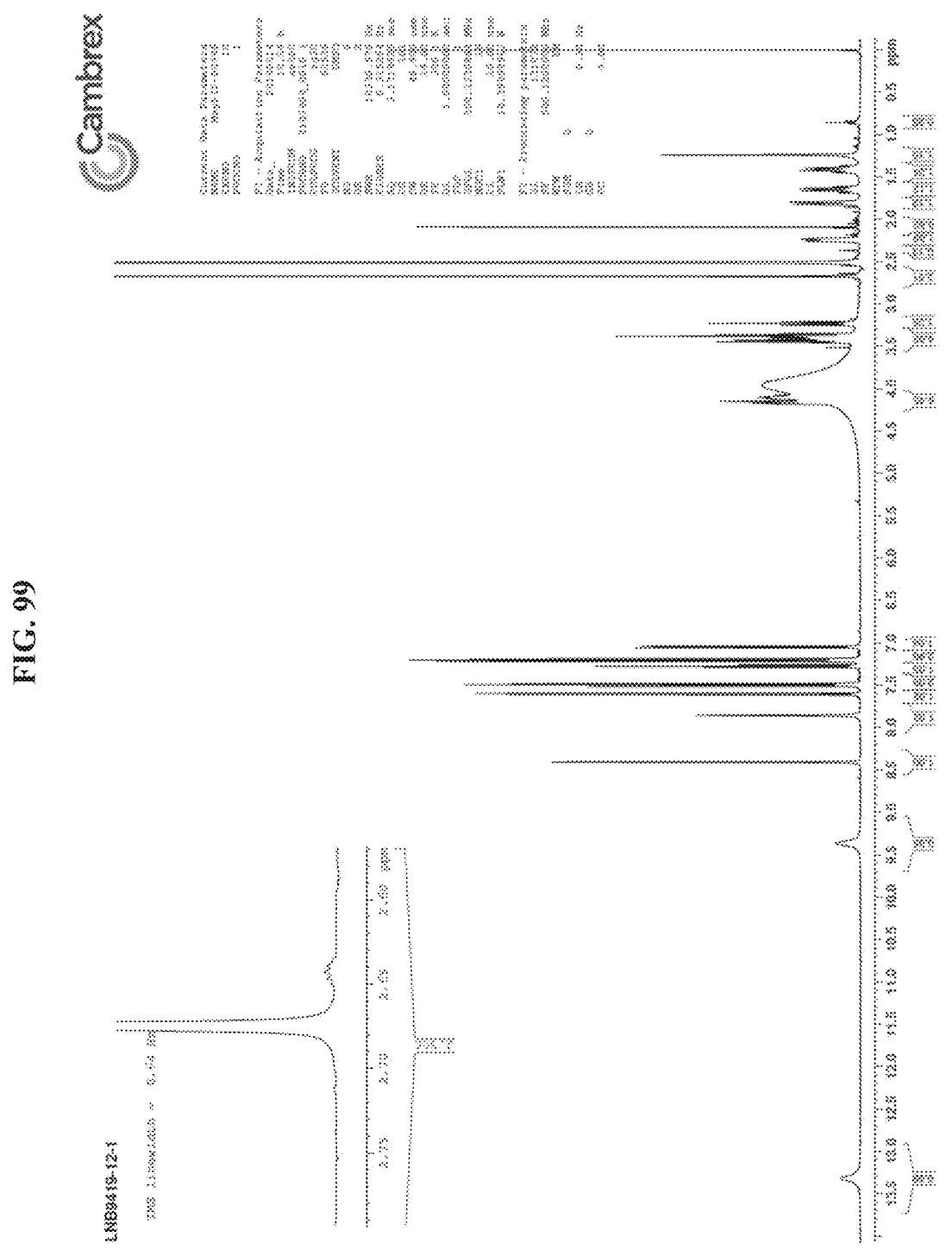

FIG. 99 sets forth a $^1$H NMR spectroscopic analysis of edisylate Form 1.

Figure 113:
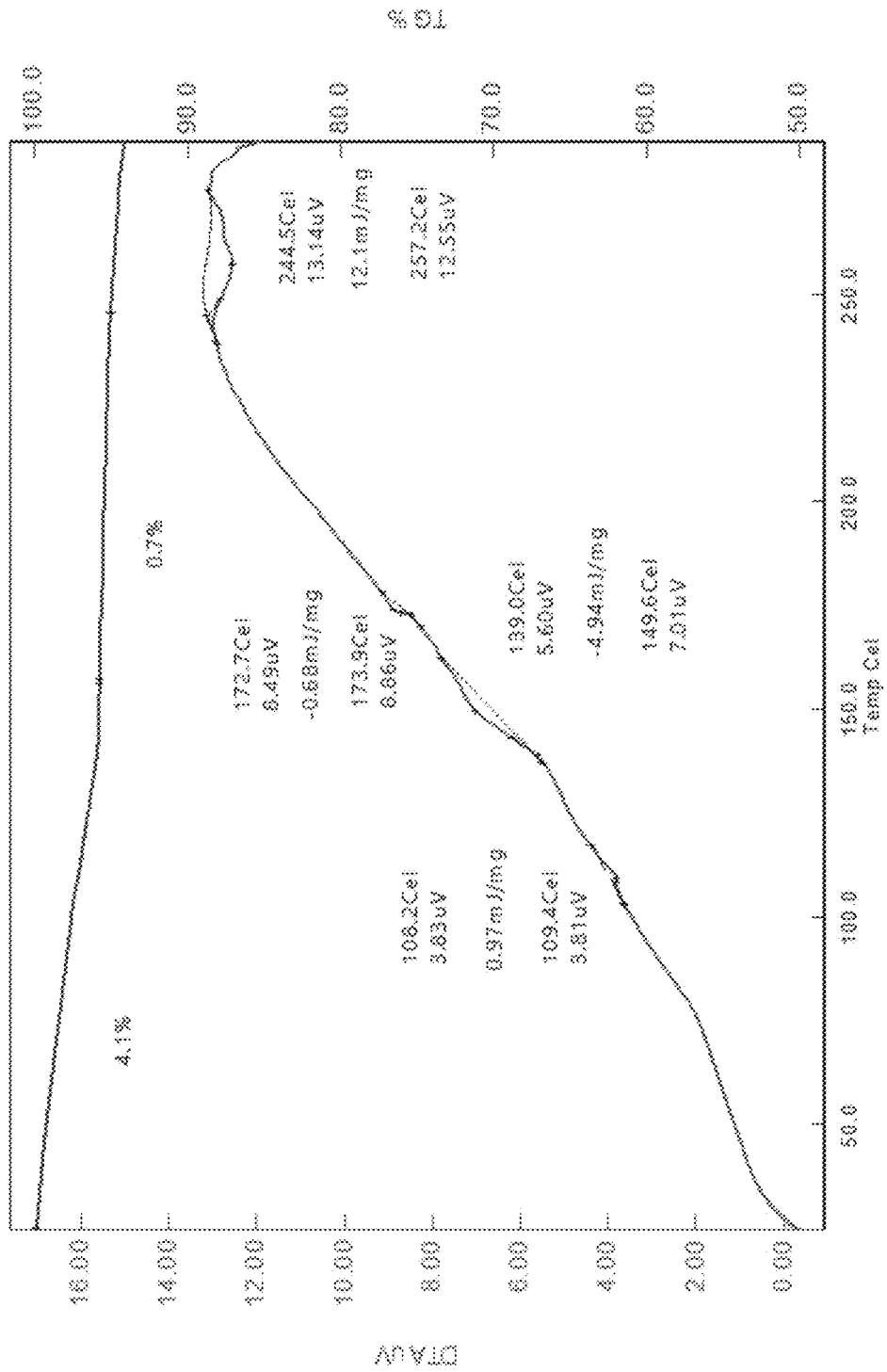

FIG. 113 sets forth a thermal analysis by TG/DTA of naphthalene-2-sulfonic salt.

Figure 114:
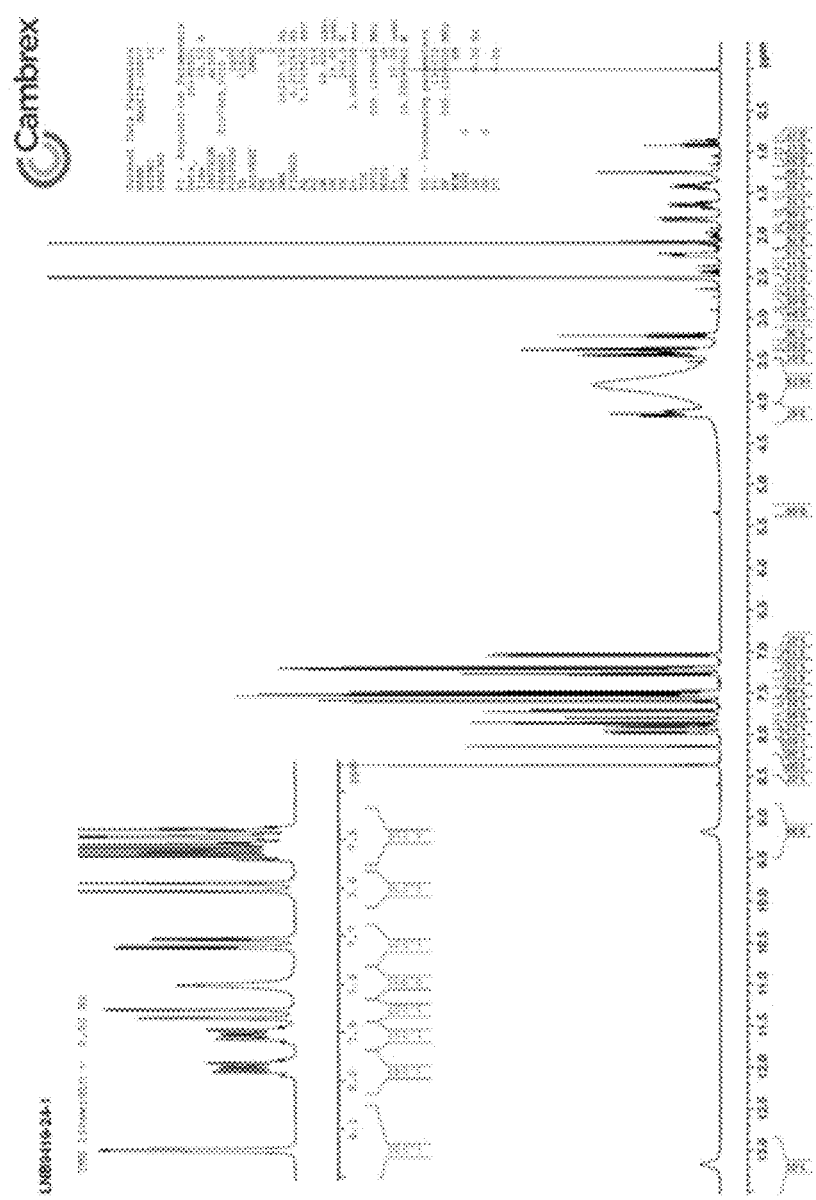

FIG. 114 sets forth a $^1$H NMR spectroscopic analysis of naphthalene-2-sulfonic acid salt.

Figure 115:
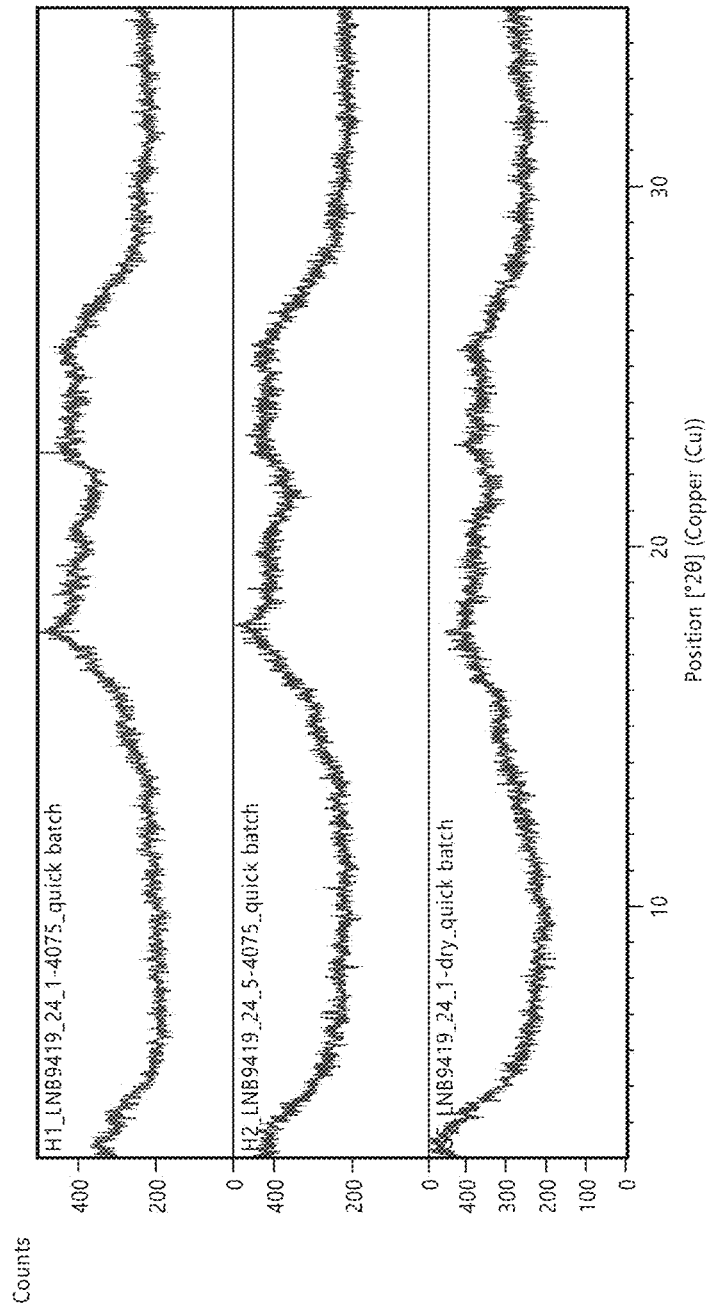

FIG. 115 sets forth XRPD patterns of naphthalene-2-sulfonic acid salt from evaporation of acetone or methyl ethyl ketone after storage at 40° C./75% RH.

Figure 116:
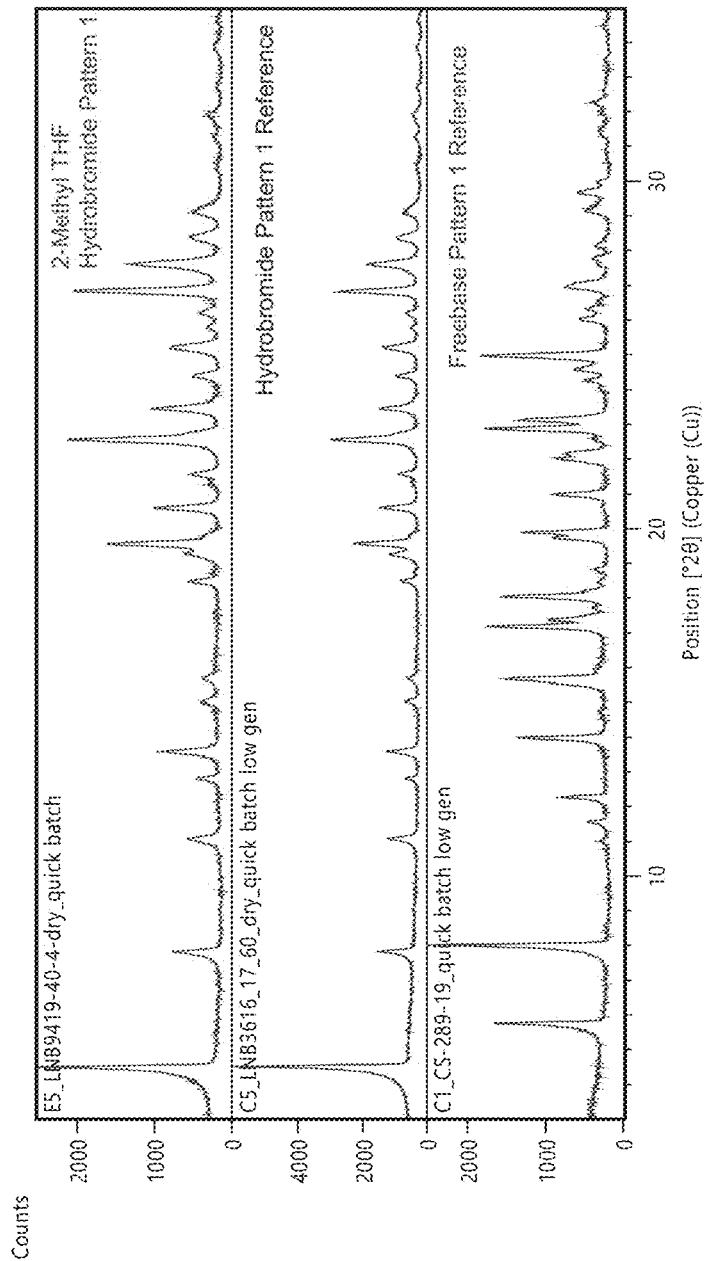

FIG. 116 sets forth comparative XRPD patterns of freebase Form 1 and hydrobromide Form 1.

Figure 117:
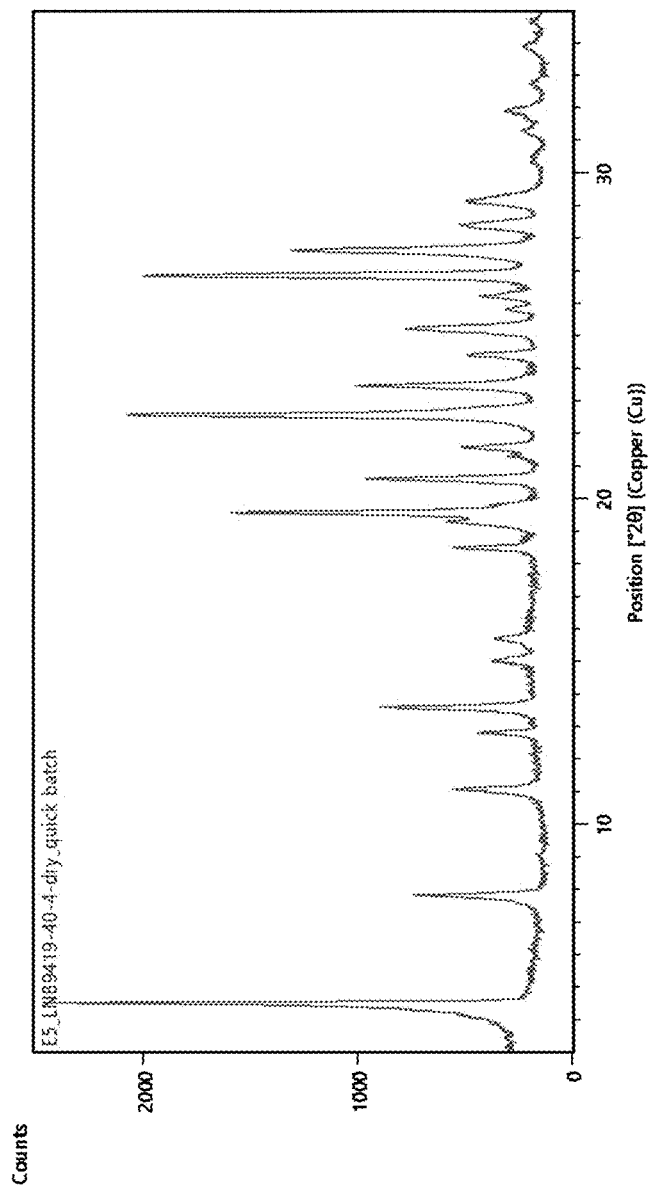

FIG. 117 sets forth an XRPD pattern of hydrobromide Form 1 from evaporation of 2-methyl THF.

Figure 118:
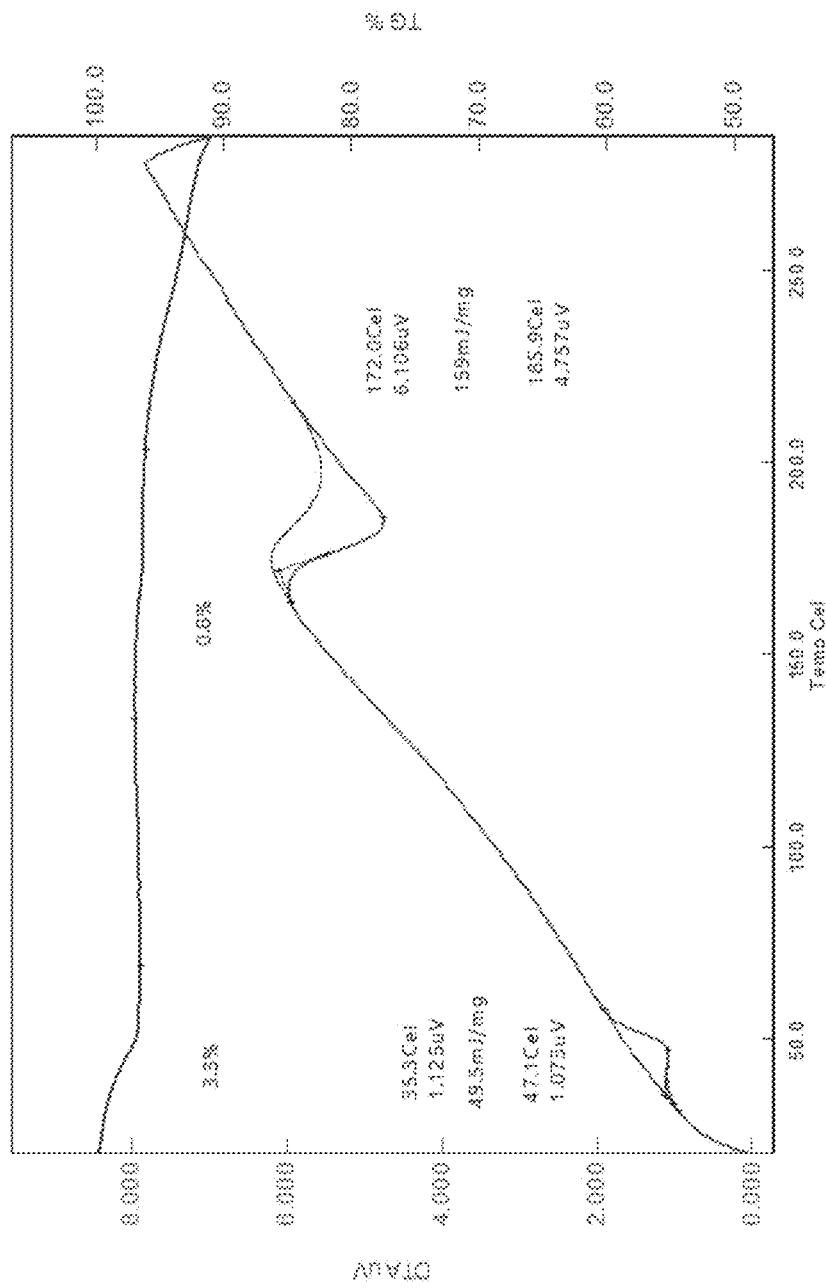

FIG. 118 sets forth a thermal analysis by TG/DTA of hydrobromide Form 1.

Figure 119:
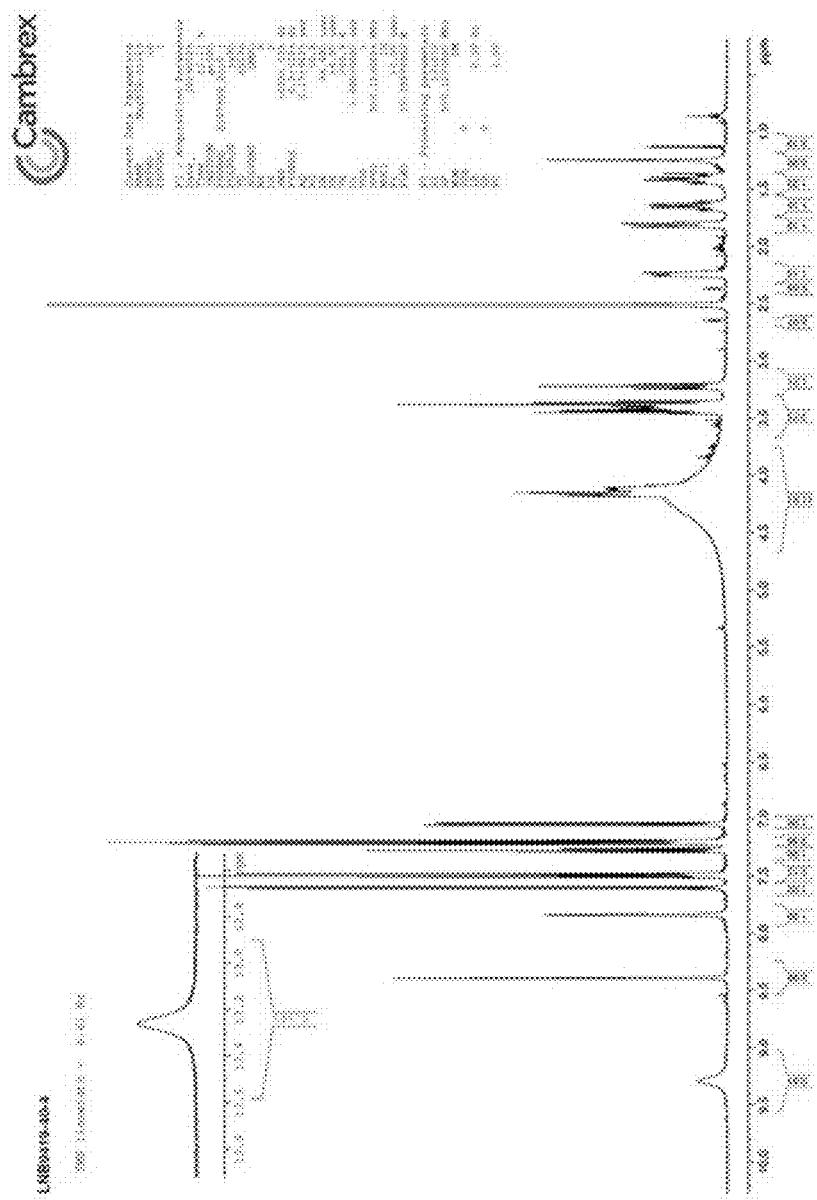

FIG. 119 sets forth a $^1$H NMR spectroscopic analysis of hydrobromide Form 1.

Figure 120:
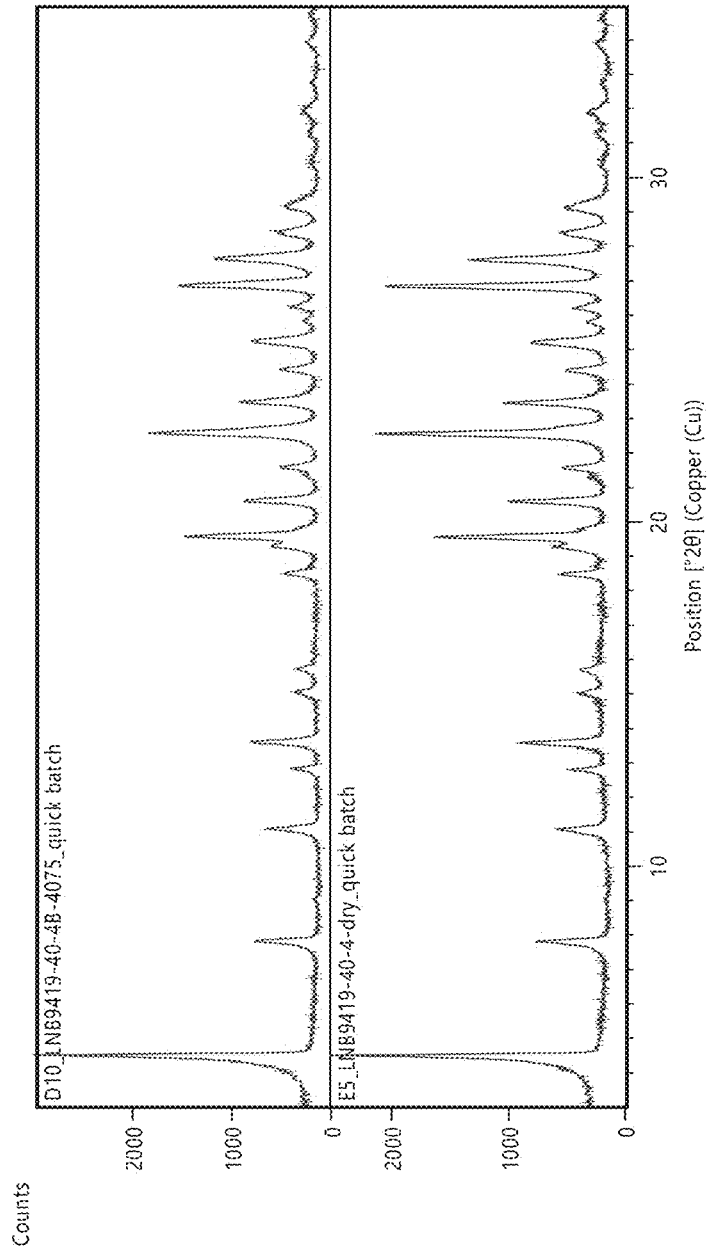

FIG. 120 sets forth XRPD patterns of hydrobromide Form 1 before and after storage at 40° C./75% RH.

Figure 121:
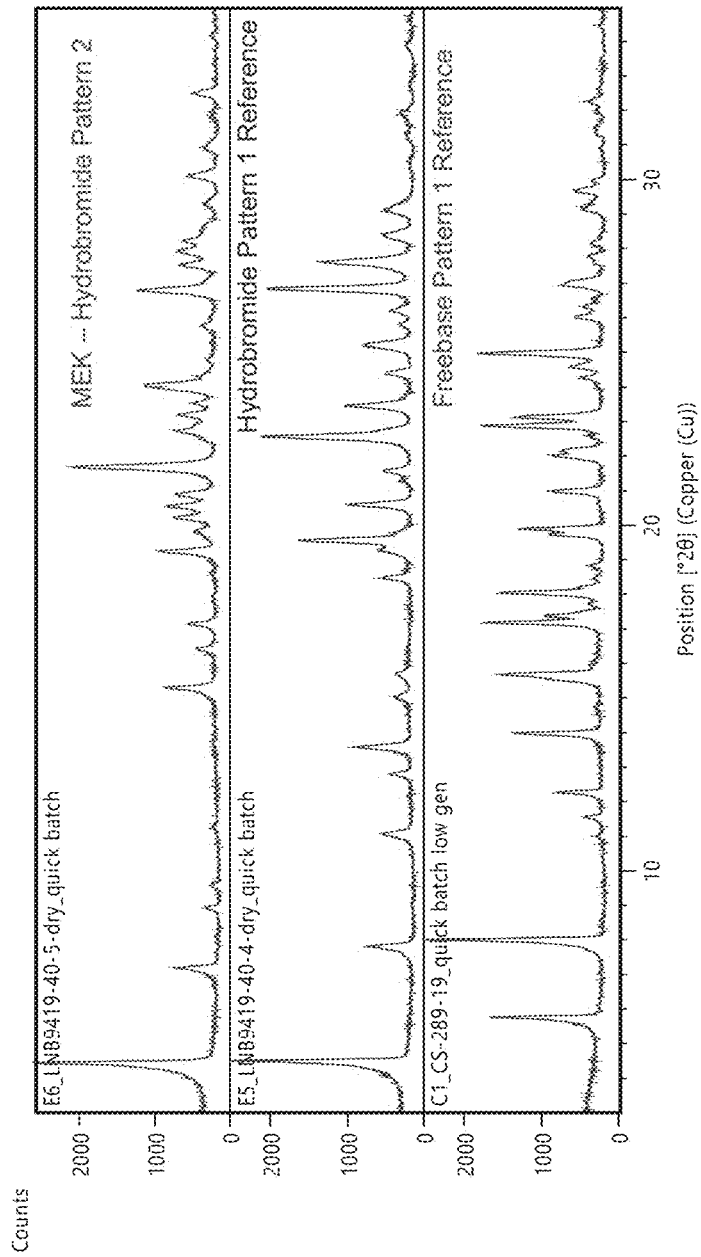

FIG. 121 sets forth comparative XRPD patterns of hydrobromide Form 2, hydrobromide Form 1, and freebase Form 1.

Figure 122:
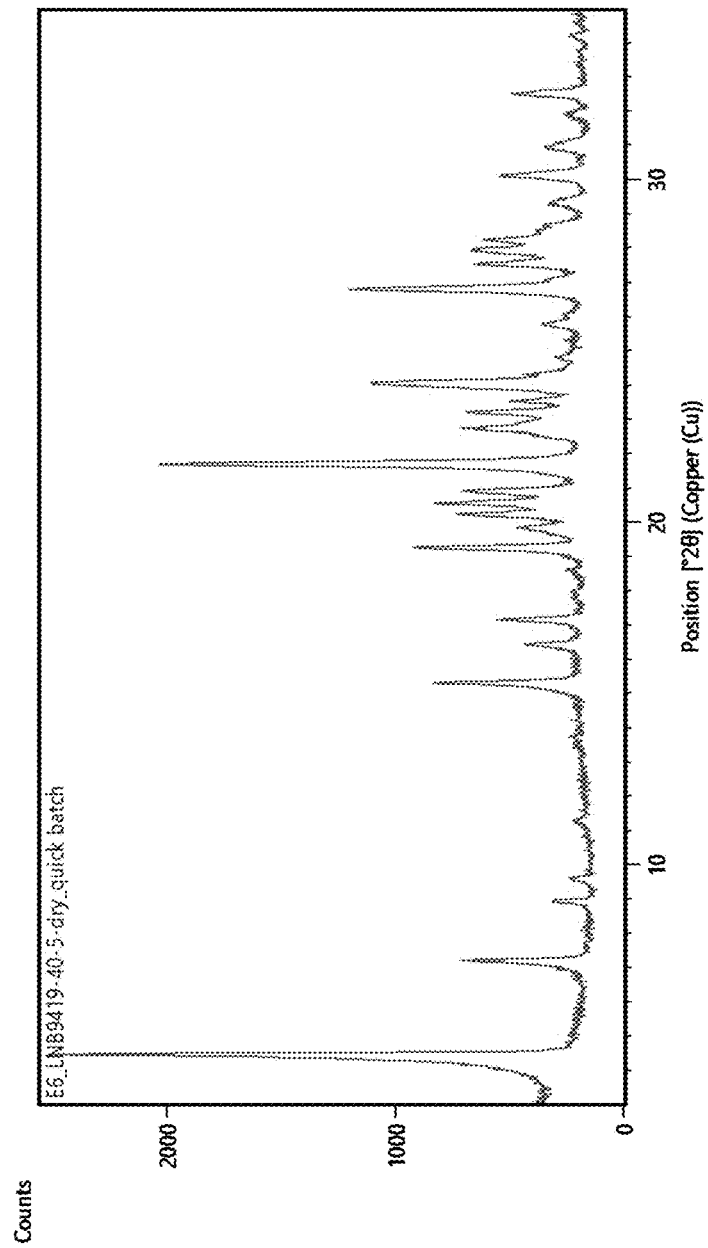

FIG. 122 sets forth an XRPD pattern of hydrobromide Form 2.

Figure 123:
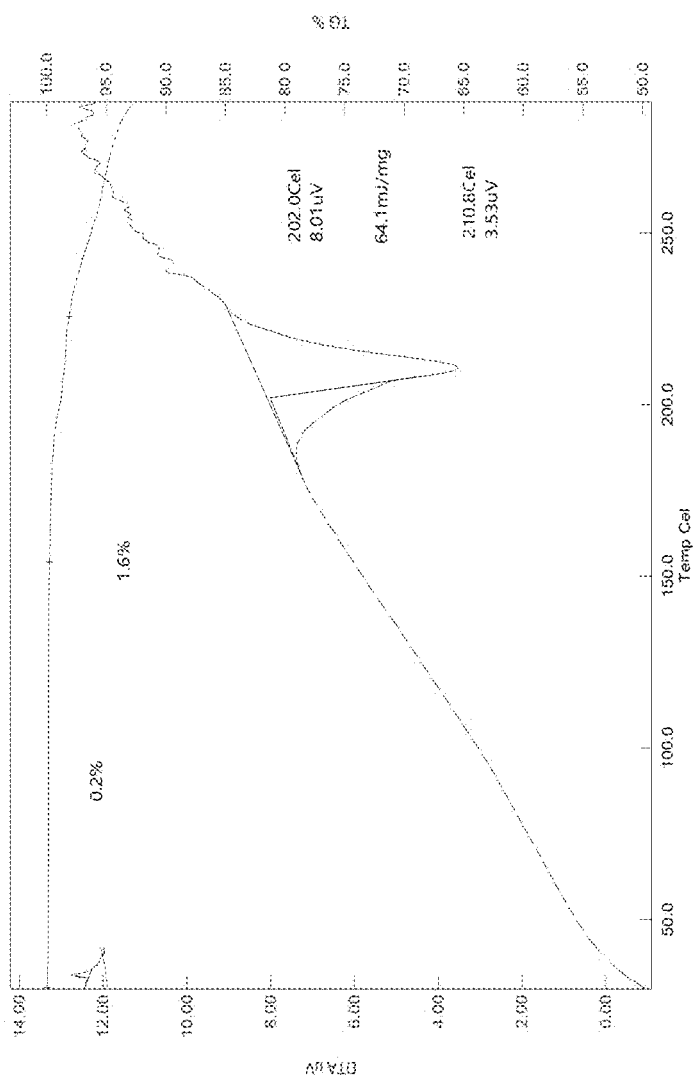

FIG. 123 sets forth a thermal analysis by TG/DTA of hydrobromide Form 2.

Figure 124:
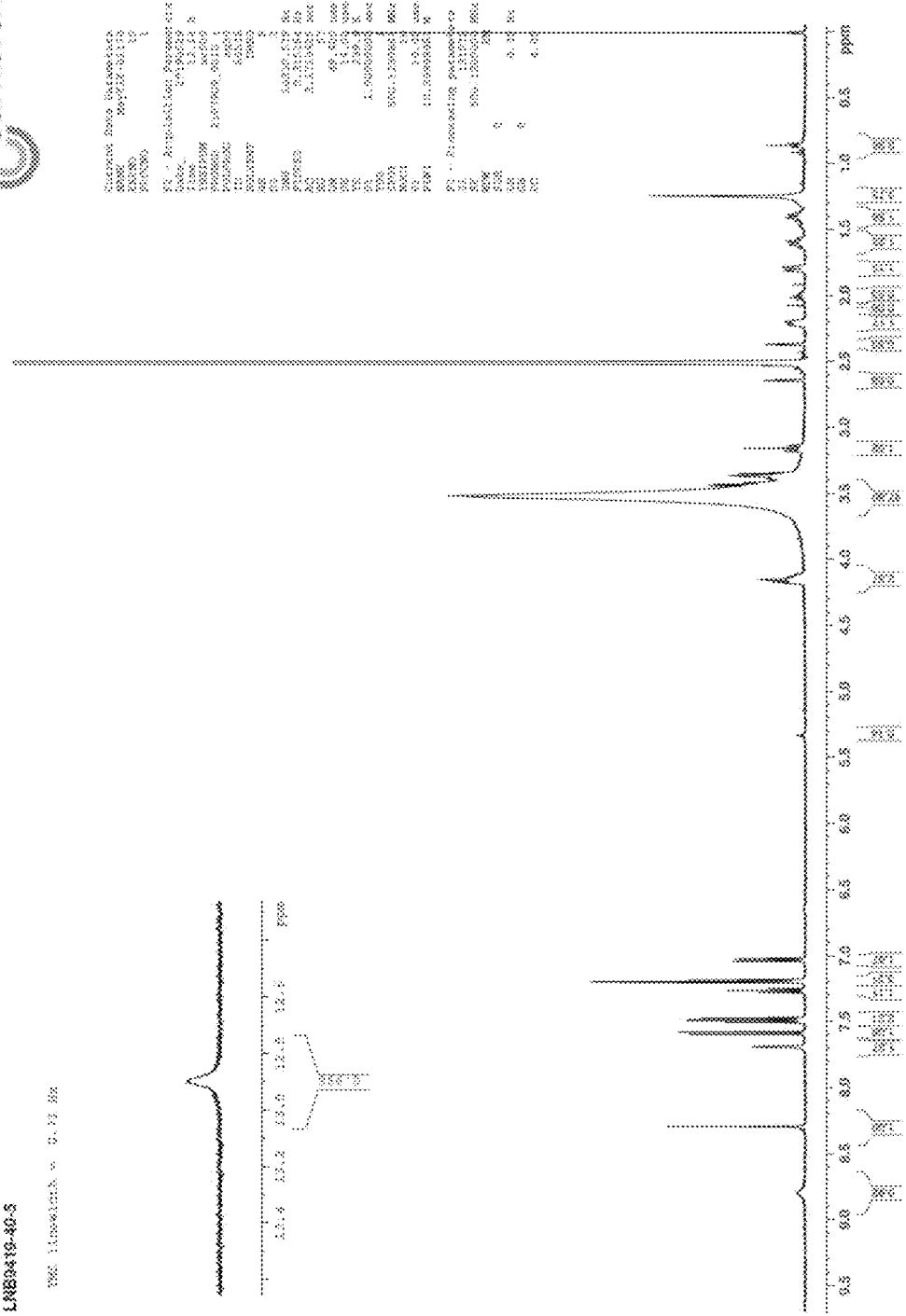

FIG. 124 sets forth a $^1$H NMR spectroscopic analysis of hydrobromide Form 2.

Figure 125:
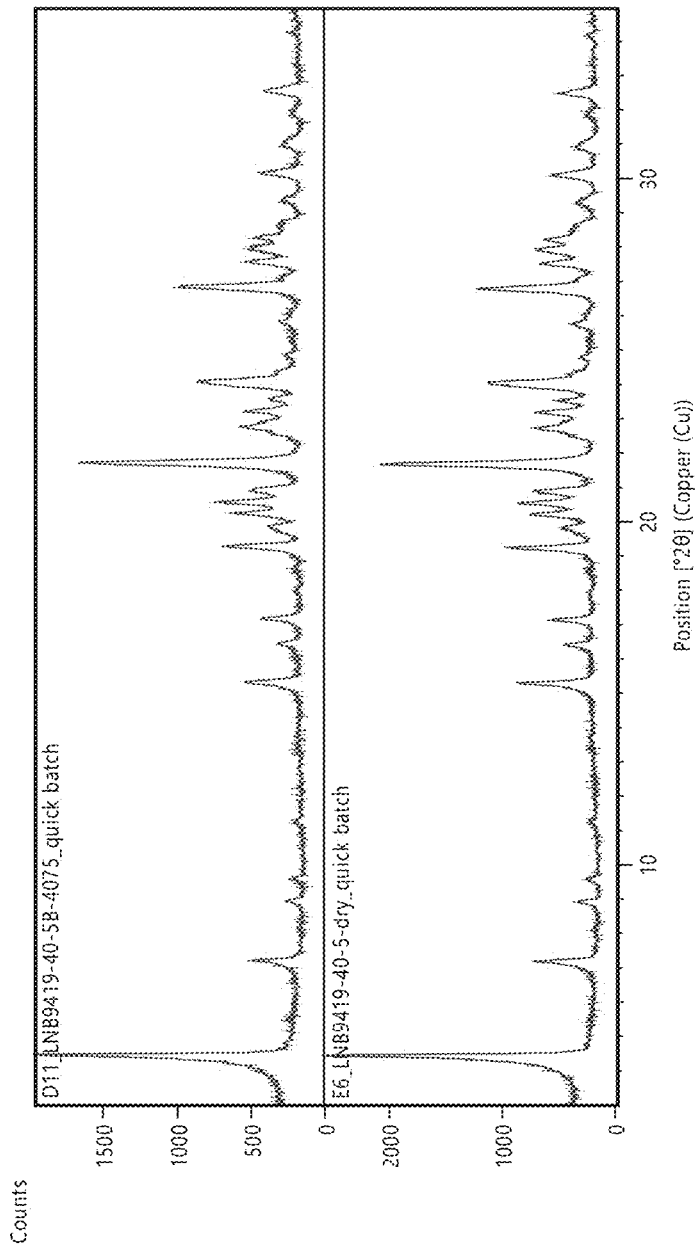

FIG. 125 sets forth XRPD patterns of hydrobromide Form 2 before and after storage at 40° C./75% RH.

Figure 126:
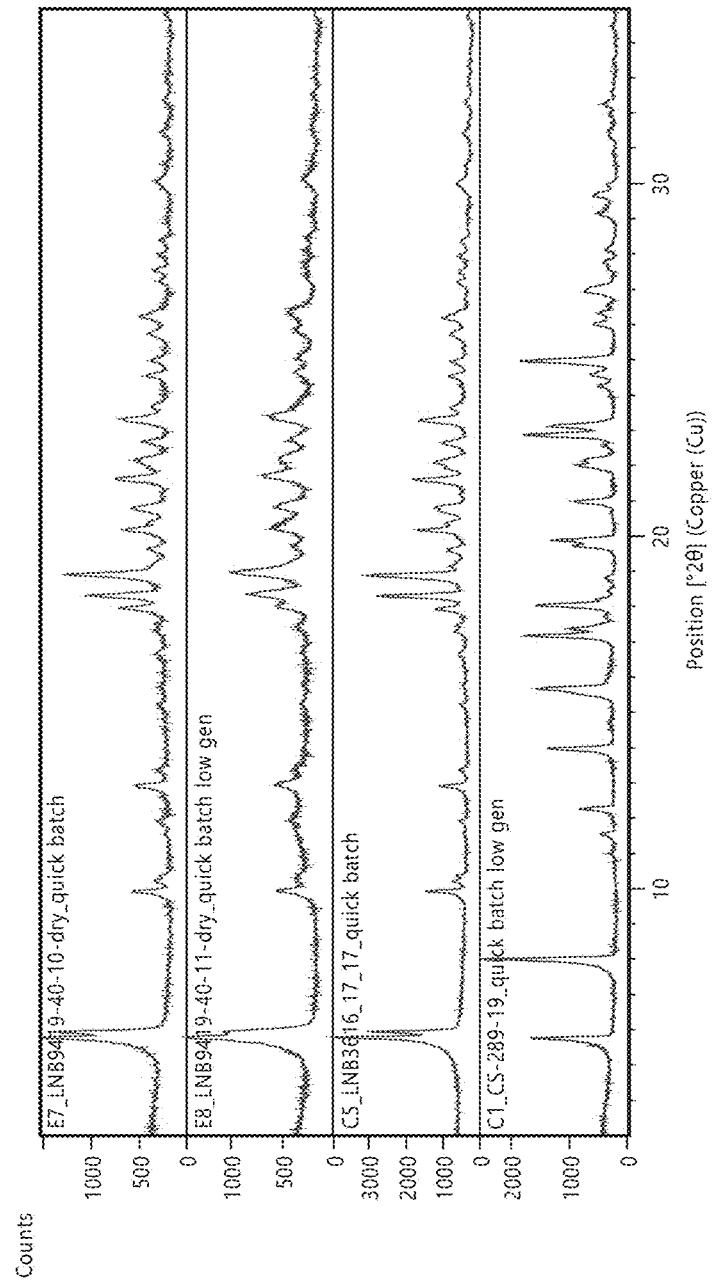

FIG. 126 sets forth comparative XRPD patterns of besylate Form 1 from THF or methyl ethyl ketone and freebase Form 1.

Figure 127:
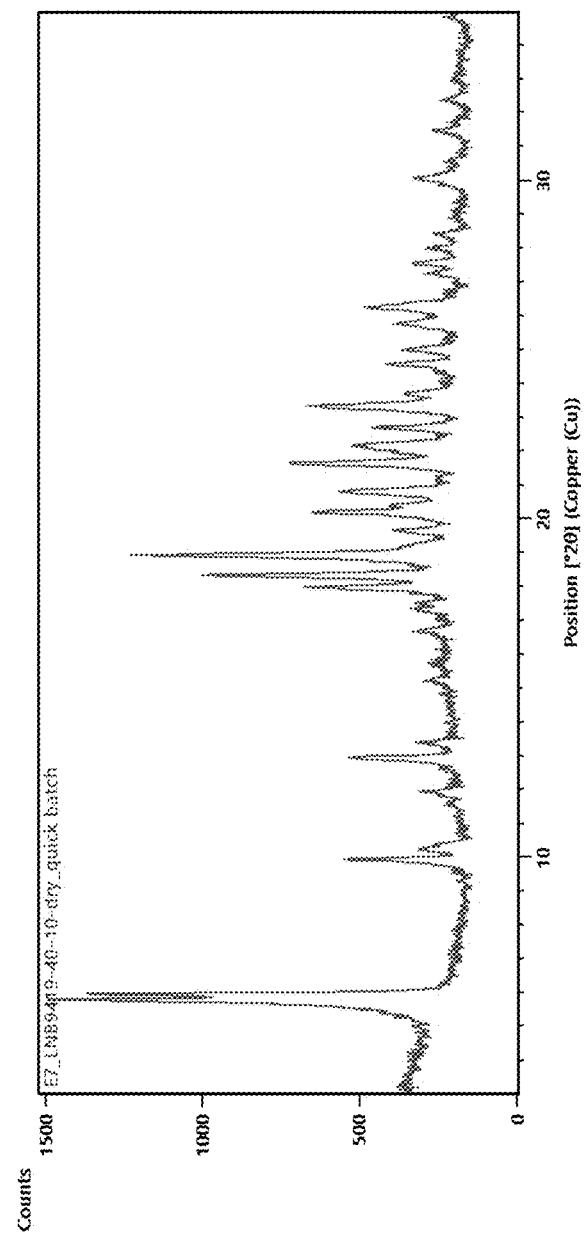

FIG. 127 sets forth an XRPD pattern of besylate Form 1 from evaporation of 2-methyl THF.

Figure 128:
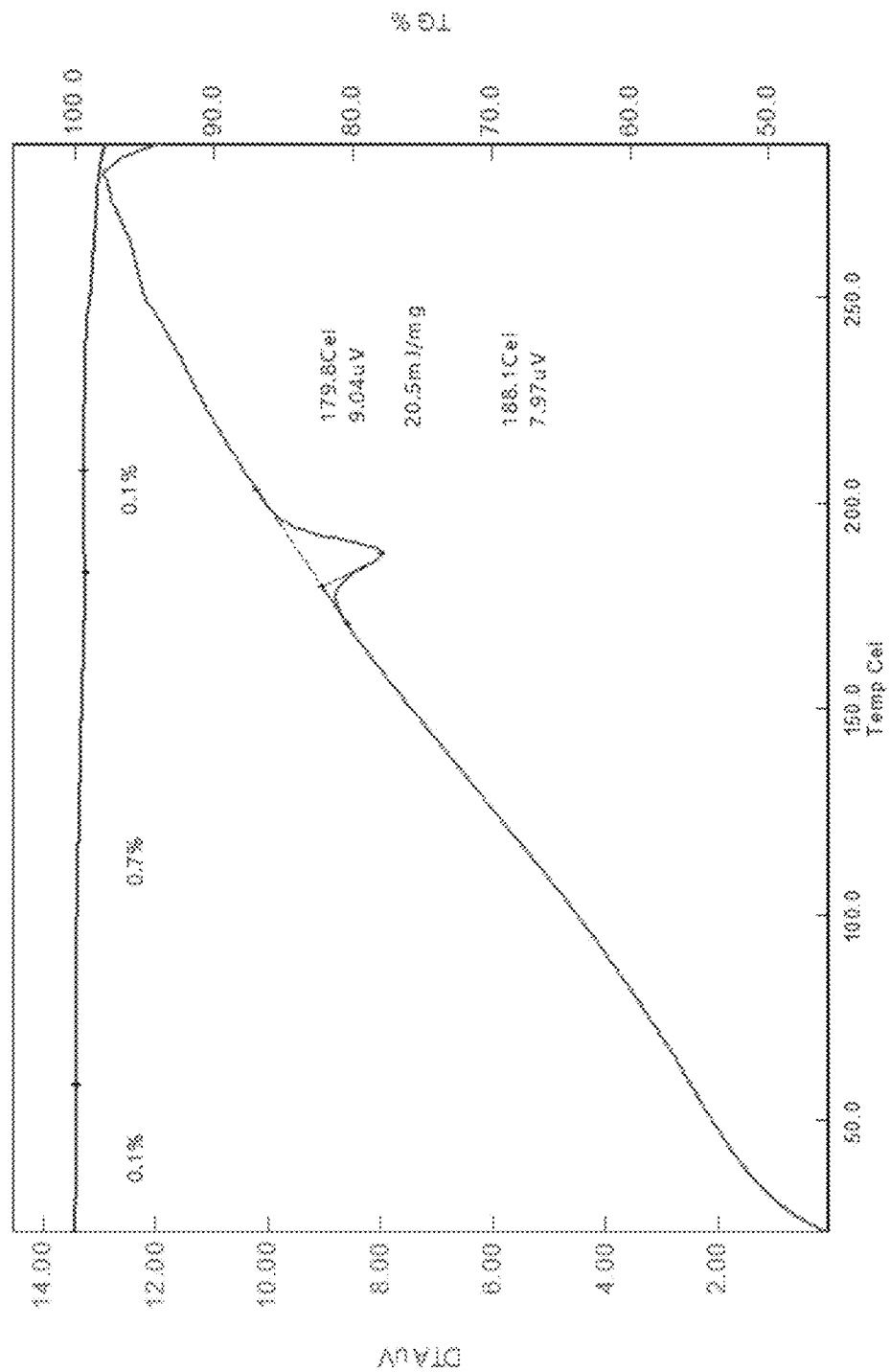

FIG. 128 sets forth a thermal analysis by TG/DTA of besylate Form 1.

Figure 129:
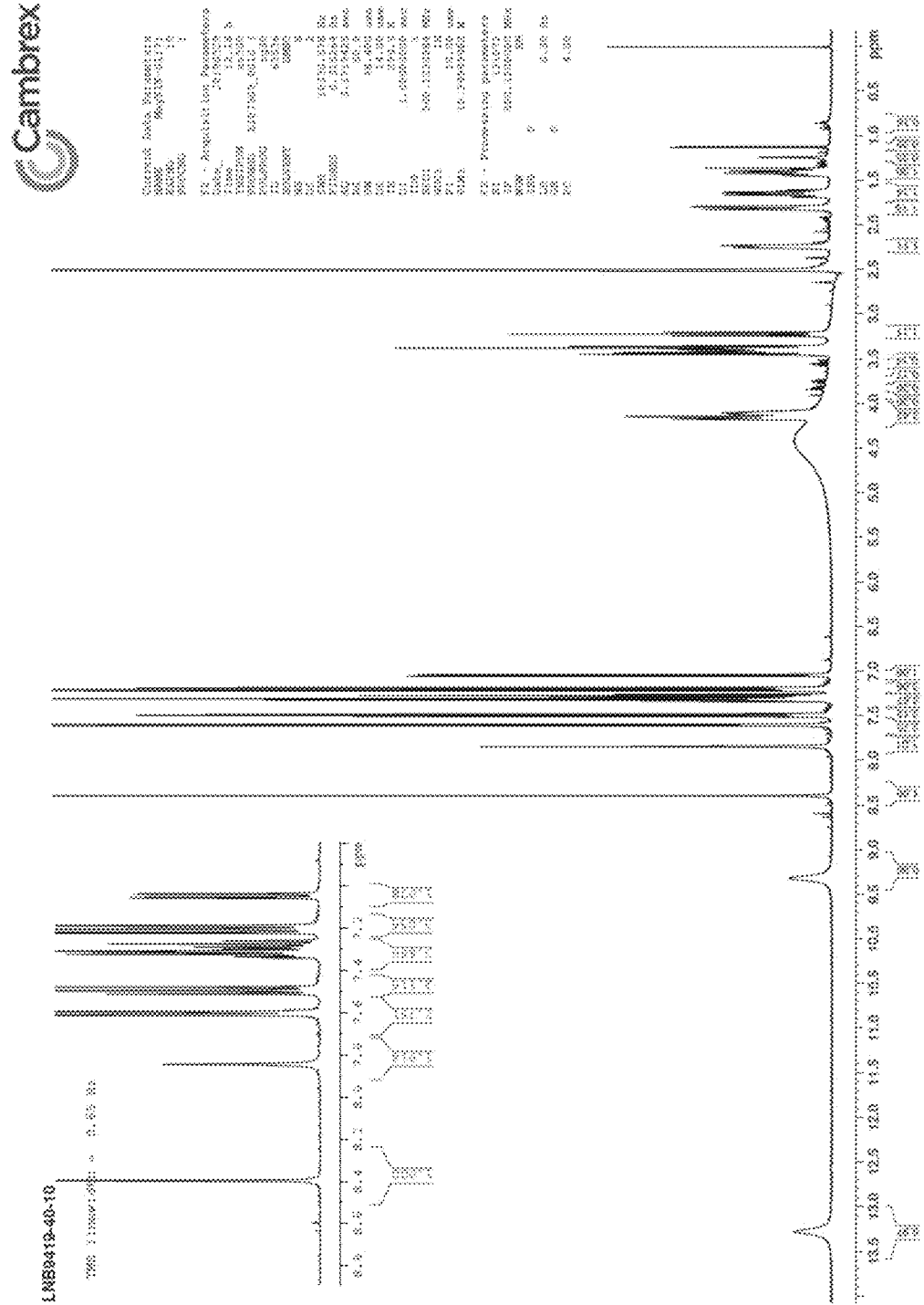

FIG. 129 sets forth a $^1$H NMR spectroscopic analysis of besylate Form 1.

Figure 130:
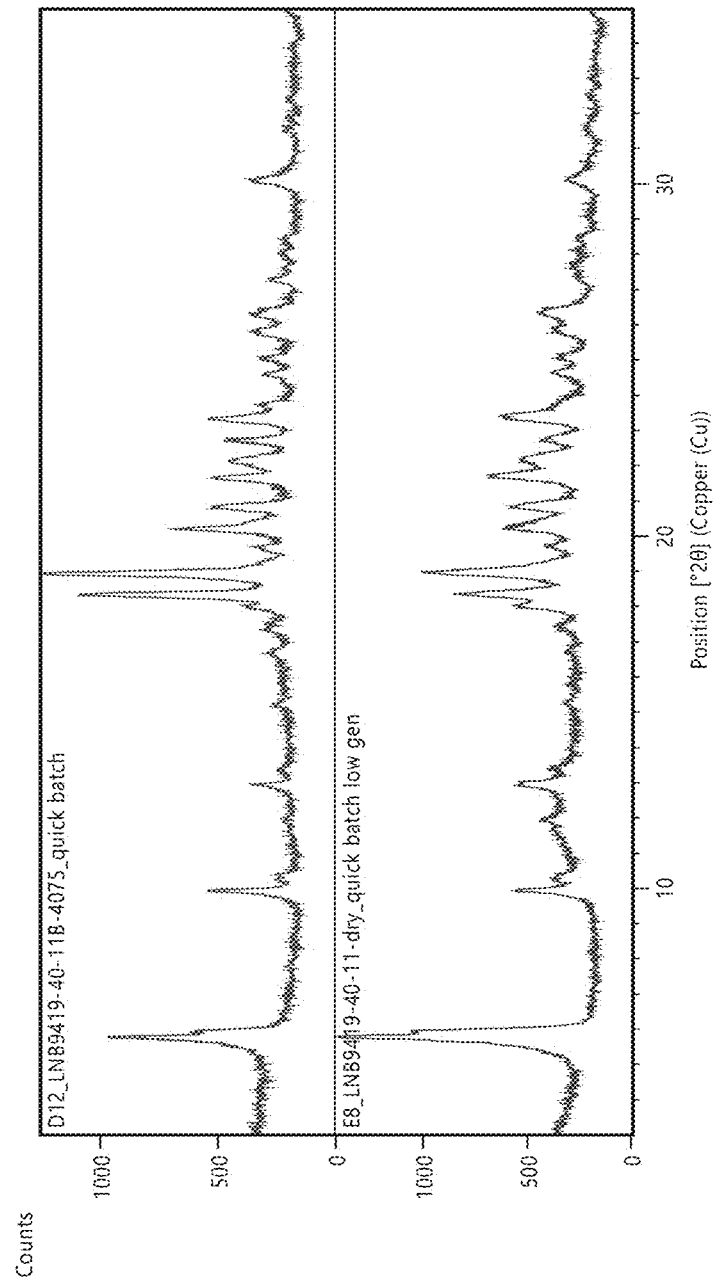

FIG. 130 sets forth XRPD patterns of besylate Form 1 before and after storage at 40° C./75% RH.

Figure 131:
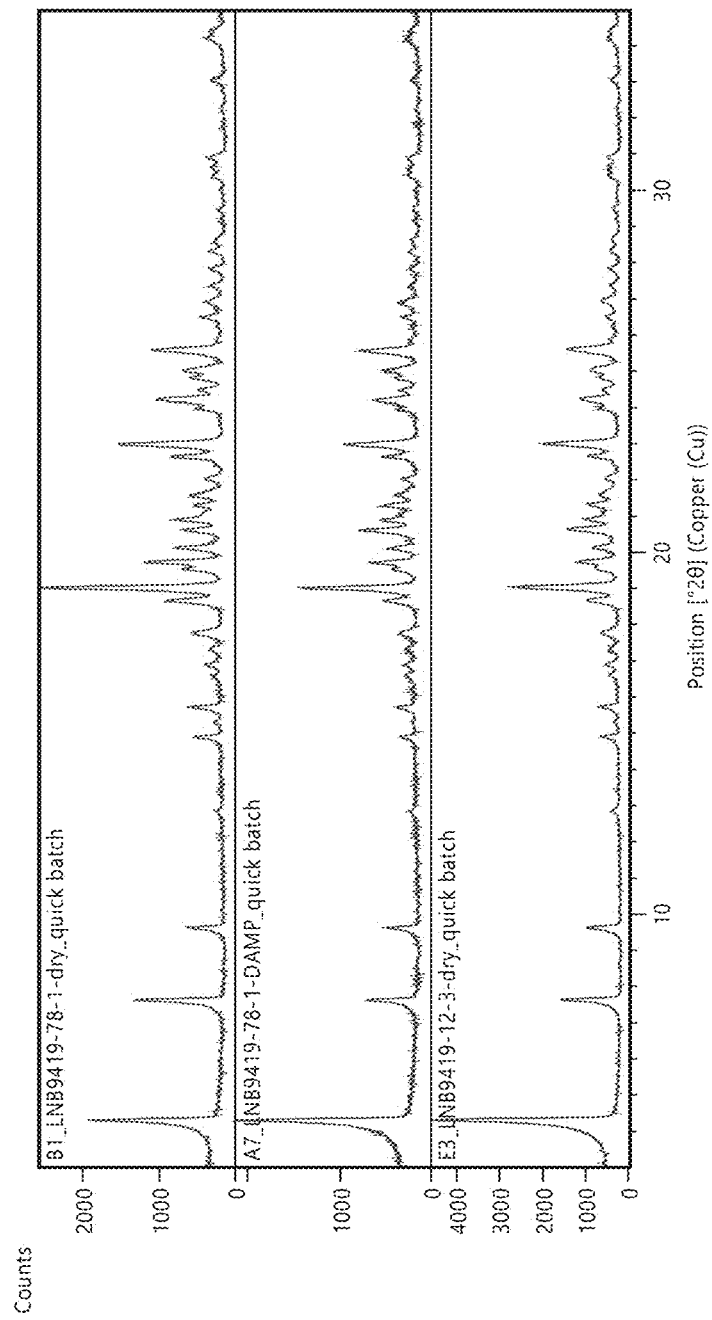

FIG. 131 sets forth XRPD patterns of edisylate Form 1 obtained from 400 mg scale-up.

Figure 132B:
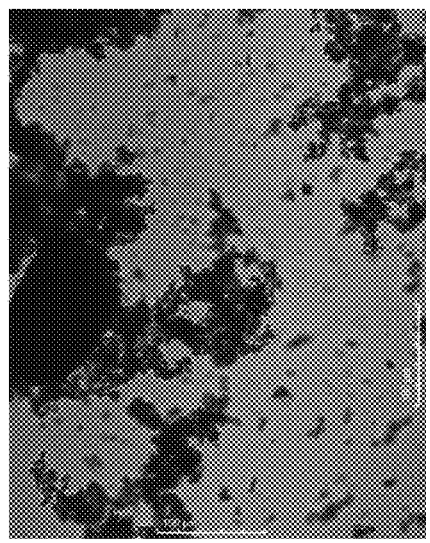
Figure 132A:
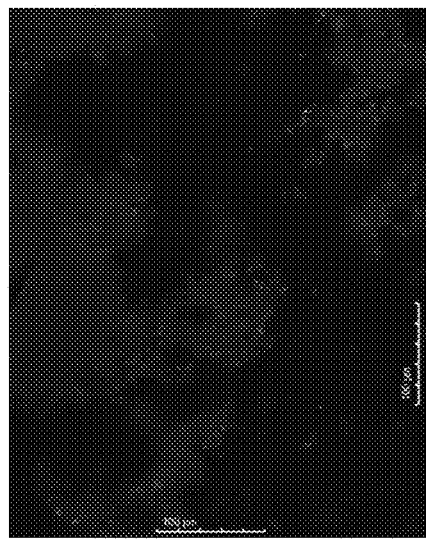

FIG. 132A sets forth a PLM image of edisylate Form 1 obtained from 400 mg scale-up.

FIG. 132B sets forth a PLM image of edisylate Form 1 obtained from 400 mg scale-up.

Figure 133:
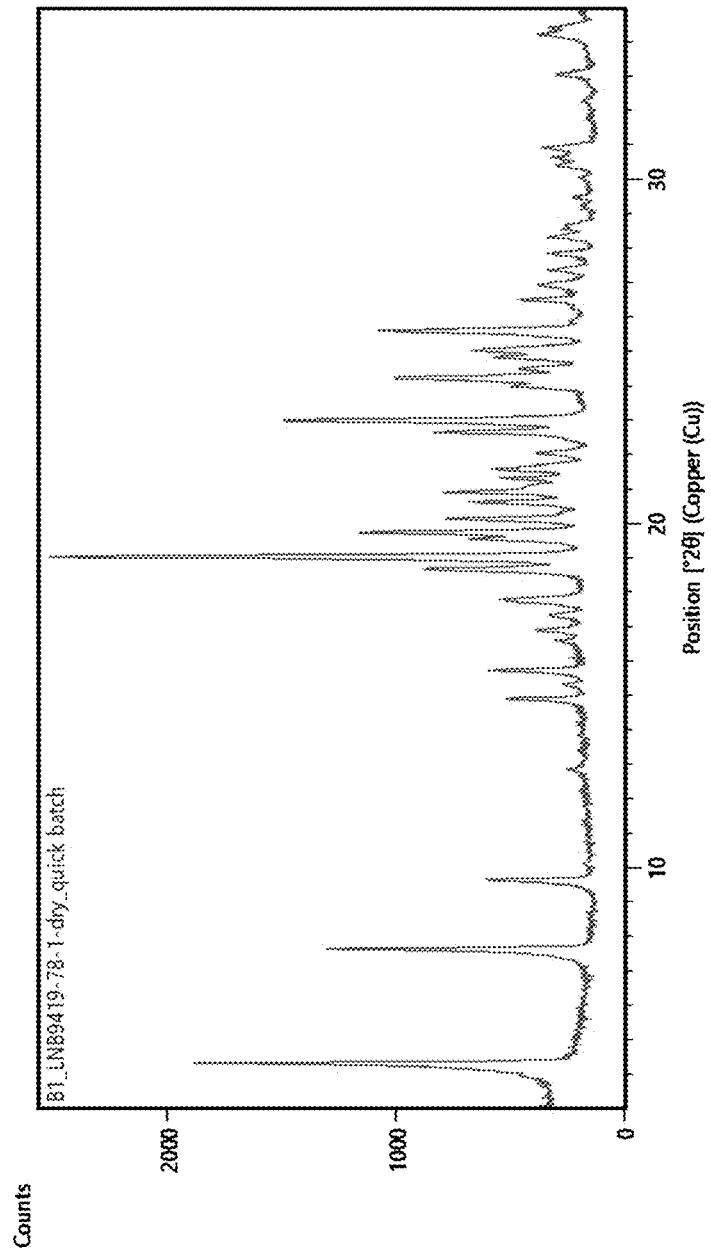

FIG. 133 sets forth an XRPD pattern of edisylate Form 1 obtained from 400 mg scale-up.

Figure 134:
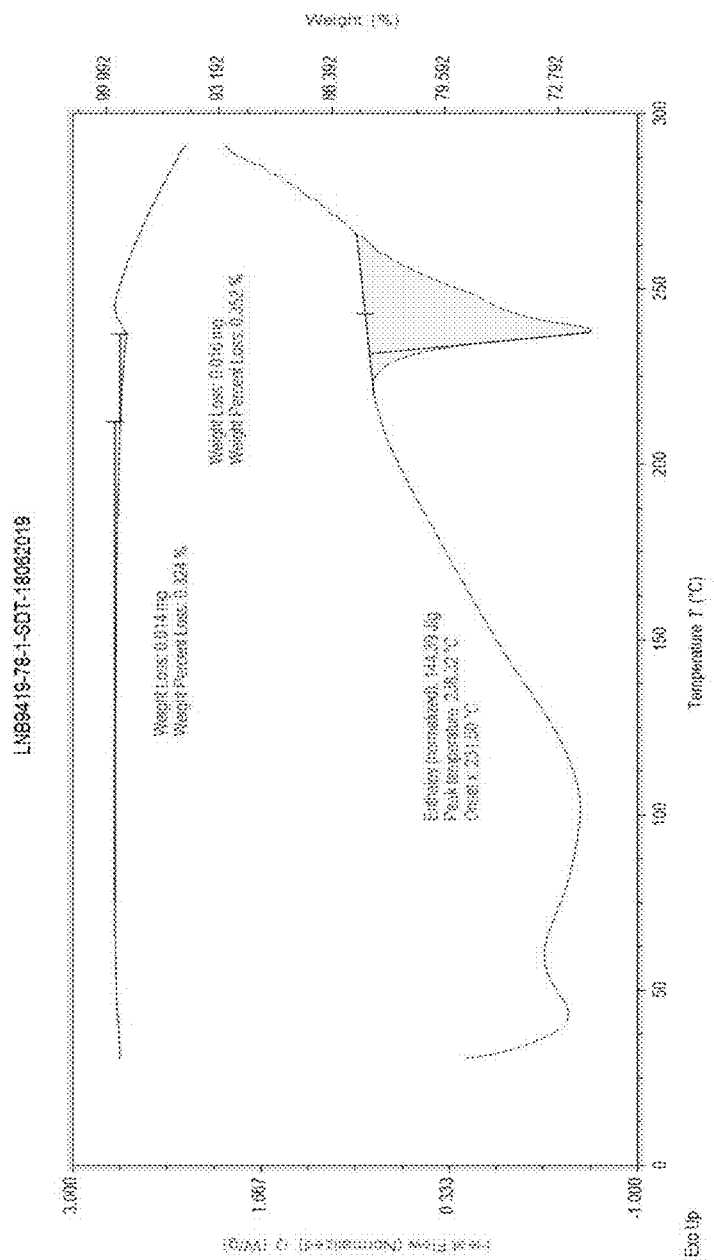

FIG. 134 sets forth a thermal analysis by TG/DTA of edisylate Form 1 obtained from 400 mg scale-up.

Figure 135:
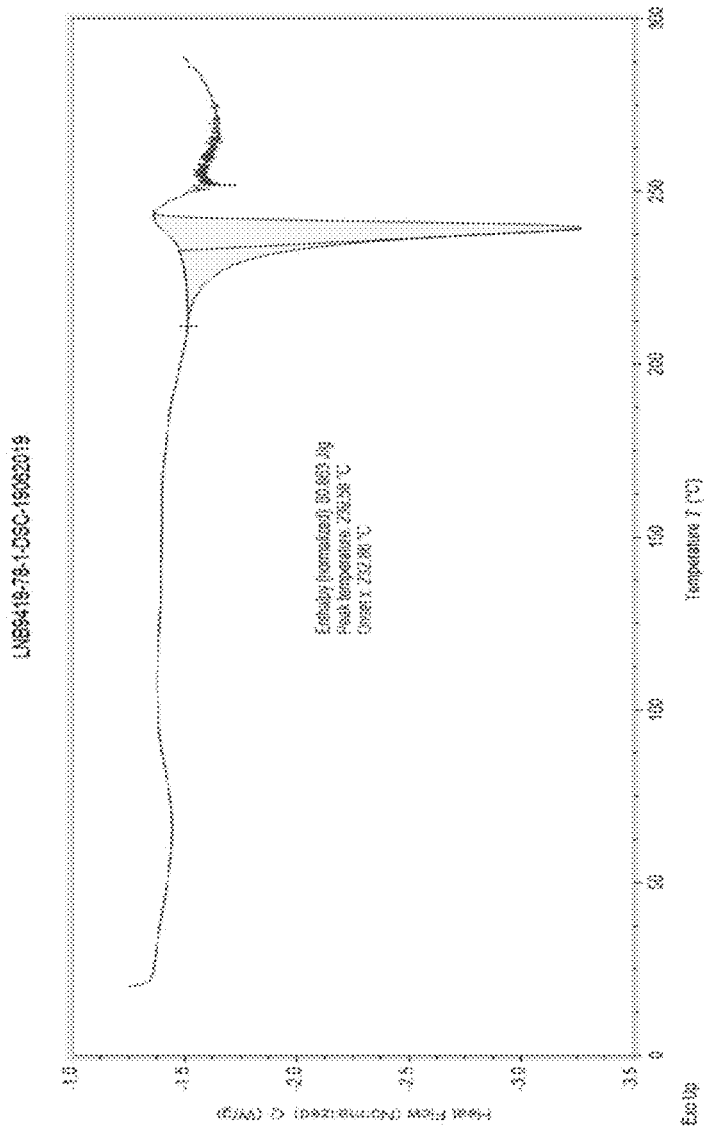

FIG. 135 sets forth a thermal analysis by a first heat DSC of edisylate Form 1 obtained from 400 mg scale-up.

Figure 136:
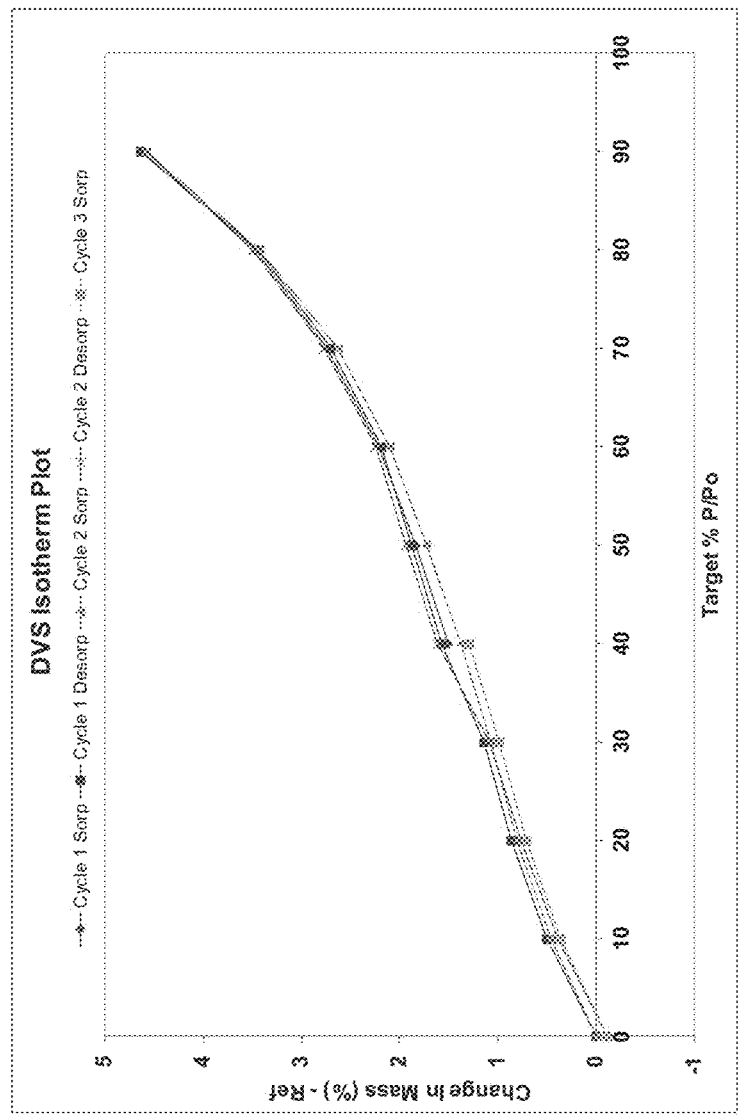

FIG. 136 sets forth a DVS isothermal analysis of edisylate Form 1 obtained from 400 mg scale-up.

Figure 137:
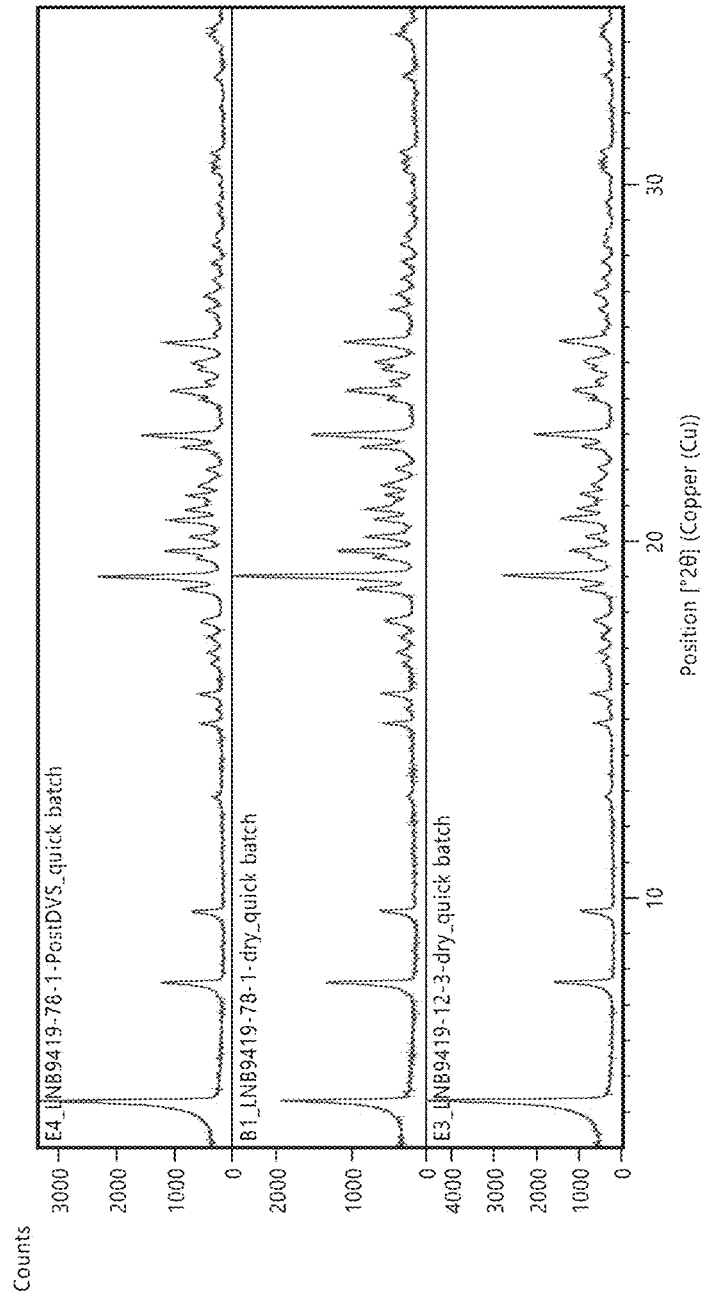

FIG. 137 sets forth comparative XRPD patterns of edisylate Form 1 obtained from 400 mg scale-up before and after DVS.

Figure 138:
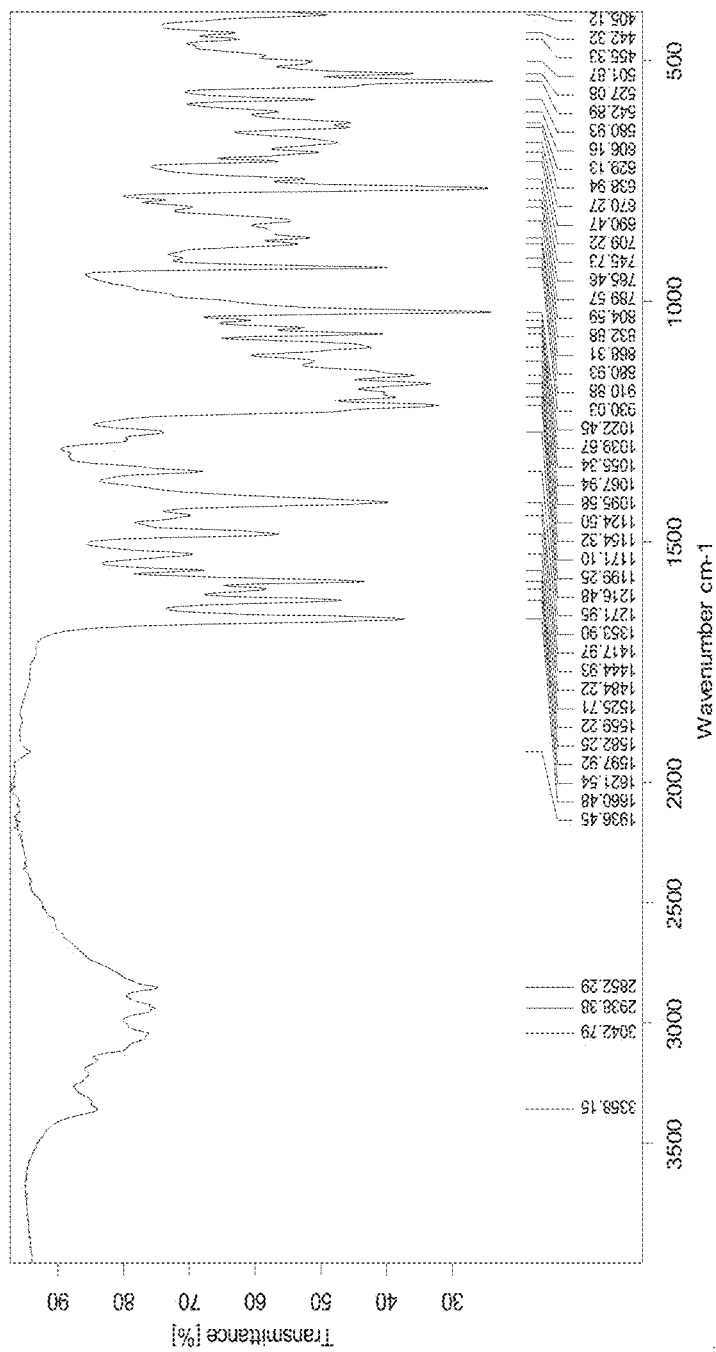

FIG. 138 sets forth an IR spectroscopic analysis of edisylate Form 1 obtained from 400 mg scale-up.

Figure 139:
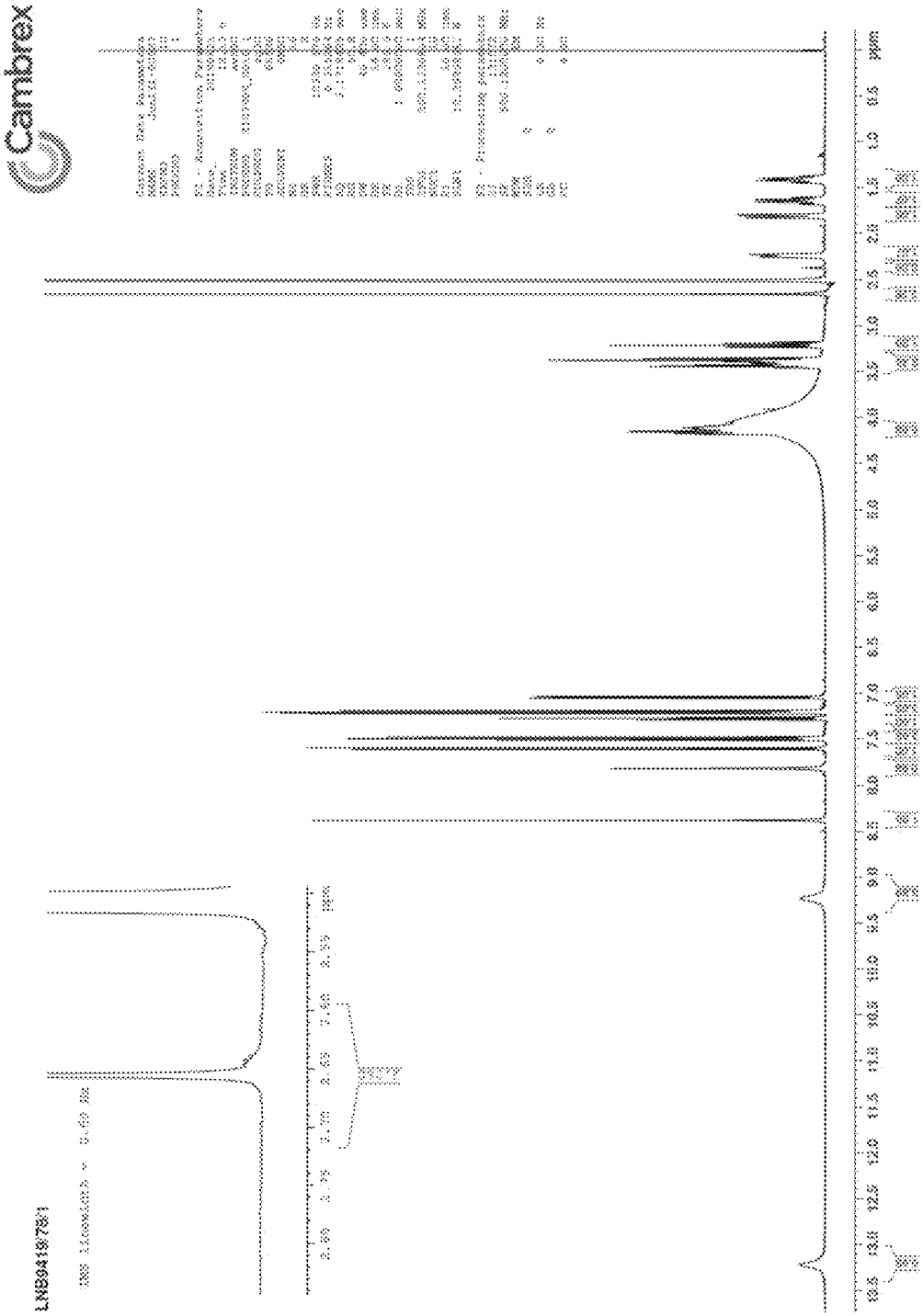

FIG. 139 sets forth a $^1$H NMR spectroscopic analysis of edisylate Form 1.

Figure 140:
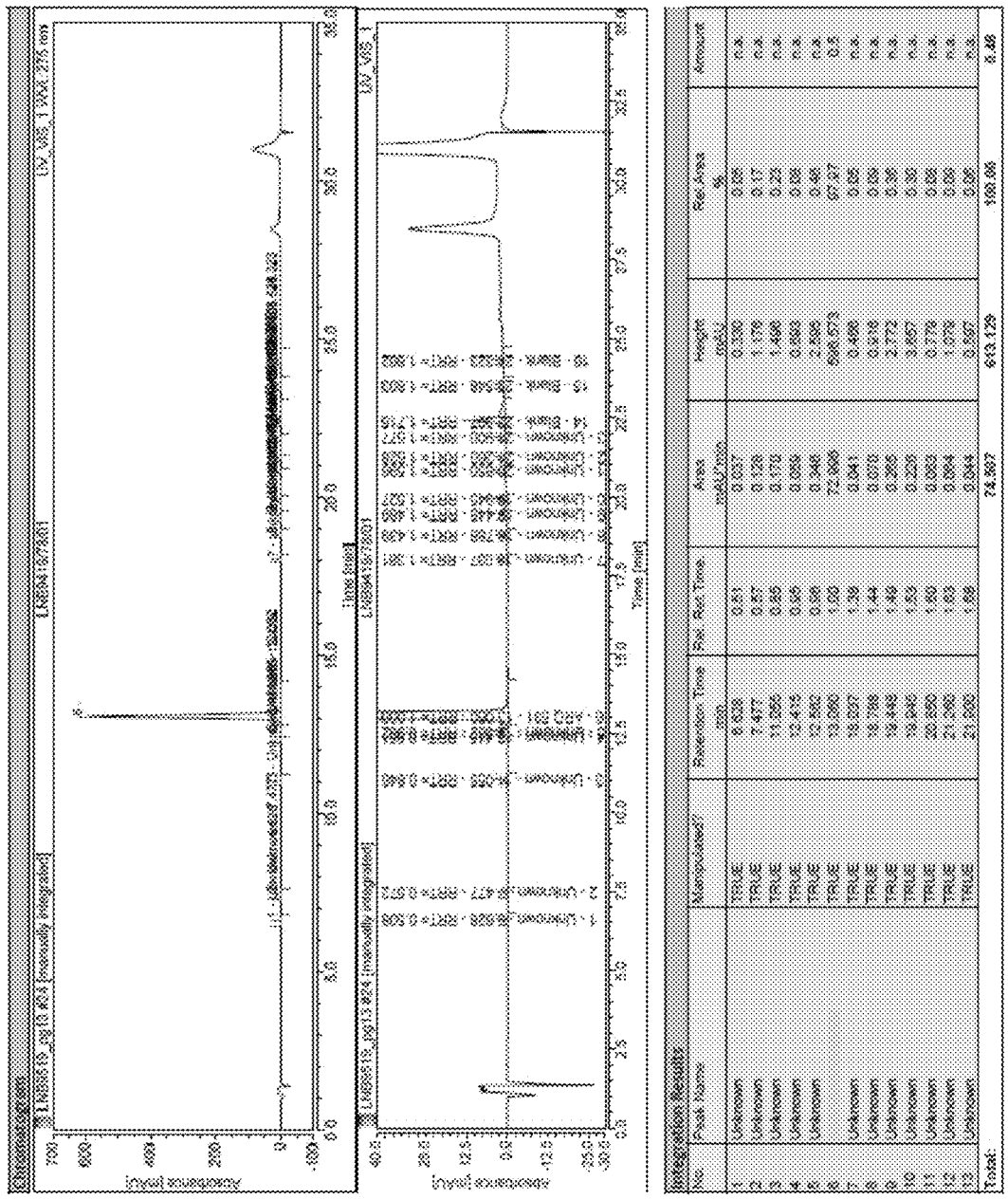

FIG. 140 sets forth an HPLC-UV chromatogram of edisylate Form 1 obtained from 400 mg scale-up.

Figure 141:
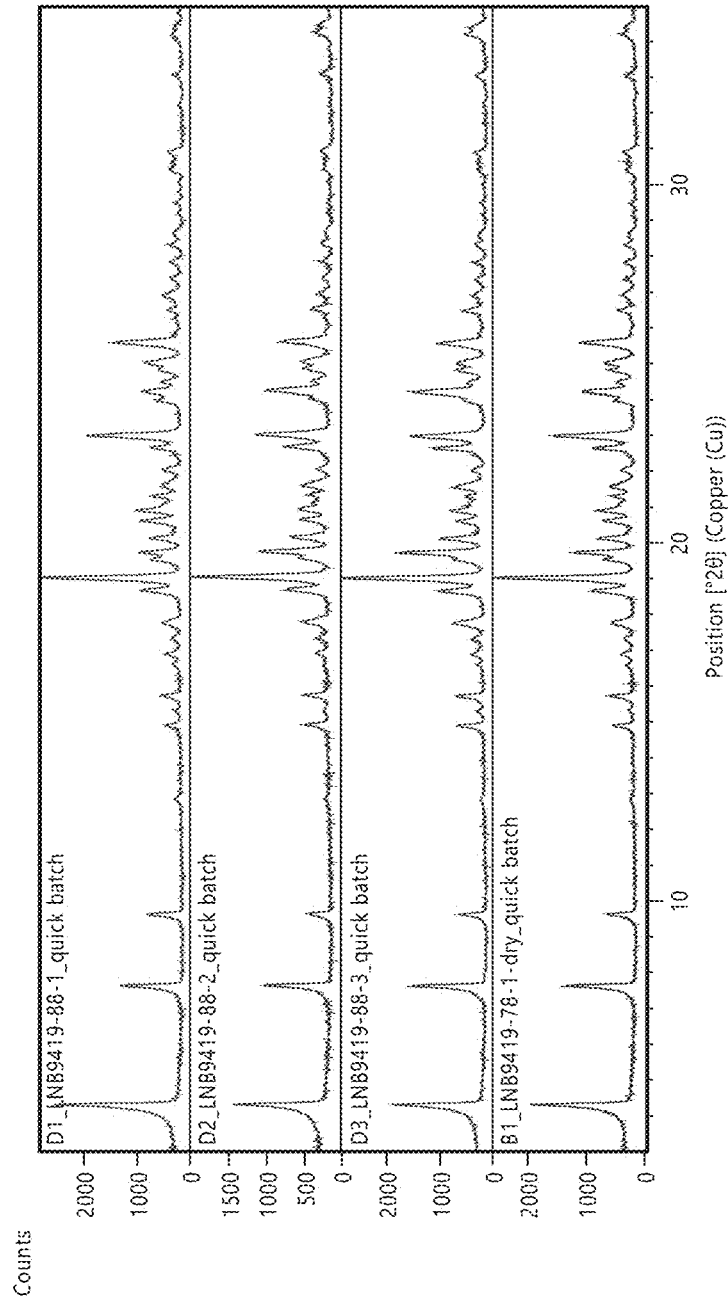

FIG. 141 sets forth XRPD patterns of edisylate Form 1 obtained from 400 mg scale-up after 1 week stability studies.

Figure 142:
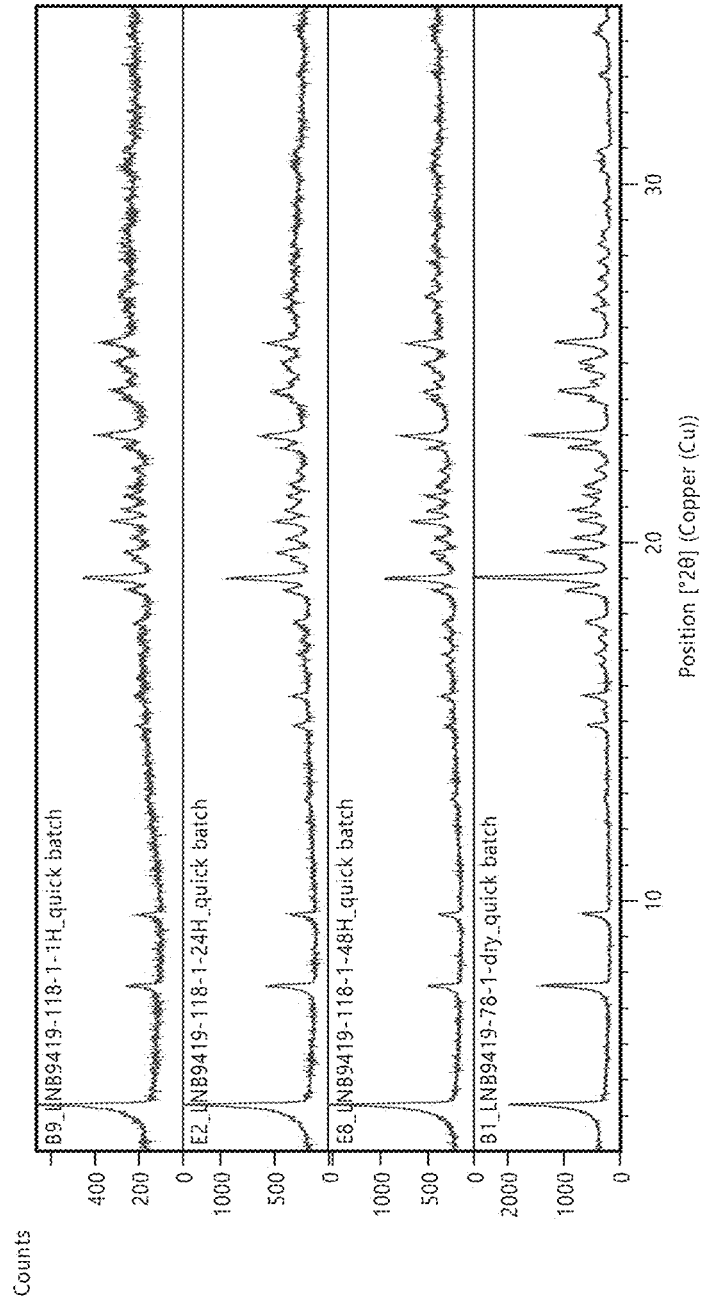

FIG. 142 sets forth XRPD patterns of edisylate Form 1 obtained from 400 mg scale-up after salt disproportionation experiments.

Figure 143:
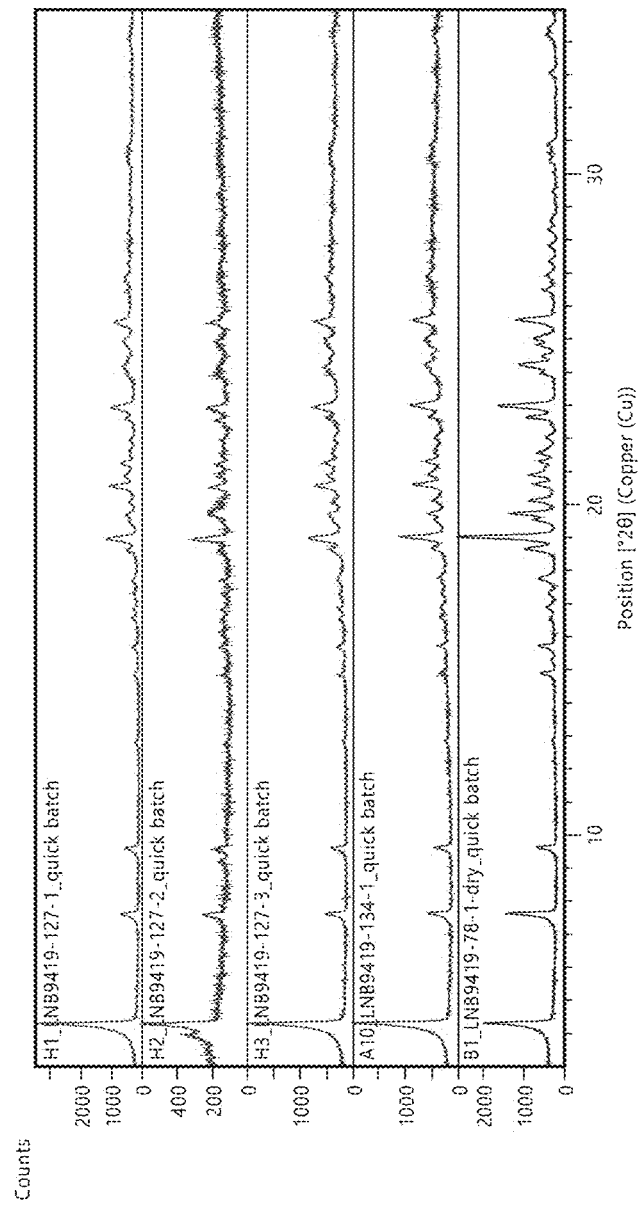

FIG. 143 sets forth XRPD patterns of edisylate Form 1 obtained from 400 mg scale-up after thermodynamic solubility experiments.

Figure 144:
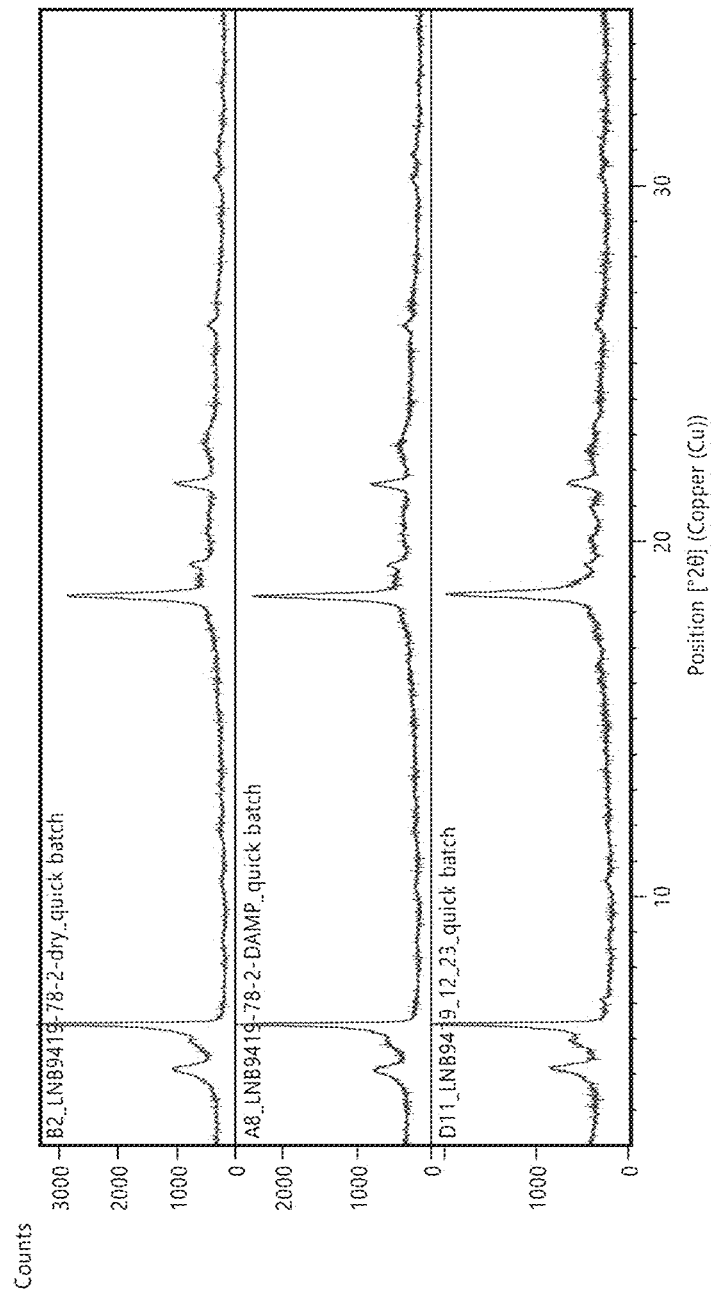

FIG. 144 sets forth XRPD patterns of cyclamate Form 1 obtained from 400 mg scale-up.

Figure 145B:
Figure 145A:
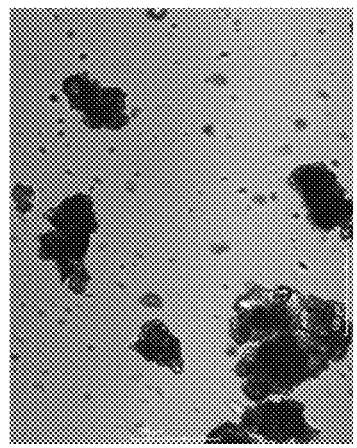

FIG. 145A sets forth a PLM image of cyclamate Form 1 obtained from 400 mg scale-up.

FIG. 145B sets forth a PLM image of cyclamate Form 1 obtained from 400 mg scale-up.

Figure 146:
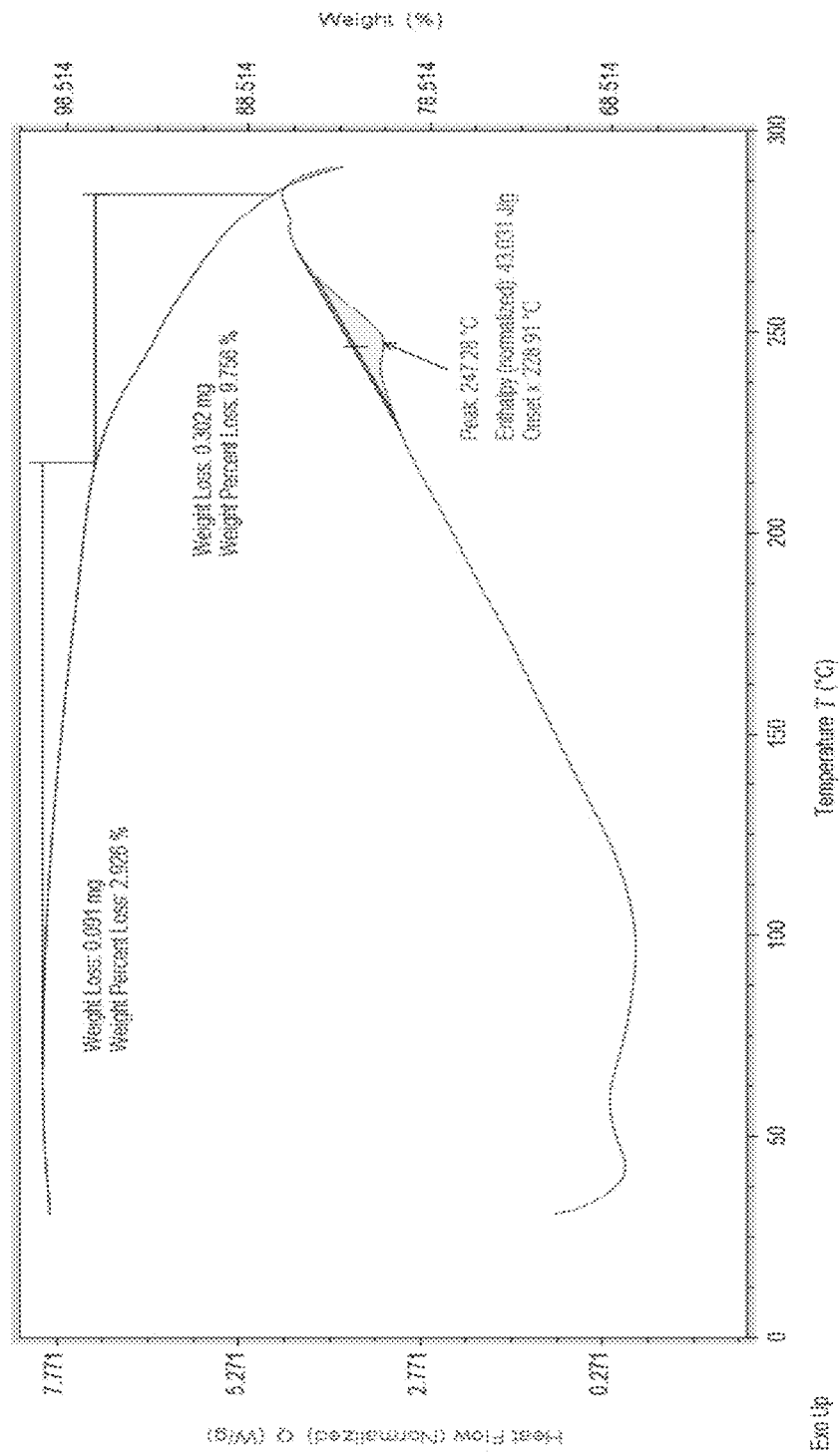

FIG. 146 sets forth a thermal analysis by TG/DTA of cyclamate Form 1 obtained from 400 mg scale-up.

Figure 147:
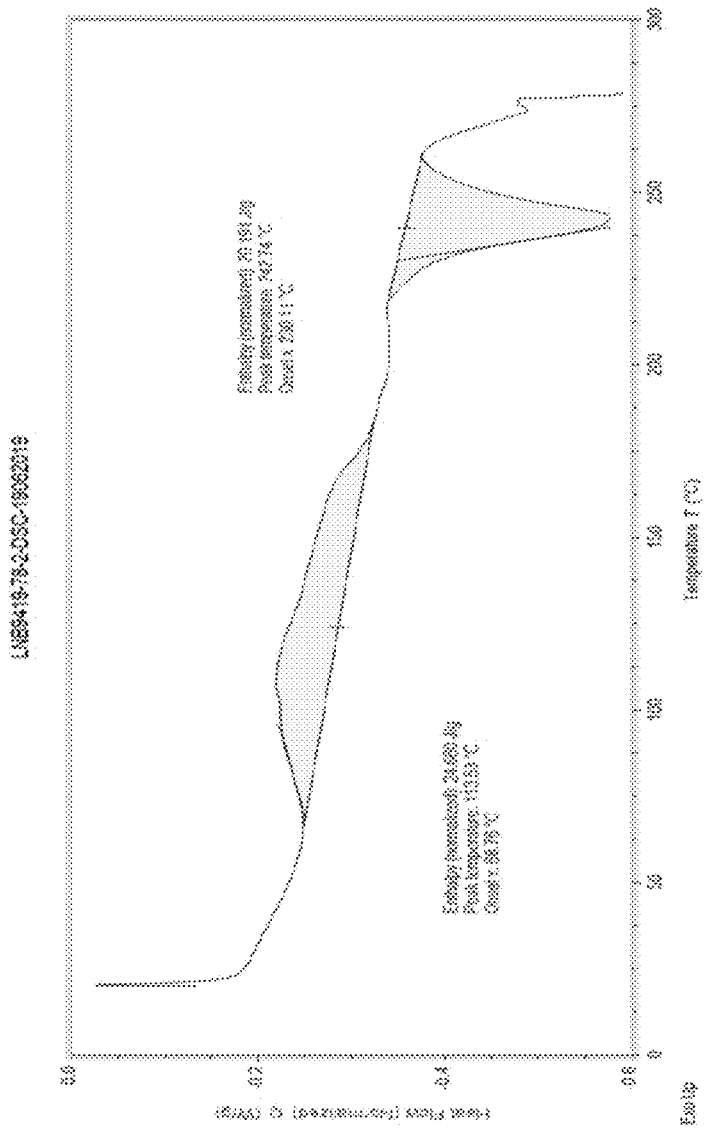

FIG. 147 sets forth a thermal analysis by a first heat DSC of cyclamate Form 1 obtained from 400 mg scale-up.

Figure 148:
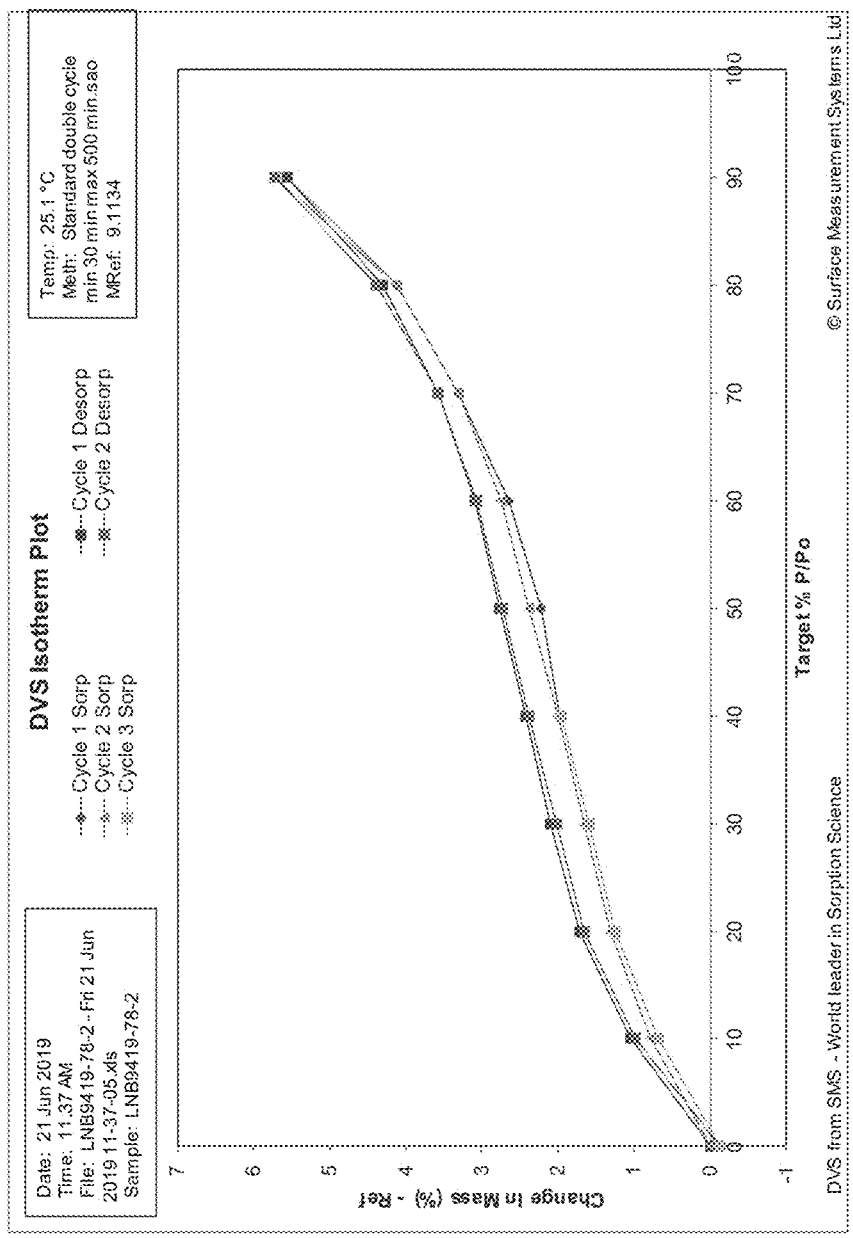

FIG. 148 sets forth a DVS isothermal analysis of cyclamate Form 1 obtained from 400 mg scale-up.

Figure 149:
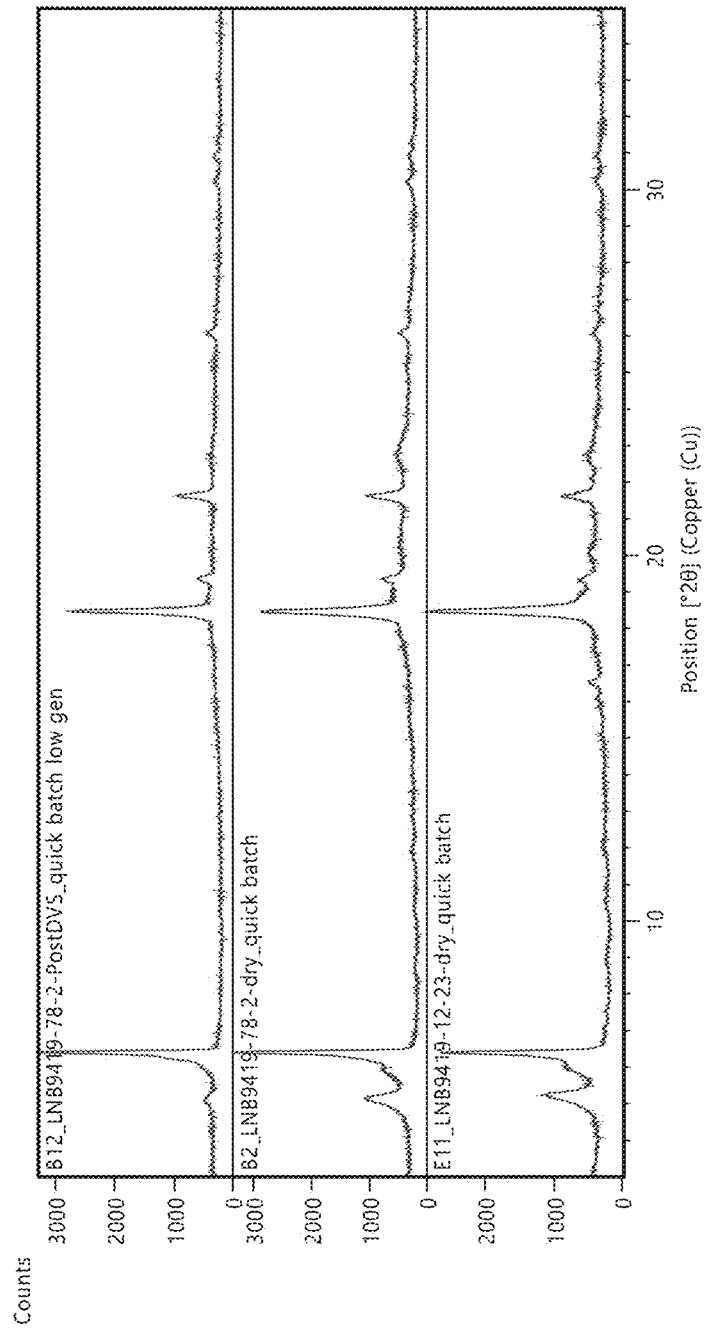

FIG. 149 sets forth comparative XRPD patterns of cyclamate Form 1 obtained from 400 mg scale-up before and after DVS.

Figure 150:
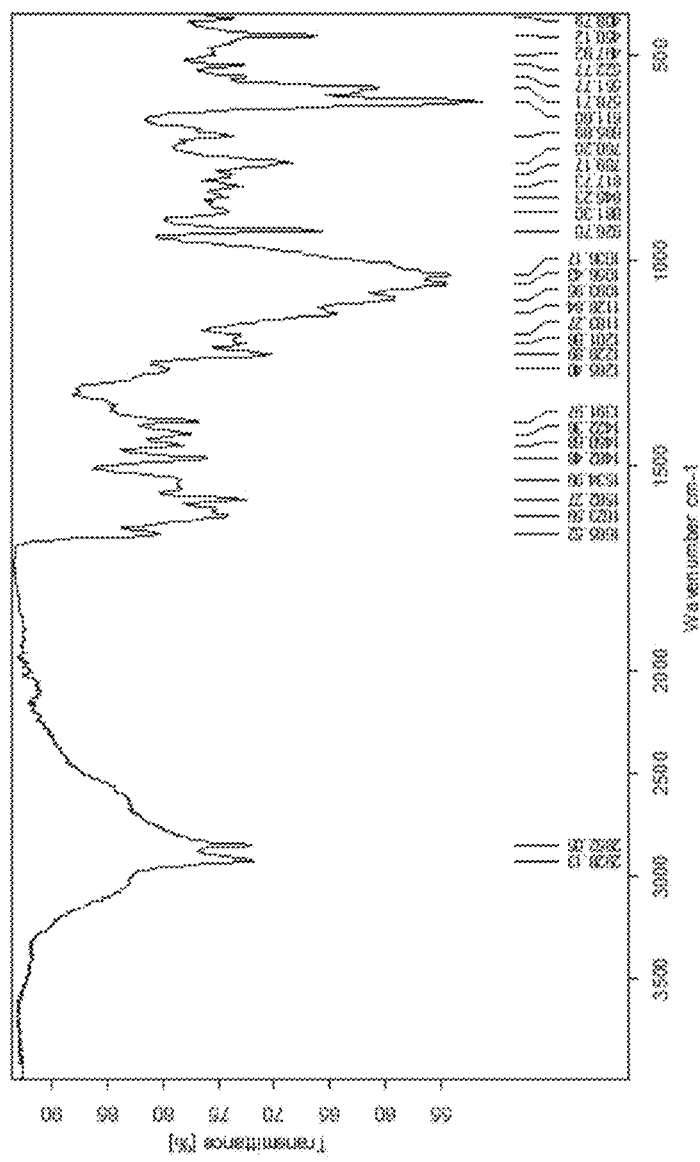

FIG. 150 sets forth an IR spectroscopic analysis of cyclamate Form 1 obtained from 400 mg scale-up.

Figure 151:
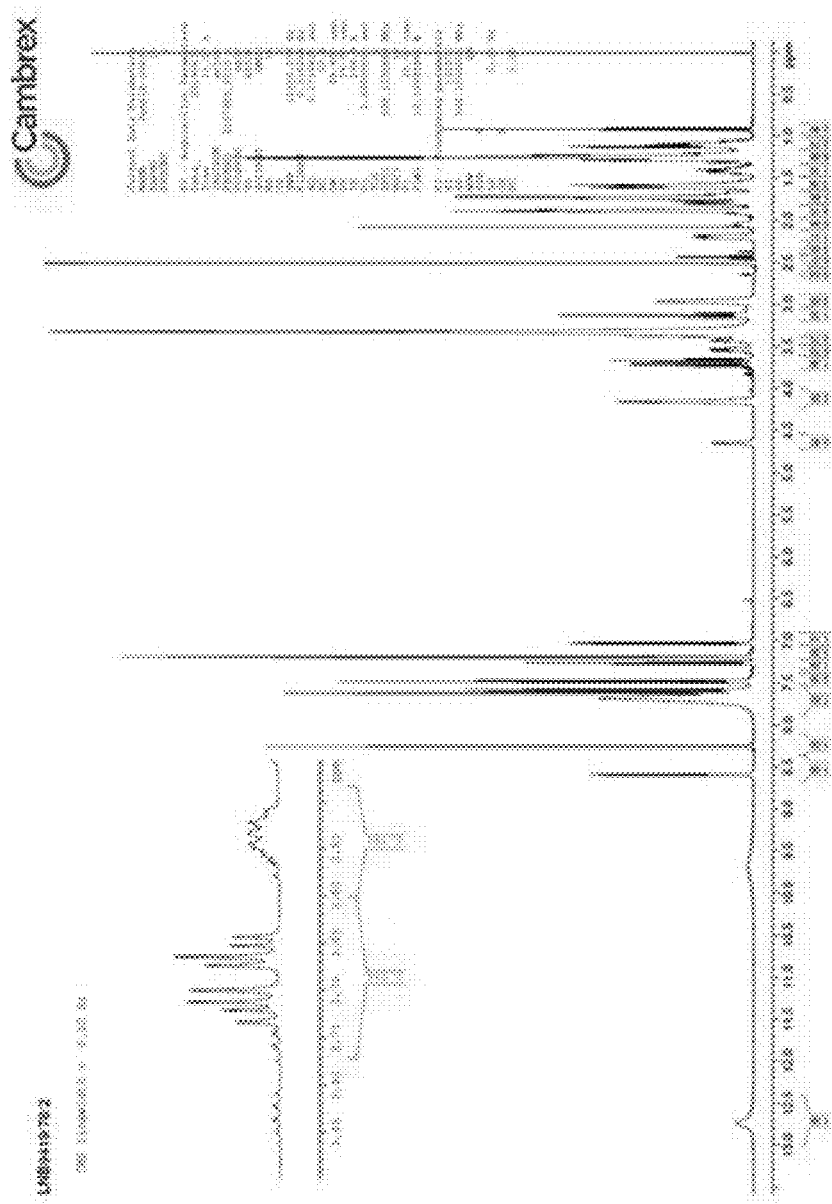

FIG. 151 sets forth a $^1$H NMR spectroscopic analysis of cyclamate Form 1 obtained from 400 mg scale-up.

Figure 152:
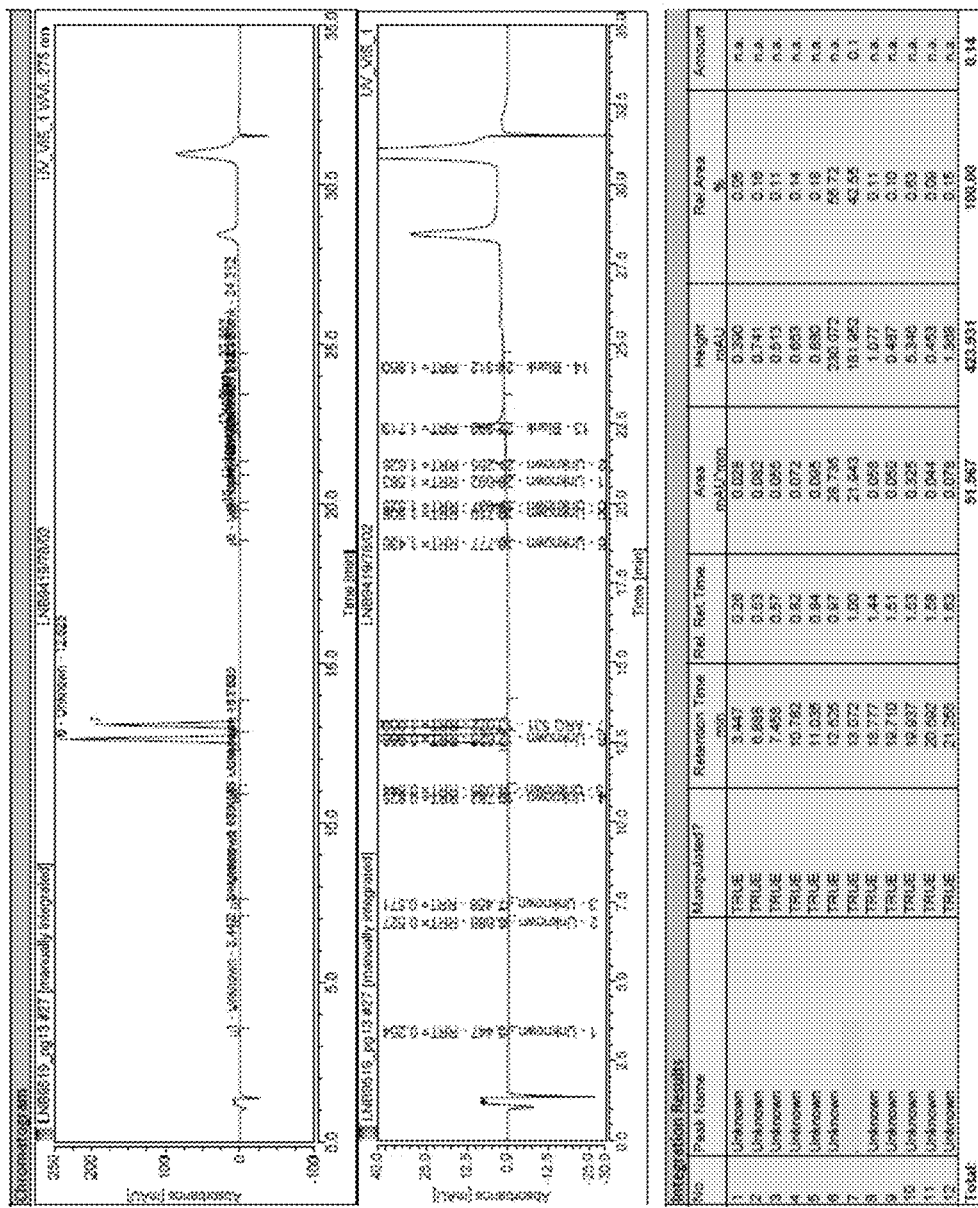

FIG. 152 sets forth an HPLC-UV chromatogram of cyclamate Form 1 obtained from 400 mg scale-up.

Figure 153:
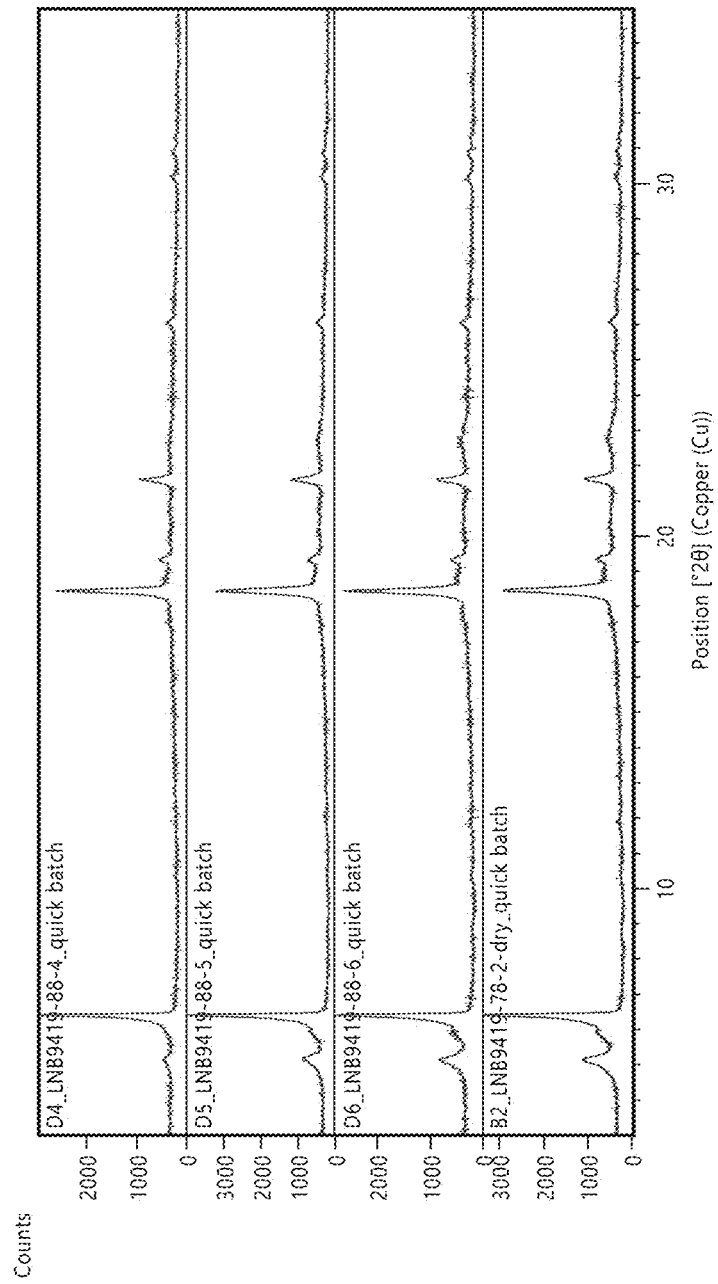

FIG. 153 sets forth XRPD patterns of cyclamate Form 1 obtained from 400 mg scale-up after 1 week stability studies.

Figure 154:
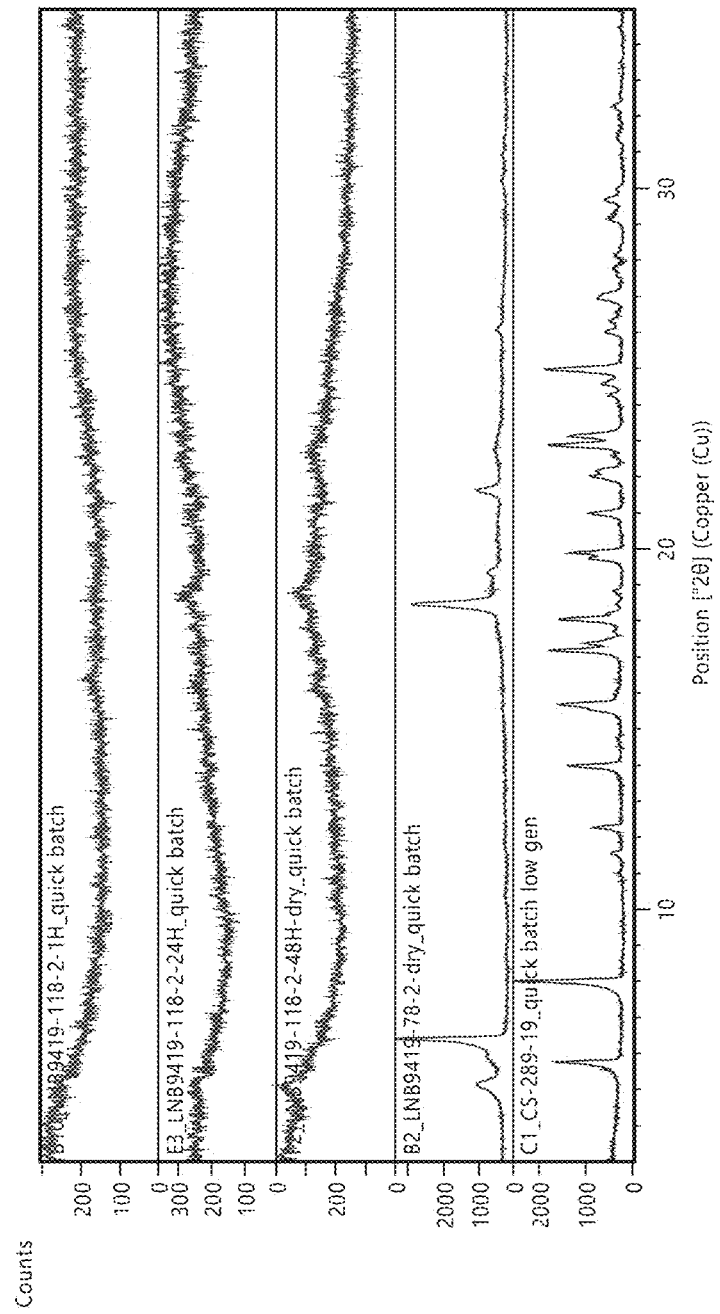

FIG. 154 sets forth XRPD patterns of cyclamate Form 1 obtained from 400 mg scale-up after salt disproportionation experiments.

Figure 155:
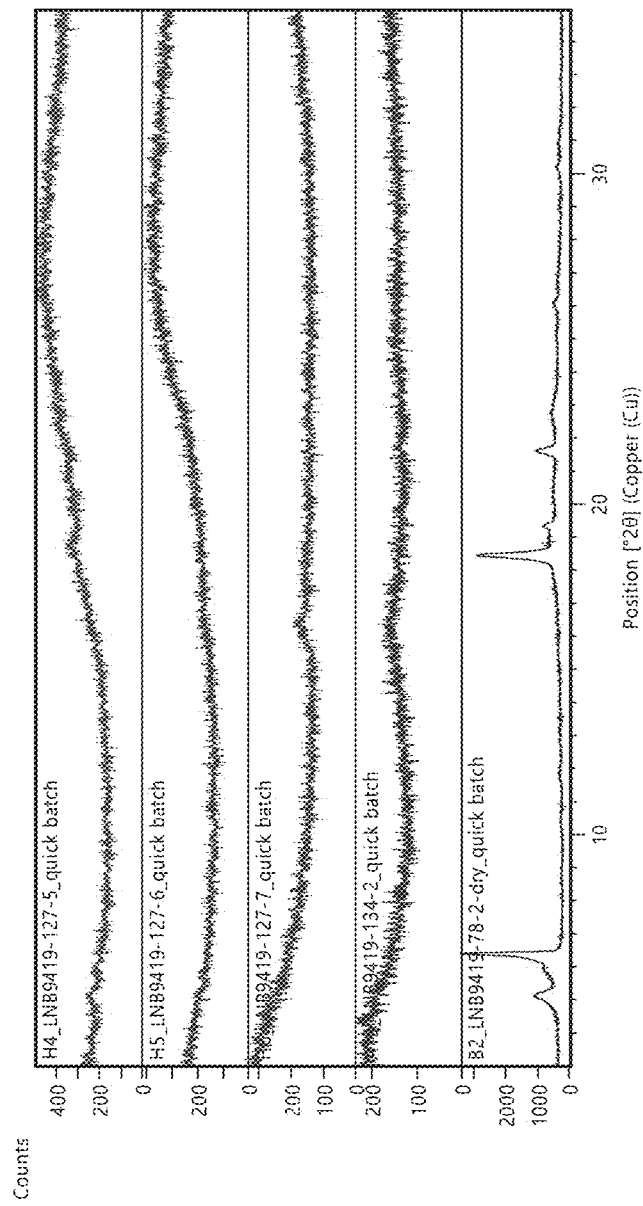

FIG. 155 sets forth XRPD patterns of cyclamate Form 1 obtained from 400 mg scale-up after thermodynamic solubility experiments.

Figure 156:
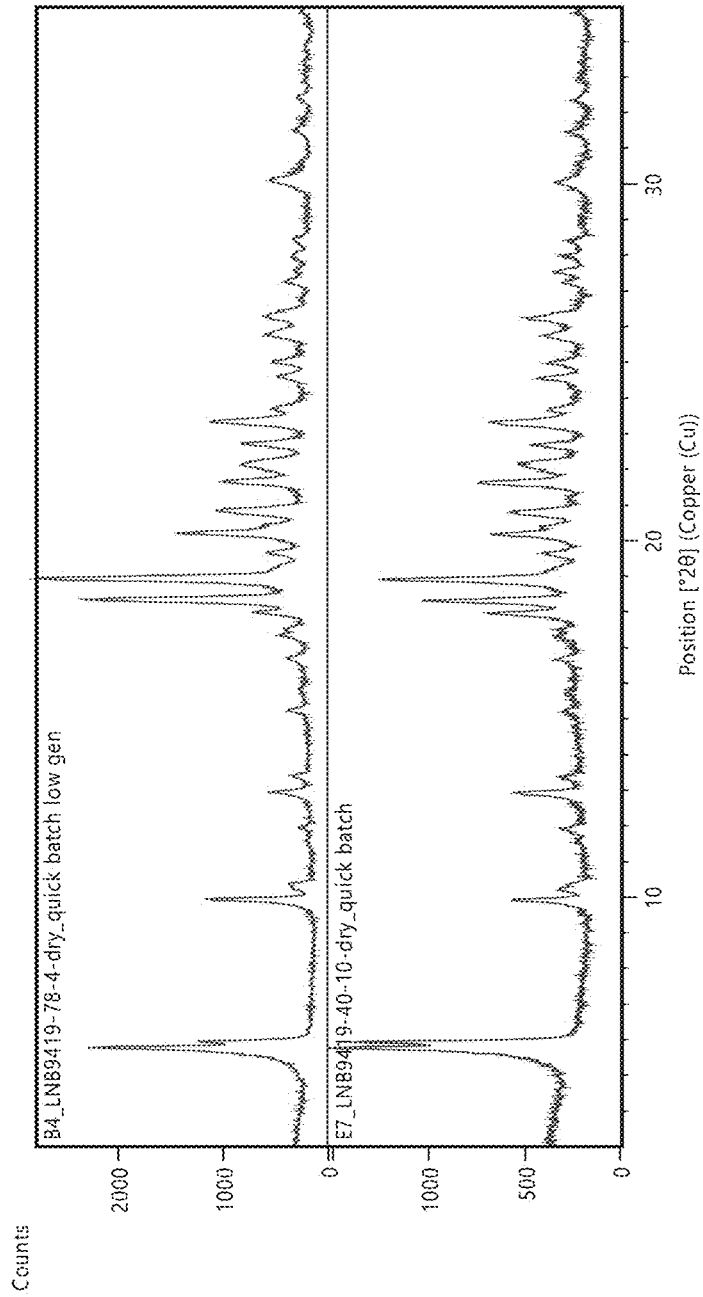

FIG. 156 sets forth XRPD patterns of besylate Form 1 obtained from 400 mg scale-up.

Figure 157B:
Figure 157A:
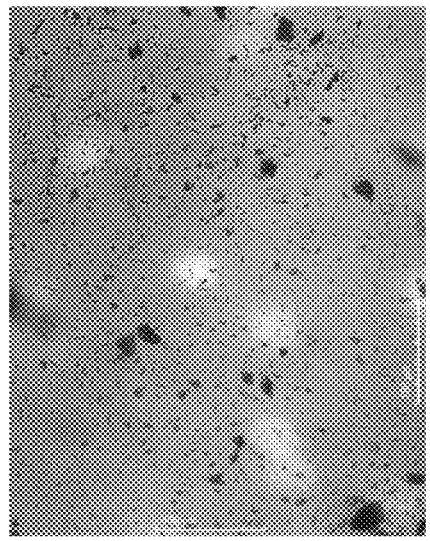

FIG. 157A sets forth a PLM image of besylate Form 1 obtained from 400 mg scale-up.

FIG. 157B sets forth a PLM image of besylate Form 1 obtained from 400 mg scale-up.

Figure 158:
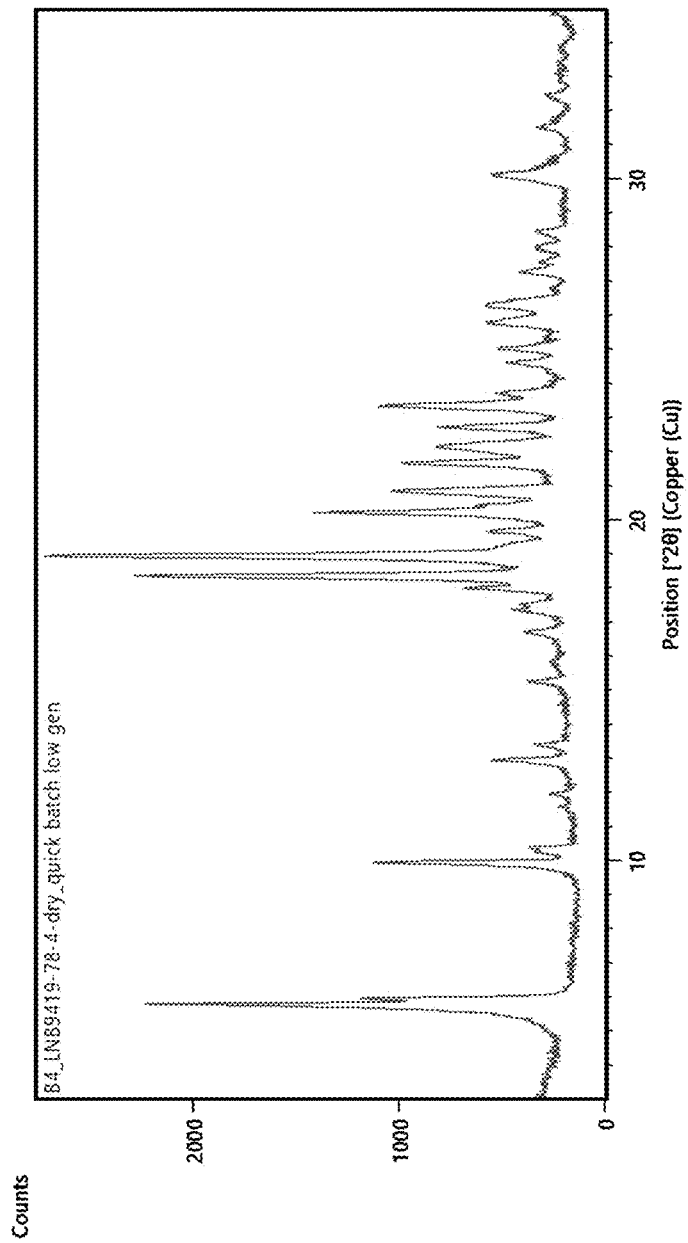

FIG. 158 sets forth XRPD patterns of besylate Form 1 obtained from 400 mg scale-up.

Figure 159:
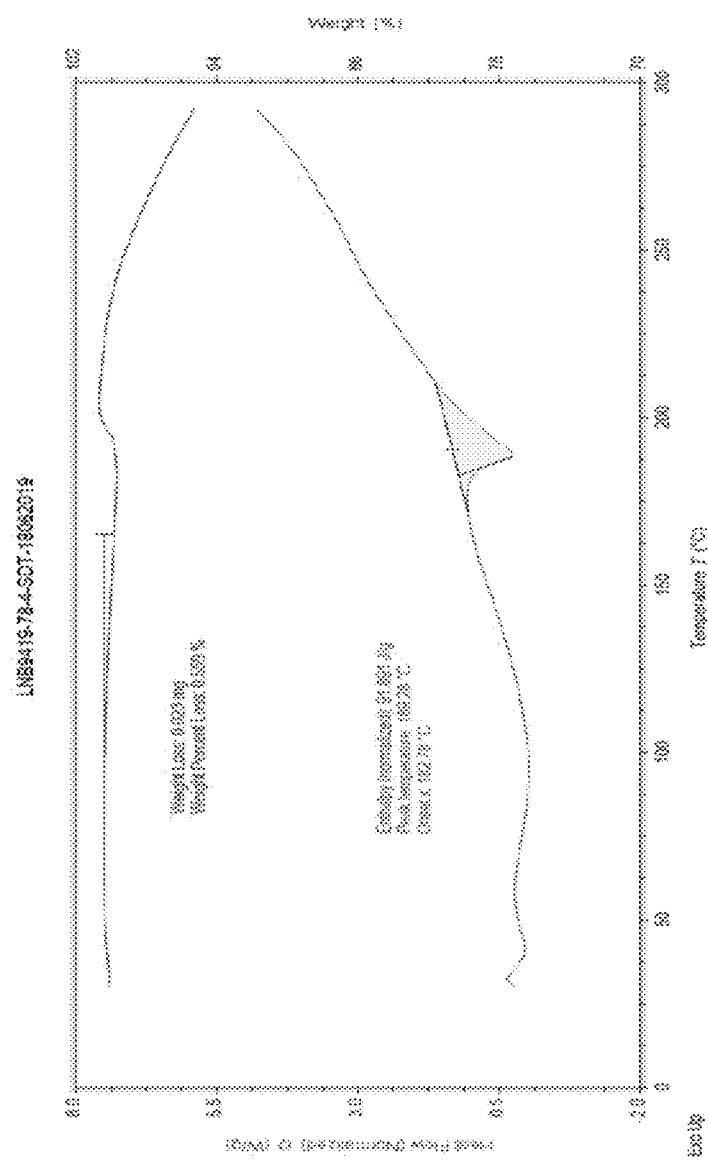

FIG. 159 sets forth a thermal analysis by TG/DTA of besylate Form 1 obtained from 400 mg scale-up.

Figure 160:
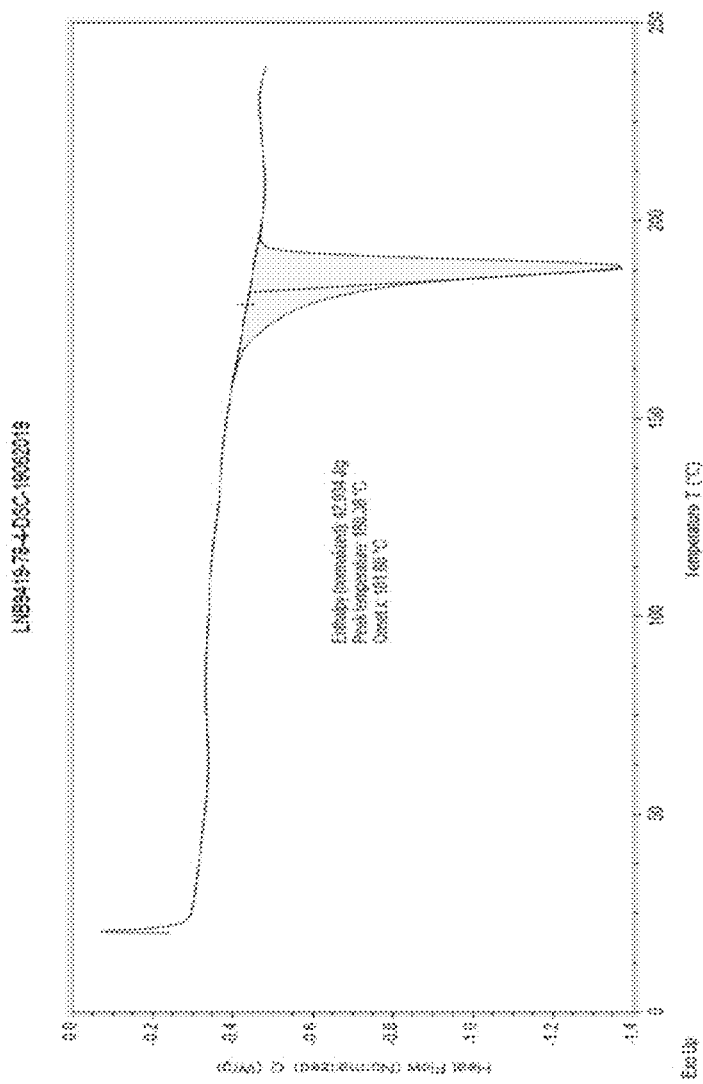

FIG. 160 sets forth a thermal analysis by a first heat DSC of besylate Form 1 obtained from 400 mg scale-up.

Figure 161:
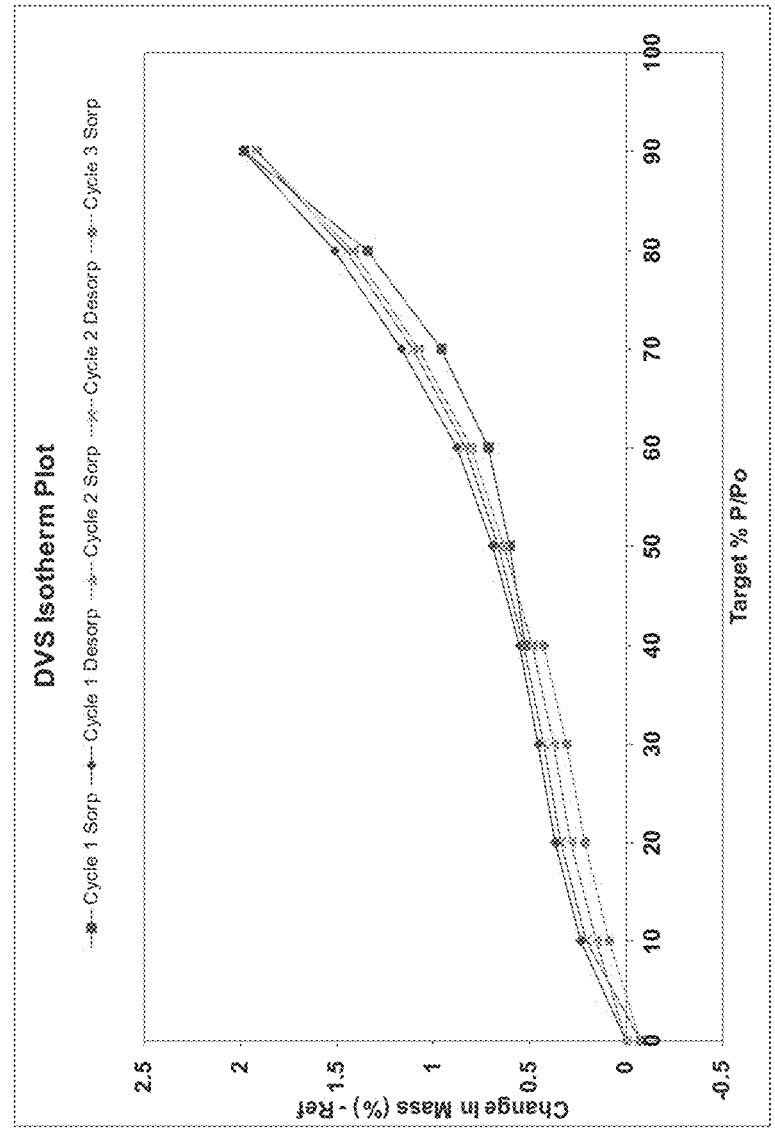

FIG. 161 sets forth a DVS isothermal analysis of besylate Form 1 obtained from 400 mg scale-up.

Figure 162:
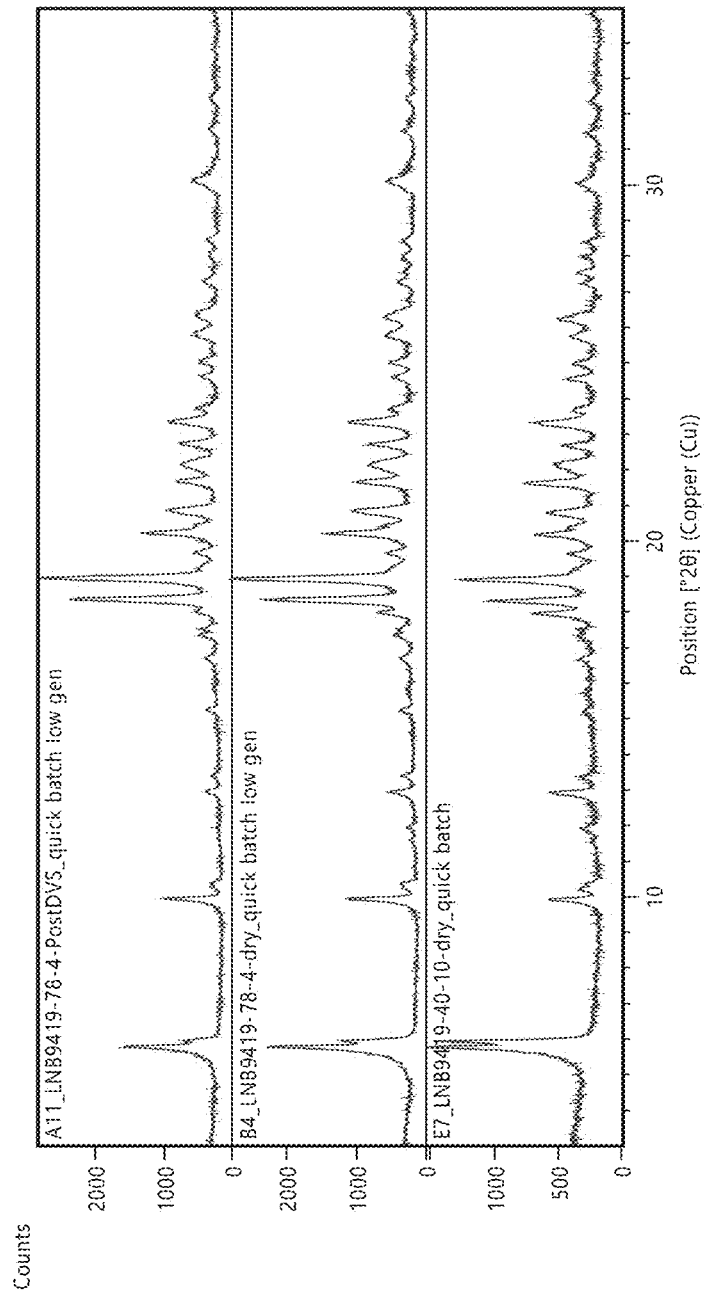

FIG. 162 sets forth comparative XRPD patterns of besylate Form 1 obtained from 400 mg scale-up before and after DVS.

Figure 163:
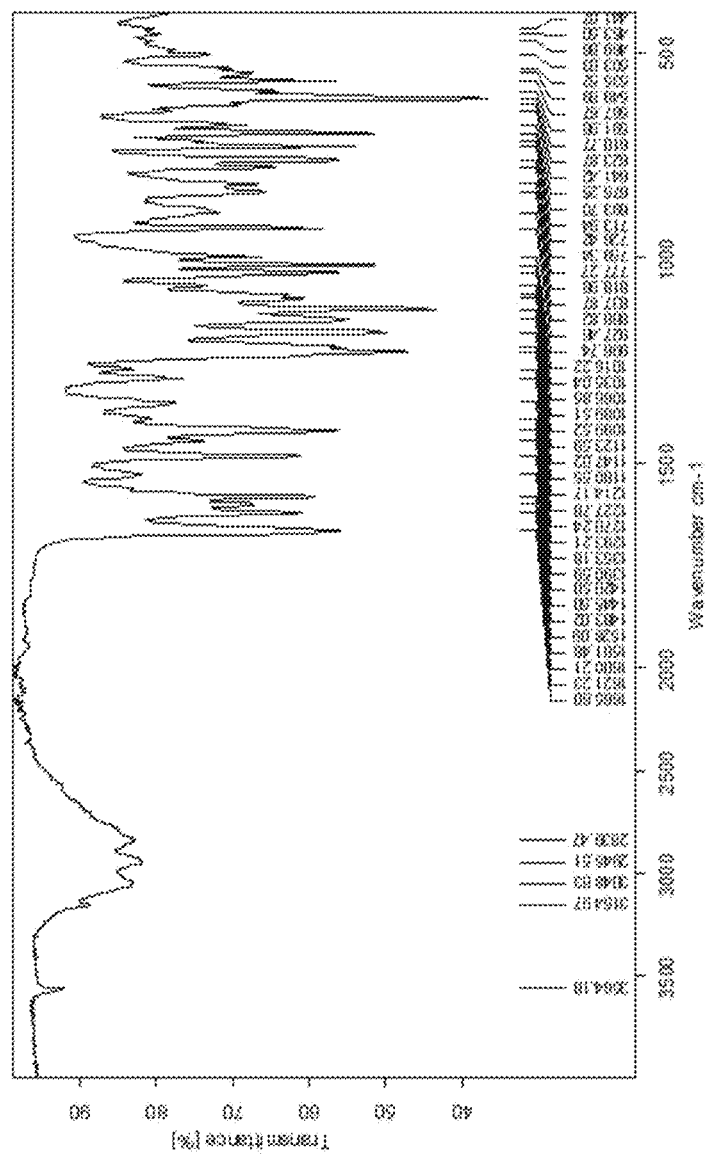

FIG. 163 sets forth an IR spectroscopic analysis of besylate Form 1 obtained from 400 mg scale-up.

Figure 164:
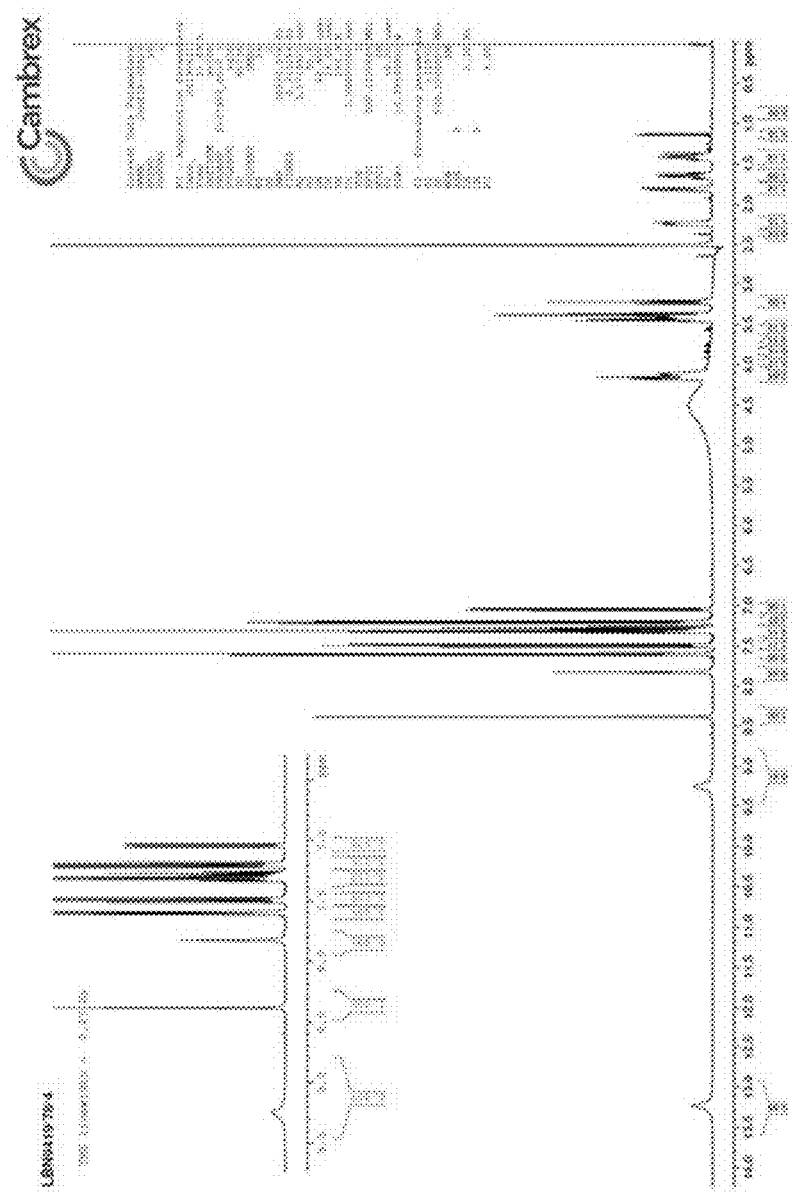

FIG. 164 sets forth a $^1$H NMR spectroscopic analysis of besylate Form 1 obtained from 400 mg scale-up.

Figure 165:
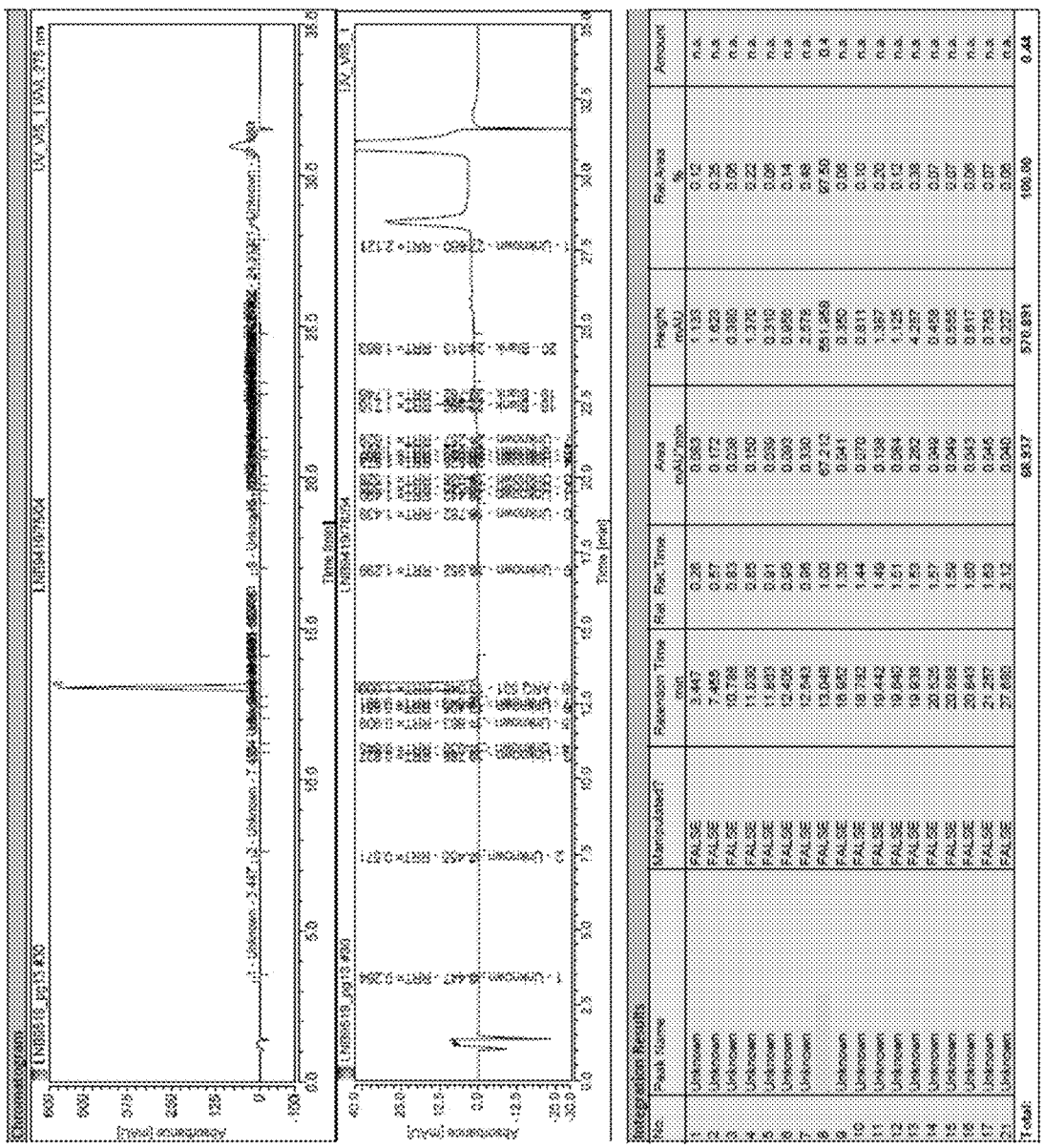

FIG. 165 sets forth an HPLC-UV chromatogram of besylate Form 1 obtained from 400 mg scale-up.

Figure 166:
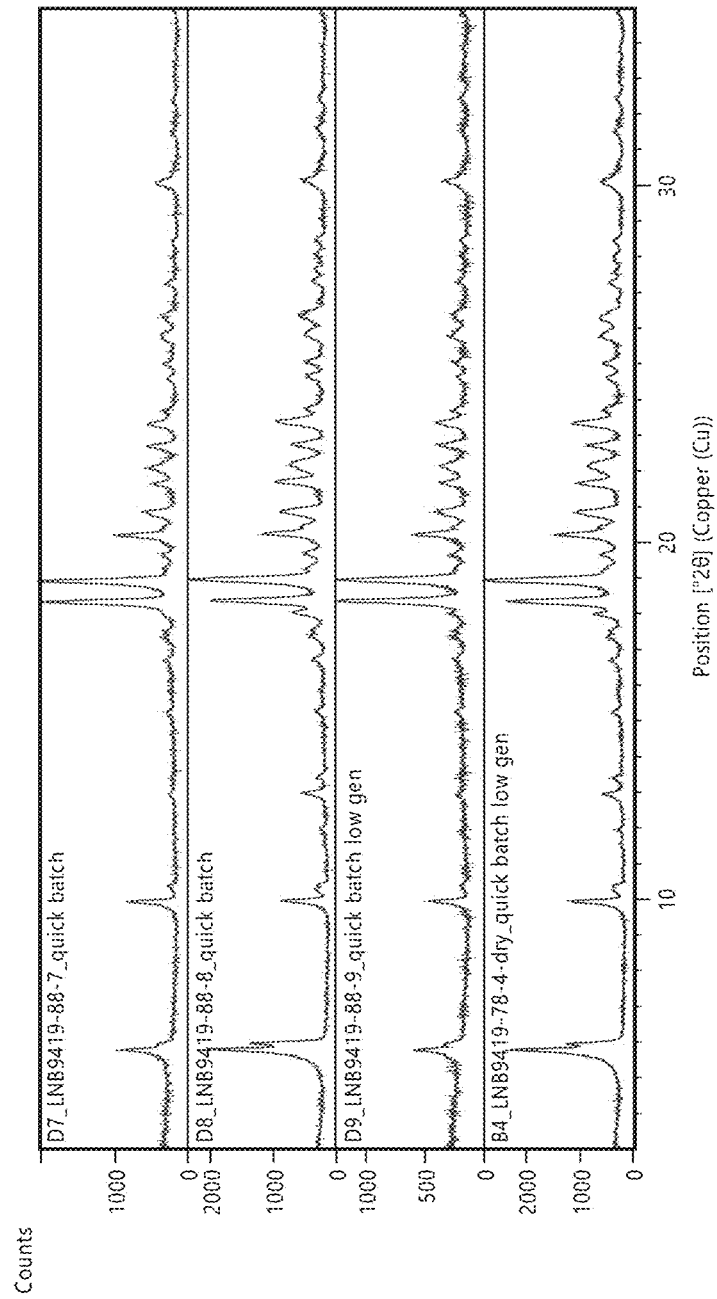

FIG. 166 sets forth XRPD patterns of besylate Form 1 obtained from 400 mg scale-up after 1 week stability studies.

Figure 167:
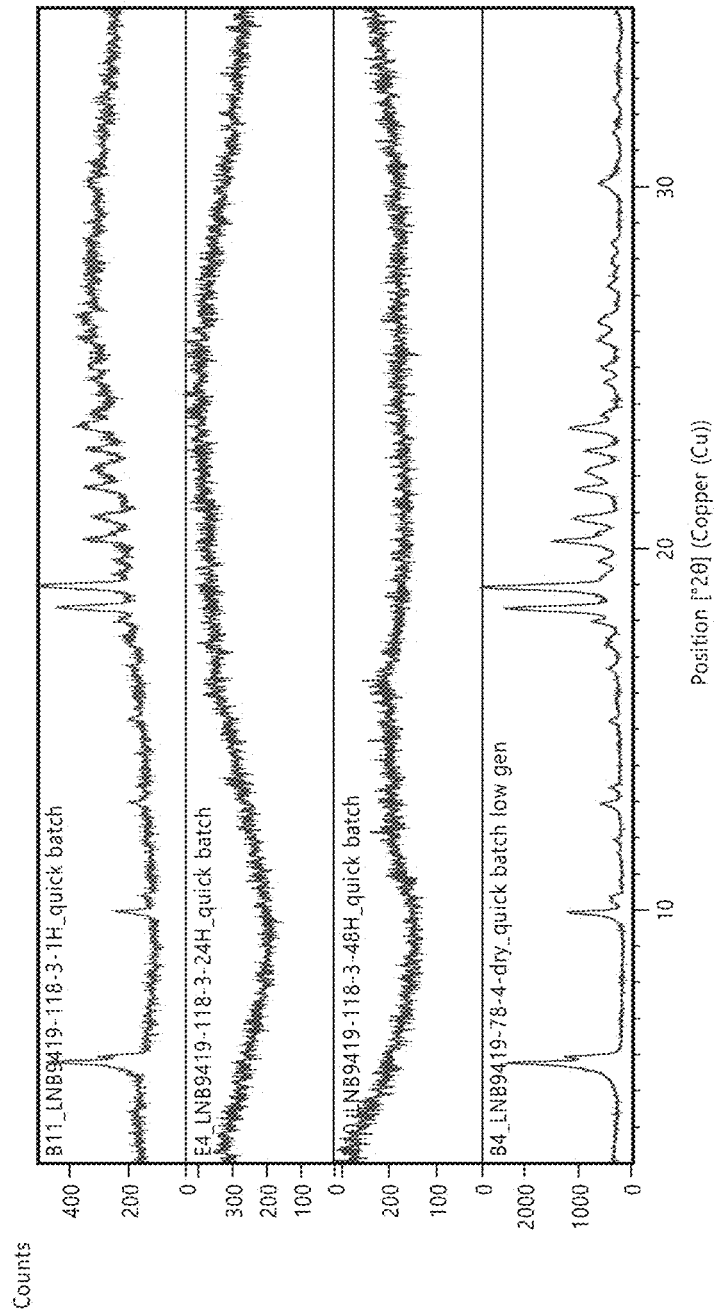

FIG. 167 sets forth XRPD patterns of besylate Form 1 obtained from 400 mg scale-up after salt disproportionation experiments.

Figure 168:
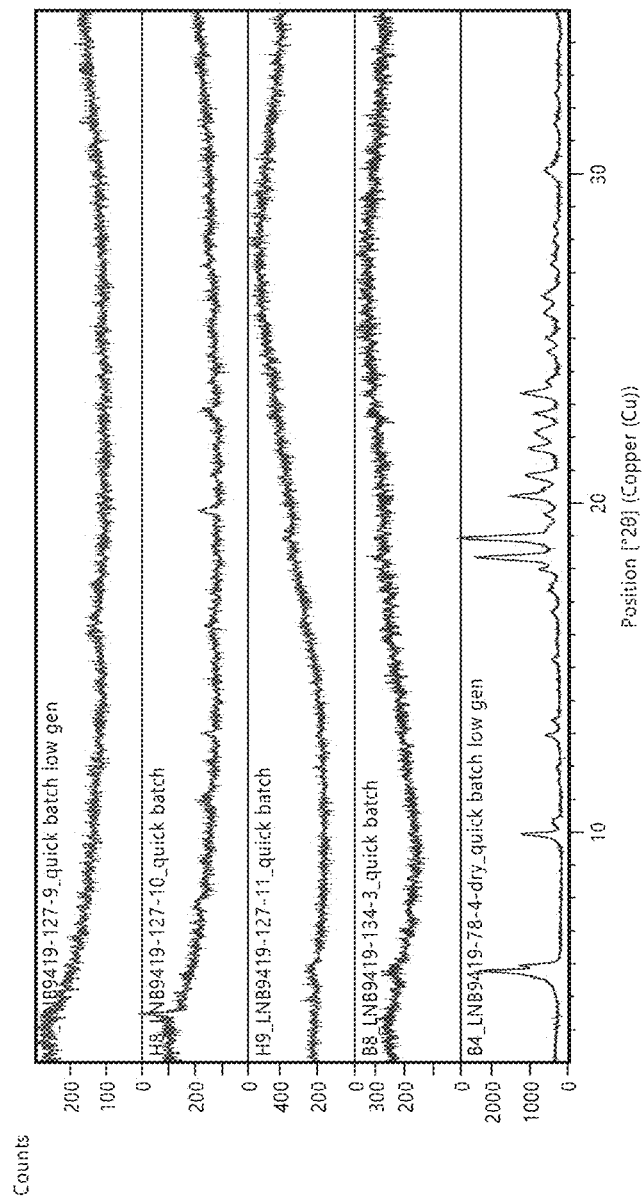

FIG. 168 sets forth XRPD patterns of besylate Form 1 obtained from 400 mg scale-up after thermodynamic solubility experiments.

Figure 169:
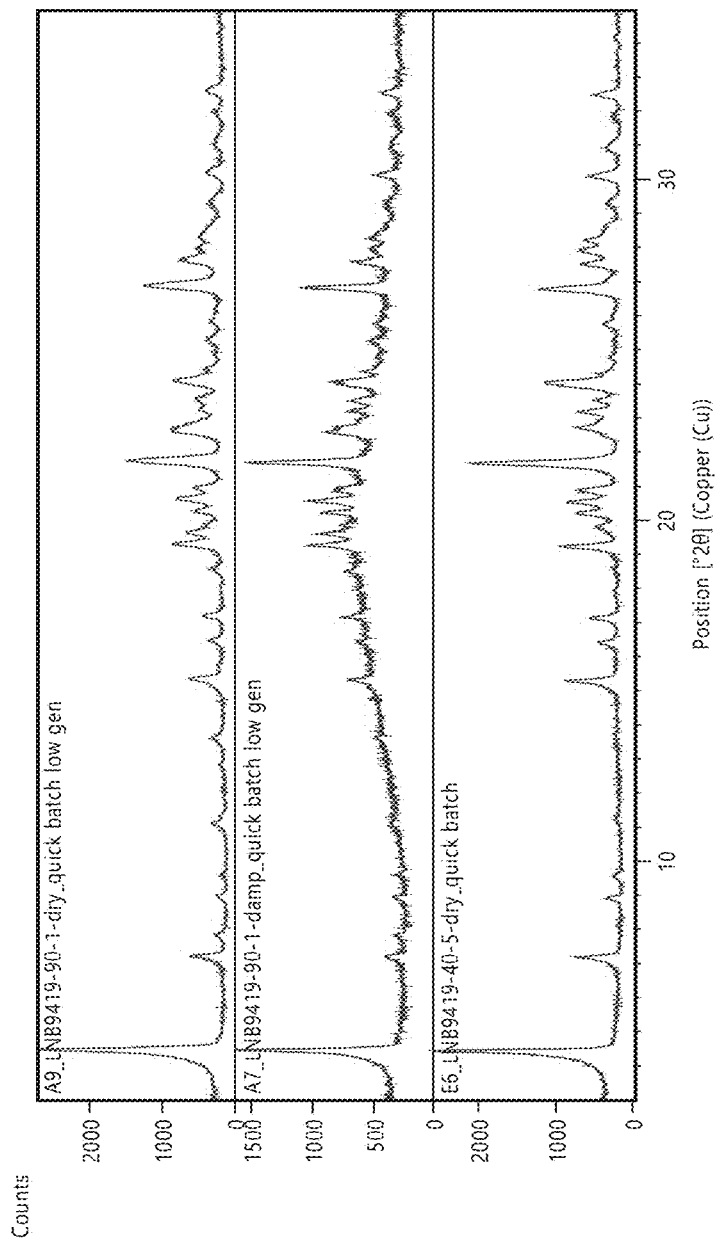

FIG. 169 sets forth XRPD patterns of hydrobromide Form 2 obtained from 400 mg scale-up.

Figure 170B:
Figure 170A:
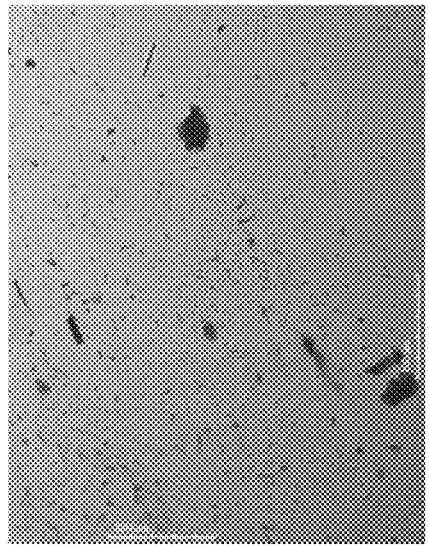

FIG. 170A sets forth a PLM image of hydrobromide Form 2 obtained from 400 mg scale-up.

FIG. 170B sets forth a PLM image of hydrobromide Form 2 obtained from 400 mg scale-up.

Figure 171:
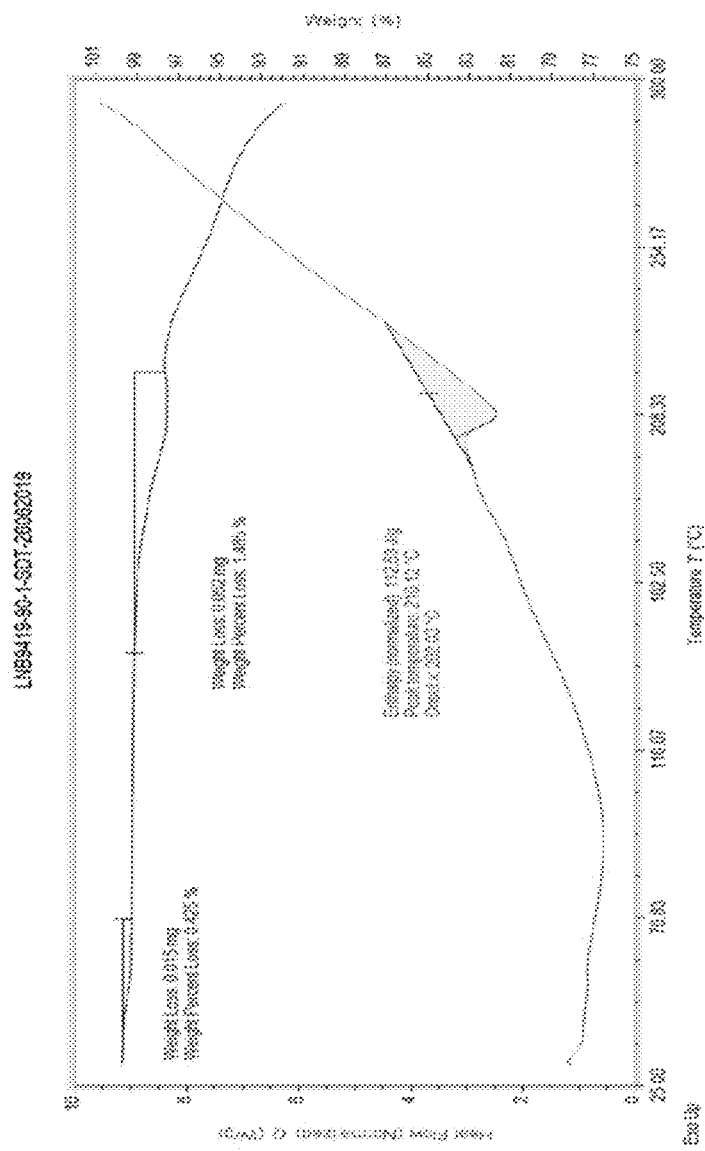

FIG. 171 sets forth a thermal analysis by TG/DTA of hydrobromide Form 2 obtained from 400 mg scale-up.

Figure 172:
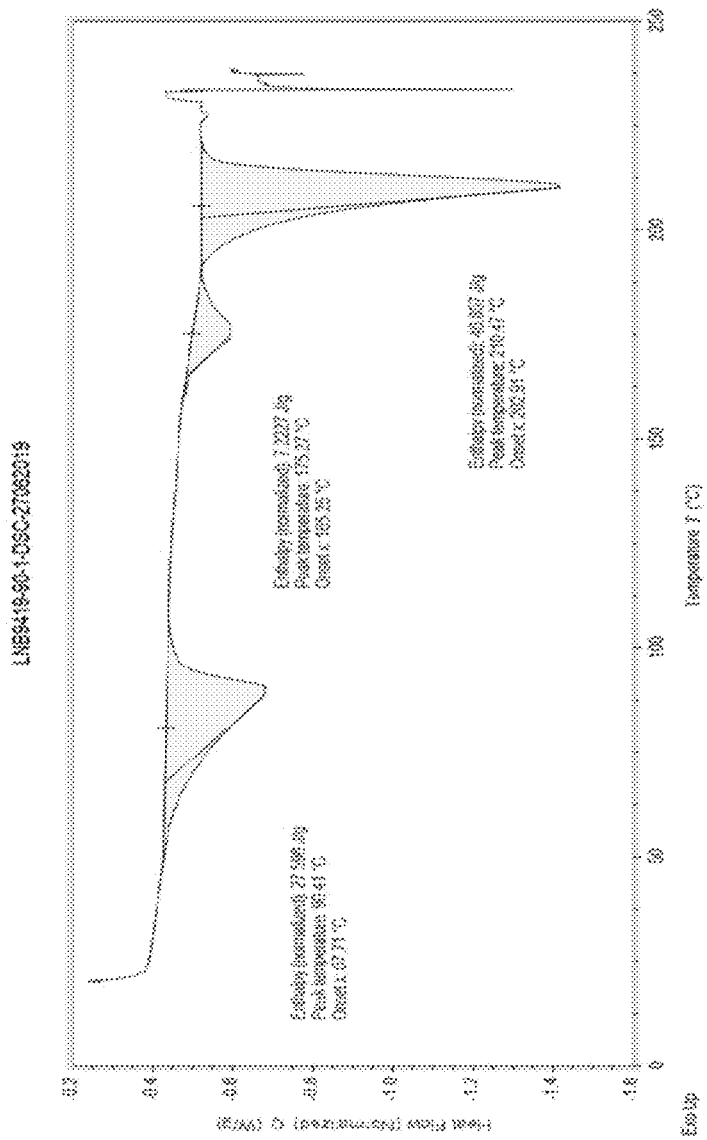

FIG. 172 sets forth a thermal analysis by a first heat DSC of hydrobromide Form 2 obtained from 400 mg scale-up.

Figure 173:
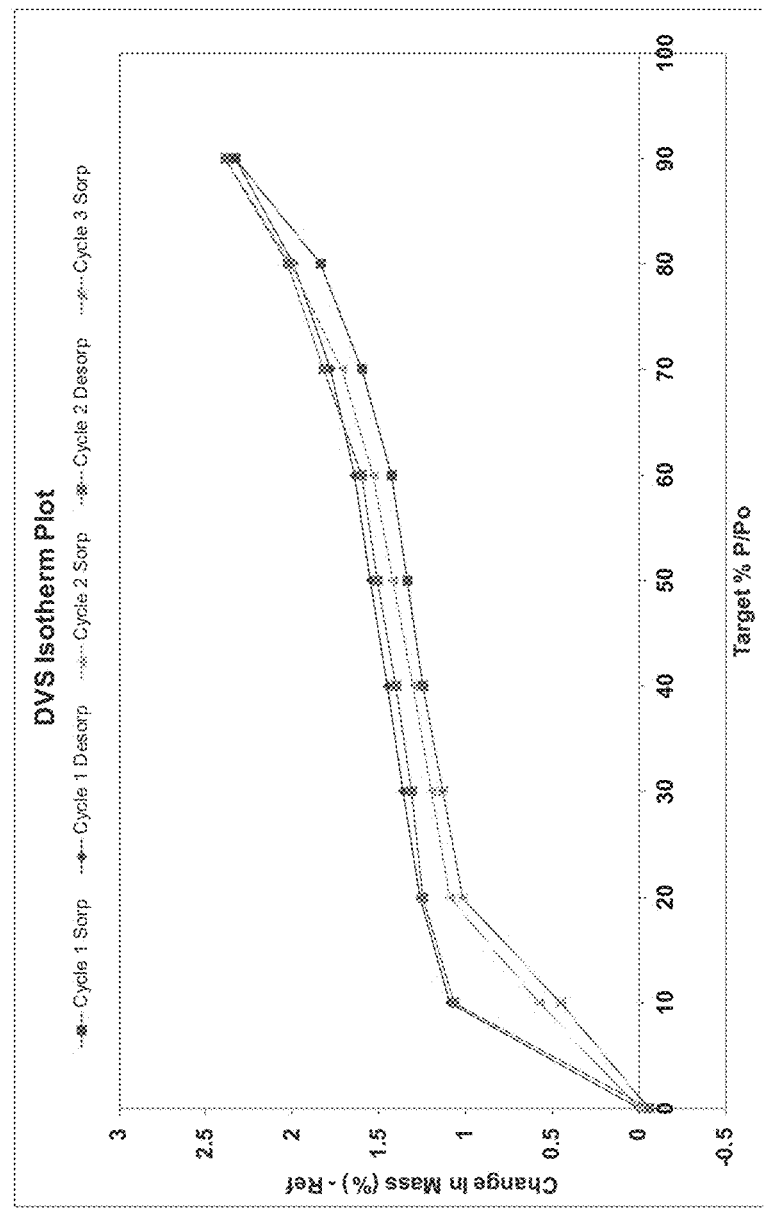

FIG. 173 sets forth a DVS isothermal analysis of hydrobromide Form 2 obtained from 400 mg scale-up.

Figure 174:
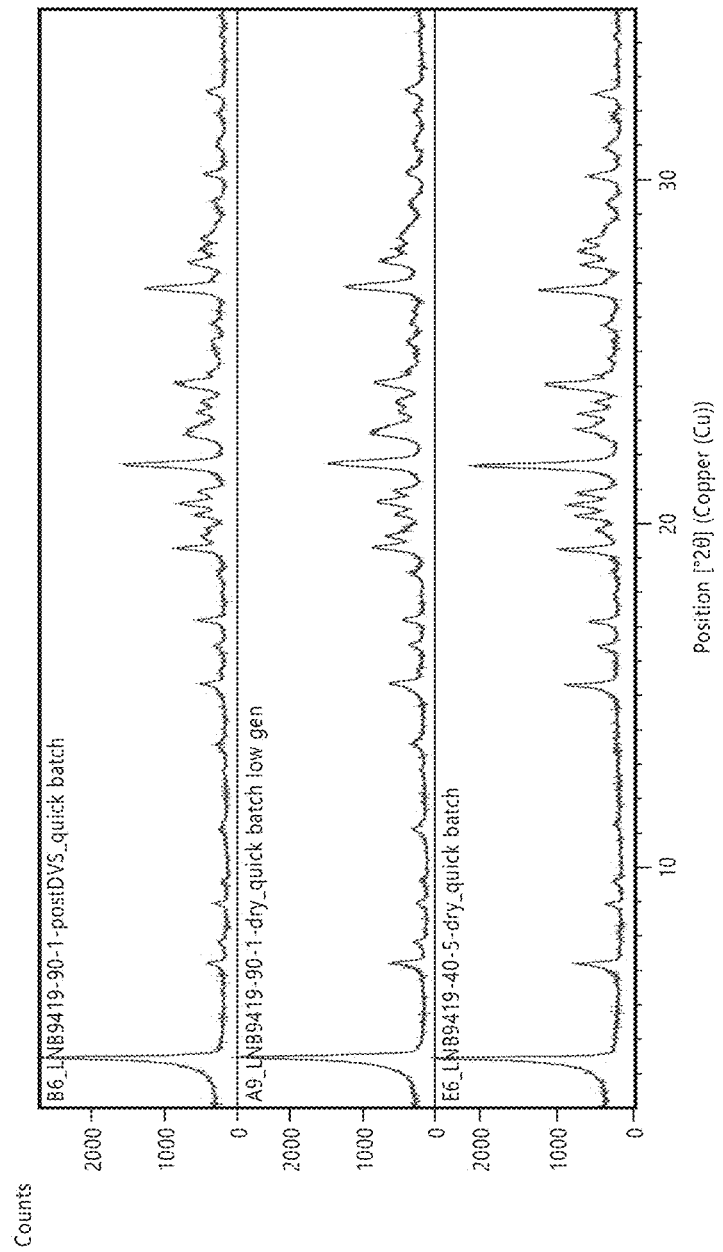

FIG. 174 sets forth comparative XRPD patterns of hydrobromide Form 2 obtained from 400 mg scale-up before and after DVS.

Figure 175:
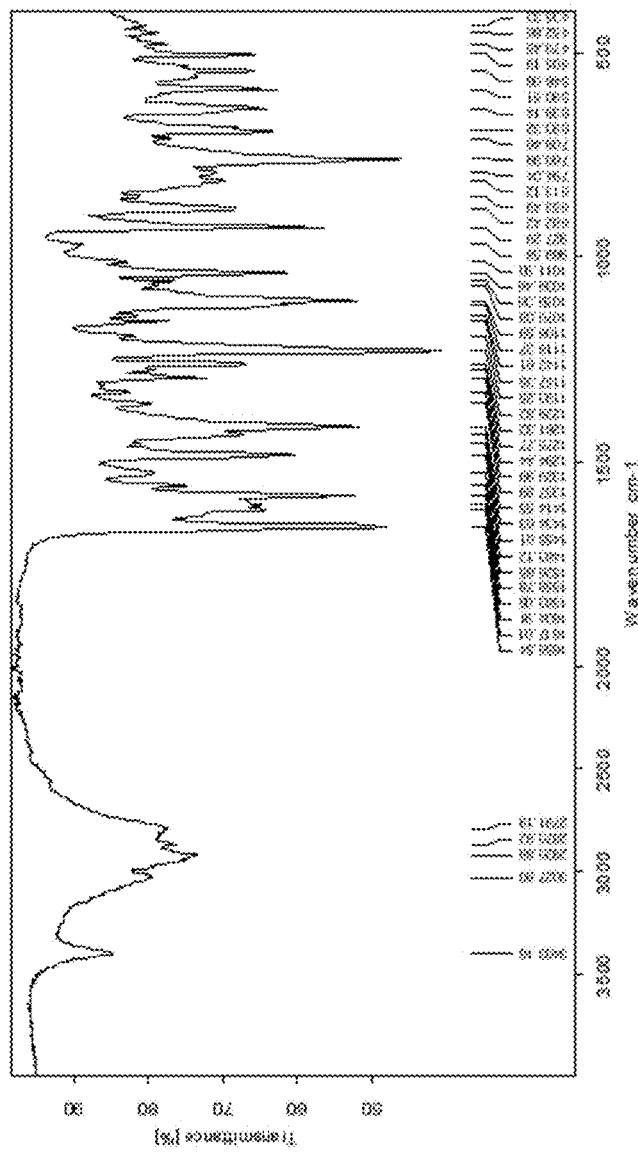

FIG. 175 sets forth an IR spectroscopic analysis of hydrobromide Form 2 obtained from 400 mg scale-up.

Figure 176:
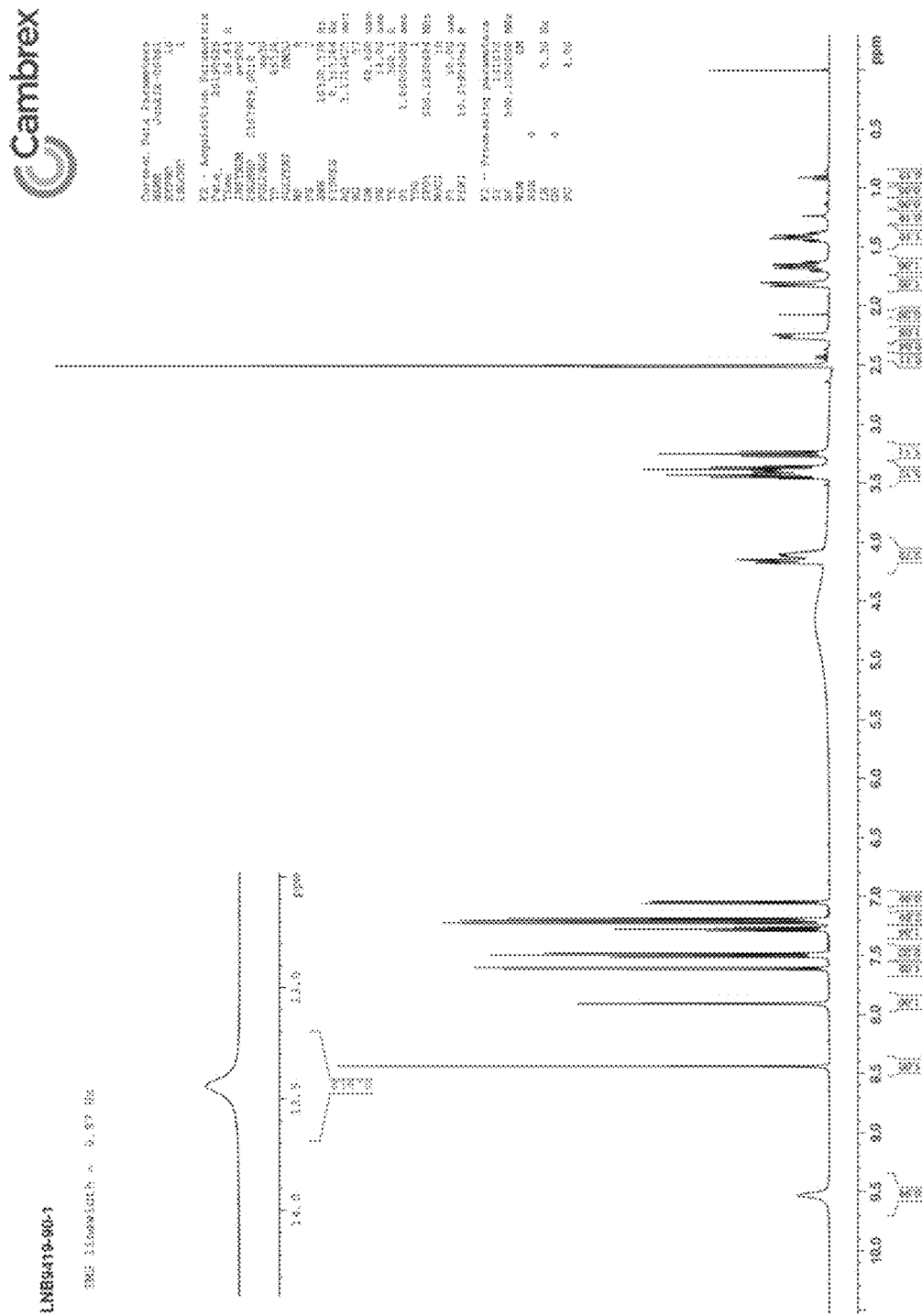

FIG. 176 sets forth a $^1$H NMR spectroscopic analysis of hydrobromide Form 2 obtained from 400 mg scale-up.

Figure 177:
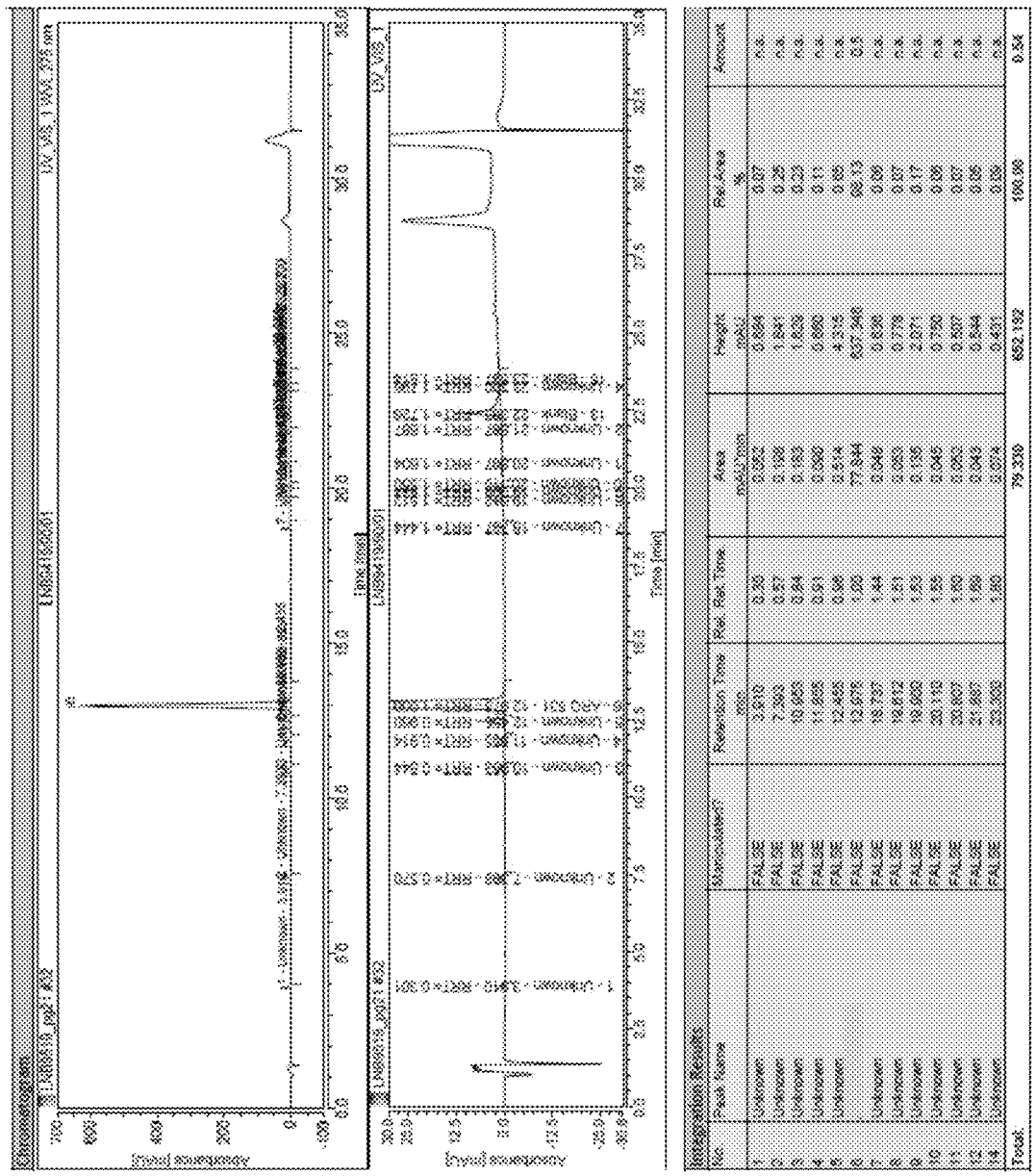

FIG. 177 sets forth an HPLC-UV chromatogram of hydrobromide Form 2 obtained from 400 mg scale-up.

Figure 178:
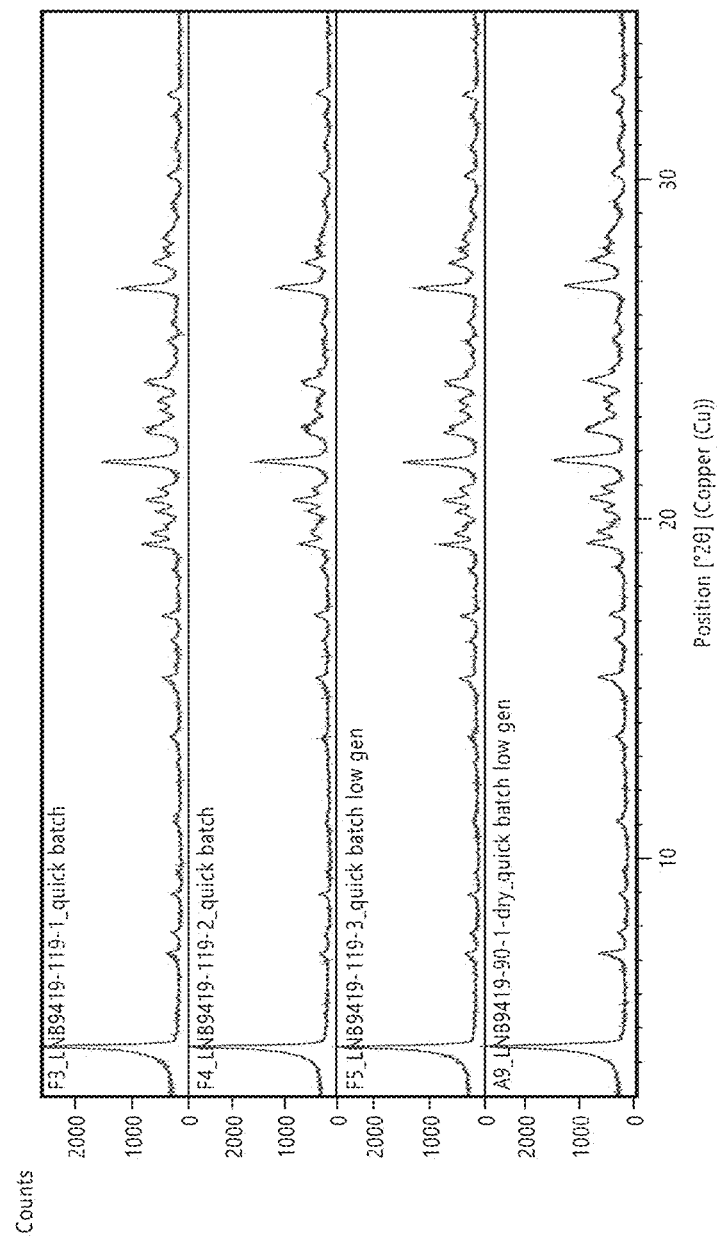

FIG. 178 sets forth XRPD patterns of hydrobromide Form 2 obtained from 400 mg scale-up after 1 week stability studies.

Figure 179:
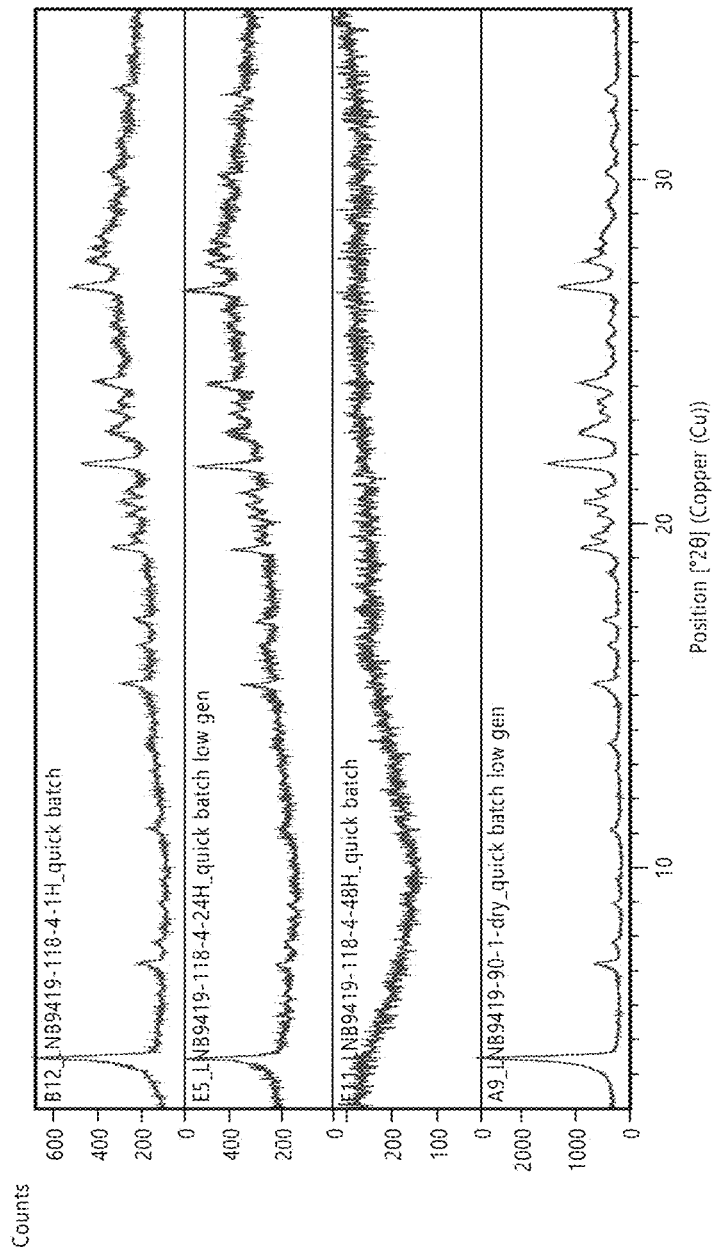

FIG. 179 sets forth XRPD patterns of hydrobromide Form 2 obtained from 400 mg scale-up after salt disproportionation experiments.

Figure 180:
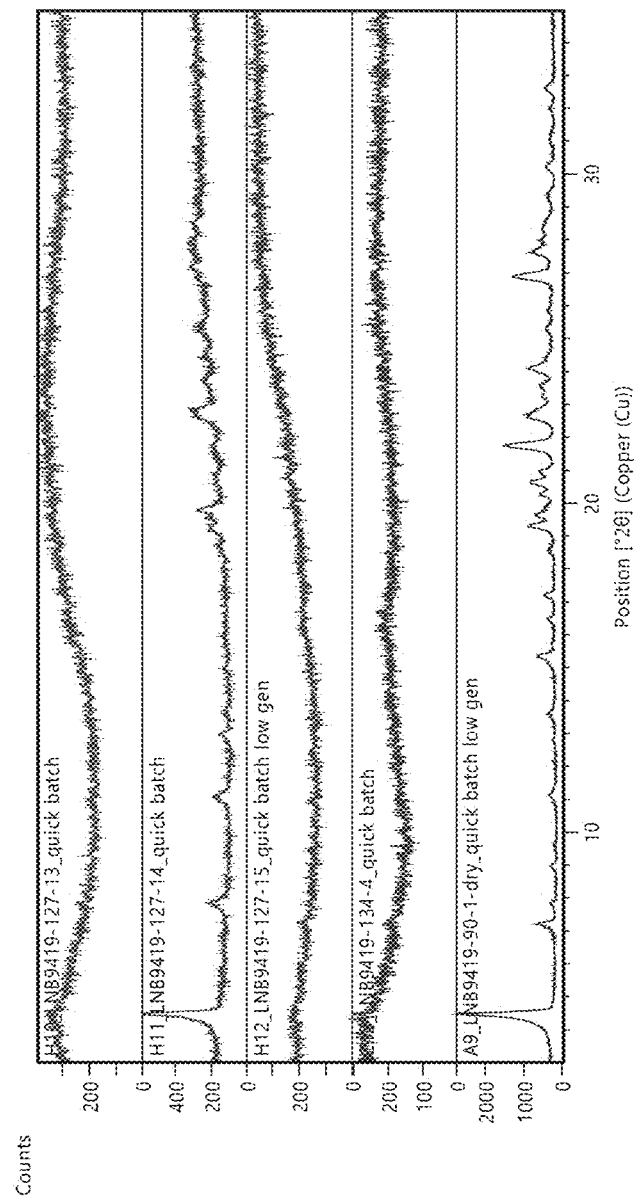

FIG. 180 sets forth XRPD patterns of hydrobromide Form 2 obtained from 400 mg scale-up after thermodynamic solubility experiments.

Figure 181:
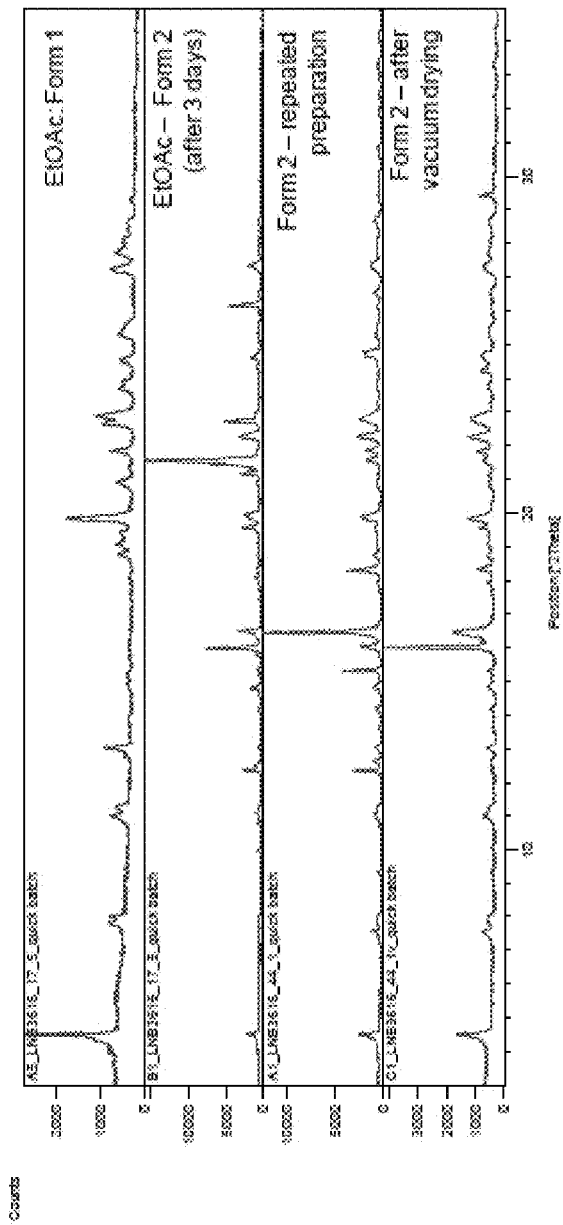

FIG. 181 sets forth XRPD patterns of hydrochloride Form 1 and Form 2.

Figures 182A, 182B:
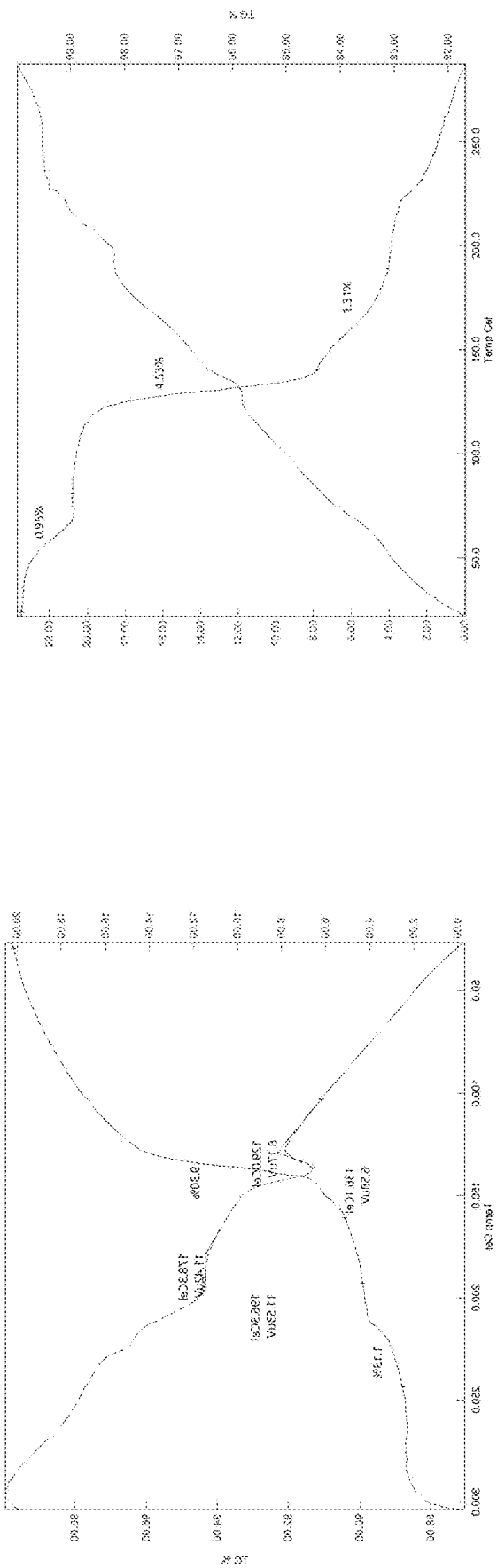

FIG. 182A sets forth a thermal analysis by TG/DTA of hydrochloride Form 2 before drying.

FIG. 182B sets forth a thermal analysis by TG/DTA of hydrochloride Form 2 after drying.

Figure 183E:
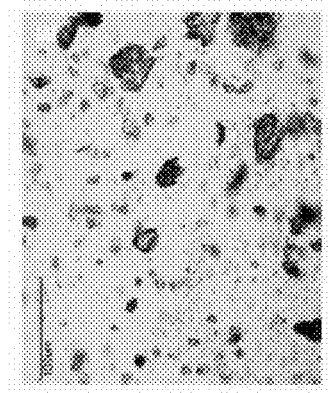
Figure 183C:
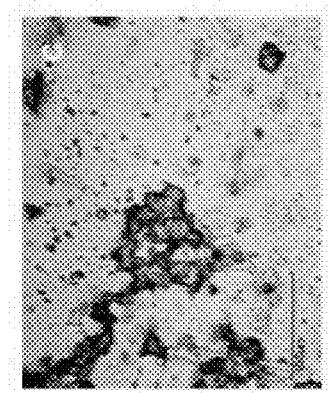
Figure 183A:
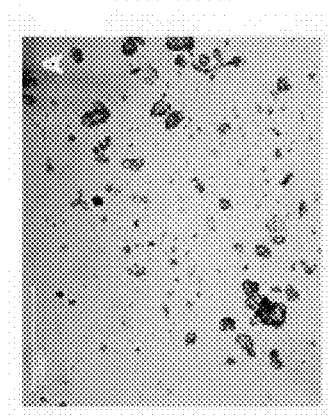

FIG. 183A sets forth PLM images of hydrochloride Form 2 under non-polarized light.

Figure 183F:
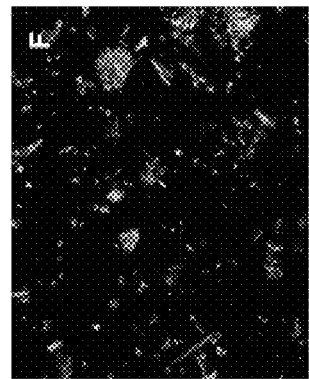
Figure 183D:
Figure 183B:
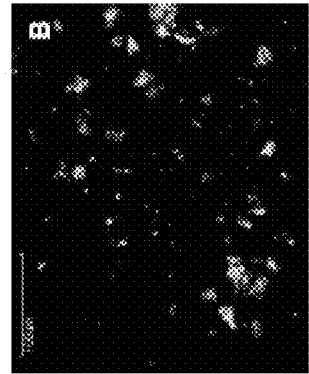

FIG. 183B sets forth PLM images of hydrochloride Form 2 under polarized light.

FIG. 183C sets forth PLM images of hydrochloride Form 2 under non-polarized light.

FIG. 183D sets forth PLM images of hydrochloride Form 2 under polarized light.

FIG. 183E sets forth PLM images of hydrochloride Form 2 after drying under vacuum under non-polarized light.

FIG. 183F sets forth PLM images of hydrochloride Form 2 after drying under vacuum under polarized light.

Figure 184:
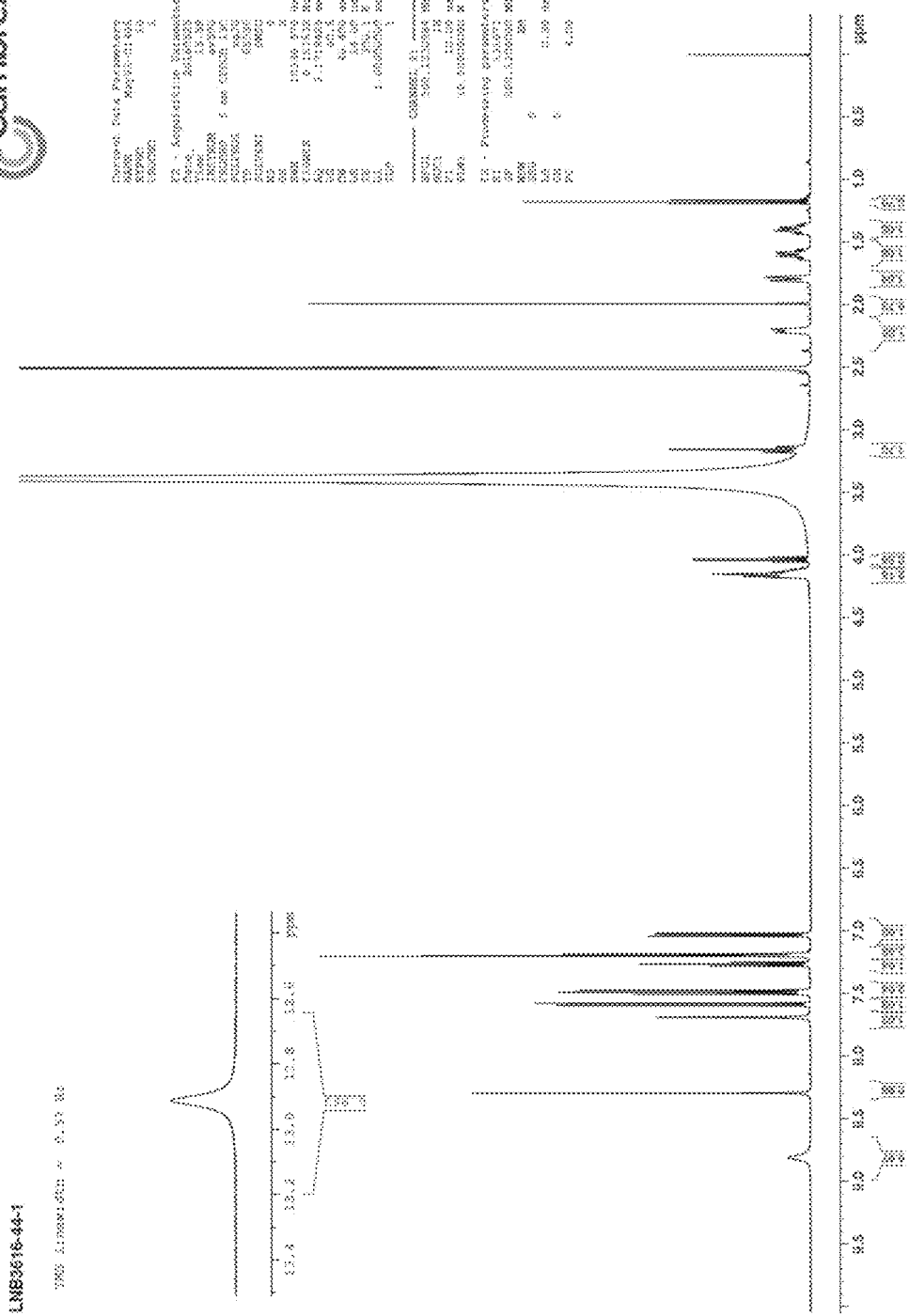

FIG. 184 sets forth a $^1$H NMR spectroscopic analysis of hydrochloride Form 2.

Figure 185:
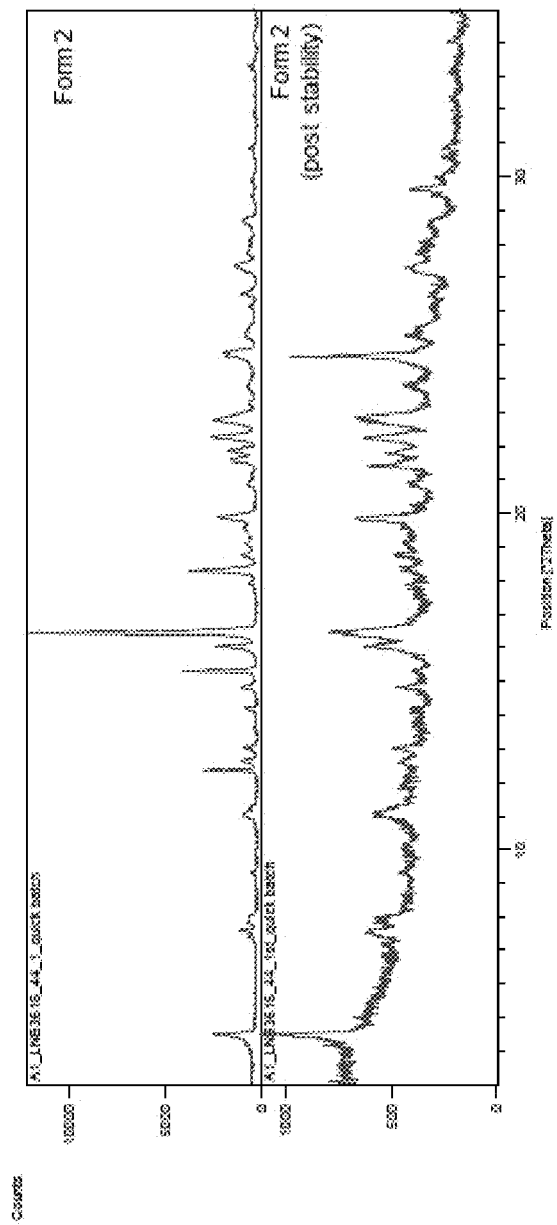

FIG. 185 sets forth XRPD patterns of hydrochloride Form 2 before and after the stability experiment.

Figure 186:
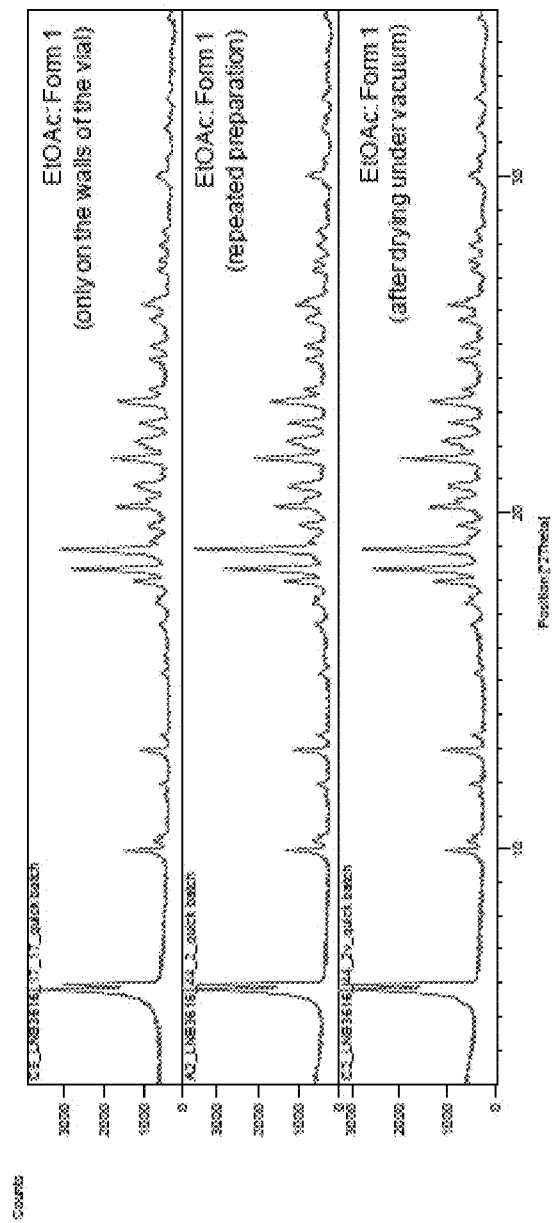

FIG. 186 sets forth XRPD patterns of besylate Form 1.

Figure 187:
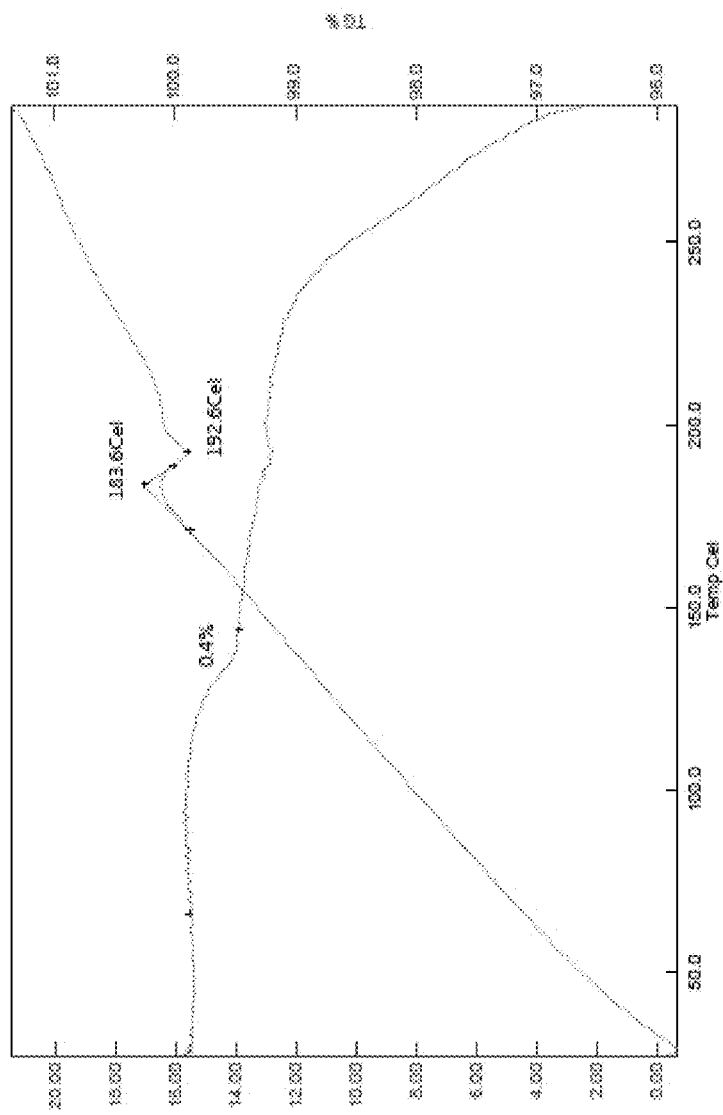

FIG. 187 sets forth a thermal analysis by TG/DTA of besylate Form 1.

Figure 188E:
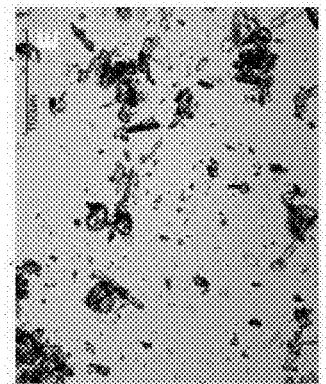
Figure 188C:
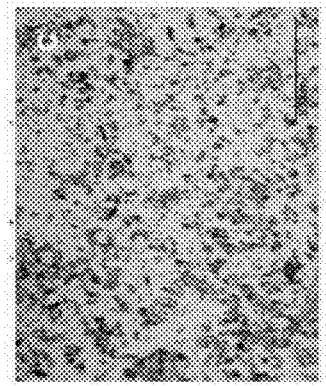
Figure 188A:
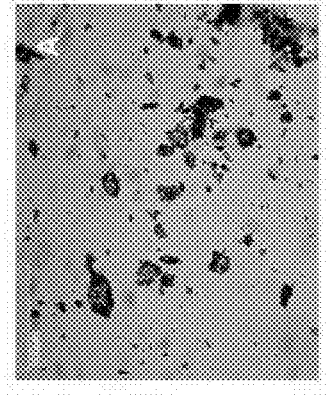

FIG. 188A sets forth PLM images of besylate Form 1 under non-polarized light.

Figure 188F:
Figure 188D:
Figure 188B:

FIG. 188B sets forth PLM images of besylate Form 1 under polarized light.

FIG. 188C sets forth PLM images of besylate Form 1 under non-polarized light.

FIG. 188D sets forth PLM images of besylate Form 1 under polarized light.

FIG. 188E sets forth PLM images of besylate Form 1 after drying under vacuum under non-polarized light.

FIG. 188F sets forth PLM images of besylate Form 1 after drying under vacuum under polarized light.

Figure 189:
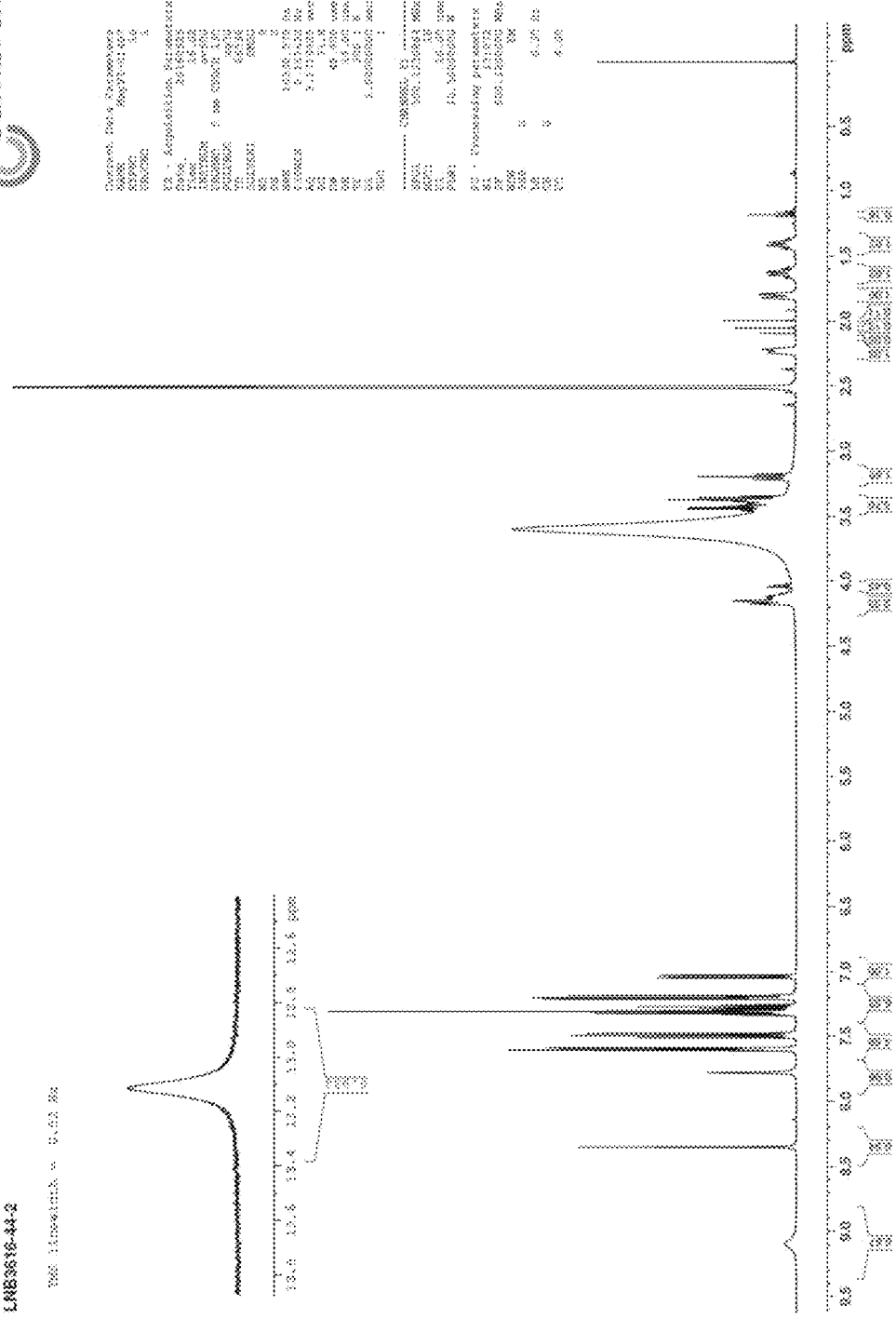

FIG. 189 sets forth a $^1$H NMR spectroscopic analysis of besylate Form 1.

Figure 190:
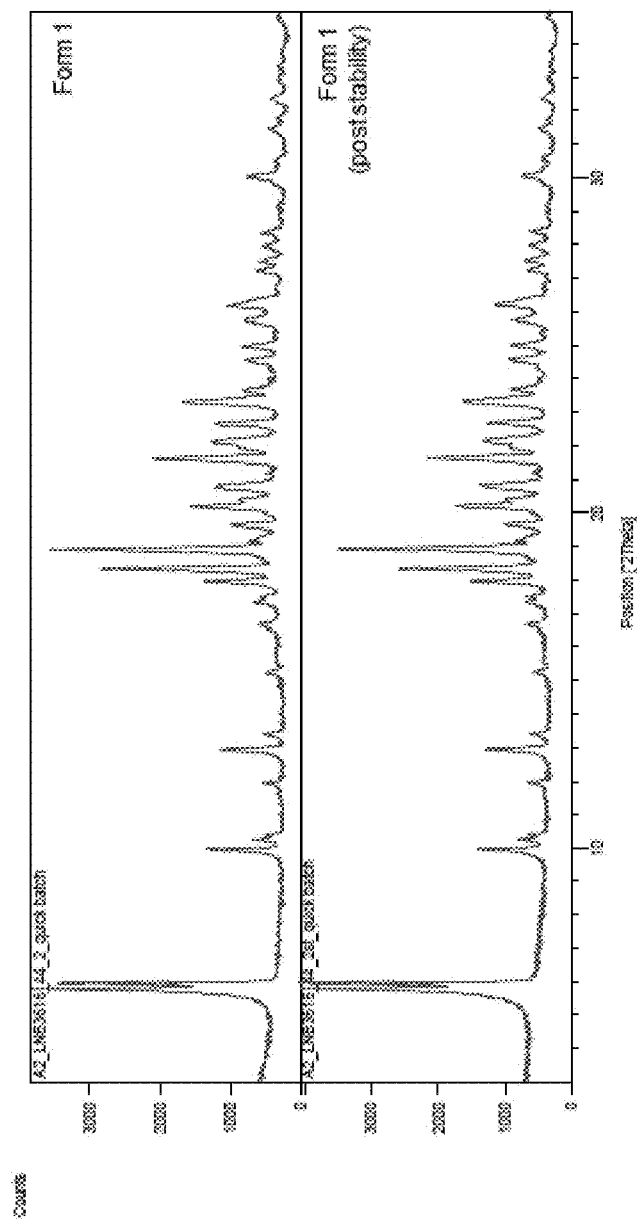

FIG. 190 sets forth XRPD patterns of besylate Form 1 before and after the stability experiment.

Figure 191:
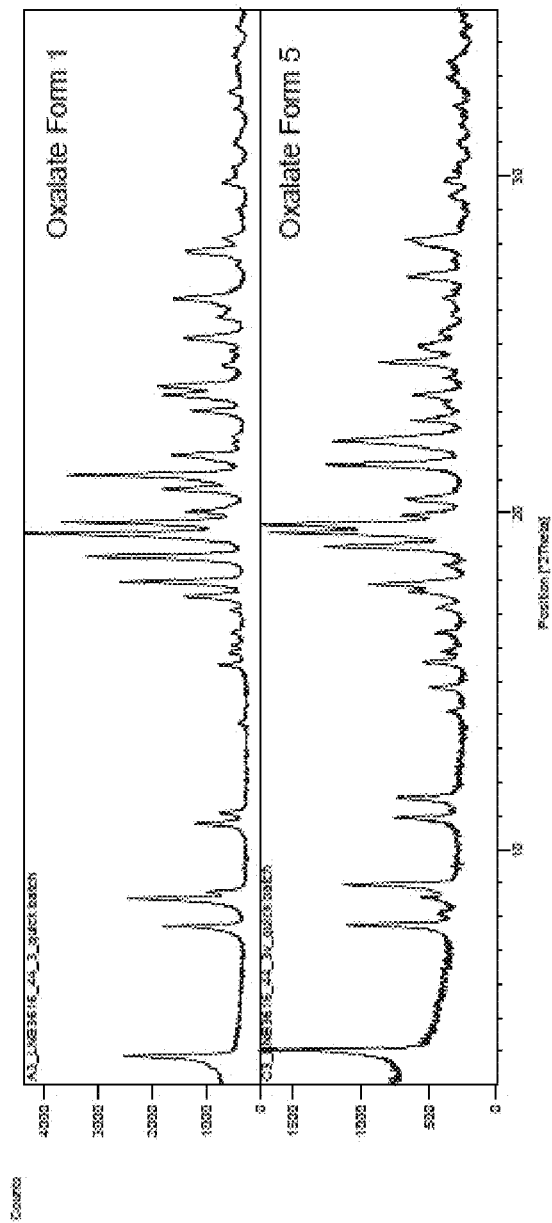

FIG. 191 sets forth XRPD patterns of oxalate Form 1 and Form 5.

Figure 192:
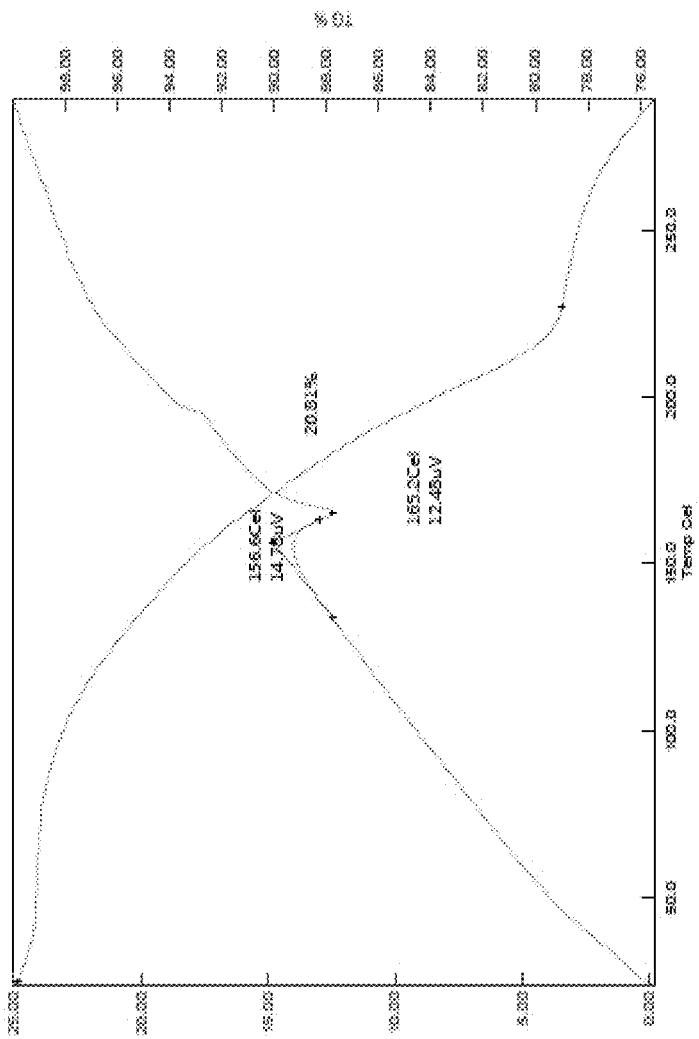

FIG. 192 sets forth a thermal analysis by TG/DTA of oxalate Form 1.

Figure 193C:
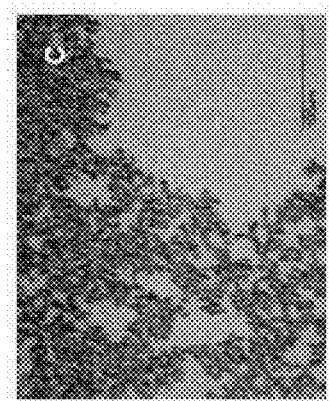
Figure 193D:
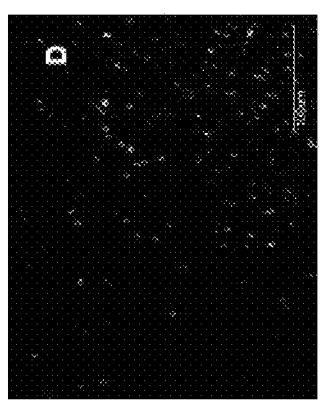
Figure 193A:
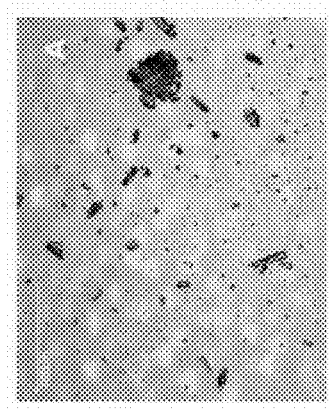

FIG. 193A sets forth PLM images of oxalate Form 1 under non-polarized light.

Figure 193B:
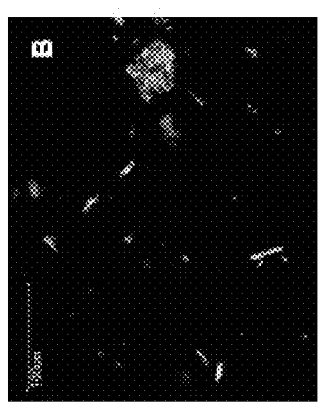

FIG. 193B sets forth PLM images of oxalate Form 1 under polarized light.

FIG. 193C sets forth PLM images of oxalate Form 1 after drying under vacuum under non-polarized light.

FIG. 193D sets forth PLM images of oxalate Form 1 after drying under vacuum under polarized light (D).

Figure 194:
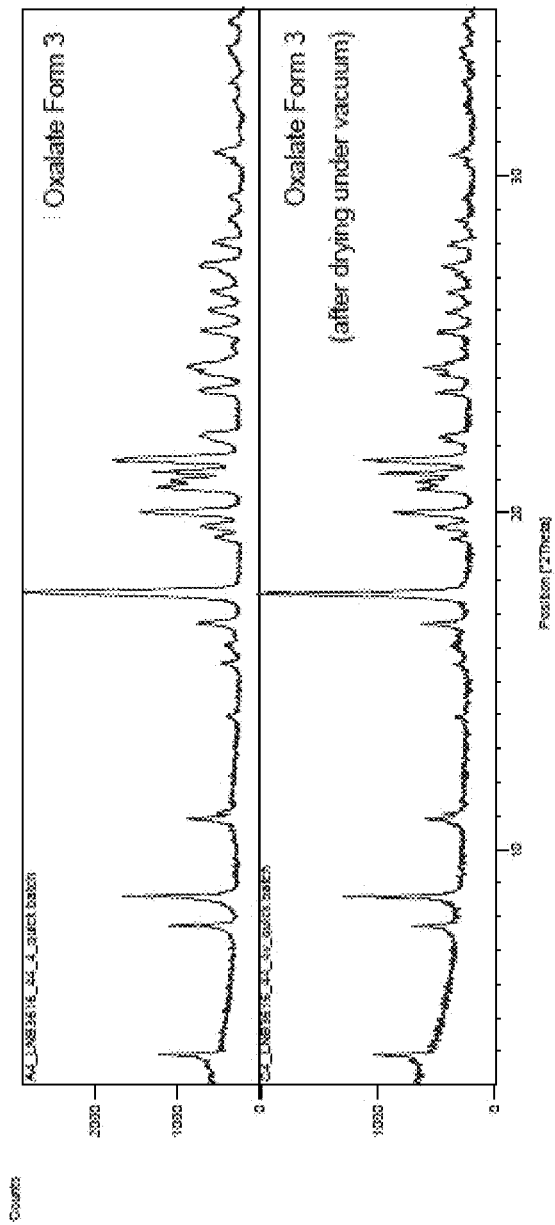

FIG. 194 sets forth XRPD patterns of oxalate Form 3 before and after drying under vacuum.

Figure 195:
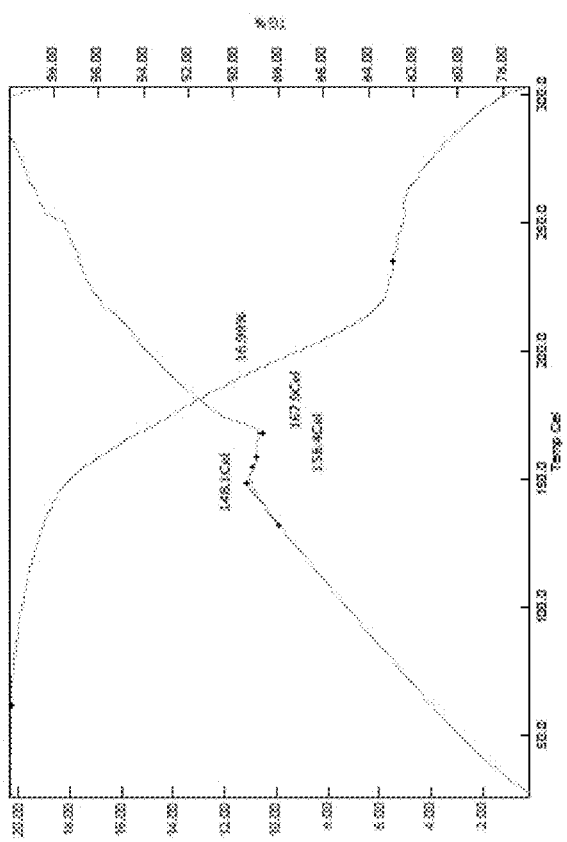

FIG. 195 sets forth a thermal analysis by TG/DTA of oxalate Form 3.

Figure 196:
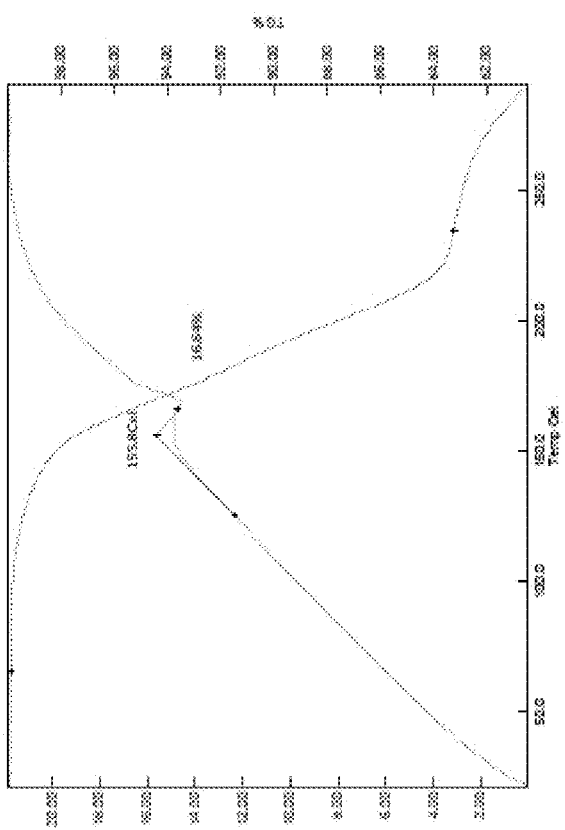

FIG. 196 sets forth a thermal analysis by TG/DTA of oxalate Form 3 after drying under vacuum.

FIG. 197A sets forth PLM images of oxalate Form 3 under non-polarized light.

FIG. 197B sets forth PLM images of oxalate Form 3 under polarized light.

FIG. 197C sets forth PLM images of oxalate Form 3 under non-polarized light.

FIG. 197D sets forth PLM images of oxalate Form 3 under polarized light.

FIG. 197E sets forth PLM images of oxalate Form 3 after drying under vacuum under non-polarized light.

FIG. 197F sets forth PLM images of oxalate Form 3 after drying under vacuum under polarized light.

Figure 198:
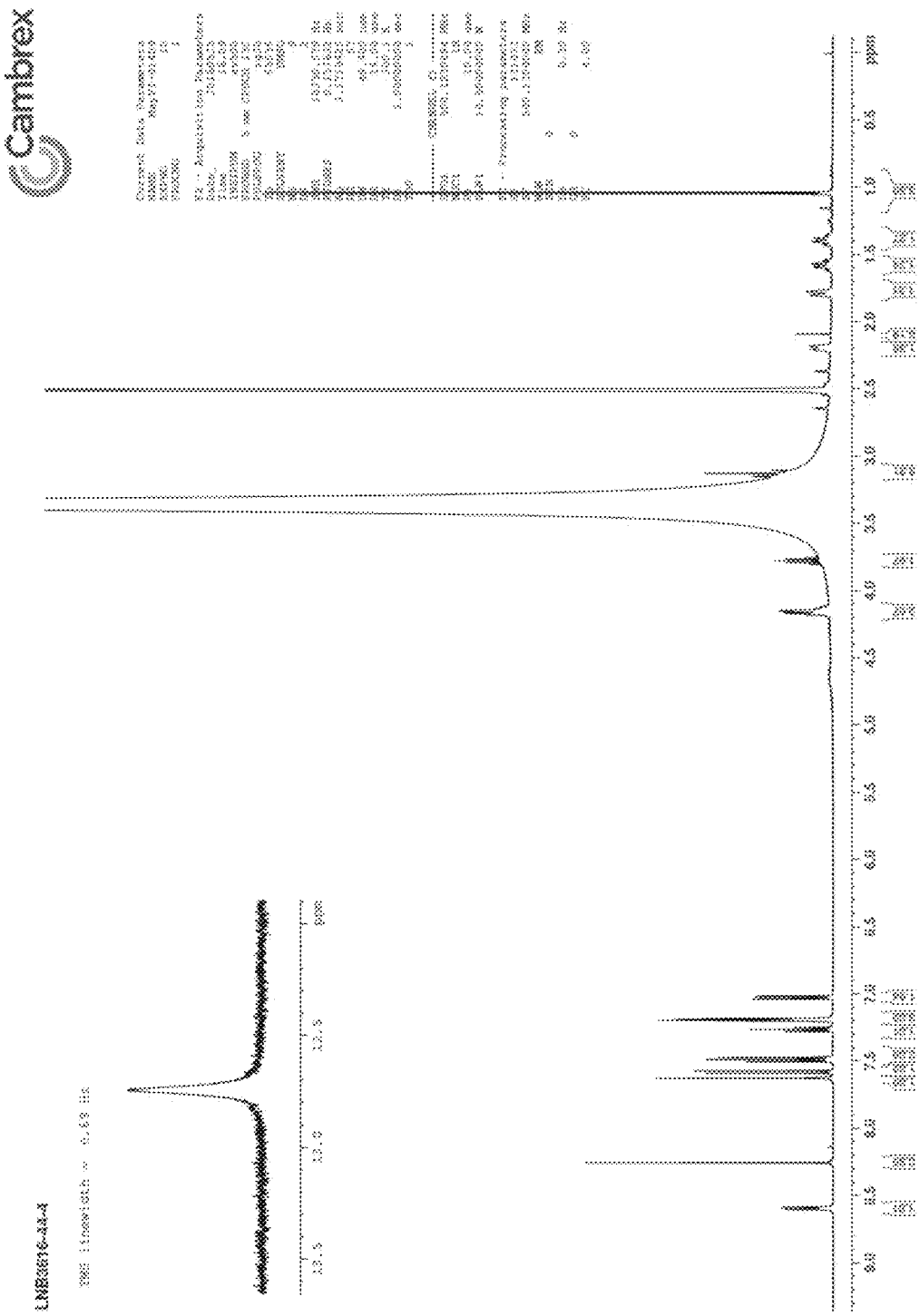

FIG. 198 sets forth a $^1$H NMR spectroscopic analysis of oxalate Form 3.

Figure 199:
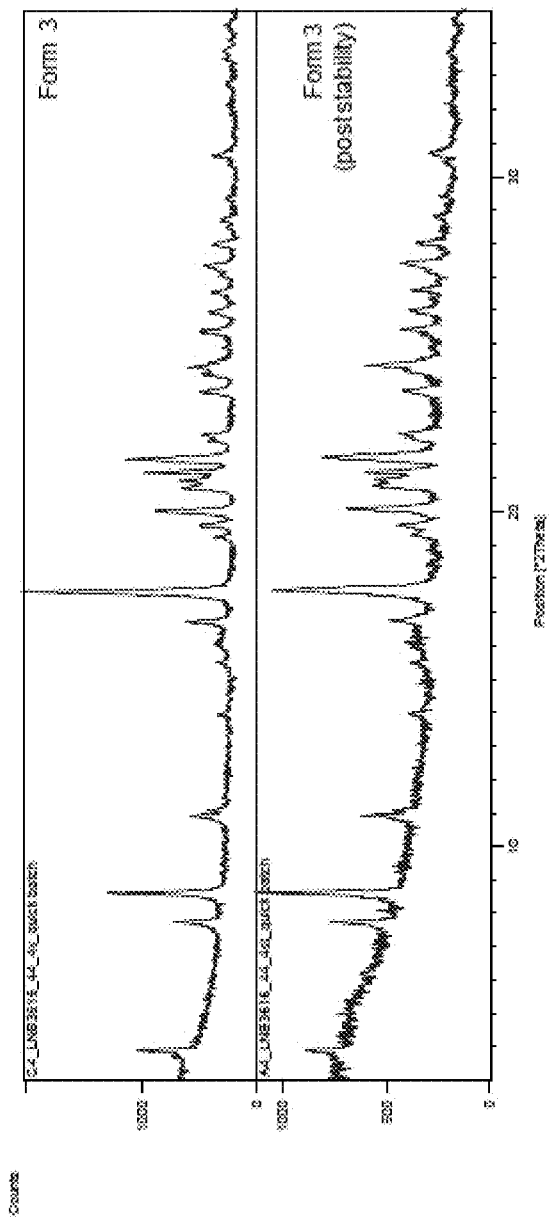

FIG. 199 sets forth XRPD patterns of oxalate Form 3 before and after the stability experiment.

Figure 200:
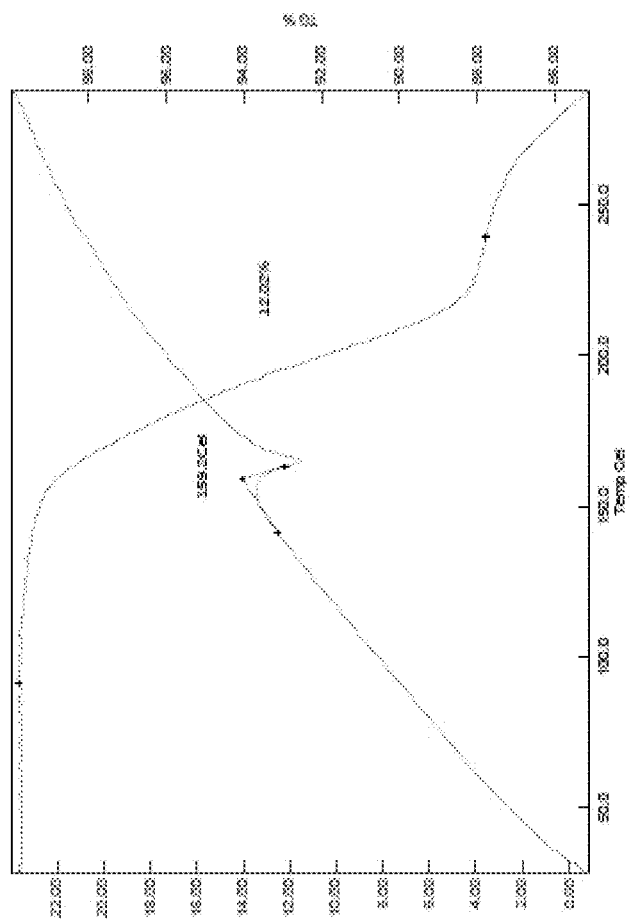

FIG. 200 sets forth a thermal analysis by TG/DTA of oxalate Form 5 after drying under vacuum.

Figures 201A, 201B:
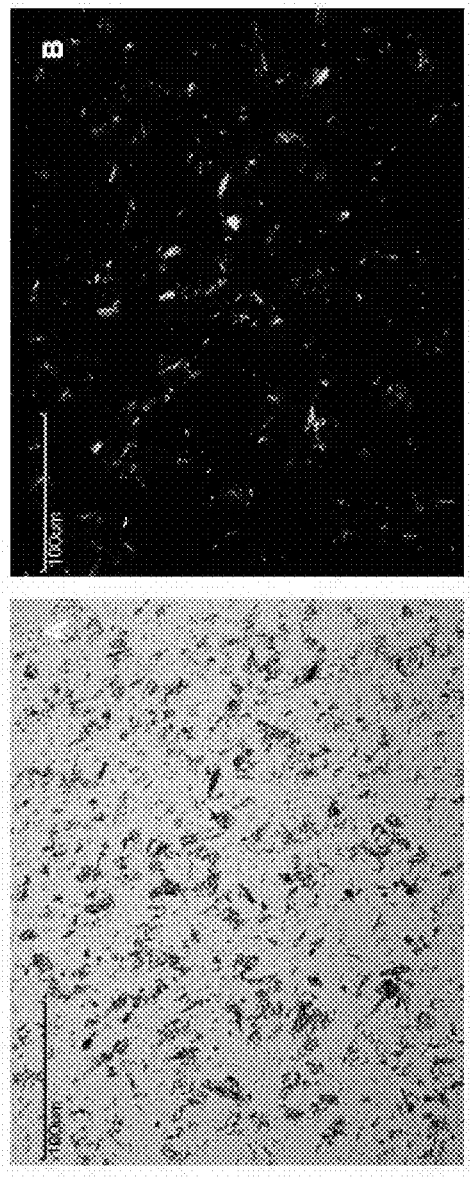

FIG. 201A sets forth PLM images of oxalate Form 5 under non-polarized light.

FIG. 201B sets forth PLM images of oxalate Form 5 under polarized light.

Figure 202:
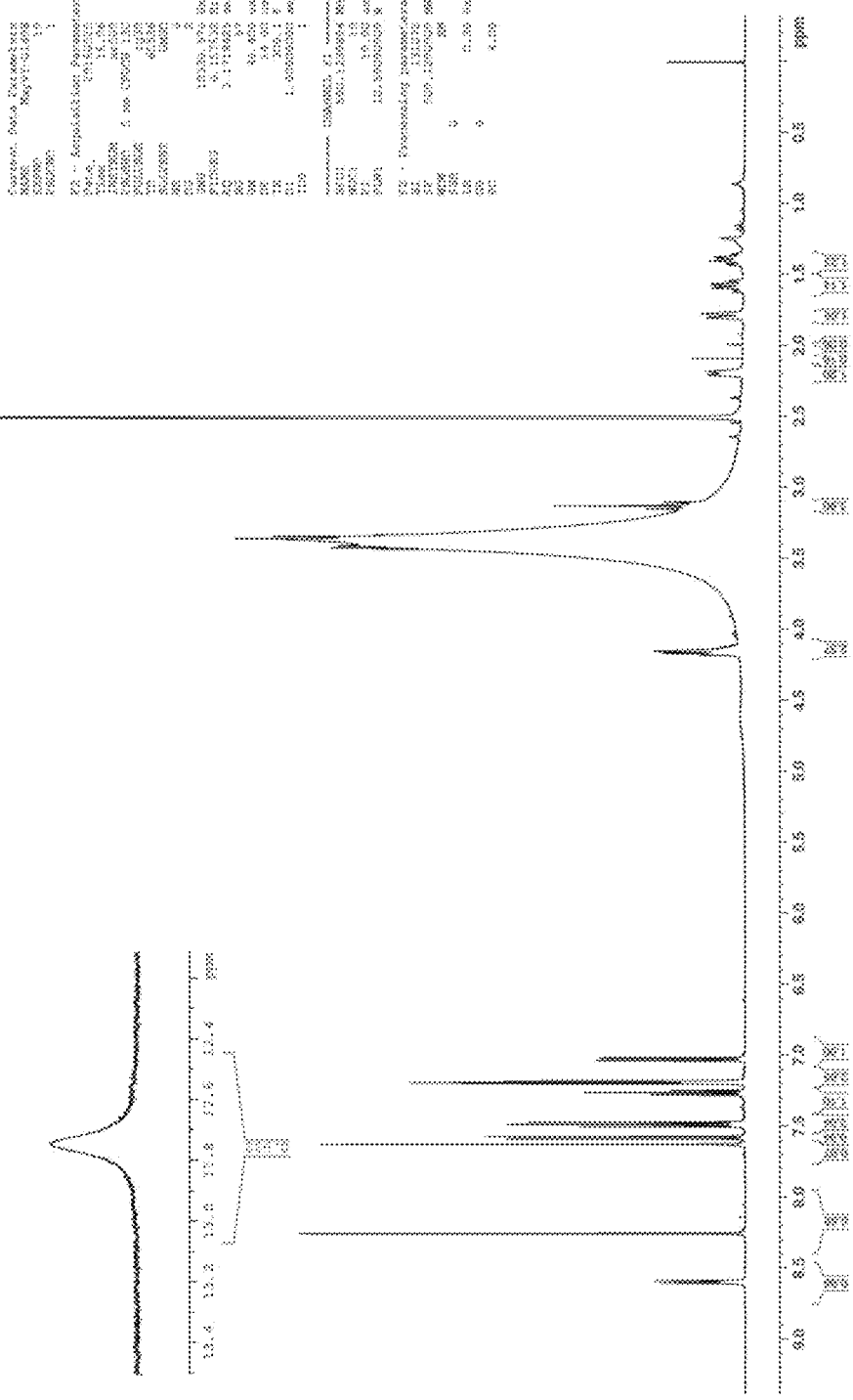

FIG. 202 sets forth a $^1$H NMR spectroscopic analysis of oxalate Form 5.

Figure 203:
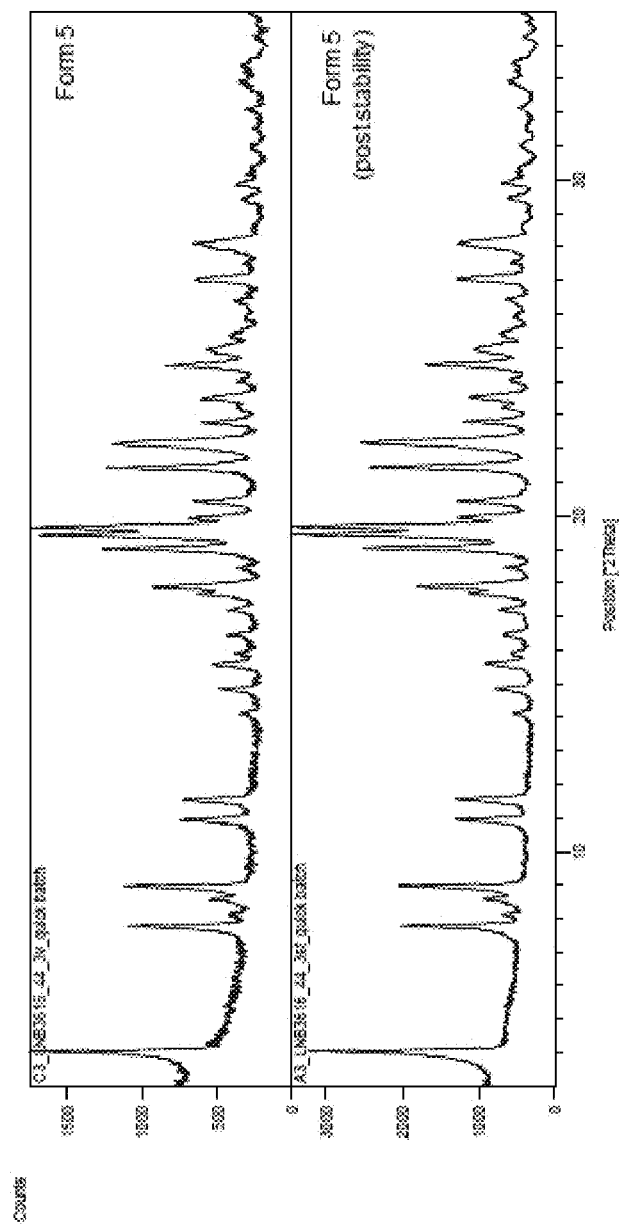

FIG. 203 sets forth XRPD patterns of oxalate Form 5 before and after the stability experiment.

Figure 204:
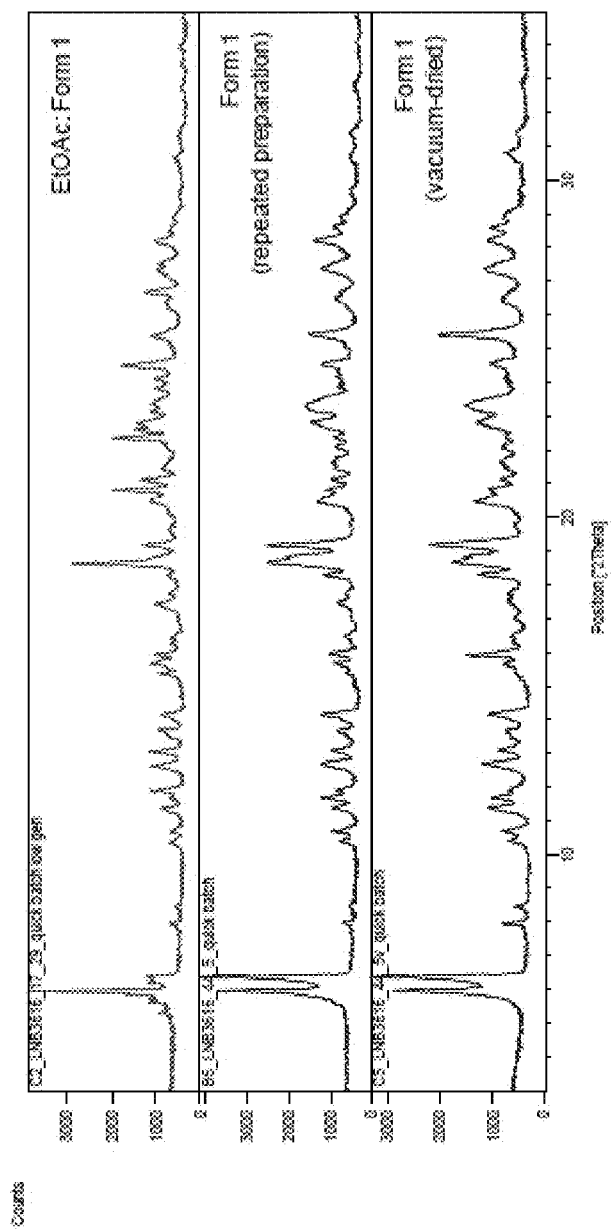

FIG. 204 sets forth XRPD patterns of maleate Form 1.

Figure 205:
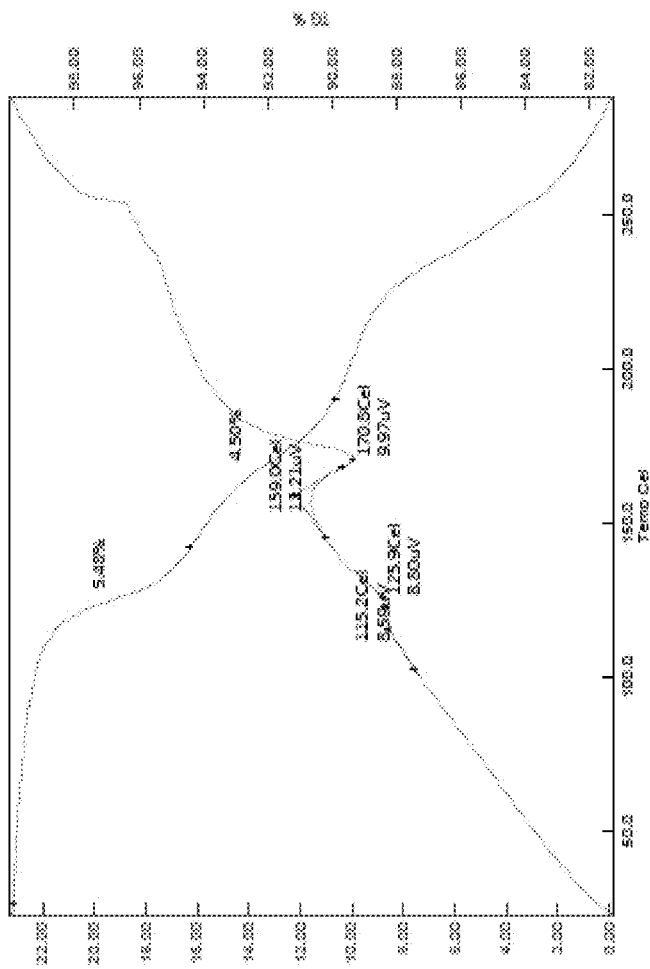

FIG. 205 sets forth a thermal analysis by TG/DTA of maleate Form 1 before drying under vacuum.

Figure 206:
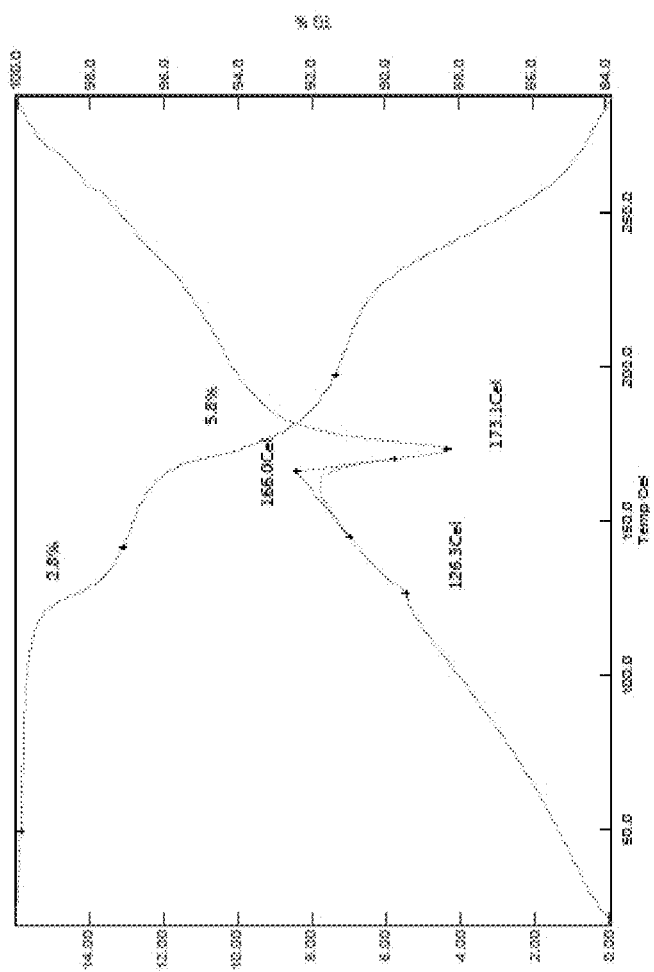

FIG. 206 sets forth a thermal analysis by TG/DTA of maleate Form 1 after drying under vacuum.

Figure 207A:
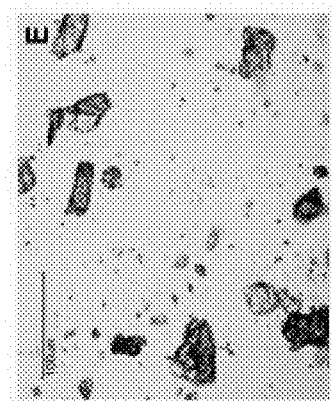

FIG. 207A sets forth PLM images of maleate Form 1 under non-polarized light.

Figure 207C:
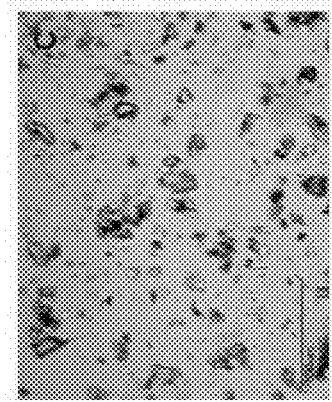
Figure 207E:
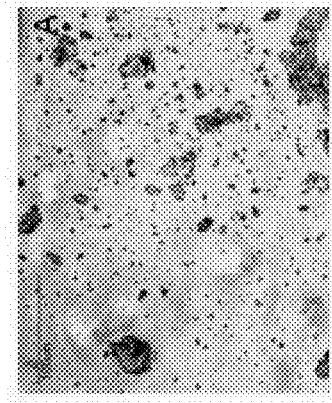
Figure 207B:
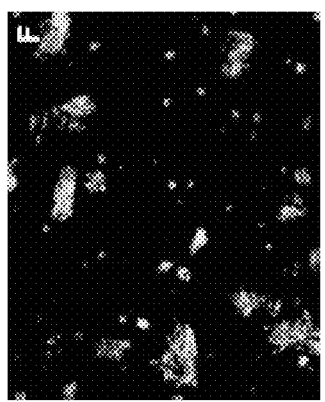

FIG. 207B sets forth PLM images of maleate Form 1 under polarized light.

FIG. 207C sets forth PLM images of maleate Form 1 under non-polarized light.

Figure 207D:
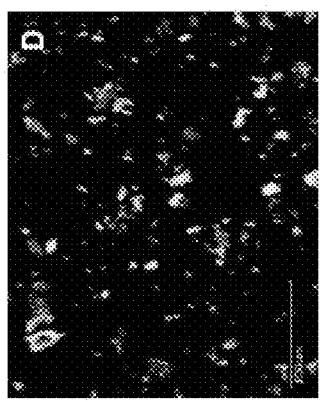

FIG. 207D sets forth PLM images of maleate Form 1 under polarized light.

FIG. 207E sets forth PLM images of maleate Form 1 after drying under vacuum under non-polarized light.

Figure 207F:
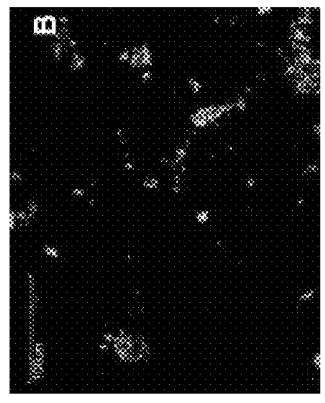

FIG. 207F sets forth PLM images of maleate Form 1 after drying under vacuum under polarized light.

Figure 208:
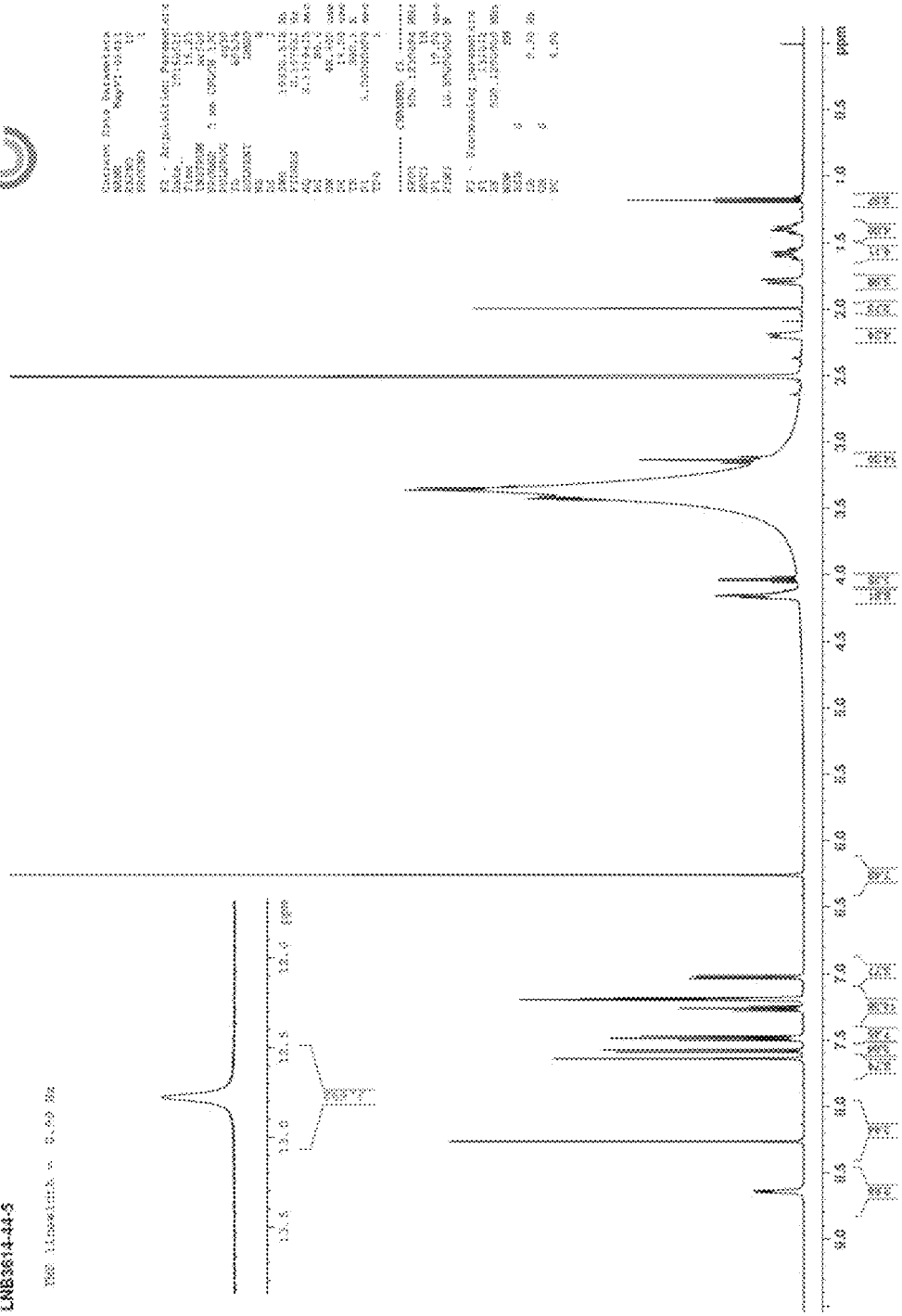

FIG. 208 sets forth a $^1$H NMR spectroscopic analysis of maleate Form 1.

Figure 209:
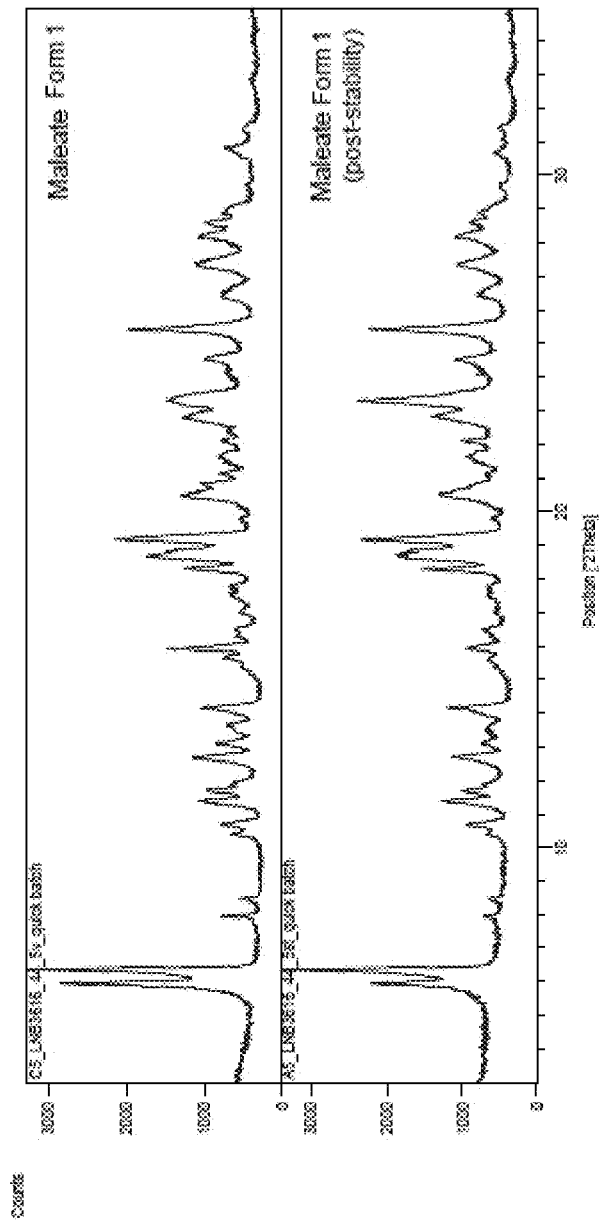

FIG. 209 sets forth XRPD patterns of maleate Form 1 before and after the stability experiment.

Figure 210:
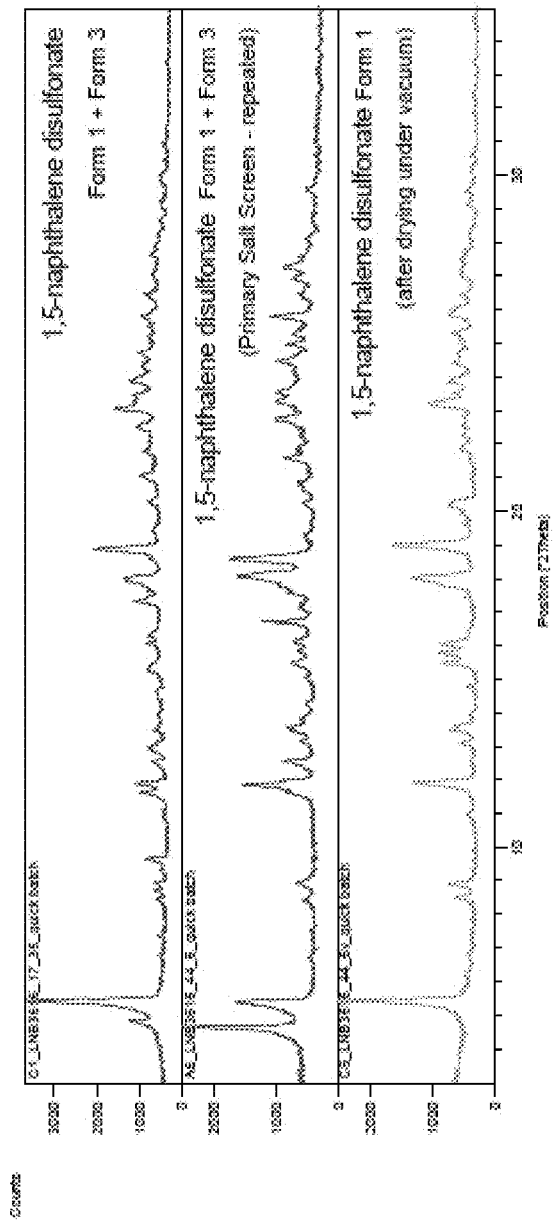

FIG. 210 sets forth XRPD patterns of 1,5-naphthalene disulfonate Form 1 and Form 3.

Figure 211:
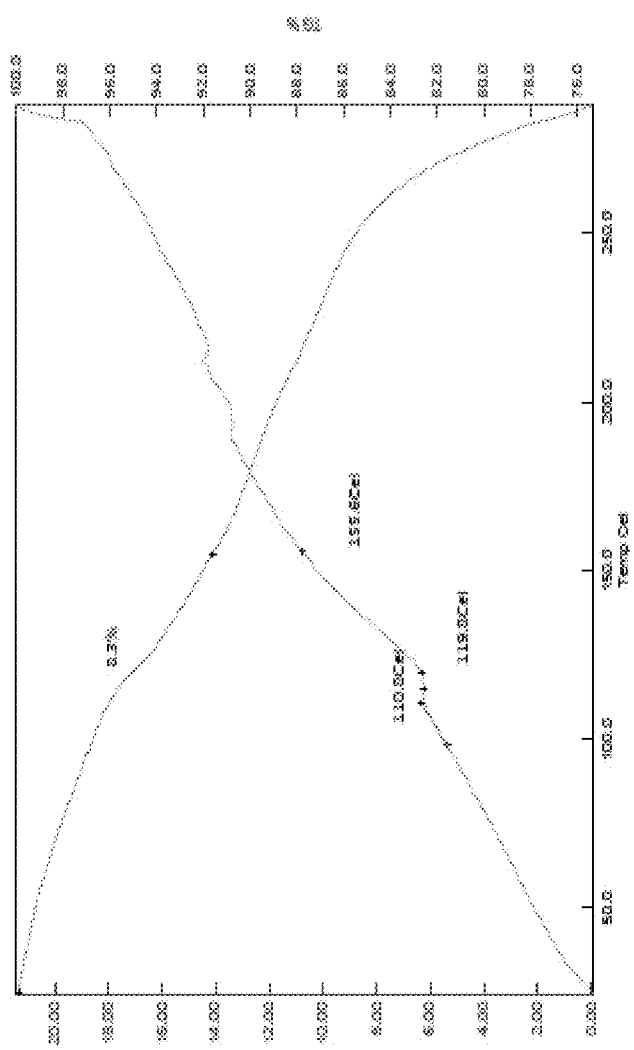

FIG. 211 sets forth a thermal analysis by TG/DTA of 1,5-naphthalene disulfonate Form 1 and Form 3 mixture.

Figure 212:
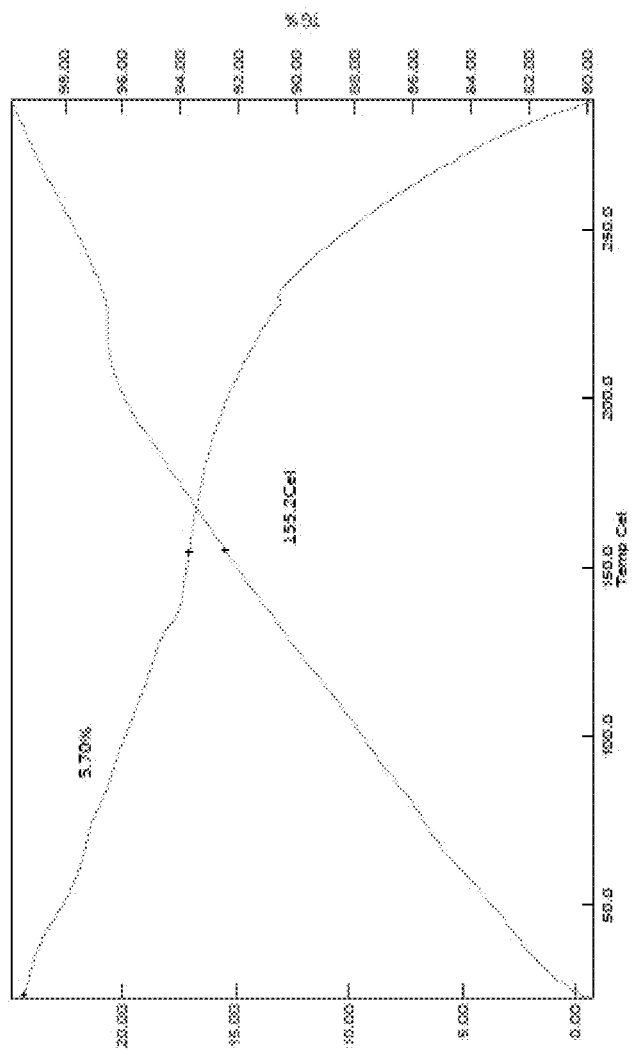

FIG. 212 sets forth a thermal analysis by TG/DTA of 1,5-naphthalene disulfonate Form 1.

FIG. 213A sets forth PLM images of 1,5-naphthalene disulfonate Form 1 and Form 3 mixture under non-polarized light.

FIG. 213B sets forth PLM images of 1,5-naphthalene disulfonate Form 1 and Form 3 mixture under polarized light.

FIG. 213C sets forth PLM images of 1,5-naphthalene disulfonate Form 1 and Form 3 mixture under non-polarized light.

FIG. 213D sets forth PLM images of 1,5-naphthalene disulfonate Form 1 and Form 3 mixture under polarized light.

FIG. 213E sets forth PLM images of 1,5-naphthalene disulfonate Form 1 and Form 3 mixture after drying under vacuum under non-polarized light.

FIG. 213F sets forth PLM images of 1,5-naphthalene disulfonate Form 1 and Form 3 mixture after drying under vacuum under polarized light.

Figure 214:
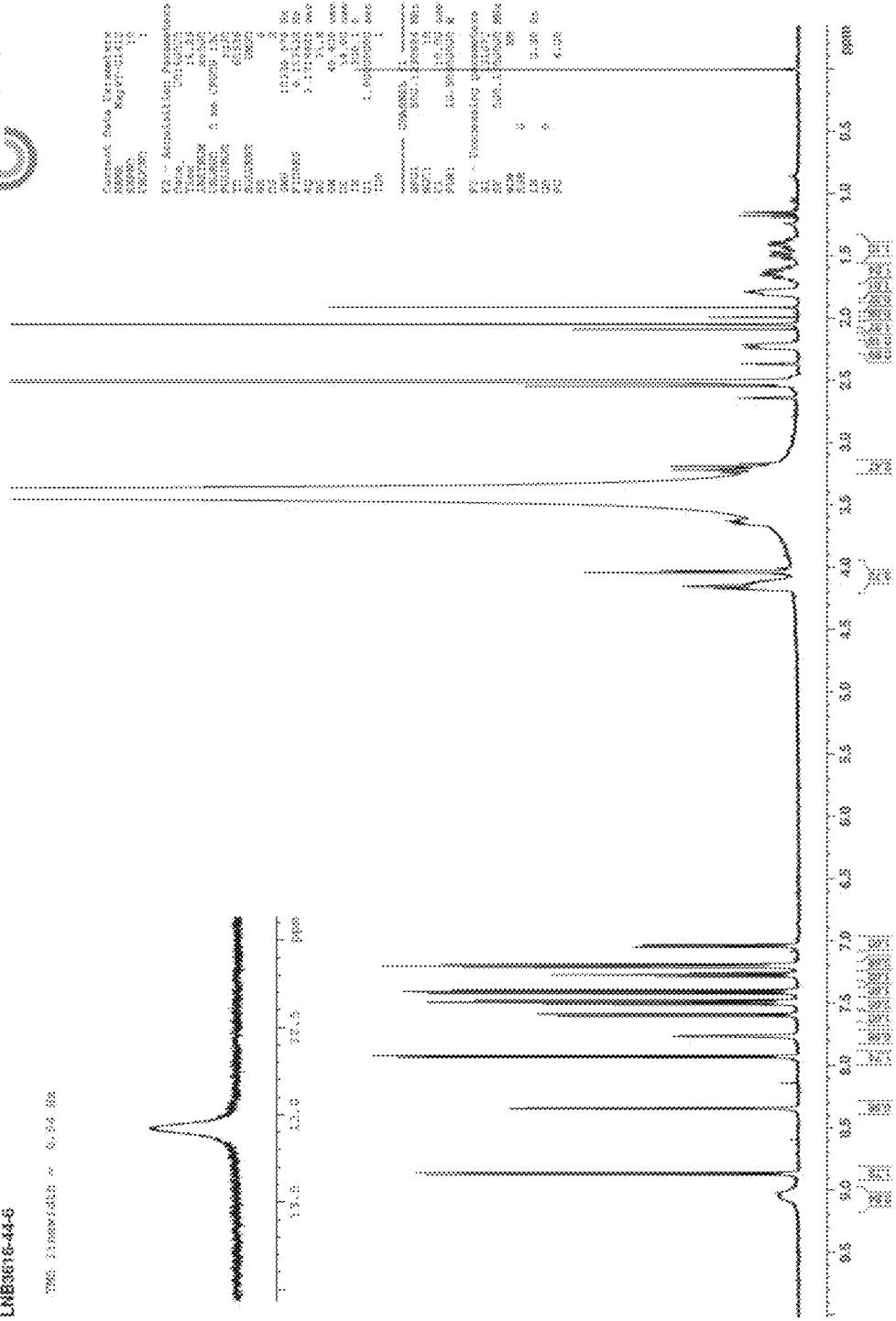

FIG. 214 sets forth a $^1$H NMR spectroscopic analysis of 1,5-naphthalene disulfonate Form 1.

Figure 215:
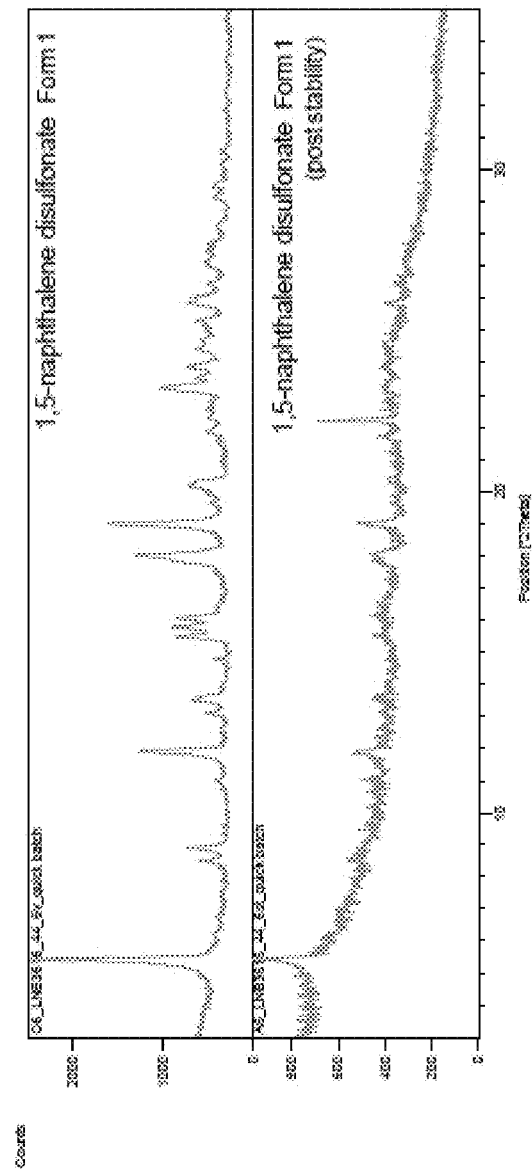

FIG. 215 sets forth XRPD patterns of 1,5-naphthalene disulfonate Form 1 before and after the stability experiment.

Figure 216:
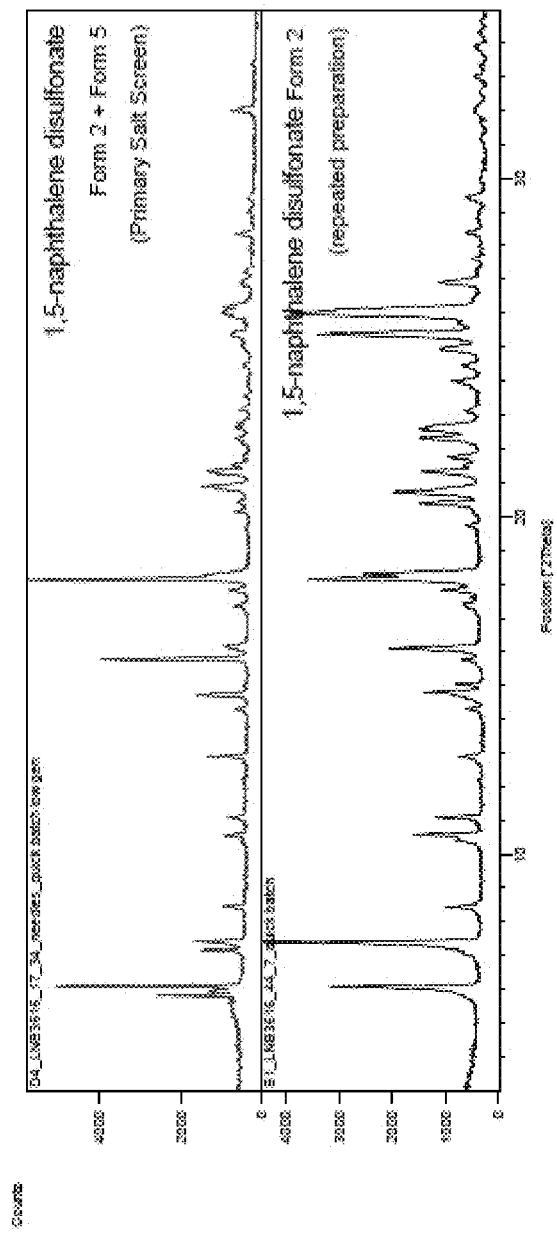

FIG. 216 sets forth XRPD patterns of 1,5-naphthalene disulfonate Form 2 and Form 5 mixture and Form 2.

Figure 217:
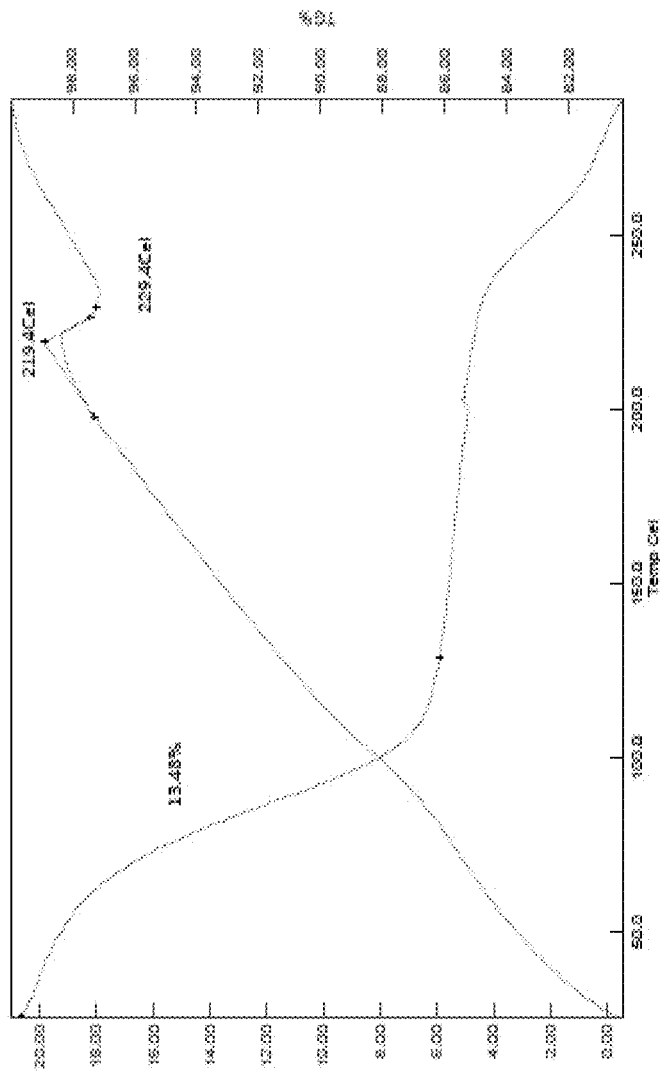

FIG. 217 sets forth a thermal analysis by TG/DTA of 1,5-naphthalene disulfonate Form 2 and Form 5.

Figure 218B:
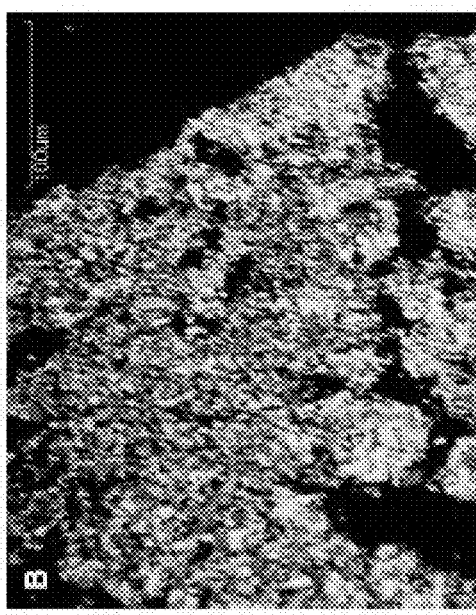
Figure 218A:

FIG. 218A sets forth PLM images of 1,5-naphthalene disulfonate Form 2 under non-polarized light.

FIG. 218B sets forth PLM images of 1,5-naphthalene disulfonate Form 2 under polarized light.

Figure 219:
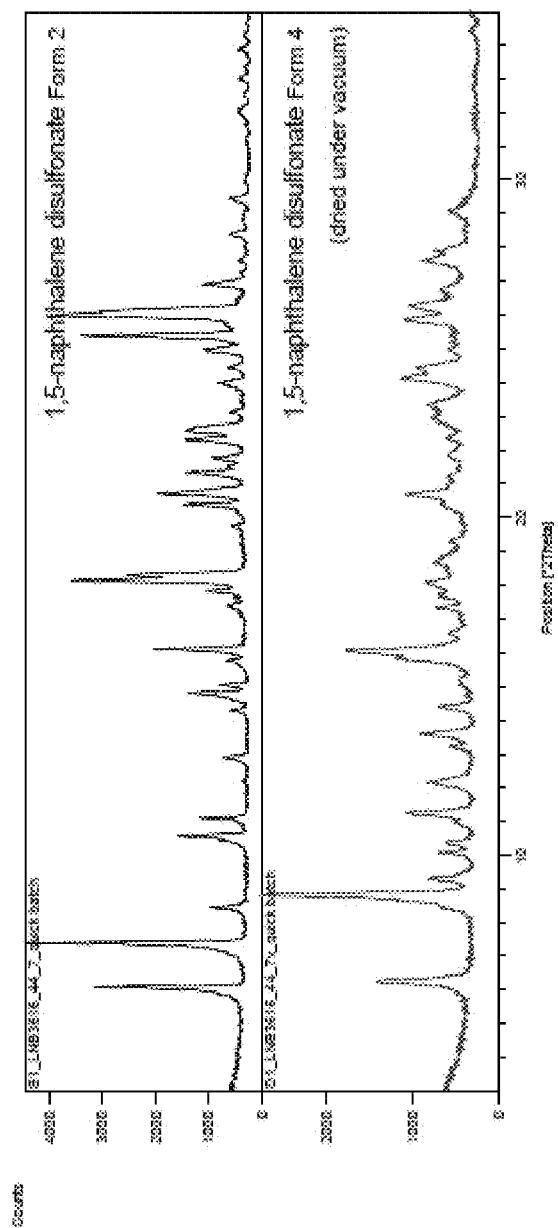

FIG. 219 sets forth XRPD patterns of 1,5-naphthalene disulfonate Form 2 and Form 4.

Figure 220:
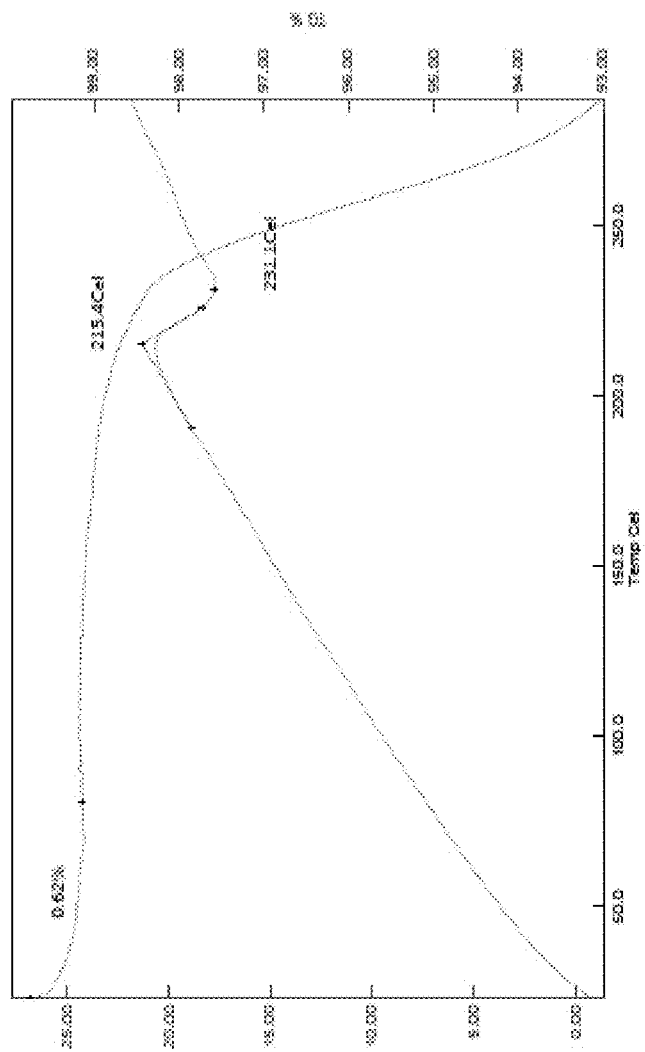

FIG. 220 sets forth a thermal analysis by TG/DTA of 1,5-naphthalene disulfonate Form 4.

Figure 221B:

Figure 221A:

FIG. 221A sets forth PLM images of 1,5-naphthalene disulfonate Form 4 under non-polarized light.

FIG. 221B sets forth PLM images of 1,5-naphthalene disulfonate Form 4 under polarized light.

Figure 222:
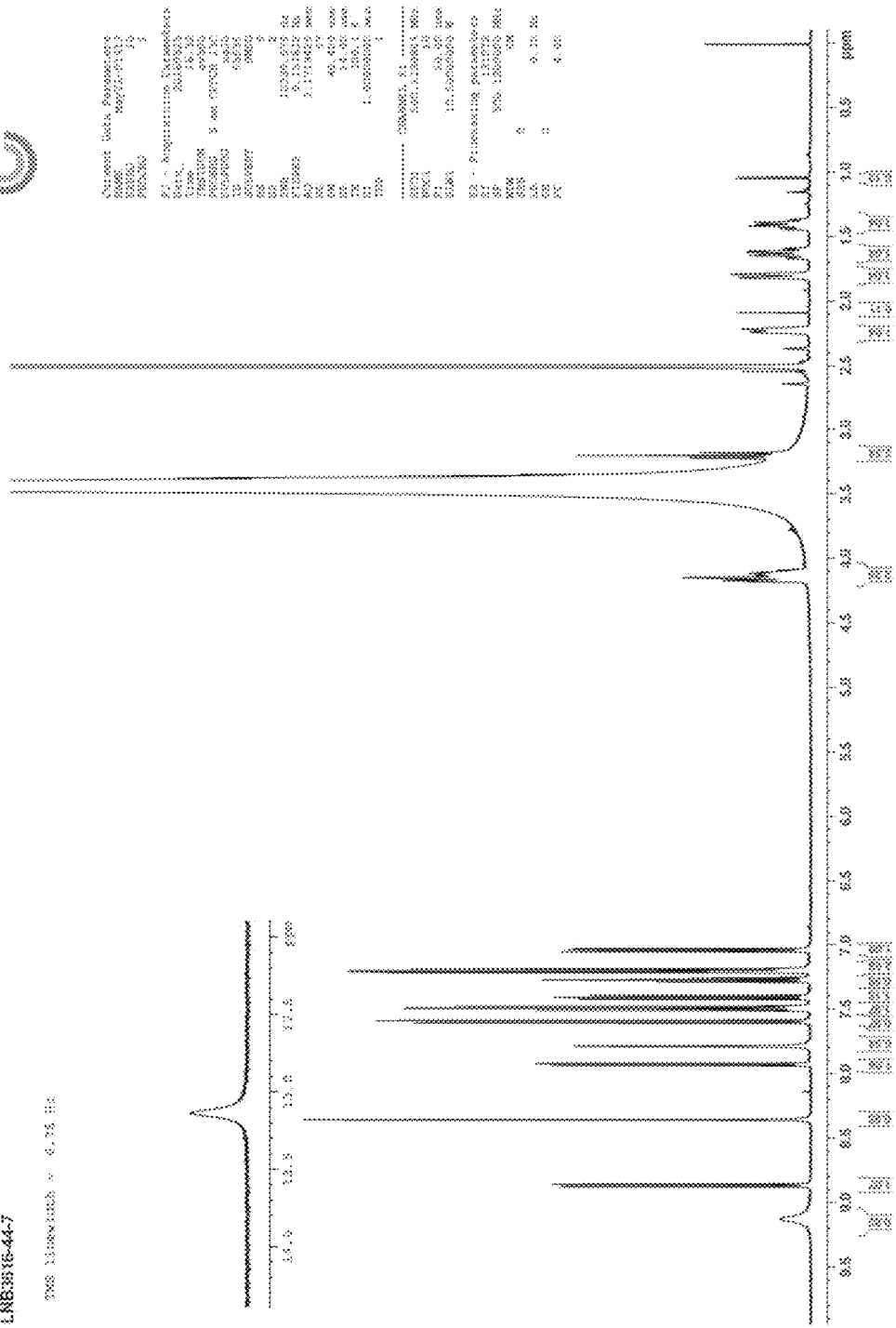

FIG. 222 sets forth a $^1$H NMR spectroscopic analysis of 1,5-naphthalene disulfonate Form 4.

Figure 223:
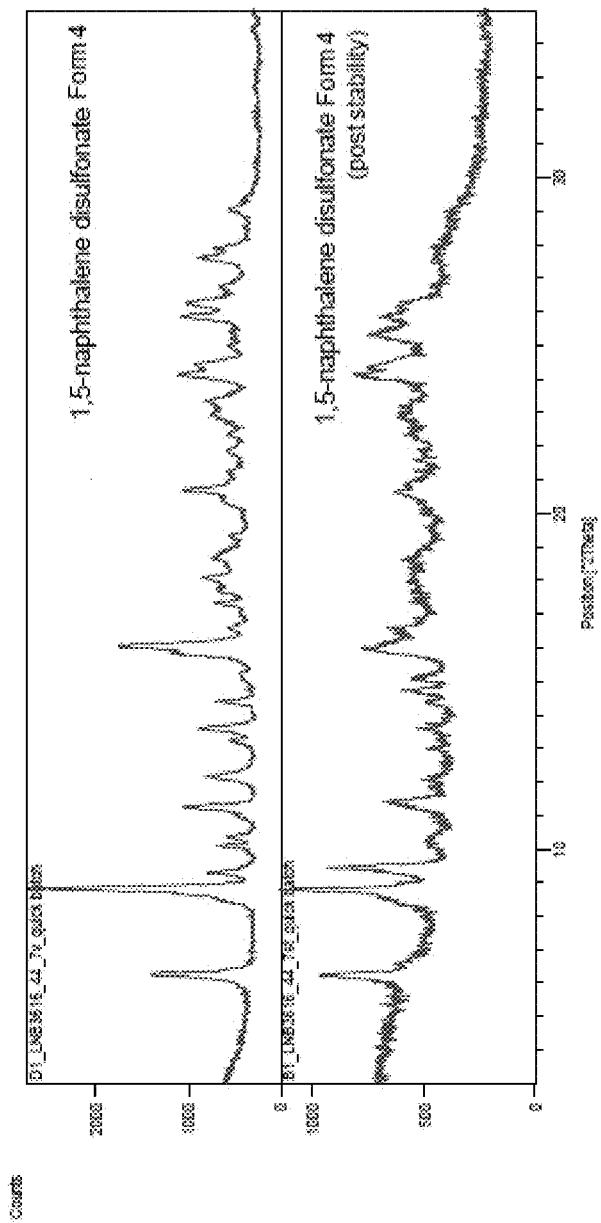

FIG. 223 sets forth XRPD patterns of 1,5-naphthalene disulfonate Form 4 before and after the stability experiment.

Figure 224:
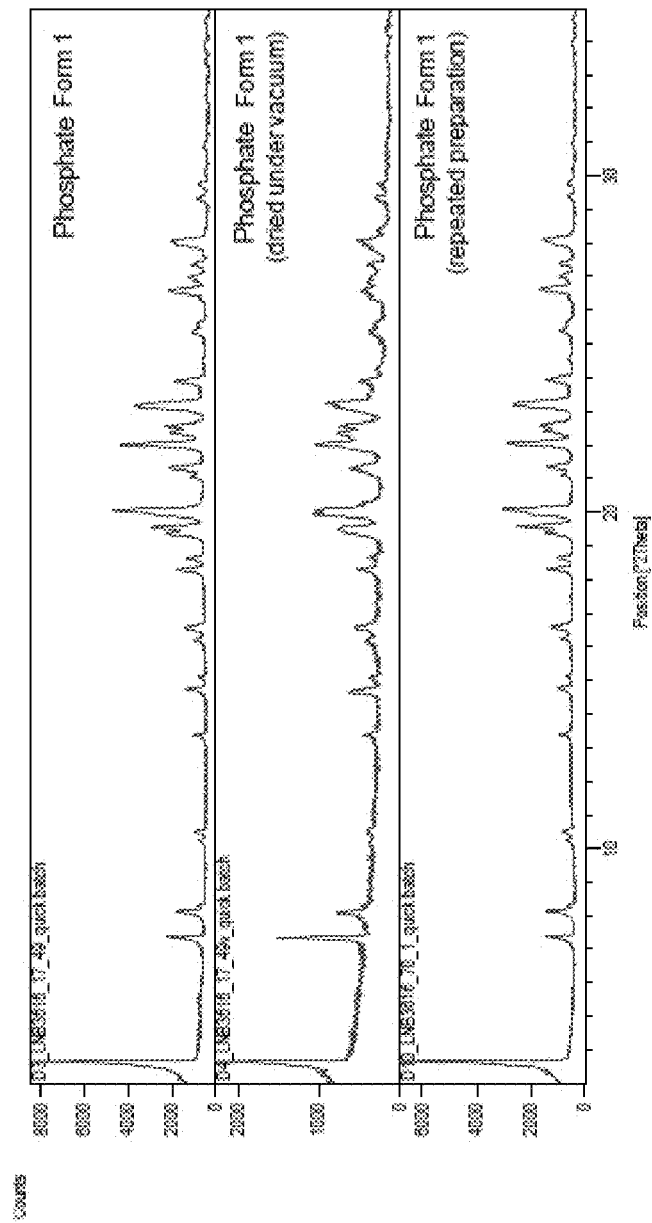

FIG. 224 sets forth XRPD patterns of phosphate Form 1.

Figure 225:
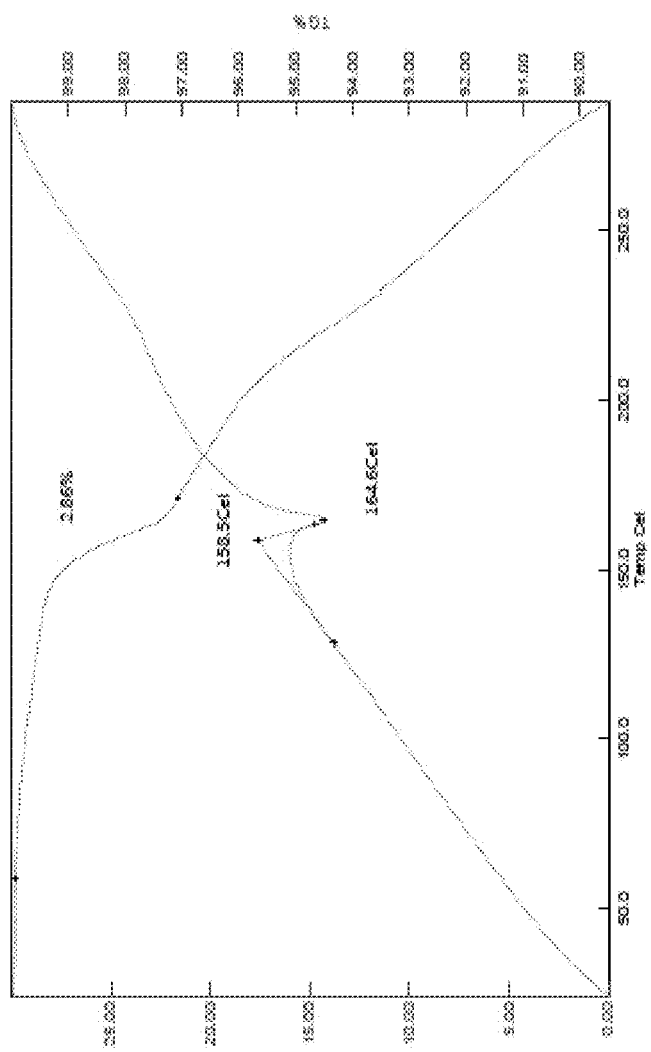

FIG. 225 sets forth a thermal analysis by TG/DTA of phosphate Form 1.

Figure 226:
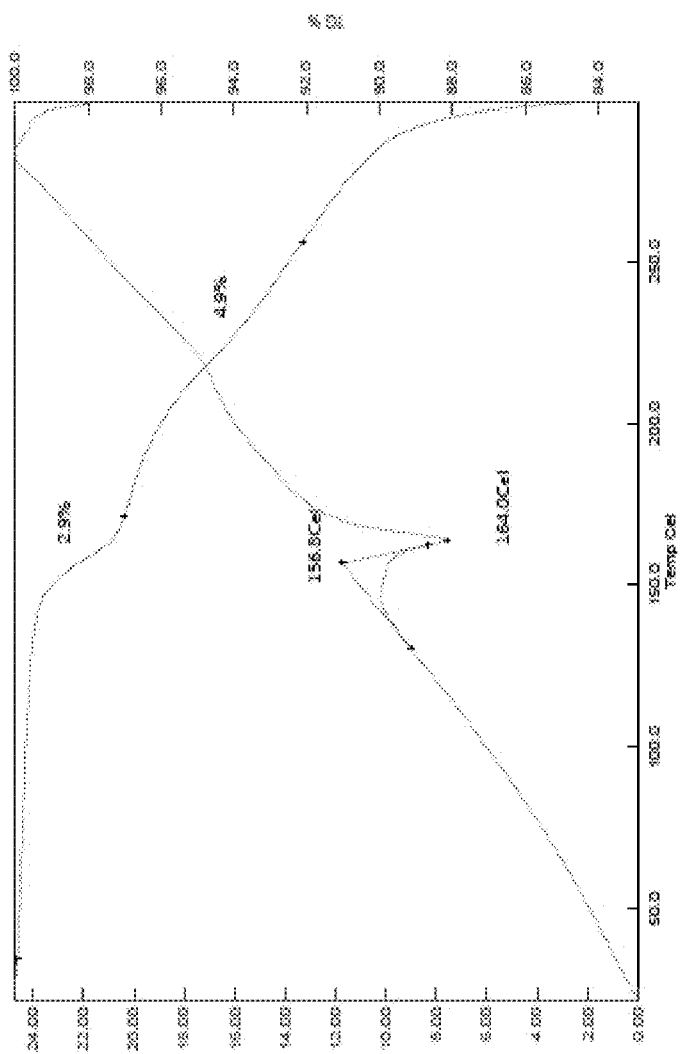

FIG. 226 sets forth a thermal analysis by TG/DTA of phosphate Form 1 after drying under vacuum for 24 hours.

Figure 227:
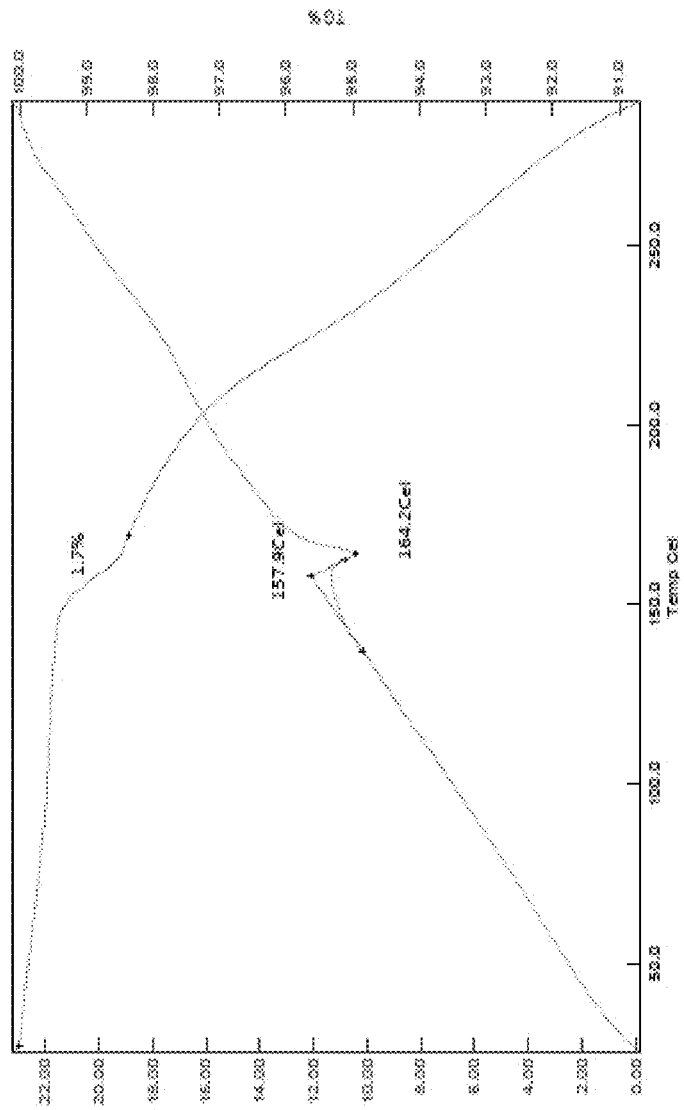

FIG. 227 sets forth a thermal analysis by TG/DTA of phosphate Form 1 after drying under vacuum for 72 hours.

Figure 228C:
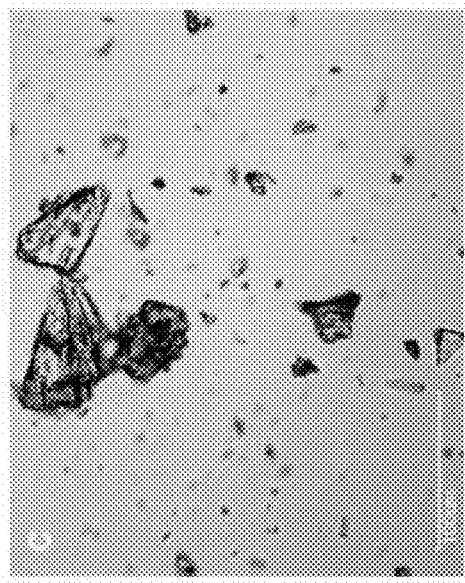
Figure 228D:
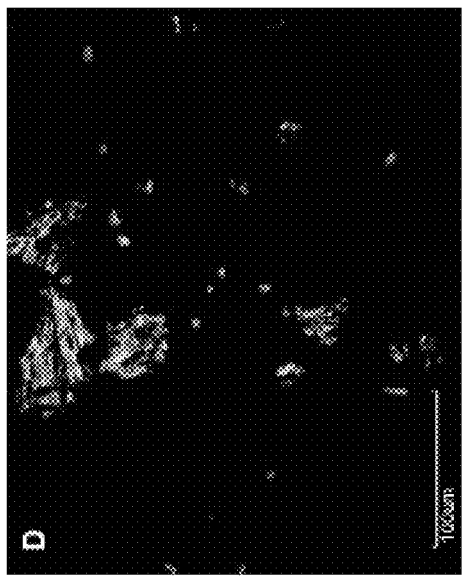
Figure 228A:
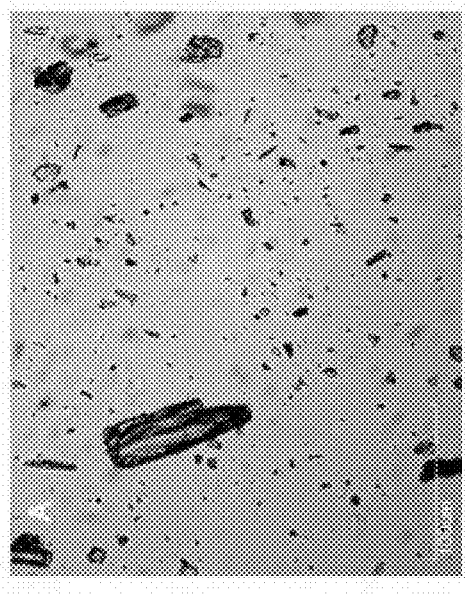

FIG. 228A sets forth PLM images of phosphate Form 1 before drying under vacuum under non-polarised light.

Figure 228B:
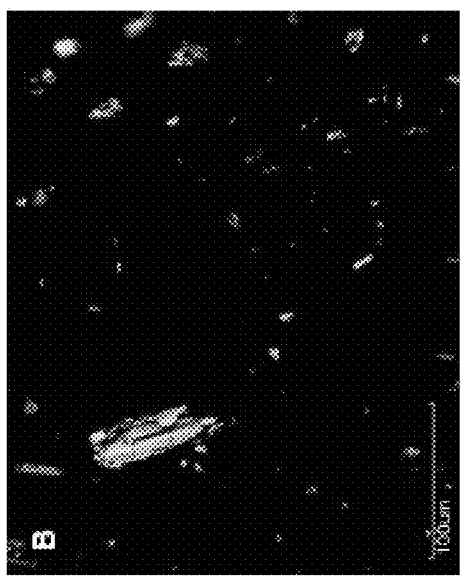

FIG. 228B sets forth PLM images of phosphate Form 1 before drying under polarised light.

FIG. 228C sets forth PLM images of phosphate Form 1 after drying under vacuum under nonpolarised light.

FIG. 228D sets forth PLM images of phosphate Form 1 after drying under vacuum under polarised light (D).

Figure 229:
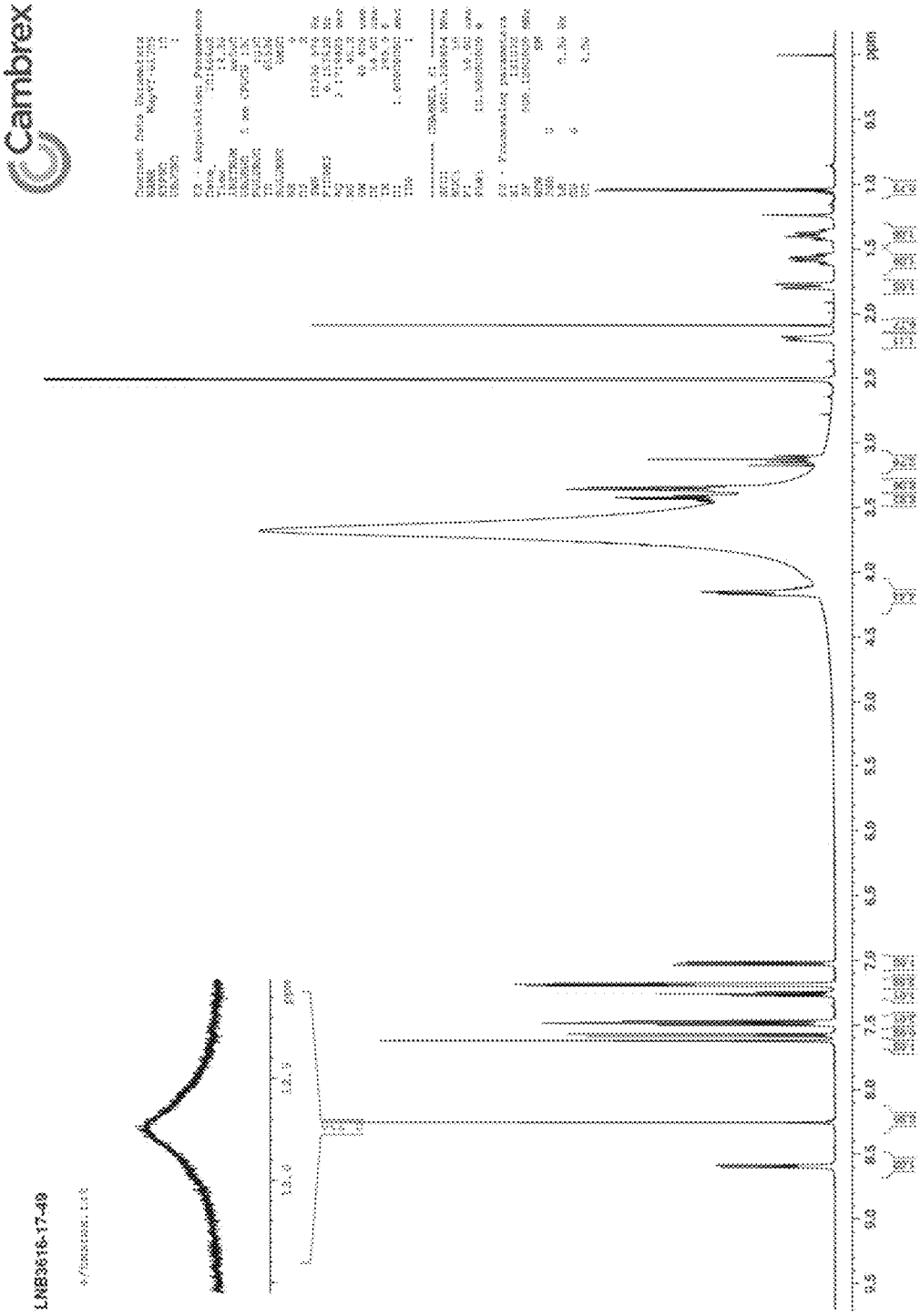

FIG. 229 sets forth a $^1$H NMR spectroscopic analysis of phosphate Form 1.

Figure 230:
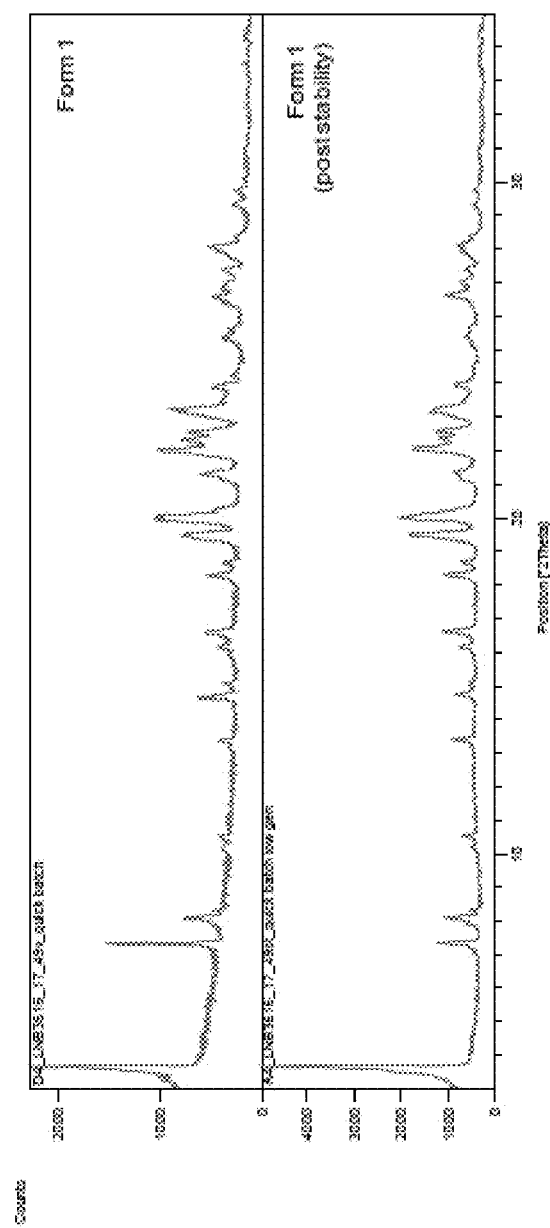

FIG. 230 sets forth XRPD patterns of phosphate Form 1 before and after the stability experiment.

Figure 231:
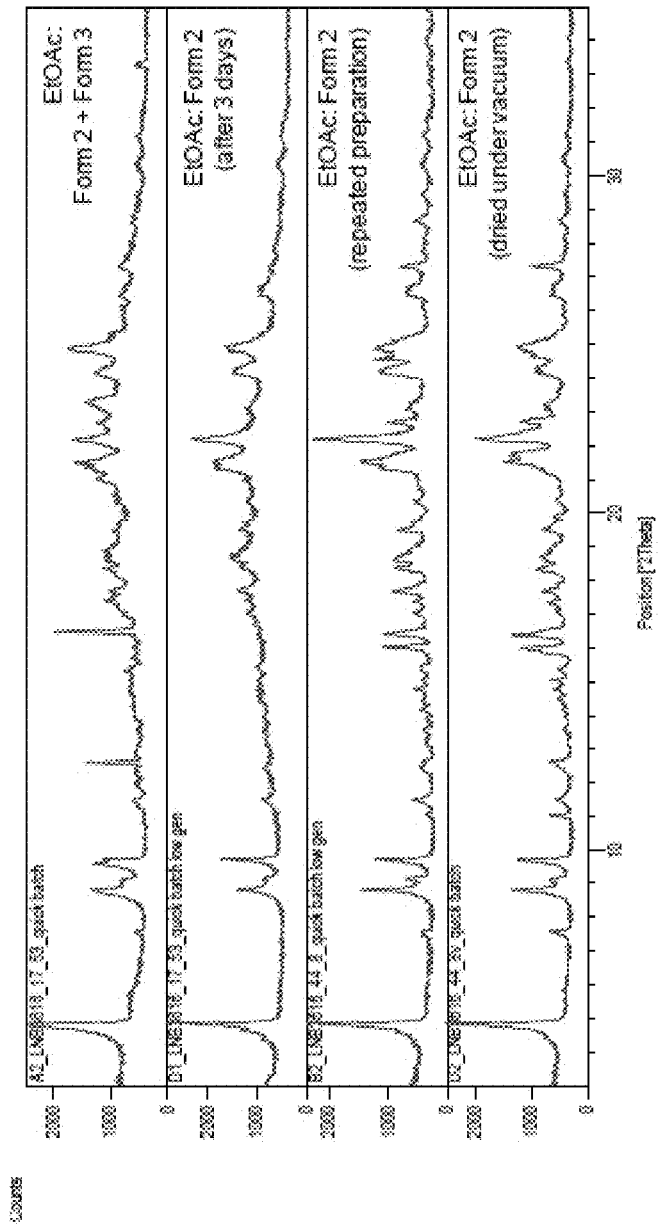

FIG. 231 sets forth XRPD patterns of phosphate Form 2 and Form 3.

Figure 232:
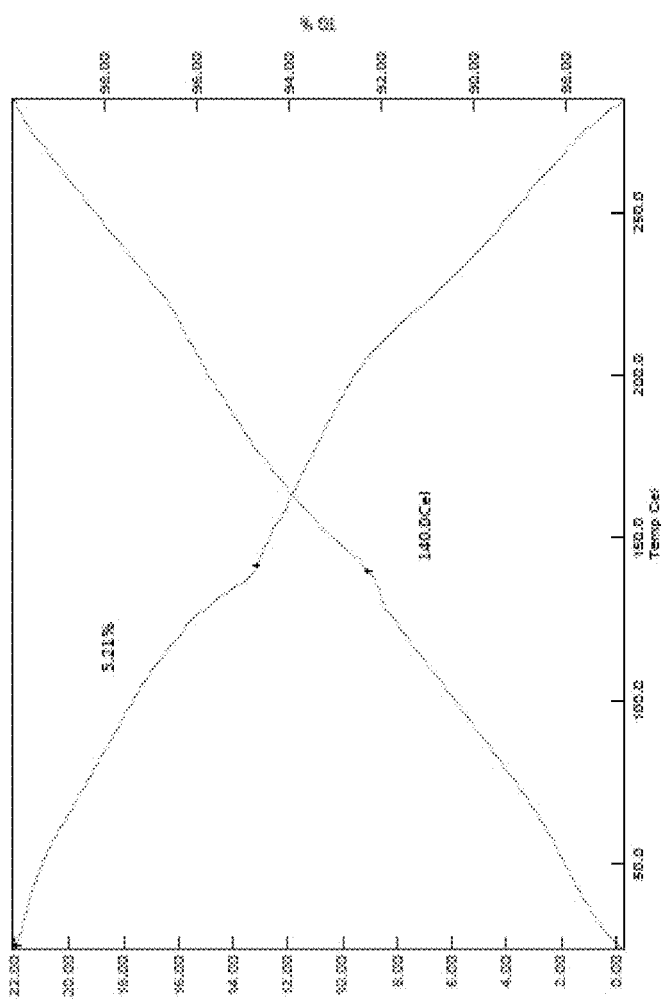

FIG. 232 sets forth a thermal analysis by TG/DTA of phosphate Form 2.

Figure 233:
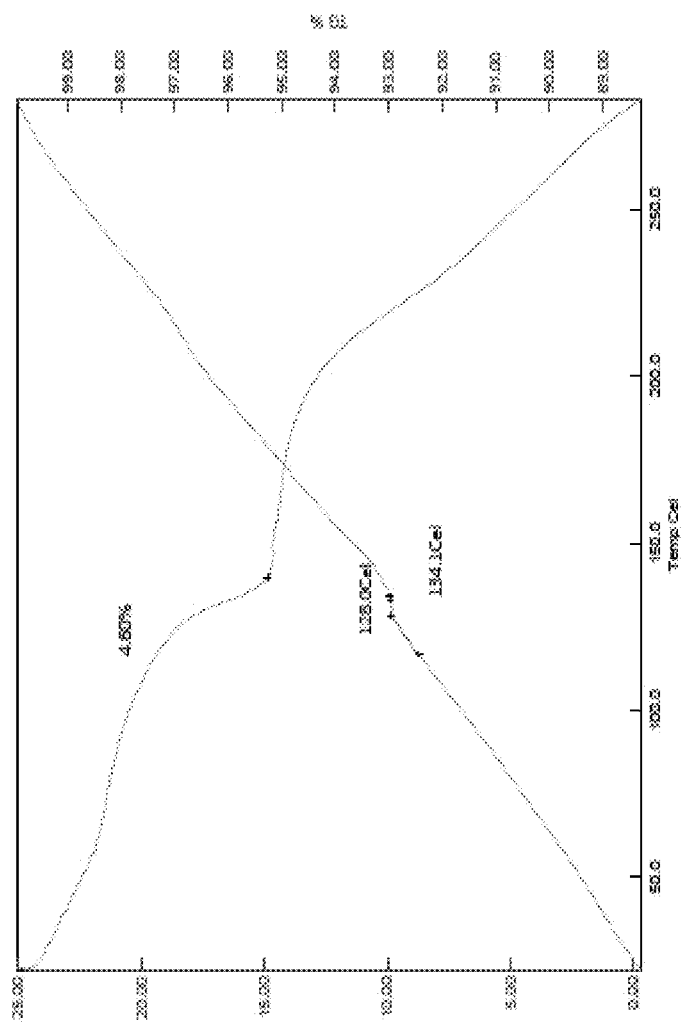

FIG. 233 sets forth a thermal analysis by TG/DTA of phosphate Form 2 after drying under vacuum for 24 hours.

Figure 234A:
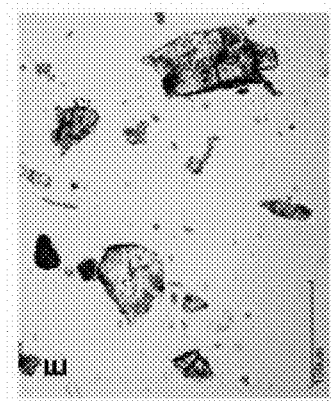

FIG. 234A sets forth PLM images of phosphate Form 2 under non-polarized light.

Figure 234C:
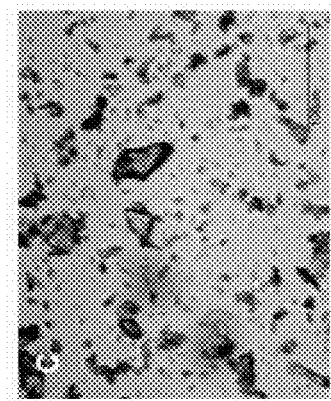
Figure 234E:
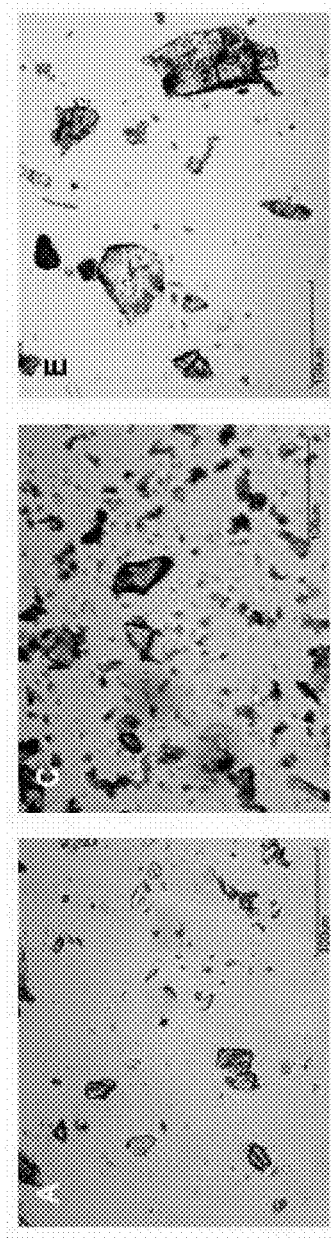
Figure 234B:

FIG. 234B sets forth PLM images of phosphate Form 2 under polarized light.

FIG. 234C sets forth PLM images of phosphate Form 2 under non-polarized light.

Figure 234D:

FIG. 234D sets forth PLM images of phosphate Form 2 under polarized light.

FIG. 234E sets forth PLM images phosphate Form 2 after drying under vacuum under non-polarized light.

Figure 234F:

FIG. 234F sets forth PLM images of phosphate Form 2 after drying under vacuum under polarized light.

Figure 235:
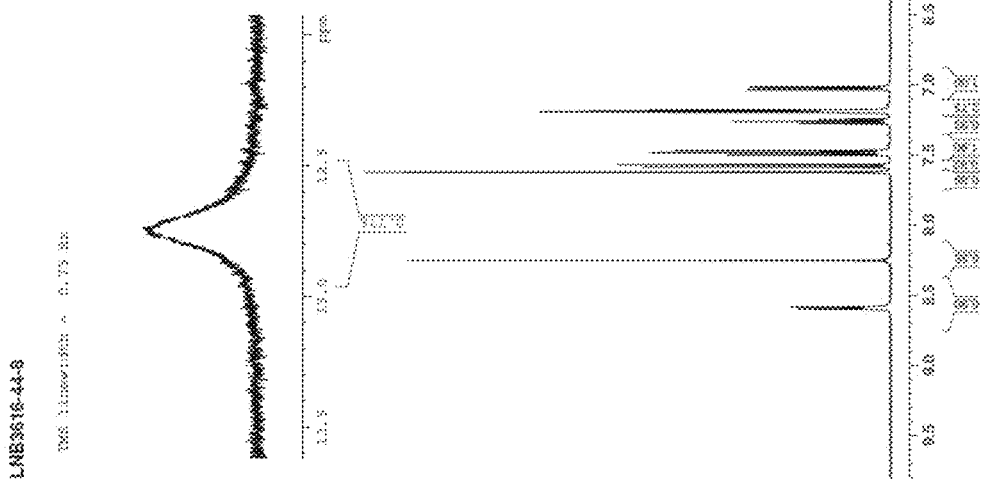

FIG. 235 sets forth a $^1$H NMR spectroscopic analysis of phosphate Form 2.

Figure 236:
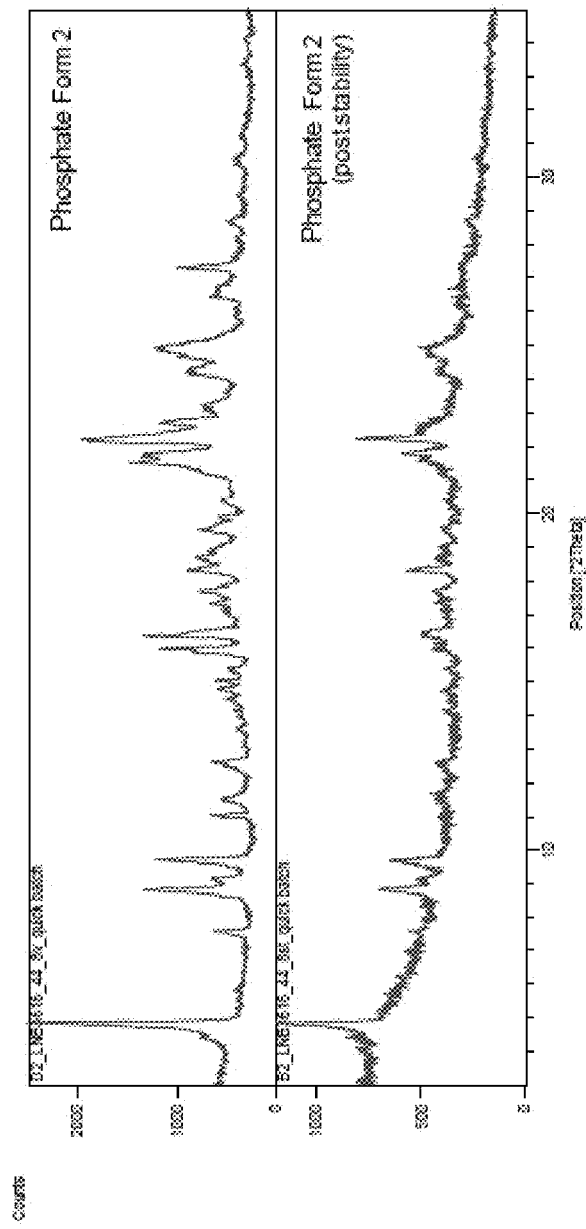

FIG. 236 sets forth XRPD patterns of phosphate Form 2 before and after the stability experiment.

Figure 237:
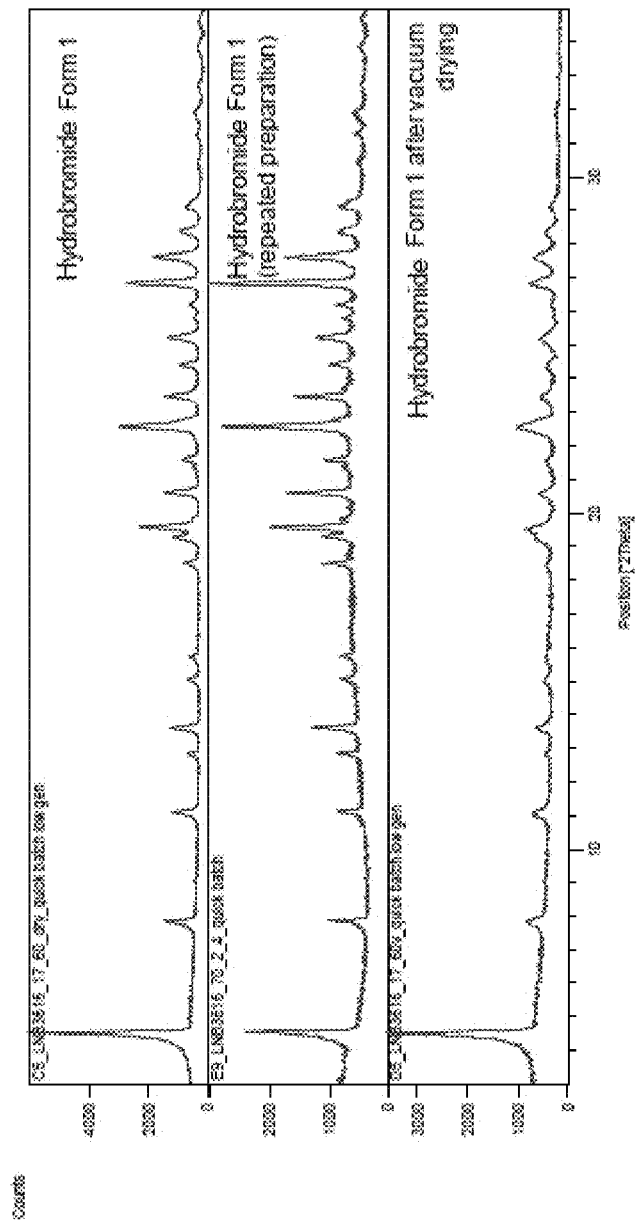

FIG. 237 sets forth XRPD patterns of hydrobromide Form 1.

Figure 238:
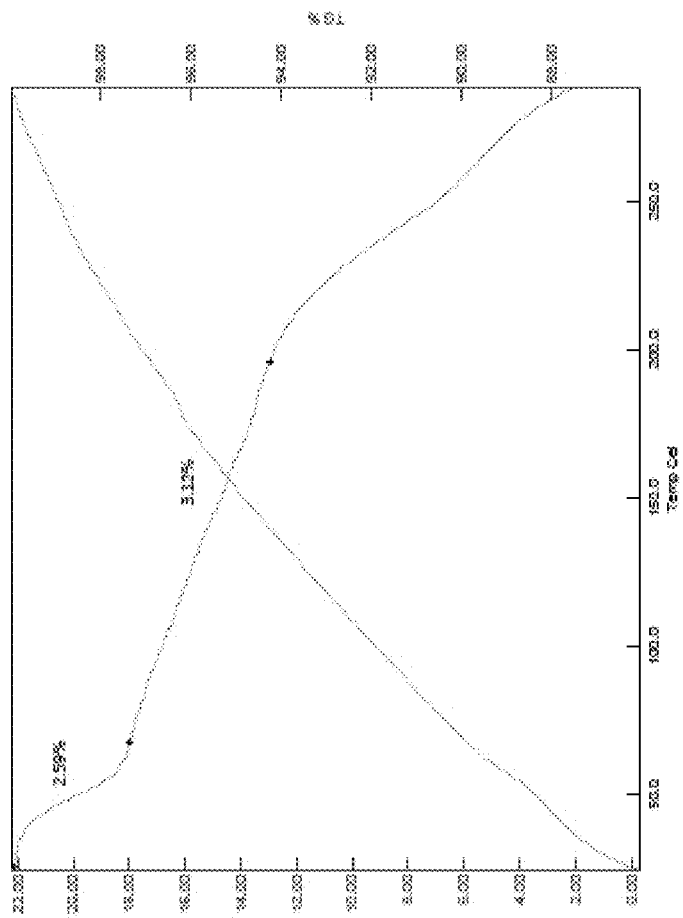

FIG. 238 sets forth a thermal analysis by TG/DTA of hydrobromide Form 1.

Figure 239:
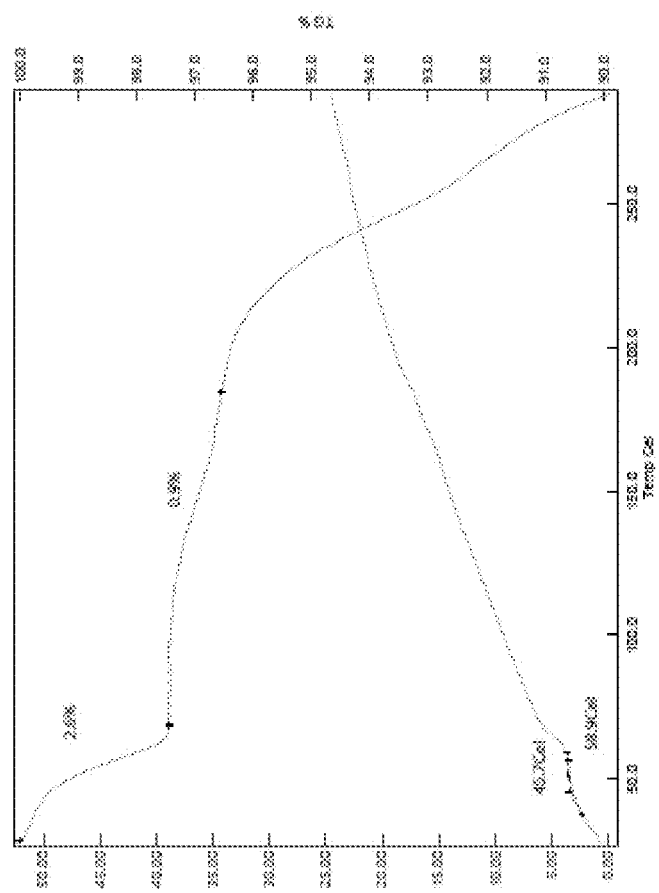

FIG. 239 sets forth a thermal analysis by TG/DTA of hydrobromide Form 1 after drying under vacuum for 24 hours.

Figure 240:
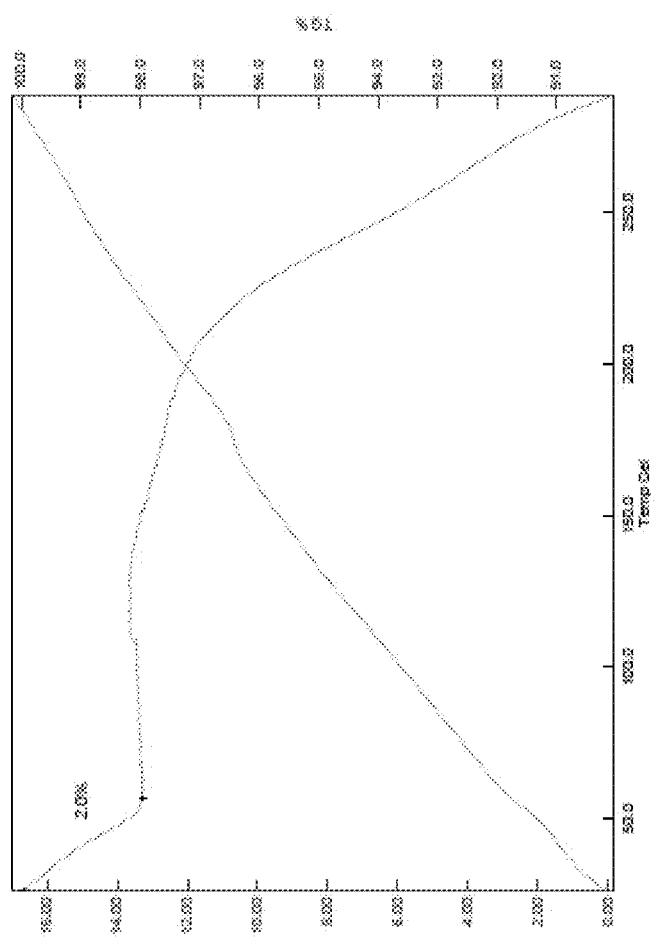

FIG. 240 sets forth a thermal analysis by TG/DTA of hydrobromide Form 1 after drying under vacuum for 72 hours.

Figure 241C:
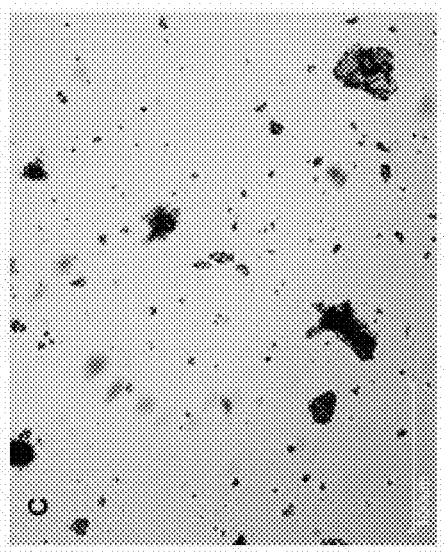
Figure 241A:
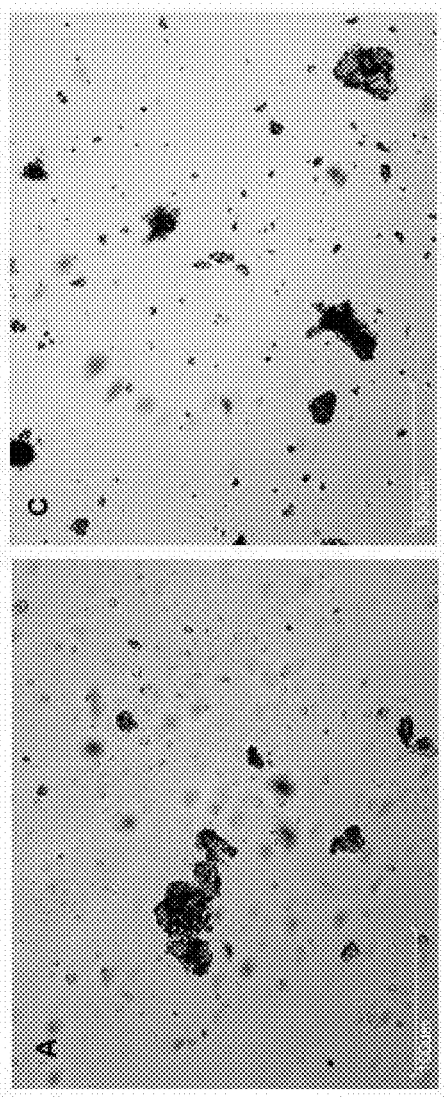

FIG. 241A sets forth PLM images of hydrobromide Form 1 before drying under vacuum under non-polarized light.

Figure 241D:
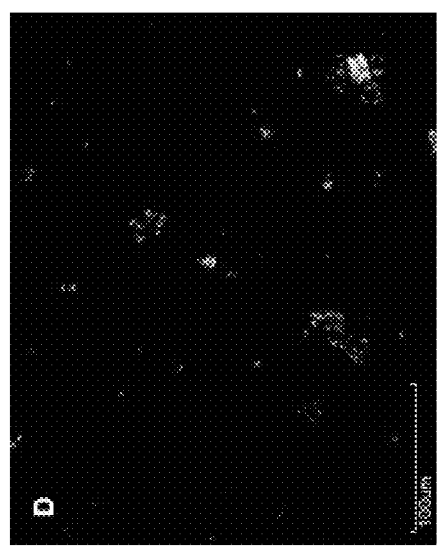
Figure 241B:
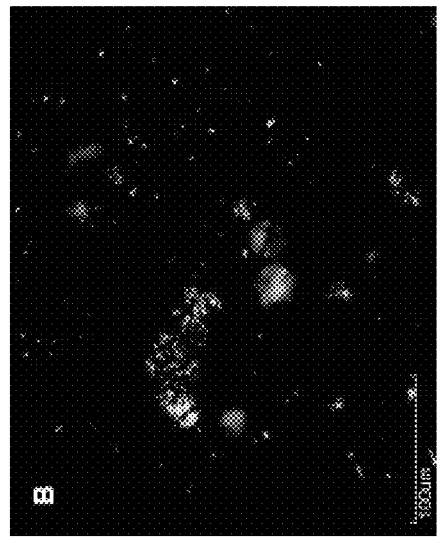

FIG. 241B sets forth PLM images of hydrobromide Form 1 before drying under polarised light.

FIG. 241C sets forth PLM images of hydrobromide Form 1 after drying under vacuum under nonpolarised light.

FIG. 241D sets forth PLM images of hydrobromide Form 1 after drying under vacuum under polarised light.

Figure 242:
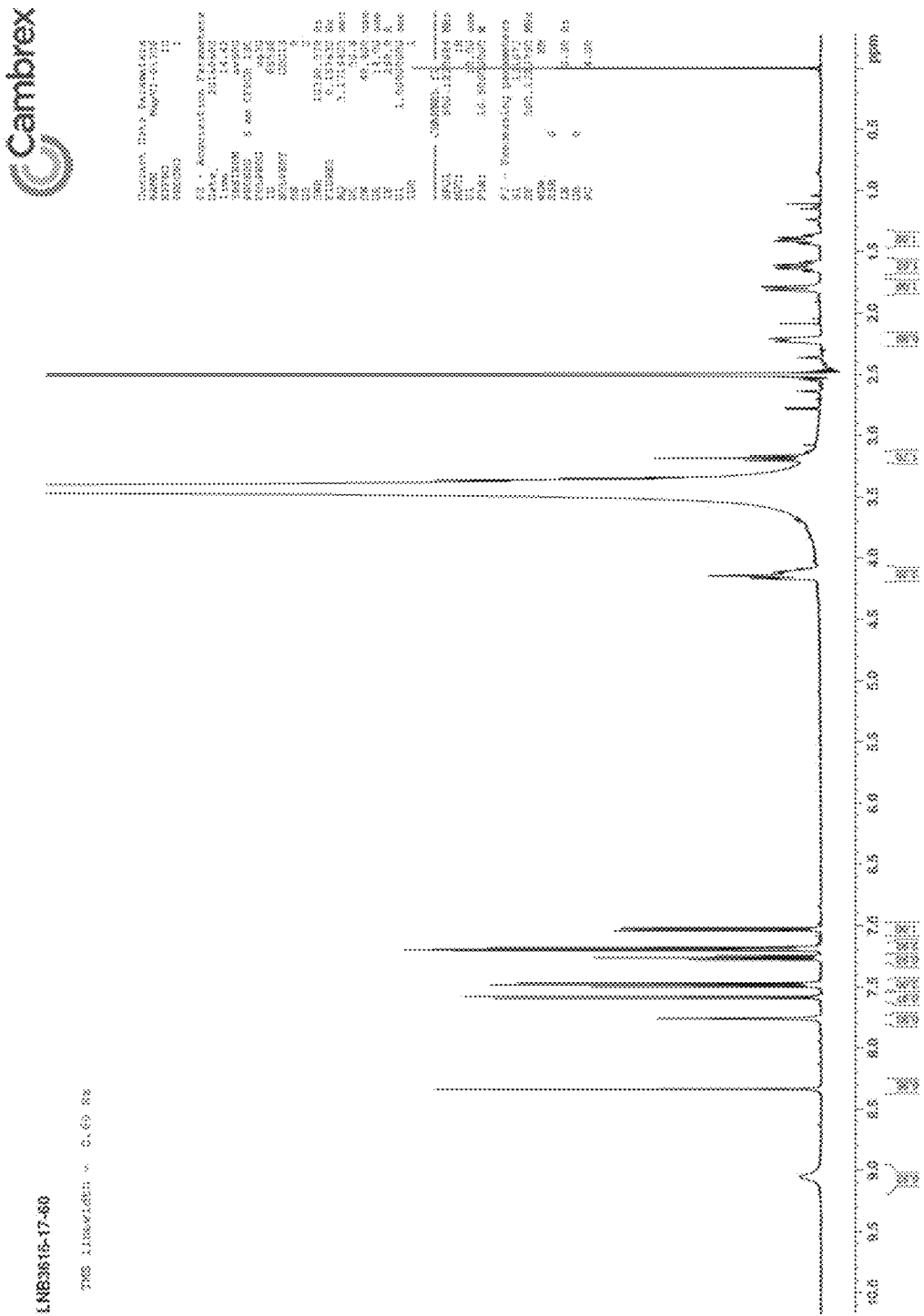

FIG. 242 sets forth a $^1$H NMR spectroscopic analysis of hydrobromide Form 1.

Figure 243:
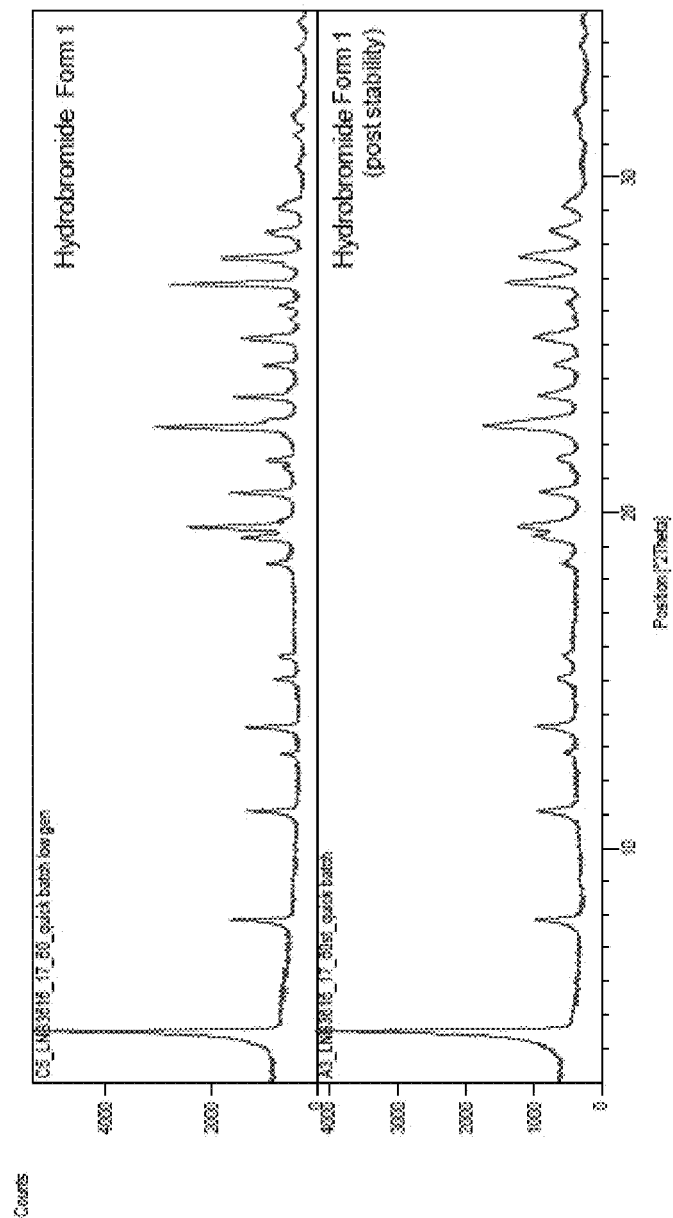

FIG. 243 sets forth XRPD patterns of hydrobromide Form 1 before and after the stability experiment.

Figure 244:
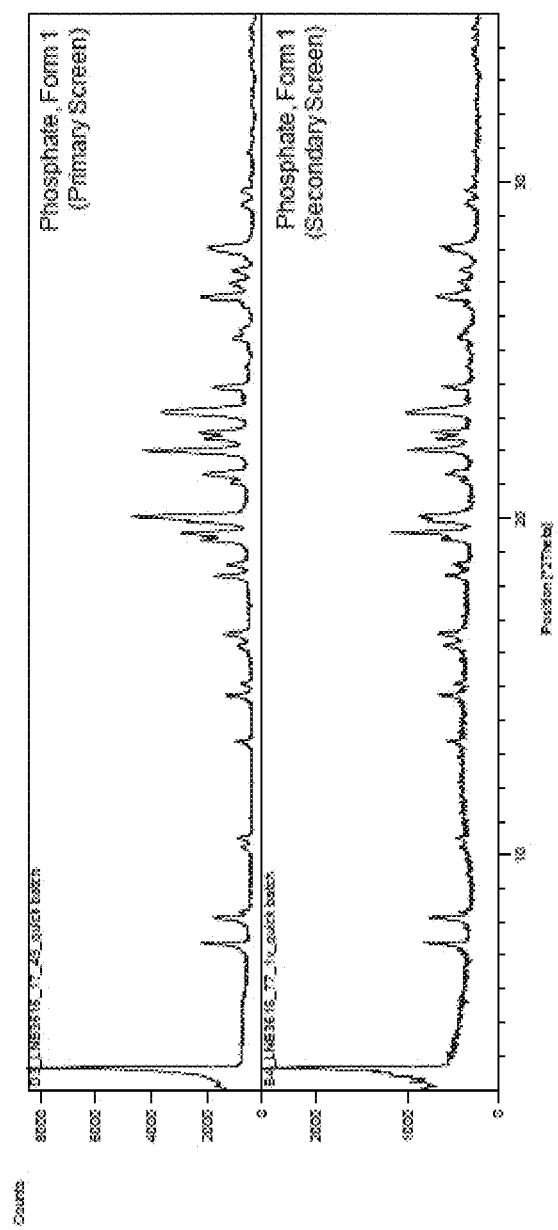

FIG. 244 sets forth XRPD patterns of phosphate Form 1 obtained from 500 mg scale-up.

Figure 245B:
Figure 245A:
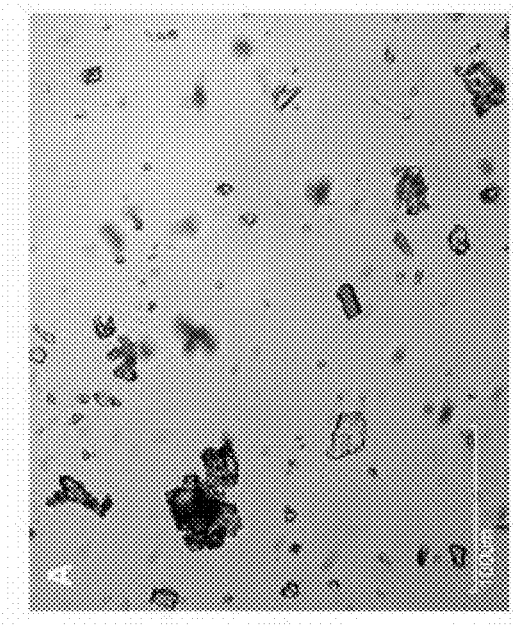

FIG. 245A sets forth PLM images of phosphate Form 1 obtained from 500 mg scale-up under non-polarized light.

FIG. 245B sets forth PLM images of phosphate Form 1 obtained from 500 mg scale-up under polarized light.

Figure 246:
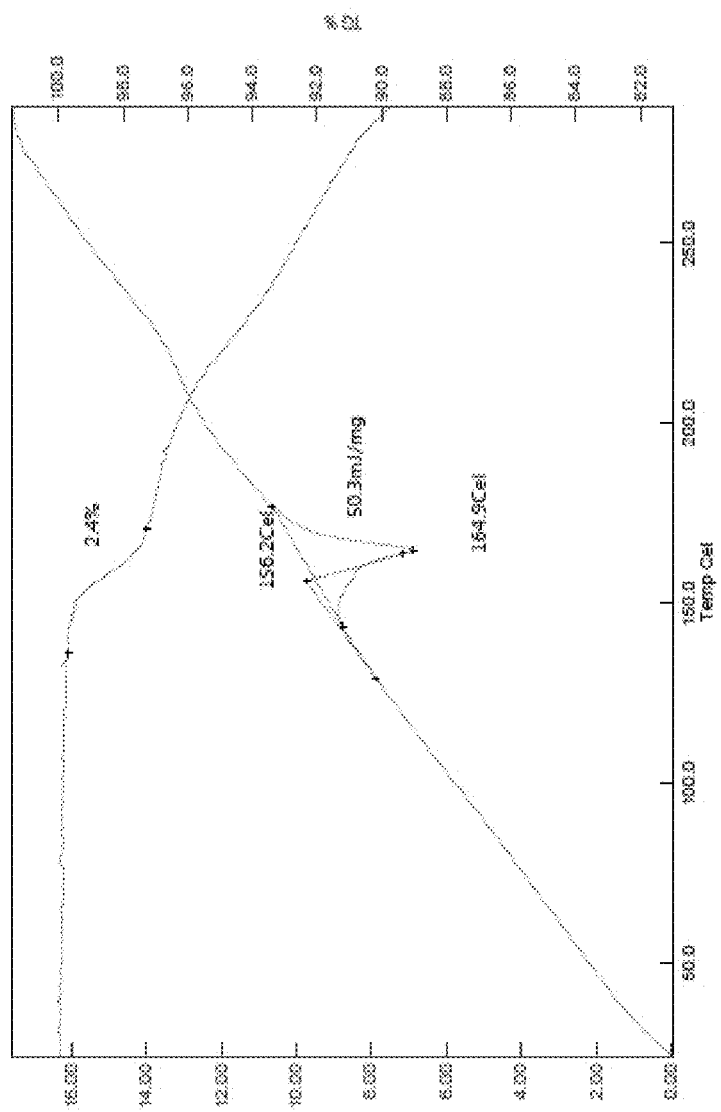

FIG. 246 sets forth a thermal analysis by TG/DTA of phosphate Form 1 obtained from 500 mg scale-up.

Figure 247:
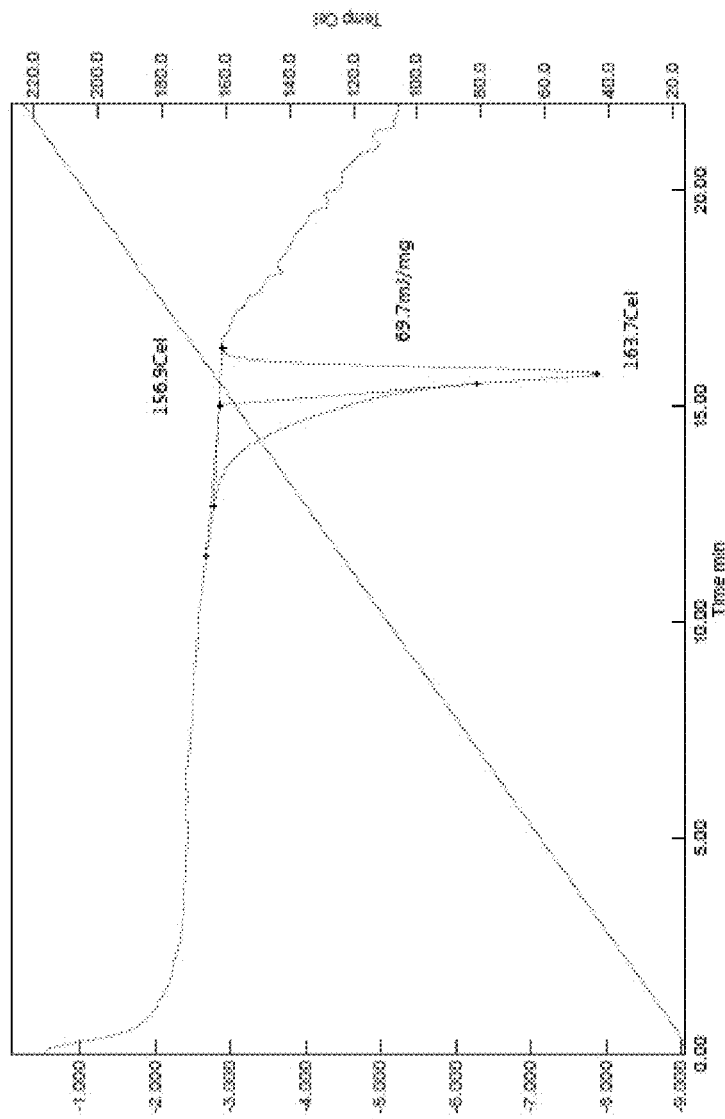

FIG. 247 sets forth a thermal analysis by DSC of phosphate Form 1 obtained from 500 mg scale-up.

Figure 248:
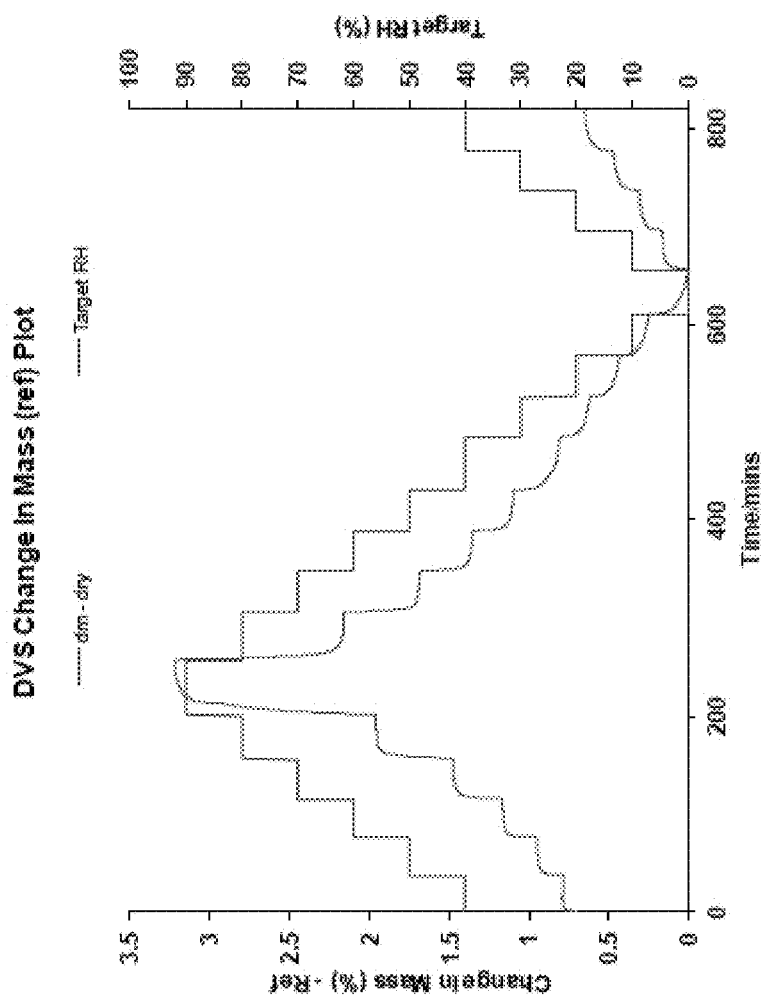

FIG. 248 sets forth a DVS kinetic analysis of phosphate Form 1 obtained from 500 mg scale-up.

Figure 249:
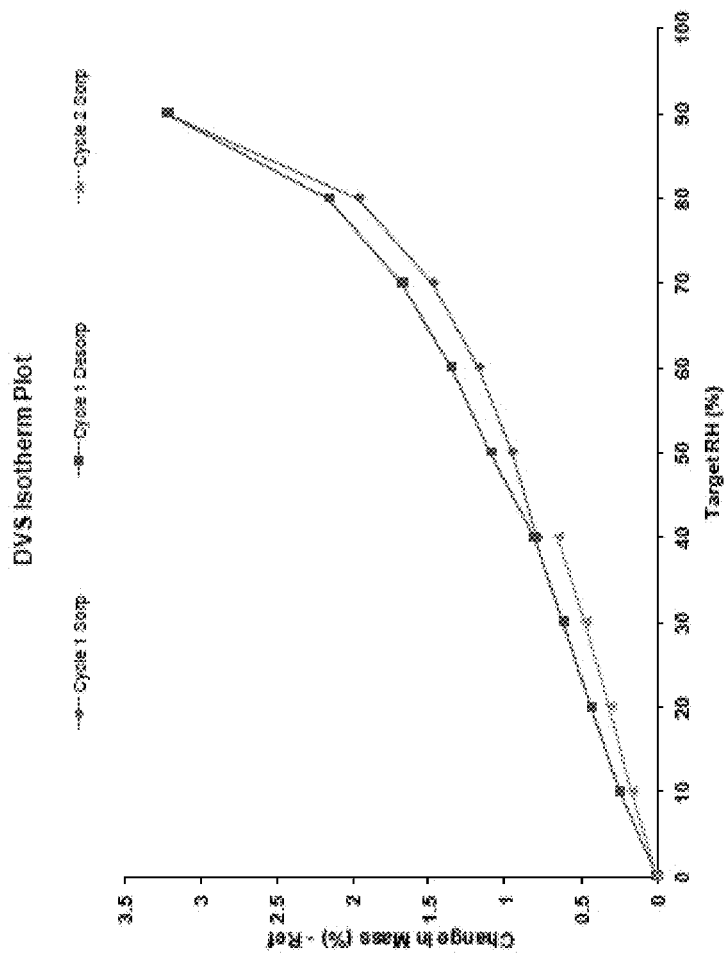

FIG. 249 sets forth a DVS isothermal analysis of phosphate Form 1 obtained from 500 mg scale-up.

Figure 250:
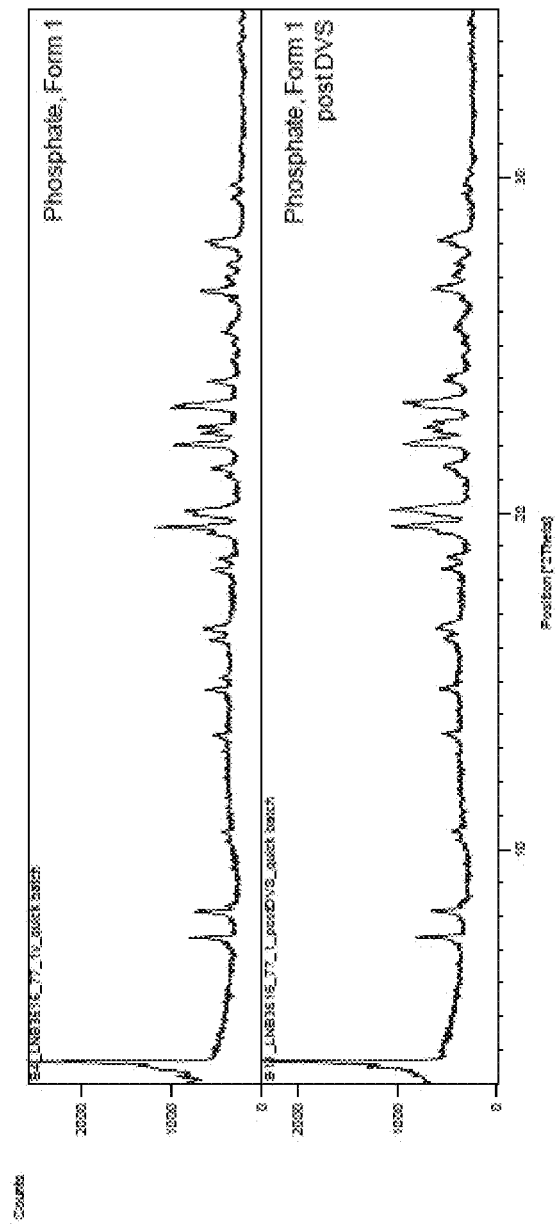

FIG. 250 sets forth comparative XRPD pattern of phosphate Form 1 obtained from 500 mg scale-up post-DVS.

Figure 251:
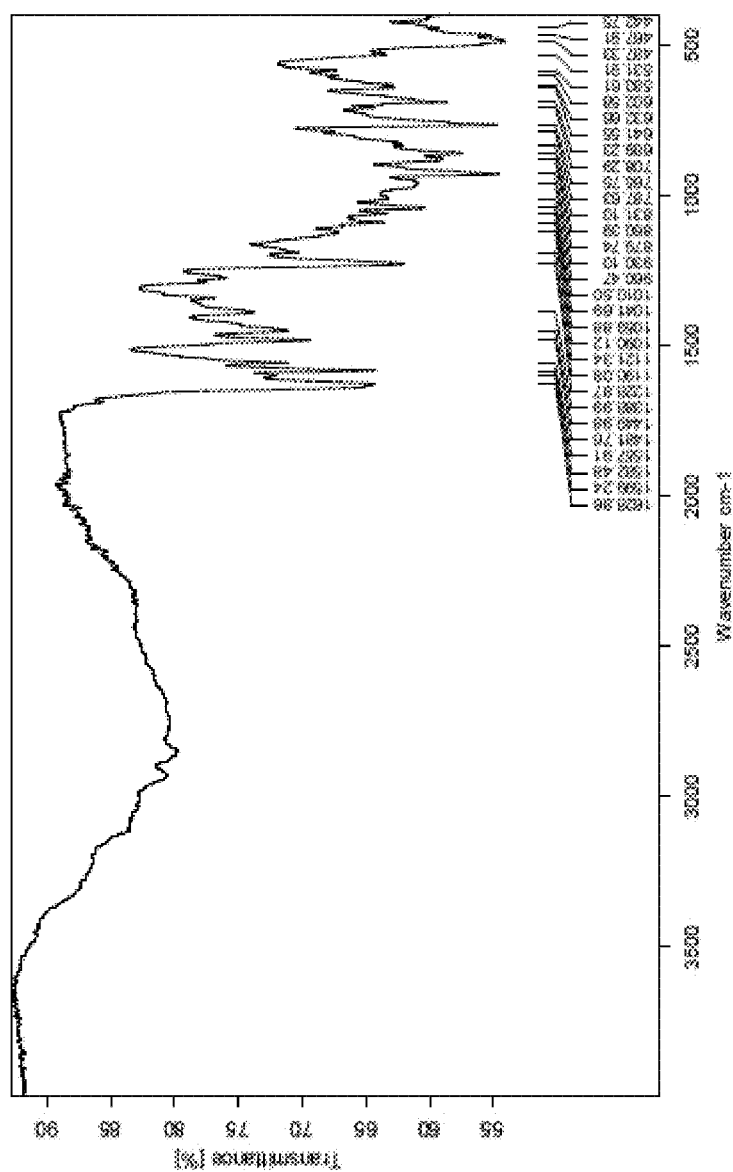

FIG. 251 sets forth comparative IR spectra of phosphate Form 1 obtained from 500 mg scale-up.

Figure 252:
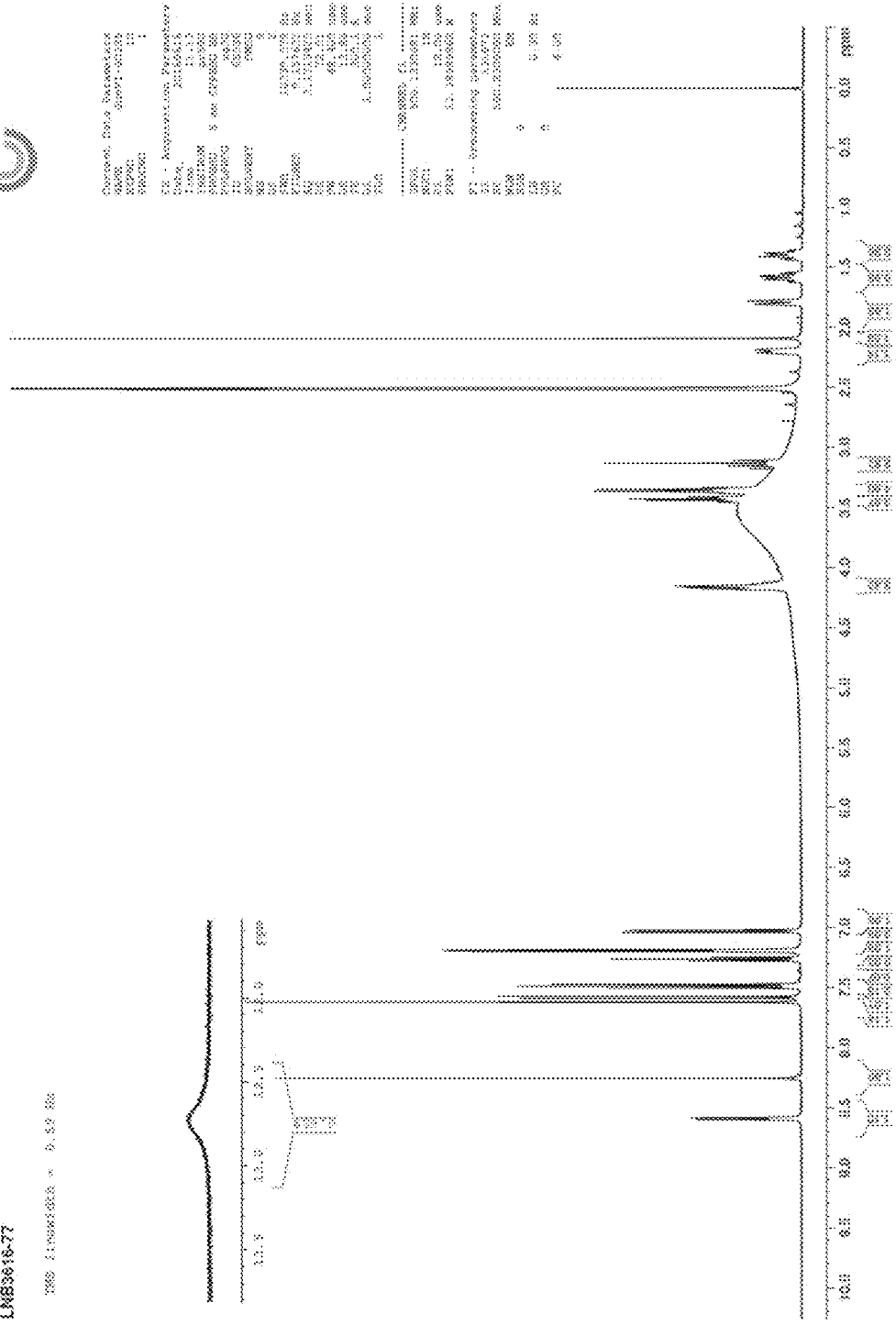

FIG. 252 sets forth a $^1$H NMR spectroscopic analysis of phosphate Form 1.

Figure 253:
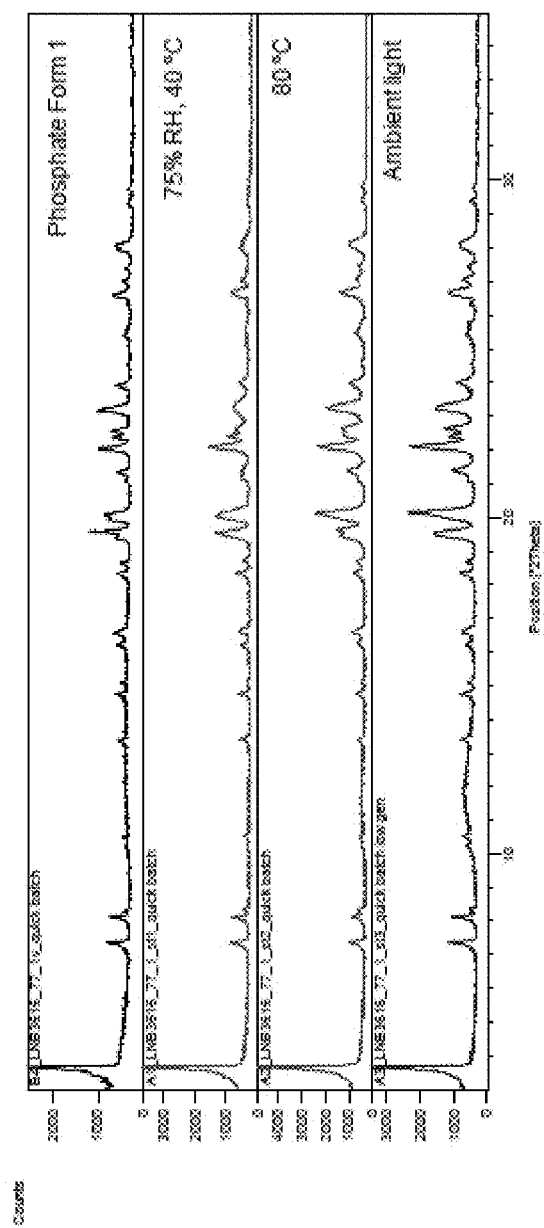

FIG. 253 sets forth XRPD patterns of phosphate Form 1 obtained from 500 mg scale-up after stability studies.

Figure 254:
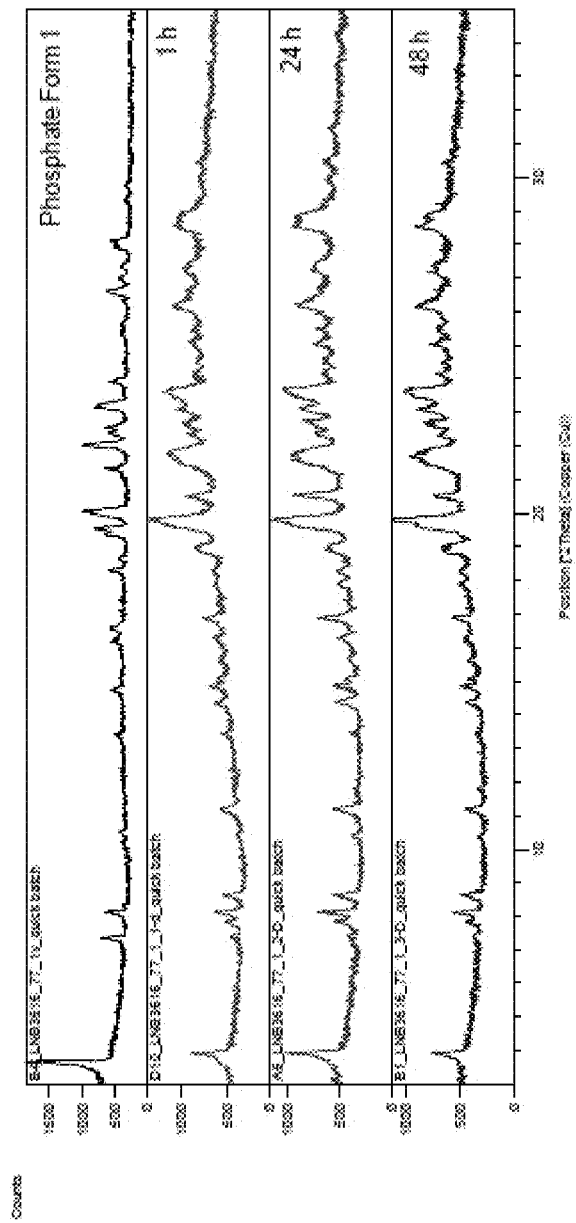

FIG. 254 sets forth XRPD patterns of phosphate Form 1 obtained from 500 mg scale-up after salt disproportionation experiments.

Figure 255:
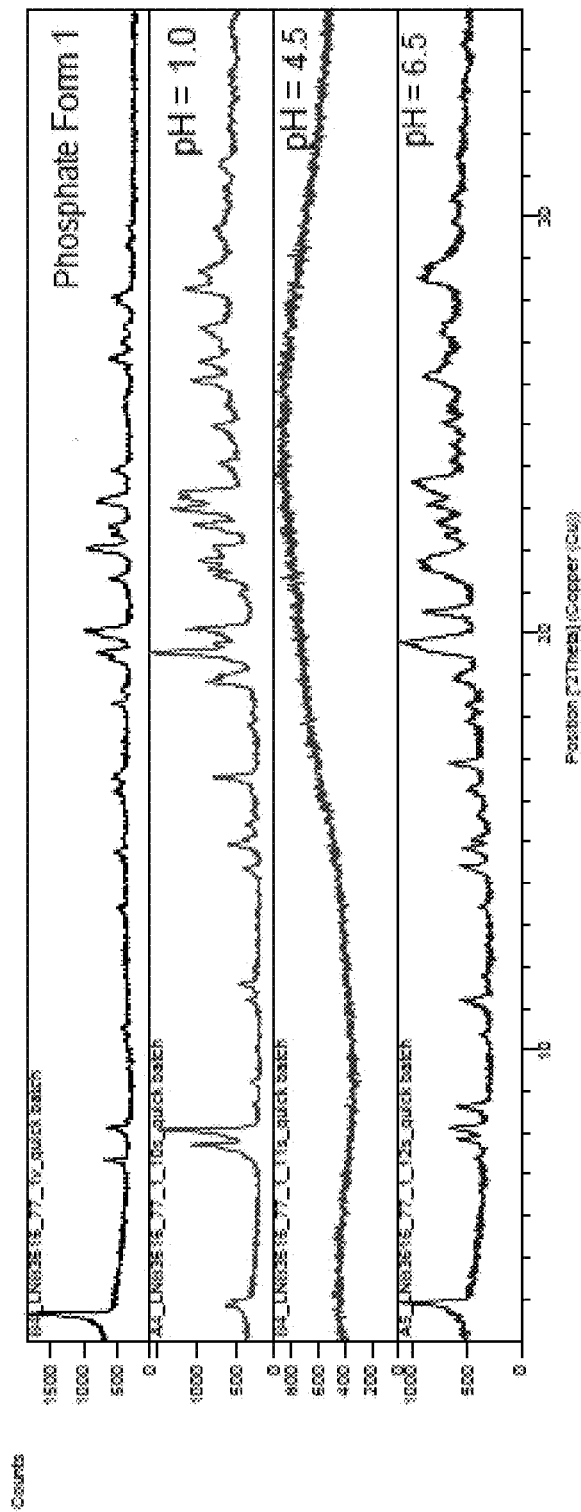

FIG. 255 sets forth XRPD patterns of phosphate Form 1 obtained from 500 mg scale-up after thermodynamic solubility experiments.

Figure 256:
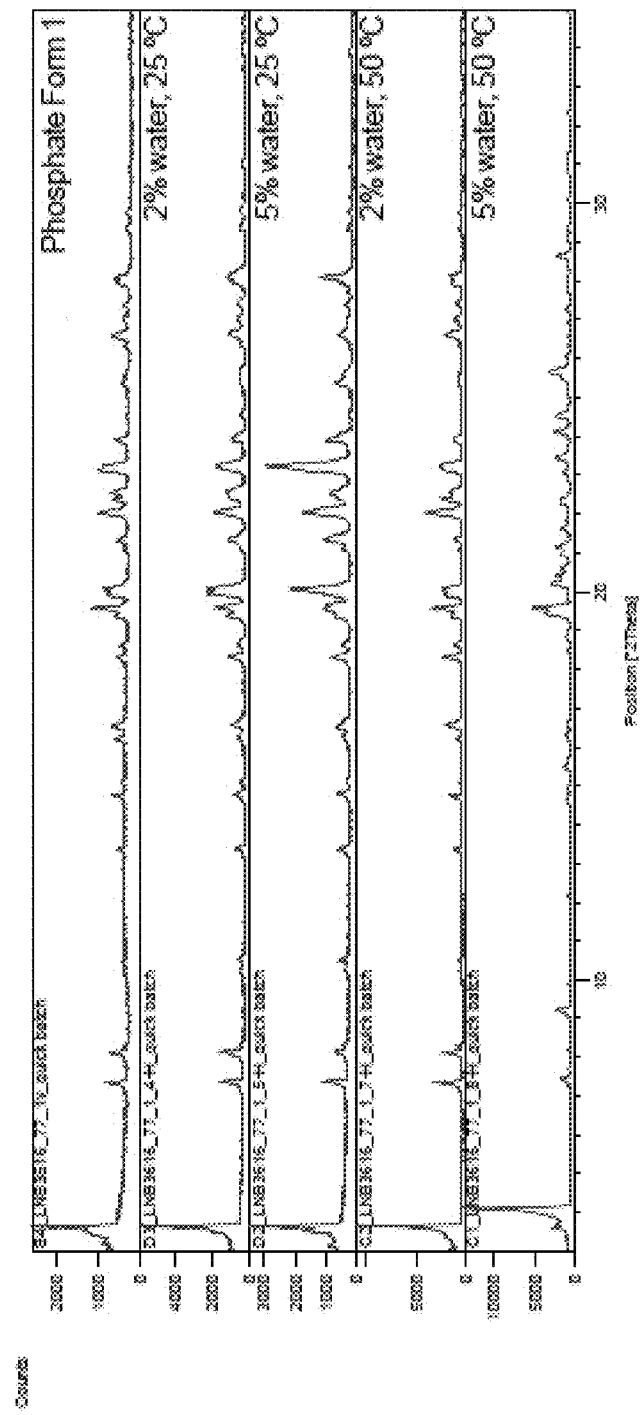

FIG. 256 sets forth XRPD patterns of phosphate Form 1 obtained from 500 mg scale-up after hydration experiments.

Figure 257:
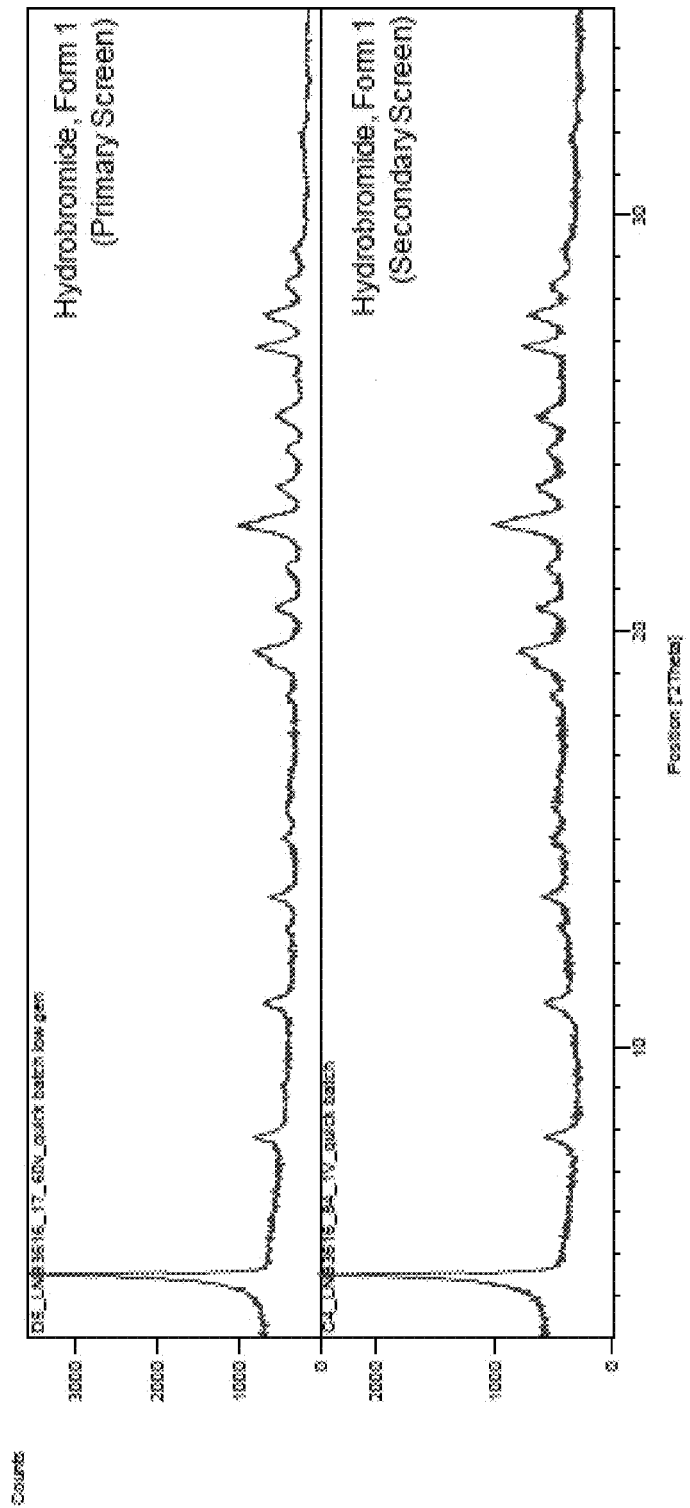

FIG. 257 sets forth XRPD patterns of hydrobromide Form 1 obtained from 500 mg scale-up.

Figure 258B:
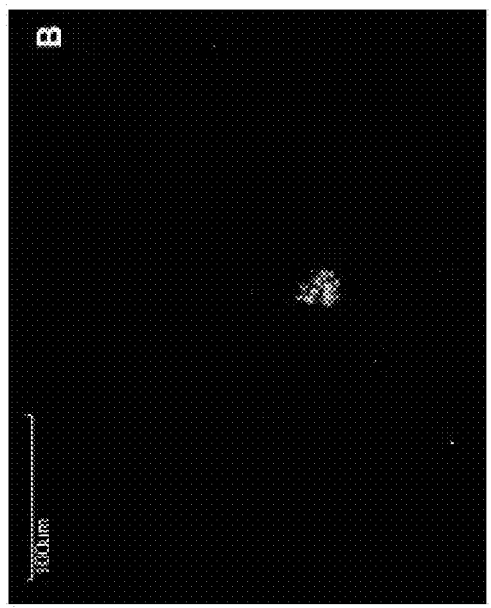
Figure 258A:
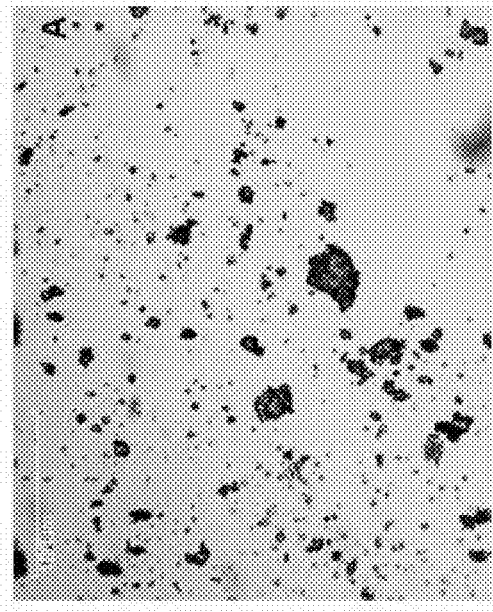

FIG. 258A sets forth PLM images of hydrobromide Form 1 obtained from 500 mg scale-up under non-polarized light.

FIG. 258B sets forth PLM images of hydrobromide Form 1 obtained from 500 mg scale-up under polarized light.

Figure 259:
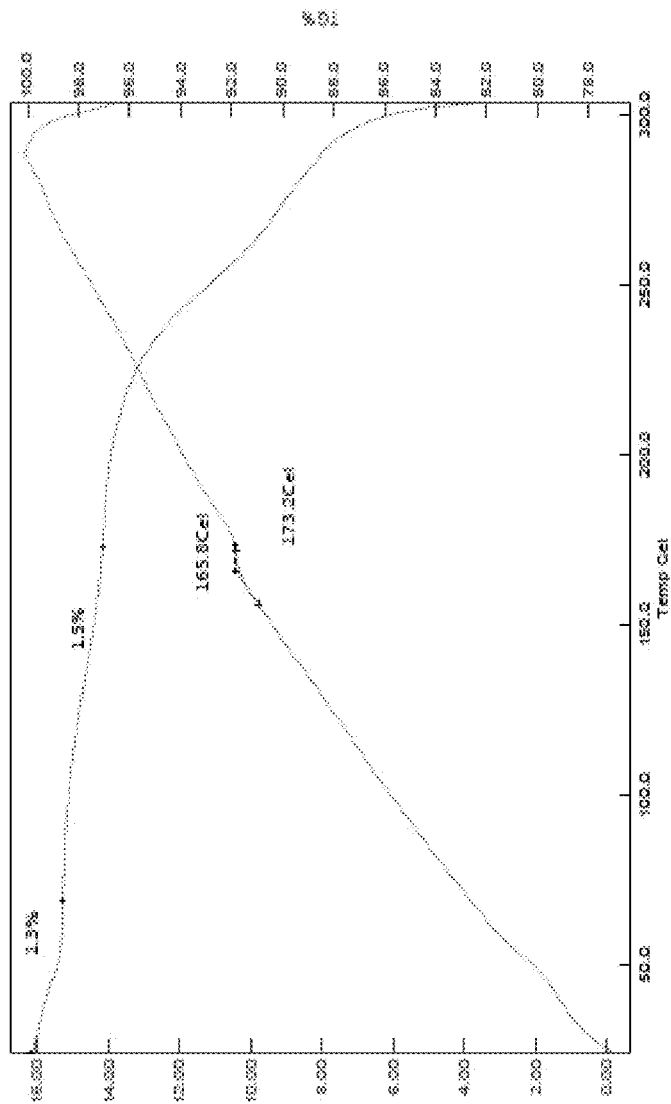

FIG. 259 sets forth a thermal analysis by TG/DTA of hydrobromide Form 1 obtained from 500 mg scale-up.

Figure 260:
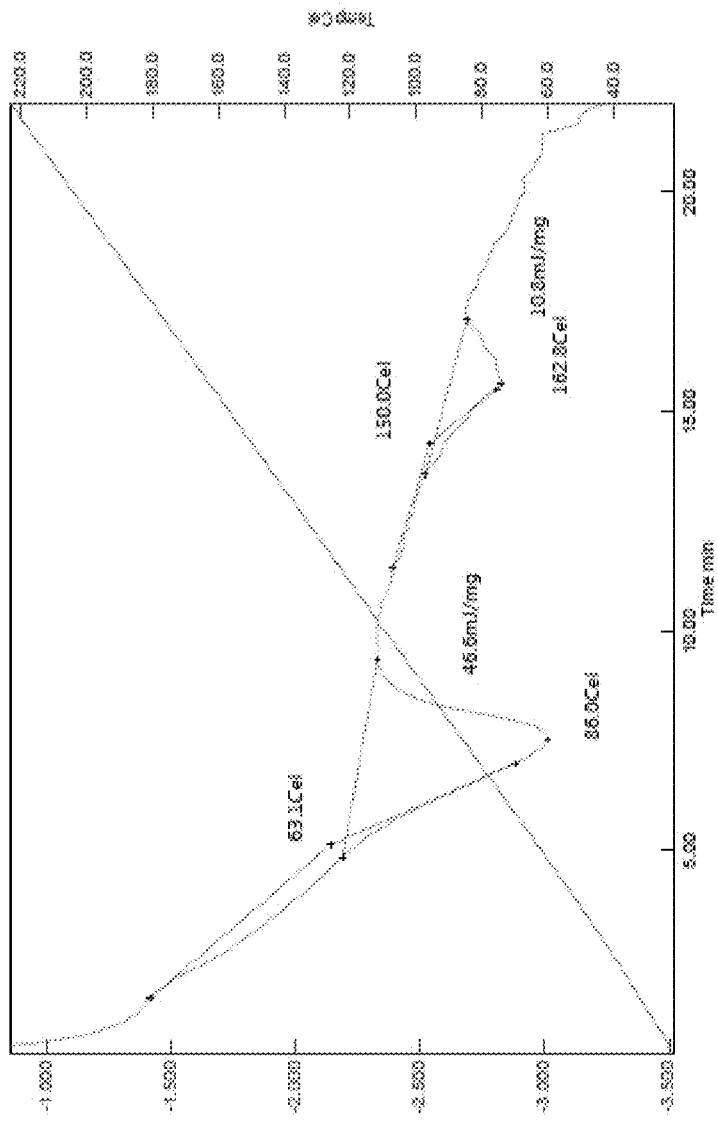

FIG. 260 sets forth a thermal analysis by DSC of hydrobromide Form 1 obtained from 500 mg scale-up.

Figure 261:
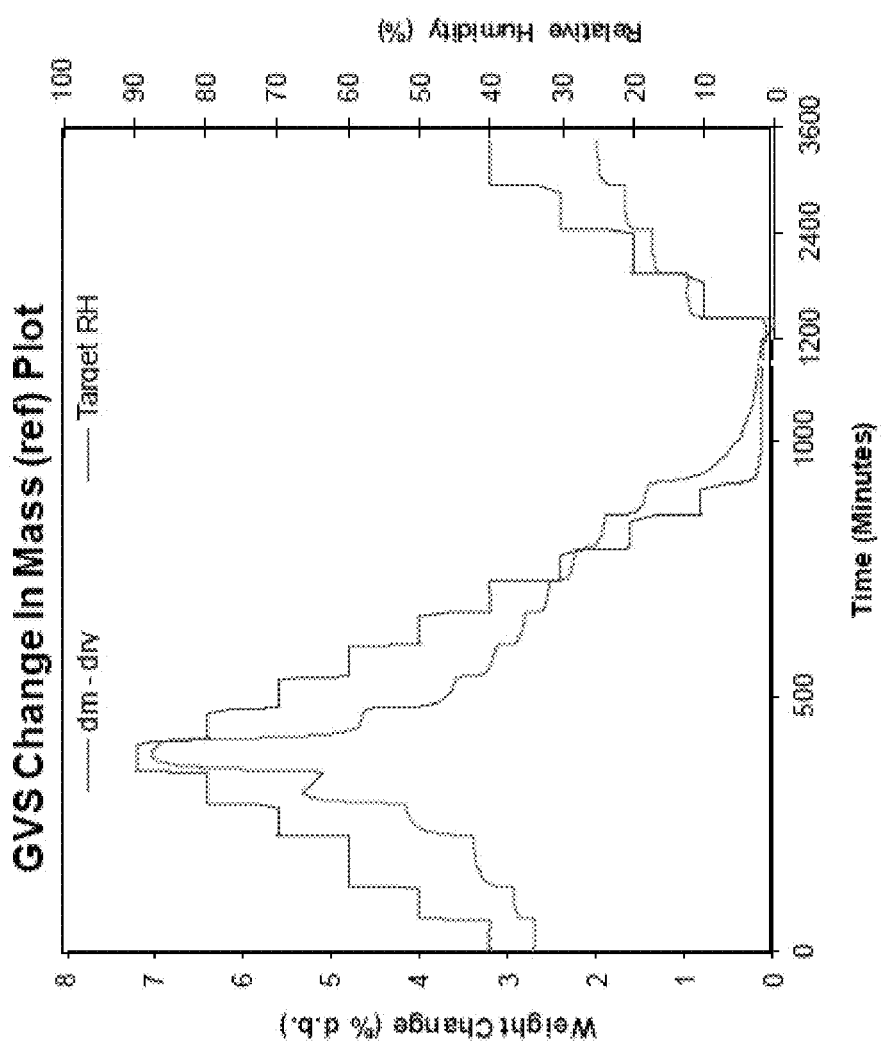

FIG. 261 sets forth a DVS kinetic analysis of hydrobromide Form 1 obtained from 500 mg scale-up.

Figure 262:
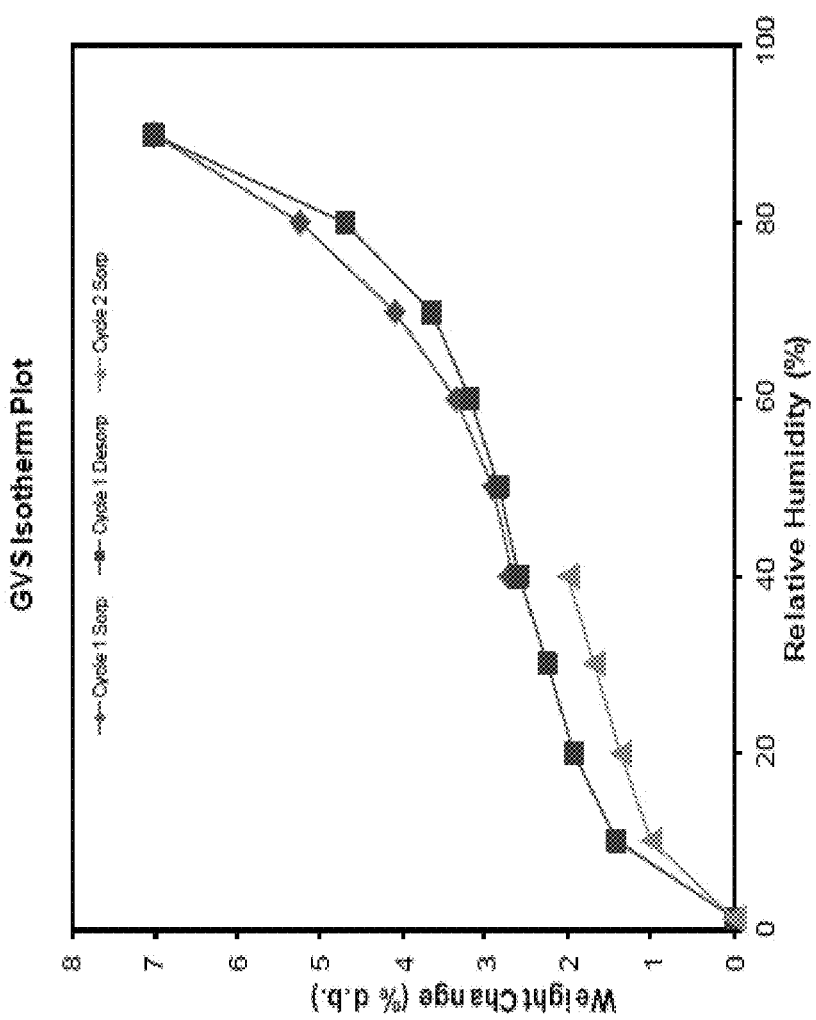

FIG. 262 sets forth a DVS isothermal analysis of hydrobromide Form 1 obtained from 500 mg scale-up.

Figure 263:
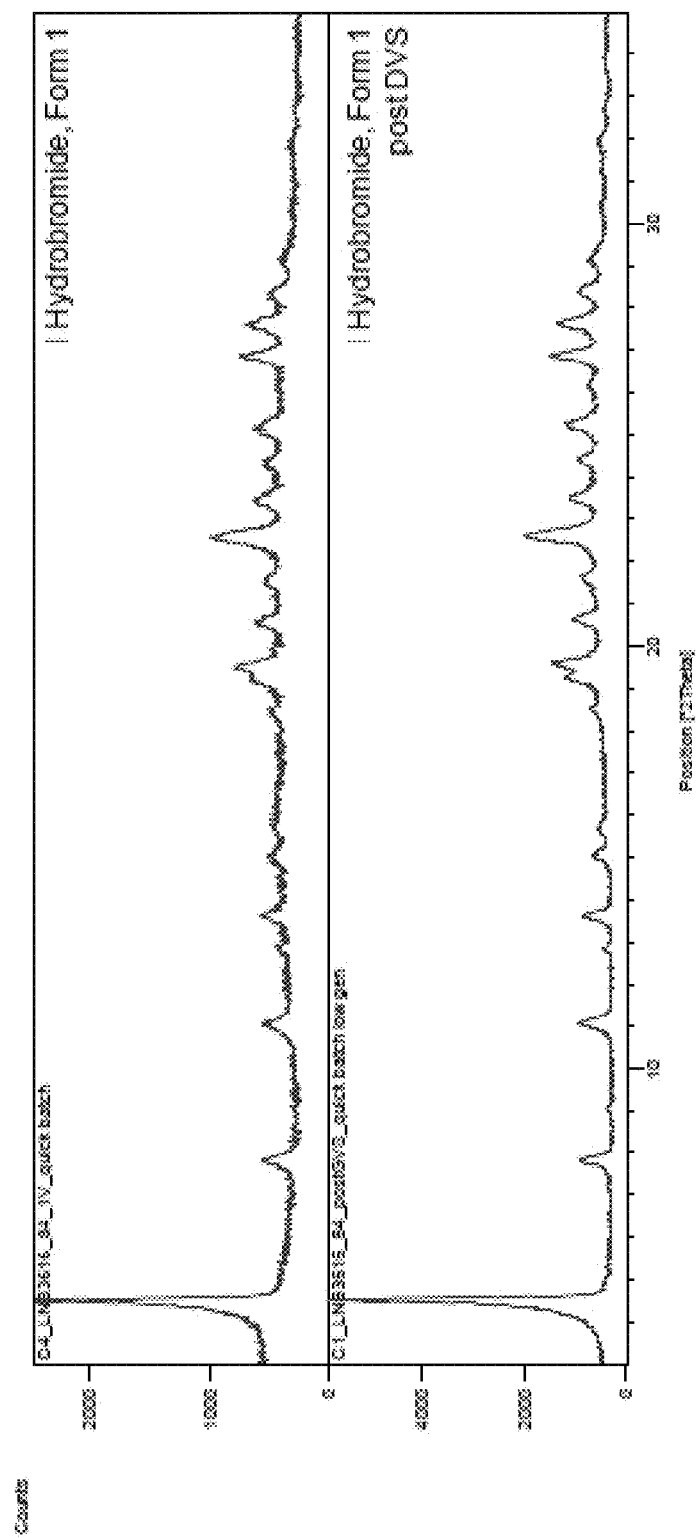

FIG. 263 sets forth comparative XRPD pattern of hydrobromide Form 1 obtained from 500 mg scale-up post-DVS.

Figure 264:
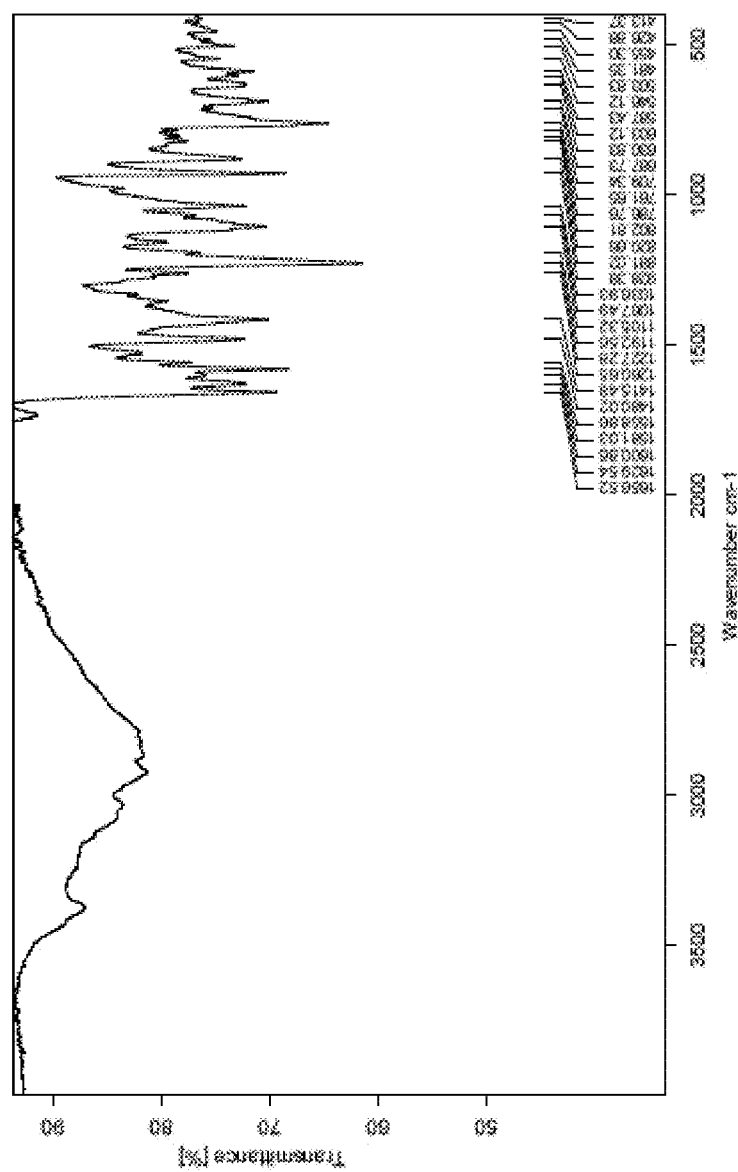

FIG. 264 sets forth comparative IR spectra of hydrobromide Form 1 obtained from 500 mg scale-up.

Figure 265:
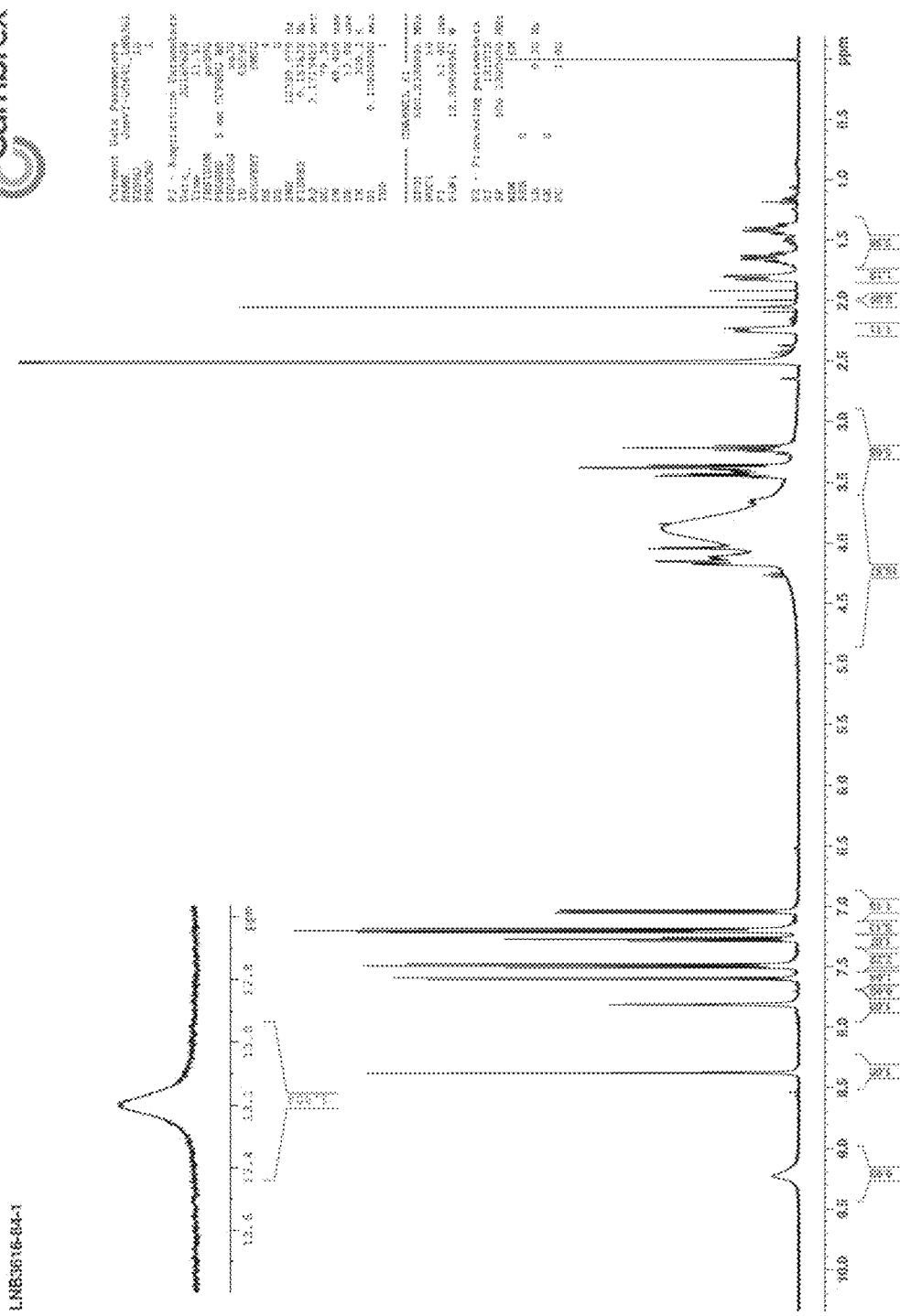

FIG. 265 sets forth a ¹H NMR spectroscopic analysis of hydrobromide Form 1.

Figure 266:
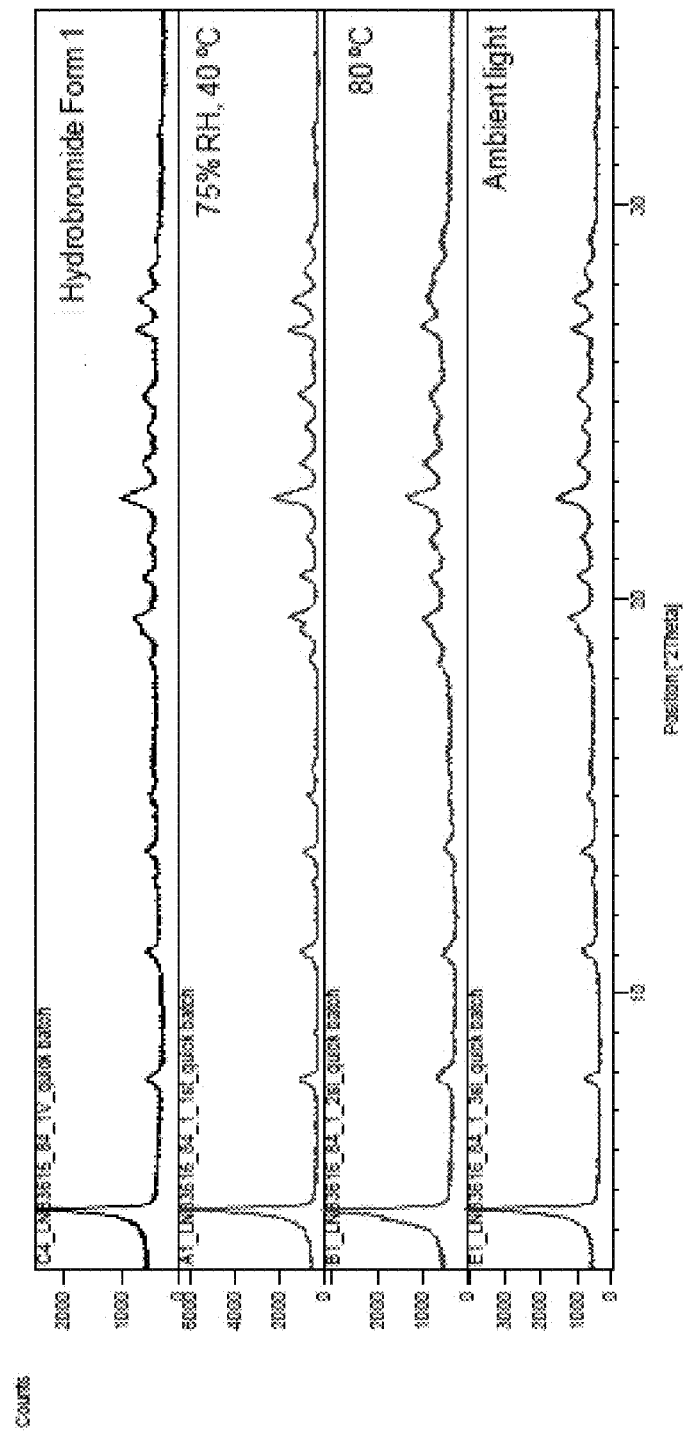

FIG. 266 sets forth XRPD patterns of hydrobromide Form 1 obtained from 500 mg scale-up after stability studies.

Figure 267:
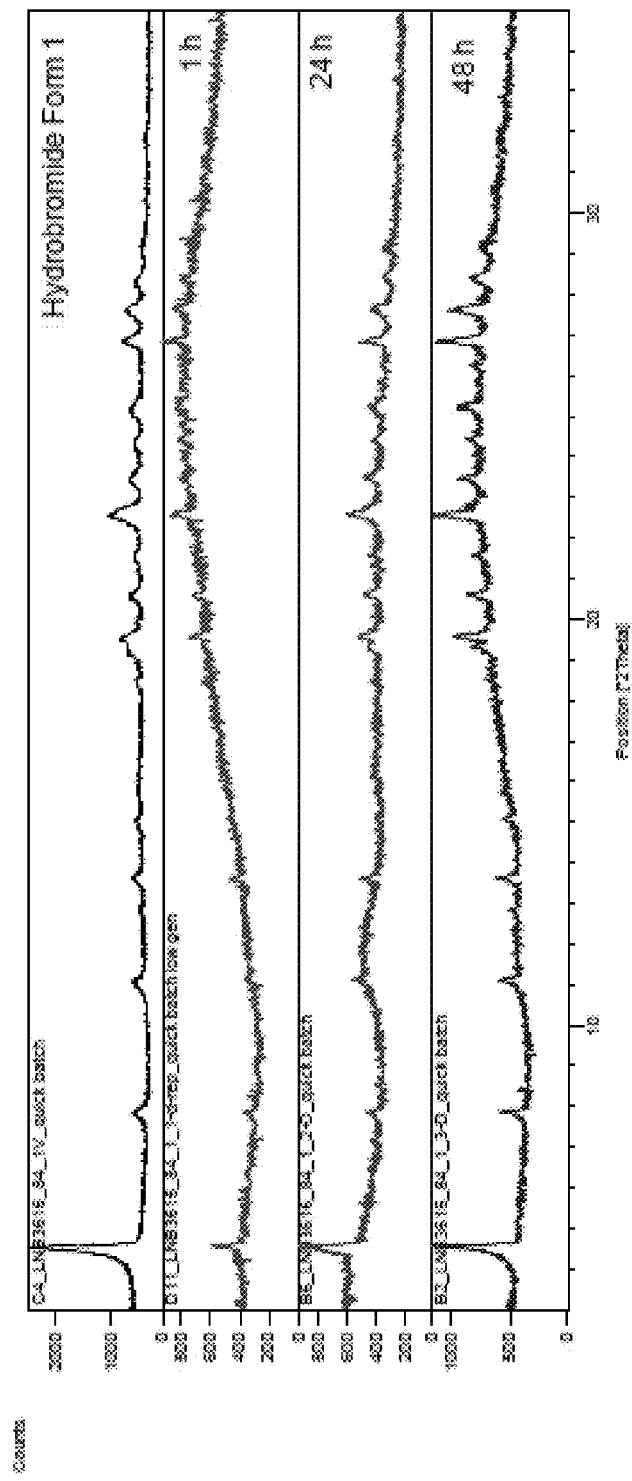

FIG. 267 sets forth XRPD patterns of hydrobromide Form 1 obtained from 500 mg scale-up after salt disproportionation experiments.

Figure 268:
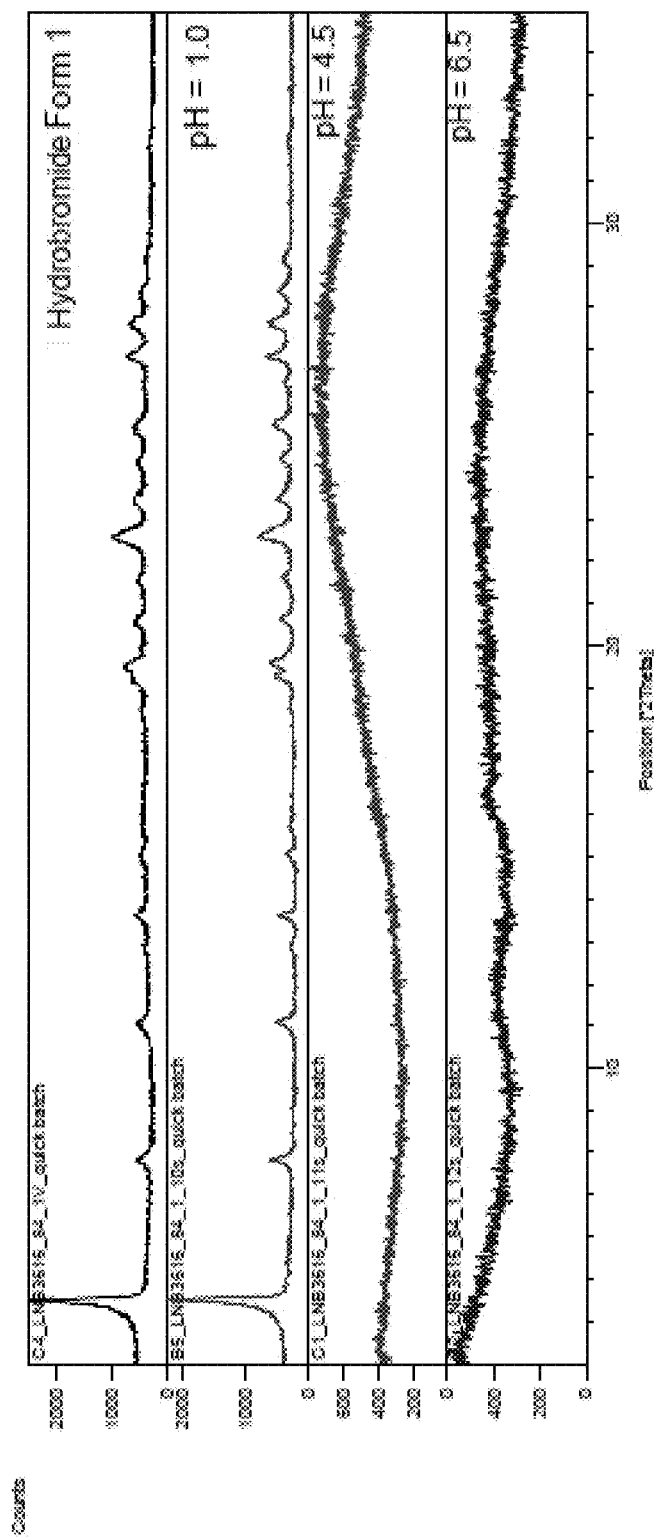

FIG. 268 sets forth XRPD patterns of hydrobromide Form 1 obtained from 500 mg scale-up after thermodynamic solubility experiments.

Figure 269:
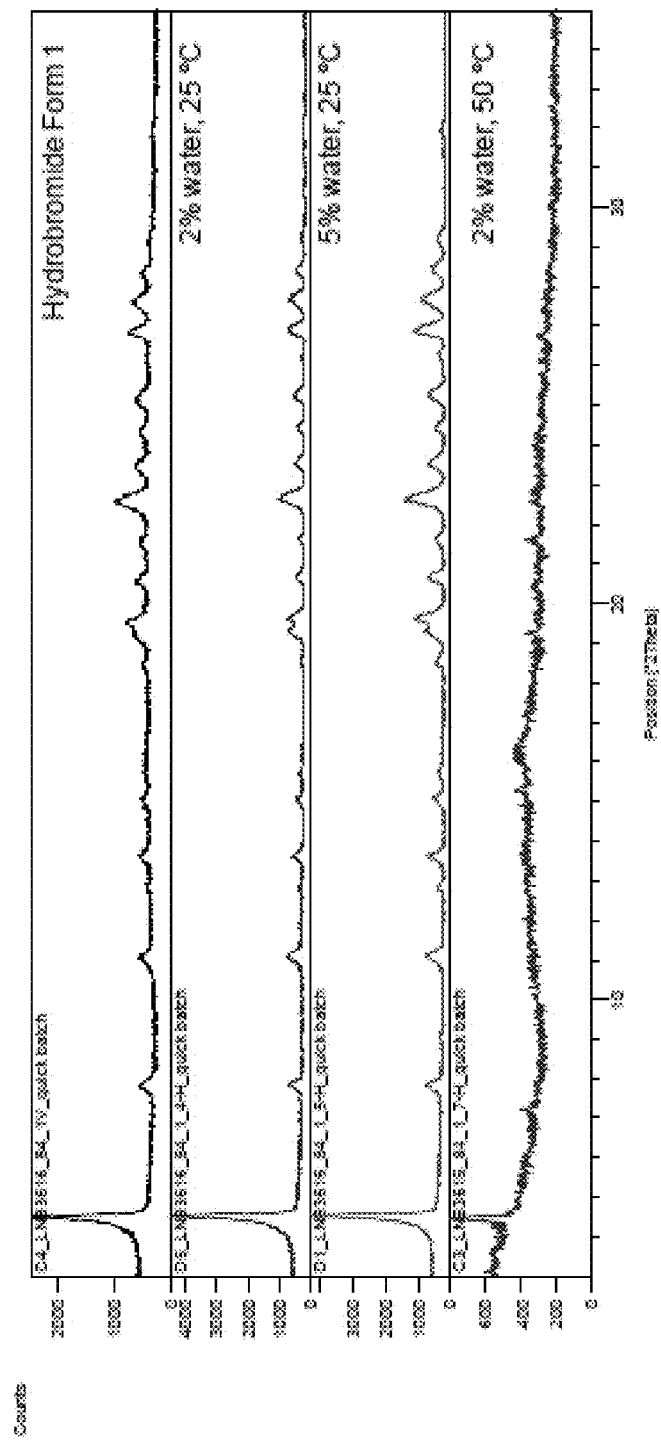

FIG. 269 sets forth XRPD patterns of hydrobromide Form 1 obtained from 500 mg scale-up after hydration experiments.

Figure 270:
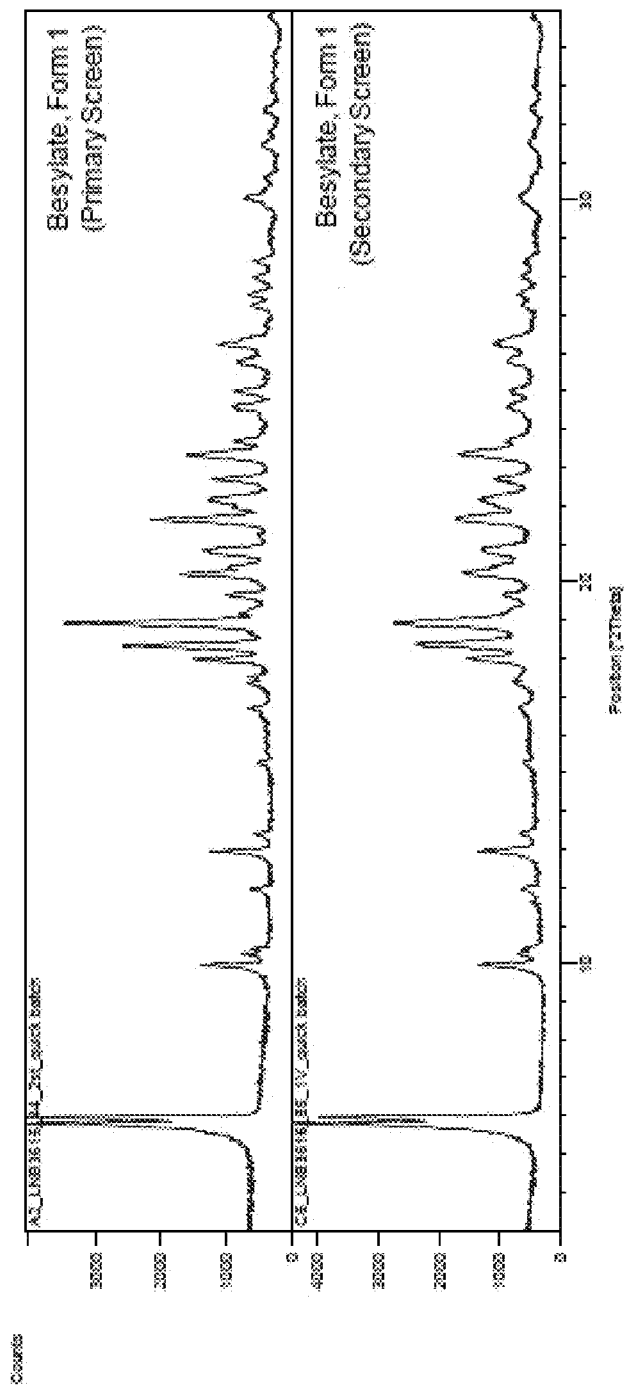

FIG. 270 sets forth XRPD patterns of besylate Form 1 obtained from 500 mg scale-up.

Figure 271A:
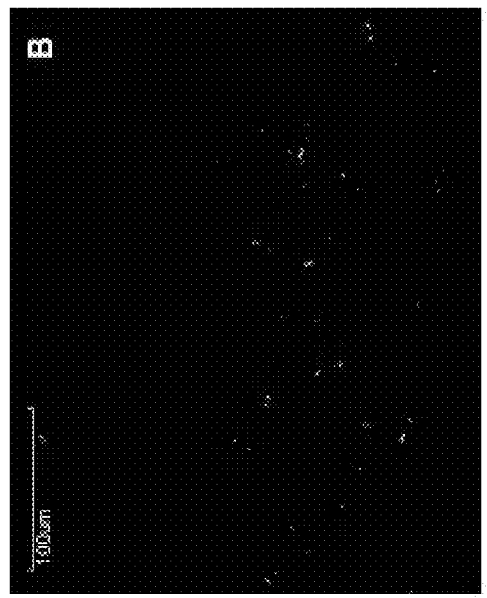

FIG. 271A sets forth PLM images of besylate Form 1 obtained from 500 mg scale-up under non-polarized light.

Figure 271B:
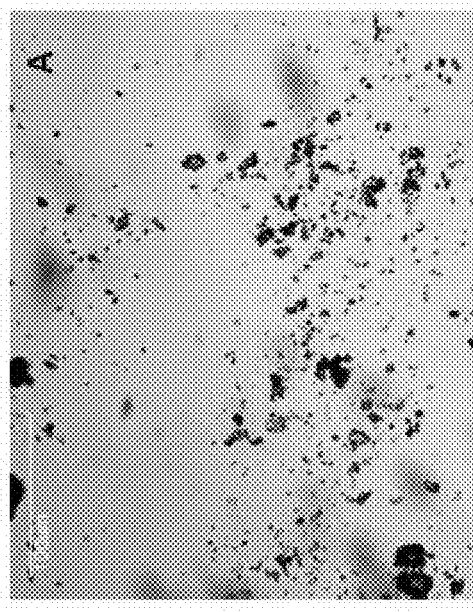

FIG. 271B sets forth PLM images of besylate Form 1 obtained from 500 mg scale-up under polarized light.

Figure 272:
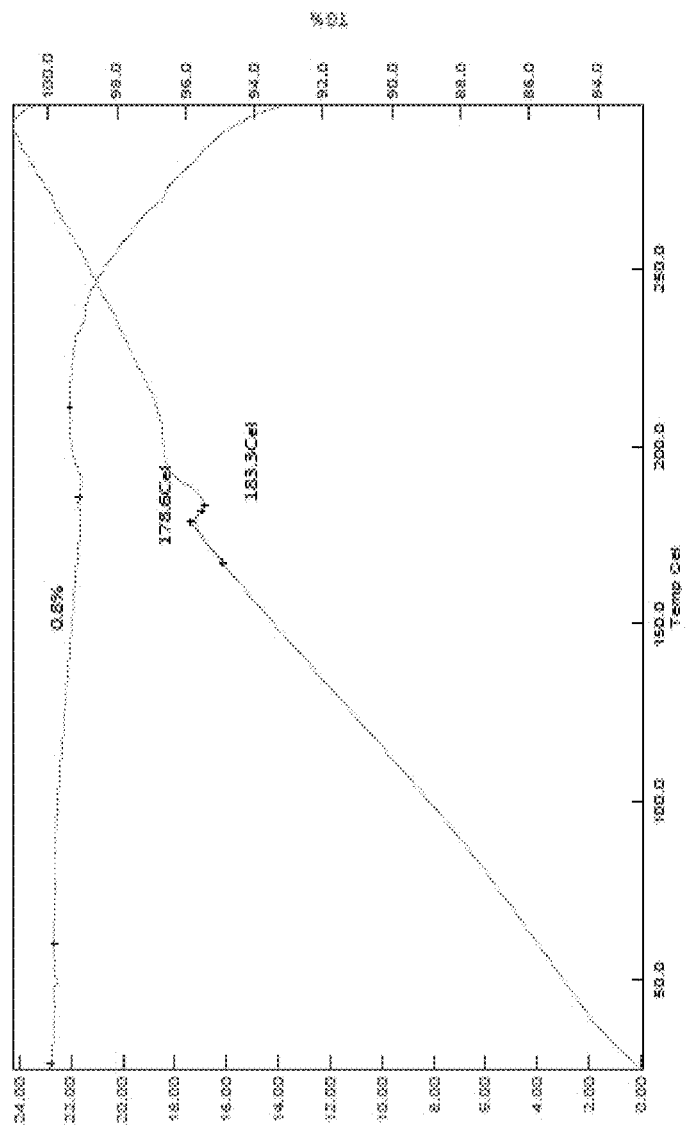

FIG. 272 sets forth a thermal analysis by TG/DTA of besylate Form 1 obtained from 500 mg scale-up.

Figure 273:
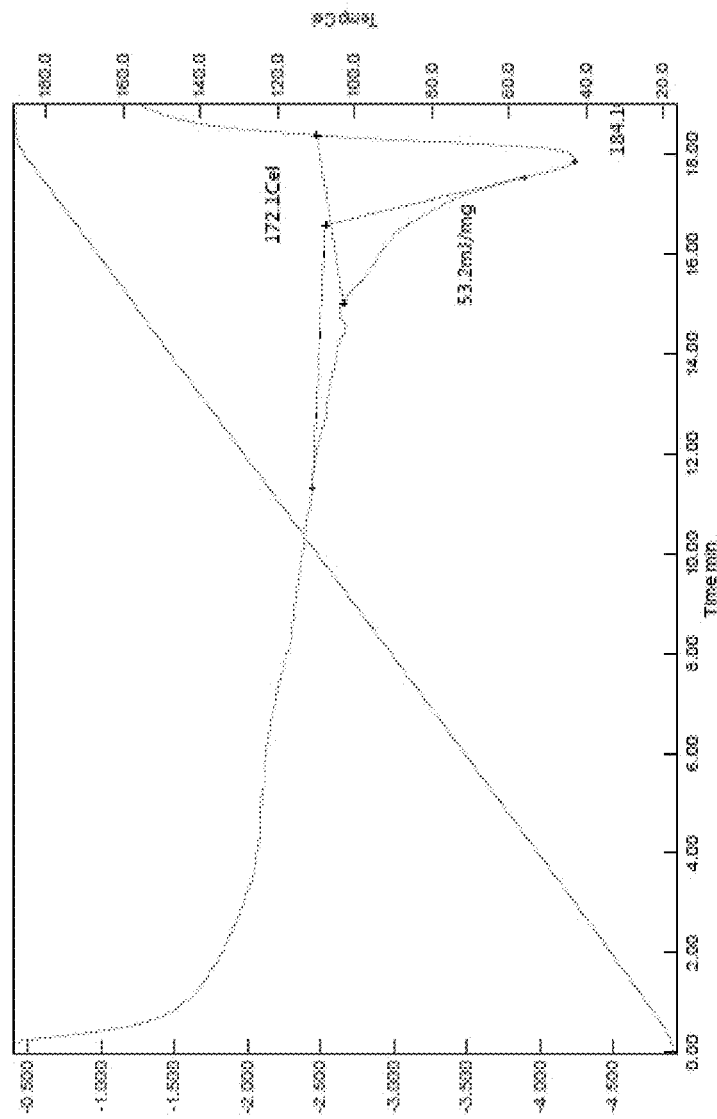

FIG. 273 sets forth a thermal analysis by DSC of besylate Form 1 obtained from 500 mg scale-up.

Figure 274:
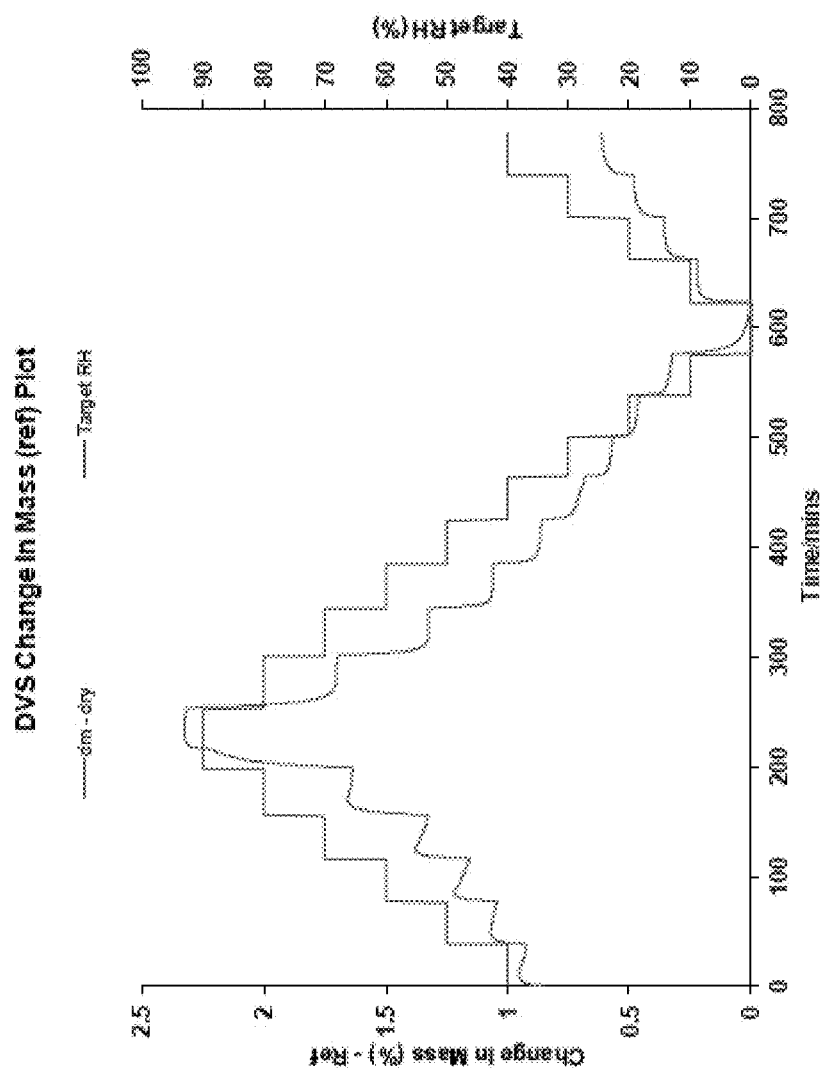

FIG. 274 sets forth a DVS kinetic analysis of besylate Form 1 obtained from 500 mg scale-up.

Figure 275:
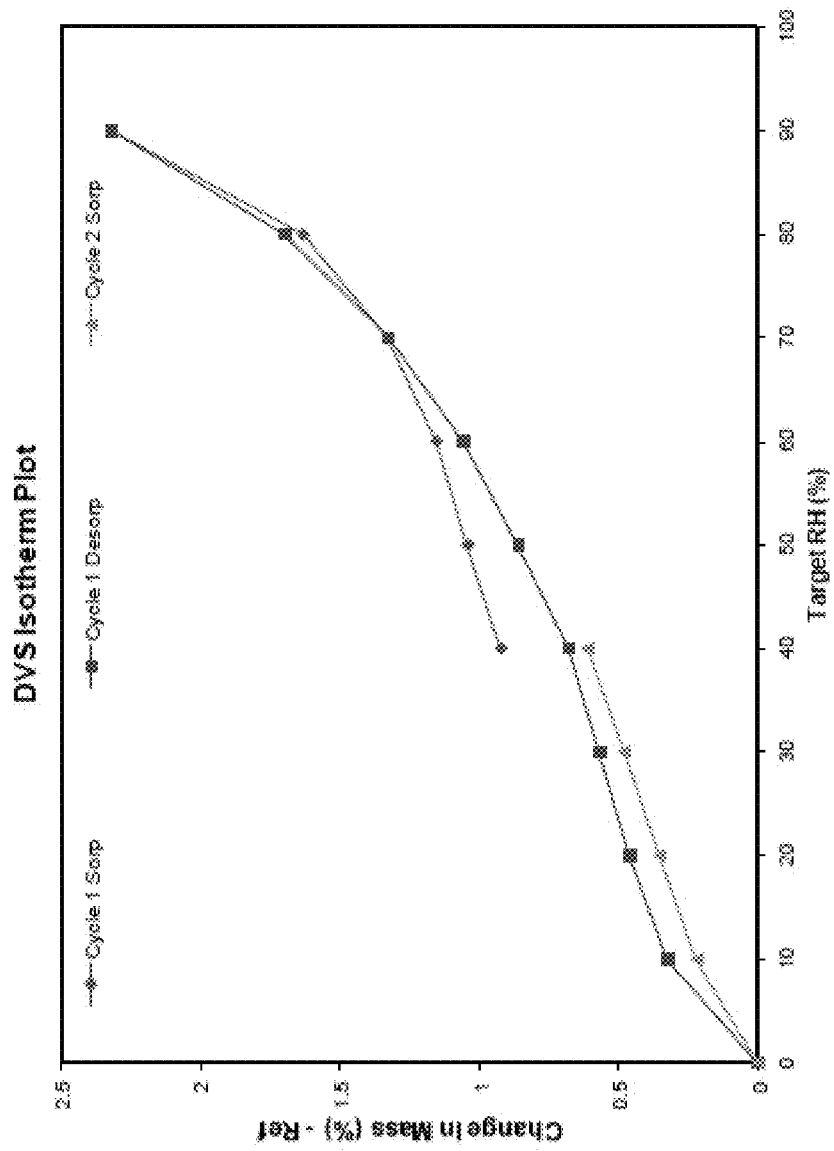

FIG. 275 sets forth a DVS isothermal analysis of besylate Form 1 obtained from 500 mg scale-up.

Figure 276:
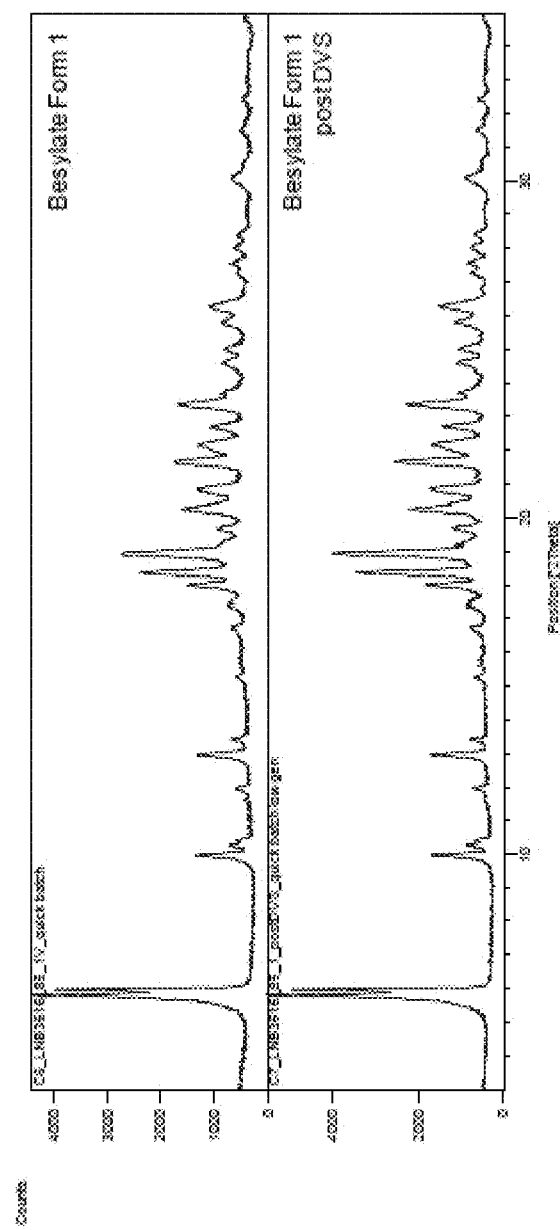

FIG. 276 sets forth comparative XRPD pattern of besylate Form 1 obtained from 500 mg scale-up post-DVS.

Figure 277:
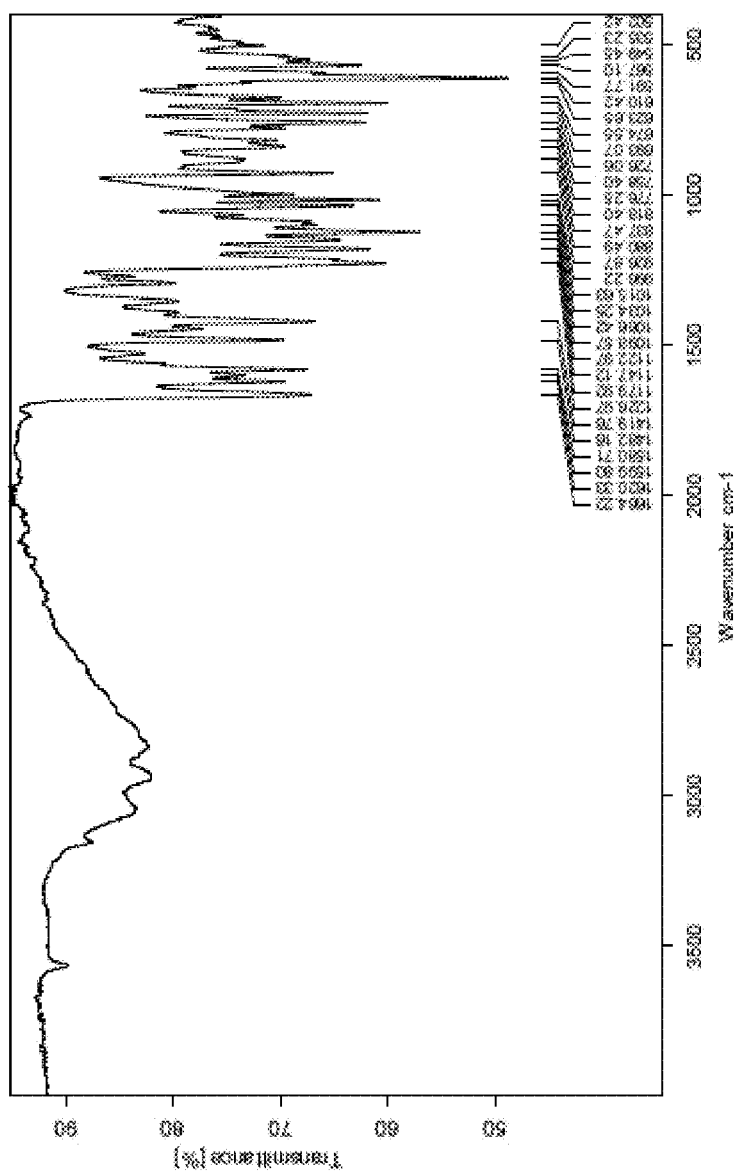

FIG. 277 sets forth comparative infrared (IR) spectra of an amorphous form of besylate Form 1 obtained from 500 mg scale-up.

Figure 278:
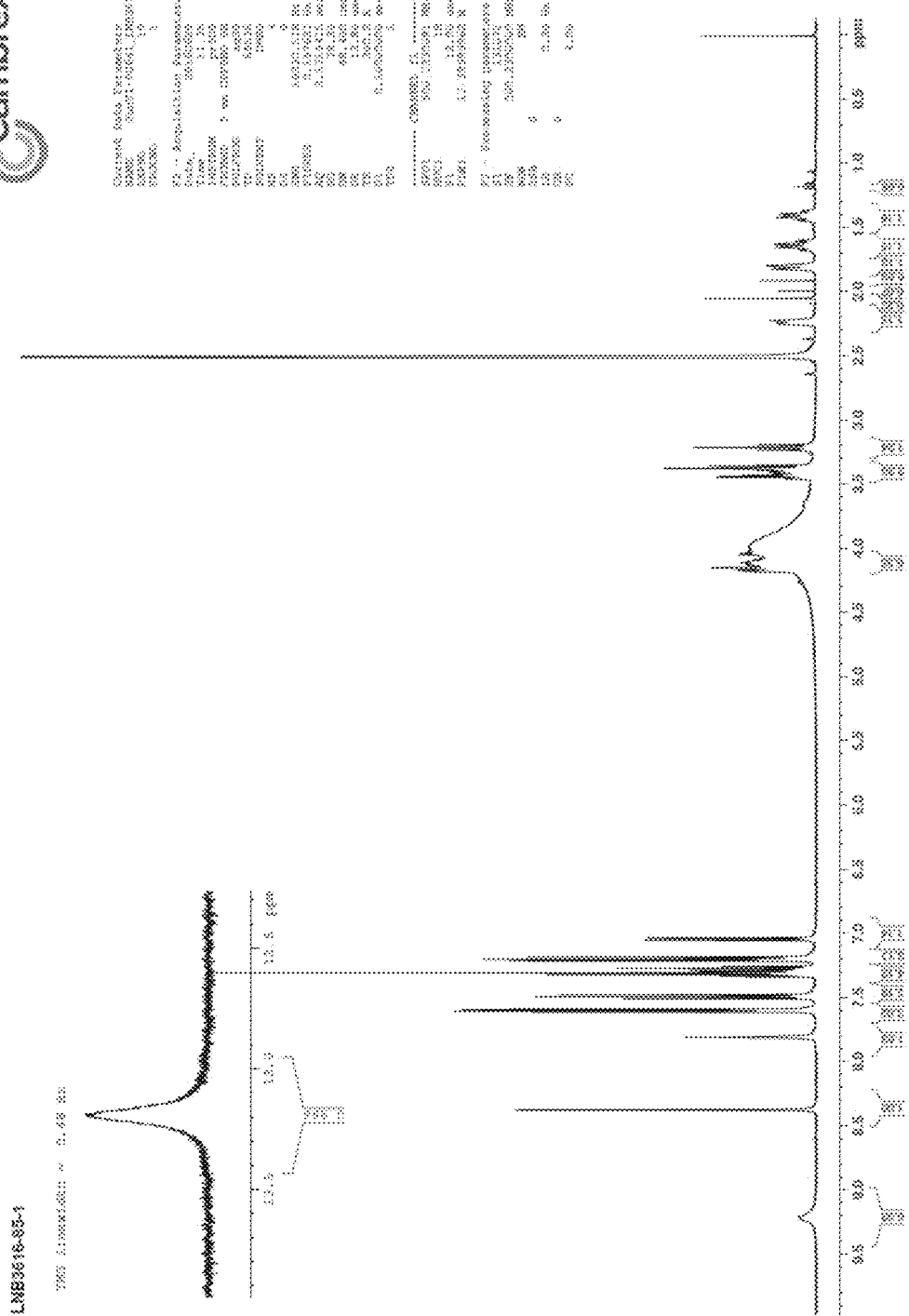

FIG. 278 sets forth a ¹H NMR spectroscopic analysis of besylate Form 1.

Figure 279:
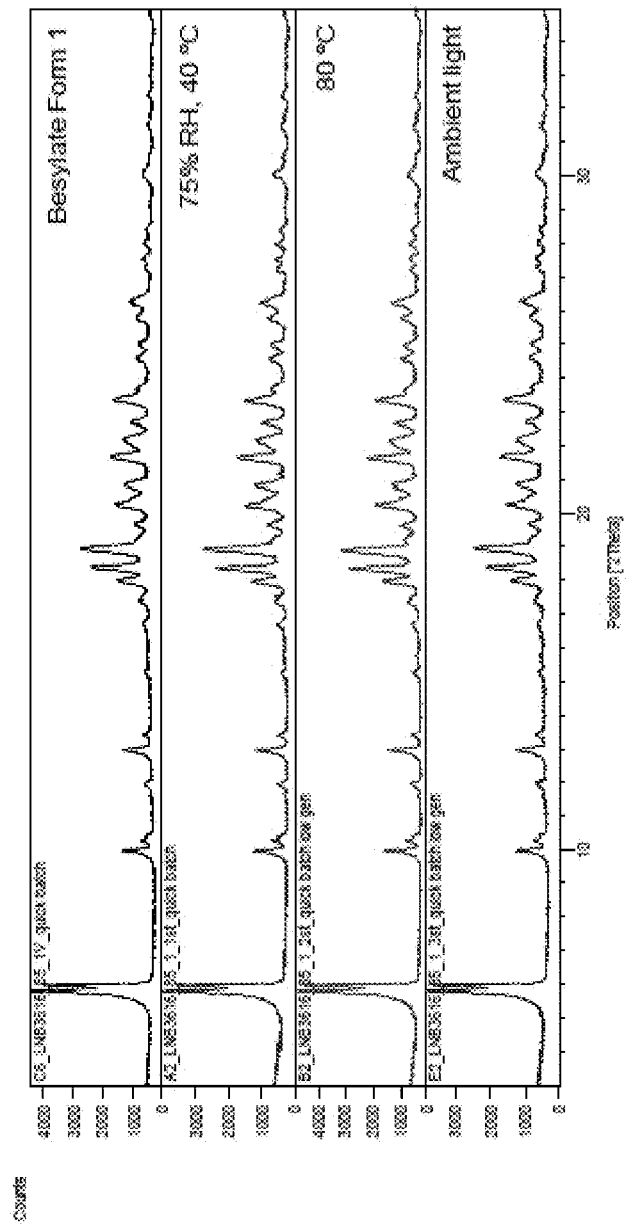

FIG. 279 sets forth XRPD patterns of besylate Form 1 obtained from 500 mg scale-up after stability studies.

Figure 280:
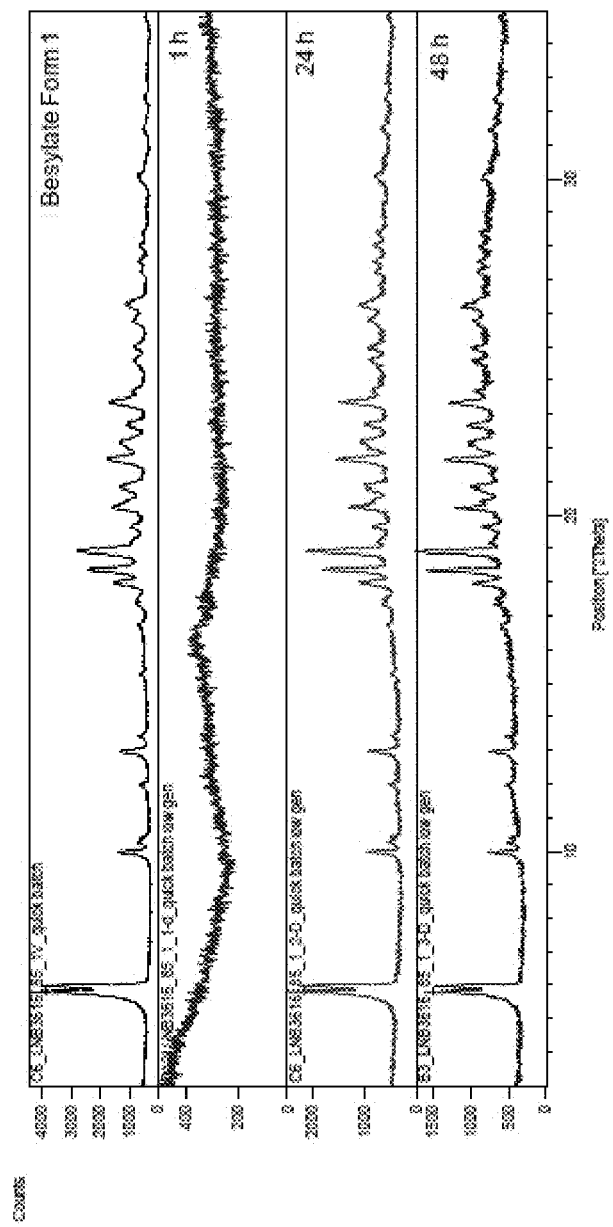

FIG. 280 sets forth XRPD patterns of besylate Form 1 obtained from 500 mg scale-up after salt disproportionation experiments.

Figure 281:
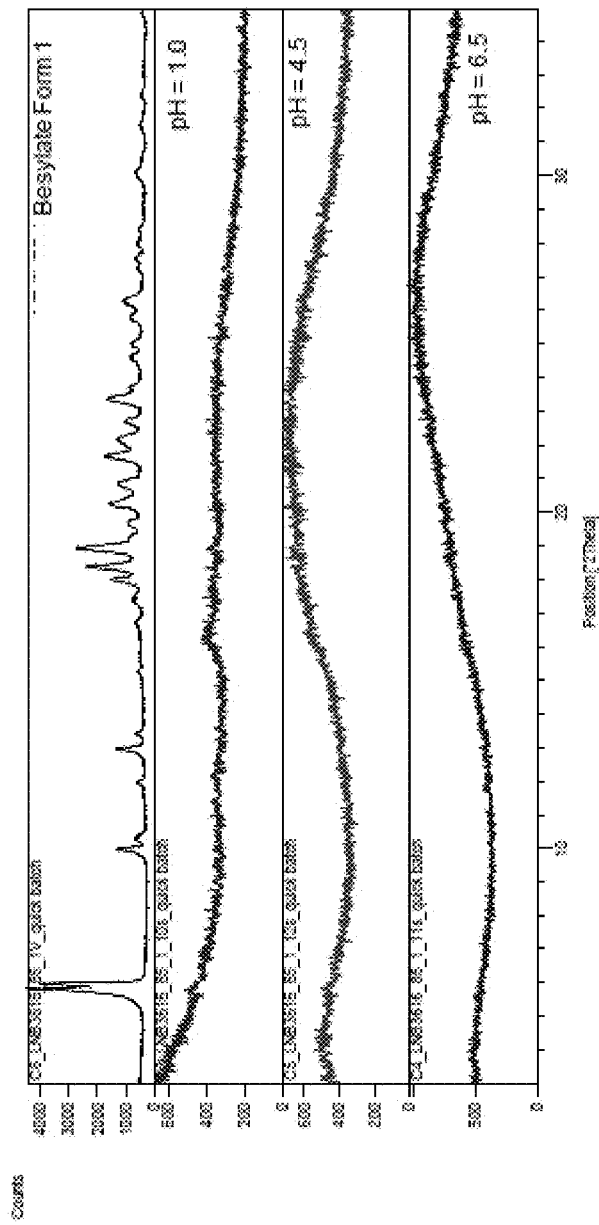

FIG. 281 sets forth XRPD patterns of besylate Form 1 obtained from 500 mg scale-up after thermodynamic solubility experiments.

Figure 282:
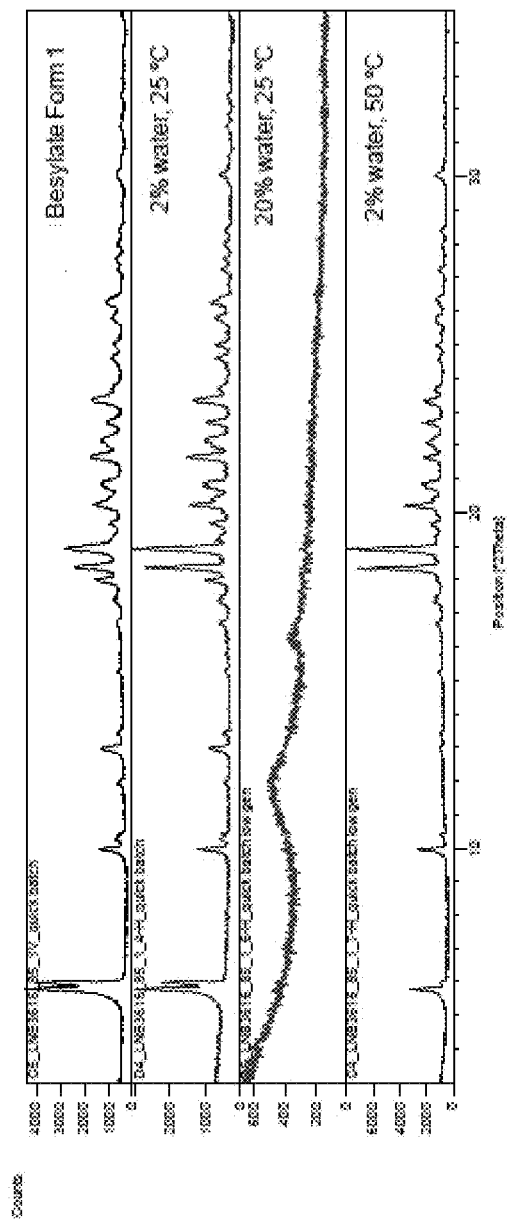

FIG. 282 sets forth XRPD patterns of besylate Form 1 obtained from 500 mg scale-up after hydration experiments.

Figure 283:
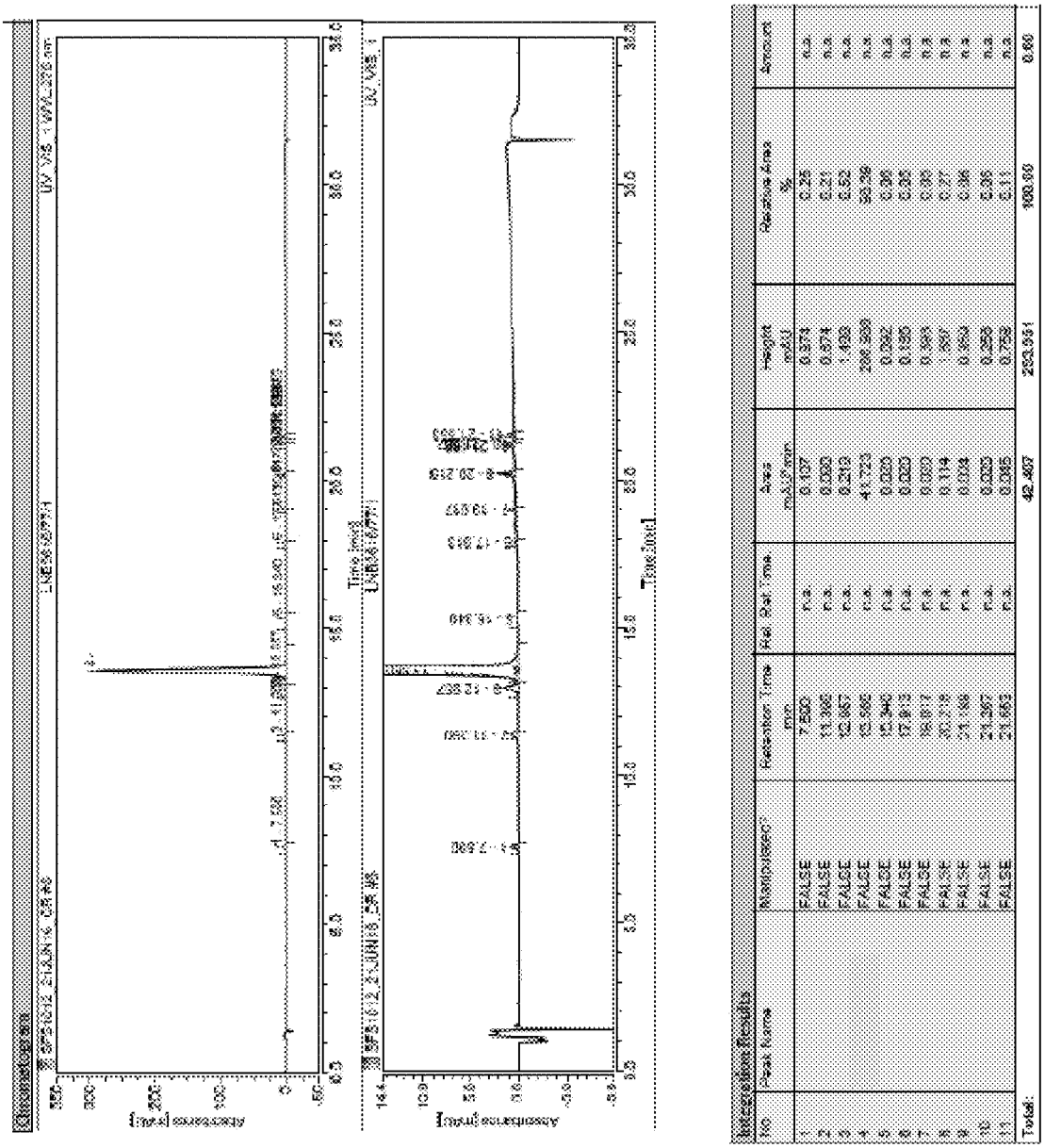

FIG. 283 sets forth a HPLC-UV chromatogram of phosphate Form 1 obtained from 500 mg scale-up.

Figure 284:
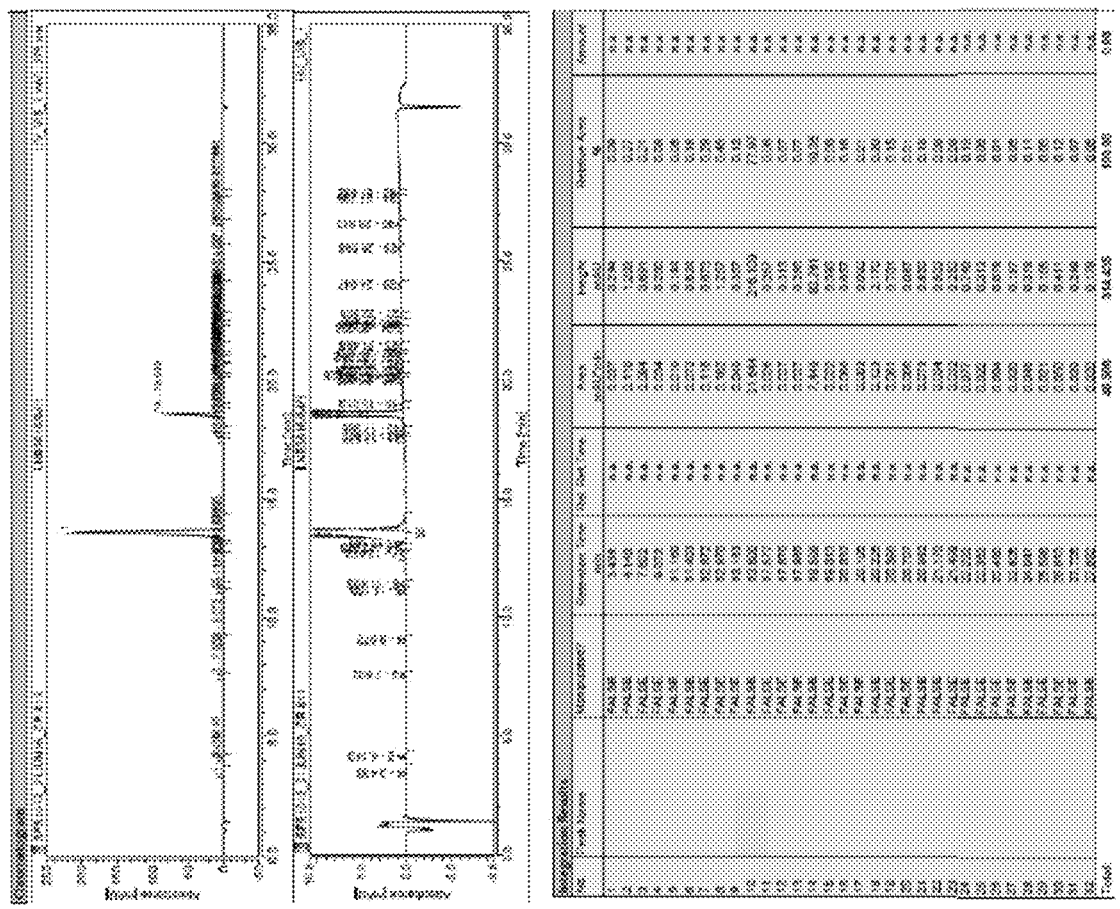

FIG. 284 sets forth a HPLC-UV chromatogram of hydrobromide Form 1 obtained from 500 mg scale-up.

Figure 285:
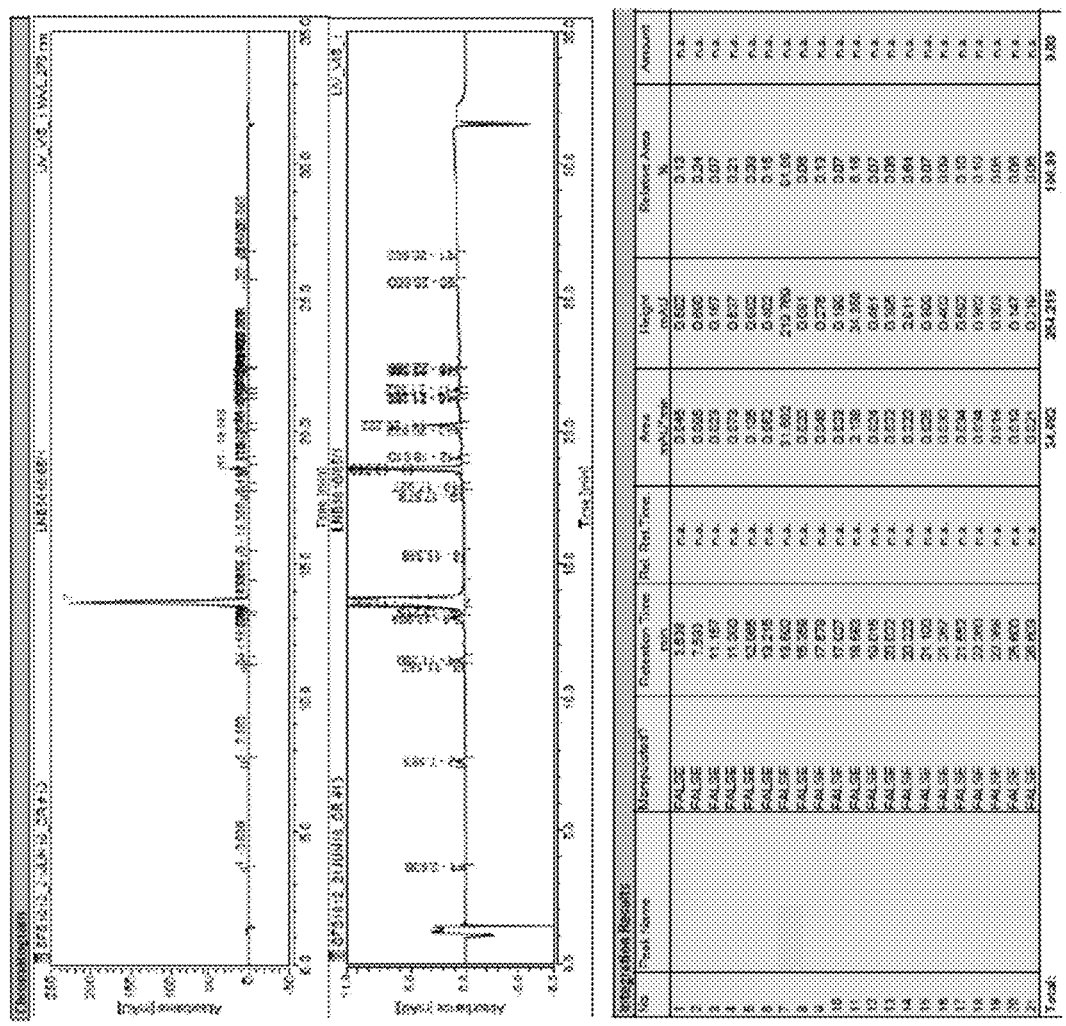

FIG. 285 sets forth a HPLC-UV chromatogram of besylate Form 1 obtained from 500 mg scale-up.

DETAILED DESCRIPTION

Solid Forms

Amorphous Form

The present application provides solid forms of (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone free base (Compound A) of the following structure:

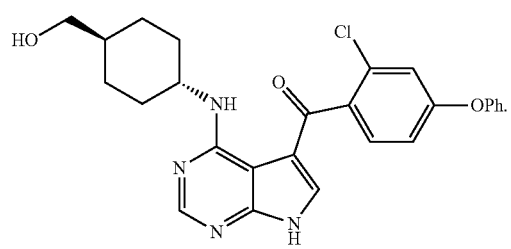 [SMILES: O=C(c1ccc(Oc2ccccc2)cc1Cl)c1c[nH]c2ncnc(N[C@H]3CC[C@H](CO)CC3)c12]

Figure 6:
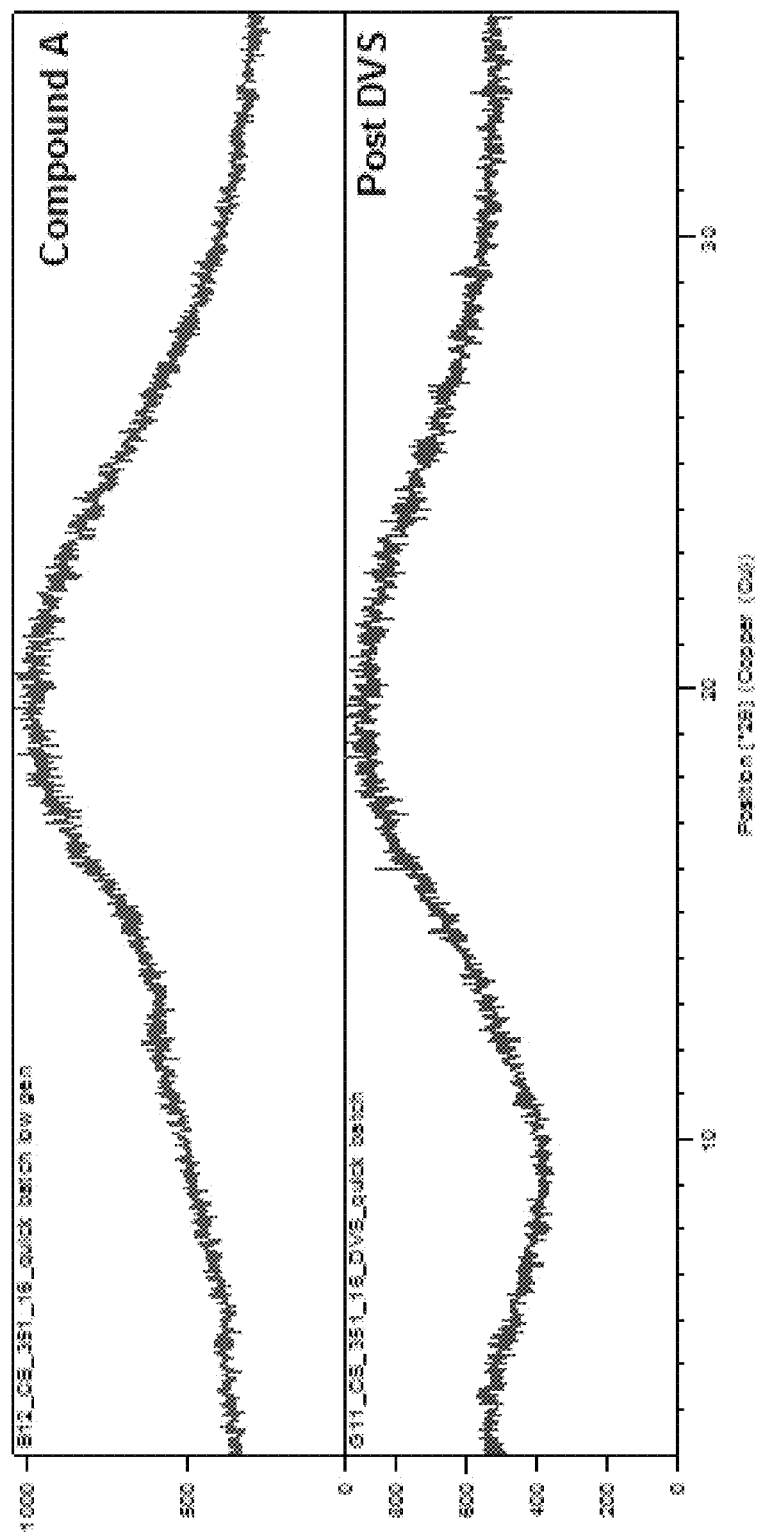
FIG. 6 sets forth XRPD patterns of an amorphous form of Compound A before (top panel) and after (bottom panel) DVS.
Figure 50:
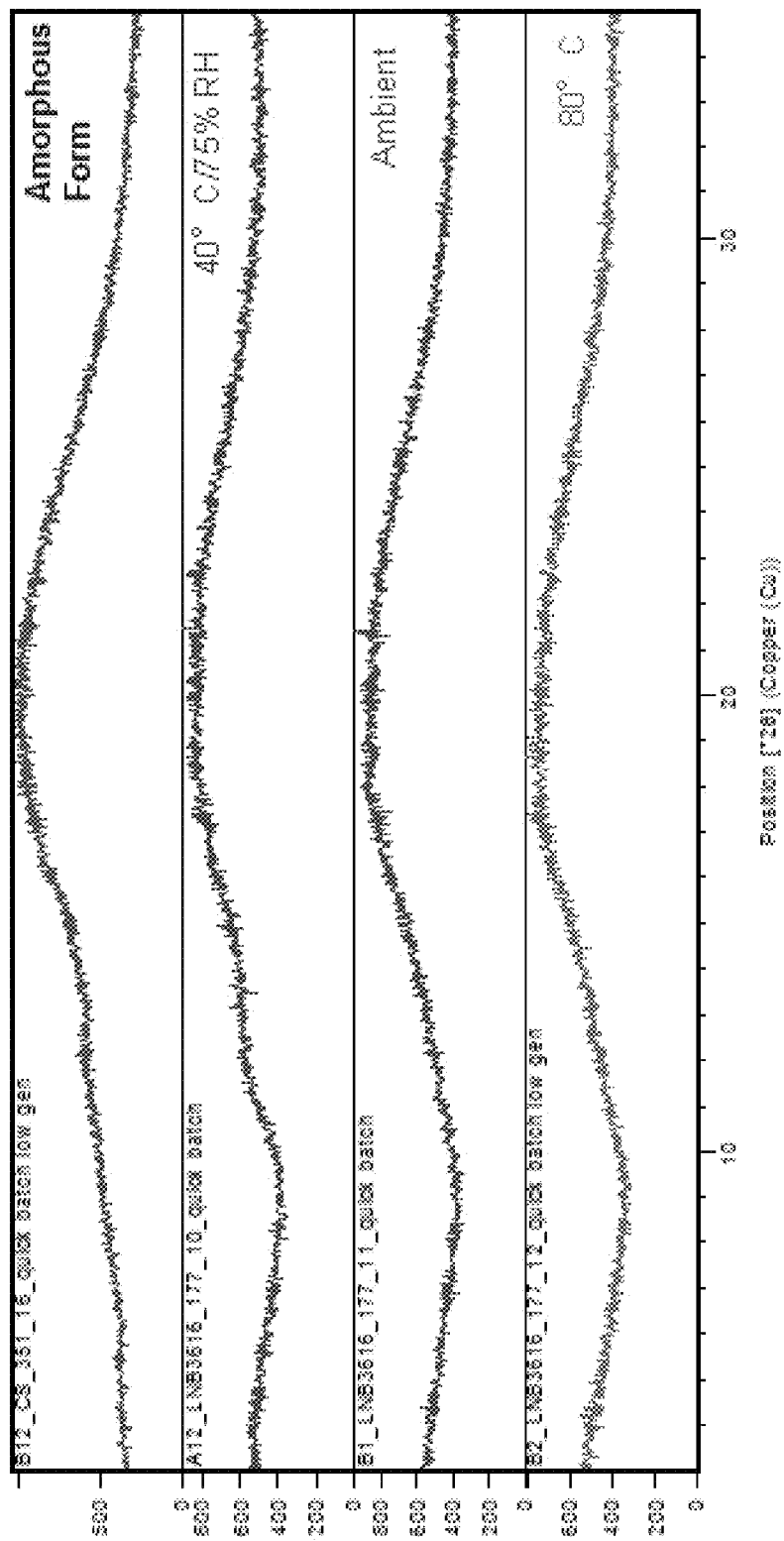
FIG. 50 sets forth XRPD patterns of an amorphous form of Compound A before (top panel) and after storage at: i) 40° C./75% relative humidity (RH) (second row from top), ii) ambient (approximately 25° C.) (third row from top), and iii) 80° C. (bottom panel).

In one embodiment, the present application provides an amorphous form of Compound A. In one embodiment, the amorphous form of Compound A is characterized by an XRPD pattern substantially similar to that set forth in FIG. 1, FIG. 6, or FIG. 50. In one embodiment, the amorphous form of Compound A is characterized by an XRPD pattern substantially similar to that set forth in FIG. 1.

In one embodiment, the amorphous form of Compound A is characterized by an endothermic event with onset at approximately 226° C. as measured by differential thermal analysis (DTA) or differential scanning calorimetry (DSC). In one embodiment, the amorphous form of Compound A is characterized by an endothermic event with a peak between approximately 228° C. and approximately 229° C. as measured by DTA or DSC. In one embodiment, the amorphous form of Compound A is characterized by an exothermic event with onset between approximately 179° C. and approximately 181° C. as measured by DTA or DSC. In one embodiment, the amorphous form of Compound A is characterized by an exothermic event with a peak between approximately 185° C. and approximately 189° C. as measured by DTA or DSC.

In one embodiment, the amorphous form of Compound A is characterized by an endothermic event with onset at approximately 226° C. as measured by DTA. In one embodiment, the amorphous form of Compound A is characterized by an endothermic event with a peak at approximately 228° C. as measured by DTA. In one embodiment, the amorphous form of Compound A is characterized by an exothermic event with onset at approximately 181° C. as measured by DTA. In one embodiment, the amorphous form of Compound A is characterized by an exothermic event with a peak at approximately 189° C. as measured by DTA. In one embodiment, the amorphous form of Compound A is characterized by a DTA thermogram substantially similar to that set forth in FIG. 3.

In one embodiment, the amorphous form of Compound A is characterized by an endothermic event with onset at approximately 226° C. as measured by DSC. In one embodiment, the amorphous form of Compound A is characterized by an endothermic event with a peak at approximately 229° C. as measured by DSC. In one embodiment, the amorphous form of Compound A is characterized by an exothermic event with onset at approximately 179° C. as measured by DSC. In one embodiment, the amorphous form of Compound A is characterized by an exothermic event with a peak at approximately 185° C. as measured by DSC. In one embodiment, the amorphous form of Compound A is characterized by a DSC thermogram substantially similar to that set forth in FIG. 4.

In one embodiment, the amorphous form of Compound A is characterized by weight losses of approximately 1.3% between about 25° C. and about 190° C. and approximately 0.5% between about 200° C. and about 270° C., as measured by thermogravimetric analysis (TGA).

In one embodiment, the amorphous form of Compound A is hygroscopic. In one embodiment, the amorphous form of Compound A displays moderate hygroscopicity between 0 and 70% relative humidity (RH) at 25° C. (e.g., about 0.5% w/w water uptake to about 3.0% w/w water uptake). In one embodiment, the amorphous form of Compound A displays significant hygroscopicity between 70% relative humidity (RH) and 90% relative humidity (RH) at 25° C. (e.g., about 2.0% w/w water uptake to about 5.0% w/w water uptake). In one embodiment, the amorphous form of Compound A displays significant hygroscopicity at 90% relative humidity (RH) at 25° C. (e.g., about 3.9% w/w water uptake).

In one embodiment, the amorphous form of Compound A is stable (e.g., no decrease in HPLC area % purity or form changes) under various storage conditions. In one embodiment, the amorphous form of Compound A is stable (e.g., no decrease in HPLC area % purity or form changes) between approximately 20° C. and approximately 90° C. (e.g., 22° C., 25° C., 40° C., or 80° C.) for at least one week, preferably at least two weeks, preferably at least three weeks, preferably at least one month, preferably at least two months, preferably at least three months, preferably at least four months, preferably at least six months, preferably at least one year. In one embodiment, the amorphous form of Compound A is stable (e.g., no decrease in HPLC area % purity or form changes) between approximately 20% relative humidity (RH) and approximately 98% relative humidity (RH) (e.g., 40% RH, 60% RH, 75% RH, or 96% RH) for at least one week, preferably at least two weeks, preferably at least three weeks, preferably at least one month, preferably at least two months, preferably at least three months, preferably at least four months, preferably at least six months, preferably at least one year. In one embodiment, the amorphous form of Compound A is stable (e.g., no decrease in HPLC area % purity or form changes) under 40° C./75% relative humidity (RH) for at least one week, preferably at least two weeks, preferably at least three weeks, preferably at least one month, preferably at least two months, preferably at least three months, preferably at least four months, preferably at least six months, preferably at least one year.

Crystalline Forms

In one embodiment, the present application provides crystalline forms of Compound A. In one embodiment, the present application provides polymorphs of Compound A. In one embodiment, the crystalline form of Compound A is a solvate. In one embodiment, the crystalline form of Compound A is a mono-solvate. In one embodiment, the crystalline form of Compound A is a hemi-solvate. In one embodiment, the crystalline form of Compound A is a hydrate. In one embodiment, the crystalline form of Compound A is a mono-hydrate. In one embodiment, the crystalline form of Compound A is a hemi-hydrate.

In one embodiment, the crystalline form of Compound A is an acetone solvate, an acetonitrile solvate, a methyl acetate solvate, an ethyl acetate solvate, a methyl ethyl ketone solvate, or a N-methyl-2-pyrrolidone solvate. In one embodiment, the crystalline form of Compound A is a mono-acetone solvate, a mono-acetonitrile solvate, a mono-methyl acetate solvate, a mono-ethyl acetate solvate, a mono-methyl ethyl ketone solvate, or a mono-N-methyl-2-pyrrolidone solvate. In one embodiment, the crystalline form of Compound A is a hemi-acetone solvate, a hemi-acetonitrile solvate, a hemi-methyl acetate solvate, a hemi-ethyl acetate solvate, a hemi-methyl ethyl ketone solvate, or a hemi-N-methyl-2-pyrrolidone solvate.

In one embodiment, the crystalline form of Compound A is a tetrahydrofuran (THF) solvate or a 2-methyltetrahydrofuran (2-Me-THF) solvate. In one embodiment, the crystalline form of Compound A is a mono-tetrahydrofuran (THF) solvate or a mono-2-methyltetrahydrofuran (2-Me-THF) solvate. In one embodiment, the crystalline form of Compound A is a hemi-tetrahydrofuran (THF) solvate or a hemi-2-methyltetrahydrofuran (2-Me-THF) solvate.

Form 1

In one embodiment, the present application provides a Form 1 polymorph of Compound A ("Form 1") characterized by an XRPD pattern comprising peaks at approximately 8.0, 22.9, and 25.0° 2θ using Cu Kα radiation. In one embodiment, Form 1 is characterized by an XRPD pattern comprising peaks at approximately 5.8, 8.0, 18.0, 22.9, and 25.0° 2θ using Cu Kα radiation. In one embodiment, Form 1 is characterized by an XRPD pattern comprising peaks at approximately 5.8, 8.0, 14.0, 15.7, 17.2, 17.4, 18.0, 19.7, 19.9, 22.0, 22.9, 23.1, and 25.0° 2θ using Cu Kα radiation. In one embodiment, Form 1 is characterized by an XRPD pattern comprising peaks at approximately 5.8, 8.0, 12.3, 14.0, 15.5, 15.7, 17.2, 17.4, 18.0, 19.7, 19.9, 21.0, 22.0, 22.2, 22.9, 23.1, 24.6, 25.0, 26.0, 26.9, and 29.7° 2θ using Cu Kα radiation. In one embodiment, Form 1 is characterized by an XRPD pattern comprising peaks at approximately the positions shown in the table below:

| Peak List | | | | |
|---|---|---|---|---|
| Pos. [°2θ] | Height [cts] | FWHM Left [°2θ] | d-spacing [Å] | Rel. Int. [%] |
| 5.7874 | 2444.00 | 0.0768 | 15.27114 | 57.97 |
| 8.0235 | 4215.96 | 0.0768 | 11.01952 | 100.00 |
| 8.5802 | 56.77 | 0.1535 | 10.30580 | 1.35 |
| 11.0115 | 120.93 | 0.1535 | 8.03513 | 2.87 |
| 11.5802 | 489.04 | 0.0895 | 7.64180 | 11.60 |
| 12.2899 | 918.25 | 0.0640 | 7.20203 | 21.78 |
| 13.9752 | 1897.10 | 0.0895 | 6.33711 | 45.00 |
| 14.7317 | 168.20 | 0.1535 | 6.01335 | 3.99 |
| 15.5247 | 1158.31 | 0.0768 | 5.70791 | 27.47 |
| 15.6895 | 2189.78 | 0.1151 | 5.64832 | 51.94 |
| 17.2003 | 2316.55 | 0.0895 | 5.15545 | 54.95 |
| 17.3935 | 1353.70 | 0.1023 | 5.09864 | 32.11 |
| 18.0358 | 2736.60 | 0.0895 | 4.91847 | 64.91 |
| 18.4444 | 277.47 | 0.1023 | 4.81042 | 6.58 |
| 18.8348 | 408.63 | 0.0512 | 4.71160 | 9.69 |
| 19.7307 | 1292.72 | 0.0895 | 4.49963 | 30.66 |
| 19.8810 | 2004.40 | 0.0895 | 4.46595 | 47.54 |
| 20.9791 | 1259.52 | 0.1023 | 4.23461 | 29.87 |
| 22.0128 | 1281.05 | 0.0640 | 4.03804 | 30.39 |
| 22.1774 | 801.38 | 0.0768 | 4.00844 | 19.01 |
| 22.8561 | 2851.34 | 0.1023 | 3.89093 | 67.63 |
| 23.1096 | 2011.69 | 0.0768 | 3.84882 | 47.72 |
| 24.2374 | 591.64 | 0.0768 | 3.67221 | 14.03 |
| 24.5675 | 833.93 | 0.1151 | 3.62362 | 19.78 |
| 24.9619 | 2940.44 | 0.1279 | 3.56725 | 69.75 |
| 26.0135 | 805.19 | 0.1151 | 3.42538 | 19.10 |
| 26.3284 | 486.87 | 0.0640 | 3.38513 | 11.55 |
| 26.9060 | 1006.38 | 0.0640 | 3.31375 | 23.87 |
| 27.7514 | 497.59 | 0.1023 | 3.21470 | 11.80 |
| 28.1483 | 350.34 | 0.1535 | 3.17026 | 8.31 |
| 29.1264 | 672.66 | 0.1279 | 3.06599 | 15.96 |
| 29.6538 | 806.03 | 0.1023 | 3.01265 | 19.12 |
| 29.9468 | 379.92 | 0.1023 | 2.98384 | 9.01 |
| 31.4175 | 358.94 | 0.2303 | 2.84744 | 8.51 |
| 32.2607 | 464.50 | 0.1535 | 2.77491 | 11.02 |
| 33.4252 | 218.45 | 0.2047 | 2.68086 | 5.18 |
| 34.4119 | 221.80 | 0.2047 | 2.60621 | 5.26 |

In one embodiment, Form 1 is characterized by an XRPD pattern substantially similar to that set forth in FIG. 8, FIG. 20, FIG. 25, FIG. 28, FIG. 29, FIG. 30, FIG. 39, or FIG. 57. In one embodiment, Form 1 is characterized by an XRPD pattern substantially similar to that set forth in FIG. 8, FIG.

Figure 28:
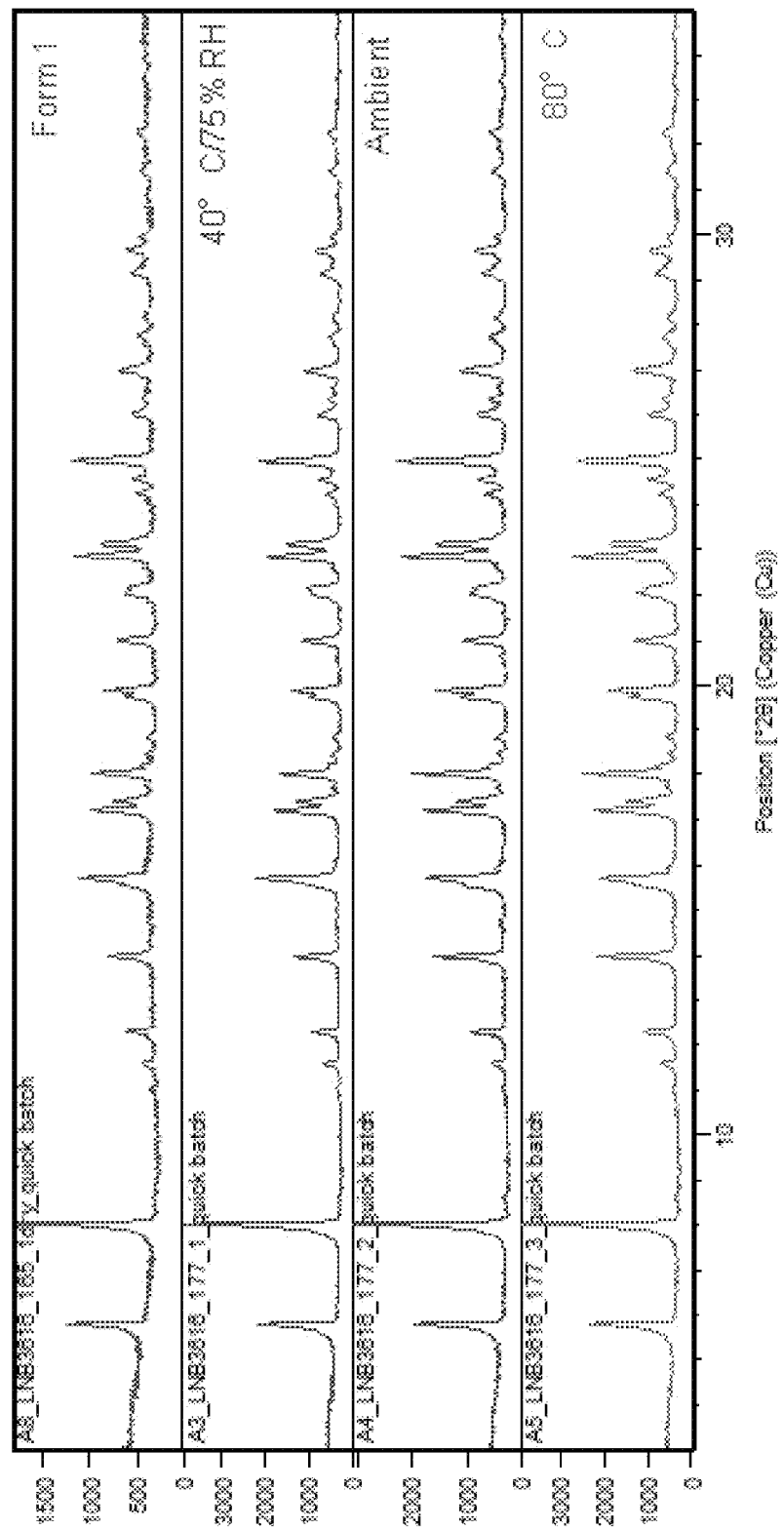
FIG. 28 sets forth XRPD patterns of Form 1 before (top panel) and after storage at: i) 40° C./75% relative humidity (RH) (second row from top), ii) ambient (approximately 25° C.) (third row from top), and iii) 80° C. (bottom panel).
Figure 29:
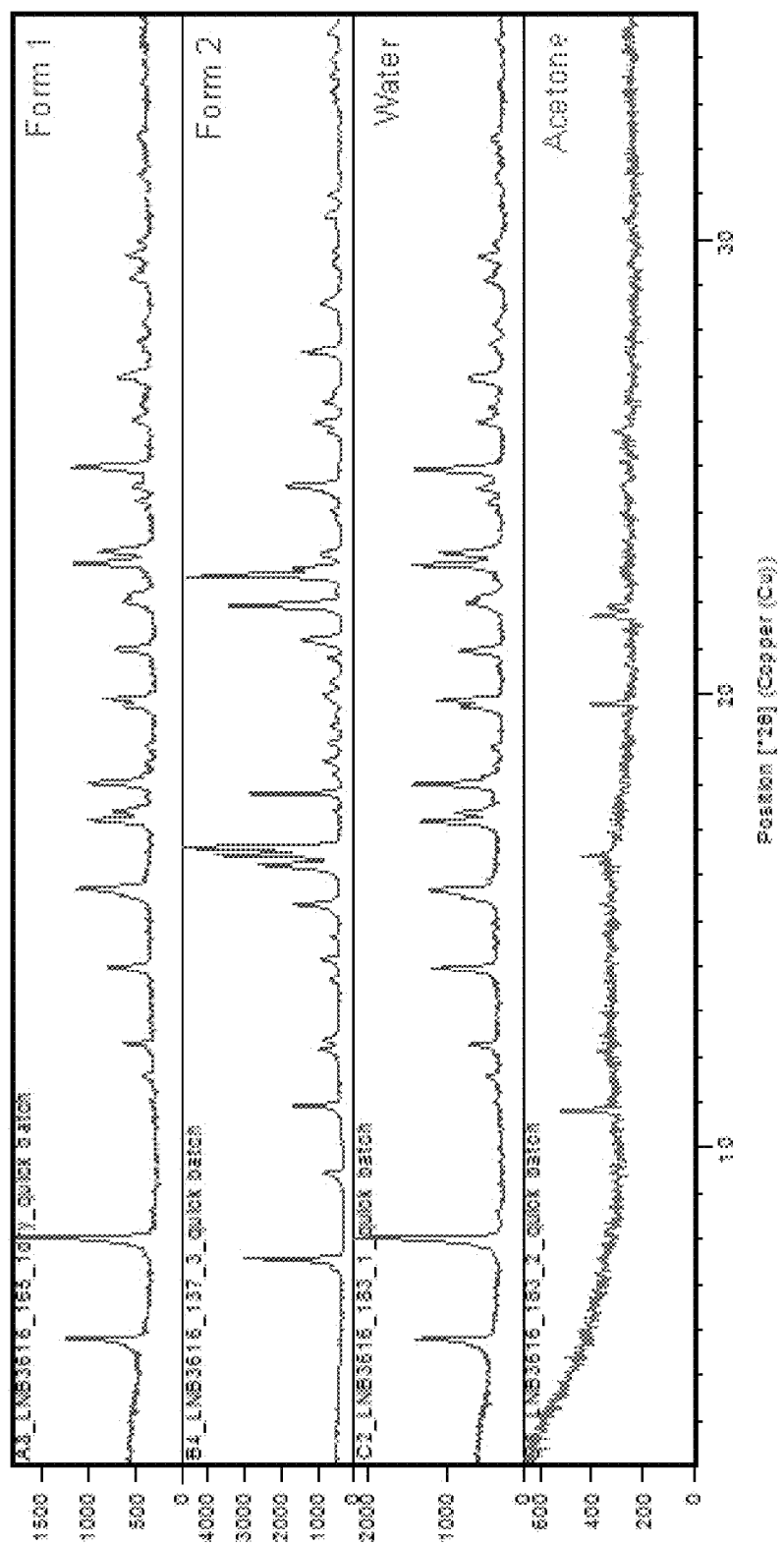
FIG. 29 sets forth XRPD patterns of Form 1 (top panel) and Form 2 (second row from top) as reference samples and Form 1 after aqueous solubility determination (third row from top) and after acetone solubility determination (bottom panel).
Figure 57:
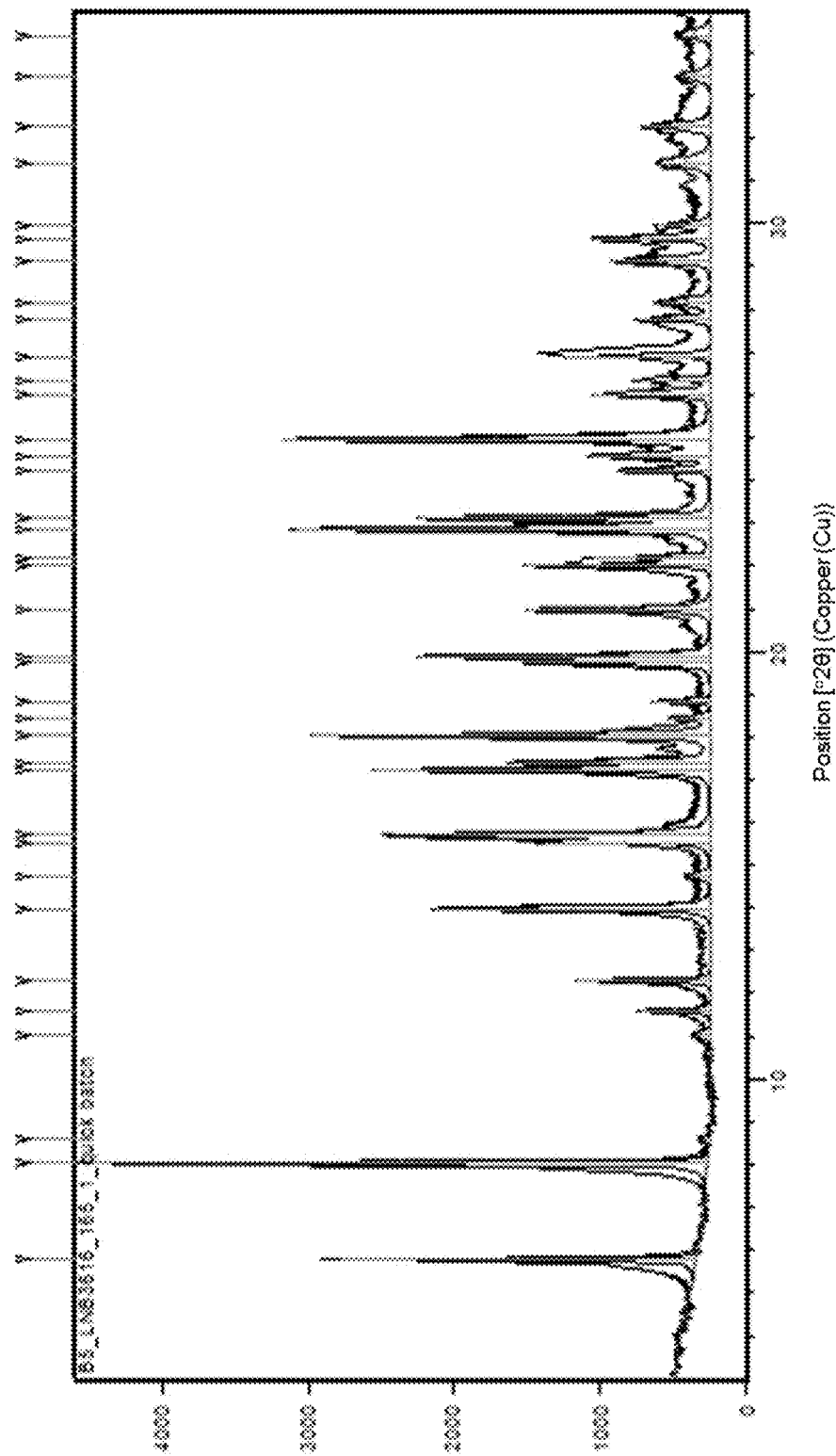
FIG. 57 sets forth an XRPD pattern of Form 1 from temperature cycling in 2-propanol.
Figure 58:
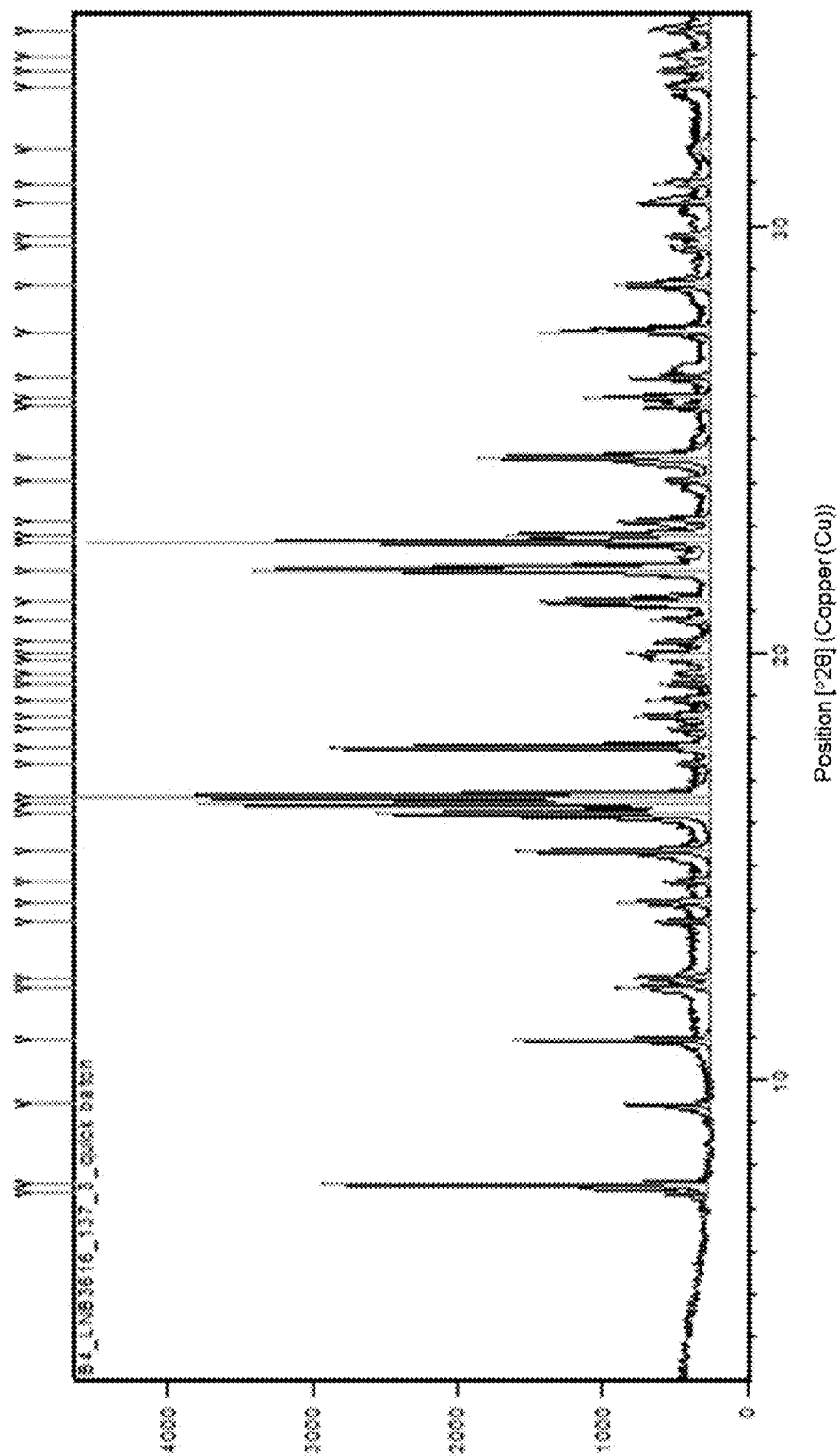
FIG. 58 sets forth an XRPD pattern of Form 2 from temperature cycling in acetone.

20, FIG. 28, FIG. 29, or FIG. 57. In one embodiment, Form 1 is characterized by an XRPD pattern substantially similar to that set forth in FIG. 57.

In one embodiment, Form 1 is characterized by endothermic events with onset between approximately 208° C. and approximately 230° C. as measured by DTA or DSC. In one embodiment, Form 1 is characterized by an exothermic event with onset between approximately 210° C. and approximately 230° C. as measured by DTA or DSC.

In one embodiment, Form 1 is characterized by 2 to 3 endothermic events and an exothermic event between approximately 210° C. and approximately 230° C. as measured by DTA. In one embodiment, Form 1 is characterized by 2 endothermic events and an exothermic event between approximately 210° C. and approximately 230° C. as measured by DTA. In one embodiment, Form 1 is characterized by 3 endothermic events and an exothermic event between approximately 210° C. and approximately 230° C. as measured by DTA. In one embodiment, Form 1 is characterized by an exothermic event with a peak at approximately 221° C. as measured by DTA. In one embodiment, Form 1 is characterized by endothermic events with onsets at approximately 210° C. and approximately 213° C. as measured by DTA. In one embodiment, Form 1 is characterized by endothermic events with peaks at approximately 211° C., approximately 216° C., and approximately 228° C. as measured by DTA. In one embodiment, Form 1 is characterized by a DTA thermogram substantially similar to that set forth in FIG. 11 or FIG. 22. In one embodiment, Form 1 is characterized by a DTA thermogram substantially similar to that set forth in FIG. 11. In one embodiment, Form 1 is characterized by a DTA thermogram substantially similar to FIG. 22.

Figure 23:
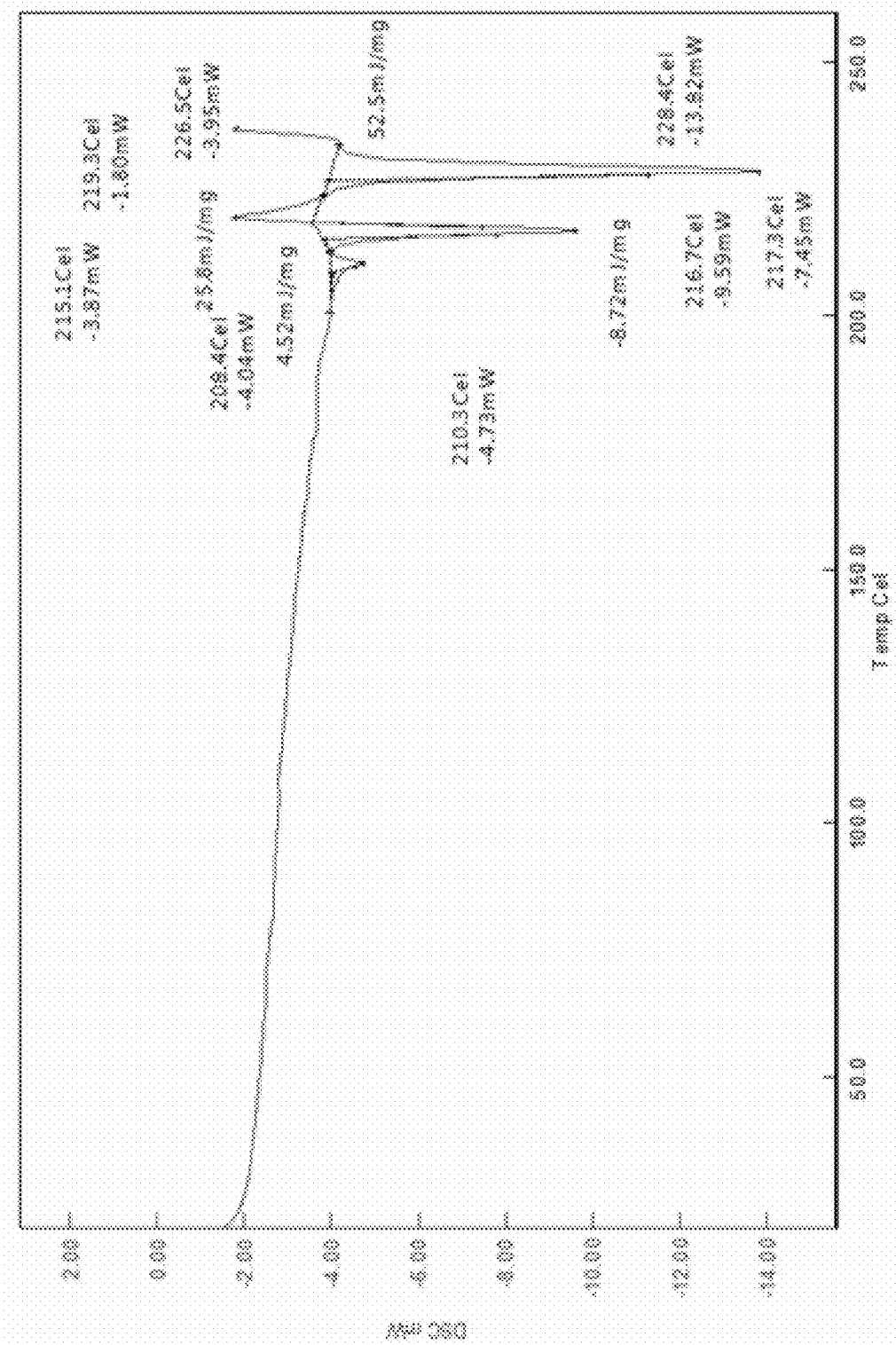
FIG. 23 sets forth a thermal analysis by DSC of Form 1.

In one embodiment, Form 1 is characterized by endothermic events with onsets at approximately 208° C., approximately 215° C., and approximately 227° C. as measured by DSC. In one embodiment, Form 1 is characterized by endothermic events with peaks at approximately 210° C., approximately 217° C., and approximately 228° C. as measured by DSC. In one embodiment, Form 1 is characterized by an exothermic event with onset at approximately 217° C. as measured by DSC. In one embodiment, Form 1 is characterized by an exothermic event with peak at approximately 219° C. as measured by DSC. In one embodiment, Form 1 is characterized by a DSC thermogram substantially similar to that set forth in FIG. 23.

In one embodiment, Form 1 shows a weight loss of between approximately 0.1% and approximately 0.3% between approximately 25° C. and approximately 300° C. as measured by TGA. In one embodiment, Form 1 shows a weight loss of approximately 0.3% between approximately 25° C. and approximately 170° C. as measured by TGA. In one embodiment, Form 1 shows a weight loss of approximately 0.1% between approximately 25° C. and approximately 300° C. as measured by TGA.

In one embodiment, Form 1 is non-hygroscopic. In one embodiment, Form 1 displays non-hygroscopicity between 0% and 90% relative humidity (RH) at approximately 25° C. (e.g., less than 0.2% w/w water uptake). In one embodiment, Form 1 displays non-hygroscopicity between 0% and 70% relative humidity (RH) at approximately 25° C. (e.g., less than 0.2% w/w water uptake).

In one embodiment, Form 1 is stable (e.g., no decrease in HPLC area % purity or form changes) under various storage conditions. In one embodiment, Form 1 is stable (e.g., no decrease in HPLC area % purity or form changes) between approximately 20° C. and approximately 90° C. (e.g., 22° C., 25° C., 40° C., or 80° C.) for at least one week, preferably at least two weeks, preferably at least three weeks, preferably at least one month, preferably at least two months, preferably at least three months, preferably at least four months, preferably at least six months, preferably at least one year. In one embodiment, Form 1 is stable (e.g., no decrease in HPLC area % purity or form changes) between approximately 20% relative humidity (RH) and approximately 98% relative humidity (RH) (e.g., 40% RH, 60% RH, 75% RH, or 96% RH) for at least one week, preferably at least two weeks, preferably at least three weeks, preferably at least one month, preferably at least two months, preferably at least three months, preferably at least four months, preferably at least six months, preferably at least one year. In one embodiment, Form 1 is stable (e.g., no decrease in HPLC area % purity or form changes) under 40° C./75% relative humidity (RH) for at least one week, preferably at least two weeks, preferably at least three weeks, preferably at least one month, preferably at least two months, preferably at least three months, preferably at least four months, preferably at least six months, preferably at least one year.

In one embodiment, Form 1 is not soluble in an aqueous solution.

In one embodiment, Form 1 is not a hydrate. In one embodiment, Form 1 is not a solvate.

In one embodiment, Form 1 is an anhydrous solid form.

In one embodiment, Form 1 is a non-hygroscopic solid form.

In one embodiment, Form 1 is an anhydrous and non-hygroscopic solid form.

In one embodiment, Form 1 is prepared by slurrying Compound A (e.g., an amorphous form of Compound A) in a solvent. In one embodiment, Form 1 is prepared by slurrying Compound A (e.g., an amorphous form of Compound A) in a solvent selected from the group consisting of anisole, dichloromethane, ethanol, 2-ethoxy ethanol, methanol, 2-methyltetrahydrofuran (2-Me-THF), methyl isobutyl ketone, 1-propanol, 2-propanol, a mixture of 2-propanol and water (e.g., 90:10 v/v), toluene, water, and mixtures thereof. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25°

C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 1 is prepared by dissolving Compound A (e.g., an amorphous form of Compound A) in a solvent, followed by slow evaporation of the solvent. In one embodiment, Form 1 is prepared by dissolving compound A (e.g., an amorphous form of Compound A) in a solvent selected from the group consisting of anisole, 1-butanol, dimethylformamide (DMF), dimethylsulfoxide (DMSO), ethanol, 2-ethoxy ethanol, methanol, 2-methyltetrahydrofuran (2-Me-THF), methyl isobutyl ketone, 1-propanol, 2-propanol, a mixture of 2-propanol and water (e.g., 90:10 v/v), and mixtures thereof, followed by slow evaporation of the solvent. In one embodiment, the evaporation is conducted at ambient temperature (e.g., approximately 20° C. to approximately 25° C.). In one embodiment, preparation of Form 1 further comprises heating the sample. In one embodiment, preparation of Form 1 further comprises heating the sample to or above approximately 40° C. In one embodiment, the evaporation is conducted with continuous agitation.

In one embodiment, Form 1 is prepared by a method comprising dissolving Compound A (e.g., an amorphous form of Compound A) in a first solvent to form a solution; and adding an anti-solvent to the solution to form a slurry; and optionally isolating Form 1. In one embodiment, the anti-solvent is added with continuous agitation. In one embodiment, the first solvent is selected from the group consisting of acetic acid, dichloromethane, dimethylformamide (DMF), 1,4-dioxane, 2-ethoxy ethanol, toluene, and mixtures thereof. In one embodiment, the anti-solvent is selected from the group consisting of tert-butyl methyl ether (t-BME), isobutyl acetate, and heptane. In one embodiment, the anti-solvent is tert-butyl methyl ether (t-BME). In one embodiment, the addition of anti-solvent is conducted at ambient temperature (e.g., approximately 20° C. to approximately 25° C.). In one embodiment, the addition of anti-solvent is conducted at ambient temperature (e.g., approximately 20° C. to approximately 25° C.) and the first solvent is selected from the group consisting of dichloromethane, dimethylformamide (DMF), 2-ethoxy ethanol, toluene, and mixtures thereof. In one embodiment, preparation of Form 1 further comprises heating the solution during the addition of anti-solvent. In one embodiment, preparation of Form 1 further comprises heating the solution during the addition of anti-solvent to or above approximately 50° C. In one embodiment, preparation of Form 1 further comprises heating the solution during the addition of anti-solvent to or above approximately 50° C. and the first solvent is selected from the group consisting of acetic acid, dichloromethane, dimethylformamide (DMF), 1,4-dioxane, 2-ethoxy ethanol, and mixtures thereof.

In one embodiment, Form 1 is prepared by a method comprising: dissolving Compound A (e.g., an amorphous form of Compound A) in a solvent to form a solution; and cooling the solution; and optionally isolating Form 1. In one embodiment, the solvent is 1-propanol. In one embodiment, the solution is cooled to a temperature of approximately or below 10° C., or approximately or below 5° C. In one embodiment, the solution is cooled to approximately 2° C. In one embodiment, the cooling comprises multiple steps of cooling. In one embodiment, the cooling comprises cooling to a first temperature, followed by cooling to a second temperature. In one embodiment, the cooling comprises cooling to approximately 5° C., or approximately 2° C., or approximately 0° C., then cooling to approximately −15° C., or approximately −18° C., or approximately −20° C. In one embodiment, the cooling comprises a third step of cooling to a third temperature. In one embodiment, the cooling is conducted with continuous agitation.

In one embodiment, a mixture of Form 1 and Form 2 is prepared by slurrying Compound A (e.g., an amorphous form of Compound A) in a solvent. In one embodiment, a mixture of Form 1 and Form 2 is prepared by slurrying Compound A (e.g., an amorphous form of Compound A) in acetonitrile. In one embodiment, a mixture of Form 1 and Form 4 is prepared by slurrying Compound A (e.g., an amorphous form of Compound A) in a solvent. In one embodiment, a mixture of Form 1 and Form 4 is prepared by slurrying Compound A (e.g., an amorphous form of Compound A) in 1-butanol. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, a mixture of Form 1 and Form 4 is prepared by a method comprising: dissolving Compound A (e.g., an amorphous form of Compound A) in a first solvent to form a solution; and adding an anti-solvent to the solution to form a slurry. In one embodiment, the first solvent is a mixture of 2-propanol and water (e.g., 90:10 v/v). In one embodiment, a mixture of Form 1 and Form 5 is prepared by a method comprising: dissolving Compound A (e.g., an amorphous form of Compound A) in a first solvent to form a solution; and adding an anti-solvent to the solution to form a slurry. In one embodiment, the first solvent is 2-methyltetrahydrofuran (2-Me-THF). In one embodiment, a mixture of Form 1 and Form 6 is prepared by a method comprising: dissolving Compound A (e.g., an amorphous form of Compound A) in a first solvent to form a solution; and adding an anti-solvent to the solution to form a slurry. In one embodiment, the first solvent is N-methyl-2-pyrrolidone (NMP). In one embodiment, the anti-solvent is tert-butyl methyl ether (t-BME) or isobutyl acetate. In one embodiment, the anti-solvent is tert-butyl methyl ether (t-BME). In one embodiment, Compound A (e.g., an amorphous form of Compound A) is dissolved in the first solvent at ambient temperature (e.g., approximately 20° C. to approximately 25° C.). In one embodiment, Compound A (e.g., an amorphous form of Compound A) is dissolved in the first solvent at or above approximately 50° C. In one embodiment, the anti-solvent is added with continuous agitation. In one embodiment, the anti-solvent is added at ambient temperature (e.g., approximately 20° C. to approximately 25° C.). In one embodiment, the anti-solvent is added at or above approximately 50° C. In one embodiment, the anti-solvent is added with continuous agitation.

In one embodiment, Form 1 is converted to the Form 2 polymorph of Compound A upon slurrying in a solvent. In one embodiment, Form 4 is converted to the Form 1 polymorph of Compound A upon slurrying in a solvent. In one embodiment, Form 1 is converted to the Form 2 polymorph of Compound A upon slurrying in acetone. In one embodiment, Form 4 is converted to the Form 1 polymorph of Compound A upon slurrying in acetone. In one embodiment, the slurrying is conducted at ambient temperature (e.g., approximately 20° C. to approximately 25° C.). In one embodiment, the slurrying is conducted at or above approximately 40° C. In one embodiment, the slurrying is conducted with continuous agitation.

Form 2

In one embodiment, the present application provides a Form 2 polymorph of Compound A ("Form 2") characterized by an XRPD pattern comprising peaks at approximately 16.4, 16.6, and 22.6° 2θ using Cu Kα radiation. In one embodiment, Form 2 is characterized by an XRPD pattern comprising peaks at approximately 7.6, 16.4, 16.6, 21.9, and 22.6° 2θ using Cu Kα radiation. In one embodiment, Form 2 is characterized by an XRPD pattern comprising peaks at approximately 7.6, 10.9, 15.4, 16.2, 16.4, 16.6, 17.8, 21.2, 21.9, 22.6, 22.8, 24.6, and 27.5° 2θ using Cu Kα radiation. In one embodiment, Form 2 is characterized by an XRPD pattern comprising peaks at approximately 7.6, 10.9, 12.2, 14.2, 15.4, 16.2, 16.4, 16.6, 17.8, 21.2, 21.9, 22.6, 22.8, 24.6, 26.0, 27.5 and 28.6° 2θ using Cu Kα radiation. In one embodiment, Form 2 is characterized by an XRPD pattern comprising peaks at approximately the positions shown in the table below:

Peak List

| Pos. [°2θ] | Height [cts] | FWHM Left [°2θ] | d-spacing [Å] | Rel. Int. [%] |
|---|---|---|---|---|
| 7.3586 | 298.73 | 0.0384 | 12.01373 | 6.79 |
| 7.5672 | 2653.76 | 0.0512 | 11.68295 | 60.28 |
| 9.4401 | 591.03 | 0.0512 | 9.36881 | 13.42 |
| 10.9354 | 1358.21 | 0.0512 | 8.09090 | 30.85 |
| 12.1742 | 621.26 | 0.0512 | 7.27026 | 14.11 |
| 12.3997 | 532.23 | 0.0640 | 7.13850 | 12.09 |
| 13.7060 | 349.98 | 0.0640 | 6.46095 | 7.95 |
| 14.1619 | 641.31 | 0.0768 | 6.25400 | 14.57 |
| 14.6418 | 291.47 | 0.0768 | 6.05006 | 6.62 |
| 15.3597 | 1324.82 | 0.0768 | 5.76887 | 30.09 |
| 16.2254 | 2289.41 | 0.0768 | 5.46295 | 52.00 |
| 16.4451 | 3547.50 | 0.0640 | 5.39047 | 80.58 |
| 16.6238 | 4402.45 | 0.0895 | 5.33292 | 100.00 |
| 17.4197 | 222.73 | 0.0768 | 5.09102 | 5.06 |
| 17.8023 | 2584.90 | 0.0768 | 4.98247 | 58.72 |
| 18.2407 | 282.63 | 0.0768 | 4.86370 | 6.42 |
| 18.5264 | 512.95 | 0.0895 | 4.78933 | 11.65 |
| 18.9177 | 418.13 | 0.0640 | 4.69112 | 9.50 |
| 19.2843 | 342.96 | 0.0512 | 4.60277 | 7.79 |
| 19.5268 | 209.65 | 0.1023 | 4.54615 | 4.76 |
| 19.8679 | 392.69 | 0.1535 | 4.46888 | 8.92 |
| 20.0003 | 544.97 | 0.0640 | 4.43958 | 12.38 |
| 20.2670 | 362.75 | 0.1023 | 4.38176 | 8.24 |
| 20.7901 | 414.63 | 0.0384 | 4.27269 | 9.42 |
| 21.2013 | 1137.73 | 0.1407 | 4.19073 | 25.84 |
| 21.9454 | 3143.18 | 0.1151 | 4.05029 | 71.40 |
| 22.5952 | 4315.00 | 0.0384 | 3.93525 | 98.01 |
| 22.7640 | 1398.19 | 0.0640 | 3.90646 | 31.76 |
| 23.0951 | 606.17 | 0.0512 | 3.85119 | 13.77 |
| 24.0310 | 299.29 | 0.1023 | 3.70328 | 6.80 |
| 24.5783 | 1591.68 | 0.1151 | 3.62205 | 36.15 |
| 25.7590 | 453.88 | 0.0512 | 3.45864 | 10.31 |
| 25.9660 | 855.83 | 0.0512 | 3.43154 | 19.44 |
| 26.4353 | 552.27 | 0.0512 | 3.37168 | 12.54 |
| 27.5153 | 1203.77 | 0.0512 | 3.24175 | 27.34 |
| 28.5993 | 645.58 | 0.1023 | 3.12129 | 14.66 |
| 29.5181 | 258.05 | 0.1023 | 3.02619 | 5.86 |
| 29.7531 | 286.09 | 0.1023 | 3.00283 | 6.50 |
| 30.5176 | 439.64 | 0.0640 | 2.92932 | 9.99 |
| 30.9707 | 380.01 | 0.0640 | 2.88749 | 8.63 |
| 31.7700 | 133.94 | 0.3070 | 2.81665 | 3.04 |
| 33.2544 | 284.96 | 0.1279 | 2.69424 | 6.47 |
| 33.6031 | 354.69 | 0.1023 | 2.66707 | 8.06 |
| 33.9742 | 346.15 | 0.1023 | 2.63878 | 7.86 |
| 34.5559 | 406.19 | 0.0640 | 2.59568 | 9.23 |

In one embodiment, Form 2 is characterized by an XRPD pattern substantially similar to that set forth in FIG. 8, FIG. 29, FIG. 49, or FIG. 58. In one embodiment, Form 2 is characterized by an XRPD pattern substantially similar to that set forth in FIG. 58.

In one embodiment, Form 2 is characterized by endothermic events with onsets at approximately 116° C., approximately 207° C., approximately 215° C., and approximately 228° C. as measured by DTA. In one embodiment, Form 2 is characterized by endothermic events with peaks at approximately 122° C., approximately 211° C., approximately 217° C., and approximately 230° C. as measured by DTA. In one embodiment, Form 2 is characterized by a DTA thermogram substantially similar to that set forth in FIG. 12.

In one embodiment, Form 2 shows weight losses of approximately 0.1% between about 25° C. and about 90° C., approximately 5.4% (e.g., about one half a mole equivalent of acetone approximately 5.27%) between about 90° C. and about 150° C., and approximately 0.2% between 150° C. and 250° C., as measured by TGA.

In one embodiment, Form 2 is a solvate. In one embodiment, Form 2 is a hemi-solvate. In one embodiment, Form 2 is an acetone solvate or an acetonitrile solvate. In one embodiment, Form 2 is an acetone hemi-solvate or an acetonitrile hemi-solvate. In one embodiment, Form 2 is an acetone solvate. In one embodiment, Form 2 is an acetone hemi-solvate. In one embodiment, Form 2 is an acetonitrile solvate. In one embodiment, Form 2 is an acetonitrile hemi-solvate.

In one embodiment, Form 2 is prepared by slurrying an amorphous form of Compound A in a solvent. In one embodiment, the amorphous form of Compound A is slurried in acetone, methyl acetate, ethyl acetate, or methyl ethyl ketone, or a mixture thereof. In one embodiment, the amorphous form of Compound A is slurried in acetone. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 2 is prepared by a method comprising dissolving Compound A (e.g., an amorphous form of Compound A) in a first solvent to form a solution; and adding an anti-solvent to the solution to form a slurry; and optionally isolating Form 2. In one embodiment, the anti-solvent is added with continuous agitation. In one embodiment, the first solvent is selected acetone and methyl ethyl ketone. In one embodiment, the anti-solvent is heptane. In one embodiment, the addition of anti-solvent is conducted at ambient temperature (e.g., approximately 20° C. to approximately 25° C.). In one embodiment, preparation of Form 2 further comprises heating the solution during the addition of anti-solvent. In one embodiment, preparation of Form 2 further comprises heating the solution during the addition of anti-solvent to or above approximately 50° C. In one embodiment, preparation of Form 2 further comprises heating the solution during the addition of anti-solvent to or above approximately 50° C.

In one embodiment, a mixture of Form 2 and Form 6 is prepared by dissolving Compound A (e.g., an amorphous form of Compound A) in a solvent, followed by slow evaporation of the solvent from the solution. In one embodiment, a mixture of Form 2 and Form 6 is prepared by dissolving Compound A (e.g., an amorphous form of Compound A) in N-methyl-2-pyrrolidone (NMP), followed by slow evaporation of N-methyl-2-pyrrolidone (NMP) from the solution. In one embodiment, the evaporation is conducted at ambient temperature (e.g., approximately 20° C. to approximately 25° C.). In one embodiment, preparation of a mixture of Form 2 and Form 6 further comprises heating the sample. In one embodiment, preparation of a mixture of Form 2 and Form 6 further comprises heating the sample to or above approximately 40° C. In one embodiment, the evaporation is conducted with continuous agitation.

In one embodiment, a mixture of Form 2 and Form 1 is prepared by slurrying Compound A (e.g., an amorphous form of Compound A) in a solvent. In one embodiment, a mixture of Form 2 and Form 1 is prepared by slurrying Compound A (e.g., an amorphous form of Compound A) in acetonitrile. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 1 is converted to the Form 2 polymorph of Compound A upon slurrying in a solvent. In one embodiment, Form 8 is converted to the Form 2 polymorph of Compound A upon slurrying in a solvent. In one embodiment, Form 1 is converted to the Form 2 polymorph of Compound A upon slurrying in acetone. In one embodiment, Form 8 is converted to the Form 2 polymorph of Compound A upon slurrying in acetone. In one embodiment, the slurrying is conducted at ambient temperature (e.g., approximately 20° C. to approximately 25° C.). In one embodiment, the slurrying is conducted at or above approximately 40° C. In one embodiment, the slurrying is conducted with continuous agitation.

Form 3

In one embodiment, the present application provides a Form 3 polymorph of Compound A ("Form 3") characterized by an XRPD pattern comprising peaks at approximately 16.0, 16.4, and 22.2° 2θ using Cu Kα radiation. In one embodiment, Form 3 is characterized by an XRPD pattern comprising peaks at approximately 14.0, 14.8, 16.0, 16.4, and 22.2° 2θ using Cu Kα radiation. In one embodiment, Form 3 is characterized by an XRPD pattern comprising peaks at approximately 14.0, 14.8, 16.0, 16.4, 19.8, 22.2, and 24.7° 2θ using Cu Kα radiation. In one embodiment, Form 3 is characterized by an XRPD pattern comprising peaks at approximately 14.0, 14.8, 16.0, 16.4, 18.4, 19.8, 22.2, 24.7, 27.3, and 28.6° 2θ using Cu Kα radiation. In one embodiment, Form 3 is characterized by an XRPD pattern comprising peaks at approximately the positions shown in the table below:

| Peak List | | | | |
|---|---|---|---|---|
| Pos. [°2θ] | Height [cts] | FWHM Left [°2θ] | d-spacing [Å] | Rel. Int. [%] |
| 14.0147 | 130.52 | 0.0512 | 6.31934 | 58.29 |
| 14.7952 | 151.66 | 0.0768 | 5.98767 | 67.73 |
| 15.9645 | 184.14 | 0.1023 | 5.55164 | 82.24 |
| 16.3846 | 223.90 | 0.2047 | 5.41023 | 100.00 |
| 18.3563 | 44.05 | 0.6140 | 4.83331 | 19.67 |
| 19.8022 | 106.35 | 0.2047 | 4.48354 | 47.50 |
| 22.2163 | 197.99 | 0.1535 | 4.00151 | 88.43 |
| 24.6927 | 69.24 | 0.3070 | 3.60553 | 30.92 |
| 27.3059 | 50.40 | 0.3070 | 3.26612 | 22.51 |
| 28.6128 | 22.83 | 0.3070 | 3.11985 | 10.20 |

Figure 59:
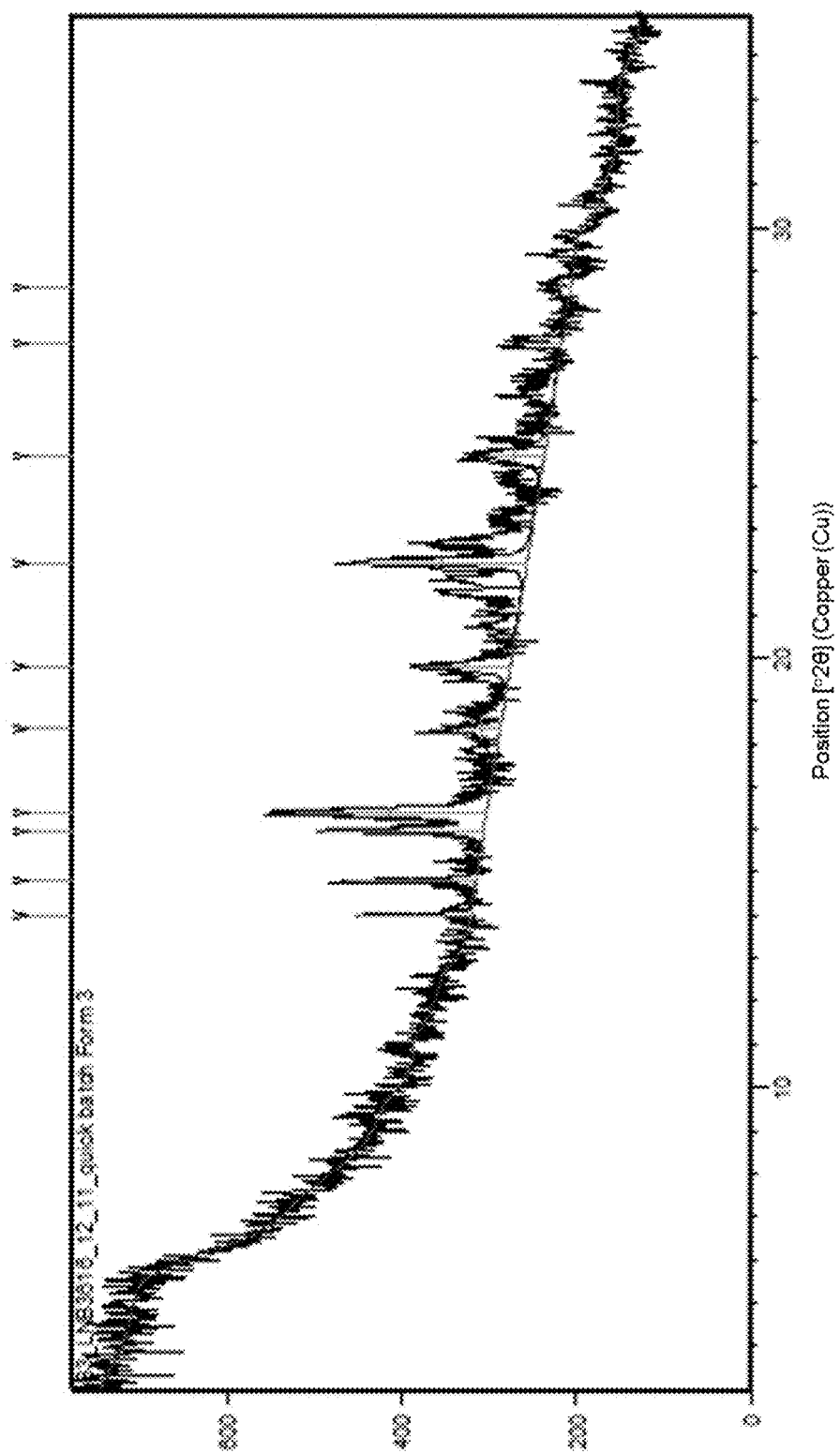
FIG. 59 sets forth an XRPD pattern of Form 3.
Figure 60:
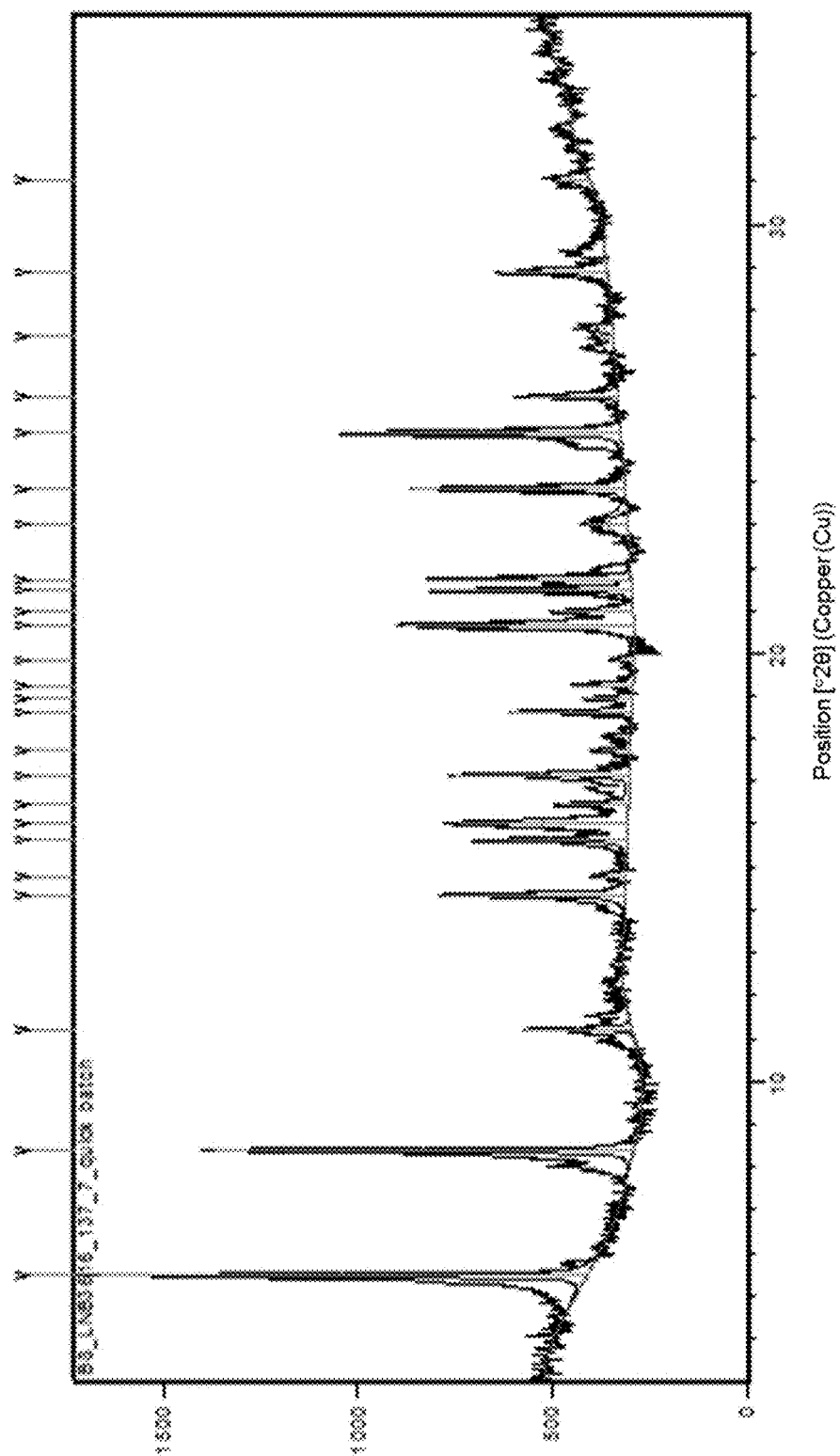
FIG. 60 sets forth an XRPD pattern of Form 4 from temperature cycling in diisopropyl ether (DIPE).

In one embodiment, Form 3 is characterized by an XRPD pattern substantially similar to that set forth in FIG. 59.

In one embodiment, Form 3 is prepared by slurrying Compound A (e.g., an amorphous form of Compound A) in a solvent. In one embodiment, Compound A (e.g., an amorphous form of Compound A) is slurried in ethyl acetate. In one embodiment, the slurrying is conducted at ambient temperature (e.g., approximately 20° C. to approximately 25° C.). In one embodiment, the slurrying is conducted at or above approximately 40° C. In one embodiment, the slurrying is conducted with continuous agitation.

In one embodiment, Form 3 is prepared by dissolving Compound A (e.g., an amorphous form of Compound A) in a solvent, followed by slow evaporation of the solvent from the solution. In one embodiment, Form 3 is prepared by dissolving Compound A (e.g., an amorphous form of Compound A) in ethyl acetate (EtOAc), followed by slow evaporation of ethyl acetate from the solution. In one embodiment, the evaporation is conducted at ambient temperature (e.g., approximately 20° C. to approximately 25° C.). In one embodiment, preparation of Form 3 further comprises heating the sample. In one embodiment, preparation of Form 3 further comprises heating the sample to or above approximately 40° C. In one embodiment, the evaporation is conducted with continuous agitation.

Form 4

In one embodiment, the present application provides a Form 4 polymorph of Compound A ("Form 4") characterized by an XRPD pattern comprising peaks at approximately 5.5, 8.4, and 25.1° 2θ using Cu Kα radiation. In one embodiment, Form 4 is characterized by an XRPD pattern comprising peaks at approximately 5.5, 8.4, 20.7, 23.8, and 25.1° 2θ using Cu Kα radiation. In one embodiment, Form 4 is characterized by an XRPD pattern comprising peaks at approximately 5.5, 8.4, 14.3, 15.6, 16.0, 17.1, 20.7, 21.5, 21.7, 23.8, and 25.1° 2θ using Cu Kα radiation. In one embodiment, Form 4 is characterized by an XRPD pattern comprising peaks at approximately 5.5, 8.4, 11.2, 14.3, 15.6, 16.0, 16.4, 17.1, 18.6, 20.7, 21.0, 21.5, 21.7, 23.8, 25.1, 26.0, and 28.9° 2θ using Cu Kα radiation. In one embodiment, Form 4 is characterized by an XRPD pattern comprising peaks at approximately the positions shown in the table below:

| Peak List | | | | |
|---|---|---|---|---|
| Pos. [°2θ] | Height [cts] | FWHM Left [°2θ] | d-spacing [Å] | Rel. Int. [%] |
| 5.4762 | 1252.51 | 0.0768 | 16.13818 | 100.00 |
| 8.3847 | 1081.32 | 0.0768 | 10.54564 | 86.33 |
| 11.2217 | 279.25 | 0.0640 | 7.88513 | 22.29 |

-continued

| Peak List | | | | |
|---|---|---|---|---|
| Pos. [°2θ] | Height [cts] | FWHM Left [°2θ] | d-spacing [Å] | Rel. Int. [%] |
| 14.3340 | 467.76 | 0.1023 | 6.17927 | 37.35 |
| 14.7825 | 63.50 | 0.1535 | 5.99280 | 5.07 |
| 15.6227 | 396.58 | 0.0768 | 5.67233 | 31.66 |
| 16.0068 | 433.41 | 0.1791 | 5.53706 | 34.60 |
| 16.4488 | 178.52 | 0.1023 | 5.38927 | 14.25 |
| 17.1437 | 451.18 | 0.0768 | 5.17236 | 36.02 |
| 17.7390 | 80.60 | 0.1535 | 5.00010 | 6.44 |
| 18.6369 | 312.28 | 0.0640 | 4.76118 | 24.93 |
| 18.9441 | 127.75 | 0.1023 | 4.68465 | 10.20 |
| 19.2671 | 159.97 | 0.0895 | 4.60683 | 12.77 |
| 19.8444 | 47.37 | 0.1535 | 4.47411 | 3.78 |
| 20.6547 | 593.64 | 0.1535 | 4.30039 | 47.40 |
| 20.9708 | 204.82 | 0.1023 | 4.23626 | 16.35 |
| 21.4638 | 514.70 | 0.0640 | 4.14006 | 41.09 |
| 21.7371 | 530.35 | 0.0512 | 4.08863 | 42.34 |
| 23.0300 | 101.22 | 0.3582 | 3.86194 | 8.08 |
| 23.8377 | 549.93 | 0.0768 | 3.73288 | 43.91 |
| 25.1390 | 721.23 | 0.0895 | 3.54252 | 57.58 |
| 26.0061 | 227.68 | 0.0768 | 3.42634 | 18.18 |
| 27.3959 | 46.48 | 0.6140 | 3.25560 | 3.71 |
| 28.8914 | 270.83 | 0.1279 | 3.09039 | 21.62 |
| 31.0505 | 89.59 | 0.2047 | 2.88025 | 7.15 |

In one embodiment, Form 4 is characterized by an XRPD pattern substantially similar to that set forth in FIG. 8, FIG. 30, FIG. 35, FIG. 38, FIG. 39, or FIG. 60. In one embodiment, Form 4 is characterized by an XRPD pattern substantially similar to that set forth in FIG. 8, FIG. 30, FIG. 35, FIG. 38, or FIG. 60. In one embodiment, Form 4 is characterized by an XRPD pattern substantially similar to that set forth in FIG. 60.

In one embodiment, Form 4 is characterized by endothermic events with onsets between approximately 194° C. and approximately 209° C., and approximately 226° C. as measured by DTA or DSC. In one embodiment, Form 4 is characterized by an exothermic event with onset between approximately 213° C. and approximately 215° C. as measured by DTA or DSC.

In one embodiment, Form 4 is characterized by endothermic events with onsets at approximately 209° C. and approximately 226° C. as measured by DTA. In one embodiment, Form 4 is characterized by endothermic events with peaks at approximately 212° C. and approximately 228° C. as measured by DTA. In one embodiment, Form 4 is characterized by an exothermic event with onset at approximately 215° C. as measured by DTA. In one embodiment, Form 4 is characterized by an exothermic event with peak at approximately 218° C. as measured by DTA. In one embodiment, Form 4 is characterized by a DTA thermogram substantially similar to that set forth in FIG. 13 or FIG. 32. In one embodiment, Form 4 is characterized by a DTA thermogram substantially similar to that set forth in FIG. 13. In one embodiment, Form 4 is characterized by a DTA thermogram substantially similar to that set forth in FIG. 32.

Figure 33:
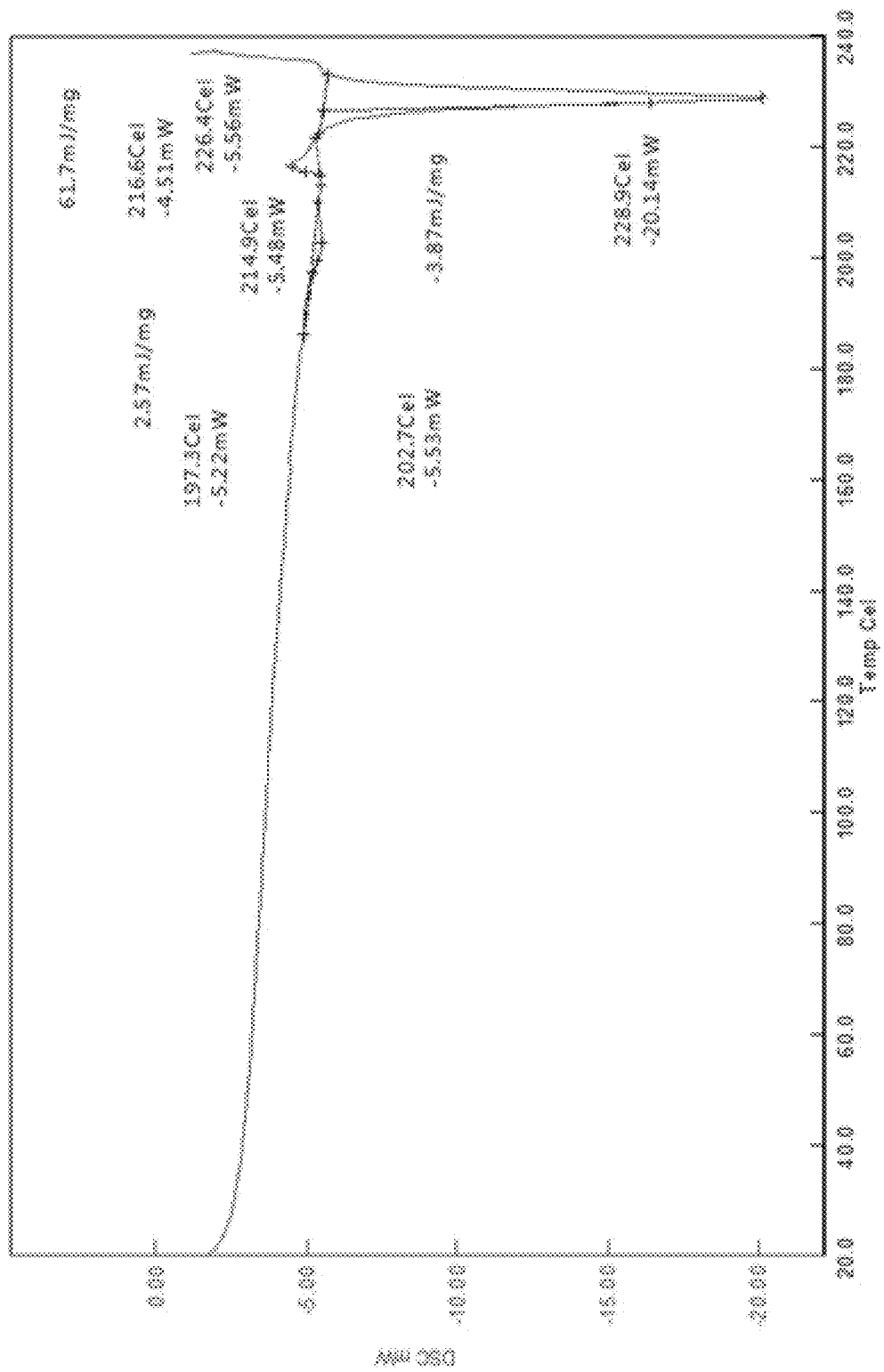
FIG. 33 sets forth a thermal analysis by DSC of Form 4.

In one embodiment, Form 4 is characterized by endothermic events with onsets at approximately 197° C. and approximately 226° C. as measured by DSC. In one embodiment, Form 4 is characterized by endothermic events with peaks at approximately 203° C. and approximately 229° C. as measured by DSC. In one embodiment, Form 4 is characterized by an exothermic event with onset at approximately 215° C. as measured by DSC. In one embodiment, Form 4 is characterized by an exothermic event with peak at approximately 217° C. as measured by DSC. In one embodiment, Form 4 is characterized by a DSC thermogram substantially similar to that set forth in FIG. 33.

In one embodiment, Form 4 shows a weight loss of between approximately 0.5% and approximately 0.7% between approximately 25° C. and approximately 300° C. as measured by TGA. In one embodiment, Form 4 shows a weight loss of approximately 0.7% between approximately 25° C. and approximately 300° C. as measured by TGA. In one embodiment, Form 4 shows a weight loss of approximately 0.5% between approximately 25° C. and approximately 300° C. as measured by TGA.

In one embodiment, Form 4 is non-hygroscopic. In one embodiment, Form 4 displays non-hygroscopicity between 0% and 90% relative humidity (RH) at approximately 25° C. (e.g., less than 0.5% w/w water uptake, less than 0.4% w/w water uptake). In one embodiment, Form 1 displays non-hygroscopicity between 0% and 70% relative humidity (RH) at approximately 25° C. (e.g., less than 0.5% w/w water uptake, less than 0.4% w/w water uptake).

In one embodiment, Form 4 is stable (e.g., no decrease in HPLC area % purity or form changes) under various storage conditions. In one embodiment, Form 4 is stable (e.g., no decrease in HPLC area % purity or form changes) between approximately 20° C. and approximately 90° C. (e.g., 22° C., 25° C., 40° C., or 80° C.) for at least one week, preferably at least two weeks, preferably at least three weeks, preferably at least one month, preferably at least two months, preferably at least three months, preferably at least four months, preferably at least six months, preferably at least one year. In one embodiment, Form 4 is stable (e.g., no decrease in HPLC area % purity or form changes) between 20% relative humidity (RH) and approximately 98% relative humidity (RH) (e.g., 40% RH, 60% RH, 75% RH, or 96% RH) for at least one week, preferably at least two weeks, preferably at least three weeks, preferably at least one month, preferably at least two months, preferably at least three months, preferably at least four months, preferably at least six months, preferably at least one year. In one embodiment, Form 4 is stable (e.g., no decrease in HPLC area % purity or form changes) under 40° C./75% relative humidity (RH) for at least one week, preferably at least two weeks, preferably at least three weeks, preferably at least one month, preferably at least two months, preferably at least three months, preferably at least four months, preferably at least six months, preferably at least one year.

In one embodiment, Form 4 is not soluble in an aqueous solution.

In one embodiment, Form 4 is not a hydrate. In one embodiment, Form 4 is not a solvate.

In one embodiment, Form 4 is an anhydrous solid form.

In one embodiment, Form 4 is a non-hygroscopic solid form.

In one embodiment, Form 4 is an anhydrous and non-hygroscopic solid form.

In one embodiment, Form 4 is prepared by slurrying Compound A (e.g., an amorphous form of Compound A) in a solvent. In one embodiment, Form 4 is prepared by slurrying Compound A (e.g., an amorphous form of Compound A) in diisopropyl ether (DIPE). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 4 is prepared by a method comprising dissolving Compound A (e.g., an amorphous form of Compound A) in a first solvent to form a solution; and adding an anti-solvent to the solution to form a slurry; and optionally isolating Form 4. In one embodiment, the anti-solvent is added with continuous agitation. In one embodiment, the first solvent is selected from the group consisting of dichloromethane, methyl isobutyl ketone, and mixtures thereof. In one embodiment, the anti-solvent is selected from the group consisting of tert-butyl methyl ether (t-BME), isobutyl acetate, and heptane. In one embodiment, the anti-solvent is heptane. In one embodiment, the addition of anti-solvent is conducted at ambient temperature (e.g., approximately 20° C. to approximately 25° C.). In one embodiment, the addition of anti-solvent is conducted at ambient temperature (e.g., approximately 20° C. to approximately 25° C.). In one embodiment, preparation of Form 4 further comprises heating the solution during the addition of anti-solvent. In one embodiment, preparation of Form 4 further comprises heating the solution during the addition of anti-solvent to or above approximately 50° C.

In one embodiment, a mixture of Form 4 and Form 1 is prepared by slurrying Compound A (e.g., an amorphous form of Compound A) in a solvent. In one embodiment, a mixture of Form 4 and Form 1 is prepared by slurrying Compound A (e.g., an amorphous form of Compound A) in 1-butanol. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C.

and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, a mixture of Form 4 and Form 1 is prepared by a method comprising: dissolving Compound A (e.g., an amorphous form of Compound A) in a first solvent to form a solution; and adding an anti-solvent to the solution to form a slurry. In one embodiment, the first solvent is a mixture of 2-propanol and water (e.g., 90:10 v/v). In one embodiment, the first solvent is 2-ethoxy ethanol and the anti-solvent is heptane. In one embodiment, a mixture of Form 4 and Form 5 is prepared by a method comprising: dissolving Compound A (e.g., an amorphous form of Compound A) in a first solvent to form a solution; and adding an anti-solvent to the solution to form a slurry. In one embodiment, the first solvent is 2-methyltetrahydrofuran (2-Me-THF). In one embodiment, the anti-solvent is tert-butyl methyl ether (t-BME) or isobutyl acetate. In one embodiment, the anti-solvent is tert-butyl methyl ether (t-BME). In one embodiment, Compound A (e.g., an amorphous form of Compound A) is dissolved in the first solvent at ambient temperature (e.g., approximately 20° C. to approximately 25° C.). In one embodiment, Compound A (e.g., an amorphous form of Compound A) is dissolved in the first solvent at or above approximately 50° C. In one embodiment, the anti-solvent is added with continuous agitation. In one embodiment, the anti-solvent is added at ambient temperature (e.g., approximately 20° C. to approximately 25° C.). In one embodiment, the anti-solvent is added at or above approximately 50° C. In one embodiment, the anti-solvent is added with continuous agitation.

In one embodiment, Form 4 is converted to the Form 1 polymorph of Compound A upon slurrying in a solvent. In one embodiment, Form 4 is converted to the Form 1 polymorph of Compound A upon slurrying in acetone. In one embodiment, the slurrying is conducted at ambient temperature (e.g., approximately 20° C. to approximately 25° C.). In one embodiment, the slurrying is conducted at or above approximately 40° C. In one embodiment, the slurrying is conducted with continuous agitation.

Form 5

In one embodiment, the present application provides a Form 5 polymorph of Compound A ("Form 5") characterized by an XRPD pattern comprising peaks at approximately 4.5, 4.7, and 20.8° 2θ using Cu Kα radiation. In one embodiment, Form 5 is characterized by an XRPD pattern comprising peaks at approximately 4.5, 4.7, 7.7, 19.1, and 20.8° 2θ using Cu Kα radiation. In one embodiment, Form 5 is characterized by an XRPD pattern comprising peaks at approximately 4.4, 4.5, 4.7, 7.7, 14.1, 16.3, 19.1, 19.9, 20.8, 21.3, and 23.2° 2θ using Cu Kα radiation. In one embodiment, Form 5 is characterized by an XRPD pattern comprising peaks at approximately 4.2, 4.4, 4.5, 4.7, 7.7, 13.0, 14.1, 16.3, 16.8, 18.7, 19.1, 19.9, 20.8, 21.3, 23.0, 23.3, 24.6, and 28.5° 2θ using Cu Kα radiation. In one embodiment, Form 5 is characterized by an XRPD pattern comprising peaks at approximately the positions shown in the table below:

| Peak List | | | | |
|---|---|---|---|---|
| Pos. [°2θ] | Height [cts] | FWHM Left [°2θ] | d-spacing [Å] | Rel. Int. [%] |
| 4.1545 | 1235.91 | 0.0384 | 21.26885 | 12.03 |
| 4.3621 | 1500.05 | 0.0512 | 20.25720 | 14.60 |
| 4.5061 | 2405.76 | 0.0384 | 19.61015 | 23.41 |
| 4.6675 | 10276.59 | 0.0768 | 18.93253 | 100.00 |
| 5.1700 | 517.94 | 0.0895 | 17.09330 | 5.04 |
| 5.4219 | 439.22 | 0.1791 | 16.29988 | 4.27 |
| 7.6925 | 1943.25 | 0.0640 | 11.49285 | 18.91 |
| 9.3248 | 540.01 | 0.0512 | 9.48439 | 5.25 |
| 9.5624 | 196.03 | 0.0768 | 9.24934 | 1.91 |
| 10.6157 | 79.04 | 0.1535 | 8.33382 | 0.77 |
| 11.1142 | 426.77 | 0.0512 | 7.96110 | 4.15 |
| 12.9799 | 865.30 | 0.0768 | 6.82069 | 8.42 |
| 14.1182 | 1297.78 | 0.0768 | 6.27322 | 12.63 |
| 14.8953 | 505.51 | 0.0895 | 5.94767 | 4.92 |
| 15.2647 | 443.32 | 0.0768 | 5.80455 | 4.31 |
| 15.9618 | 776.76 | 0.0640 | 5.55258 | 7.56 |
| 16.2546 | 1430.79 | 0.0895 | 5.45321 | 13.92 |
| 16.7593 | 1060.71 | 0.0512 | 5.29010 | 10.32 |
| 16.9997 | 447.94 | 0.1023 | 5.21584 | 4.36 |
| 17.5668 | 670.57 | 0.0640 | 5.04871 | 6.53 |
| 18.6836 | 1094.48 | 0.0895 | 4.74939 | 10.65 |
| 19.0813 | 2153.84 | 0.1151 | 4.65128 | 20.96 |
| 19.9258 | 1762.28 | 0.1279 | 4.45602 | 17.15 |
| 20.7532 | 4320.72 | 0.1023 | 4.28019 | 42.04 |
| 21.2973 | 1294.60 | 0.0895 | 4.17205 | 12.60 |
| 22.3235 | 767.86 | 0.2047 | 3.98253 | 7.47 |
| 23.0381 | 852.62 | 0.1023 | 3.86059 | 8.30 |
| 23.2376 | 1348.91 | 0.1023 | 3.82790 | 13.13 |
| 24.4076 | 643.36 | 0.0768 | 3.64699 | 6.26 |
| 24.6446 | 1247.54 | 0.0640 | 3.61245 | 12.14 |
| 25.7666 | 504.45 | 0.1791 | 3.45765 | 4.91 |
| 26.6151 | 764.11 | 0.0512 | 3.34930 | 7.44 |
| 27.7862 | 472.14 | 0.1023 | 3.21075 | 4.59 |
| 28.4642 | 1025.08 | 0.0640 | 3.13580 | 9.97 |
| 29.3519 | 211.72 | 0.1791 | 3.04295 | 2.06 |
| 30.5194 | 393.53 | 0.1791 | 2.92916 | 3.83 |
| 31.5985 | 173.36 | 0.2047 | 2.83154 | 1.69 |
| 32.4180 | 60.49 | 0.4093 | 2.76181 | 0.59 |
| 33.0511 | 92.72 | 0.2047 | 2.71034 | 0.90 |

Figure 8A:
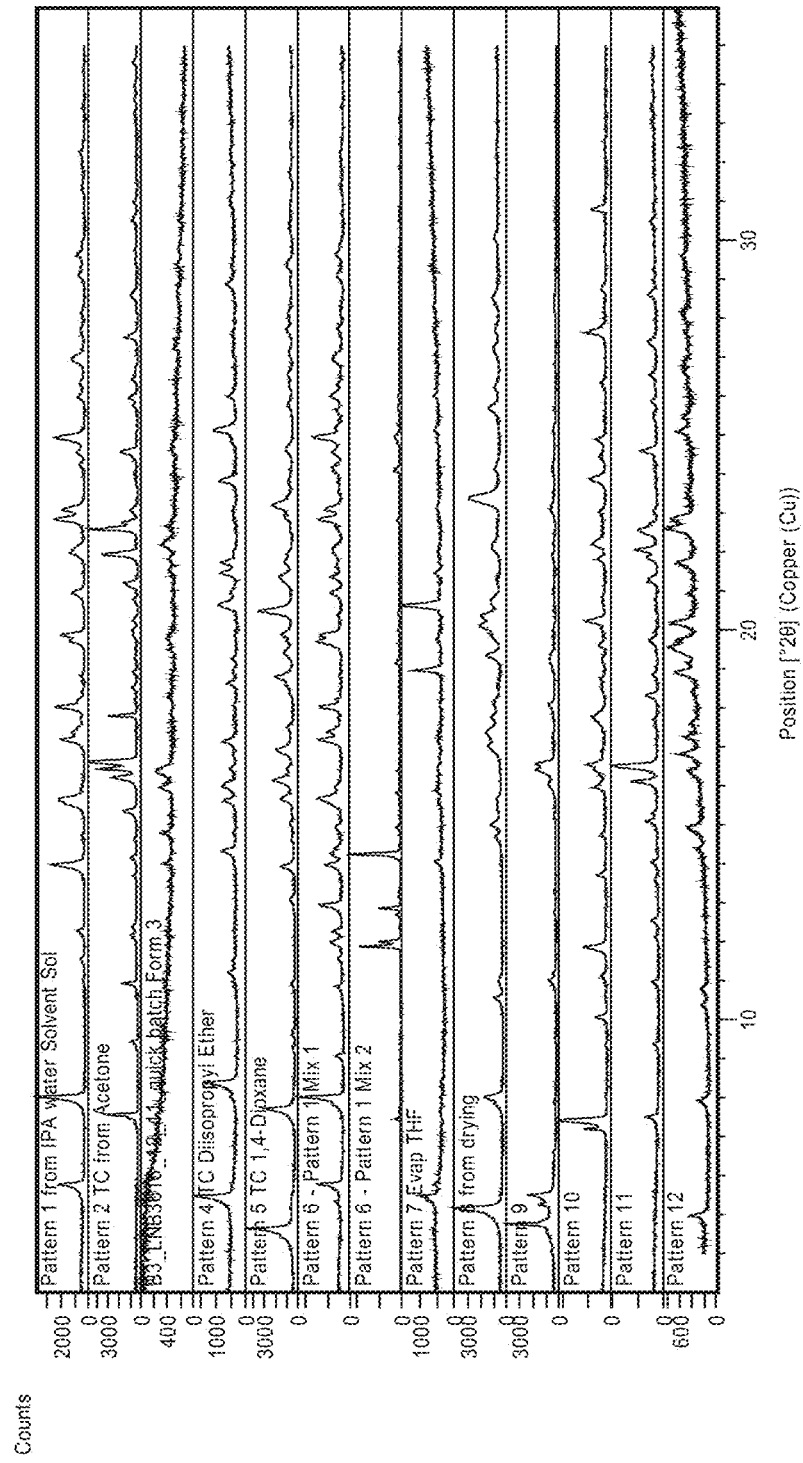
FIG. 8A sets forth comparative XRPD patterns of Form 1, Form 2, Form 3, Form 4, Form 5, Form 1 and Form 6, Form 2 and Form 6, Form 7, Form 8, Form 9, Form 10, Form 11, and Form 12 as indicated.
Figure 8B:
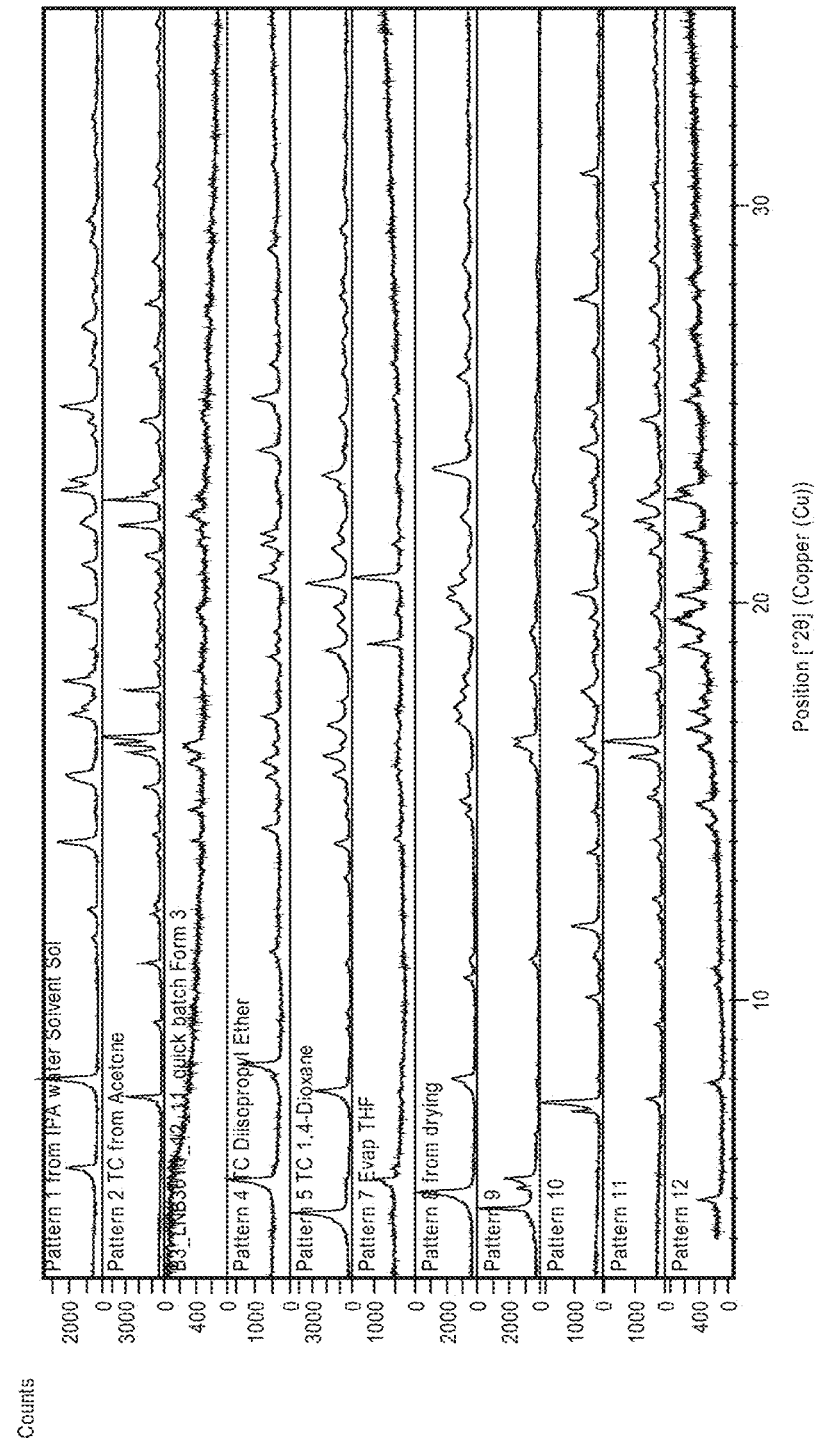
FIG. 8B sets forth comparative XRPD patterns of Form 1, Form 2, Form 3, Form 4, Form 5, Form 7, Form 8, Form 9, Form 10, Form 11, and Form 12 as indicated.
Figure 10:
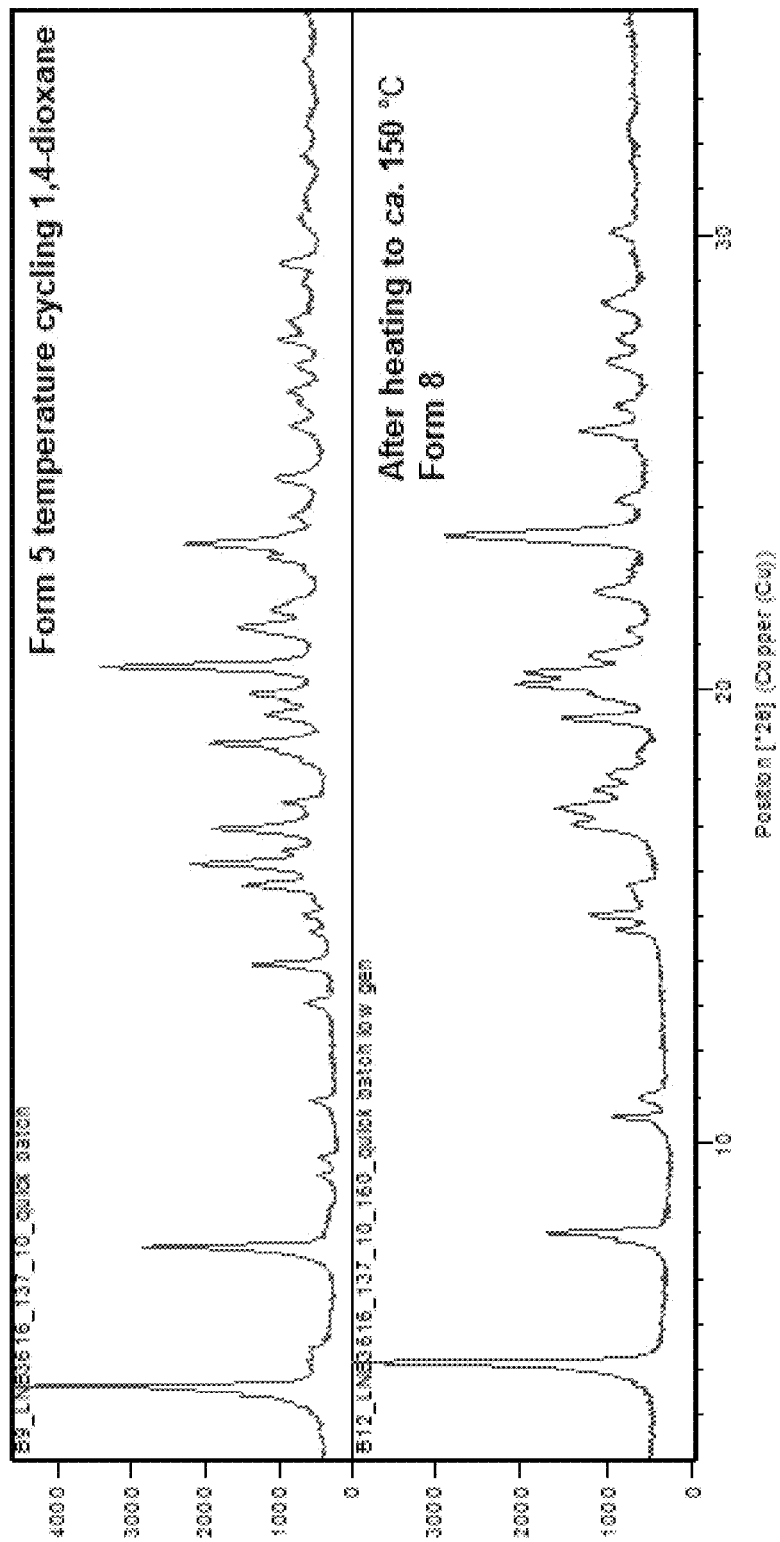
FIG. 10 sets forth XRPD patterns of Form 5 from temperature cycling in 1,4-dioxane before (top panel) and after (bottom panel) heating to approximately 150° C., after which Form 5 is desolvated to Form 8.
Figure 61:
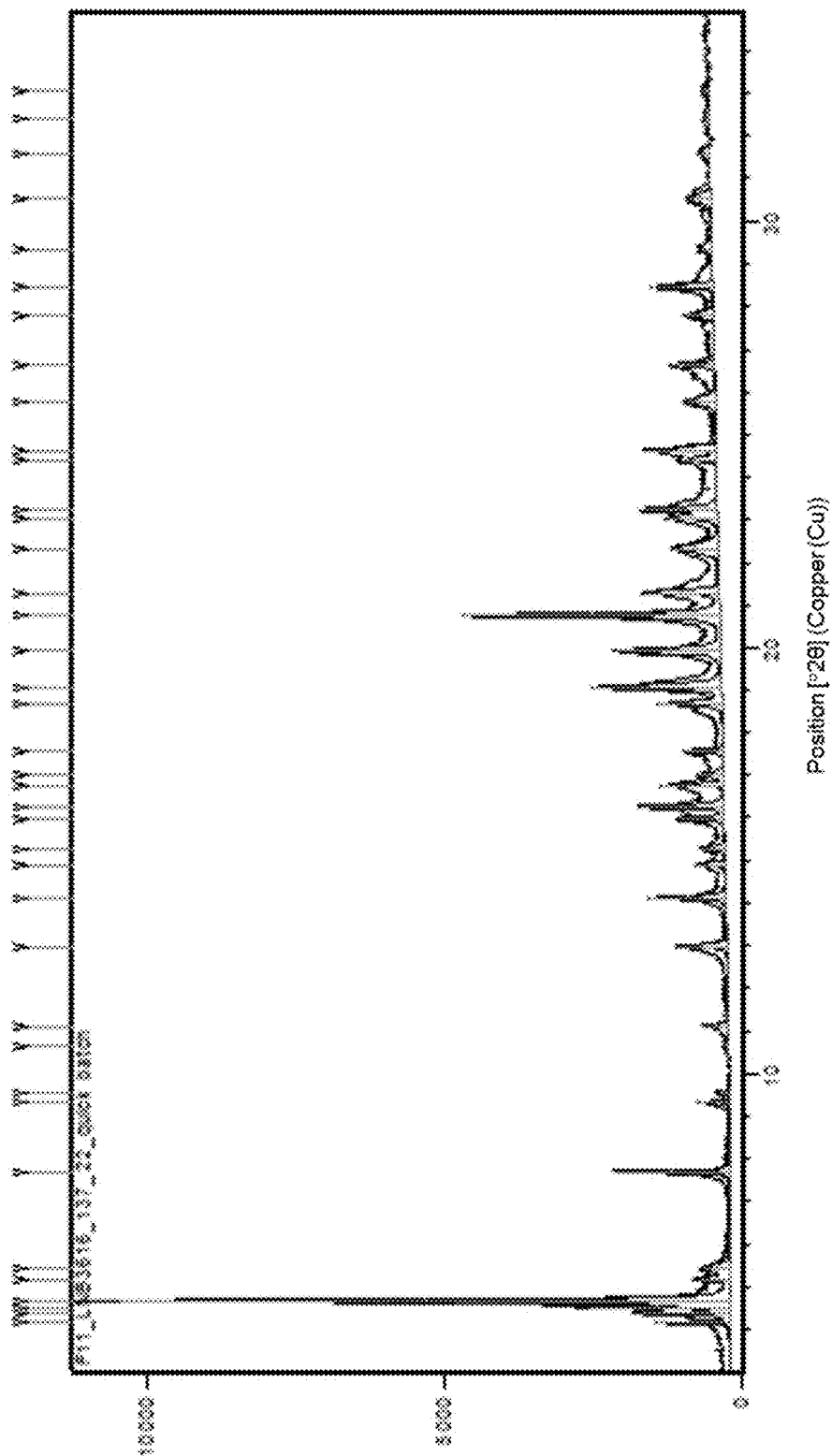
FIG. 61 sets forth an XRPD pattern of Form 5 from temperature cycling in THF.

In one embodiment, Form 5 is characterized by an XRPD pattern substantially similar to that set forth in FIG. 8, FIG. 10, or FIG. 61. In one embodiment, Form 5 is characterized by an XRPD pattern substantially similar to that set forth in FIG. 61.

In one embodiment, Form 5 is characterized by endothermic events with onset between approximately 94° C. and approximately 104° C., and between approximately 225° C. and approximately 226° C. as measured by DTA. In one embodiment, Form 5 is characterized by endothermic events with peaks between approximately 99° C. and approximately 110° C., and approximately 228° C. as measured by DTA. In one embodiment, Form 5 is characterized by endothermic events with onsets at approximately 94° C. and approximately 226° C. as measured by DTA. In one embodiment, Form 5 is characterized by endothermic events with onsets at approximately 104° C. and approximately 225° C. as measured by DTA. In one embodiment, Form 5 is characterized by endothermic events with peaks at approximately 99° C. and approximately 228° C. as measured by DTA. In one embodiment, Form 5 is characterized by endothermic events with peaks at approximately 110° C. and approximately 228° C. as measured by DTA. In one embodiment, Form 5 is characterized by an exothermic event with onset at approximately 73° C. as measured by DTA. In one embodiment, Form 5 is characterized by an exothermic event with peak at approximately 74° C. as measured by DTA. In one embodiment, Form 5 is characterized by a DTA thermogram substantially similar to FIG. 14, FIG. 15, or FIG. 16. In one embodiment, Form 5 is characterized by a DTA thermogram substantially similar to FIG. 14. In one embodiment, Form 5 is characterized by a DTA thermogram substantially similar to FIG. 15. In one embodiment, Form 5 is characterized by a DTA thermogram substantially similar to FIG. 16.

In one embodiment, Form 5 shows a weight loss of approximately 1.3% between about 25° C. and about 110° C., as measured by TGA. In one embodiment, Form 5 shows weight losses of approximately 0.1% between about 25° C. and about 70° C. and approximately 2.4% between about 70° C. and about 140° C., as measured by TGA. In one embodiment, Form 5 shows a weight loss of approximately 2.2% between about 25° C. and about 150° C., as measured by TGA.

In one embodiment, Form 5 is a solvate. In one embodiment, Form 5 is a hemi-solvate. In one embodiment, Form 5 is a tetrahydrofuran (THF) solvate or 1,4-dioxane solvate. In one embodiment, Form 5 is a THF hemi-solvate or a 1,4-dioxane hemi-solvate. In one embodiment, Form 5 is a THF solvate. In one embodiment, Form 5 is a THF hemi-solvate. In one embodiment, Form 5 is a THF mono-solvate. In one embodiment, Form 5 is a 1,4-dioxane solvate. In one embodiment, Form 5 is a 1,4-dioxane hemi-solvate. In one embodiment, Form 5 is a 1,4-dioxane mono-solvate.

In one embodiment, Form 5 is prepared by slurrying Compound A (e.g., an amorphous form of Compound A) in a solvent. In one embodiment, Form 5 is prepared by slurrying Compound A (e.g., an amorphous form of Compound A) in tetrahydrofuran (THF), 1,4-dioxane, or mixtures thereof. In one embodiment, Form 5 is prepared by slurrying Compound A (e.g., an amorphous form of Compound A) in tetrahydrofuran (THF). In one embodiment, Form 5 is prepared by slurrying Compound A (e.g., an amorphous form of Compound A) in 1,4-dioxane. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 5 is prepared by a method comprising: dissolving Compound A (e.g., an amorphous form of Compound A) in a solvent to form a solution; and cooling the solution; and optionally isolating Form 5. In one embodiment, the solvent is tetrahydrofuran (THF). In one embodiment, the solution is cooled to a temperature of approximately or below 10° C., or approximately or below 5° C. In one embodiment, the solution is cooled to approximately 2° C. In one embodiment, the cooling comprises multiple steps of cooling. In one embodiment, the cooling comprises cooling to a first temperature, followed by cooling to a second temperature. In one embodiment, the cooling comprises cooling to approximately 5° C., or approximately 2° C., or approximately 0° C., then cooling to approximately −15° C., or approximately −18° C., or approximately −20° C. In one embodiment, the cooling comprises a third step of cooling to a third temperature. In one embodiment, the cooling is conducted with continuous agitation.

In one embodiment, a mixture of Form 5 and Form 4 is prepared by a method comprising: dissolving Compound A (e.g., an amorphous form of Compound A) in a first solvent to form a solution; and adding an anti-solvent to the solution to form a slurry. In one embodiment, a mixture of Form 5 and Form 1 is prepared by a method comprising: dissolving Compound A (e.g., an amorphous form of Compound A) in a first solvent to form a solution; and adding an anti-solvent to the solution to form a slurry. In one embodiment, the first solvent is 2-methyltetrahydrofuran (2-Me-THF). In one embodiment, the anti-solvent is tert-butyl methyl ether (t-BME) or isobutyl acetate. In one embodiment, the anti-solvent is tert-butyl methyl ether (t-BME). In one embodiment, Compound A (e.g., an amorphous form of Compound A) is dissolved in the first solvent at ambient temperature (e.g., approximately 20° C. to approximately 25° C.). In one embodiment, Compound A (e.g., an amorphous form of Compound A) is dissolved in the first solvent at or above approximately 50° C. In one embodiment, the anti-solvent is added with continuous agitation. In one embodiment, the anti-solvent is added at ambient temperature (e.g., approximately 20° C. to approximately 25° C.). In one embodiment, the anti-solvent is added at or above approximately 50° C. In one embodiment, the anti-solvent is added with continuous agitation.

In one embodiment, Form 5 is converted to Form 8 by desolvation. In one embodiment, Form 8 is prepared by preparing Form 5 and desolvating Form 5. In one embodiment, Form 8 is prepared by desolvation of Form 5. In one embodiment, Form 8 is prepared by heating Form 5 to a temperature of greater than 100° C., preferably greater than 110° C., preferably greater than 115° C., preferably greater than 120° C., preferably greater than 125° C., preferably greater than 130° C., preferably greater than 140° C., preferably greater than 150° C., preferably greater than 160° C. In one embodiment, Form 8 is prepared by heating Form 5 to a temperature of greater than 150° C. under vacuum pressure.

Form 6

In one embodiment, the present application provides a Form 6 polymorph of Compound A ("Form 6"). In one embodiment, a mixture of Form 6 and Form 1 is characterized by an XRPD pattern substantially similar to that set forth in FIG. 8.

In one embodiment, a mixture of Form 6 and Form 1 is prepared by a method comprising: dissolving Compound A (e.g., an amorphous form of Compound A) in a first solvent to form a solution; and adding an anti-solvent to the solution to form a slurry. In one embodiment, the first solvent is N-methyl-2-pyrrolidone (NMP). In one embodiment, the anti-solvent is tert-butyl methyl ether (t-BME) or isobutyl acetate. In one embodiment, the anti-solvent is tert-butyl methyl ether (t-BME). In one embodiment, Compound A (e.g., an amorphous form of Compound A) is dissolved in the first solvent at ambient temperature (e.g., approximately 20° C. to approximately 25° C.). In one embodiment, Compound A (e.g., an amorphous form of Compound A) is dissolved in the first solvent at or above approximately 50° C. In one embodiment, the anti-solvent is added with continuous agitation. In one embodiment, the anti-solvent is added at ambient temperature (e.g., approximately 20° C. to approximately 25° C.). In one embodiment, the anti-solvent is added at or above approximately 50° C. In one embodiment, the anti-solvent is added with continuous agitation.

In one embodiment, a mixture of Form 6 and Form 2 is prepared by dissolving Compound A (e.g., an amorphous form of Compound A) in a solvent, followed by slow evaporation of the solvent from the solution. In one embodiment, a mixture of Form 6 and Form 2 is prepared by dissolving Compound A (e.g., an amorphous form of Compound A) in N-methyl-2-pyrrolidone (NMP), followed by slow evaporation of N-methyl-2-pyrrolidone (NMP) from the solution. In one embodiment, the evaporation is conducted at ambient temperature (e.g., approximately 20° C. to approximately 25° C.). In one embodiment, preparation of a mixture of Form 6 and Form 2 further comprises heating the sample. In one embodiment, preparation of a mixture of Form 6 and Form 2 further comprises heating the sample to or above approximately 40° C. In one embodiment, the evaporation is conducted with continuous agitation.

Form 7

In one embodiment, the present application provides a Form 7 polymorph of Compound A ("Form 7") characterized by an XRPD pattern comprising peaks at approximately 5.5, 19.0, and 20.6° 2θ using Cu Kα radiation. In one embodiment, Form 7 is characterized by an XRPD pattern comprising peaks at approximately 5.5, 14.1, 19.0, 20.6, and 21.5° 2θ using Cu Kα radiation. In one embodiment, Form 7 is characterized by an XRPD pattern comprising peaks at approximately 5.5, 5.8, 14.1, 16.0, 19.0, 20.6, and 21.5° 2θ using Cu Kα radiation. In one embodiment, Form 7 is characterized by an XRPD pattern comprising peaks at approximately 5.5, 5.8, 14.1, 16.0, 19.0, 20.6, 21.5, 25.2, and 26.0.° 2θ using Cu Kα radiation. In one embodiment, Form 7 is characterized by an XRPD pattern comprising peaks at approximately the positions shown in the table below:

Peak List

| Pos. [°2θ] | Height [cts] | FWHM Left [°2θ] | d-spacing [Å] | Rel. Int. [%] |
|---|---|---|---|---|
| 5.4816 | 551.49 | 0.0512 | 16.12253 | 50.54 |
| 5.7609 | 148.96 | 0.0768 | 15.34146 | 13.65 |
| 7.6403 | 51.44 | 0.2047 | 11.57127 | 4.71 |
| 14.0593 | 192.70 | 0.1023 | 6.29939 | 17.66 |
| 15.9904 | 106.97 | 0.6140 | 5.54270 | 9.80 |
| 18.9693 | 795.85 | 0.0640 | 4.67849 | 72.94 |
| 19.7926 | 77.87 | 0.2047 | 4.48569 | 7.14 |
| 20.6324 | 1091.11 | 0.1151 | 4.30498 | 100.00 |
| 21.4759 | 163.30 | 0.1023 | 4.13776 | 14.97 |
| 23.1308 | 61.31 | 0.3070 | 3.84534 | 5.62 |
| 25.1626 | 98.90 | 0.1279 | 3.53925 | 9.06 |
| 26.0193 | 99.44 | 0.1023 | 3.42463 | 9.11 |

Figure 62:
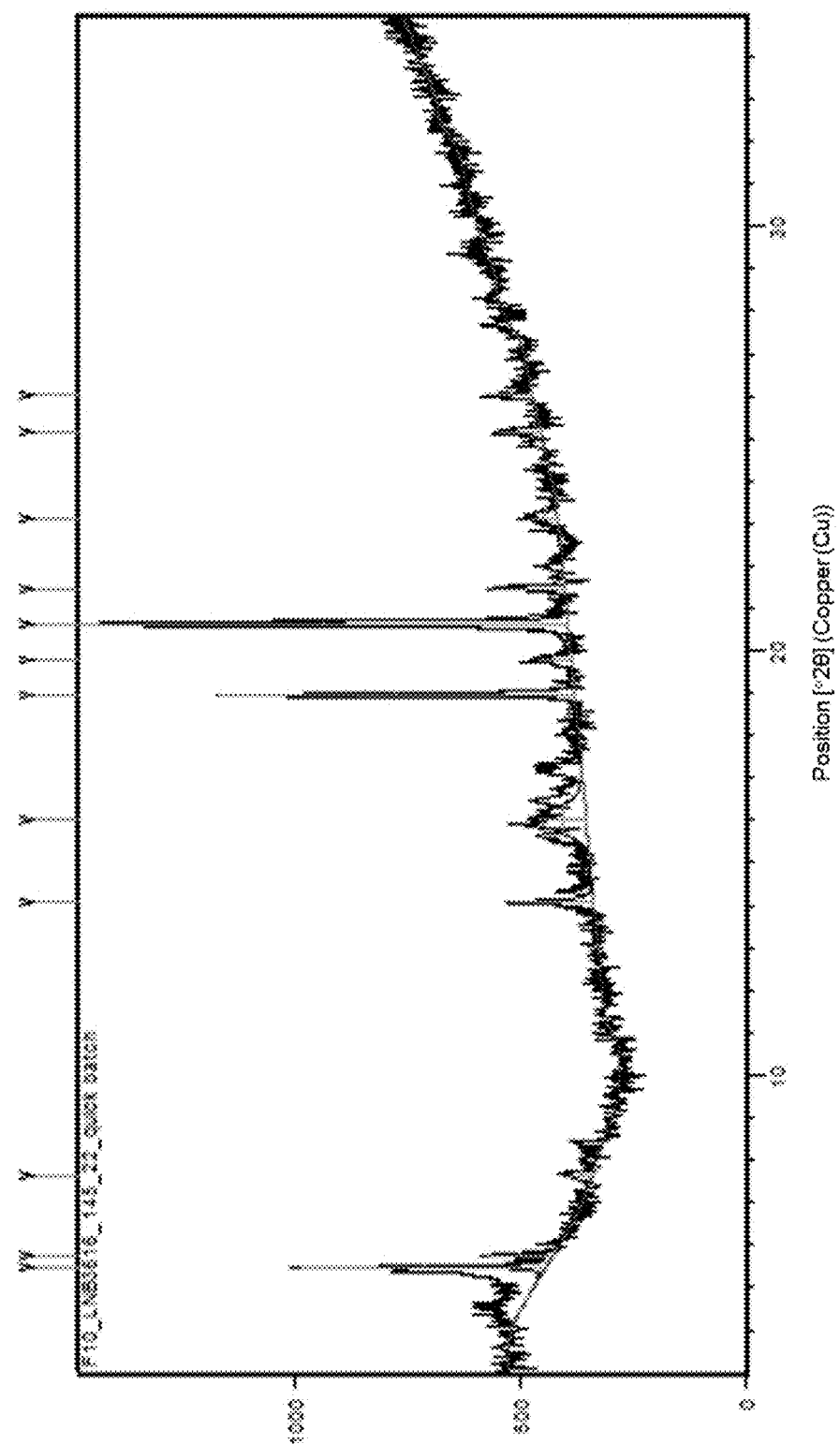
FIG. 62 sets forth an XRPD pattern of Form 7 from THF evaporation.
Figure 63:
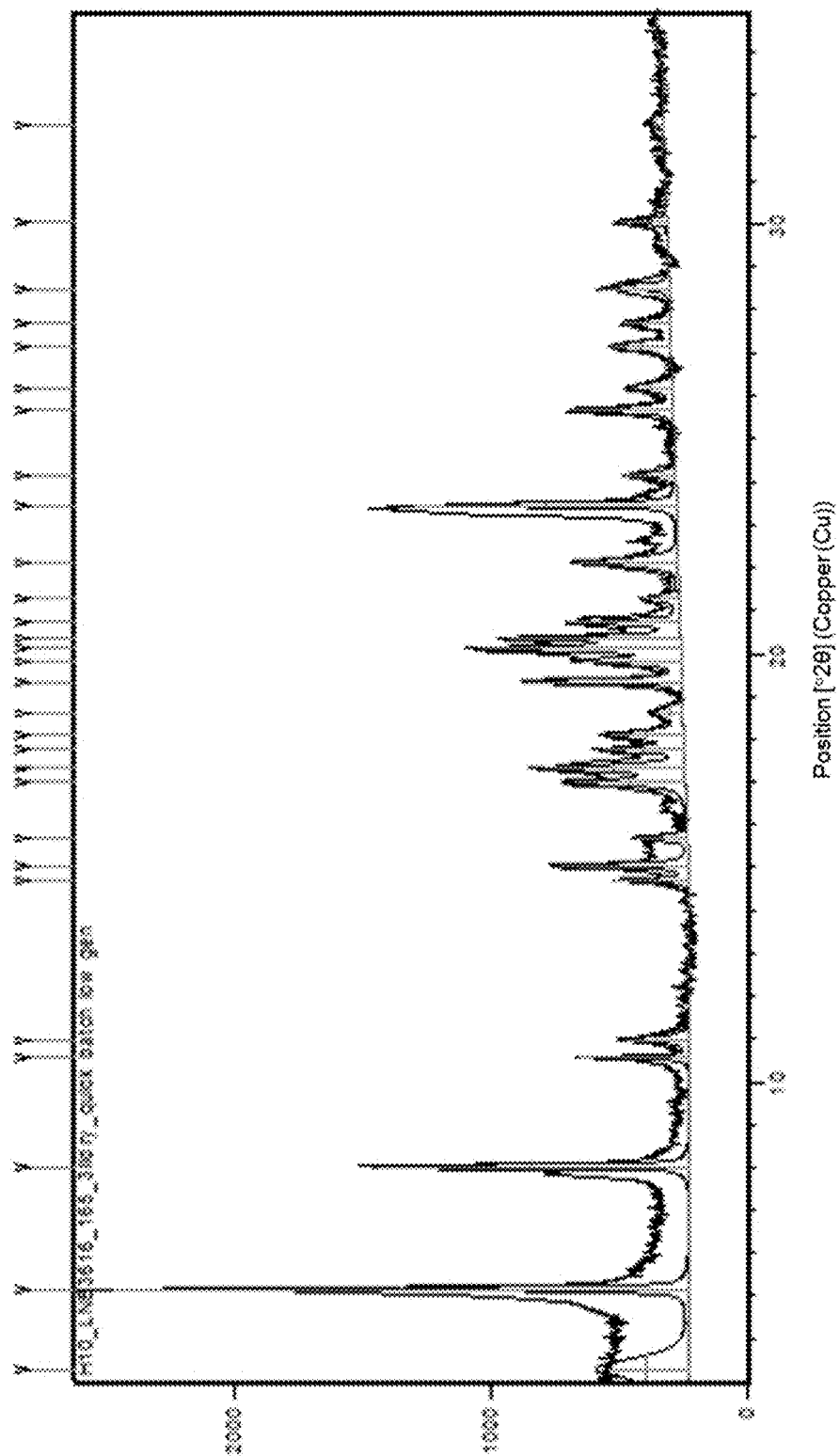
FIG. 63 sets forth an XRPD pattern of Form 8 from temperature cycling in THF and drying at ca. 150° C.
Figure 64:
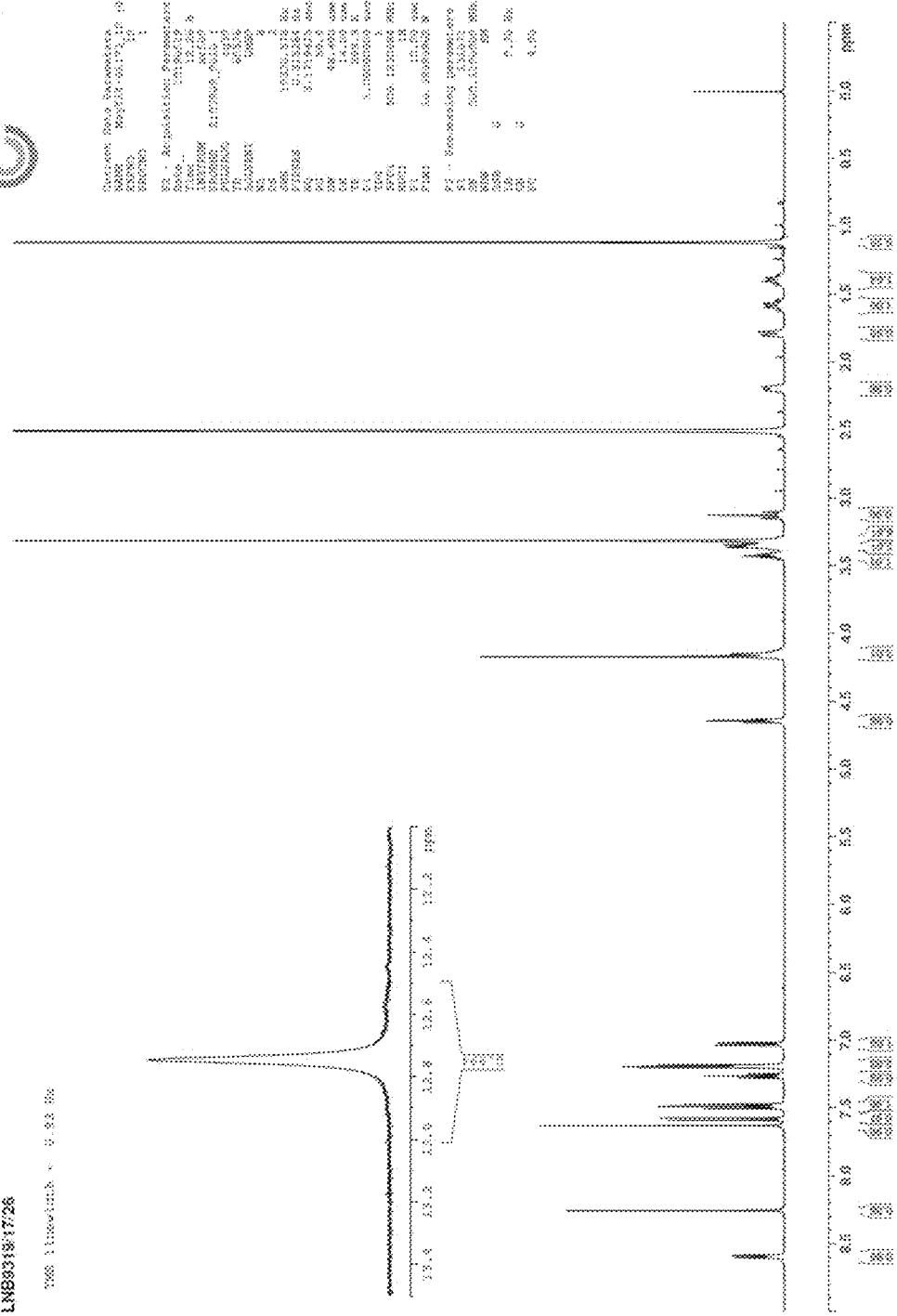
FIG. 64 sets forth a $^1$H NMR spectroscopic analysis of Form 9.

In one embodiment, Form 7 is characterized by an XRPD pattern substantially similar to that set forth in FIG. 8 or FIG. 62. In one embodiment, Form 7 is characterized by an XRPD pattern substantially similar to that set forth in FIG. 62.

In one embodiment, Form 7 is characterized by an endothermic event with onset at approximately 225° C. as measured by DTA. In one embodiment, Form 7 is characterized by a DTA thermogram substantially similar to that set forth in FIG. 19.

In one embodiment, Form 7 shows weight losses of approximately 2.5% between about 25° C. and about 140° C., and approximately 0.4% between about 140° C. and about 300° C., as measured by TGA.

In one embodiment, Form 7 is a solvate. In one embodiment, Form 7 is a mono-solvate. In one embodiment, Form 7 is a hemi-solvate. In one embodiment, Form 7 is a tetrahydrofuran (THF) solvate. In one embodiment, Form 7 is a mono-tetrahydrofuran (THF) solvate. In one embodiment, Form 7 is a hemi-tetrahydrofuran (THF) solvate. In one embodiment, Form 7 is a hydrate. In one embodiment, Form 7 is a mono-hydrate. In one embodiment, Form 7 is a hemi-hydrate.

In one embodiment, Form 7 is prepared by dissolving Compound A (e.g., an amorphous form of Compound A) in a solvent, followed by slow evaporation of the solvent from the solution. In one embodiment, Form 7 is prepared by dissolving Compound A (e.g., an amorphous form of Compound A) in tetrahydrofuran (THF), followed by slow evaporation of tetrahydrofuran (THF) from the solution. In one embodiment, the evaporation is conducted at ambient temperature (e.g., approximately 20° C. to approximately 25° C.). In one embodiment, preparation of Form 7 further comprises heating the sample. In one embodiment, preparation of Form 7 further comprises heating the sample to or above approximately 40° C. In one embodiment, the evaporation is conducted with continuous agitation.

Form 8

In one embodiment, the present application provides a Form 8 polymorph of Compound A ("Form 8") characterized by an XRPD pattern comprising peaks at approximately 5.2, 8.0, and 23.4° 2θ using Cu Kα radiation. In one embodiment, Form 8 is characterized by an XRPD pattern comprising peaks at approximately 5.2, 8.0, 20.1, 20.3, and 23.4° 2θ using Cu Kα radiation. In one embodiment, Form 8 is characterized by an XRPD pattern comprising peaks at approximately 5.2, 8.0, 10.6, 15.0, 17.0, 17.3, 19.3, 20.1, 20.3, 20.7 and 23.4° 2θ using Cu Kα radiation. In one embodiment, Form 8 is characterized by an XRPD pattern comprising peaks at approximately 5.2, 8.0, 10.6, 14.7, 15.0, 17.0, 17.3, 17.8, 18.1, 19.3, 19.8, 20.1, 20.3, 20.7, 22.1, 23.4, 25.7, and 28.5° 2θ using Cu Kα radiation. In one embodiment, Form 8 is characterized by an XRPD pattern comprising peaks at approximately the positions shown in the table below:

Peak List

| Pos. [°2θ] | Height [cts] | FWHM Left [°2θ] | d-spacing [Å] | Rel. Int. [%] |
|---|---|---|---|---|
| 5.1616 | 2242.80 | 0.0768 | 17.12105 | 100.00 |
| 8.0205 | 1220.59 | 0.0895 | 11.02367 | 54.42 |
| 10.5577 | 432.25 | 0.0768 | 8.37947 | 19.27 |
| 10.9740 | 247.27 | 0.1535 | 8.06251 | 11.03 |
| 14.6855 | 287.89 | 0.0895 | 6.03213 | 12.84 |
| 15.0229 | 506.25 | 0.1151 | 5.89742 | 22.57 |
| 15.6678 | 194.97 | 0.1279 | 5.65609 | 8.69 |
| 16.9638 | 431.47 | 0.1791 | 5.22681 | 19.24 |
| 17.3001 | 549.83 | 0.1791 | 5.12594 | 24.52 |
| 17.7504 | 318.01 | 0.1279 | 4.99690 | 14.18 |
| 18.0871 | 289.60 | 0.2047 | 4.90465 | 12.91 |
| 18.6089 | 114.40 | 0.2558 | 4.76827 | 5.10 |
| 19.3364 | 616.19 | 0.1151 | 4.59048 | 27.47 |
| 19.8096 | 382.99 | 0.1535 | 4.48188 | 17.08 |
| 20.1004 | 796.83 | 0.1279 | 4.41770 | 35.53 |
| 20.3377 | 669.66 | 0.1279 | 4.36669 | 29.86 |
| 20.7048 | 440.57 | 0.1151 | 4.29008 | 19.64 |
| 21.2604 | 143.55 | 0.1535 | 4.17922 | 6.40 |
| 22.1097 | 392.52 | 0.2047 | 4.02056 | 17.50 |
| 23.4290 | 1023.49 | 0.0895 | 3.79707 | 45.63 |
| 24.1327 | 189.23 | 0.1279 | 3.68792 | 8.44 |
| 25.6527 | 396.25 | 0.1279 | 3.47274 | 17.67 |
| 26.1731 | 163.43 | 0.1791 | 3.40486 | 7.29 |
| 27.1375 | 229.39 | 0.2047 | 3.28601 | 10.23 |
| 27.6747 | 174.14 | 0.2303 | 3.22343 | 7.76 |
| 28.5047 | 269.40 | 0.1023 | 3.13143 | 12.01 |
| 30.0396 | 190.49 | 0.0768 | 2.97483 | 8.49 |
| 32.2971 | 52.23 | 0.4093 | 2.77187 | 2.33 |

In one embodiment, Form 8 is characterized by an XRPD pattern substantially similar to that set forth in FIG. 8, FIG. 10, FIG. 40, FIG. 48, FIG. 49, or FIG. 63. In one embodiment, Form 8 is characterized by an XRPD pattern substantially similar to that set forth in FIG. 63.

In one embodiment, Form 8 is characterized by an endothermic event with onset between approximately 224° C. and approximately 225° C. as measured by DTA or DSC. In one embodiment, Form 8 is characterized by an endothermic event with peak between approximately 227° C. and approximately 229° C. as measured by DTA or DSC.

In one embodiment, Form 8 is characterized by an endothermic event with onset between approximately 224° C. and approximately 225° C. as measured by DTA. In one embodiment, Form 8 is characterized by an endothermic event with onset at approximately 224° C. as measured by DTA. In one embodiment, Form 8 is characterized by an endothermic event with onset at approximately 225° C. as measured by DTA. In one embodiment, Form 8 is characterized by an endothermic event with peak at approximately 227° C. as measured by DTA. In one embodiment, Form 8 is characterized by a DTA thermogram substantially similar to that set forth in FIG. 17 or FIG. 42. In one embodiment, Form 8 is characterized by a DTA thermogram substantially similar to that set forth in FIG. 17. In one embodiment, Form 1 is characterized by a DTA thermogram substantially similar to FIG. 42.

Figure 43:
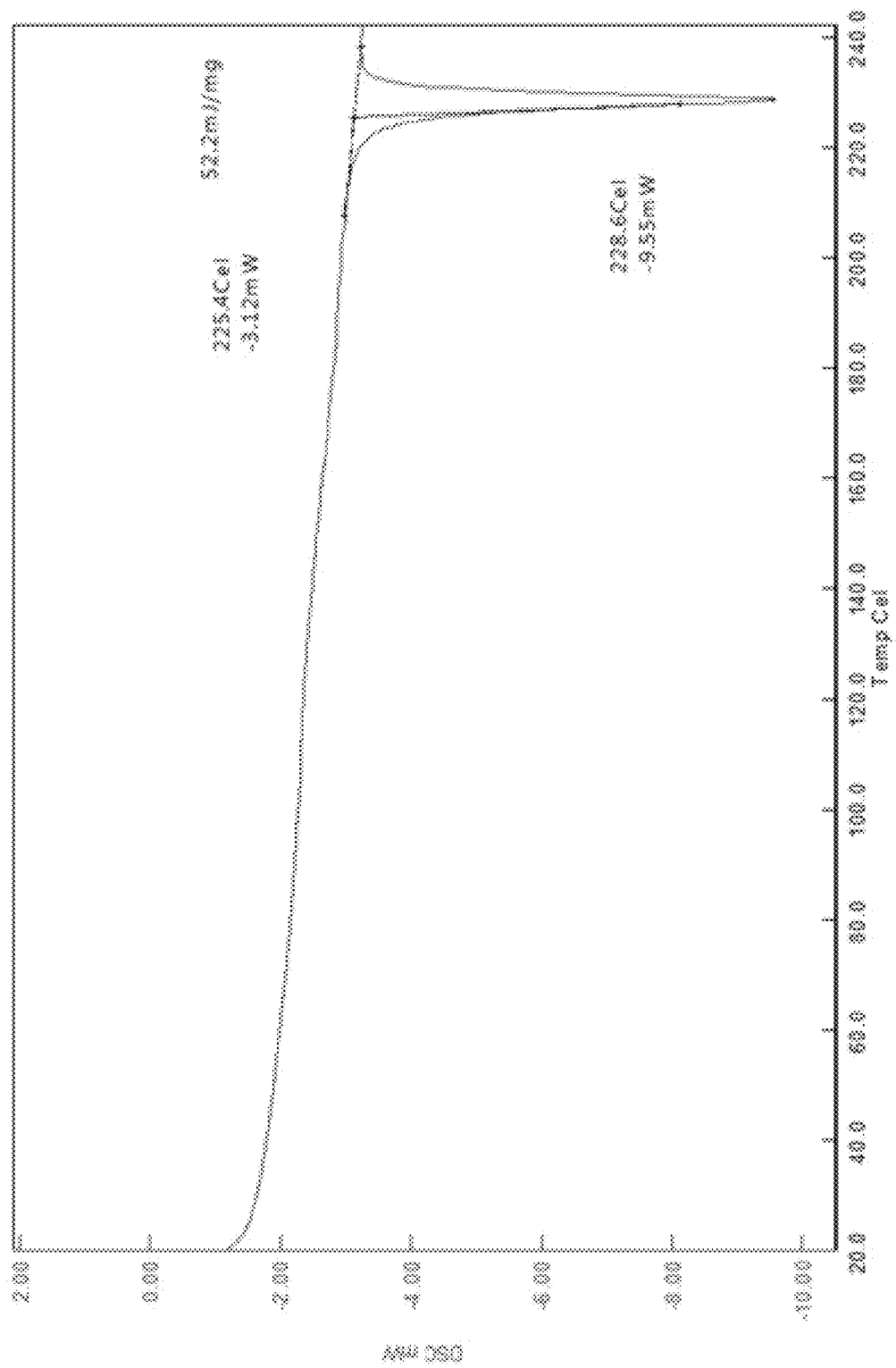
FIG. 43 sets forth a thermal analysis by DSC of Form 8.

In one embodiment, Form 8 is characterized by an endothermic event with onset at approximately 225° C. as measured by DSC. In one embodiment, Form 8 is characterized by an endothermic event with peak at approximately 229° C. as measured by DSC. In one embodiment, Form 8 is characterized by a DSC thermogram substantially similar to that set forth in FIG. 43.

In one embodiment, Form 8 shows a weight loss of approximately 0.2% between approximately 25° C. and 300° C. as measured by TGA. In one embodiment, Form 8 shows a weight loss of approximately 0.1% between approximately 25° C. and approximately 200° C. as measured by TGA. In one embodiment, Form 8 shows a weight loss of approximately 0.1% between approximately 200° C. and approximately 300° C. as measured by TGA.

In one embodiment, Form 8 is non-hygroscopic. In one embodiment, Form 1 displays non-hygroscopicity between 0% and 90% relative humidity (RH) at approximately 25° C. (e.g., less than 0.9% w/w water uptake, less than 0.85% w/w water uptake, less than 0.8% w/w water uptake). In one embodiment, Form 1 displays non-hygroscopicity between 0% and 70% relative humidity (RH) at approximately 25° C. (e.g., less than 0.2% w/w water uptake, less than 0.85% w/w water uptake, less than 0.8% w/w water uptake).

In one embodiment, Form 8 is stable (e.g., no decrease in HPLC area % purity or form changes) under various storage conditions. In one embodiment, Form 8 is stable (e.g., no decrease in HPLC area % purity or form changes) between approximately 20° C. and approximately 90° C. (e.g., 22° C., 25° C., 40° C., or 80° C.) for at least one week, preferably at least two weeks, preferably at least three weeks, preferably at least one month, preferably at least two months, preferably at least three months, preferably at least four months, preferably at least six months, preferably at least one year. In one embodiment, Form 8 is stable (e.g., no decrease in HPLC area % purity or form changes) between approximately 20% relative humidity (RH) and approximately 98% relative humidity (RH) (e.g., 40% RH, 60% RH, 75% RH, or 96% RH) for at least one week, preferably at least two weeks, preferably at least three weeks, preferably at least one month, preferably at least two months, preferably at least three months, preferably at least four months, preferably at least six months, preferably at least one year. In one embodiment, Form 8 is stable (e.g., no decrease in HPLC area % purity or form changes) under 40° C./75% relative humidity (RH) for at least one week, preferably at least two weeks, preferably at least three weeks, preferably at least one month, preferably at least two months, preferably at least three months, preferably at least four months, preferably at least six months, preferably at least one year.

In one embodiment, Form 8 is not soluble in an aqueous solution.

In one embodiment, Form 8 is not a hydrate. In one embodiment, Form 8 is not a solvate.

In one embodiment, Form 8 is a desolvated form of Form 5.

In one embodiment, Form 8 is an anhydrous solid form.

In one embodiment, Form 8 is a non-hygroscopic solid form.

In one embodiment, Form 8 is an anhydrous and non-hygroscopic solid form.

In one embodiment, Form 8 is prepared by preparing Form 5 and desolvating Form 5. In one embodiment, Form 8 is prepared by desolvation of Form 5. In one embodiment, Form 8 is prepared by heating Form 5 to a temperature of greater than 100° C., preferably greater than 110° C., preferably greater than 115° C., preferably greater than 120° C., preferably greater than 125° C., preferably greater than 130° C., preferably greater than 140° C., preferably greater than 150° C., preferably greater than 160° C. In one embodiment, Form 8 is prepared by heating Form 5 to a temperature of greater than 150° C. under vacuum pressure.

In one embodiment, Form 8 is converted to the Form 2 polymorph of Compound A upon slurrying in a solvent. In one embodiment, Form 8 is converted to the Form 2 polymorph of Compound A upon slurrying in acetone. In one embodiment, the slurrying is conducted at ambient temperature (e.g., approximately 20° C. to approximately 25° C.). In one embodiment, the slurrying is conducted at or above approximately 40° C. In one embodiment, the slurrying is conducted with continuous agitation.

Form 9

In one embodiment, the present application provides a Form 9 polymorph of Compound A ("Form 9") characterized by an XRPD pattern comprising peaks at approximately 4.9, 16.4, and 16.6° 2θ using Cu Kα radiation. In one embodiment, Form 9 is characterized by an XRPD pattern comprising peaks at approximately 4.9, 5.5, 16.4, 16.6, and 17.2° 2θ using Cu Kα radiation. In one embodiment, Form 9 is characterized by an XRPD pattern comprising peaks at approximately 4.9, 5.5, 11.1, 11.2, 15.8, 16.4, 16.6, 17.2, 18.2, 19.4, 20.1, 23.3, 24.4, and 28.4° 2θ using Cu Kα radiation. In one embodiment, Form 9 is characterized by an XRPD pattern comprising peaks at approximately 4.9, 5.5, 6.6, 11.1, 11.2, 15.8, 16.4, 16.6, 17.2, 17.6, 17.9, 18.2, 19.0, 19.4, 19.7, 20.1, 21.0, 21.9, 23.3, 24.3, and 28.4° 2θ using Cu Kα radiation. In one embodiment, Form 9 is characterized by an XRPD pattern comprising peaks at approximately the positions shown in the table below:

| Pos. [°2θ] | Height [cts] | d-spacing [Å] | Rel. Int. [%] |
| --- | --- | --- | --- |
| 4.9088 | 1704.77 | 18.00237 | 62.12 |
| 5.5259 | 1188.63 | 15.99314 | 43.32 |
| 6.6233 | 230.7 | 13.34557 | 8.41 |
| 8.0533 | 100.85 | 10.97878 | 3.67 |
| 9.7761 | 90.87 | 9.04758 | 3.31 |
| 11.0569 | 500.32 | 8.00223 | 18.23 |
| 11.1863 | 407.66 | 7.90995 | 14.86 |
| 12.1513 | 192.39 | 7.28388 | 7.01 |
| 13.2963 | 111.11 | 6.6591 | 4.05 |
| 15.076 | 162.08 | 5.87677 | 5.91 |
| 15.7701 | 757.7 | 5.61966 | 27.61 |
| 16.4154 | 2744.12 | 5.40014 | 100 |
| 16.6373 | 1238.34 | 5.32864 | 45.13 |
| 17.1705 | 839.77 | 5.16434 | 30.6 |
| 17.6291 | 285.68 | 5.02685 | 10.41 |
| 17.8945 | 344.35 | 4.957 | 12.55 |
| 18.2253 | 411.13 | 4.86776 | 14.98 |
| 18.9574 | 332.65 | 4.68139 | 12.12 |
| 19.429 | 390.25 | 4.56881 | 14.22 |
| 19.7204 | 345.15 | 4.50197 | 12.58 |
| 20.0833 | 380.61 | 4.42142 | 13.87 |
| 20.6682 | 177.75 | 4.29405 | 6.48 |
| 20.978 | 225.31 | 4.23484 | 8.21 |
| 21.8665 | 271.21 | 4.06473 | 9.88 |
| 23.3 | 609.77 | 3.81779 | 22.22 |
| 24.3126 | 394.6 | 3.66103 | 14.38 |
| 25.3477 | 149.07 | 3.51383 | 5.43 |
| 26.7561 | 73.77 | 3.33198 | 2.69 |
| 28.4157 | 330.32 | 3.14104 | 12.04 |
| 30.0705 | 87.33 | 2.97185 | 3.18 |
| 32.9264 | 48.71 | 2.72032 | 1.77 |

Figure 65:
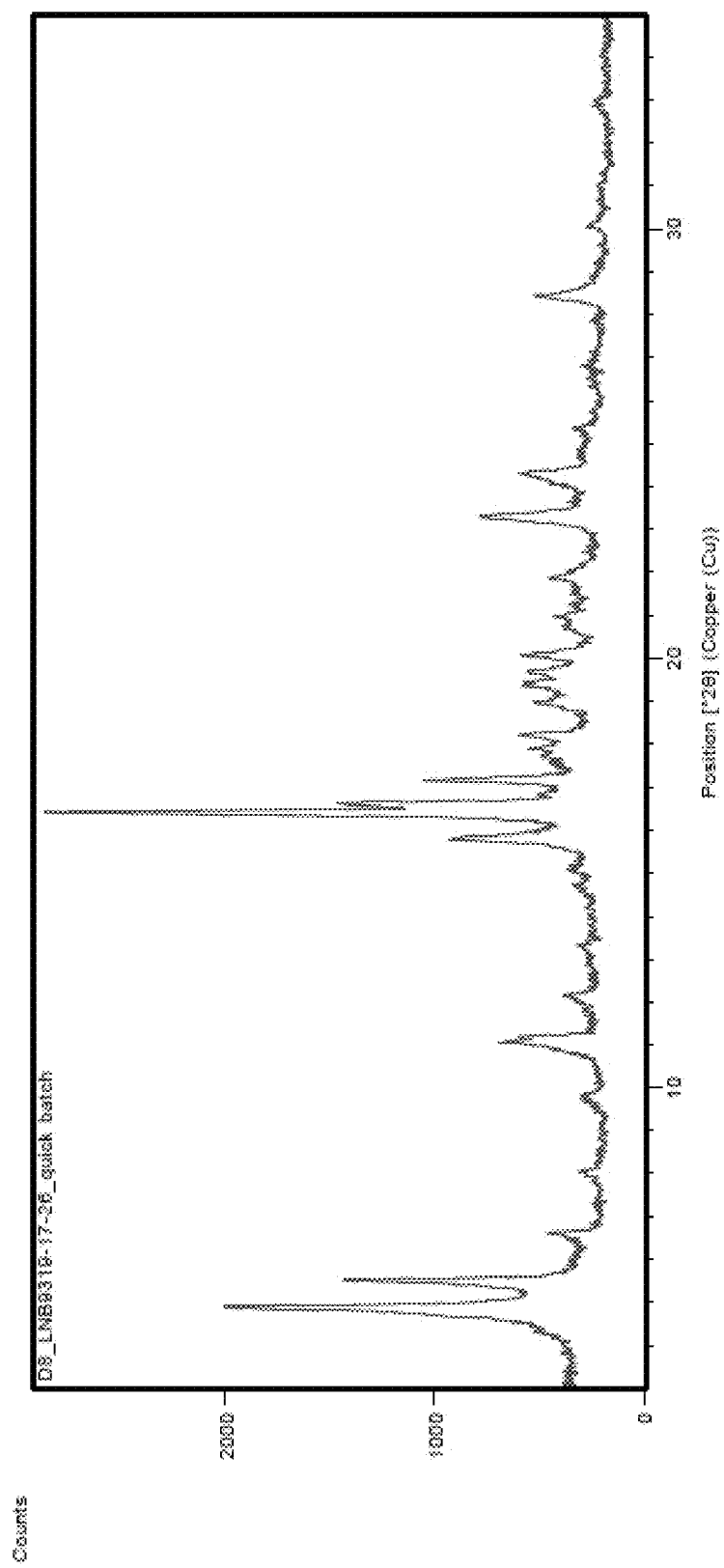
FIG. 65 sets forth an XRPD pattern of Form 9.

In one embodiment, Form 9 is characterized by an XRPD pattern substantially similar to that set forth in FIG. 65.

In one embodiment, Form 9 is characterized by endothermic events with onsets at approximately 69° C. and approximately 218° C. as measured by DSC. In one embodiment, Form 9 is characterized by endothermic events with peaks at approximately 96° C. and approximately 223° C. as measured by DSC. In one embodiment, Form 9 is characterized by a DSC thermogram substantially similar to that set forth in FIG. 66.

Figure 66:
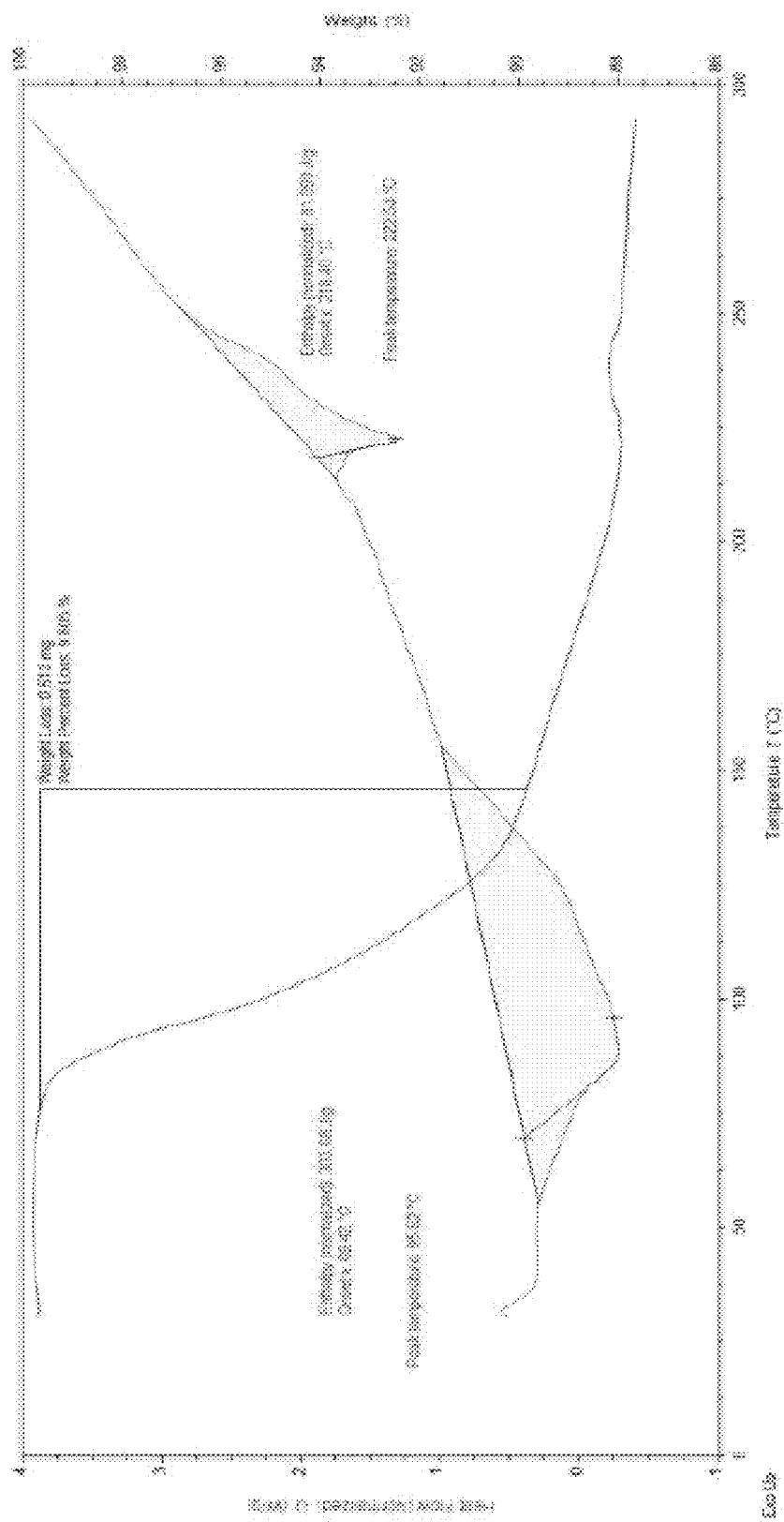
FIG. 66 sets forth a thermal analysis by thermogravimetric/differential scanning calorimetry (TG/DSC) of Form 9.
Figure 67:
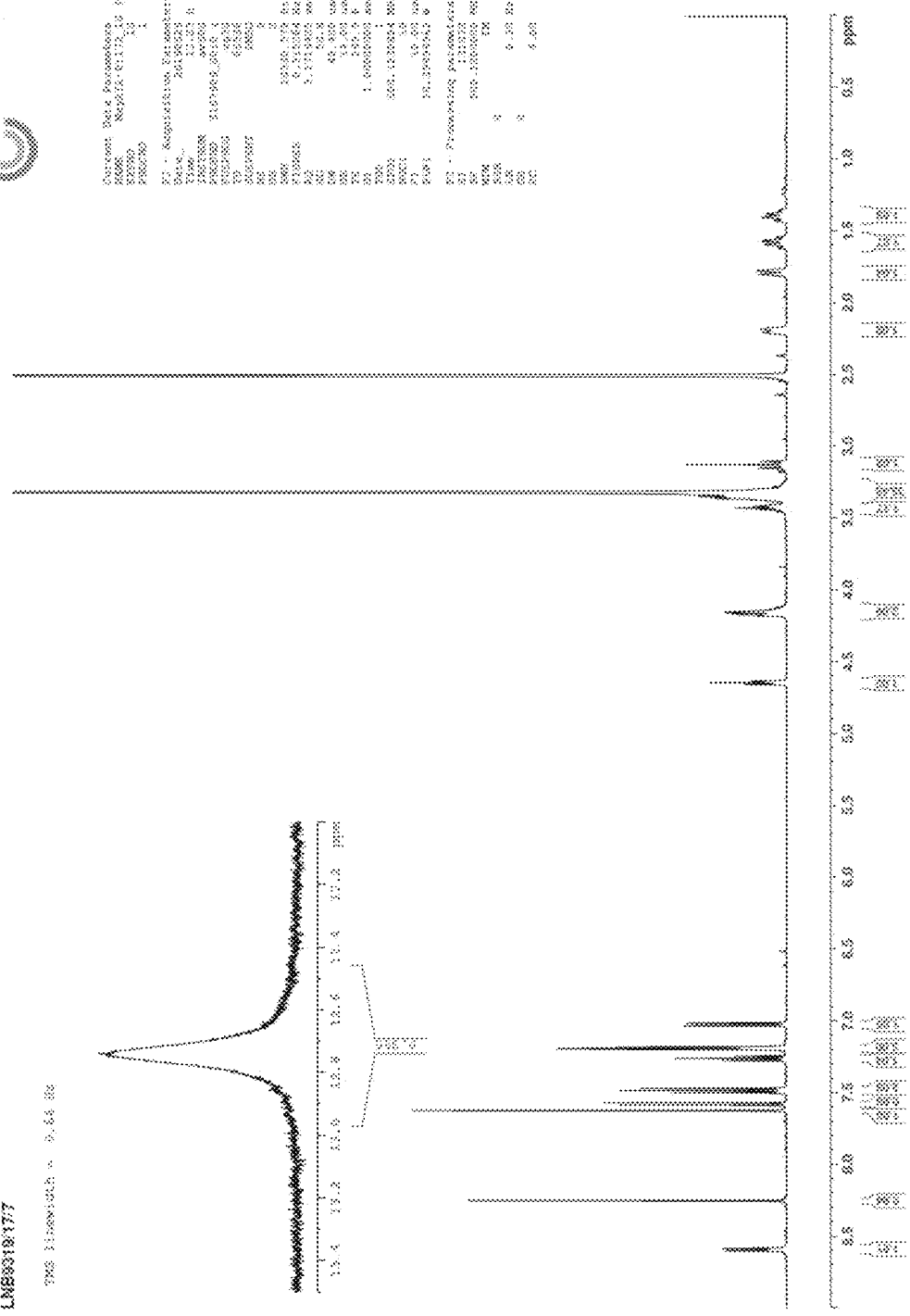
FIG. 67 sets forth a $^1$H NMR spectroscopic analysis of Form 10.

In one embodiment, Form 9 shows a weight loss of approximately 9.8% between approximately 50° C. and approximately 160° C. as measured by TGA (FIG. 66).

In one embodiment, Form 9 is prepared by slurrying Compound A (e.g., an amorphous form of Compound A) in a solvent. In one embodiment, Form 9 is prepared by slurrying Compound A in 2-methyl-1-propanol. In one embodiment, Form 9 is prepared by slurrying Compound A in tert-butanol. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or 4 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 9 is prepared by dissolving Compound A (e.g., an amorphous form of Compound A) in a solvent, followed by slow evaporation of the solvent. In one embodiment, Form 9 is prepared by dissolving compound A in 2-methyl-1-propanol, followed by slow evaporation of the solvent. In one embodiment, Form 9 is prepared by dissolving compound A in tert-butanol, followed by slow evaporation of the solvent. In one embodiment, the evaporation is conducted at ambient temperature (e.g., approximately 20° C. to approximately 25° C.). In one embodiment, preparation of Form 9 further comprises heating the sample. In one embodiment, preparation of Form 9 further comprises heating the sample to or above approximately 40° C.

Form 10

In one embodiment, the present application provides a Form 10 polymorph of Compound A ("Form 10") characterized by an XRPD pattern comprising peaks at approximately 7.2, 7.4, and 11.9° 2θ using Cu Kα radiation. In one embodiment, Form 10 is characterized by an XRPD pattern comprising peaks at approximately 7.2, 7.4, 11.9, 20.2, and 27.6° 2θ using Cu Kα radiation. In one embodiment, Form 10 is characterized by an XRPD pattern comprising peaks at approximately 7.2, 7.4, 10.0, 11.9, 13.7, 16.0, 16.6, 17.8, 20.2, 21.8, 22.2, 23.9, 27.6, and 30.8° 2θ using Cu Kα radiation. In one embodiment, Form 10 is characterized by an XRPD pattern comprising peaks at approximately 7.2, 7.4, 10.0, 11.9, 13.7, 14.8, 16.0, 16.6, 17.8, 19.6, 20.2, 21.8, 22.2, 23.0, 23.9, 24.5, 24.9, 26.4, 27.6, 28.8 and 30.8° 2θ using Cu Kα radiation. In one embodiment, Form 10 is characterized by an XRPD pattern comprising peaks at approximately the positions shown in the table below:

| Pos. [°2θ] | Height [cts] | d-spacing [Å] | Rel. Int. [%] |
|---|---|---|---|
| 7.2004 | 938 | 12.27728 | 49.09 |
| 7.4371 | 1910.84 | 11.88704 | 100 |
| 9.3561 | 51.69 | 9.45276 | 2.71 |
| 10.0699 | 451.88 | 8.78422 | 23.65 |
| 10.584 | 151.09 | 8.35179 | 7.91 |
| 11.1622 | 186.98 | 7.92702 | 9.78 |
| 11.8695 | 950.58 | 7.45615 | 49.75 |
| 13.7078 | 413.77 | 6.46011 | 21.65 |
| 14.7523 | 241.19 | 6.00497 | 12.62 |
| 15.9667 | 602.79 | 5.55088 | 31.55 |
| 16.5595 | 800.74 | 5.35348 | 41.91 |
| 16.8924 | 150.76 | 5.24439 | 7.89 |
| 17.7989 | 582.7 | 4.9834 | 30.49 |
| 18.4609 | 188.21 | 4.80618 | 9.85 |
| 18.7432 | 226.75 | 4.73442 | 11.87 |
| 19.2266 | 173.94 | 4.61645 | 9.1 |
| 19.6175 | 317.02 | 4.52533 | 16.59 |
| 20.2385 | 868.17 | 4.38787 | 45.43 |
| 20.812 | 153.5 | 4.26824 | 8.03 |
| 21.8357 | 416.71 | 4.0704 | 21.81 |
| 22.2015 | 592.73 | 4.00414 | 31.02 |
| 23.0485 | 293.4 | 3.85887 | 15.35 |
| 23.9065 | 631.4 | 3.7223 | 33.04 |
| 24.4735 | 233.35 | 3.63733 | 12.21 |
| 24.8965 | 413.11 | 3.57648 | 21.62 |
| 26.3699 | 191.26 | 3.37989 | 10.01 |
| 27.6278 | 864.16 | 3.22879 | 45.22 |
| 28.3119 | 132.07 | 3.14971 | 6.91 |
| 28.7523 | 209.04 | 3.10503 | 10.94 |
| 29.7873 | 67.08 | 2.99946 | 3.51 |
| 30.7899 | 600.14 | 2.90403 | 31.41 |
| 32.4204 | 48 | 2.76161 | 2.51 |

Figure 68:
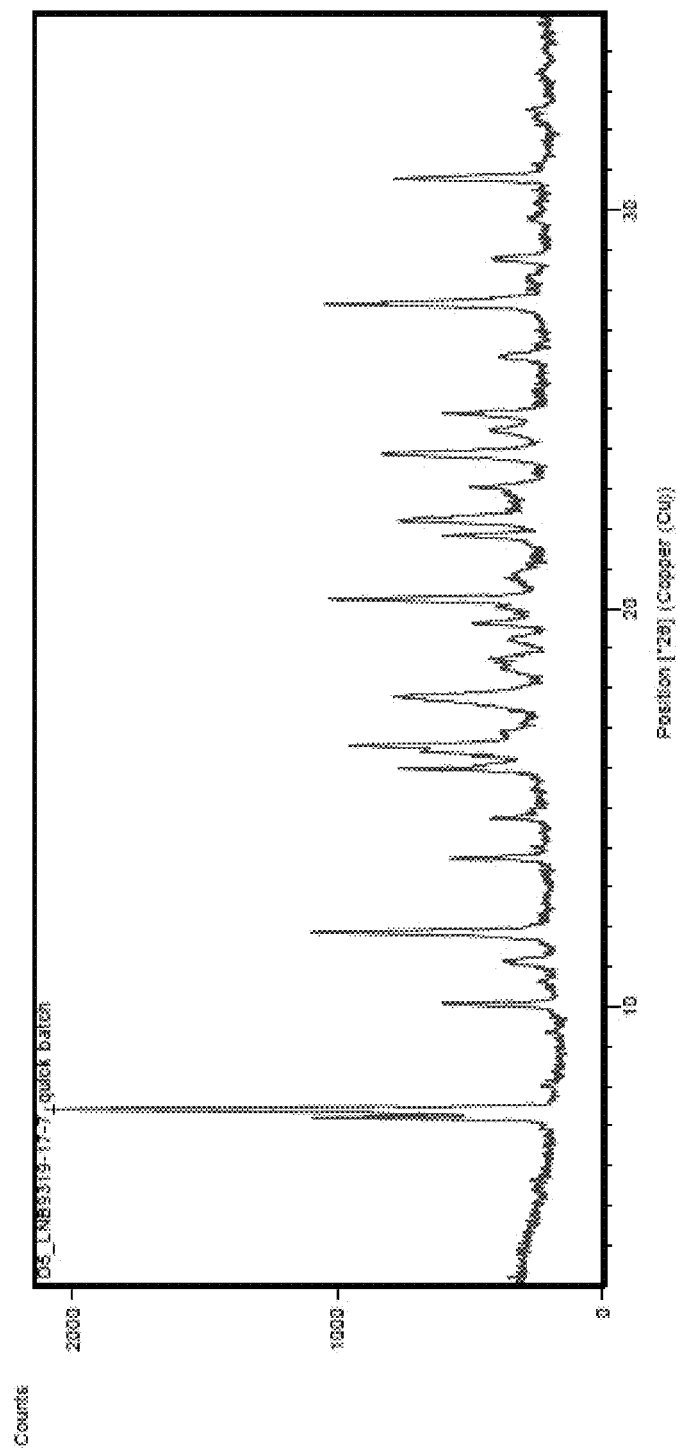
FIG. 68 sets forth an XRPD pattern of Form 10.
Figure 70:
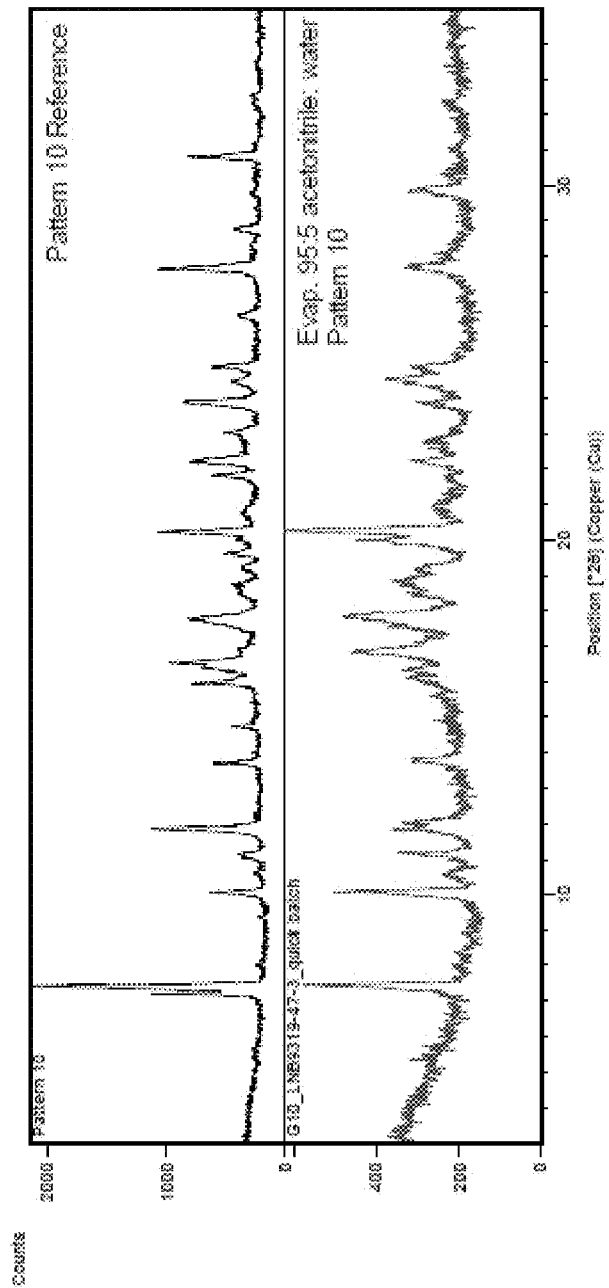
FIG. 70 sets forth comparative XRPD patterns of Form 10 with the XRPD pattern of Form 10 from 200 mg scale-up.

In one embodiment, Form 10 is characterized by an XRPD pattern substantially similar to that set forth in FIG. 68 or FIG. 70. In one embodiment, Form 10 is characterized by an XRPD pattern substantially similar to that set forth in FIG. 68.

In one embodiment, Form 10 is characterized by endothermic events with onsets at approximately 106° C., approximately 206° C., and approximately 213° C. as measured by DSC. In one embodiment, Form 10 is characterized by endothermic events with peaks at approximately 147° C., approximately 207° C., and approximately 251° C. In one embodiment, Form 10 is characterized by a DSC thermogram substantially similar to that set forth in FIG. 71.

In one embodiment, Form 10 is characterized by endothermic events with onsets at approximately 195° C. and approximately 230° C. as measured by DSC. In one embodiment, Form 10 is characterized by endothermic events with peaks at approximately 201° C. and approximately 231° C. In one embodiment, Form 10 is characterized by a DSC thermogram substantially similar to that set forth in FIG. 75.

In one embodiment, Form 10 shows a weight loss of approximately 0.5% between approximately 70° C. and approximately 150° C., and a weight loss of approximately 1.7% between approximately 150° C. and approximately 300° C. as measured by TGA.

In one embodiment, Form 10 shows a weight loss of approximately 0.9% between approximately 70° C. and approximately 150° C., and a weight loss of approximately 1.9% between approximately 150° C. and approximately 300° C. as measured by TGA.

Figure 83:
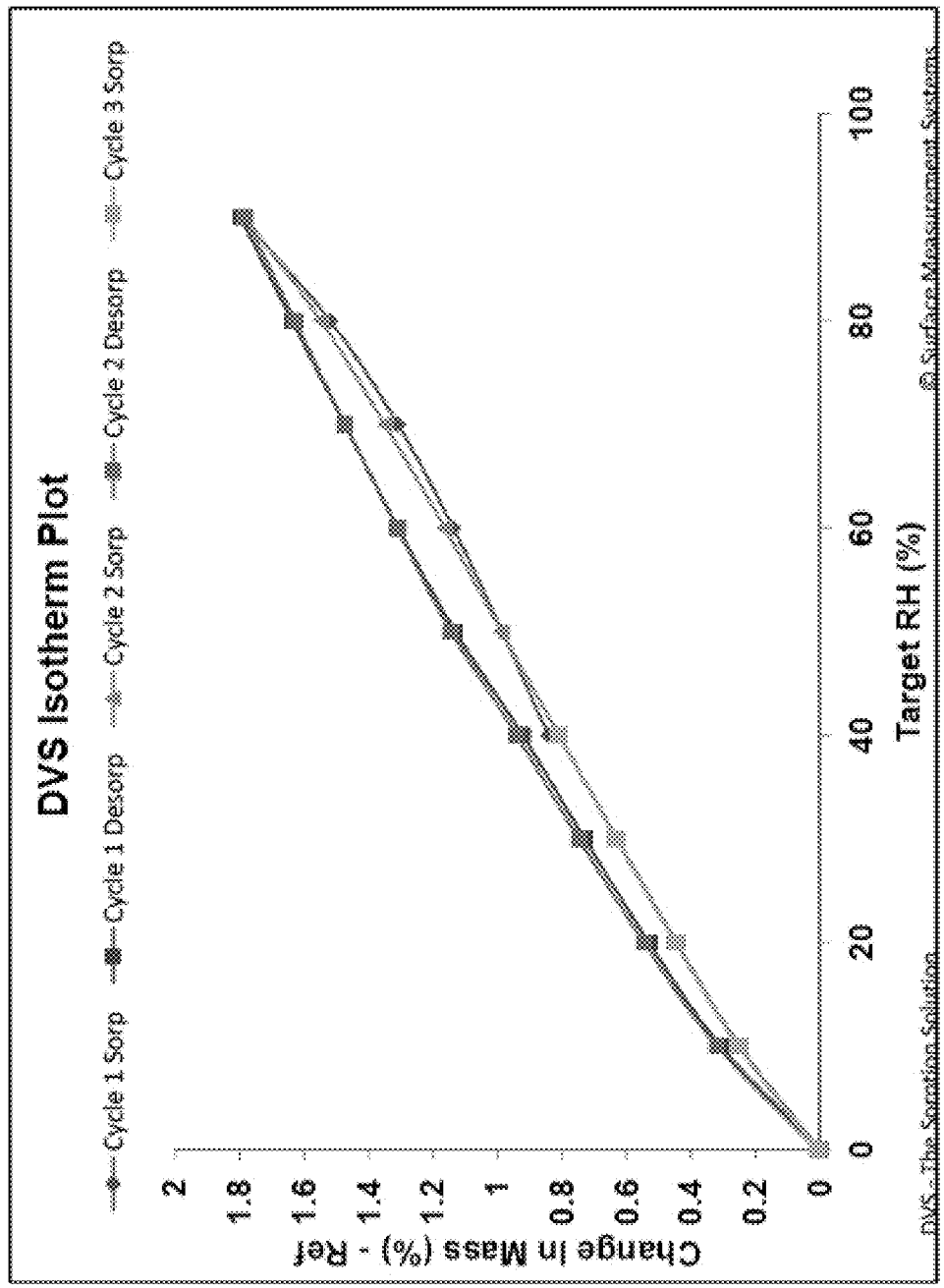
FIG. 83 sets forth a DVS isothermal analysis of Form 10 obtained from 400 mg scale-up.
Figure 84:
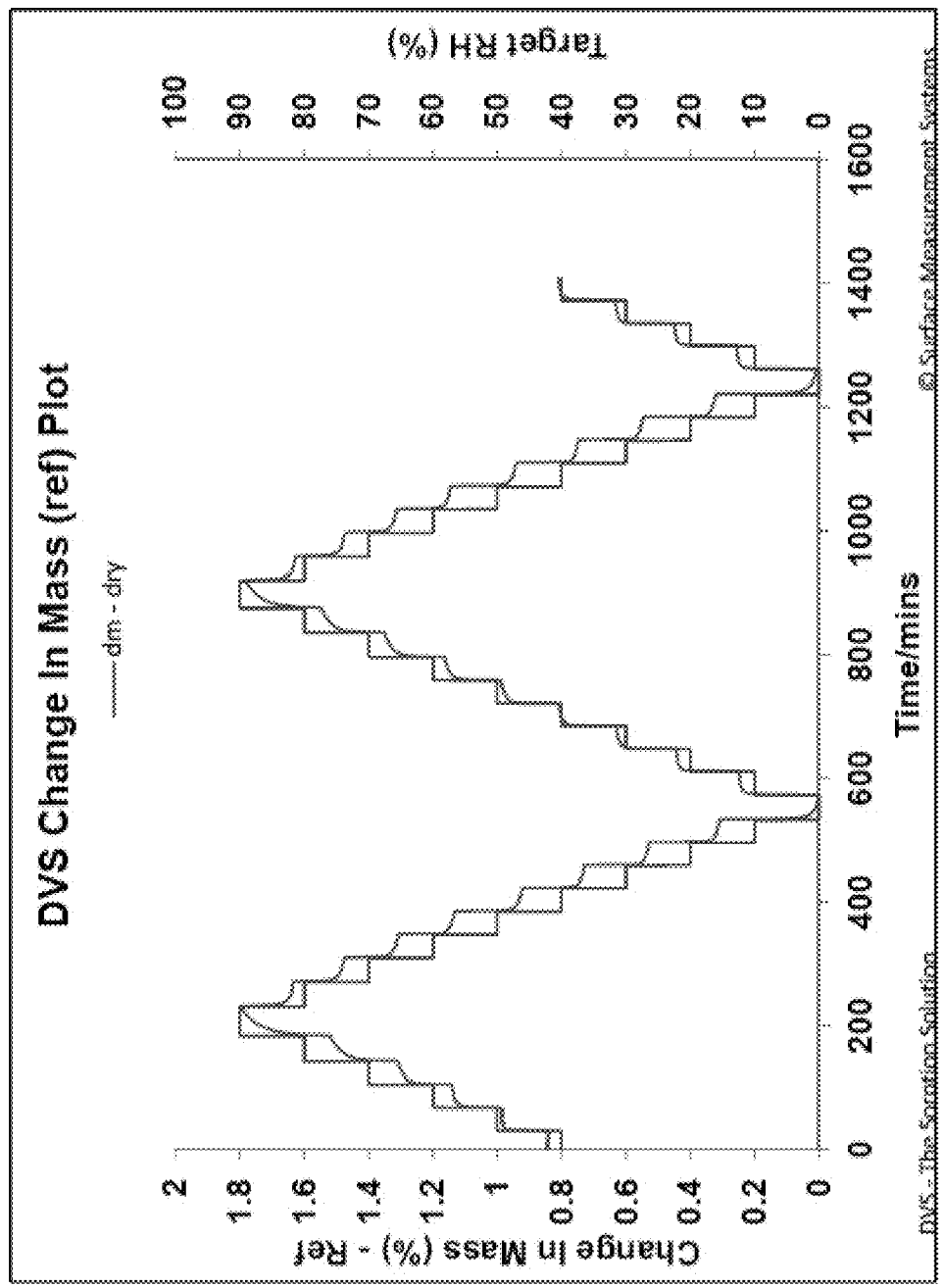
FIG. 84 sets forth a DVS kinetic analysis of Form 10 obtained from 400 mg scale-up.

In one embodiment, Form 10 was shown to be slightly hygroscopic with a mass increase of 0.94% at 90% relative humidity (RH) as measured by DVS analysis (FIG. 83 and FIG. 84).

In one embodiment, Form 10 is prepared by slurrying Compound A (e.g., an amorphous form of Compound A) in a solvent. In one embodiment, Form 10 is prepared by slurrying Compound A in a mixture of acetonitrile and water (e.g., 95:5 v/v). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 10 is prepared by dissolving Compound A (e.g., an amorphous form of Compound A) in a solvent, followed by slow evaporation of the solvent. In one embodiment, Form 10 is prepared by dissolving Compound A in a mixture of acetonitrile and water (e.g., 95:5 v/v) or a mixture of N-methyl-2-pyrrolidone:water (e.g., 90:10 v/v). In one embodiment, the dissolving is conducted at ambient temperature (e.g., approximately 20° C. to approximately 25° C.). In one embodiment, the dissolving is conducted with temperature cycle, as described herein. In one embodiment, preparation (e.g., dissolving) of Form 10 further comprises heating the sample. In one embodiment, preparation (e.g., dissolving) of Form 10 further comprises heating the sample to or above approximately 40° C.

In one embodiment, Form 10 is prepared by dissolving Compound A (e.g., an amorphous form of Compound A) in a first solvent to form a solution; and adding an anti-solvent to the solution to form a slurry. In one embodiment, the first solvent is a mixture of acetonitrile and water (e.g., 95:5 v/v). In one embodiment, the anti-solvent is a mixture of N-methyl-2-pyrrolidone:water (e.g., 90:10 v/v). In one embodiment, Compound A (e.g., an amorphous form of Compound A) is dissolved in the first solvent at ambient temperature (e.g., approximately 20° C. to approximately 25° C.). In one embodiment, Compound A (e.g., an amorphous form of Compound A) is dissolved in the first solvent at an elevated temperature (e.g., 40° C.). In one embodiment, the anti-solvent is added with continuous agitation. In one embodiment, the anti-solvent is added at ambient temperature (e.g., approximately 20° C. to approximately 25° C.).

Form 11

In one embodiment, the present application provides a Form 11 polymorph of Compound A ("Form 11") characterized by an XRPD pattern comprising peaks at approximately 16.1, 16.6, and 21.7° 2θ using Cu Kα radiation. In one embodiment, Form 11 is characterized by an XRPD pattern comprising peaks at approximately 16.1, 16.6, 21.7, 22.1, and 22.6° 2θ using Cu Kα radiation. In one embodiment, Form 11 is characterized by an XRPD pattern comprising peaks at approximately 7.5, 15.1, 16.1, 16.6, 18.4, 21.3, 21.7, 22.1, 22.6, 22.8, 24.6, and 28.2° 2θ using Cu Kα radiation. In one embodiment, Form 11 is characterized by an XRPD pattern comprising peaks at approximately 7.5, 12.6, 14.1, 15.1, 15.3, 16.1, 16.6, 18.4, 19.8, 21.3, 21.7, 22.1, 22.6, 22.8, 23.7, 24.6, 25.5, 27.4, 28.2, 28.7, and 31.1° 2θ using Cu Kα radiation. In one embodiment, Form 11 is characterized by an XRPD pattern comprising peaks at approximately the positions shown in the table below:

| Position (°2θ) | Height (counts) | d-spacing (Å) | Relative Intensity (%) |
|---|---|---|---|
| 7.534 | 1030.640 | 11.735 | 27.360 |
| 9.405 | 398.730 | 9.404 | 10.590 |
| 11.001 | 508.340 | 8.043 | 13.500 |
| 11.782 | 152.100 | 7.511 | 4.040 |
| 12.142 | 313.200 | 7.290 | 8.320 |
| 12.564 | 649.010 | 7.046 | 17.230 |
| 13.642 | 348.130 | 6.491 | 9.240 |
| 14.085 | 591.590 | 6.288 | 15.710 |
| 14.544 | 126.440 | 6.091 | 3.360 |
| 15.124 | 967.020 | 5.858 | 25.680 |
| 15.307 | 602.220 | 5.789 | 15.990 |
| 16.136 | 2322.980 | 5.493 | 61.680 |
| 16.564 | 3766.330 | 5.352 | 100.000 |
| 17.361 | 414.510 | 5.108 | 11.010 |
| 17.723 | 396.420 | 5.005 | 10.530 |
| 18.370 | 989.920 | 4.830 | 26.280 |
| 18.901 | 442.360 | 4.695 | 11.750 |
| 19.455 | 225.990 | 4.563 | 6.000 |
| 19.794 | 729.890 | 4.485 | 19.380 |
| 20.540 | 183.340 | 4.324 | 4.870 |
| 20.806 | 302.060 | 4.269 | 8.020 |
| 21.306 | 983.590 | 4.170 | 26.120 |
| 21.670 | 1908.850 | 4.101 | 50.680 |
| 22.112 | 1725.680 | 4.020 | 45.820 |
| 22.585 | 183.410 | 3.937 | 48.680 |
| 22.804 | 1068.790 | 3.900 | 28.380 |
| 23.077 | 387.270 | 3.854 | 10.280 |
| 23.286 | 288.560 | 3.820 | 7.660 |
| 23.727 | 611.120 | 3.750 | 16.230 |
| 24.136 | 225.360 | 3.687 | 5.980 |
| 24.595 | 1166.430 | 3.620 | 30.970 |
| 25.508 | 759.370 | 3.492 | 20.160 |
| 25.906 | 444.840 | 3.439 | 11.810 |
| 26.170 | 487.070 | 3.405 | 12.930 |
| 26.591 | 532.110 | 3.352 | 14.130 |
| 26.997 | 205.330 | 3.303 | 5.450 |
| 27.403 | 669.600 | 3.255 | 17.780 |
| 28.223 | 962.730 | 3.162 | 25.560 |
| 28.656 | 661.630 | 3.115 | 17.570 |
| 29.006 | 182.050 | 3.078 | 4.830 |
| 29.354 | 140.710 | 3.043 | 3.740 |
| 29.983 | 181.570 | 2.980 | 4.820 |
| 30.514 | 354.410 | 2.930 | 9.410 |
| 31.131 | 790.400 | 2.873 | 20.990 |
| 31.804 | 81.100 | 2.814 | 2.150 |
| 32.300 | 172.110 | 2.772 | 4.570 |
| 33.002 | 131.150 | 2.714 | 3.480 |
| 33.473 | 231.370 | 2.677 | 6.140 |
| 33.970 | 142.300 | 2.639 | 3.780 |
| 34.588 | 321.550 | 2.593 | 8.540 |

In one embodiment, the present application provides a Form 11 polymorph of Compound A ("Form 11") characterized by an XRPD pattern comprising peaks at approximately 16.1, 16.5, and 22.6° 2θ using Cu Kα radiation. In one embodiment, Form 11 is characterized by an XRPD pattern comprising peaks at approximately 7.5, 16.1, 16.5, 22.1, and 22.6° 2θ using Cu Kα radiation. In one embodiment, Form 11 is characterized by an XRPD pattern comprising peaks at approximately 7.5, 12.6, 15.1, 16.1, 16.5, 18.3, 19.8, 21.3, 21.8, 22.1, and 22.6° 2θ using Cu Kα radiation. In one embodiment, Form 11 is characterized by an XRPD pattern comprising peaks at approximately 7.5, 12.6, 14.1, 15.1, 15.3, 16.1, 16.5, 18.3, 19.8, 21.3, 21.8, 22.1, 22.6, 25.9, 26.6, 27.3, 27.4, and 28.6° 2θ using Cu Kα radiation. In one embodiment, Form 11 is characterized by an XRPD pattern comprising peaks at approximately the positions shown in the table below:

| Pos. [°2θ] | Height [cts] | d-spacing [Å] | Rel. Int. [%] |
|---|---|---|---|
| 7.5385 | 1700.73 | 11.7274 | 24.98 |
| 9.3925 | 389.38 | 9.4162 | 5.72 |
| 9.7844 | 87.53 | 9.03993 | 1.29 |
| 10.9862 | 653.8 | 8.0536 | 9.6 |
| 12.1411 | 472.42 | 7.29 | 6.94 |
| 12.573 | 1193.63 | 7.04052 | 17.53 |
| 13.6169 | 511.48 | 6.50304 | 7.51 |
| 14.0768 | 996.6 | 6.29161 | 14.64 |
| 14.5488 | 240.85 | 6.08852 | 3.54 |
| 15.0955 | 1253.37 | 5.86921 | 18.41 |
| 15.3222 | 755.84 | 5.78288 | 11.1 |
| 16.1421 | 2880.5 | 5.49096 | 42.31 |
| 16.5394 | 6808.7 | 5.35995 | 100 |
| 17.728 | 537.54 | 5.00317 | 7.89 |
| 18.3285 | 1580.64 | 4.84057 | 23.21 |
| 18.8396 | 401.08 | 4.71041 | 5.89 |
| 19.089 | 292.2 | 4.64942 | 4.29 |
| 19.4395 | 406.6 | 4.56637 | 5.97 |
| 19.7688 | 1386.27 | 4.49104 | 20.36 |
| 20.5382 | 319.25 | 4.3245 | 4.69 |
| 20.8314 | 565.47 | 4.2643 | 8.31 |
| 21.3281 | 1815.36 | 4.16611 | 26.66 |
| 21.8235 | 1364.94 | 4.07265 | 20.05 |
| 22.0531 | 2435.77 | 4.03075 | 35.77 |
| 22.6081 | 2712.47 | 3.93304 | 39.84 |
| 22.7532 | 1089.41 | 3.90829 | 16 |
| 23.0888 | 583.32 | 3.85224 | 8.57 |
| 23.7289 | 374.12 | 3.74975 | 5.49 |
| 24.099 | 455.87 | 3.69299 | 6.7 |
| 24.5787 | 2247.14 | 3.622 | 33 |
| 25.1808 | 410.7 | 3.53382 | 6.03 |
| 25.5642 | 390.81 | 3.48456 | 5.74 |
| 25.8768 | 766.64 | 3.44317 | 11.26 |
| 26.2885 | 372.94 | 3.39018 | 5.48 |
| 26.5576 | 863.42 | 3.35643 | 12.68 |
| 27.3091 | 775.8 | 3.26305 | 11.39 |
| 27.4093 | 1055.44 | 3.25404 | 15.5 |
| 27.9813 | 148.17 | 3.1888 | 2.18 |
| 28.5876 | 1261.14 | 3.12254 | 18.52 |
| 28.979 | 318.56 | 3.08125 | 4.68 |
| 29.3121 | 307.68 | 3.04699 | 4.52 |
| 29.5806 | 226.46 | 3.01994 | 3.33 |
| 30.5007 | 634.8 | 2.93091 | 9.32 |
| 30.949 | 223.61 | 2.88946 | 3.28 |
| 31.7746 | 172.68 | 2.81624 | 2.54 |
| 33.0083 | 281.39 | 2.71375 | 4.13 |
| 33.4503 | 427.44 | 2.67891 | 6.28 |
| 33.9574 | 295.37 | 2.64005 | 4.34 |
| 34.3201 | 281.64 | 2.61298 | 4.14 |
| 34.5481 | 237.61 | 2.59625 | 3.49 |

In one embodiment, Form 11 is characterized by an XRPD pattern substantially similar to that set forth in FIG. 87, FIG. 88, FIG. 90, or FIG. 92. In one embodiment, Form 11 is characterized by an XRPD pattern substantially similar to that set forth in FIG. 87 or FIG. 92. In one embodiment, Form 11 is characterized by an XRPD pattern substantially similar to that set forth in FIG. 87.

In one embodiment, Form 11 is characterized by endothermic events with onsets at approximately 112° C., approximately 197° C., and approximately 221° C. as measured by DSC. In one embodiment, Form 11 is characterized by endothermic events with peaks at approximately 125° C., approximately 204° C., and approximately 262° C. In one embodiment, Form 11 is characterized by a DSC thermogram substantially similar to that set forth in FIG. 89.

In one embodiment, Form 11 is characterized by endothermic events with onsets at approximately 119° C., approximately 195° C., approximately 210° C., and approximately 224° C. as measured by DSC. In one embodiment, Form 11 is characterized by endothermic events with peaks at approximately 128° C., approximately 202° C., approximately 213° C., and approximately 226° C. In one embodiment, Form 11 is characterized by a DSC thermogram substantially similar to that set forth in FIG. 93.

Figure 89:
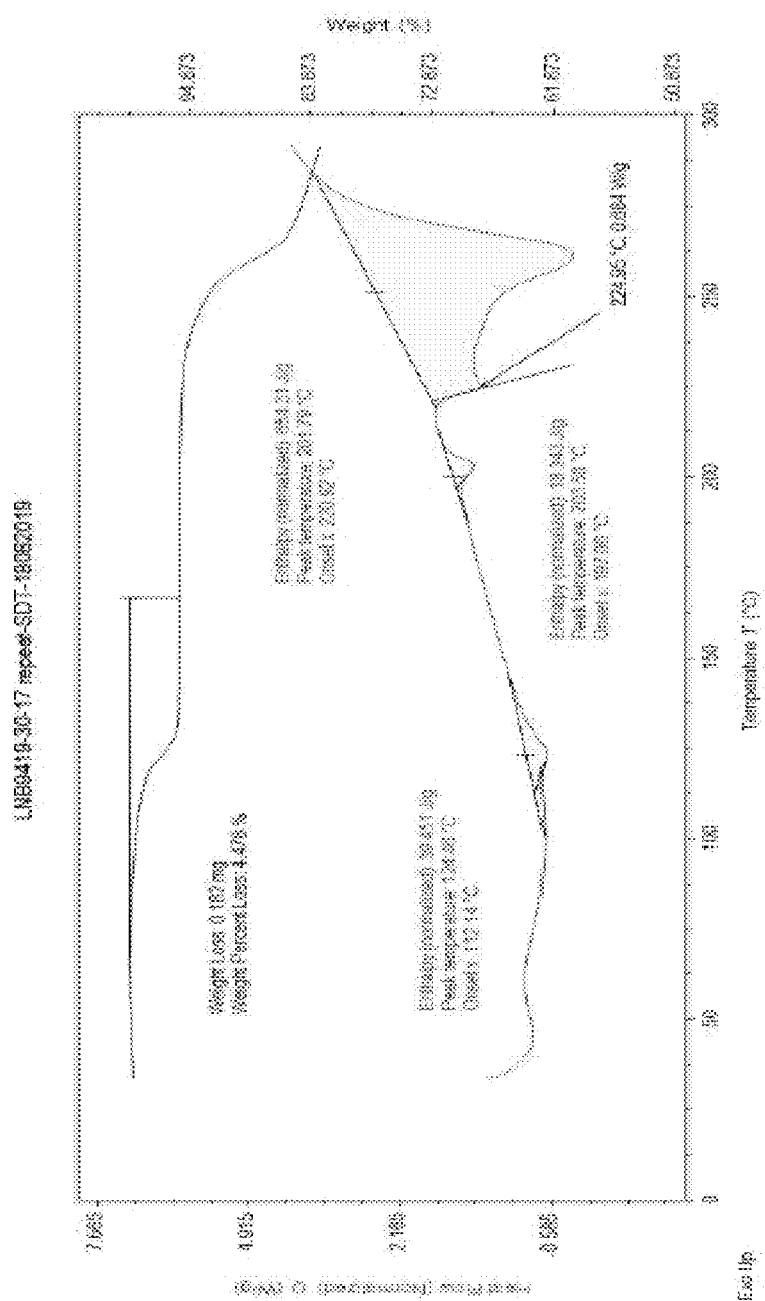
FIG. 89 sets forth a thermal analysis by TG/DSC of Form 11.
Figure 90:
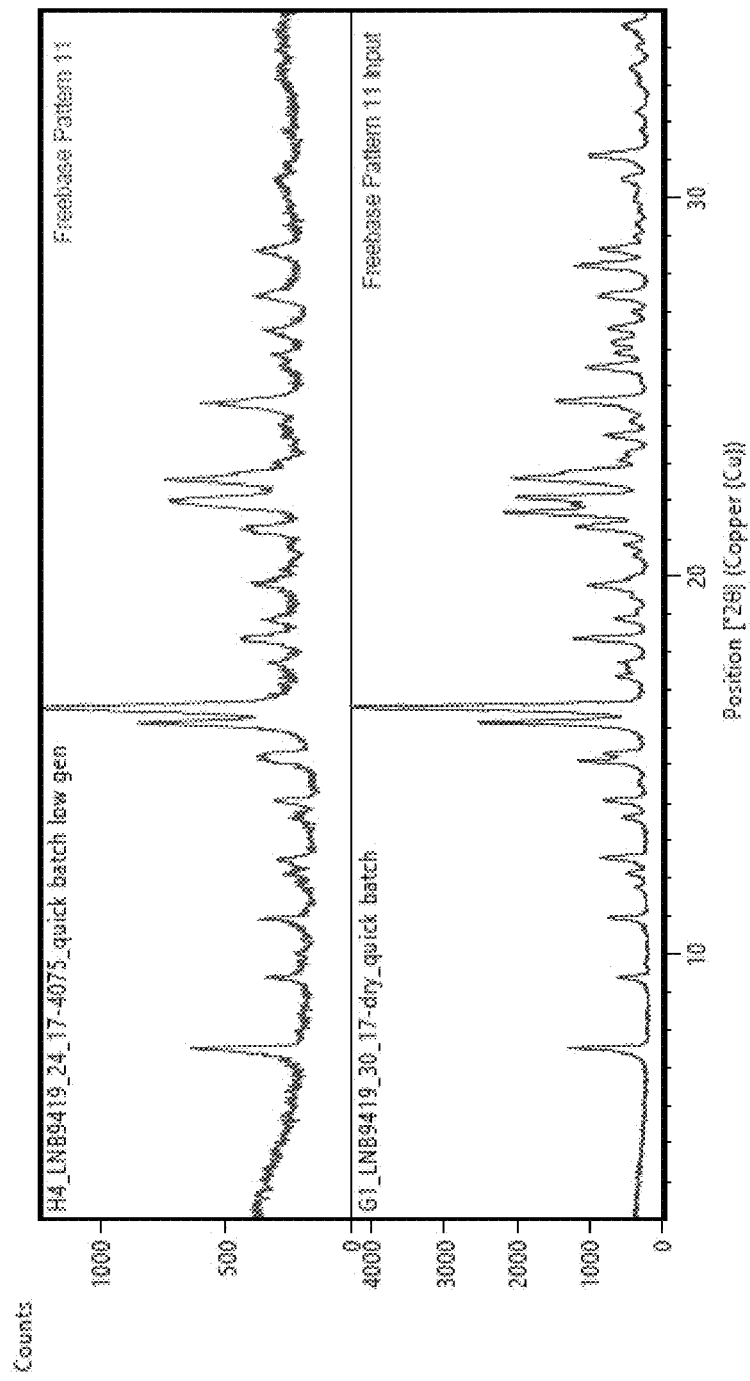
FIG. 90 sets forth XRPD patterns of Form 11 before (bottom panel) and after storage at 40° C./75% relative humidity (RH).

In one embodiment, Form 11 shows a weight loss of approximately 4.5% between approximately 50° C. and approximately 165° C. as measured by TGA (FIG. 89).

Figure 93:
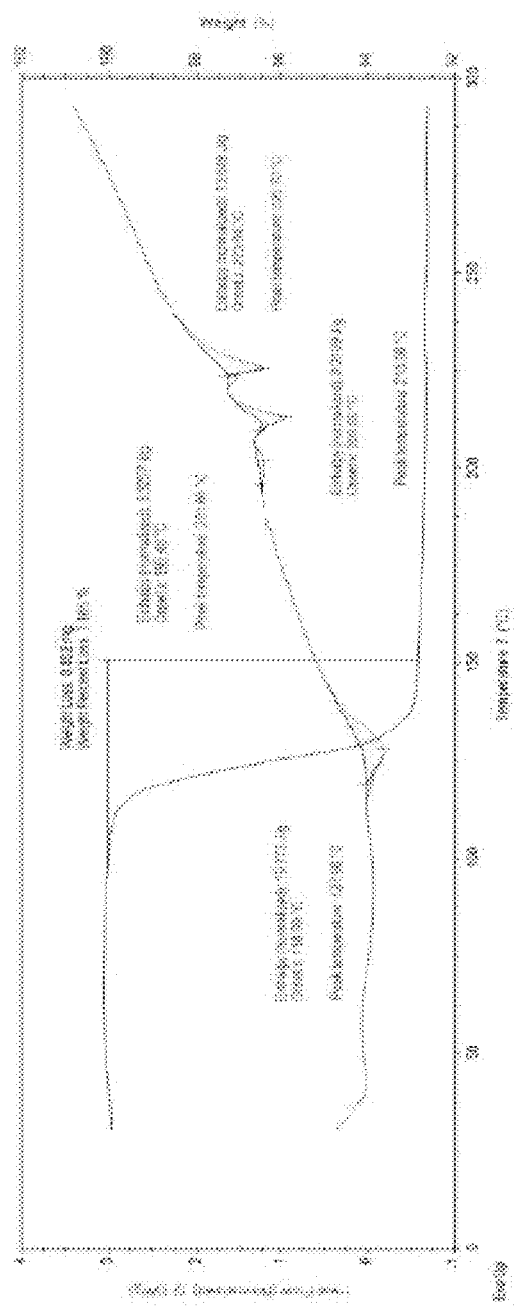
FIG. 93 sets forth a thermal analysis by TG/DSC of Form 11 obtained from 200 mg scale-up.
Figure 94:
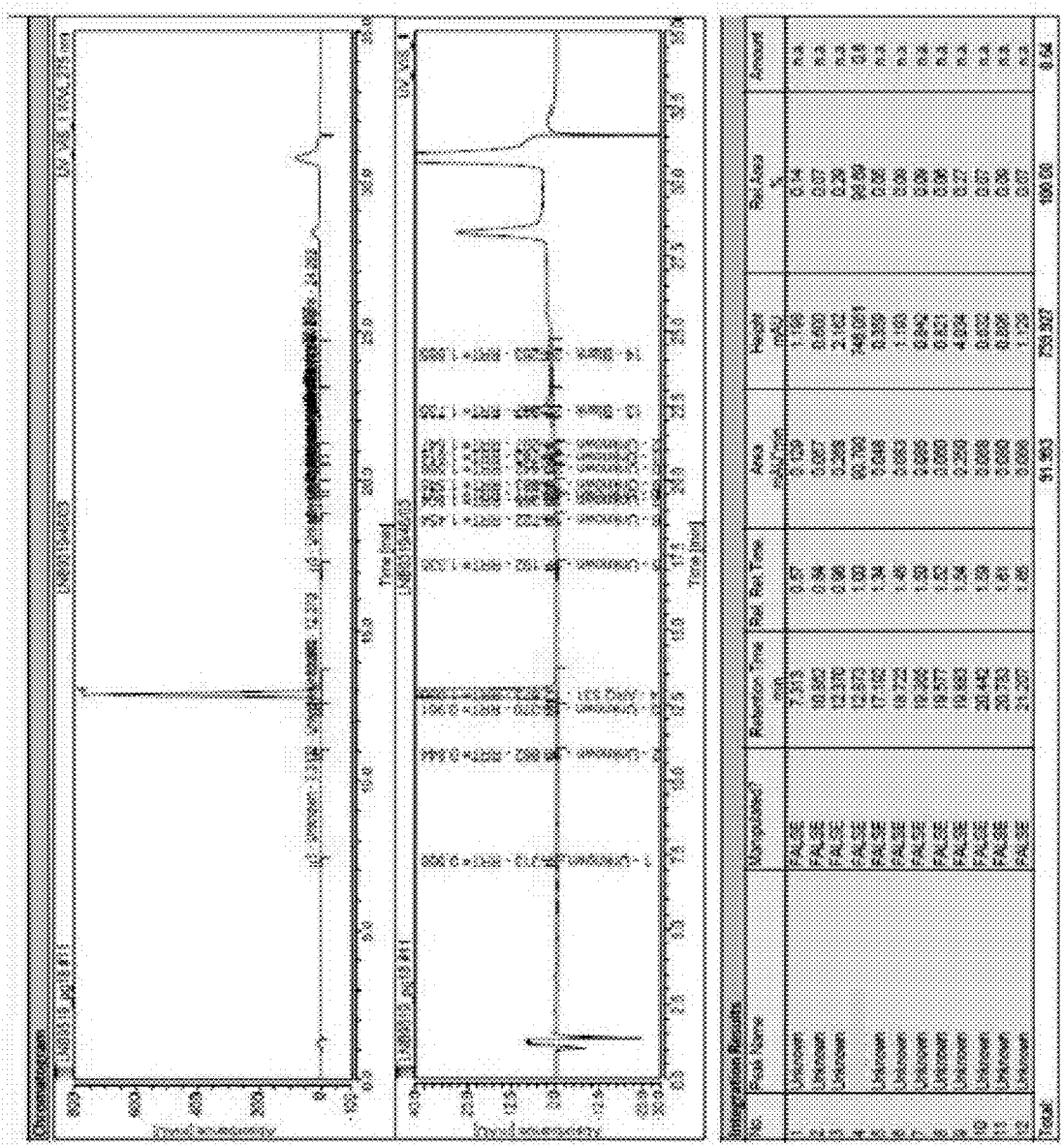
FIG. 94 sets forth an HPLC-UV chromatogram of Form 11 obtained from 200 mg scale-up.

In one embodiment, Form 11 shows a weight loss of approximately 7.2% between approximately 100° C. and approximately 150° C., and a weight loss of approximately 1.7% between approximately 150° C. and approximately 300° C. as measured by TGA (FIG. 93).

In one embodiment, Form 11 is prepared by slurrying Compound A (e.g., an amorphous form of Compound A) in a solvent. In one embodiment, Form 11 is prepared by slurrying Compound A in methyl ethyl ketone. In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C.

In one embodiment, Form 11 is prepared by dissolving Compound A (e.g., an amorphous form of Compound A) in a solvent, followed by slow evaporation of the solvent. In one embodiment, Form 11 is prepared by slurrying Compound A in methyl ethyl ketone. In one embodiment, the evaporation is conducted at 40° C. under vacuum.

Form 12

In one embodiment, the present application provides a Form 12 polymorph of Compound A ("Form 12") characterized by an XRPD pattern comprising peaks at approximately 19.6, 20.2, and 22.6° 2θ using Cu Kα radiation. In one embodiment, Form 12 is characterized by an XRPD pattern comprising peaks at approximately 18.9, 19.6, 20.2, 22.6 and 22.9° 2θ using Cu Kα radiation. In one embodiment, Form 12 is characterized by an XRPD pattern comprising peaks at approximately 5.0, 16.8, 17.3, 18.9, 19.6, 19.8, 20.2, 21.7, 22.6, 22.9, and 25.1° 2θ using Cu Kα radiation. In one embodiment, Form 12 is characterized by an XRPD pattern comprising peaks at approximately 5.0, 7.9, 15.0, 16.4, 16.8, 17.3, 17.6, 18.9, 19.6, 19.8, 20.2, 21.7, 22.6, 22.9, 25.1, and 25.5° 2θ using Cu Kα radiation. In one embodiment, Form 12 is characterized by an XRPD pattern comprising peaks at approximately the positions shown in the table below:

| Pos. [°2θ] | d-spacing [Å] | Height [cts] | Rel. Int. [%] |
|---|---|---|---|
| 4.9636 | 17.80381 | 307.21 | 64.45 |
| 7.925 | 11.1563 | 170.08 | 35.68 |
| 10.3853 | 8.5182 | 95.26 | 19.99 |
| 10.7952 | 8.19568 | 88.26 | 18.52 |
| 14.3758 | 6.1614 | 121.41 | 25.47 |
| 14.9758 | 5.91587 | 217.01 | 45.53 |
| 16.3962 | 5.40644 | 218.48 | 45.84 |
| 16.8252 | 5.26953 | 309.28 | 64.89 |
| 17.2535 | 5.13969 | 249.79 | 52.41 |
| 17.626 | 5.03189 | 132.56 | 27.81 |
| 18.4047 | 4.82073 | 113.79 | 23.87 |
| 18.9142 | 4.692 | 375.56 | 78.79 |
| 19.5739 | 4.53531 | 469.41 | 98.48 |
| 19.7601 | 4.49301 | 323.1 | 67.79 |
| 20.1812 | 4.40019 | 426.12 | 89.4 |
| 20.9409 | 4.24226 | 111.09 | 23.31 |
| 21.7341 | 4.08919 | 287.49 | 60.32 |
| 22.5958 | 3.93516 | 476.64 | 100 |
| 22.8844 | 3.88617 | 345.65 | 72.52 |
| 23.4773 | 3.78935 | 101.66 | 21.33 |
| 25.0968 | 3.54838 | 246.64 | 51.74 |
| 25.4819 | 3.49563 | 128.75 | 27.01 |
| 26.8605 | 3.31926 | 101.95 | 21.39 |
| 28.1058 | 3.17496 | 93.48 | 19.61 |
| 29.6288 | 3.01514 | 70.63 | 14.82 |

Figure 95:
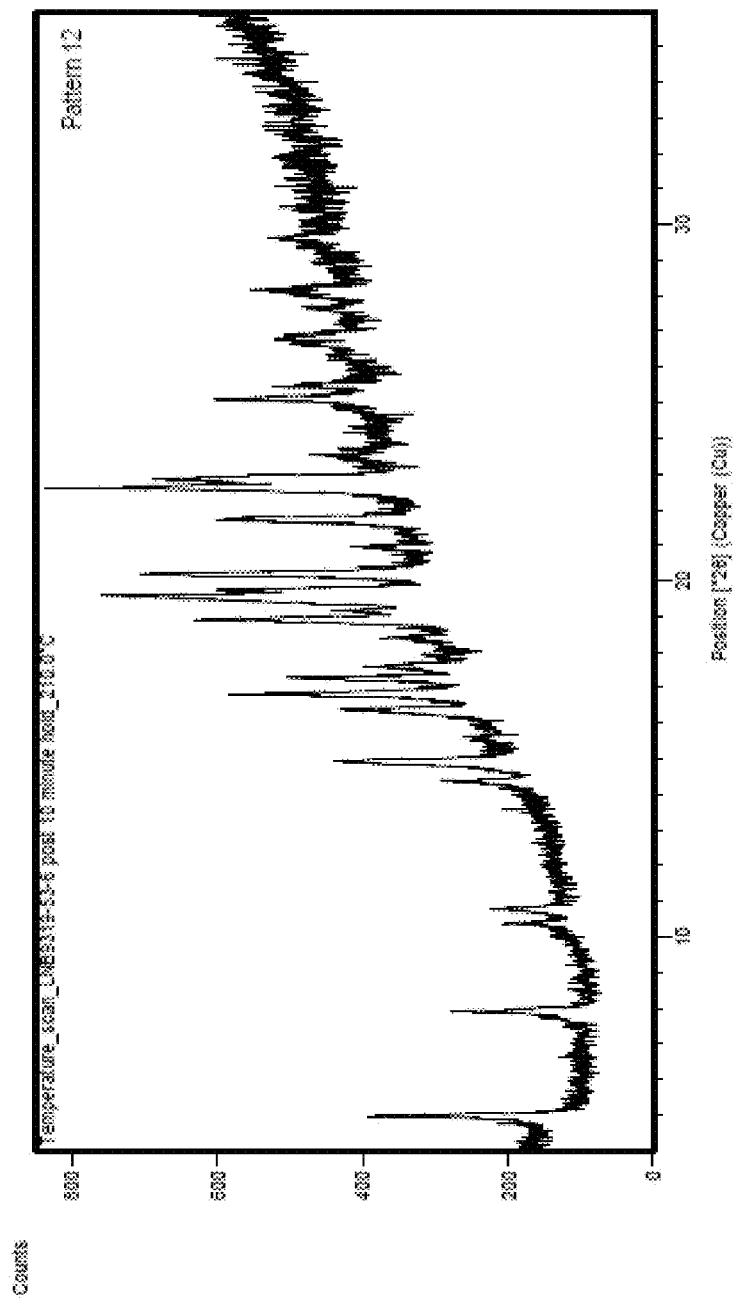
FIG. 95 sets forth an XRPD pattern of Form 12 obtained from 200 mg scale-up.
Figure 96:
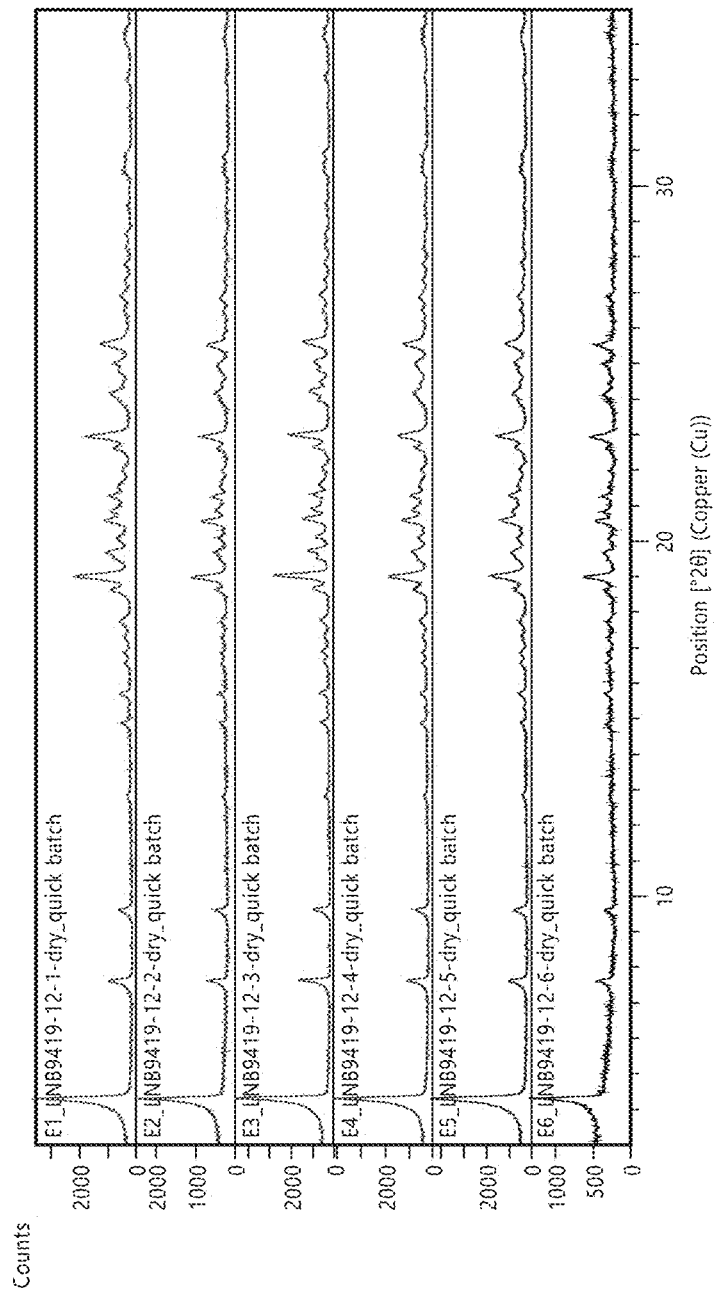
FIG. 96 sets forth comparative XRPD patterns of edisylate Form 1 obtained from evaporation of acetone, dichloromethane, methanol, isopropyl alcohol:water (90:10 v:v), methyl ethyl ketone, or THF.

In one embodiment, Form 12 is characterized by an XRPD pattern substantially similar to that set forth in FIG. 95.

In one embodiment, Form 12 is prepared by performing variable temperature experiments on Compound A (e.g., an amorphous form of Compound A). In one embodiment, Form 12 is prepared by performing variable temperature X-ray powder diffraction (VT-XRPD) on Form 10. In one embodiment, the temperature is varied from 30° C. to about 230° C., from about 30° C. to about 220° C., from about 30° C. to about 210° C., from about 30° C. to about 200° C., from about 30° C. to about 190° C., from about 30° C. to about 180° C., from about 30° C. to about 170° C., from about 30° C. to about 160° C., from about 30° C. to about 150° C., from about 30° C. to about 140° C., from about 30° C. to about 130° C., from about 30° C. to about 120° C., from about 30° C. to about 110° C., from about 30° C. to about 100° C., from about 30° C. to about 90° C., from about 30° C. to about 80° C., from about 30° C. to about 70° C., from about 30° C. to about 60° C., from about 30° C. to about 50° C., from about 30° C. to about 40° C., from about 40° C. to about 230° C., from about 50° C. to about 230° C., from about 60° C. to about 230° C., from about 70° C. to about 230° C., from about 80° C. to about 230° C., from about 90° C. to about 230° C., from about 100° C. to about 230° C., from about 110° C. to about 230° C., from about 120° C. to about 230° C., from about 130° C. to about 230° C., from about 140° C. to about 230° C., from about 150° C. to about 230° C., from about 160° C. to about 230° C., from about 170° C. to about 230° C., from about 180° C. to about 190° C., from about 200° C. to about 230° C., from about 210° C. to about 230° C., or from about 220° C. to about 230° C.

Polymorphs of Salts of Compound A

Edisylate Form 1

In one embodiment, the present application provides an edisylate Form 1 polymorph of Compound A ("edisylate Form 1") characterized by an XRPD pattern comprising peaks at approximately 4.3, 19.0, and 22.9° 2θ using Cu Kα radiation. In one embodiment, edisylate Form 1 is characterized by an XRPD pattern comprising peaks at approximately 4.3, 19.0, 20.6, 22.9, and 25.5° 2θ using Cu Kα radiation. In one embodiment, edisylate Form 1 is characterized by an XRPD pattern comprising peaks at approximately 4.3, 7.6, 18.6, 19.0, 19.7, 20.6, 20.9, 21.3, 22.9, 24.2, and 25.5° 2θ using Cu Kα radiation. In one embodiment, edisylate Form 1 is characterized by an XRPD pattern comprising peaks at approximately 4.3, 7.6, 9.6, 15.7, 17.8, 18.6, 19.0, 19.5, 19.7, 20.1, 20.6, 20.9, 21.3, 21.6, 22.6, 22.9, 24.2, 24.8, 25.0, 25.5, and 26.9° 2θ using Cu Kα radiation. In one embodiment, edisylate Form 1 is characterized by an XRPD pattern comprising peaks at approximately the positions shown in the table below:

| Position (°2θ) | d-spacing (Å) | Height (counts) | Relative Intensity (%) |
| --- | --- | --- | --- |
| 4.324 | 20.436 | 3034.440 | 100.000 |
| 7.639 | 11.573 | 769.110 | 25.350 |
| 9.625 | 9.189 | 455.950 | 15.030 |
| 12.826 | 6.902 | 137.590 | 4.530 |
| 14.882 | 5.953 | 282.170 | 9.300 |
| 15.708 | 5.642 | 372.610 | 12.280 |
| 16.582 | 5.346 | 210.900 | 6.950 |
| 16.886 | 5.251 | 224.710 | 7.410 |
| 17.346 | 5.112 | 211.390 | 6.970 |
| 17.760 | 4.994 | 404.040 | 13.320 |
| 18.629 | 4.763 | 685.860 | 22.600 |
| 19.020 | 4.666 | 1942.850 | 64.030 |
| 19.488 | 4.555 | 549.000 | 18.090 |
| 19.682 | 4.511 | 889.070 | 29.300 |
| 20.089 | 4.420 | 431.560 | 14.220 |
| 20.578 | 4.316 | 915.610 | 30.170 |
| 20.854 | 4.260 | 693.030 | 22.840 |
| 21.300 | 4.172 | 723.900 | 23.860 |
| 21.555 | 4.123 | 450.520 | 14.850 |
| 22.035 | 4.034 | 299.850 | 9.880 |
| 22.613 | 3.932 | 604.000 | 19.900 |
| 22.941 | 3.877 | 1477.090 | 48.680 |
| 24.186 | 3.680 | 672.010 | 22.150 |
| 24.769 | 3.595 | 430.980 | 14.200 |
| 25.010 | 3.560 | 576.470 | 19.000 |
| 25.546 | 3.487 | 998.780 | 32.910 |
| 26.537 | 3.359 | 247.760 | 8.160 |
| 26.899 | 3.315 | 355.130 | 11.700 |
| 27.329 | 3.263 | 230.780 | 7.610 |
| 27.797 | 3.210 | 227.830 | 7.510 |
| 28.280 | 3.156 | 192.060 | 6.330 |
| 28.685 | 3.112 | 139.540 | 4.600 |
| 29.427 | 3.035 | 123.880 | 4.080 |
| 30.384 | 2.942 | 212.790 | 7.010 |
| 30.890 | 2.895 | 211.580 | 6.970 |
| 33.016 | 2.713 | 125.310 | 4.130 |
| 34.111 | 2.629 | 222.540 | 7.330 |

Figure 97:
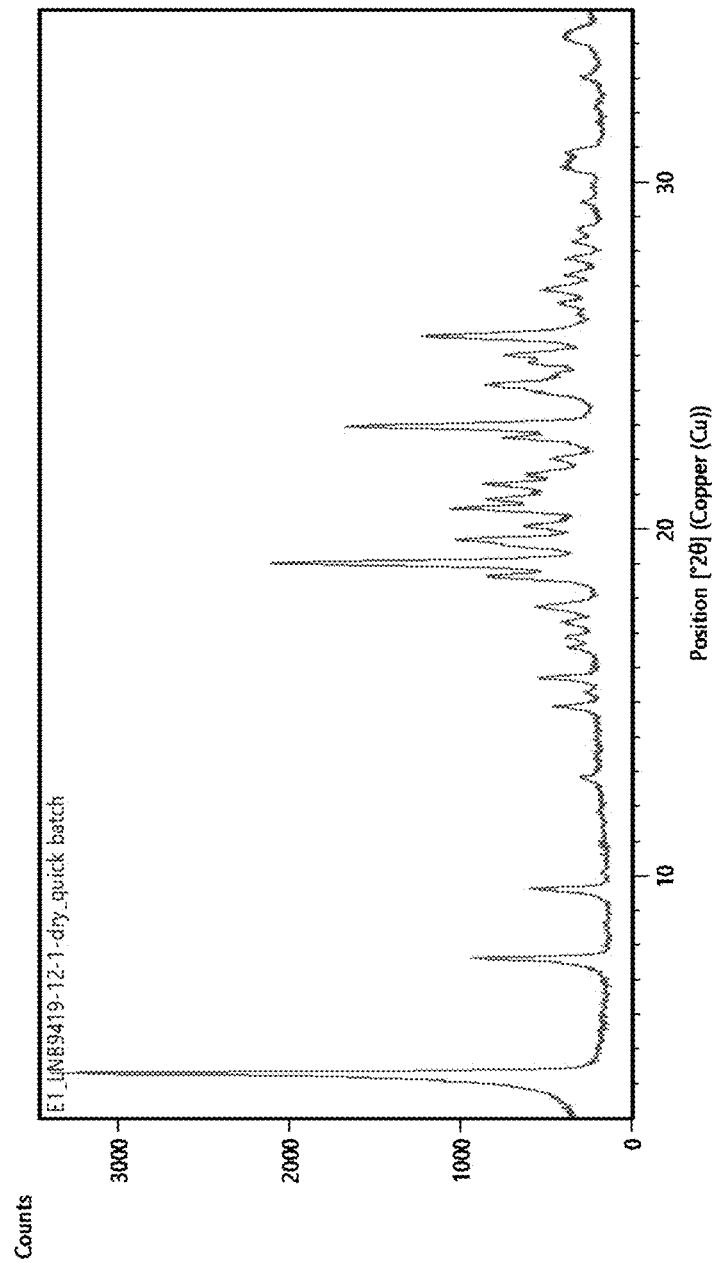
FIG. 97 sets forth an XRPD pattern of edisylate Form 1.

In one embodiment, edisylate Form 1 is characterized by an XRPD pattern substantially similar to that set forth in FIG. 97.

In one embodiment, edisylate Form 1 is characterized by an endothermic event with an onset at approximately 229° C. or approximately 230° C. as measured by DTA. In one embodiment, edisylate Form 1 is characterized by an endothermic event with a peak at approximately 235° C. In one embodiment, edisylate Form 1 is characterized by a DTA thermogram substantially similar to that set forth in FIG. 98.

In one embodiment, edisylate Form 1 shows a weight loss of approximately 0.5% between approximately 25° C. and approximately 70° C., a weight loss of 0.3% between approximately 80° C. and approximately 180° C., and a weight loss of 0.6% between approximately 180° C. and approximately 240° C. as measured by TGA.

In one embodiment, edisylate Form 1 is prepared by slurrying or dissolving Compound A (e.g., an amorphous form of Compound A) in a solvent. In one embodiment, edisylate Form 1 is prepared by slurrying or dissolving Compound A (e.g., an amorphous form of Compound A) in a solvent selected from the group consisting of acetone, dichloromethane, methanol, 2-propanol:water (90:10 v/v), methyl ethyl ketone, and tetrahydrofuran, and mixtures thereof. In one embodiment, edisylate Form 1 is prepared by adding a solution or slurry of 1,2-ethane disulfonic acid (1.1 equivalents based on the weight of Compound A freebase) to a slurry or solution of Compound A. In one embodiment, the mixture (e.g., slurry) of 1,2-ethane disulfonic acid and Compound A is heated to approximately 40° C. In one embodiment, the mixing (e.g., slurrying) is conducted with continuous agitation. In one embodiment, the mixture (e.g., slurry) is temperature cycled. In one embodiment, the mixture (e.g., slurry) is temperature cycled in 0.5-8-hour cycles, preferably 1.0-6.0-hour cycles, preferably 1.5-4.0-hour cycles, preferably about 2.0-hour cycles or about 4.0-hour cycles, for 12-144 hours, preferably 24-120 hours, preferably 36-96 hours, preferably 48-84 hours, or preferably about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, edisylate Form 1 is prepared by separating the solid by centrifugation. In one embodiment, edisylate Form 1 was prepared by drying the damp solid at 40° C. under vacuum for about 18 hours.

Cyclamate Form 1

In one embodiment, the present application provides a cyclamate Form 1 polymorph of Compound A ("cyclamate Form 1") characterized by an XRPD pattern comprising peaks at approximately 5.3, 6.4, and 18.5° 2θ using Cu Kα radiation. In one embodiment, cyclamate Form 1 is characterized by an XRPD pattern comprising peaks at approximately 5.3, 6.0, 6.4, 18.5, and 21.6° 2θ using Cu Kα radiation. In one embodiment, cyclamate Form 1 is characterized by an XRPD pattern comprising peaks at approximately 5.3, 6.0, 6.4, 16.6, 18.5, 19.3, 21.6, and 22.6° 2θ using Cu Kα radiation. In one embodiment, cyclamate Form 1 is characterized by an XRPD pattern comprising peaks at approximately the positions shown in the table below:

| Position (°2θ) | d-spacing (Å) | Height (counts) | Relative Intensity (%) |
| --- | --- | --- | --- |
| 5.286 | 16.717 | 777.910 | 30.760 |
| 6.014 | 14.697 | 550.330 | 21.760 |
| 6.416 | 13.777 | 2348.300 | 92.860 |
| 8.948 | 9.883 | 43.620 | 1.730 |
| 10.490 | 8.433 | 39.110 | 1.550 |
| 12.042 | 7.350 | 52.320 | 2.070 |
| 16.555 | 5.355 | 176.450 | 6.980 |
| 18.460 | 4.806 | 2528.900 | 100.000 |
| 19.325 | 4.593 | 302.410 | 11.960 |
| 20.094 | 4.419 | 153.100 | 6.050 |
| 21.604 | 4.113 | 567.650 | 22.450 |
| 22.572 | 3.939 | 161.780 | 6.400 |
| 26.084 | 3.416 | 79.610 | 3.150 |
| 30.213 | 2.958 | 103.720 | 4.100 |
| 30.959 | 2.889 | 83.380 | 3.300 |

Figure 102:
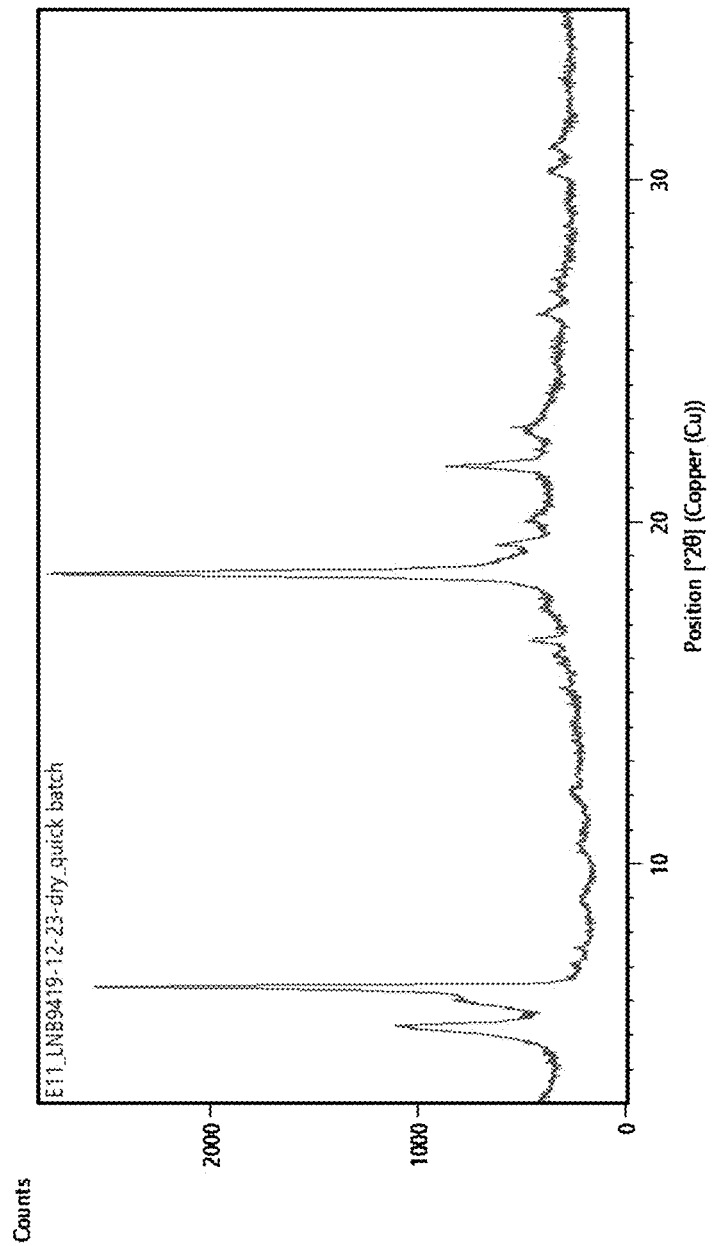
FIG. 102 sets forth an XRPD pattern of cyclamate Form 1.

In one embodiment, cyclamate Form 1 is characterized by an XRPD pattern substantially similar to that set forth in FIG. 102.

In one embodiment, cyclamate Form 1 is characterized by an endothermic event with an onset at approximately 220° C. as measured by DTA. In one embodiment, cyclamate Form 1 is characterized by an endothermic event with a peak at approximately 232° C. In one embodiment, cyclamate Form 1 is characterized by a DTA thermogram substantially similar to that set forth in FIG. 103.

In one embodiment, cyclamate Form 1 shows a weight loss of approximately 1.4% between approximately 25° C. and approximately 120° C., and a weight loss of approximately 2.4% between approximately 140° C. and approximately 260° C. as measured by TGA.

In one embodiment, cyclamate Form 1 is prepared by slurrying Compound A (e.g., an amorphous form of Compound A) in a solvent. In one embodiment, cyclamate Form 1 is prepared by slurrying Compound A (e.g., an amorphous form of Compound A) in a solvent selected from the group consisting of acetone, methyl ethyl ketone, and tetrahydrofuran, and mixtures thereof. In one embodiment, cyclamate Form 1 is prepared by adding a slurry or solution of freebase Form 1 is added to a solution of cyclamic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, cyclamate Form 1 was prepared by separating the solid by centrifugation. In one embodiment, cyclamate Form 1 was prepared by drying the damp solid at 40° C. under vacuum for ca. 18 hours.

Cyclamate Form 2

In one embodiment, the present application provides a cyclamate Form 2 polymorph of Compound A ("cyclamate Form 2") characterized by an XRPD pattern comprising peaks at approximately 7.1, 18.5, and 21.6° 2θ using Cu Kα radiation. In one embodiment, cyclamate Form 2 is characterized by an XRPD pattern comprising peaks at approximately 5.3, 6.1, 7.1, 18.5, 20.1, and 21.6° 2θ using Cu Kα radiation. In one embodiment, cyclamate Form 2 is characterized by an XRPD pattern comprising peaks at approximately the positions shown in the table below:

| Position (°2θ) | d-spacing (Å) | Height (counts) | Relative Intensity (%) |
| --- | --- | --- | --- |
| 5.262 | 16.795 | 31.790 | 58.140 |
| 6.130 | 14.418 | 30.530 | 55.830 |
| 7.069 | 12.504 | 54.680 | 100.000 |
| 16.431 | 5.395 | 23.250 | 42.510 |
| 17.376 | 5.104 | 12.280 | 22.470 |
| 18.510 | 4.793 | 53.220 | 97.330 |
| 19.540 | 4.543 | 19.300 | 35.300 |
| 20.087 | 4.421 | 27.550 | 50.390 |
| 21.558 | 4.122 | 42.180 | 77.130 |

Figure 107:
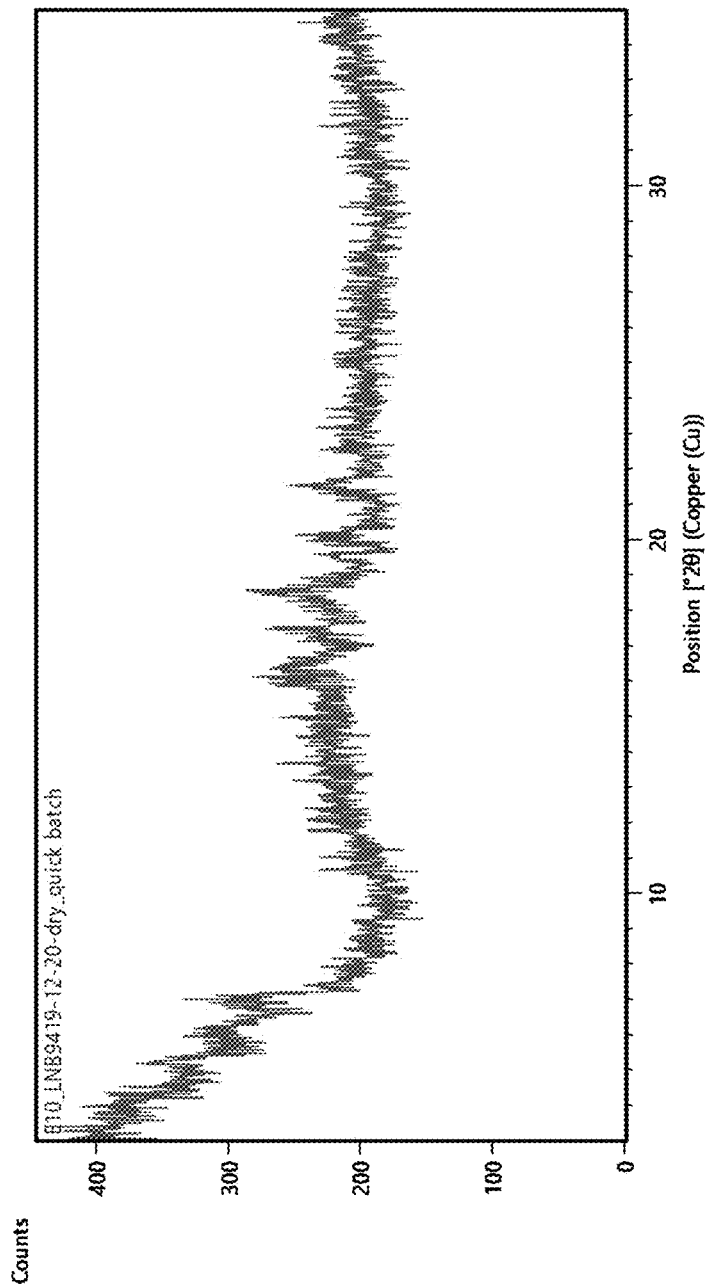
FIG. 107 sets forth an XRPD pattern of cyclamate Form 2.

In one embodiment, cyclamate Form 2 is characterized by an XRPD pattern substantially similar to that set forth in FIG. 107.

In one embodiment, cyclamate Form 2 is characterized by no thermal events as measured by DTA. Possible thermal events are noted at 145° C. and 177° C. by DTA. In one embodiment, cyclamate Form 2 is characterized by a DTA thermogram substantially similar to that set forth in FIG. 108.

In one embodiment, cyclamate Form 2 shows a weight loss of approximately 1.4% between approximately 25° C. and approximately 110° C., and a weight loss of approximately 1.8% between approximately 110° C. and approximately 210° C. as measured by TGA.

In one embodiment, cyclamate Form 2 is prepared by slurrying Compound A (e.g., an amorphous form of Compound A) in a solvent. In one embodiment, cyclamate Form 2 is prepared by slurrying Compound A (e.g., an amorphous form of Compound A) in dichloromethane. In one embodiment, cyclamate Form 2 is prepared by adding a slurry or solution of freebase Form 2 is added to a solution of cyclamic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, cyclamate Form 2 was prepared by separating the solid by centrifugation. In one embodiment, cyclamate Form 2 was prepared by drying the damp solid at 40° C. under vacuum for ca. 18 hours.

Naphthalene-2-Sulfonic Acid Salt Polymorph

In one embodiment, the present application provides a naphthalene-2-sulfonic acid salt polymorph of Compound A ("naphthalene-2-sulfonic acid salt polymorph") characterized by an XRPD pattern comprising peaks at approximately 17.5, 22.8, and 25.5° 2θ using Cu Kα radiation. In one embodiment, naphthalene-2-sulfonic acid salt polymorph is characterized by an XRPD pattern comprising peaks at approximately the positions shown in the table below:

| Position (°2θ) | d-spacing (Å) | Height (counts) | Relative Intensity (%) |
|---|---|---|---|
| 17.498 | 5.069 | 49.65 | 92.41 |
| 22.750 | 3.910 | 51.57 | 95.99 |
| 25.545 | 3.487 | 53.72 | 100.00 |

Figure 112:
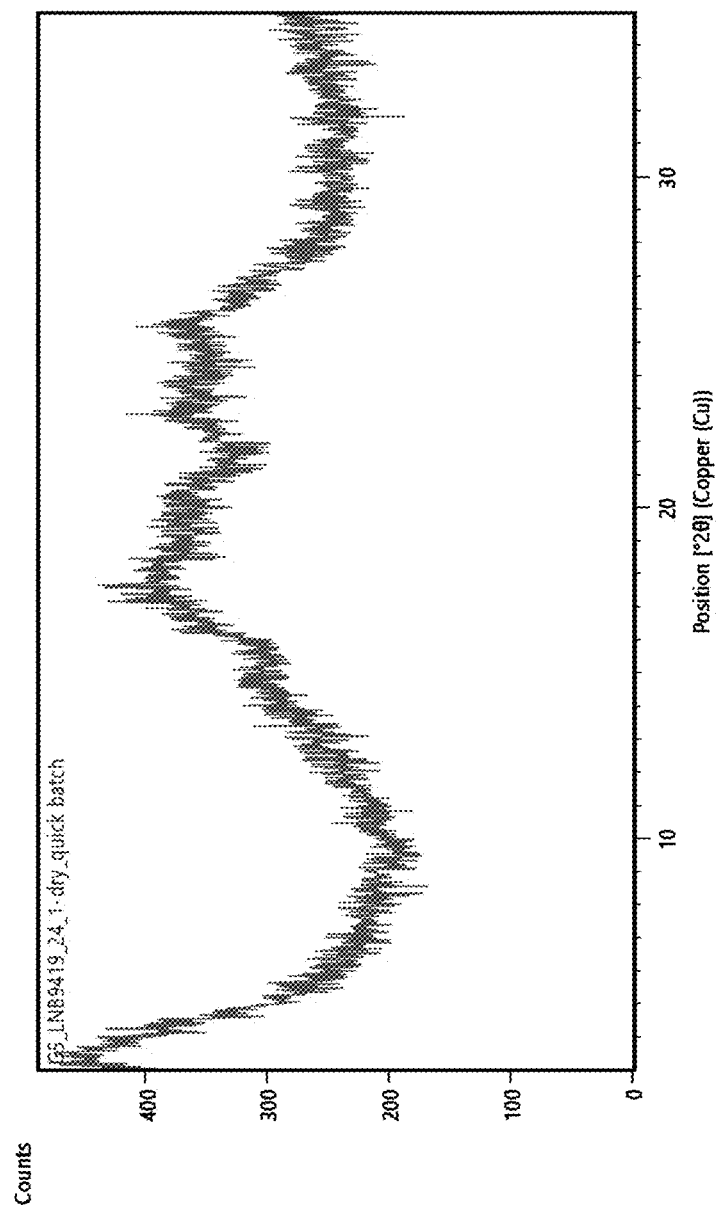
FIG. 112 sets forth an XRPD pattern of naphthalene-2-sulfonic acid salt.

In one embodiment, naphthalene-2-sulfonic acid salt polymorph is characterized by an XRPD pattern substantially similar to that set forth in FIG. 112.

In one embodiment, naphthalene-2-sulfonic acid salt polymorph is characterized by endothermic events with onsets at approximately 108° C., approximately 139° C., approximately 173° C., and approximately 244° C. as measured by DTA. In one embodiment, naphthalene-2-sulfonic acid salt polymorph is characterized by endothermic events with peaks at approximately 109° C., approximately 150° C., approximately 174° C., and approximately 257° C. In one embodiment, naphthalene-2-sulfonic acid salt polymorph is characterized by a DTA thermogram substantially similar to that set forth in FIG. 113.

In one embodiment, naphthalene-2-sulfonic acid salt polymorph shows a weight loss of approximately 4.1% between approximately 25° C. and approximately 150° C., and a weight loss of approximately 0.7% between approximately 150° C. and approximately 240° C. as measured by TGA.

In one embodiment, naphthalene-2-sulfonic acid salt polymorph is prepared by slurrying Compound A (e.g., an amorphous form of Compound A) in a solvent. In one embodiment, naphthalene-2-sulfonic acid salt polymorph is prepared by slurrying Compound A (e.g., an amorphous form of Compound A) in a solvent selected from the group consisting of acetone and methyl ethyl ketone, and mixtures thereof. In one embodiment, naphthalene-2-sulfonic acid salt polymorph is prepared by adding a slurry or solution of freebase is added to a solution of naphthalene-2-sulfonic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, naphthalene-2-sulfonic acid salt polymorph was prepared by separating the solid by centrifugation. In one embodiment, naphthalene-2-sulfonic acid salt polymorph was prepared by drying the damp solid at 40° C. under vacuum for ca. 18 hours.

Hydrobromide Form 1

In one embodiment, the present application provides a hydrobromide Form 1 polymorph of Compound A ("hydrobromide Form 1") characterized by an XRPD pattern comprising peaks at approximately 4.5, 22.6, and 26.8° 2θ using Cu Kα radiation. In one embodiment, hydrobromide Form 1 is characterized by an XRPD pattern comprising peaks at approximately 4.5, 19.6, 22.6, 26.8, and 27.6° 2θ using Cu Kα radiation. In one embodiment, hydrobromide Form 1 is characterized by an XRPD pattern comprising peaks at approximately 4.5, 7.8, 13.6, 19.6, 20.6, 22.6, 24.4, 26.8, and 27.6° 2θ using Cu Kα radiation. In one embodiment, hydrobromide Form 1 is characterized by an XRPD pattern comprising peaks at approximately 4.5, 7.8, 11.1, 13.6, 18.5, 19.3, 19.6, 20.6, 21.6, 22.6, 23.5, 24.4, 25.2, 26.8, 27.6, 28.4, and 29.1° 2θ using Cu Kα radiation. In one embodiment, hydrobromide Form 1 is characterized by an XRPD pattern comprising peaks at approximately the positions shown in the table below:

| Position (°2θ) | d-spacing (Å) | Height (counts) | Relative Intensity (%) |
|---|---|---|---|
| 4.522 | 19.542 | 2195.550 | 100.000 |
| 7.830 | 11.292 | 597.940 | 27.230 |
| 11.078 | 7.987 | 430.920 | 19.630 |
| 12.802 | 6.915 | 315.580 | 14.370 |
| 13.611 | 6.506 | 703.140 | 32.030 |
| 15.018 | 5.899 | 238.690 | 10.870 |
| 15.706 | 5.642 | 237.360 | 10.810 |
| 18.468 | 4.804 | 397.940 | 18.120 |
| 19.280 | 4.604 | 453.220 | 20.640 |
| 19.558 | 4.539 | 1483.160 | 67.550 |
| 20.600 | 4.312 | 853.780 | 38.890 |
| 21.589 | 4.116 | 389.610 | 17.750 |
| 22.572 | 3.939 | 1968.810 | 89.670 |
| 23.465 | 3.791 | 893.290 | 40.690 |
| 24.414 | 3.646 | 359.470 | 16.370 |
| 25.237 | 3.529 | 628.790 | 28.640 |
| 25.812 | 3.452 | 183.290 | 8.350 |
| 26.206 | 3.401 | 301.340 | 13.730 |
| 26.835 | 3.322 | 1900.950 | 86.580 |
| 27.611 | 3.231 | 1193.970 | 54.380 |
| 28.428 | 3.140 | 372.350 | 16.960 |
| 29.111 | 3.068 | 333.530 | 15.190 |
| 30.446 | 2.936 | 48.800 | 2.220 |
| 31.252 | 2.862 | 92.180 | 4.200 |
| 31.931 | 2.803 | 163.650 | 7.450 |
| 32.758 | 2.734 | 57.700 | 2.630 |
| 33.902 | 2.644 | 95.620 | 4.360 |

In one embodiment, hydrobromide Form 1 is characterized by an XRPD pattern substantially similar to that set forth in FIG. 117, FIG. 237, or FIG. 257.

In one embodiment, hydrobromide Form 1 is characterized by endothermic events with onsets at approximately 35° C. and approximately 172° C. as measured by DTA. In one embodiment, hydrobromide Form 1 is characterized by endothermic events with peaks at approximately 47° C. and approximately 186° C. In one embodiment, hydrobromide Form 1 is characterized by a DTA thermogram substantially similar to that set forth in FIG. 118.

In one embodiment, hydrobromide Form 1 is characterized by an endothermic event with an onset at approximately 46° C. as measured by DTA. In one embodiment, hydrobromide Form 1 is characterized by an endothermic event with a peak at approximately 59° C. In one embodiment, hydrobromide Form 1 is characterized by a DTA thermogram substantially similar to that set forth in FIG. 238.

In one embodiment, hydrobromide Form 1 shows a weight loss of approximately 3.3% between approximately 25° C. and approximately 80° C., and a weight loss of approximately 0.8% between approximately 140° C. and approximately 200° C. as measured by TGA.

In one embodiment, hydrobromide Form 1 shows a weight loss of approximately 2.6% up to 60° C., a gradual weight loss of approximately 3.1% from about 60° C. to about 200° C. before drying as measured by TGA (FIG. 238). A weight loss of approximately 0.9% was observed after drying under vacuum at 40° C. for 1 day as measured by TGA (FIG. 239). A weight loss of approximately 2% below 60° C. was observed after 3 days of drying under vacuum as measured by TGA (FIG. 240).

In one embodiment, hydrobromide Form 1 is characterized by a $^1$H-NMR spectrum showing changes in chemical shift in the region from about 7.6 to 8.7 ppm compared to the amorphous form, indicating salt formation and the presence of water. In one embodiment, hydrobromide Form 1 is characterized by a $^1$H-NMR spectrum substantially similar to that set forth in FIG. 242.

In one embodiment, PLM analysis of hydrobromide Form 1 shows small, irregular particles of various size, exhibiting birefringence (FIG. 241).

In one embodiment, hydrobromide Form 1 is stable under accelerated storage conditions (e.g., 75% RH/40° C. for 72 hours). No change in crystallinity is observed (FIG. 243).

In one embodiment, hydrobromide Form 1 is prepared by slurrying Compound A (e.g., an amorphous form of Compound A) in a solvent. In one embodiment, hydrobromide Form 1 is prepared by slurrying Compound A (e.g., an amorphous form of Compound A) in 2-methyl tetrahydrofuran or tetrahydrofuran. In one embodiment, hydrobromide Form 1 is prepared by adding a slurry or solution of freebase is added to a solution of hydrobromic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, hydrobromide Form 1 was prepared by separating the solid by centrifugation. In one embodiment, hydrobromide Form 1 was prepared by drying the damp solid at 40° C. under vacuum for ca. 18 hours.

In one embodiment, hydrobromide Form 1 is prepared by slurrying Compound A (e.g., an amorphous form of Compound A) in a solvent. In one embodiment, hydrobromide Form 1 is prepared by slurrying Compound A (e.g., an amorphous form of Compound A) in tetrahydrofuran. In one embodiment, hydrobromide Form 1 is prepared by adding hydrobromic acid (1.1 equivalents based on the weight of the freebase) to the slurry. In one embodiment, hydrobromide Form 1 is prepared by temperature cycling the slurry between about 5° C. and about 40° C. in 2 hour cycles for ca. 3 days. In one embodiment, hydrobromide Form 1 is prepared by addition of an anti-solvent to the slurry. In one embodiment, hydrobromide Form 1 is prepared by the addition of tert-butyl methyl ether to the slurry. In one embodiment, hydrobromide Form 1 is prepared by maintaining the sample at 5° C. for ca. 10 days. In one embodiment, hydrobromide Form 1 is prepared by filtering the resulting solid by centrifuge filter.

In one embodiment, hydrobromide Form 1 is prepared by slurrying Compound A (e.g., an amorphous form of Compound A) in a solvent. In one embodiment, hydrobromide Form 1 is prepared by slurrying Compound A (e.g., an amorphous form of Compound A) in ethyl acetate. In one embodiment, hydrobromide Form 1 is prepared by adding hydrobromic acid (1.1 equivalents based on the weight of the freebase) to the slurry. In one embodiment, hydrobromide Form 1 is prepared by adding hydrobromide Form 1 seed crystals to the slurry while stirring at ambient temperature. In one embodiment, hydrobromide Form 1 is prepared by transferring the sample to a reaction block and stirring at 5° C. for ca. 1 day.

In one embodiment, hydrobromide Form 1 is prepared by slurrying Compound A (e.g., an amorphous form of Compound A) in a solvent. In one embodiment, hydrobromide Form 1 is prepared by slurrying Compound A (e.g., an amorphous form of Compound A) in a solvent selected from acetone, dichloromethane, methanol, 2-propanol:water (9:1 v/v), ethyl acetate, and tetrahydrofuran. In one embodiment, hydrobromide Form 1 is prepared by slurrying Compound A (e.g., an amorphous form of Compound A) in tetrahydrofuran. In one embodiment, hydrobromide Form 1 is prepared by adding hydrobromic acid (1.1 equivalents based on the weight of the freebase) to the slurry. In one embodiment, hydrobromide Form 1 is prepared by temperature cycling the slurry between ambient temperature and about 40° C. in 2 hour cycles for ca. 72 hours. In one embodiment, hydrobromide Form 1 is prepared by evaporating the solvent and re-dissolving in tetrahydrofuran. In one embodiment, hydrobromide Form 1 is prepared by precipitating from tetrahydrofuran by adding anti-solvent. In one embodiment, hydrobromide Form 1 is prepared by addition of an anti-solvent selected from water and tert-butyl methyl ether.

Hydrobromide Form 2

In one embodiment, the present application provides a hydrobromide Form 2 polymorph of Compound A ("hydrobromide Form 2") characterized by an XRPD pattern comprising peaks at approximately 4.5, 21.7, and 26.8° 2θ using Cu Kα radiation. In one embodiment, hydrobromide Form 2 is characterized by an XRPD pattern comprising peaks at approximately 4.5, 19.3, 21.7, 24.1, and 26.8° 2θ using Cu Kα radiation. In one embodiment, hydrobromide Form 2 is characterized by an XRPD pattern comprising peaks at approximately 4.5, 15.3, 19.3, 20.5, 21.7, 24.1, and 26.8° 2θ using Cu Kα radiation. In one embodiment, hydrobromide Form 2 is characterized by an XRPD pattern comprising peaks at approximately 4.5, 7.2, 15.3, 19.3, 20.2, 20.5, 20.9, 21.7, 22.7, 23.2, 24.1, 26.8, 27.5, and 28.0° 2θ using Cu Kα radiation. In one embodiment, hydrobromide Form 2 is characterized by an XRPD pattern comprising peaks at approximately 4.5, 7.2, 15.3, 16.4, 17.1, 19.2, 19.8, 20.2, 20.5, 20.9, 21.7, 22.7, 23.2, 23.5, 24.1, 26.8, 27.5, 28.0, 28.3, 30.1, and 32.5° 2θ using Cu Kα radiation. In one embodiment, hydrobromide Form 2 is characterized by an XRPD pattern comprising peaks at approximately the positions shown in the table below:

| Position (°2θ) | d-spacing (Å) | Height (counts) | Relative Intensity (%) |
|---|---|---|---|
| 4.466 | 19.787 | 2265.090 | 100.000 |
| 7.196 | 12.284 | 529.080 | 23.360 |
| 8.941 | 9.891 | 163.230 | 7.210 |
| 9.589 | 9.224 | 78.540 | 3.470 |
| 11.283 | 7.842 | 53.820 | 2.380 |
| 15.310 | 5.787 | 644.390 | 28.450 |
| 16.439 | 5.393 | 239.480 | 10.570 |
| 17.161 | 5.167 | 364.300 | 16.080 |
| 19.262 | 4.608 | 740.650 | 32.700 |
| 19.849 | 4.473 | 267.070 | 11.790 |
| 20.232 | 4.389 | 546.340 | 24.120 |
| 20.548 | 4.322 | 660.700 | 29.170 |
| 20.920 | 4.247 | 517.060 | 22.830 |
| 21.697 | 4.096 | 1876.480 | 82.840 |
| 22.724 | 3.913 | 500.820 | 22.110 |
| 23.205 | 3.833 | 504.200 | 22.260 |
| 23.528 | 3.781 | 295.010 | 13.020 |
| 24.074 | 3.697 | 945.720 | 41.750 |
| 24.805 | 3.589 | 107.970 | 4.770 |
| 25.771 | 3.457 | 173.330 | 7.650 |
| 26.797 | 3.327 | 1013.790 | 44.760 |
| 27.524 | 3.241 | 478.680 | 21.130 |
| 27.955 | 3.192 | 481.440 | 21.250 |
| 28.250 | 3.159 | 409.740 | 18.090 |
| 28.690 | 3.112 | 157.140 | 6.940 |
| 29.295 | 3.049 | 128.250 | 5.660 |
| 30.104 | 2.969 | 356.560 | 15.740 |
| 30.907 | 2.893 | 153.120 | 6.760 |
| 31.906 | 2.805 | 63.340 | 2.800 |
| 32.479 | 2.757 | 296.370 | 13.080 |
| 34.177 | 2.624 | 50.450 | 2.230 |

In one embodiment, hydrobromide Form 2 is characterized by an XRPD pattern substantially similar to that set forth in FIG. 122.

In one embodiment, hydrobromide Form 2 is characterized by an endothermic event with an onset at approximately 202° C. as measured by DTA. In one embodiment, hydrobromide Form 2 is characterized by an endothermic event with a peak at approximately 211° C. In one embodiment, hydrobromide Form 2 is characterized by a DTA thermogram substantially similar to that set forth in FIG. 123.

In one embodiment, hydrobromide Form 2 shows a weight loss of approximately 0.2% between approximately 25° C. and approximately 160° C., and a weight loss of approximately 1.6% between approximately 160° C. and approximately 220° C. as measured by TGA.

In one embodiment, hydrobromide Form 2 is prepared by slurrying Compound A (e.g., an amorphous form of Compound A) in a solvent. In one embodiment, hydrobromide Form 2 is prepared by slurrying Compound A (e.g., an amorphous form of Compound A) in methyl ethyl ketone. In one embodiment, hydrobromide Form 2 is prepared by adding a slurry or solution of freebase is added to a solution of hydrobromic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, hydrobromide Form 1 was prepared by separating the solid by centrifugation. In one embodiment, hydrobromide Form 2 was prepared by drying the damp solid at 40° C. under vacuum for ca. 18 hours.

Besylate Form 1

In one embodiment, the present application provides a besylate Form 1 polymorph of Compound A ("besylate Form 1") characterized by an XRPD pattern comprising peaks at approximately 5.8, 6.0, and 18.9° 2θ using Cu Kα radiation. In one embodiment, besylate Form 1 is characterized by an XRPD pattern comprising peaks at approximately 5.8, 6.0, 18.3, 18.9, and 21.7° 2θ using Cu Kα radiation. In one embodiment, besylate Form 1 is characterized by an XRPD pattern comprising peaks at approximately 5.8, 6.0, 9.9, 18.0, 18.3, 18.9, 20.2, 21.7, and 23.3° 2θ using Cu Kα radiation. In one embodiment, besylate Form 1 is characterized by an XRPD pattern comprising peaks at approximately 5.8, 6.0, 9.9, 13.0, 18.0, 18.3, 18.9, 19.6, 20.2, 20.9, 21.7, 22.2, 22.7, 23.3, 24.6, 25.7, and 26.2° 2θ using Cu Kα radiation. In one embodiment, besylate Form 1 is characterized by an XRPD pattern comprising peaks at approximately the positions shown in the table below:

| Position (°2θ) | d-spacing (Å) | Height (counts) | Relative Intensity (%) |
| --- | --- | --- | --- |
| 5.786 | 15.275 | 1276.690 | 100.000 |
| 5.966 | 14.815 | 1023.240 | 80.150 |
| 9.938 | 8.901 | 387.470 | 30.350 |
| 10.216 | 8.659 | 148.010 | 11.590 |
| 11.932 | 7.417 | 138.970 | 10.880 |
| 12.965 | 6.829 | 310.990 | 24.360 |
| 13.402 | 6.607 | 120.630 | 9.450 |
| 15.210 | 5.825 | 113.850 | 8.920 |
| 16.683 | 5.314 | 154.060 | 12.070 |
| 17.304 | 5.125 | 151.250 | 11.850 |
| 17.976 | 4.935 | 515.300 | 40.360 |
| 18.324 | 4.842 | 854.850 | 66.960 |

-continued

| Position (°2θ) | d-spacing (Å) | Height (counts) | Relative Intensity (%) |
| --- | --- | --- | --- |
| 18.919 | 4.691 | 1084.570 | 84.950 |
| 19.649 | 4.518 | 216.510 | 16.960 |
| 20.158 | 4.405 | 480.970 | 37.670 |
| 20.854 | 4.260 | 343.210 | 26.880 |
| 21.659 | 4.103 | 543.940 | 42.610 |
| 22.200 | 4.004 | 326.350 | 25.560 |
| 22.691 | 3.919 | 240.340 | 18.820 |
| 23.318 | 3.815 | 496.570 | 38.890 |
| 23.679 | 3.758 | 186.000 | 14.570 |
| 24.570 | 3.623 | 245.720 | 19.250 |
| 24.985 | 3.564 | 190.310 | 14.910 |
| 25.742 | 3.461 | 211.160 | 16.540 |
| 26.228 | 3.398 | 308.550 | 24.170 |
| 27.251 | 3.273 | 120.140 | 9.410 |
| 27.533 | 3.240 | 169.420 | 13.270 |
| 27.990 | 3.188 | 107.590 | 8.430 |
| 28.403 | 3.142 | 84.340 | 6.610 |
| 30.062 | 2.973 | 161.100 | 12.620 |
| 31.453 | 2.844 | 89.350 | 7.000 |
| 32.379 | 2.765 | 61.290 | 4.800 |

In one embodiment, besylate Form 1 is characterized by an XRPD pattern substantially similar to that set forth in FIG. 127, FIG. 186, or FIG. 270.

In one embodiment, besylate Form 1 is characterized by an endothermic event with an onset at approximately 180° C. as measured by DTA. In one embodiment, besylate Form 1 is characterized by an endothermic event with a peak at approximately 188° C. In one embodiment, besylate Form 1 is characterized by a DTA thermogram substantially similar to that set forth in FIG. 128.

In one embodiment, besylate Form 1 is characterized by an endothermic event with an onset at approximately 184° C. as measured by DTA. In one embodiment, besylate Form 1 is characterized by an endothermic event with a peak at approximately 193° C. In one embodiment, besylate Form 1 is characterized by a DTA thermogram substantially similar to that set forth in FIG. 187.

In one embodiment, besylate Form 1 shows a weight loss of approximately 0.8% between approximately 25° C. and approximately 180° C., and a weight gain of approximately 0.1% between approximately 180° C. and approximately 210° C. as measured by TGA.

In one embodiment, besylate Form 1 shows a weight loss of approximately 0.4% at approximately 130° C. as measured by TGA.

In one embodiment, besylate Form 1 is characterized by a $^1$H-NMR spectrum showing ethyl acetate (ca. 0.045 equivalents) and benzene sulfonic acid (ca. 0.6 equivalents) after ca. 24 hours of drying under vacuum. In one embodiment, besylate Form 1 is characterized by a 41-NMR spectrum substantially similar to that set forth in FIG. 189.

In one embodiment, PLM analysis of besylate Form 1 shows irregular particles of various size, with some rod-like crystals observed (FIG. 188).

In one embodiment, besylate Form 1 is stable under accelerated storage conditions (e.g., 75% RH/40° C. for 72 hours). In one embodiment, the XRPD after storage shows no change (FIG. 190).

In one embodiment, besylate Form 1 is prepared by slurrying Compound A (e.g., an amorphous form of Compound A) in a solvent. In one embodiment, cyclamate Form 1 is prepared by slurrying Compound A (e.g., an amorphous form of Compound A) in a solvent selected from the group consisting of ethyl acetate, acetone, or methyl ethyl ketone, or mixtures thereof. In one embodiment, besylate Form 1 is prepared by adding a slurry or solution of freebase is added to a solution of benzene sulfonic acid (1.1 equivalents based on the weight of the freebase). In one embodiment, the slurrying is conducted at approximately 40° C. In one embodiment, the slurrying is conducted with continuous agitation. In one embodiment, the slurry is temperature cycled. In one embodiment the slurry is temperature cycled in 0.5-8 hour cycles, preferably 1.0-6.0 hour cycles, preferably 1.5-4.0 hour cycles, preferably about 2.0 hour or about 4.0 hour cycles for 12-144 hours, preferably 24-120 hours, preferably 36-96 hours, preferably 48-84 hours, or about 72 hours. In one embodiment, the mixture (e.g., slurry) is temperature cycled between about 5° C. and about 50° C. In another embodiment, the mixture (e.g., slurry) is temperature cycled between about 10° C. and about 50° C., between about 15° C. and about 50° C., between about 20° C. and about 50° C., between about 25° C. and about 50° C., between about 30° C. and about 50° C., between about 35° C. and about 50° C., between about 40° C. and about 50° C., between about 5° C. and about 45° C., between about 5° C. and about 40° C., between about 5° C. and about 35° C., between about 5° C. and about 30° C., between about 5° C. and about 25° C., between about 5° C. and about 20° C., between about 5° C. and about 15° C., between about 10° C. and about 45° C., between about 10° C. and about 40° C., between about 10° C. and about 35° C., between about 10° C. and about 30° C., between about 10° C. and about 25° C., between about 10° C. and about 20° C., between about 20° C. and about 45° C., between about 20° C. and about 40° C., between about 20° C. and about 35° C., between about 20° C. and about 30° C., between about 25° C. and about 45° C., between about 25° C. and about 40° C., between about 25° C. and about 35° C., between about 30° C. and about 45° C., between about 30° C. and about 40° C., or between about 35° C. and about 45° C. In one embodiment, besylate Form 1 was prepared by separating the solid by centrifugation. In one embodiment, besylate Form 1 was prepared by drying the damp solid at 40° C. under vacuum for ca. 18 hours.

In one embodiment, besylate Form 1 is prepared by slurrying Compound A (e.g., an amorphous form of Compound A) in a solvent. In one embodiment, besylate Form 1 is prepared by slurrying Compound A (e.g., an amorphous form of Compound A) in a solvent selected from acetone, dichloromethane, methanol, 2-propanol:water (9:1 v/v), ethyl acetate, and tetrahydrofuran. In one embodiment, besylate Form 2 is prepared by slurrying Compound A (e.g., an amorphous form of Compound A) in ethyl acetate. In one embodiment, besylate Form 1 is prepared by adding benzene sulfonic acid (1.1 equivalents based on the weight of the freebase) to the slurry. In one embodiment, besylate Form 1 is prepared by temperature cycling the slurry (e.g., between ambient temperature and about 40° C. or between about 5° C. and about 40° C.) in 2 hour cycles for ca. 72 hours. In one embodiment, the preparation comprises stirring. In one embodiment, besylate Form 1 is prepared by isolating the solid by centrifuge filtration. In one embodiment, besylate Form 1 is prepared by drying the solid (e.g., under vacuum).

Hydrochloride Form 1

In one embodiment, the present application provides a hydrochloride Form 1 polymorph of Compound A ("hydrochloride Form 1") characterized by an XRPD pattern comprising peaks at approximately 4.6, 19.8, and 22.7° 2θ using Cu Kα radiation. In one embodiment, hydrochloride Form 1 is characterized by an XRPD pattern substantially similar to that set forth in FIG. 181.

In one embodiment, hydrochloride Form 1 gradually converts to hydrochloride Form 2 under ambient conditions.

In one embodiment, hydrochloride Form 1 is prepared by slurrying Compound A (e.g., an amorphous form of Compound A) in a solvent. In one embodiment, hydrochloride Form 1 is prepared by slurrying Compound A (e.g., an amorphous form of Compound A) in ethyl acetate. In one embodiment, hydrochloride Form 1 is prepared by adding hydrochloric acid (1.1 equivalents based on the weight of the freebase) to the slurry. In one embodiment, hydrochloride Form 1 is prepared by temperature cycling the slurry (e.g., between ambient temperature and about 40° C. or between about 5° C. and about 40° C.) in 2 hour cycles for ca. 72 hours. In one embodiment, hydrochloride Form 1 is prepared by isolating the solid by centrifuge filtration.

Hydrochloride Form 2

In one embodiment, the present application provides a hydrochloride Form 2 polymorph of Compound A ("hydrochloride Form 2") characterized by an XRPD pattern comprising peaks at approximately 16.0, 16.4, and 21.6° 2θ using Cu Kα radiation. In one embodiment, hydrochloride Form 2 is characterized by an XRPD pattern substantially similar to that set forth in FIG. 181 or FIG. 185.

In one embodiment, hydrochloride Form 2 is characterized by an endothermic event with an onset at approximately 129° C. as measured by DTA. In one embodiment, hydrochloride Form 2 is characterized by an endothermic event with a peak at approximately 136° C. In one embodiment, hydrochloride Form 2 is characterized by a DTA thermogram substantially similar to that set forth in FIG. 182.

In one embodiment, hydrochloride Form 2 shows a weight loss of approximately 9.3% at approximately 129° C. as measured by TGA. In one embodiment, hydrochloride Form 2 shows weight losses of approximately 1% at approximately 60° C., approximately 4.5% at approximately 130° C., and approximately 1.3% from approximately 130° C. to approximately 170° C. while drying under vacuum.

In one embodiment, hydrochloride Form 2 is characterized by a $^1$H-NMR spectrum showing changes (ca. 0.1 ppm) in chemical shift in the region from about 7.6 to 9.0 ppm compared to the amorphous form. In one embodiment, the $^1$H-NMR spectrum shows ethyl acetate (0.23 equivalents) after ca. 24 hours of drying under vacuum. In one embodiment, hydrochloride Form 2 is characterized by a $^1$H-NMR spectrum substantially similar to that set forth in FIG. 184.

In one embodiment, PLM analysis of hydrochloride Form 2 shows small, irregular particles up to 50 μm in size, exhibiting birefringence (FIG. 183).

In one embodiment, after tested under accelerated storage conditions (e.g., 75% RH/40° C. for 72 hours), hydrochloride Form 2 shows decreased crystallinity (FIG. 185).

In one embodiment, hydrochloride Form 2 is prepared by slurrying Compound A (e.g., an amorphous form of Compound A) in a solvent. In one embodiment, hydrochloride Form 2 is prepared by slurrying Compound A (e.g., an amorphous form of Compound A) in ethyl acetate. In one embodiment, hydrochloride Form 2 is prepared by adding hydrochloric acid (1.1 equivalents based on the weight of the freebase) to the slurry. In one embodiment, hydrochloride Form 2 is prepared by temperature cycling the slurry (e.g., between ambient temperature and about 40° C. or between about 5° C. and about 40° C.) in 2 hour cycles for ca. 72 hours. In one embodiment, hydrochloride Form 2 is prepared by isolating the solid by centrifuge filtration.

Oxalate Form 1

In one embodiment, the present application provides an oxalate Form 1 polymorph of Compound A ("oxalate Form 1") characterized by an XRPD pattern comprising peaks at approximately 4.1, 19.3, and 19.7° 2θ using Cu Kα radiation. In one embodiment, oxalate Form 1 is characterized by an XRPD pattern substantially similar to that set forth in FIG. 191.

In one embodiment, oxalate Form 1 is characterized by an endothermic event with an onset at approximately 157° C. as measured by DTA. In one embodiment, oxalate Form 1 is characterized by an endothermic event with a peak at approximately 165° C. In one embodiment, oxalate Form 1 is characterized by a DTA thermogram substantially similar to that set forth in FIG. 192.

In one embodiment, oxalate Form 1 shows a weight loss of approximately 20.8% between ambient and approximately 230° C. as measured by TGA.

In one embodiment, PLM analysis of oxalate Form 1 shows small, needle-like particles that exhibited birefringence (FIG. 193).

In one embodiment, oxalate Form 1 converts to oxalate Form 5 under vacuum drying conditions.

In one embodiment, oxalate Form 1 is prepared by slurrying Compound A (e.g., an amorphous form of Compound A) in a solvent. In one embodiment, oxalate Form 1 is prepared by slurrying Compound A (e.g., an amorphous form of Compound A) in acetone, dichloromethane, or ethyl acetate. In one embodiment, oxalate Form 1 is prepared by adding hydrochloric acid (1.1 equivalents based on the weight of the freebase) to the slurry. In one embodiment, oxalate Form 1 is prepared by temperature cycling the slurry (e.g., between ambient temperature and about 40° C. or between about 5° C. and about 40° C.) in 2 hour cycles for ca. 72 hours. In one embodiment, oxalate Form 1 is prepared by isolating the solid by centrifuge filtration.

Oxalate Form 3

In one embodiment, the present application provides an oxalate Form 3 polymorph of Compound A ("oxalate Form 3") characterized by an XRPD pattern comprising peaks at approximately 8.5, 17.6, and 21.6° 2θ using Cu Kα radiation. In one embodiment, oxalate Form 3 is characterized by an XRPD pattern substantially similar to that set forth in FIG. 194.

In one embodiment, oxalate Form 3 is characterized by an endothermic event with onset at approximately 148° C. or approximately 156° C. as measured by DTA. In one embodiment, oxalate Form 3 is characterized by an endothermic event with a peak at approximately 168° C. In one embodiment, oxalate Form 3 is characterized by a DTA thermogram substantially similar to that set forth in FIG. 195 or FIG. 196.

In one embodiment, oxalate Form 3 shows a weight loss of approximately 17% between ambient and approximately 230° C. as measured by TGA.

In one embodiment, oxalate Form 3 is characterized by a $^1$H-NMR spectrum showing 2-propanol (ca. 0.58 equivalents). In one embodiment, oxalate Form 3 is characterized by a 41-NMR spectrum substantially similar to that set forth in FIG. 198.

In one embodiment, PLM analysis of oxalate Form 3 shows small needle-like particles that exhibit birefringence (FIG. 197).

In one embodiment, oxalate Form 3 is stable under accelerated storage conditions (e.g., 75% RH/40° C. for 72 hours). In one embodiment, the XRPD after storage shows no change from the input material (FIG. 199).

In one embodiment, oxalate Form 3 is prepared by slurrying Compound A (e.g., an amorphous form of Compound A) in a solvent. In one embodiment, oxalate Form 3 is prepared by slurrying Compound A (e.g., an amorphous form of Compound A) in 2-propanol:water (9:1 v/v) or tetrahydrofuran. In one embodiment, oxalate Form 3 is prepared by slurrying Compound A (e.g., an amorphous form of Compound A) in tetrahydrofuran. In one embodiment, oxalate Form 3 is prepared by adding oxalic acid (1.1 equivalents based on the weight of the freebase) to the slurry. In one embodiment, oxalate Form 3 is prepared by temperature cycling the slurry (e.g., between ambient temperature and about 40° C. or between about 5° C. and about 40° C.) in 2 hour cycles for ca. 72 hours. In one embodiment, oxalate Form 3 is prepared by isolating the solid by centrifuge filtration.

Oxalate Form 5

In one embodiment, the present application provides an oxalate Form 5 polymorph of Compound A ("oxalate Form 5") characterized by an XRPD pattern comprising peaks at approximately 4.0, 19.5, and 19.8° 2θ using Cu Kα radiation. In one embodiment, oxalate Form 5 is characterized by an XRPD pattern substantially similar to that set forth in FIG. 191.

In one embodiment, oxalate Form 5 is characterized by an endothermic event with an onset at approximately 159° C. as measured by DTA. In one embodiment, oxalate Form 5 is characterized by a DTA thermogram substantially similar to that set forth in FIG. 200.

In one embodiment, oxalate Form 5 shows a weight loss of approximately 12% greater than 159° C. as measured by TGA.

In one embodiment, oxalate Form 5 is characterized by a $^1$H-NMR spectrum showing 2-propanol (ca. 0.02 equivalents). In one embodiment, oxalate Form 5 is characterized by a $^1$H-NMR spectrum substantially similar to that set forth in FIG. 202.

In one embodiment, PLM analysis of oxalate Form 5 shows small needle-like particles that exhibit birefringence (FIG. 201).

In one embodiment, oxalate Form 5 is stable under accelerated storage conditions (e.g., 75% RH/40° C. for 72 hours). In one embodiment, the XRPD after storage shows no change from the input material (FIG. 203).

In one embodiment, oxalate Form 5 is prepared by drying oxalate Form 1 under vacuum.

Maleate Form 1

In one embodiment, the present application provides a maleate Form 1 polymorph of Compound A ("maleate Form 1") characterized by an XRPD pattern comprising peaks at approximately 6.0, 6.3, and 19.1° 2θ using Cu Kα radiation. In one embodiment, maleate Form 1 is characterized by an XRPD pattern substantially similar to that set forth in FIG. 204.

In one embodiment, maleate Form 1 is characterized by an endothermic event with an onset at approximately 159° C. (peak at approximately 171° C.) or approximately 166° C. (peak at approximately 173° C.) as measured by DTA. In one embodiment, maleate Form 1 is characterized by a DTA thermogram substantially similar to that set forth in FIG. 205 or FIG. 206.

In one embodiment, maleate Form 1 shows a weight loss of approximately 5.5% at approximately 115-125° C. as measured by TGA. In one embodiment, maleate Form 1 shows a weight loss of approximately 4.5% at approximately 125-180° C. as measured by TGA. In one embodiment, maleate Form 1 shows a weight loss of approximately 5.8% at approximately 130-200° C. as measured by TGA.

In one embodiment, maleate Form 1 is characterized by a 41-NMR spectrum showing maleic acid (ca. 1 equivalent) and ca. 0.91 equivalent of ethyl acetate. In one embodiment, maleate Form 1 is characterized by a ¹H-NMR spectrum substantially similar to that set forth in FIG. 208.

In one embodiment, PLM analysis of maleate Form 1 shows small needle-like particles that exhibit birefringence (FIG. 207).

In one embodiment, maleate Form 1 is stable under accelerated storage conditions (e.g., 75% RH/40° C. for 72 hours). In one embodiment, the XRPD after storage shows no change from the input material (FIG. 209).

In one embodiment, maleate Form 1 is prepared by slurrying Compound A (e.g., an amorphous form of Compound A) in a solvent. In one embodiment, maleate Form 1 is prepared by slurrying Compound A (e.g., an amorphous form of Compound A) in ethyl acetate. In one embodiment, maleate Form 1 is prepared by adding maleic acid (1.1 equivalents based on the weight of the freebase) to the slurry. In one embodiment, maleate Form 1 is prepared by temperature cycling the slurry (e.g., between ambient temperature and about 40° C. or between about 5° C. and about 40° C.) in 2 hour cycles for ca. 72 hours. In one embodiment, maleate Form 1 is prepared by isolating the solid by centrifuge filtration.

1,5-Naphthalene Disulfonate Form 1

In one embodiment, the present application provides a 1,5-naphthalene disulfonate Form 1 polymorph of Compound A ("1,5-naphthalene disulfonic acid Form 1", "1,5-naphthalene disulfonate Form 1", "naphthalene disulfonic acid Form 1" or "naphthalene disulfonate Form 1") characterized by an XRPD pattern comprising peaks at approximately 5.2, 18.1, and 19.0° 2θ using Cu Kα radiation. In one embodiment, 1,5-naphthalene disulfonate Form 1 is characterized by an XRPD pattern substantially similar to that set forth in FIG. 210.

In one embodiment, 1,5-naphthalene disulfonate Form 1 is characterized by no thermal events as measured by DTA. In one embodiment, 1,5-naphthalene disulfonate Form 1 is characterized by a DTA thermogram substantially similar to that set forth in FIG. 212.

In one embodiment, 1,5-naphthalene disulfonate Form 1 is characterized by a ¹H-NMR spectrum showing 1,5-naphthalene sulfonic acid (0.56 equivalents) and ethyl acetate (ca. 0.02 equivalents). In one embodiment, 1,5-naphthalene disulfonate Form 1 is characterized by a 41-NMR spectrum substantially similar to that set forth in FIG. 214.

In one embodiment, 1,5-naphthalene disulfonate Form 1 shows continuous weight loss from ambient temperature until decomposition.

1,5-Naphthalene Disulfonate Form 1 and Form 3

In one embodiment, the present application provides a mixture of 1,5-naphthalene disulfonic acid Form 1 and Form 3 polymorphs of Compound A ("1,5-naphthalene disulfonic acid Form 1 and Form 3", "1,5-naphthalene disulfonate Form 1 and Form 3", "naphthalene disulfonic acid Form 1 and Form 3" or "naphthalene disulfonate Form 1 and Form 3") characterized by an XRPD pattern comprising peaks at approximately 4.7, 18.0, and 18.3° 2θ using Cu Kα radiation. In one embodiment, 1,5-naphthalene disulfonic acid Form 1 and Form 3 is characterized by an XRPD pattern substantially similar to that set forth in FIG. 210.

In one embodiment, 1,5-naphthalene disulfonic acid Form 1 and Form 3 is characterized by an endothermic event with an onset at approximately 111° C. as measured by DTA. In one embodiment, 1,5-naphthalene disulfonic acid Form 1 and Form 3 is characterized by a DTA thermogram substantially similar to that set forth in FIG. 211.

In one embodiment, 1,5-naphthalene disulfonic acid Form 1 and Form 3 shows a continuous weight loss from ambient temperature to decomposition as measured by TGA.

In one embodiment, PLM analysis of 1,5-naphthalene disulfonic acid Form 1 and Form 3 shows irregular particles of various sizes that exhibit birefringence (FIG. 213).

In one embodiment, 1,5-naphthalene disulfonate Form 1 and Form 3 shows continuous weight loss from ambient temperature until decomposition.

In one embodiment, 1,5-naphthalene disulfonic acid Form 1 and Form 3 is characterized by a ¹H-NMR spectrum showing 1,5-naphthalene disulfonic acid (ca. 0.56 equivalent) and ca. 0.026 equivalent of ethyl acetate. In one embodiment, 1,5-naphthalene disulfonic acid Form 1 and Form 3 is characterized by a ¹H-NMR spectrum substantially similar to that set forth in FIG. 214.

In one embodiment, after tested under accelerated storage conditions (e.g., 75% RH/40° C. for 72 hours), 1,5-naphthalene disulfonic acid Form 1 and Form 3 shows decreased crystallinity (FIG. 215).

In one embodiment, 1,5-naphthalene disulfonic acid Form 1 and Form 3 is prepared by slurrying Compound A (e.g., an amorphous form of Compound A) in a solvent. In one embodiment, 1,5-naphthalene disulfonic acid Form 1 and Form 3 is prepared by slurrying Compound A (e.g., an amorphous form of Compound A) in acetone or ethyl acetate. In one embodiment, 1,5-naphthalene disulfonic acid Form 1 and Form 3 is prepared by adding 1,5-naphthalene disulfonic acid (1.1 equivalents based on the weight of the freebase) to the slurry. In one embodiment, 1,5-naphthalene disulfonic acid Form 1 and Form 3 is prepared by temperature cycling the slurry (e.g., between ambient temperature and about 40° C. or between about 5° C. and about 40° C.) in 2 hour cycles for ca. 72 hours. In one embodiment, 1,5-naphthalene disulfonic acid Form 1 and Form 3 is prepared by isolating the solid by centrifuge filtration.

1,5-Naphthalene Disulfonate Form 2

In one embodiment, the present application provides 1,5-naphthalene disulfonic acid Form 2 polymorph of Compound A ("1,5-naphthalene disulfonic acid Form 2", "1,5-naphthalene disulfonate Form 2", "naphthalene disulfonic acid Form 2" or "naphthalene disulfonate Form 2") characterized by an XRPD pattern comprising peaks at approximately 7.2, 18.1, and 26.0° 2θ using Cu Kα radiation. In one embodiment, 1,5-naphthalene disulfonic acid Form 2 is characterized by an XRPD pattern substantially similar to that set forth in FIG. 216.

In one embodiment, PLM analysis of 1,5-naphthalene disulfonic acid Form 2 shows irregular particles of various sizes that exhibit birefringence (FIG. 218).

In one embodiment, 1,5-naphthalene disulfonic acid Form 2 converts 1,5-naphthalene disulfonic acid Form 4 under vacuum drying conditions (FIG. 219).

1,5-Naphthalene Disulfonate Form 2 and Form 5

In one embodiment, the present application provides a mixture of 1,5-naphthalene disulfonic acid Form 2 and Form 5 polymorph of Compound A ("1,5-naphthalene disulfonic acid Form 2 and Form 5", "1,5-naphthalene disulfonate Form 2 and Form 5", "naphthalene disulfonic acid Form 2 and Form 5" or "naphthalene disulfonate Form 2 and Form 5") characterized by an XRPD pattern comprising peaks at approximately 6.1, 15.9, and 18.1° 2θ using Cu Kα radiation. In one embodiment, 1,5-naphthalene disulfonic acid Form 2 and Form 5 is characterized by an XRPD pattern substantially similar to that set forth in FIG. 216.

In one embodiment, 1,5-naphthalene disulfonic acid Form 2 and Form 5 is characterized by an endothermic event with an onset at approximately 219° C. as measured by DTA. In one embodiment, 1,5-naphthalene disulfonic acid Form 2 and Form 5 is characterized by an endothermic event with a peak at approximately 229° C. In one embodiment, 1,5-naphthalene disulfonic acid Form 2 and Form 5 is characterized by a DTA thermogram substantially similar to that set forth in FIG. 217.

In one embodiment, 1,5-naphthalene disulfonic acid Form 2 and Form 5 shows a weight loss of 13.5% below 100° C. as measured by TGA.

In one embodiment, 1,5-naphthalene disulfonic acid Form 2 and Form 5 is prepared by slurrying Compound A (e.g., an amorphous form of Compound A) in a solvent. In one embodiment, 1,5-naphthalene disulfonic acid Form 2 and Form 5 is prepared by slurrying Compound A (e.g., an amorphous form of Compound A) in 2-propanol:water (9:1 v/v). In one embodiment, 1,5-naphthalene disulfonic acid Form 2 and Form 5 is prepared by adding 1,5-naphthalene disulfonic acid (1.1 equivalents based on the weight of the freebase) to the slurry. In one embodiment, 1,5-naphthalene disulfonic acid Form 2 and Form 5 is prepared by temperature cycling the slurry (e.g., between ambient temperature and about 40° C. or between about 5° C. and about 40° C.) in 2 hour cycles for ca. 72 hours. In one embodiment, 1,5-naphthalene disulfonic acid Form 2 and Form 5 is prepared by isolating the solid by centrifuge filtration.

1,5-Naphthalene Disulfonate Form 4

In one embodiment, the present application provides a 1,5-naphthalene disulfonate Form 4 polymorph of Compound A ("1,5-naphthalene disulfonic acid Form 4", "1,5-naphthalene disulfonate Form 4", "naphthalene disulfonic acid Form 4" or "naphthalene disulfonate Form 4") characterized by an XRPD pattern comprising peaks at approximately 6.1, 8.8, and 16.0° 2θ using Cu Kα radiation. In one embodiment, 1,5-naphthalene disulfonate Form 4 is characterized by an XRPD pattern substantially similar to that set forth in FIG. 219.

In one embodiment, 1,5-naphthalene disulfonate Form 4 is characterized by an endothermic event with an onset at approximately 215° C. as measured by DTA. In one embodiment, 1,5-naphthalene disulfonic acid Form 4 is characterized by an endothermic event with a peak at approximately 231° C. In one embodiment, 1,5-naphthalene disulfonate Form 4 is characterized by a DTA thermogram substantially similar to that set forth in FIG. 220.

In one embodiment, 1,5-naphthalene disulfonate Form 4 is characterized by a $^1$H-NMR spectrum showing 1,5-naphthalene sulfonic acid (0.5 equivalents) and 2-propanol (ca. 0.02 equivalent). In one embodiment, 1,5-naphthalene disulfonate Form 1 is characterized by a $^1$H-NMR spectrum substantially similar to that set forth in FIG. 222.

In one embodiment, 1,5-naphthalene disulfonic acid Form 4 shows a weight loss of approximately 0.6% below 100° C. as measured by TGA.

In one embodiment, PLM analysis of 1,5-naphthalene disulfonic acid Form 4 shows irregular particles of various sizes that exhibited birefringence (FIG. 221).

In one embodiment, after tested under accelerated storage conditions (e.g., 75% RH/40° C. for 72 hours), 1,5-naphthalene disulfonic acid Form 4 shows decreased crystallinity (FIG. 223).

In one embodiment, 1,5-naphthalene disulfonate Form 4 is prepared by drying 1,5-naphthalene disulfonate Form 2 under vacuum.

Phosphate Form 1

In one embodiment, the present application provides a phosphate Form 1 polymorph of Compound A ("phosphate Form 1") characterized by an XRPD pattern comprising peaks at approximately 3.7, 19.9, and 22.0° 2θ using Cu Kα radiation. In one embodiment, phosphate Form 1 is characterized by an XRPD pattern substantially similar to that set forth in FIG. 224.

In one embodiment, phosphate Form 1 is characterized by an endothermic event with an onset at approximately 157-158° C. as measured by DTA. In one embodiment, phosphate Form 1 is characterized by an endothermic event with a peak at approximately 165° C. In one embodiment, phosphate Form 1 is characterized by a DTA thermogram substantially similar to that set forth in FIG. 225.

In one embodiment, phosphate Form 1 shows a weight loss of approximately 2.9% at approximately 60-160° C., and a weight loss of 1.7% was observed below approximately 158° C. after 3 days of drying under vacuum, as measured by TGA.

In one embodiment, phosphate Form 1 is characterized by a $^1$H-NMIR spectrum showing changes (ca. 0.1 ppm) in chemical shift in the region from about 7.6 to 8.7 ppm compared to the amorphous form. In one embodiment, the $^1$H-NMR spectrum shows acetone (0.13 equivalents). In one embodiment, phosphate Form 1 is characterized by a $^1$H-NMR spectrum substantially similar to that set forth in FIG. 229.

In one embodiment, PLM analysis of phosphate Form 1 shows small, irregular particles up to 100 μm in size, exhibiting birefringence (FIG. 228).

In one embodiment, phosphate Form 1 is stable under accelerated storage conditions (e.g., 75% RH/40° C. for 72 hours). In one embodiment, the XRPD after storage shows no change from the input material (FIG. 230).

In one embodiment, phosphate Form 1 is prepared by slurrying Compound A (e.g., an amorphous form of Compound A) in a solvent. In one embodiment, phosphate Form 1 is prepared by slurrying Compound A (e.g., an amorphous form of Compound A) in acetone or 2-propanol:water (9:1 v/v). In one embodiment, phosphate Form 1 is prepared by slurrying Compound A (e.g., an amorphous form of Compound A) in acetone. In one embodiment, phosphate Form 1 is prepared by adding phosphoric acid (1.1 equivalents based on the weight of the freebase) to the slurry. In one embodiment, phosphate Form 1 is prepared by temperature cycling the slurry (e.g., between ambient temperature and about 40° C. or between about 5° C. and about 40° C.) in 2 hour cycles for ca. 72 hours. In one embodiment, phosphate Form 1 is prepared by cooling the slurry (e.g., from ambient temperature to 5° C.). In one embodiment, the slurry is stirred. In one embodiment, phosphate Form 1 is prepared by isolating the solid by centrifuge filtration.

Phosphate Form 2

In one embodiment, the present application provides a phosphate Form 2 polymorph of Compound A ("phosphate Form 2") characterized by an XRPD pattern comprising peaks at approximately 4.9, 21.4, and 22.2° 2θ using Cu Kα radiation. In one embodiment, phosphate Form 2 is characterized by an XRPD pattern substantially similar to that set forth in FIG. 231.

In one embodiment, phosphate Form 2 is characterized by an endothermic event with an onset at approximately 128° C. as measured by DTA. In one embodiment, phosphate Form 2 is characterized by an endothermic event with a peak at approximately 134° C. In one embodiment, phosphate Form 2 is characterized by a DTA thermogram substantially similar to that set forth in FIG. 232 or FIG. 233.

In one embodiment, phosphate Form 2 shows a weight loss of approximately 5.2% below 150° C., and a weight loss of 4.6% was observed below 150° C. after drying under vacuum at 40° C., as measured by TGA.

In one embodiment, phosphate Form 2 is characterized by a $^1$H-NMR spectrum showing ethyl acetate (0.24 equivalents). In one embodiment, phosphate Form 2 is characterized by a $^1$H-NMR spectrum substantially similar to that set forth in FIG. 235.

In one embodiment, PLM analysis of phosphate Form 2 shows small, irregular particles of various size, exhibiting birefringence (FIG. 234).

In one embodiment, phosphate Form 2 is stable under accelerated storage conditions (e.g., 75% RH/40° C. for 72 hours). In one embodiment, the XRPD after storage shows no change from the input material (FIG. 236).

In one embodiment, phosphate Form 2 is prepared by slurrying Compound A (e.g., an amorphous form of Compound A) in a solvent. In one embodiment, phosphate Form 2 is prepared by slurrying Compound A (e.g., an amorphous form of Compound A) in ethyl acetate.

In one embodiment, phosphate Form 2 is prepared by adding phosphoric acid (1.1 equivalents based on the weight of the freebase) to the slurry. In one embodiment, phosphate Form 2 is prepared by temperature cycling the slurry (e.g., between ambient temperature and about 40° C. or between about 5° C. and about 40° C.) in 2 hour cycles for ca. 72 hours. In one embodiment, phosphate Form 2 is prepared by isolating the solid by centrifuge filtration. In one embodiment, phosphate Form 2 is prepared by storing the solid under ambient conditions, for example, for at least 1 day, 2 days, or 3 days.

Phosphate Form 2 and Form 3

In one embodiment, the present application provides a mixture of phosphate Form 2 and Form 3 polymorph of Compound A ("phosphate Form 2 and Form 3") characterized by an XRPD pattern comprising peaks at approximately 5.0, 16.2, and 24.9° 2θ using Cu Kα radiation. In one embodiment, phosphate Form 2 and Form 3 is characterized by an XRPD pattern substantially similar to that set forth in FIG. 231.

The terms "crystalline polymorphs", "crystal polymorphs", "crystal forms", "polymorphs", or "polymorphic forms" means crystal structures in which a compound (e.g., free base, salts, or solvates thereof) can crystallize in different crystal packing arrangements, all of which have the same elemental composition. Different crystal forms usually have different X-ray diffraction patterns, infrared spectra, melting points, density, crystal shape, optical and electrical properties, stability, and solubility. Crystallization solvent, rate of crystallization, storage temperature, and other factors may cause one crystal form to dominate. Crystal polymorphs of the compounds can be prepared by crystallization under different conditions. In addition, crystal polymorphism may be present but is not limiting, but any crystal form may be a single or a crystal form mixture, or an anhydrous or hydrated crystal form.

The term "amorphous form" refers to a noncrystalline solid state form of a substance.

Additionally, the compounds of the present application (e.g., free bases and salts, and amorphous forms, crystalline forms, and polymorphs thereof), can exist in either hydrated or unhydrated (the anhydrous) form or as solvates with other solvent molecules or in an unsolvated form. Nonlimiting examples of hydrates include hemihydrates, monohydrates, dihydrates, etc. Nonlimiting examples of solvates include DMSO solvates, DMSO hemisolvates, acetone solvates, acetone hemisolvates, acetonitrile solvates, acetonitrile hemisolvates etc.

All forms of the compounds of the present application are contemplated, either in a mixture or in pure or substantially pure form, including crystalline forms of racemic mixtures and crystalline forms of individual isomers.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing solid forms of a compound, such as polymorphs, include, but are not limited to, DSC, X-ray powder diffractometry (XRPD), single crystal X-ray diffractometry, vibrational spectroscopy (e.g., IR and Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. For example, the solvate may be a DMSO solvate, a dichloromethane (DCM) solvate, a methyl ethyl ketone (MEK solvate), an acetone solvate, an acetonitrile solvate, or a tetrahydrofuran (THF) solvate.

As used herein, the terms "unsolvated" or "desolvated" refer to a solid state form (e.g., crystalline forms, amorphous forms, and polymorphs) of a substance which does not contain solvent.

As used herein, the term "pure" means about 90-100%, preferably 95-100%, more preferably 98-100% (wt./wt.), or 99-100% (wt./wt.) pure compound; e.g., less than about 10%, less than about 5%, less than about 2%, or less than about 1% impurity is present. Such impurities include, e.g., degradation products, oxidized products, solvents, and/or other undesirable impurities.

As used herein, a compound is "stable" where significant amount of degradation products are not observed under constant conditions of humidity (e.g., 10%, 20%, 30%, 40%, 50%, 60%, 70%, 75%, 80%, 85%, 90%, and 95% relative humidity [RH]), light exposure and temperatures (e.g., higher than 0° C., e.g., 20° C., 25° C., 30° C., 35° C., 40° C., 45° C., 50° C., 55° C., 60° C., 65° C., and 70° C.) over a certain period (e.g., one week, two weeks, three weeks, and four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability.

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In one embodiment, "approximately" and "about" refer to a recited amount, value, or duration ±10%, ±8%, ±6%, ±5%, ±4%, ±2%, ±1%, or ±0.5%. In another embodiment, "approximately" and "about" refer to a listed amount, value, or duration ±10%, ±8%, ±6%, ±5%, ±4%, or ±2%. In yet another embodiment, "approximately" and "about" refer to a listed amount, value, or duration ±5%. In yet another embodiment, "approximately" and "about" refer to a listed amount, value, or duration ±2% or ±1%.

When the terms "approximately" and "about" are used when reciting XRPD peaks, these terms refer to the recited XRPD peak±0.3° 2θ, ±0.2° 2θ, or ±0.1° 2θ. In another embodiment, the terms "approximately" and "about" refer to the listed XRPD peak±0.2° 2θ. In another embodiment, the terms "approximately" and "about" refer to the listed XRPD peak±0.1° 2θ.

When the terms "approximately" and "about" are used when reciting temperature or temperature range, these terms refer to the recited temperature or temperature range ±5° C., ±2° C., or ±1° C. In another embodiment, the terms "approximately" and "about" refer to the recited temperature or temperature range ±2° C.

Methods and Assays
Synthesis of Compound A

The compounds of the present application may be made by a variety of methods, including standard chemistry. A suitable synthetic route is depicted in the Schemes given below.

The compounds of the present application may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis. These groups are removed at a convenient stage of the compound synthesis using methods that are readily apparent to those skilled in the art. The selection processes, as well as the reaction conditions and order of their execution, shall be consistent with the preparation of the compounds of the present application. Standard synthetic methods and procedures for the preparation of organic molecules and functional group transformations and manipulations, including the use of protective groups, can be obtained from the relevant scientific literature of from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999.

Those skilled in the art will recognize if a stereocenter exists in the compounds of the present application. Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., Compound A) can be synthesized by following the steps outlined in General Scheme 1 which comprises a sequence of assembling intermediates 2-a to 2-h. Starting materials are either commercially available or made by known procedures in the reported literature or as illustrated.

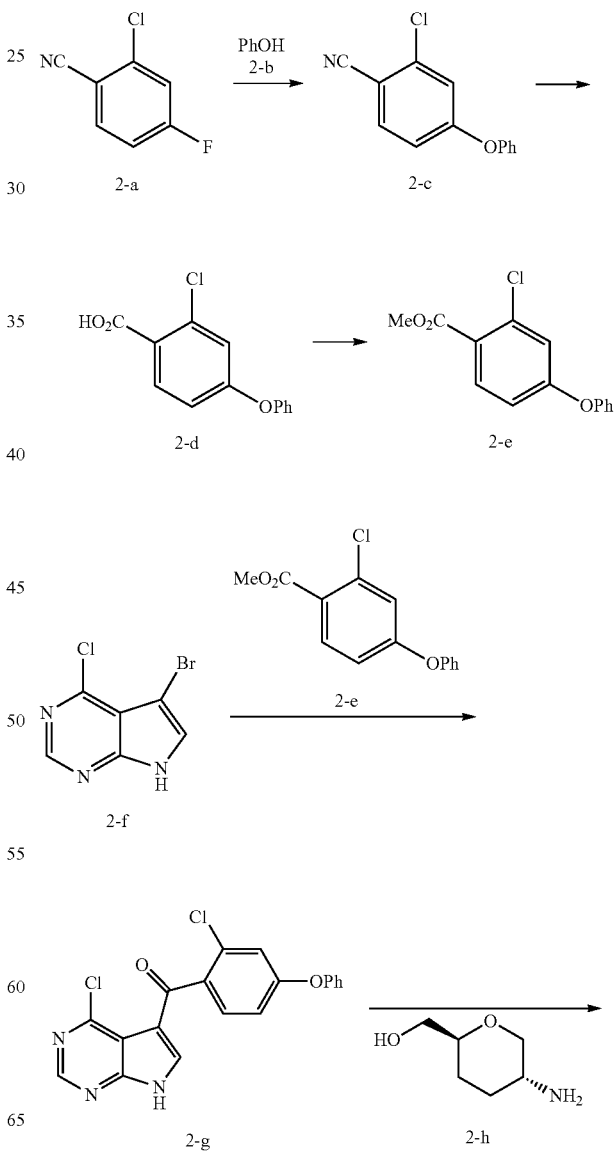

General Scheme 1

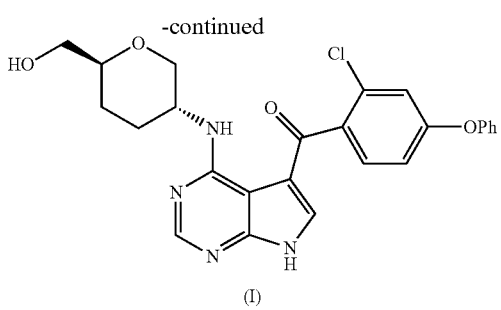

(I)

The general way of preparing Compound A by using intermediates 2-a, 2-b, 2-c, 2-d, 2-e, 2-f, 2-g, and 2-h is outlined in General Scheme 1. Nucleophilic addition of phenol 2-b to 2-chloro-4-fluorobenzonitrile 2-a using a strong base, e.g., sodium hydride (NaH), in a solvent, e.g., N,N-dimethylformamide (DMF), yields 2-c. Hydrolysis of 2-c using a base, e.g., potassium hydroxide (KOH), in a solvent, e.g., ethanol, at an elevated temperature yields carboxylic acid 2-d. Esterification of 2-d with methyl iodide using a base, e.g., potassium carbonate ($K_2CO_3$) or cesium carbonate ($Cs_2CO_3$), in a solvent, e.g., N,N-dimethylformamide (DMF), provides 2-e. Acylation of intermediate 2-f with 2-e using a strong base, e.g., n-butyl lithium (n-BuLi), in a solvent, e.g., tetrahydrofuran (THF), provides 2-g. Nucleophilic addition of amine 2-h to aryl chloride 2-g using a base, e.g., N,N-diisopropylethylamine (DIPEA), and optionally in a solvent, e.g., N,N-dimethylformamide (DMF), provides Compound A.

A mixture of enantiomers, diastereomers, cis/trans isomers resulting from the process described above can be separated into their single components by chiral salt technique, chromatography using normal phase, reverse phase or chiral column, depending on the nature of the separation.

Methods for preparing the free base of Compound A is described in U.S. Pat. No. 9,630,968, the entire contents of which are incorporated herein by reference.

Biological Assays

The present application provides methods to assess biological activities of the compounds of the application. In one method, an assay based on enzymatic activity can be utilized. In one specific enzymatic activity assay, the enzymatic activity is from a kinase (e.g., BTK). As used herein, "kinase" refers to enzymes which catalyze the transfer of the γ-phosphate from ATP to the hydroxyl group on the side chain of Ser/Thr or Tyr in proteins and peptides and are intimately involved in the control of various important cell functions, such as signal transduction, differentiation, and proliferation. Preferably, the kinase assayed is a tyrosine kinase (e.g., BTK).

A change in enzymatic activity caused by compounds of the present application can be measured in disclosed assays. The change in enzymatic activity can be characterized by the change in the extent of phosphorylation of certain substrates. As used herein "phosphorylation" refers to the addition of phosphate groups to a substrate, including proteins and organic molecules, and plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. Specific methods for assessing the biological activity of the disclosed compounds are described in the examples.

BTK Kinase Activity Assay

Test inhibitor and controls are prepared in a solvent (i.e., DMSO), and added to each well of a reaction plate. Full-length active BTK is diluted in assay buffer and added to each well. After pre-incubation, the kinase reaction is initiated by the addition of an activation mixture diluted in assay buffer containing biotinylated PLCγ2 peptide and ATP. The plates are incubated and the reactions are then stopped in the dark by the addition of stop/detection mixture prepared in assay buffer. Assay plates are incubated in the dark, and the plates are read on a plate reader.

BTK C481S Kinase Activity Assay

Test inhibitor and controls are prepared in a solvent (i.e., DMSO) at the desired final concentration, and added to each well of a reaction plate. Full-length BTKC481S is diluted in assay buffer and added to each well in a volume. After pre-incubation, the kinase reaction is initiated by the addition of an activation mixture diluted in assay buffer containing biotinylated PLCγ2 peptide, and ATP. The plates are incubated and the reactions are then stopped in the dark by the addition of a stop/detection mixture prepared in assay buffer. Assay plates are incubated in the dark, and the plates are read on a plate reader.

Anti Proliferation Assay

Cell survival is determined by a MTS assay. Briefly, cells (i.e., TMD-8 cells or Rec-1 cells) are plated in a 96-well plate, cultured in complete growth medium, and then treated with various drugs and drug combinations. MTS/PMS is added and incubated, followed by assessment of cell viability using a microplate reader. Data is normalized to untreated controls and analyzed with Microsoft Excel.

One skilled in the art may refer to general reference texts for detailed descriptions of known techniques discussed herein or equivalent techniques. The texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the disclosure.

Analytical Methods

X-Ray Powder Diffraction (XRPD)

XRPD analysis was carried out on a PANalytical X'pert pro, scanning the samples between 3° and 35° 2-theta (2θ). The material was gently compressed and loaded onto a multi-well plate with Kapton or Mylar polymer film to support the sample. The multi-well plate was then placed into a diffractometer and analyzed using Cu Kα radiation ($α_1$ λ=1.54060 Å, $α_2$=1.54443 Å, λ=1.39225 Å, $α_1$:$α_2$ ratio=0.5) running in transmission mode (step size 0.0130° 2θ) using 40 kV, 40 mA generator settings.

Variable Temperature X-Ray Powder Diffraction (VT-XRPD)

VT-XRPD analysis was carried out on a Philips X'Pert Pro Multipurpose diffractometer. The samples were scanned between 4 and 35.99° 2θ using Cu K radiation ($α_1$ λ=1.54060 Å; $α_2$=1.54443 Å; β=1.39225 Å; $α_1$:$α_2$ ratio=0.5) running in Bragg-Brentano geometry (step size 0.008° 2θ) using 40 kV/40 mA generator settings. Measurements were performed at each step of the temperature profile: 30° C. initial scan, 150° C., 200° C., 210° C., 230° C., and 30° C., final scan.

Polarized Light Microscopy (PLM)

The presence of crystallinity (birefringence) was determined using an Olympus BX50 polarizing microscope, equipped with a Motic camera and image capture software (Motic Images Plus 2.0). All images were recorded using a 20× objective, unless otherwise stated.

Thermogravimetric/Differential Thermal Analysis (TG/DTA)

Approximately 5-10 mg of material was weighted into an open aluminum pan, loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as a purge gas, at a flow rate of 300 cm$^3$/min.

Differential Scanning Calorimetry (DSC)

Approximately 1-5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 240° C., 250° C., 260° C. or 270° C. at a scan rate of 10° C./min and the resulting heat flow response monitored. Nitrogen was used as a purge gas, at a flow rate of 50 cm$^3$/min.

Alternatively, approximately 1-5 mg of material was weighed into an aluminium DSC pan and sealed non-hermetically with an aluminum lid. The sample pan was then loaded into a TA Instruments Discovery DSC 2500 differential scanning calorimeter equipped with a RC90 cooler. The sample and reference were heated to 240° C. at a scan rate of 10° C./min and the resulting heat flow response monitored. The sample was re-cooled to 20° C. and then reheated again to 240° C. all at 10° C./min. Nitrogen was used as the purge gas, at a flow rate of 50 cm$^3$/min.

Thermogravimetric/Differential Scanning Calorimetry (TG/DSC)

Alternatively, approximately 5-10 mg of material was added into a pre-tared open aluminum pan and loaded into a TA Instruments Discovery SDT 650 Auto—Simultaneous DSC and held at room temperature. The sample was then heated at a rate of 10° C./min from 30° C. to 300° C. during which time the change in sample weight was recorded along with the heat flow response (DSC). Nitrogen was used as the purge gas, at a flow rate of 300 cm$^3$/min.

Karl Fischer Coulometric Titration (KF)

Approximately 10-30 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Infrared Spectroscopy (IR)

Infrared spectroscopy (IR) was carried out on a Bruker ALPHA P spectrometer. Sufficient material was placed onto the center of the plate of the spectrometer and the spectra were obtained using the following parameters: Resolution: 4 cm$^{-1}$; Background Scan Time: 16 scans; Sample Scan Time: 16 scans; Data Collection: 4000 to 400 cm$^{-1}$; Result Spectrum: Transmittance; Software: OPUS version 6.

$^1$H Nuclear Magnetic Resonance (NMR)

Nuclear magnetic resonance (NMR) experiments were performed on a Bruker AVIIIHD spectrometer equipped with a DCH cryoprobe operating at 500.12 MHz for protons. Experiments were performed in deuterated DMSO and each sample was prepared to ca. 10 mM concentration.

Dynamic Vapor Sorption (DVS)

Approximately 10-20 mg of sample was placed into a mesh vapor sorption balance pan and loaded into a DVS-1 dynamic vapor sorption balance by Surface Measurement Systems. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis may be then carried out on any solid retained.

Gravimetric Vapor Sorption (GVS)

Approximately 10-20 mg of sample was placed into a mesh vapor sorption balance pan and loaded into an IGAS-orp Moisture Sorption Analyzer balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

High Performance Liquid Chromatography-Ultraviolet Detection (HPLC-UV)

Samples were diluted in methanol and then analyzed using the following experimental conditions: Column: Waters Sunfire C18, 4.6×150 mm, 3.5 µm; Column Temperature: 40° C.; Auto sampler Temperature: 25° C.; UV wavelength: 275 nm; Injection Volume: 5 µL; Flow Rate: 1.4 mL/min; Mobile Phase A: 0.1% TFA in H2O; Mobile Phase B: 0.1% TFA in Acetonitrile; Diluent: Methanol.

Gradient program:

| Time (minutes) | Solvent B [%] |
| --- | --- |
| 0 | 25 |
| 1.0 | 25 |
| 15 | 40 |
| 25 | 80 |
| 30 | 90 |
| 30.1 | 25 |
| 35 | 25 |

Pharmaceutical Compositions

The present application also provides pharmaceutical compositions comprising one or more compounds of the present application (e.g., solid forms, amorphous forms, crystalline forms, and polymorphs of Compound A) in combination with at least one pharmaceutically acceptable excipient or carrier.

A "pharmaceutical composition" is a formulation containing the compounds of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the one or more of the disclosed compounds) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is selected from immune disorders, cancer, cardiovascular diseases, viral infections, inflammation, metabolism/endocrine function disorders and neurological disorders. In another embodiment, the disease or condition to be treated is cancer. In another embodiment, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration to humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be express as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippan, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable composition can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tables. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from a pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a patient may be measured with reference to diameter of a tumor. Decrease in the diameter of a tumor indicates regression. Regression is also indicated by failure of tumors to reoccur after treatment has stopped. As used herein, the term "dosage effective manner" refers to an amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydoxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxyl, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formats, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs*, p 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, tautomer, prodrug, solvate, metabolite, polymorph, analog or derivative thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, tautomer, prodrug, solvate, metabolite, polymorph, analog or derivative thereof employed. An ordinarily skilled physician or veterinarian can readily determine and prescribe the effective amount of the drug required to prevent, counter or arrest the progress of the condition.

Techniques for formulation and administration of the disclosed compounds of the present application can be found in *Remington: the Science and Practice of Pharmacy*, 19th edition, Mack Publishing Co., Easton Pa. (1995). In an embodiment, the compounds described herein, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Treatment

The present application provides methods for the treatment of a cell proliferative disorder in a subject in need thereof by administering to the subject a therapeutically effective amount of one or more compounds of the present application (e.g., solid forms, amorphous forms, crystalline forms, or polymorphs). The present application also provides methods of protecting against a cell proliferative disorder in a subject in need thereof by administering to the subject a therapeutically effective amount of one or more compounds of the present application (e.g., solid forms, amorphous forms, crystalline forms, or polymorphs). The cell proliferative disorder can be cancer or a precancerous condition. The present application further provides the use of one or more compounds of the present application for the preparation of a medicament useful for the treatment or prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

A cell proliferative disorder includes a precancer or a precancerous condition. A cell proliferative disorder includes cancer. Preferably, the methods provided herein are used to treat or alleviate a symptom of cancer.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Exemplary cancers are selected from breast cancer, ovary cancer, cervix cancer, prostate cancer, testis cancer, genitourinary tract cancer, esophagus cancer, larynx cancer, glioblastoma, neuroblastoma, stomach cancer, skin cancer, keratoacanthoma, lung cancer, epidermoid carcinoma, large cell carcinoma, non-small cell lung carcinoma (NSCLC), small cell carcinoma, lung adenocarcinoma, bone cancer, colon cancer, adenoma, pancreas cancer, adenocarcinoma, follicular carcinoma, undifferentiated carcinoma, papillary carcinoma, seminoma, melanoma, sarcoma, myeloid disorders, lymphoma, cancer of hairy cells, buccal cavity, naso-pharyngeal, pharynx, lip, tongue, mouth, small intestine, colon-rectum, large intestine, rectum, brain or central nervous system, bronchus, thyroid, liver, intrahepatic bile duct, gastric, endometrial, kidney, renal pelvis, urinary bladder, uterine corpus, or uterine, glioma/glioblastoma, Hodgkin's leukemia, acute myelogenous leukemia, chronic myelogenous leukemia, lymphocytic leukemia, chronic lymphoid leukemia (CLL), Richter's Transformation, small lymphocytic lymphoma (SLL), diffuse large B-cell lymphoma (DLBCL), follicular lymphoma (FL), mantle cell lymphoma (MCL), primary central nervous system (CNS) lymphoma, secondary central nervous system (CNS) lymphoma, marginal zone lymphoma (MZL), Waldenstrom macroglobulinemia (WM), acute myeloid leukemia (AML), multiple myeloma (MM), pediatric sarcoma and pediatric brain tumors, myeloid leukemia, oral cavity and pharynx, non-Hodgkin lymphoma, B-cell non-Hodgkin lymphoma, melanoma, and villous colon adenoma.

Further exemplary cancers are selected from chronic lymphocytic leukemia (CLL), Richter's Transformation, small lymphocytic lymphoma (SLL), diffuse large B-cell lymphoma (DLBCL), follicular lymphoma (FL), mantle cell lymphoma (MCL), primary central nervous system (CNS) lymphoma, secondary central nervous system (CNS) lymphoma, marginal zone lymphoma (MZL), Waldenstrom macroglobulinemia (WM), acute myeloid leukemia (AML), multiple myeloma (MM), pediatric sarcoma, and pediatric brain tumors. In some embodiments, the cancer is a B-cell lymphoid malignancy. In some embodiments, the cancer is selected from CLL, Richter's Transformation, FL, and DLBCL.

In some embodiments, the cancer has a mutant BTK. In some embodiments, the cancer has a BTK C481 mutation. In some embodiments, the cancer has a BTK C481S mutation. In some embodiments, the cancer is relapsed or refractory to at least one prior therapy. In some embodiments, the cancer is relapsed or refractory to at least one therapy with a BTK inhibitor. For example, in some embodiments, the cancer is ibrutinib resistant.

Another aspect of the application relates to a method of treating, preventing, inhibiting, or eliminating a disease or disorder associated with modulation of BTK (e.g., inhibition of BTK). The method comprises administering to a patient in need of a treatment for diseases or disorders associated with modulation of BTK an effective amount of the compounds of the present application (e.g., solid forms, amorphous forms, crystalline forms, or polymorphs) or a pharmaceutical composition of the compounds of the present application. In one embodiment, the BTK-mediated disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to a method of treating, preventing, inhibiting, or eliminating a cell proliferative disorder, the method comprising administering to a patient in need thereof a therapeutically effective amount of the compounds of the present application (e.g., solid forms, amorphous forms, crystalline forms, or polymorphs) or a pharmaceutical composition of the compounds of the present application. In one embodiment, the cell proliferative disorder is a cancer. In some embodiments, the method further comprises administering an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the application relates to a method of modulating BTK, the method comprising administering to a patient in need thereof a therapeutically effective amount of the compounds of the present application (e.g., solid forms, amorphous forms, crystalline forms, or polymorphs) or a pharmaceutical composition of the compounds of the present application. In one embodiment, modulating BTK is inhibiting BTK. In some embodiments, the BTK is wild-type BTK. In other embodiments, the BTK is mutant BTK (e.g., BTK C481S mutant).

Another aspect of the application relates to the compounds of the present application (e.g., solid forms, amorphous forms, crystalline forms, or polymorphs), for use in a method of treating a BTK-mediated disorder. In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to a pharmaceutical composition of the compounds of the present application (e.g., solid forms, amorphous forms, crystalline forms, or polymorphs), for use in a method of treating at BTK-mediated disorder In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-typed BTK. In other embodiments, the BTK is mutant BTK (e.g., BTK C481 S mutant).

Another aspect of the application relates to the compounds of the present application (e.g., solid forms, amorphous forms, crystalline forms, or polymorphs), for use in a method of treating, preventing, inhibiting, or eliminating a cell proliferative disorder. In one embodiment, the cell proliferative disorder is a cancer.

In another aspect, the present application relates to a pharmaceutical composition of the compounds of the present application (e.g., solid forms, amorphous forms, crystalline forms, or polymorphs), for use in a method of treating, preventing, inhibiting, or eliminating a cell proliferative disorder. In one embodiment, the cell proliferative disorder is a cancer.

Another aspect of the application relates to the compounds of the present application (e.g., solid forms, amorphous forms, crystalline forms, or polymorphs), for use in modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to a pharmaceutical composition of the compounds of the present application (e.g., solid forms, amorphous forms, crystalline forms, or polymorphs), for use in modulating BTK. In one embodiment, modulating BTK is inhibiting BTK. In some embodiments, the BTK is wild-type BTK. In other embodiments, the BTK is mutant BTK (e.g., BTK C481 S mutant).

Another aspect of the application relates to the use of the compounds of the present application (e.g., solid forms, amorphous forms, crystalline forms, or polymorphs), in the manufacture of a medicament for treating a BTK-mediated disease or disorder. In one embodiment, the disease or disorder is selected from immune disorders, cancer, cardiovascular diseases, viral infections, inflammation, metabolism/endocrine function disorders and neurological disorders. In some embodiments, the treatment further comprises administering an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to the use of a pharmaceutical composition of the compounds of the present application (e.g., solid forms, amorphous forms, crystalline forms, or polymorphs), in the manufacture of a medicament for treating a BTK-mediated disease or disorder. In one embodiment, the disease or disorder is selected from immune disorders, cancer, cardiovascular disorders, viral infections, inflammation, metabolism/endocrine function disorders and neurological disorders. In some embodiments, the treatment further comprises administering an additional therapeutic agent selected from an anti-inflammatory agent, an immunomodulatory agent, a chemotherapeutic agent, a neurotropic factor, an agent for treating cardiovascular disease, and agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S).

Another aspect of the application relates to the use of the compounds of the present application (e.g., solid forms, amorphous forms, crystalline forms, or polymorphs), in the manufacture of a medicament for treating, preventing, inhibiting, or eliminating a cell proliferative disorder. In one embodiment, the cell proliferative disorder is a cancer.

In another aspect, the present application relates to the use of a pharmaceutical composition of the compounds of the present application (e.g., solid forms, amorphous forms, crystalline forms, or polymorphs), in the manufacture of a medicament for treating, preventing, inhibiting, or eliminating a cell proliferative disorder. In one embodiment, the cell proliferative disorder is a cancer.

Another aspect of the application relates to the use of the compounds of the present application (e.g., solid forms, amorphous forms, crystalline forms, or polymorphs), in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to the use of a pharmaceutical composition of the compounds of the present application (e.g., solid forms, amorphous forms, crystalline forms, or polymorphs), in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In some embodiments of the methods and uses described herein, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In some embodiments of the methods and uses described herein, the disease or disorder is an immune disorder. In one embodiment, the immune disorder is rheumatoid arthritis.

In some embodiments of the methods and uses described herein, the disease or disorder is systemic and local inflammation, arthritis, inflammation related to immune suppression, organ transplant rejection, allergies, ulcerative colitis, Crohn's disease, dermatitis, asthma, systemic lupus erythematosus, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), and psoriasis, and combinations thereof.

In one embodiment, methods of treating a disease or disorder associated with modulation of BTK including, immune disorders, cancer, cardiovascular diseases, viral infections, inflammation, metabolism/endocrine function disorders and neurological disorders, comprise administering to a patient suffering from at least one of said diseases or disorder the compounds of the present application (e.g., solid forms, amorphous forms, crystalline forms, or polymorphs).

The disclosed compound of the application can be administered in effective amounts to treat or prevent a disorder and/or prevent the development thereof in subjects.

The compound of the application can be administered in therapeutically effective amounts in a combinatorial therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. In some embodiments, the compound of the present application (e.g., solid forms, amorphous forms, crystalline forms, or polymorphs) is administered in combination with an additional therapeutic agent selected from an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the conditions being treated and so forth.

Combination therapy includes the administration of the subject compound in further combination with other biologically active ingredients (such as, but not limited to, an anti-inflammatory agent, an immunomodulatory agent, a chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

As used herein, "treating" or "treat" describes the management and care of a patient for the purpose of combating a disease, condition, or disorder, and includes the administration of a compound of the present application to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of a compound of the present application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "symptom" is defined as an indication of disease, illness, injury, or that something is not right in the body. Symptoms are felt or noticed by the individual experiencing the symptom, but may not easily be noticed by others.

As used herein, the term "sign" is also defined as an indication that something is not right in the body. However, signs are defined as things that can be seen by a doctor, nurse, or other health care professional.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Example 1: Characterization of Amorphous Compound A Free Base

The amorphous Compound A free base was characterized by XRPD, PLM, TG/DTA, DSC, DVS, $^1$H NMR and high performance liquid chromatography (HPLC) analyses with the following results observed.

Figure 1:
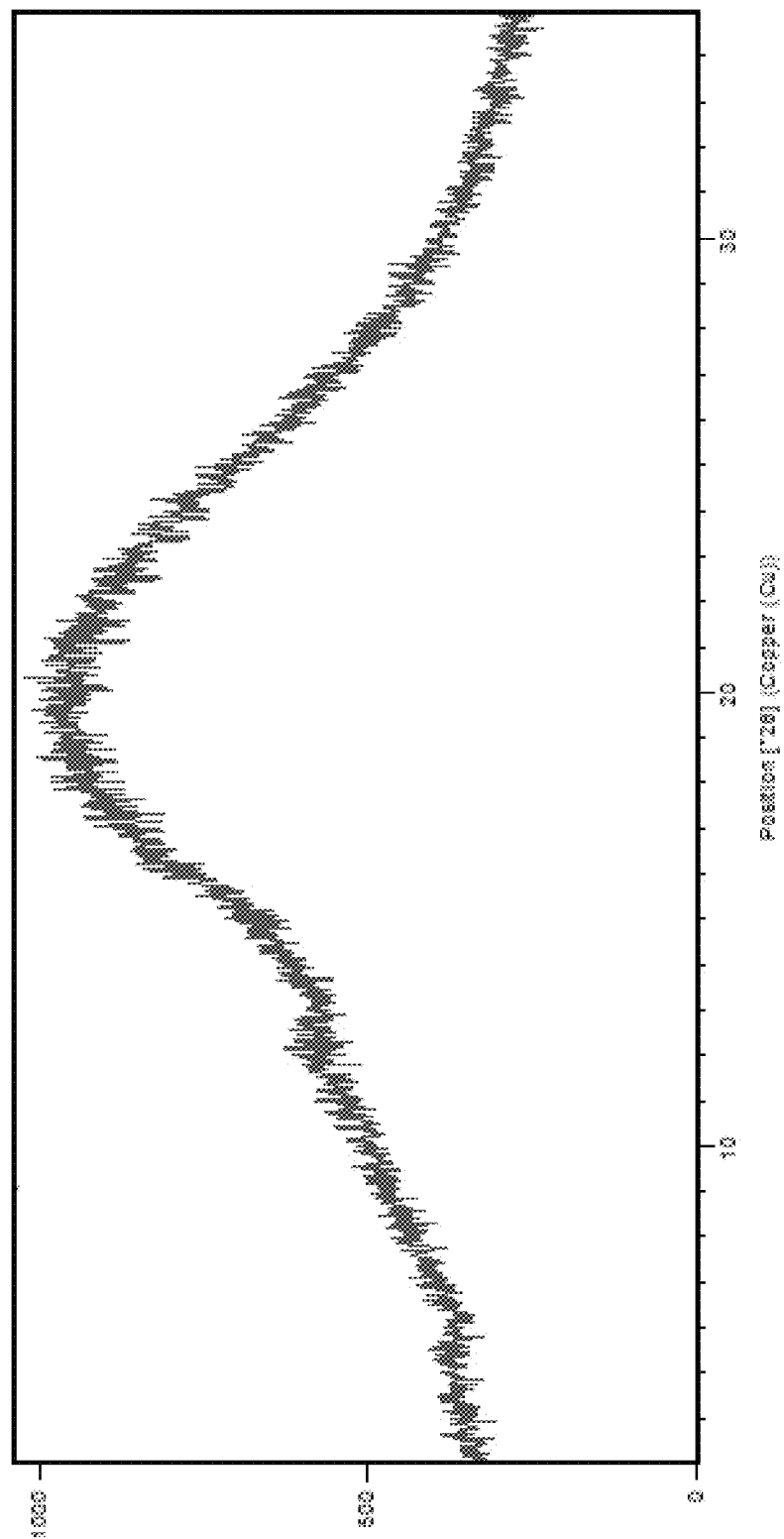
FIG. 1 sets forth an X-ray powder diffraction (XRPD) pattern of an amorphous form of Compound A.
Figure 2B:
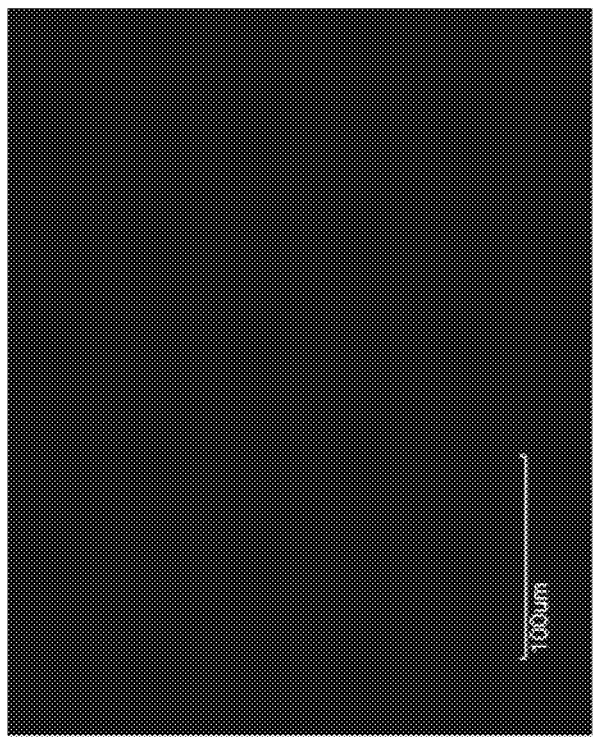
FIG. 2B sets forth a PLM image of an amorphous form of Compound A under polarized lenses.
Figure 2A:
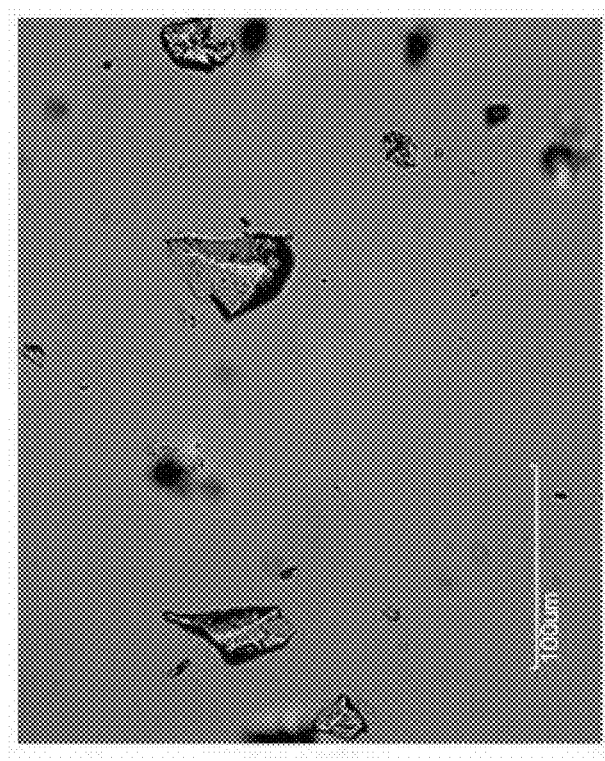
FIG. 2A sets forth a polarized light microscopy (PLM) image of an amorphous form of Compound A under non-polarized lenses.
Figure 3:
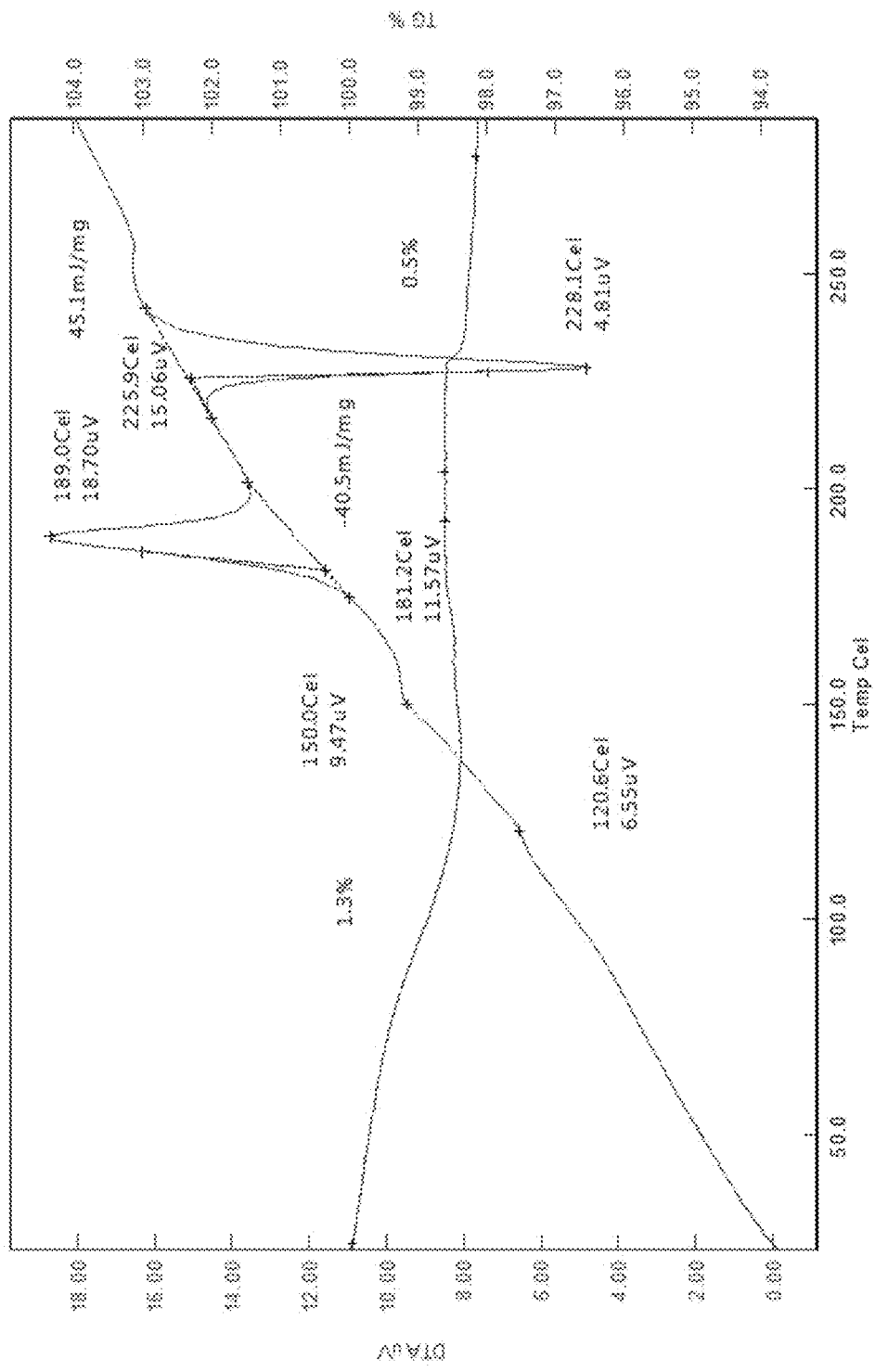
FIG. 3 sets forth a thermal analysis by Thermogravimetric/Differential Thermal Analysis (TG/DTA) of an amorphous form of Compound A.
Figure 4:
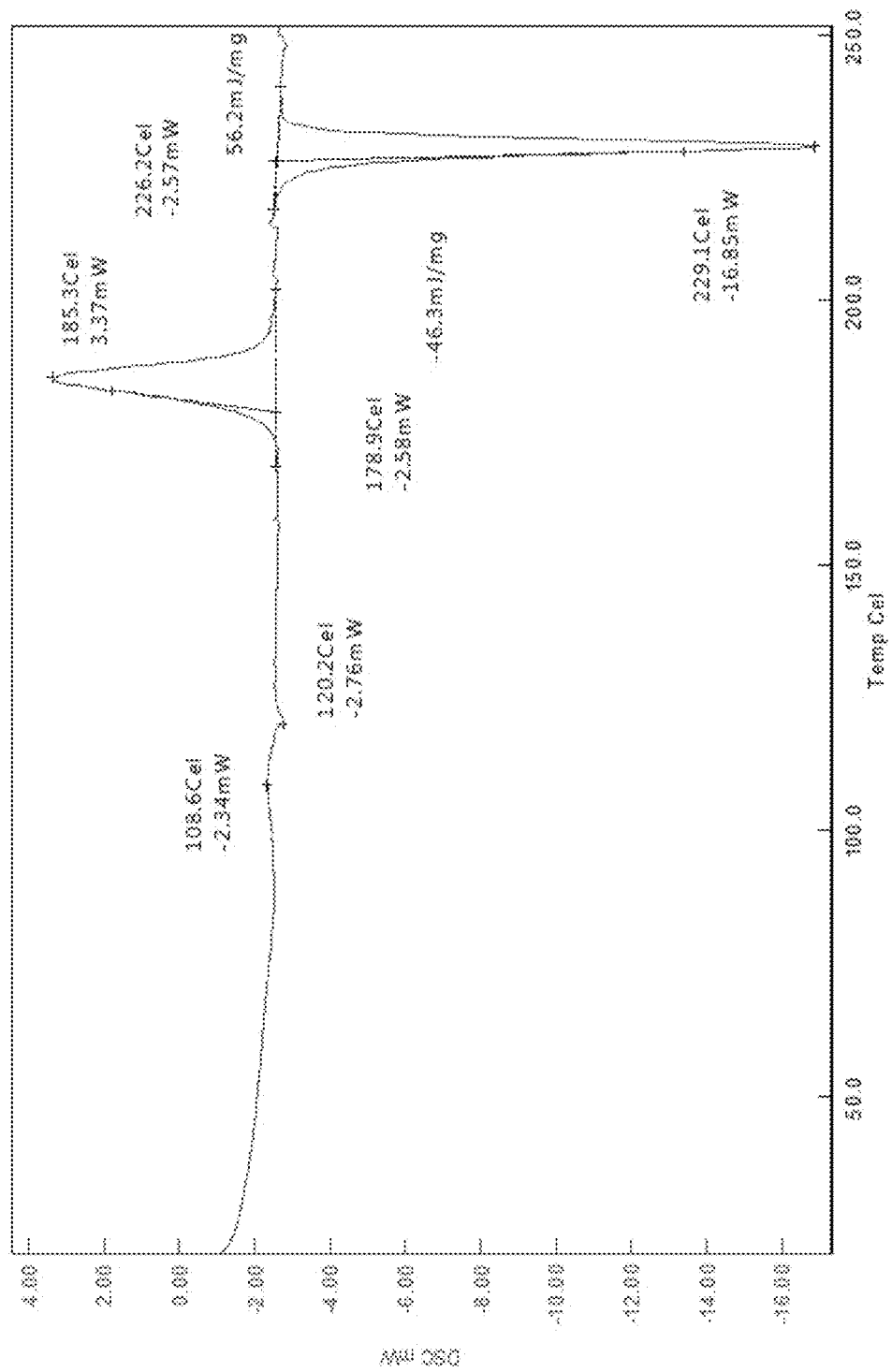
FIG. 4 sets forth a thermal analysis by differential scanning calorimetry (DSC) of an amorphous form of Compound A.
Figure 5:
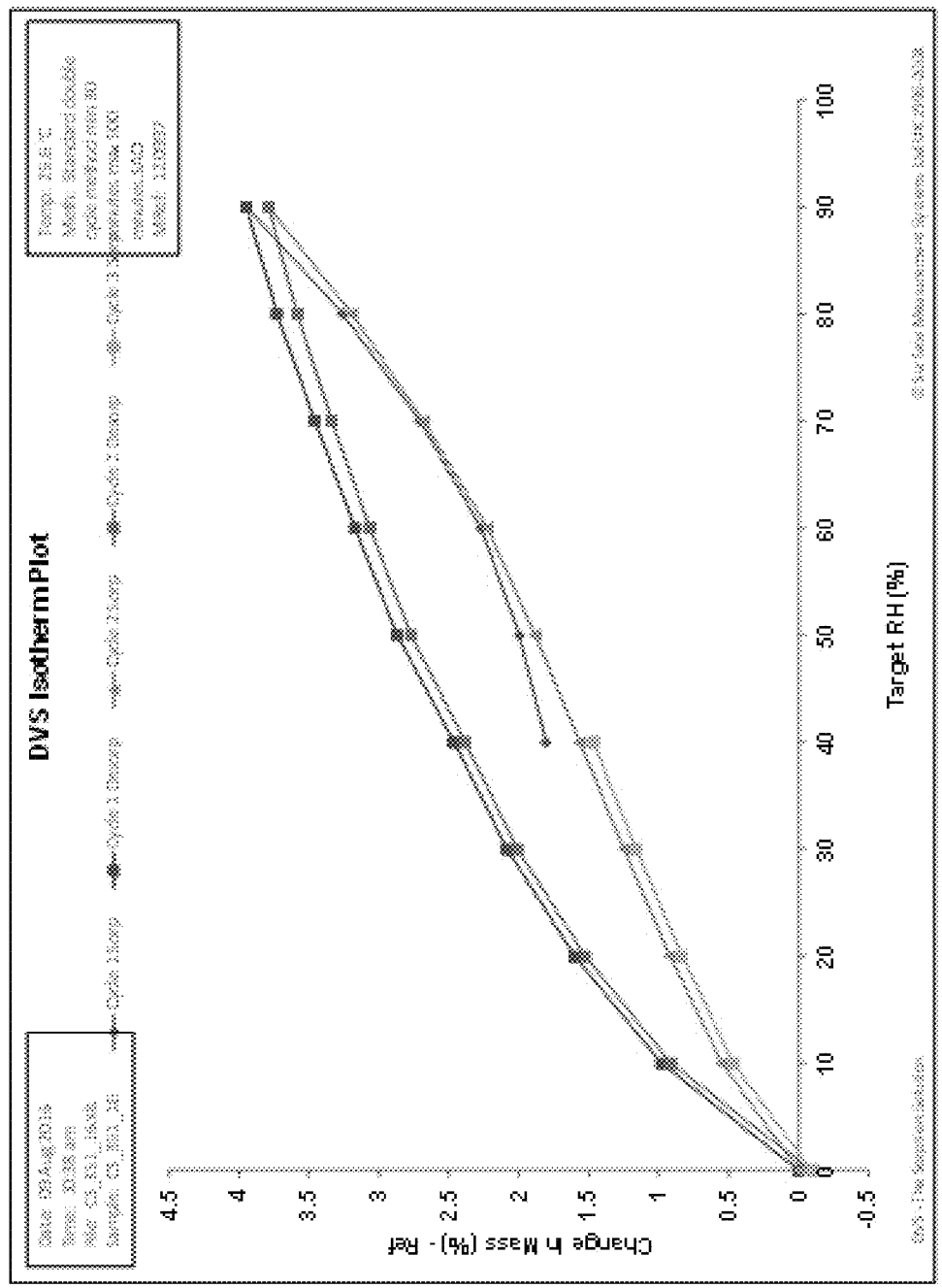
FIG. 5 sets forth a dynamic vapor sorption (DVS) analysis of an amorphous form of Compound A.
Figure 7:
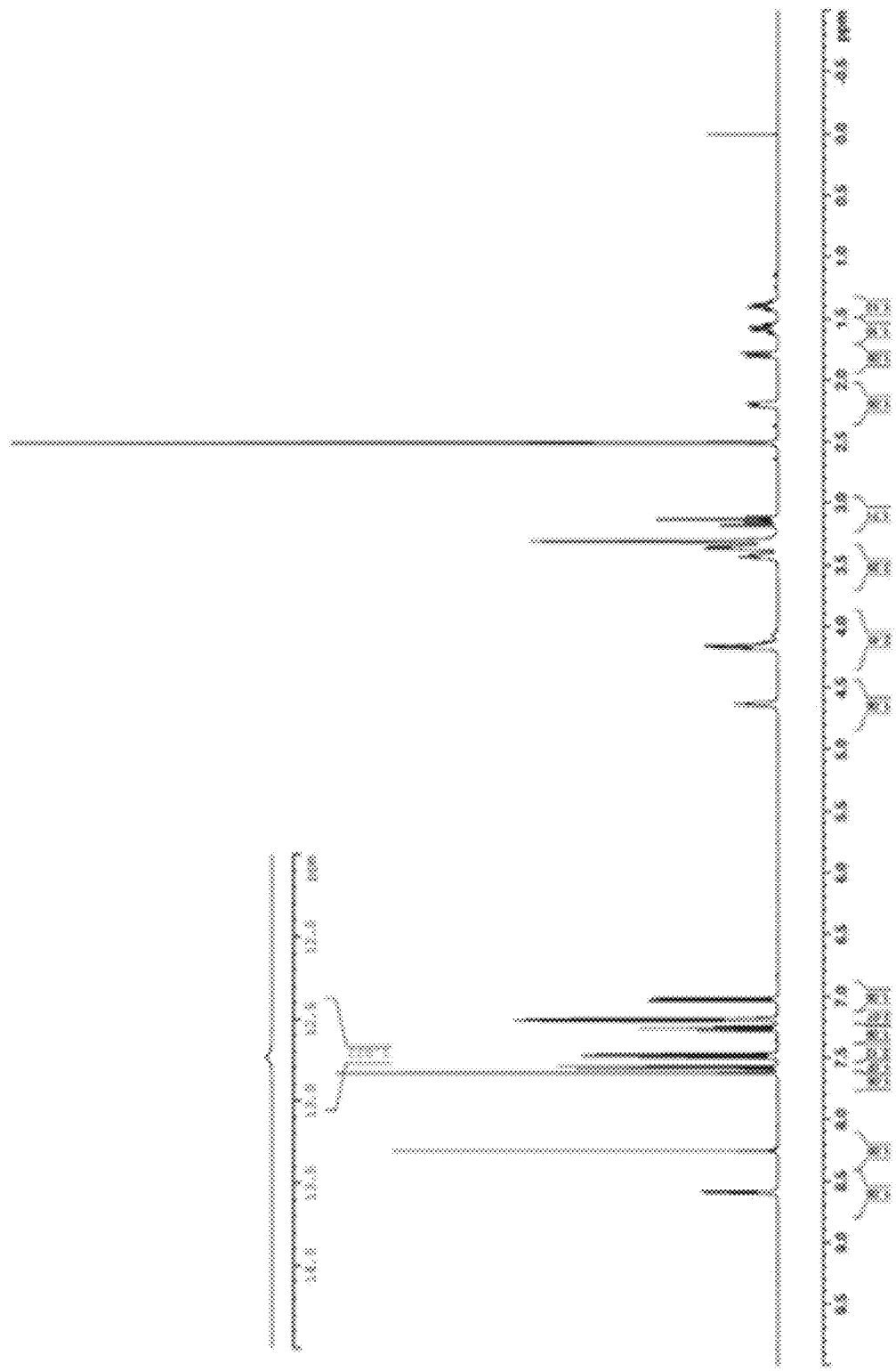
FIG. 7 sets forth a $^1$H nuclear magnetic resonance (NMR) spectroscopic analysis of an amorphous form of Compound A.

XRPD showed the material to be amorphous (FIG. 1). PLM showed glassy particles with no birefringence (FIG. 2A and FIG. 2B). TGA showed a weight loss of 1.3% between ca. 25° C. and 190° C., followed by a loss of 0.5% between ca. 200° C. and 270° C. (FIG. 3). DTA showed an exothermic event with onset ca. 181° C. and peak at 189° C., followed by an endothermic event with onset ca. 226° C. and peak at 228° C. (FIG. 3). DSC analysis showed an exothermic event with onset ca. 179° C. and peak at 185° C., followed by an endothermic event with onset ca. 226° C. and peak at 229° C. (FIG. 4). DVS analysis showed amorphous Compound A to be hygroscopic with a 3.9% uptake at 90% relative humidity (RH) (FIG. 5). Post-DVS XRPD analysis showed amorphous Compound A to remain amorphous (FIG. 6) after exposure to elevated humidity conditions. The 1H-NMR spectrum (FIG. 7) was found to be consistent with the chemical structure of Compound A. The HPLC area % purity of amorphous Compound A was 98.7%.

Example 2: Preparation of the Polymorphs of the Application

Polymorphs of the present application were prepared using the solvents listed in Table 1.

TABLE 1

Solvent for preparing the polymorphs of the application

Solvent System

| | |
|---|---|
| 1 | Acetic acid |
| 2 | Acetonitrile |
| 3 | Acetone |
| 4 | Anisole |
| 5 | 1-Butanol |
| 6 | Dichloromethane |
| 7 | Diisopropyl ether |
| 8 | Dimethylformamide |
| 9 | Dimethylsulfoxide |
| 10 | 1,4-Dioxane |
| 11 | Ethanol |
| 12 | 2-ethoxy ethanol |
| 13 | Ethyl acetate |
| 14 | Methanol |
| 15 | 2-MeTHF |
| 16 | Methyl ethyl ketone |
| 17 | Methyl isobutyl ketone |
| 18 | N-Methyl-2-pyrrolidone |
| 19 | 1-Propanol |
| 20 | 2-Propanol |
| 21 | 2-Propanol:water (90:10 v/v) |
| 22 | Tetrahydrofuran |
| 23 | Toluene |
| 24 | Water |
| 25 | 2-Methyl-1-propanol |
| 26 | Acetonitrile:water (95:5 v/v) |
| 27 | tert-butanol |
| 28 | N-methyl-2-pyrrolidone:water (90:10 v/v) |

Temperature Cycling

Slurries of amorphous Compound A were prepared in each of the solvents in Table 1 using ca. 150 mg per vial and 0.4, 3 or 5 mL of the appropriate solvent system was added depending on solubility, and the resulting mixtures were temperature cycled (between 5° C. and 40° C. in 2 hour cycles) for ca. 72 hours. Additional solids were added to form slurries if the material dissolved during the first 1 hour and 5 hours. After temperature cycling, saturated solutions and residual solids were obtained by filtration (centrifuge filtration using a 0.22 µm nylon filter, additionally using a 0.45 µm PTFE syringe filter if required). Experiments carried out in acetic acid, DMF, DMSO and NMP were solutions after temperature cycling and so were not filtered. The solutions were then split into portions for the additional screening experiments. The residual solids remaining after XRPD analysis were allowed to dry at ambient in the centrifuge filters for ca. 1 week before further analysis was carried out.

Crash Cooling

Cooling experiments were performed by placing solutions of the material in each of the solvents in Table 1 at ca. 2° C. for ca. 4 days. The experiments which were solutions (all samples apart from the tetrahydrofuran sample) were then moved to −18° C. for ca. 9 days in order to obtain sufficient solids.

Anti-Solvent Addition

Anti-solvent addition experiments were conducted at ambient temperature (ca. 22° C.) and 50° C. by adding anti-solvent to the solutions, in each of the solvents in Table 1, until precipitation was observed or no more anti-solvent could be added to the ca. 2 mL vials. The samples were stirred during the anti-solvent addition which was added slowly. Methyl tert-butyl ether (t-BME) was used as the anti-solvent for all experiments apart from the DMSO solution, where isobutyl acetate was used.

Evaporation

Evaporation experiments were conducted by allowing the solutions of the material, in each of the solvents in Table 1, to evaporate at ambient conditions in open vials. Any solid material produced was then recovered and analyzed after the solvent had evaporated to dryness.

Anti-Solvent Addition Using Heptane

Using the samples from the crash cooling experiments (very few solids were obtained from cooling experiments) further anti-solvent addition was carried out at ambient temperature using heptane. Heptane was added to the solutions at ambient temperature until precipitation was observed or no more anti-solvent could be added to the vials. The samples were stirred during the anti-solvent addition which was added slowly.

Form 1 was observed from temperature cycling in anisole, dichloromethane, ethanol, 2-ethoxy ethanol, methanol, 2-methyl THF, methyl isobutyl ketone, 1-propanol, 2-propanol, 2-propanol:water (90:10 v/v), toluene and water, also from crash cooling in 1-propanol, anti-solvent addition at 50° C. in acetic acid, dichloromethane, dimethylformamide, 1,4-dioxane and 2-ethoxy ethanol, from anti-solvent addition at ambient temperature in dichloromethane, dimethylformamide, 2-ethoxy ethanol and toluene, from evaporation experiments with anisole, 1-butanol, dimethylformamide, dimethylsulfoxide, ethanol, 2-ethoxyethanol, methanol, 2-methyl THF, methyl isobutyl ketone, 1-propanol, 2-propanol and tetrahydrofuran, or from anti-solvent addition using heptane from 2-methyl THF.

Form 2 was observed from temperature cycling in acetone, ethyl acetate and methy ethyl ketone. Form 2 was also observed from anti-solvent addition using heptane in acetone and methyl ethyl ketone.

Form 3 was observed in a solubility screen from ethyl acetate.

Form 4 was observed from temperature cycling in diisopropyl ether (DIPE), and heptane anti-solvent addition in dichloromethane and methyl isobutyl ketone.

Form 5 was observed from temperature cycling in 1,4-dioxane and tetrahydrofuran and crash cooling in tetrahydrofuran.

Form 6 was observed as a mixture with Form 1 from anti-solvent addition at 50° C. in N-methyl-2-pyrrolidone and as a mixture with Form 2 from evaporation in N-methyl-2-pyrrolidone.

Form 7 was observed from evaporation in tetrahydrofuran (THF).

Form 9 was observed from temperature cycling in 2-methyl-1-propanol or from evaporation of a solution of Compound A in 2-methyl-1-propanol.

Form 10 was observed from temperature cycling in acetonitrile:water (95:5) or from evaporation of a solution of Compound A in acetonitrile:water (95:5).

Form 11 was observed from temperature cycling in methyl ethyl ketone.

Form 12 was observed during variable temperature XRPD experiments on Form 10 at 210° C.

Edisylate Form 1 was observed from temperature cycling in acetone, dichloromethane, methanol, 2-propanol:water (90:10 v/v), methyl ethyl ketone, or tetrahydrofuran.

Cyclamate Form 1 was observed from temperature cycling in acetone, methyl ethyl ketone, or tetrahydrofuran.

Cyclamate Form 2 was observed from temperature cycling in dichloromethane.

Naphthalene sulfonic acid salt was observed from temperature cycling in acetone or methyl ethyl ketone.

Hydrobromide Form 1 was observed from temperature cycling in 2-methyl tetrahydrofuran.

Hydrobromide Form 2 was observed from temperature cycling in methyl ethyl ketone.

Besylate Form 1 was observed from temperature cycling in acetone, ethyl acetate, or methyl ethyl ketone.

Hydrochloride Form 1 and Form 2 were observed from temperature cycling in ethyl acetate.

Oxalate Form 1 was observed from temperature cycling in acetone, dichloromethane, and ethyl acetate.

Oxalate Form 3 was observed from temperature cycling in 2-propanol:water (90:10 v/v) and tetrahydrofuran.

Oxalate Form 5 was observed from drying oxalate Form 1 under vacuum.

Maleate Form 1 was observed from temperature cycling in ethyl acetate. 1,5-Naphthalene Disulfonate Form 1 and Form 3 were observed from temperature cycling in acetone and ethyl acetate.

1,5-Naphthalene Disulfonate Form 2 and Form 5 were observed from temperature cycling in 2-propanol:water (90:10 v/v).

1,5-Naphthalene Disulfonate Form 4 was observed from drying Form 2 under vacuum.

Phosphate Form 1 was observed from temperature cycling in 2-propanol:water (90:10 v/v) and acetone.

Phosphate Form 2 and Form 3 were observed from temperature cycling in ethyl acetate.

Mixtures of forms were also observed, with temperature cycling in acetonitrile giving a mixture of Form 1 and Form 2. Form 1 and Form 4 mixtures were observed from temperature cycling in 1-butanol, anti-solvent addition at 50° C. in 2-propanol:water (90:10 v/v) and heptane anti-solvent addition in 2-ethoxy ethanol. Form 5 was observed as a mixture with Form 1 from anti-solvent addition at 50° C. in 2-methyl THF. A mixture of Form 4 and Form 5 was observed from ambient anti-solvent addition in 2-methyl THF.

Example 3: Characterization of the Polymorphs of the Application

Figure 18B:
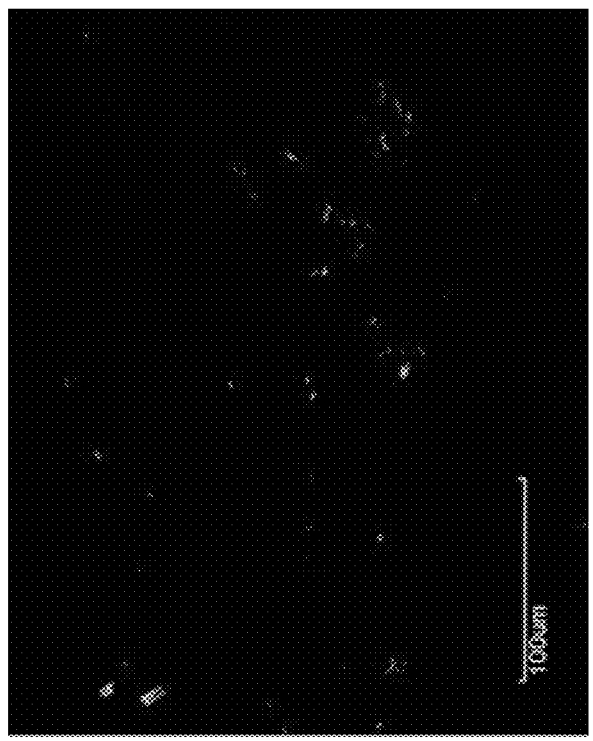
FIG. 18B sets forth a PLM image of Form 7 under polarized lenses.
Figure 18A:
FIG. 18A sets forth a PLM image of Form 7 under non-polarized lenses.
Figure 76A:
FIG. 76A sets forth a PLM image of Form 10 under non-polarized lenses obtained from 400 mg scale-up.
Figure 76B:
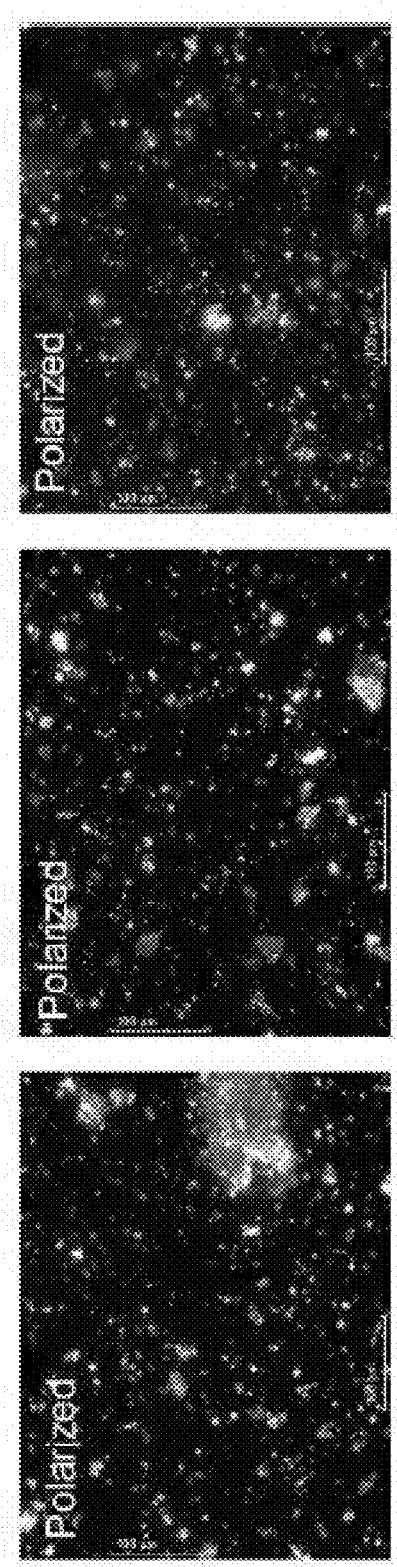
FIG. 76B sets forth a PLM image of Form 10 under polarized lenses obtained from 400 mg scale-up.

PLM analysis showed small slightly birefringent particles for Form 1 (FIG. 21A and FIG. 21B) and birefringent plate-like particles for Form 2. Birefringent needle-like particles were observed for Form 4 (FIG. 31A and FIG. 31B) and Form 5 and small birefringent particles for Form 7 (FIG. 18A and FIG. 18B). Small birefringent particles with poorly defined morphology were observed for Form 10 (FIGS. 76A and 76B). Small particles with no clear morphology were observed for edisylate Form 1 (FIG. 132). Small birefringent particles were observed for cyclamate Form 1 (FIG. 145). Small rod-like particles with agglomeration and birefringence were observed for besylate Form 1 (FIG. 157). Irregular particles of various size, but some rod-like crystals were observed for besylate Form 1 (FIG. 188 and FIG. 271). Small rod-like particles with agglomeration and birefringence were observed for hydrobromide Form 1 (FIG. 170 and FIG. 258). Small, irregular particles of various size, exhibiting birefringence were observed for hydrobromide Form 1 (FIG. 241). Small, irregular particles up to 50 μm in size, exhibiting birefringence were observed for hydrochloride Form 2 (FIG. 183). Small, needle-like particles that exhibited birefringence were observed for oxalate Form 1 (FIG. 193). Small needle-like particles that exhibited birefringence were observed for oxalate Form 3 (FIG. 197). Small needle-like particles that exhibited birefringence were observed for oxalate Form 5 (FIG. 201). Small needle-like particles that exhibited birefringence were observed for maleate Form 1 (FIG. 207). Irregular particles of various sizes that exhibited birefringence were observed for 1,5-naphthalene disulfonic acid Form 1 and Form 3 (FIG. 213). Irregular particles of various sizes that exhibited birefringence were observed for 1,5-naphthalene disulfonic acid Form 2 (FIG. 218). Irregular particles of various sizes that exhibited birefringence were observed for 1,5-naphthalene disulfonic acid Form 4 (FIG. 221). Small, irregular particles up to 100 μm in size, exhibiting birefringence were observed for phosphate Form 1 (FIG. 228 and FIG. 245). Small, irregular particles of various size, exhibiting birefringence were observed for phosphate Form 2 (FIG. 234).

Figure 11:
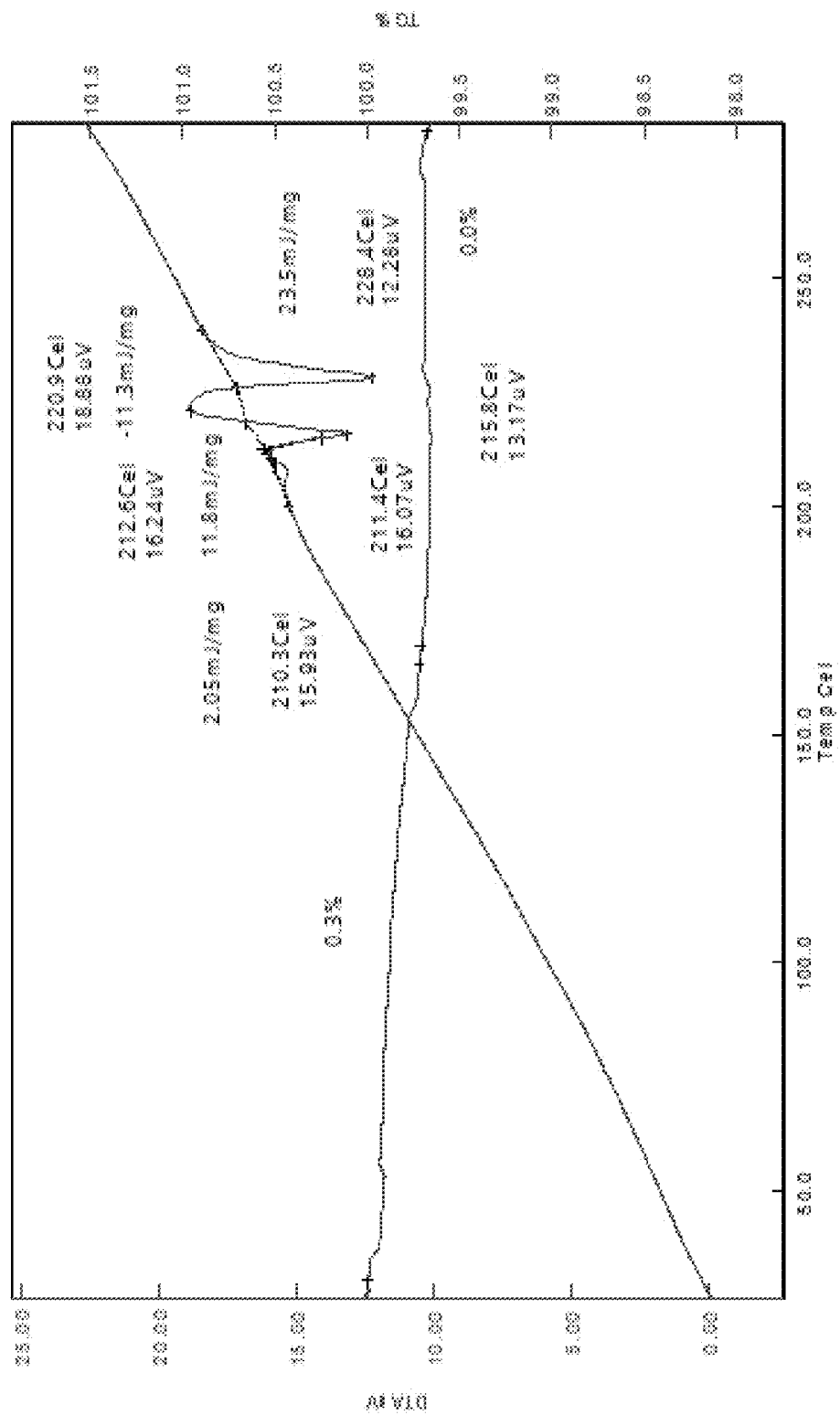
FIG. 11 sets forth a thermal analysis by TG/DTA of Form 1 from temperature cycling in 2-propanol.

TGA of the Form 1 material isolated from temperature cycling in 2-propanol showed a weight loss of 0.3% between ca. 25° C. and 170° C. (FIG. 11). DTA (FIG. 11) showed 3 endothermic events and an exothermic event between ca. 210° C. and 230° C. Endothermic events were observed with onset at ca. 210° C. and peak ca. 211° C., onset at ca. 213° C. and peak at ca. 216° C. and peak at ca. 228° C. The observed exotherm had peak at ca. 221° C. Form 1 is therefore again confirmed to be an anhydrous form.

Figure 12:
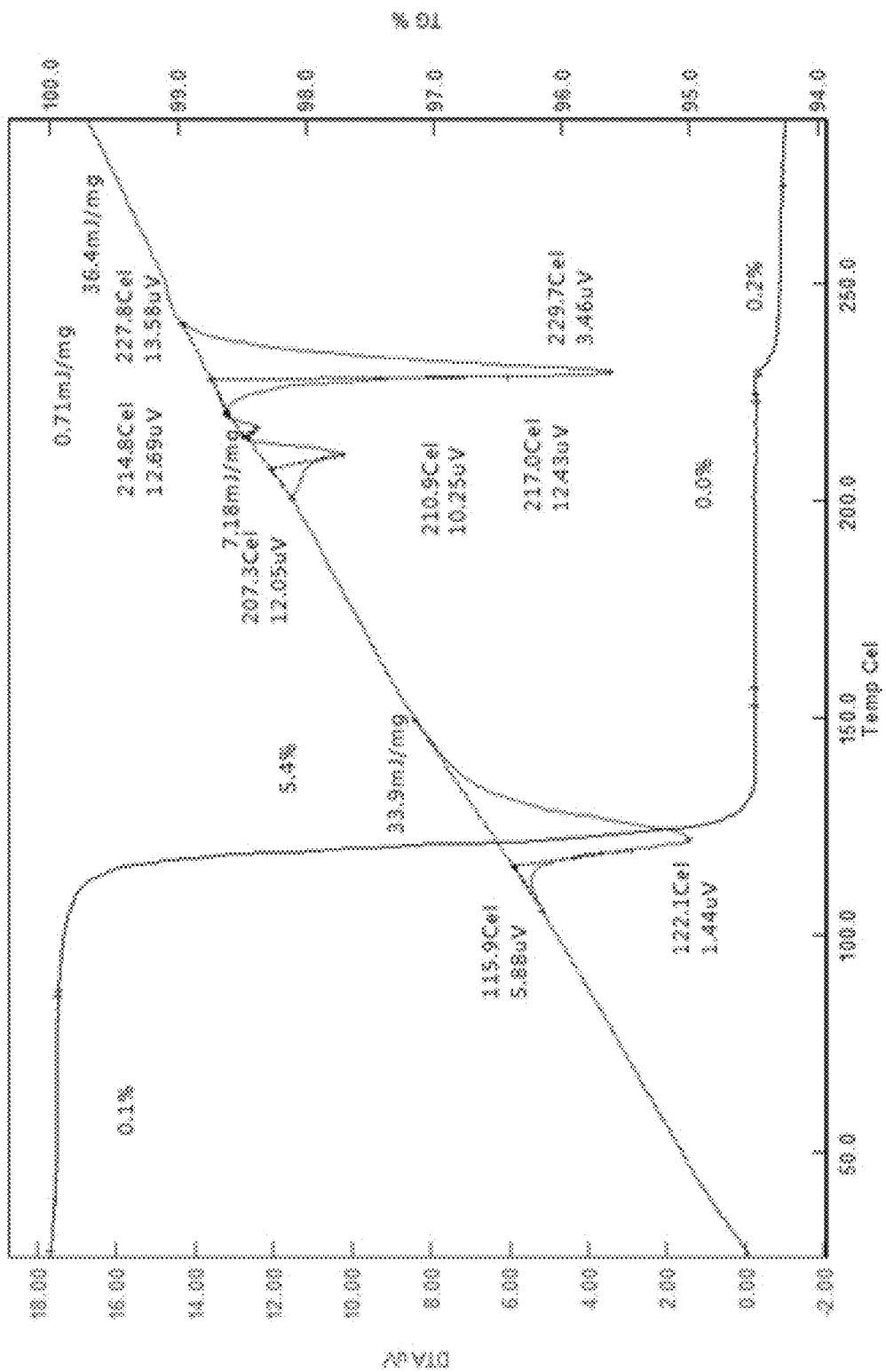
FIG. 12 sets forth a thermal analysis by TG/DTA of Form 2 from temperature cycling in acetone.

TGA of the Form 2 material isolated from temperature cycling in acetone showed a weight loss of 0.1% between ca. 25° C. and 90° C., a loss of 5.4% between ca. 90° C. and 150° C. followed by further loss of 0.2% between 150° C. and 250° C. (FIG. 12). Approximately 5.27% corresponds with half a mole equivalent of acetone. DTA (FIG. 12) showed 4 endothermic events with onsets at ca. 116° C., 207° C., 215° C. and 228° C. and peaks at 122° C., 211° C., 217° C. and 230° C. Form 2 is likely a solvate. Form 2 was obtained from multiple solvent systems, indicating the potential for isostructural solvates, however further analysis would be required for confirmation.

Figure 13:
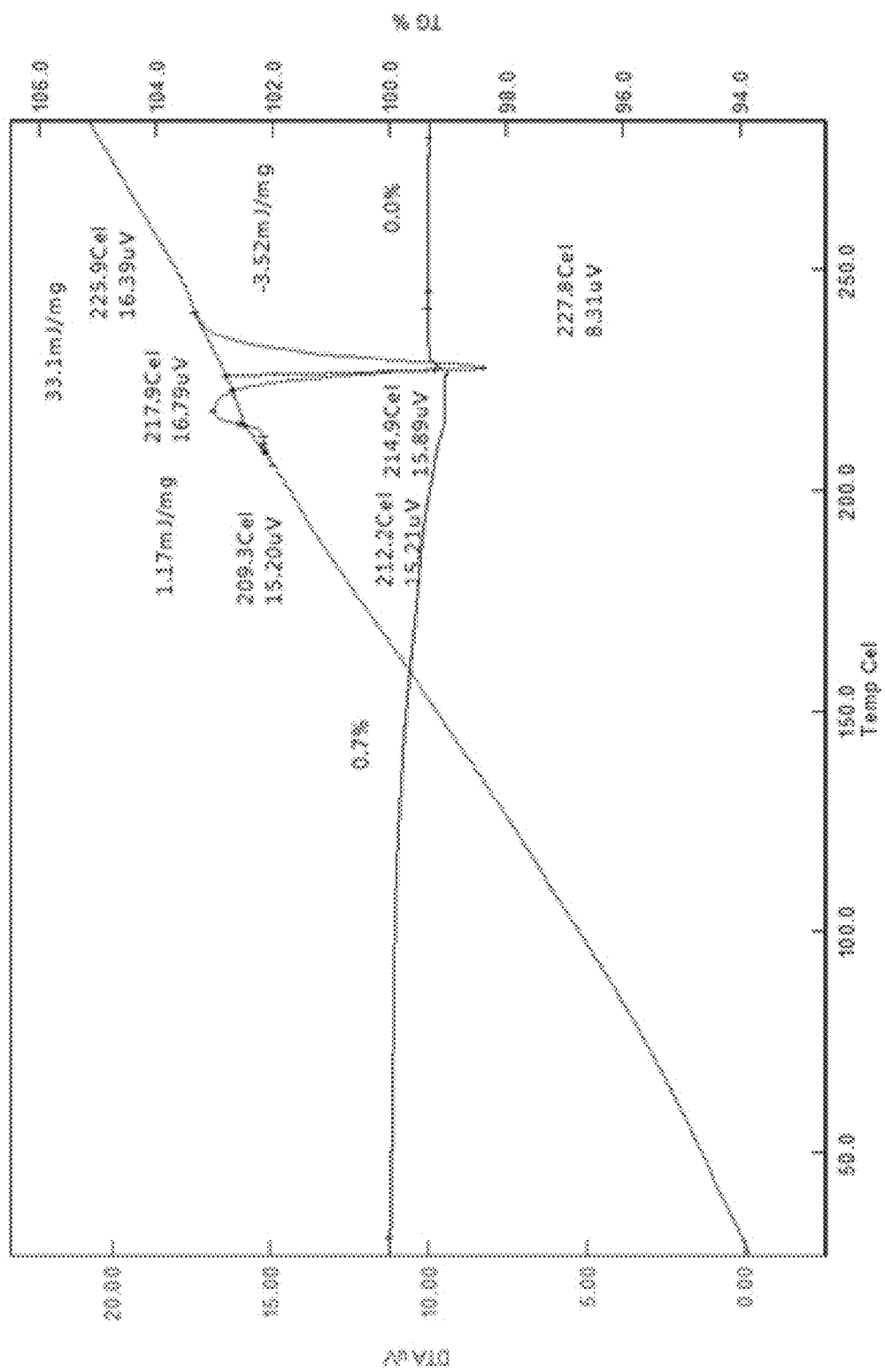
FIG. 13 sets forth a thermal analysis by TG/DTA of Form 4 from temperature cycling in diisopropyl ether (DIPE).

TGA of the Form 4 material isolated from temperature cycling in DIPE showed a weight loss of 0.7% between ca. 25° C. and 230° C. (FIG. 13). DTA (FIG. 13) showed 2 endothermic events with onsets at ca. 209° C. and 226° C. (peaks at ca. 212° C. and 228° C.) and an exothermic event with onset ca. 215° C. and peak at ca. 218° C. Based on the thermal data, Form 4 appears as an anhydrous form.

Figure 14:
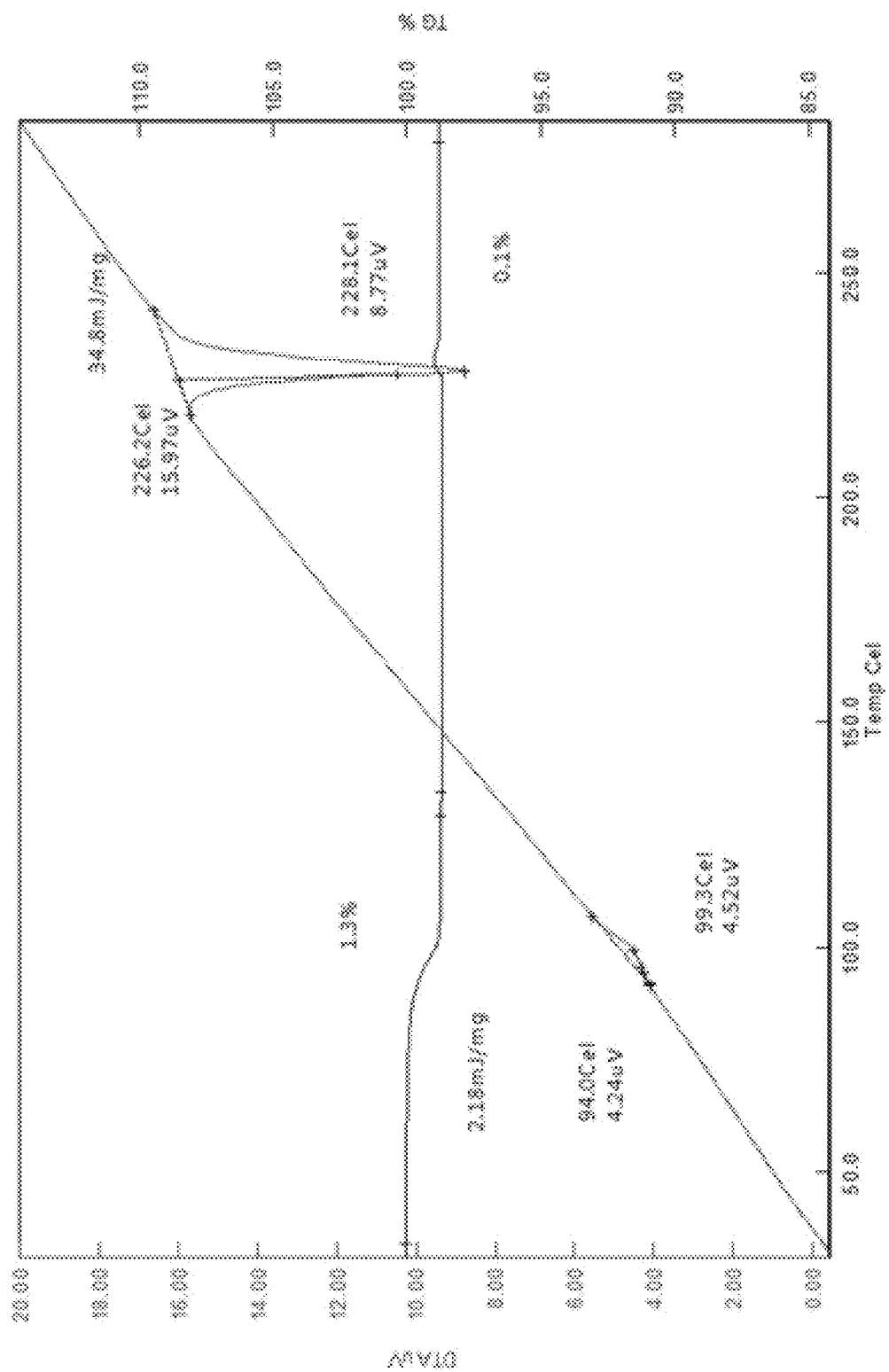
FIG. 14 sets forth a thermal analysis by TG/DTA of Form 5 from temperature cycling in THF.

TGA of the Form 5 material isolated from temperature cycling in THF showed a weight loss of 1.3% between ca. 25° C. and 110° C. (FIG. 14). DTA (FIG. 14) showed a small endothermic event with onset ca. 94° C. (peak at ca. 99° C.) and a further endothermic event with onset ca. 226° C. and peak at ca. 228° C.

Figure 15:
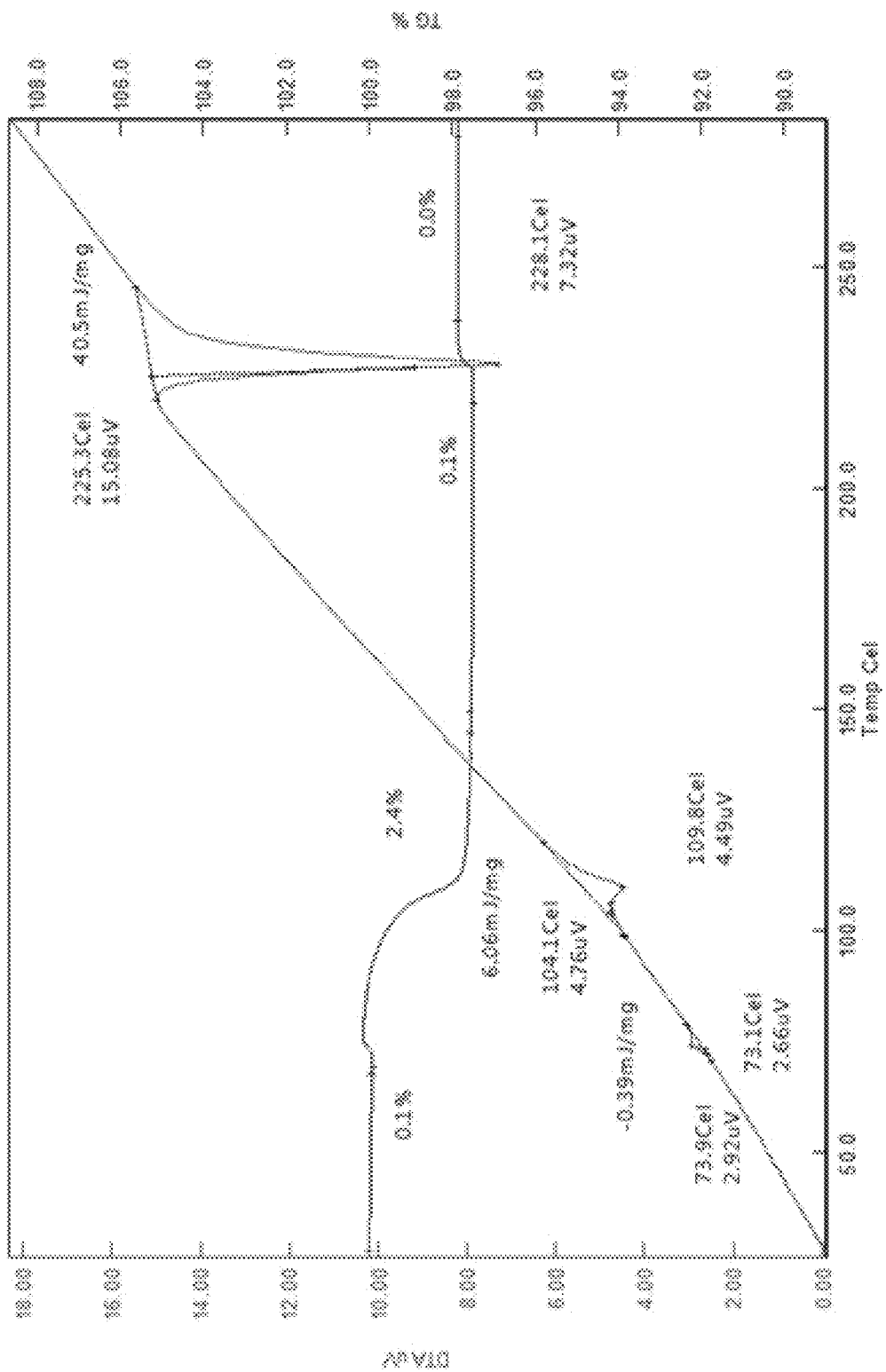
FIG. 15 sets forth a thermal analysis by TG/DTA of Form 5 from temperature cycling in 1,4-dioxane.
Figure 16:
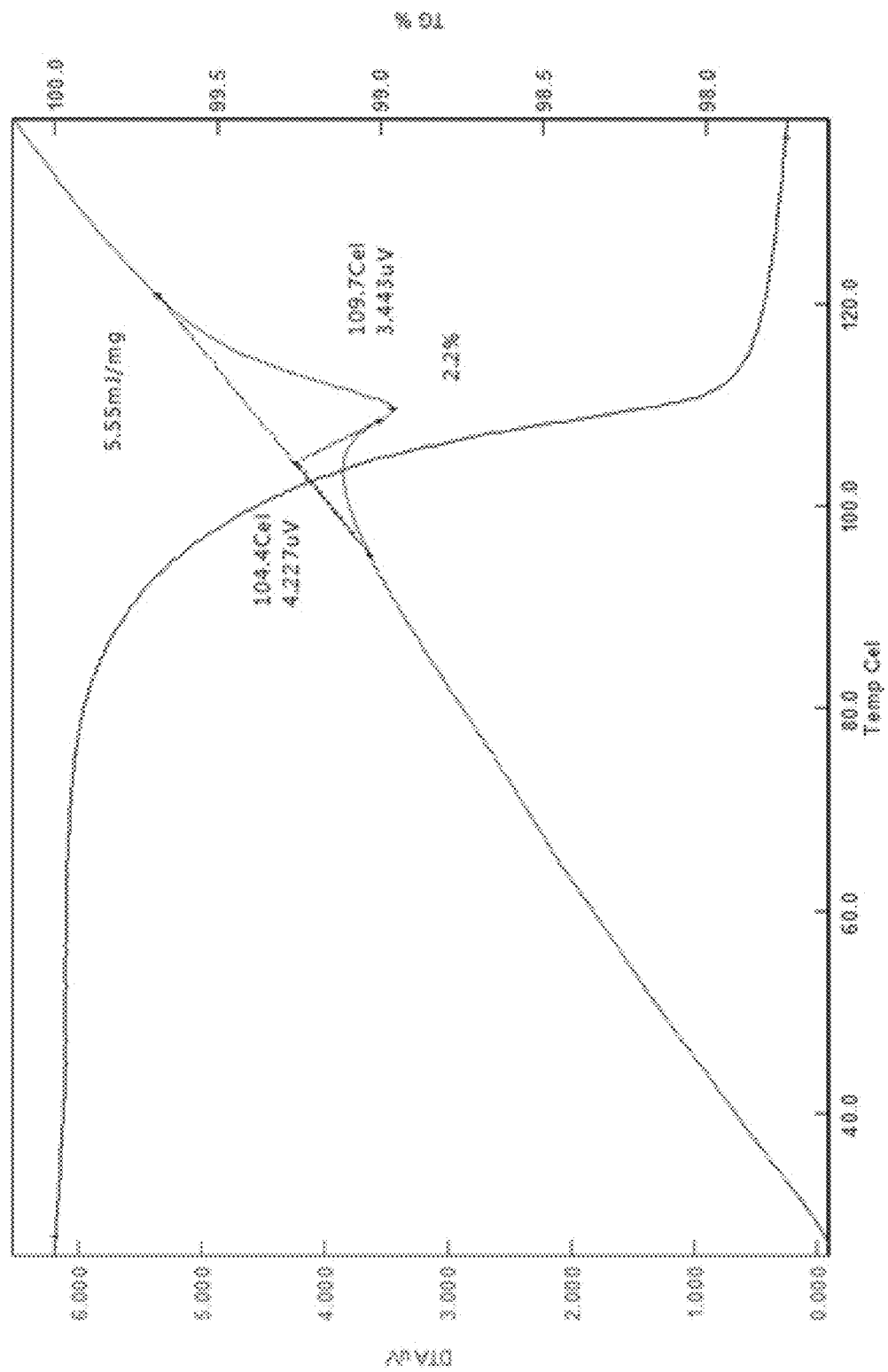
FIG. 16 sets forth a thermal analysis by TG/DTA of Form 5 from temperature cycling in 1,4-dioxane after drying.

TGA of the Form 5 material isolated from temperature cycling in 1,4-dioxane, dried under vacuum overnight at 40° C., showed a weight loss of 0.1% between ca. 25° C. and 70° C. and a loss of 2.4% between ca. 70° C. and 140° C. (FIG. 15 and FIG. 16). DTA (FIG. 15 and FIG. 16) showed a small exothermic event with onset ca. 73° C. (peak at 74° C.) and 2 endothermic events with onsets ca. 104° C. and 225° C. and peaks at 110° C. and 228° C.

The dried Form 5 material, isolated from 1,4-dioxane, was heated to ca. 150° C. by TG/DTA which showed at 2.2% weight loss by TGA and then analyzed by XRPD which indicated that this material was a unique form—Form 8 (FIG. 10).

Figure 17:
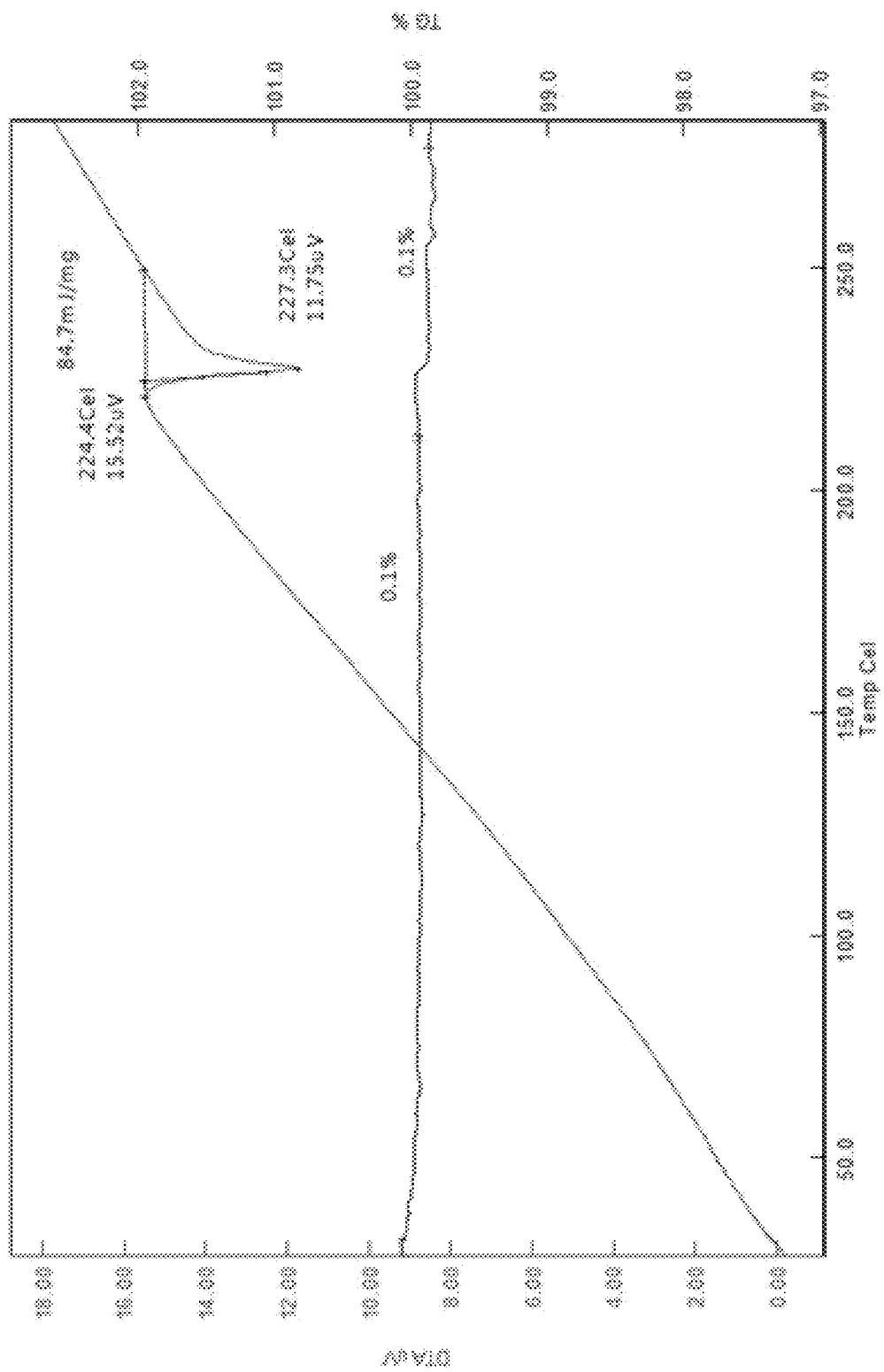
FIG. 17 sets forth a thermal analysis by TG/DTA of Form 8.

TGA of Form 8 showed a weight loss of 0.1% between ca. 25° C. and 200° C. and a loss of 0.1% between ca. 200° C. and 300° C. (FIG. 17). DTA (FIG. 17) showed a single endotherm with onset ca. 224° C. Form 5 therefore appears as a solvated material which may desolvate to anhydrous Form 8 upon heating.

Figure 19:
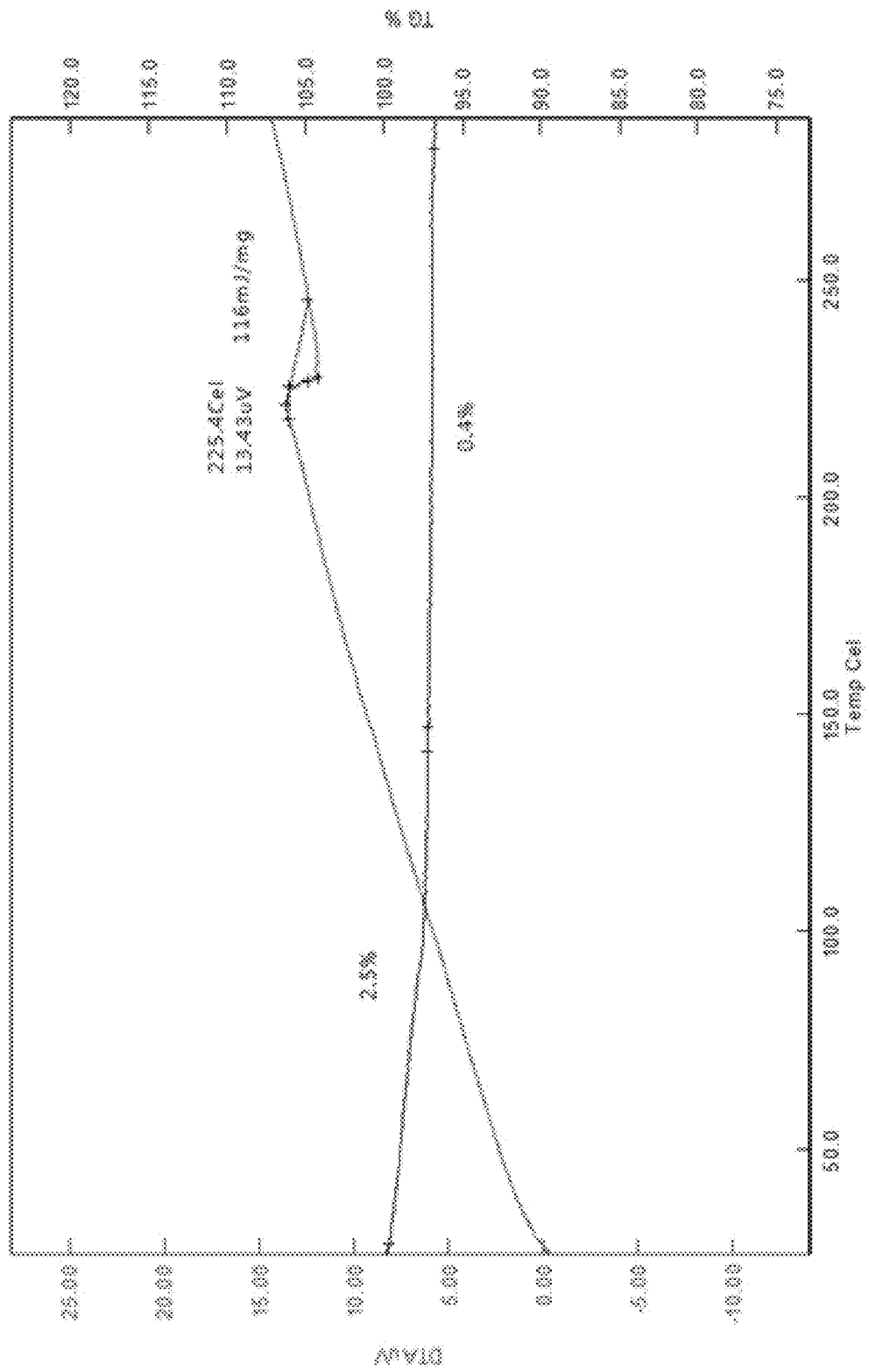
FIG. 19 sets forth a thermal analysis by TG/DTA of Form 7.

TGA of Form 7 from THF evaporation showed a weight loss of 2.5% between ca. 25° C. and 140° C. and a loss of 0.4% between ca. 140° C. and 300° C. (FIG. 19). DTA (FIG.

19) showed an endotherm with onset ca. 225° C. Further analysis of Form 7 material would be required in order to definitively assign the nature of Form 7 and assess whether the 2.5% weight loss which is observed from the outset of the TGA is due to any unbound or bound solvent/water.

TGA of the Form 9 material isolated from slurrying of 2-methyl-1-propanol showed a weight loss of 9.8% between ca. 50° C. and 160° C. (FIG. 66). DSC (FIG. 66) showed 2 endothermic events between ca. 55° C. and 260° C. Endothermic events were observed with onset at ca. 69° C. and peak ca. 96° C., and onset at ca. 218° C. and peak at ca. 223° C.

Figure 71:
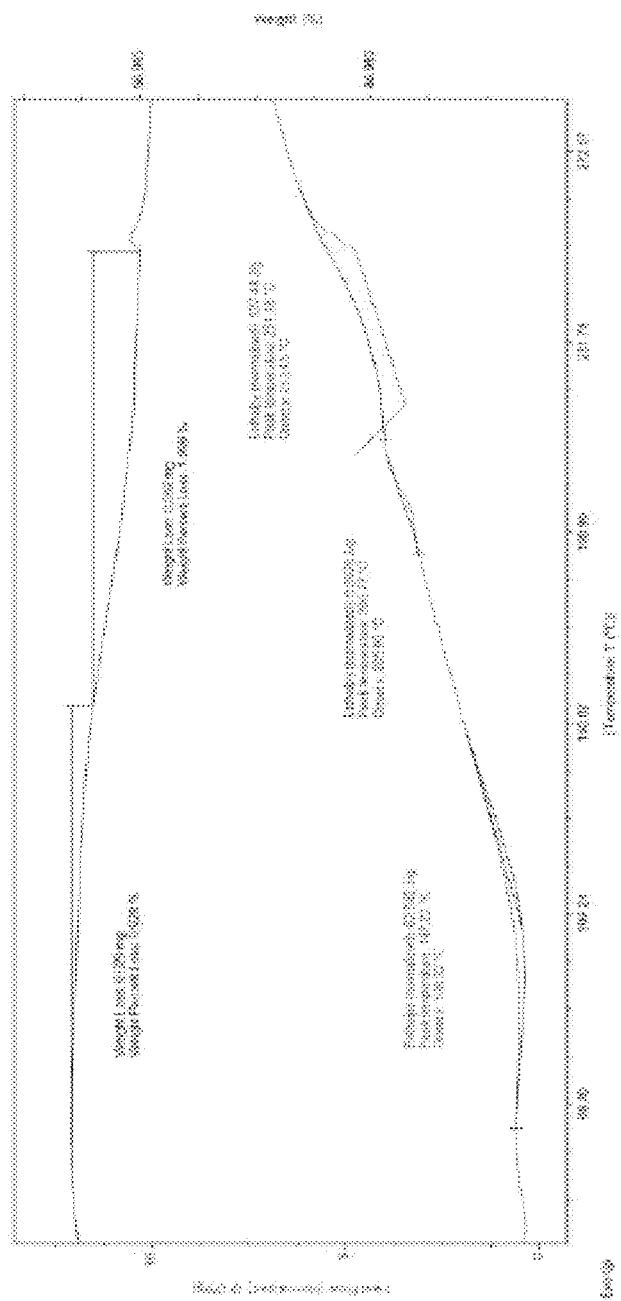
FIG. 71 sets forth a thermal analysis by TG/DSC of Form 10 obtained from 200 mg scale-up.

TGA of the Form 10 material isolated from slurrying of acetonitrile:water (95:5) showed weight losses of 0.9% between ca. 70° C. and 150° C., and 1.9% above 150° C. (FIG. 71). DSC (FIG. 71) showed 3 endothermic events at approximately 106° C., approximately 206° C., and approximately 213° C.

Figure 75:
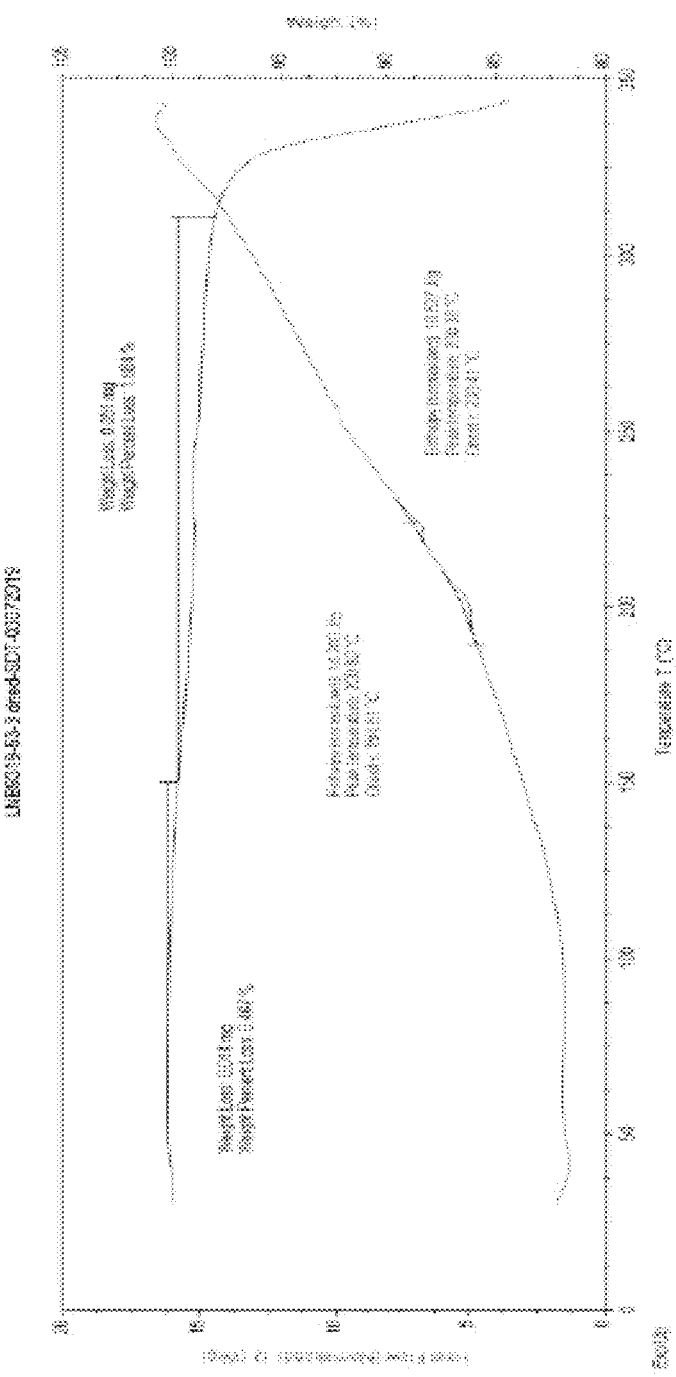
FIG. 75 sets forth a thermal analysis by TG/DSC of Form 10 obtained from 400 mg scale-up.

TGA of the Form 10 material isolated from evaporation of acetonitrile:water (95:5) showed weight losses of 0.5% between ca. 70° C. and 150° C., and 1.7% between ca. 150° C. and 300° C. (FIG. 75). DSC (FIG. 75) showed 2 endothermic events with onsets at approximately 195° C. and approximately 230° C. (peaks at approximately 201° C. and approximately 231° C.).

TGA of the Form 11 material isolated from methyl ethyl ketone showed a weight loss of approximately 4.5% between approximately 50° C. and approximately 165° C. (FIG. 89). DSC (FIG. 89) showed 3 endothermic events at ca. 112° C., ca. 197° C., and ca. 221° C. (peaks at ca. 125° C., ca. 204° C., and ca. 262° C.) as measured by scanning calorimetry (DSC). In one embodiment, Form 11 is characterized by endothermic events with peaks at approximately 125° C., approximately 204° C., and approximately 262° C.

TGA of the Form 11 material isolated from methyl ethyl ketone showed a weight loss of approximately 7.2% between approximately 100° C. and approximately 150° C., and a weight loss of approximately 1.7% between approximately 150° C. and approximately 300° C. (FIG. 93). DSC (FIG. 93) showed 4 endothermic events at ca. 119° C., ca. 195° C., ca. 210° C., and ca. 224° C. (peaks at ca. 128° C., ca. 202° C., ca. 213° C., and ca. 226° C.).

Figure 98:
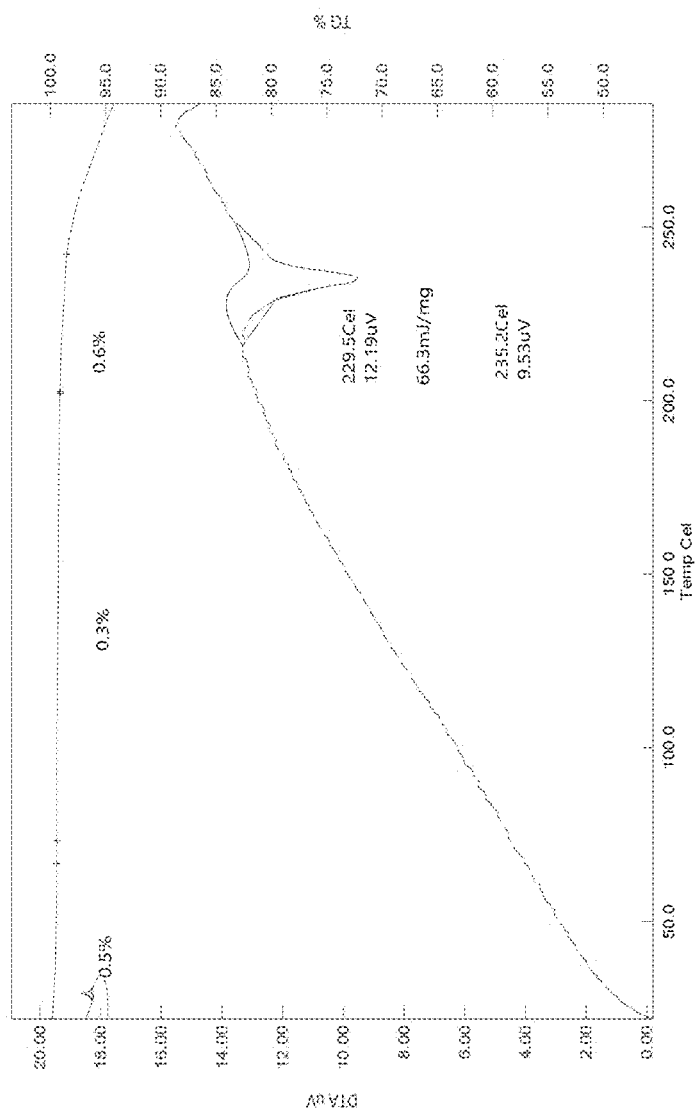
FIG. 98 sets forth a thermal analysis by TG/DTA of edisylate Form 1.
Figure 100:
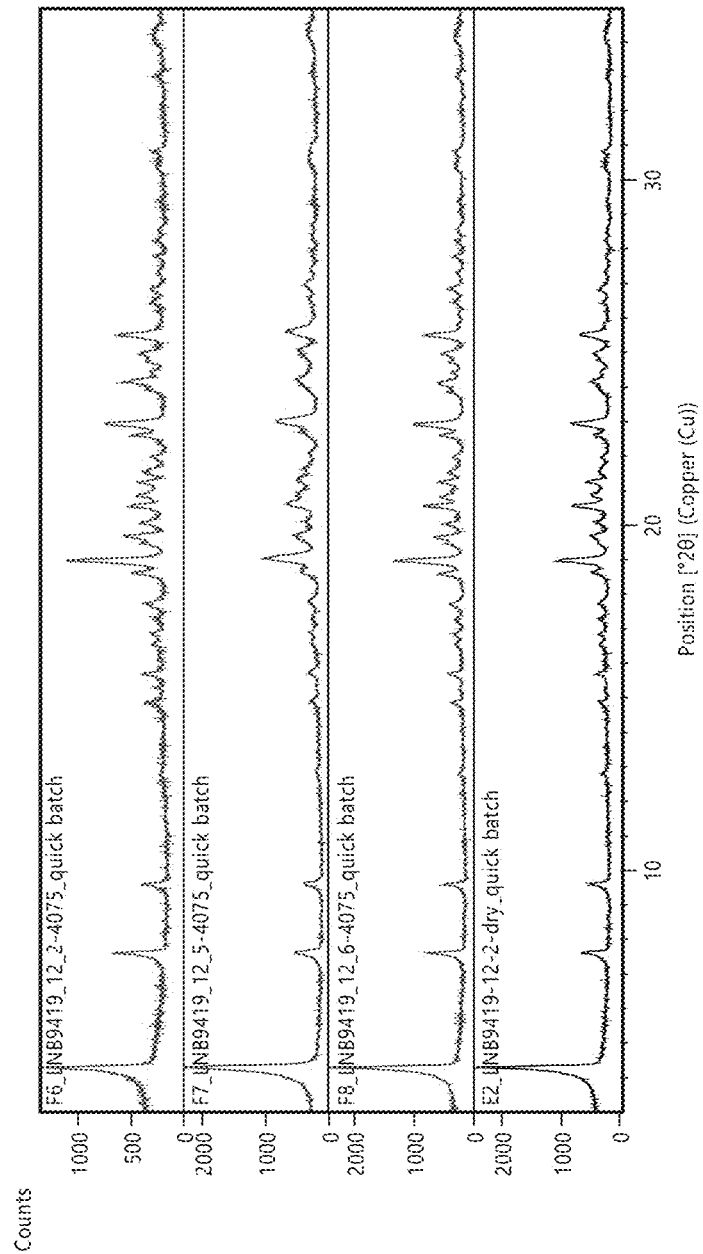
FIG. 100 sets forth comparative XRPD patterns of edisylate Form 1 from dichloromethane, methyl ethyl ketone, or THF after storage at 40° C./75% RH.
Figure 101:
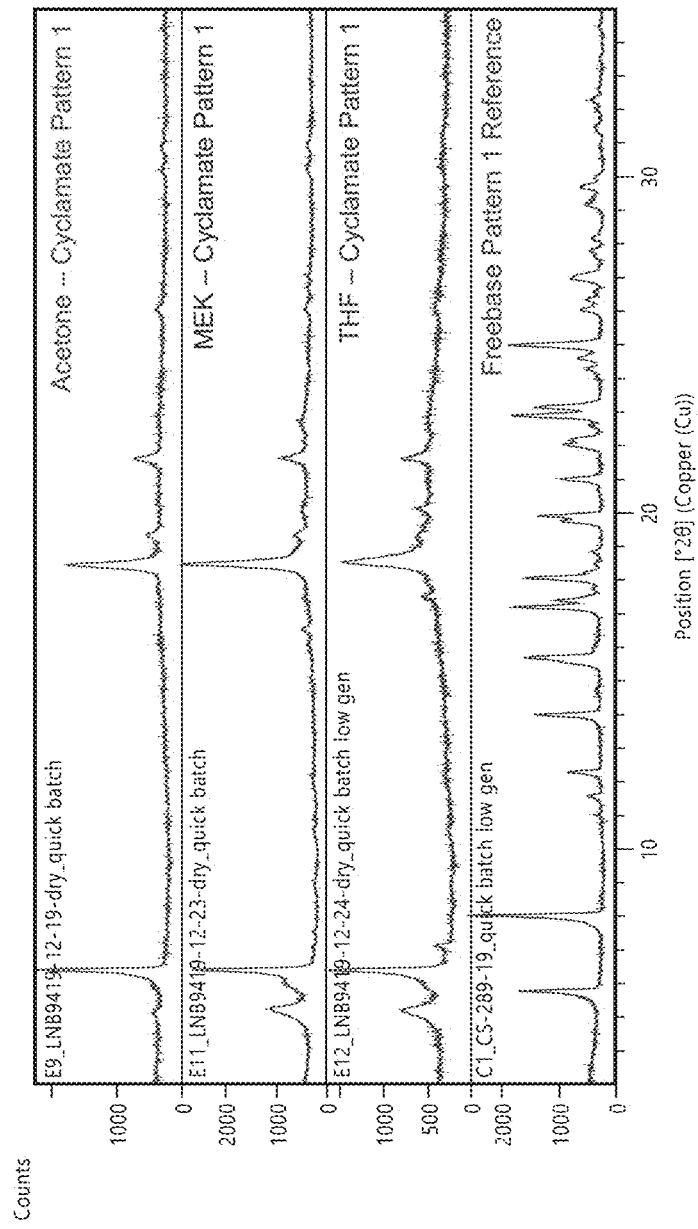
FIG. 101 sets forth comparative XRPD patterns of the freebase Form 1 and cyclamate Form 1 obtained from evaporation of acetone, methyl ethyl ketone, or THF.

TGA of the edisylate Form 1 recovered from acetone showed a weight loss of approximately 0.5% between approximately 25° C. and approximately 70° C. (FIG. 98). DTA (FIG. 93) showed an endothermic event with an onset at approximately 229° C. (peak at approximately 235° C.).

Figure 103:
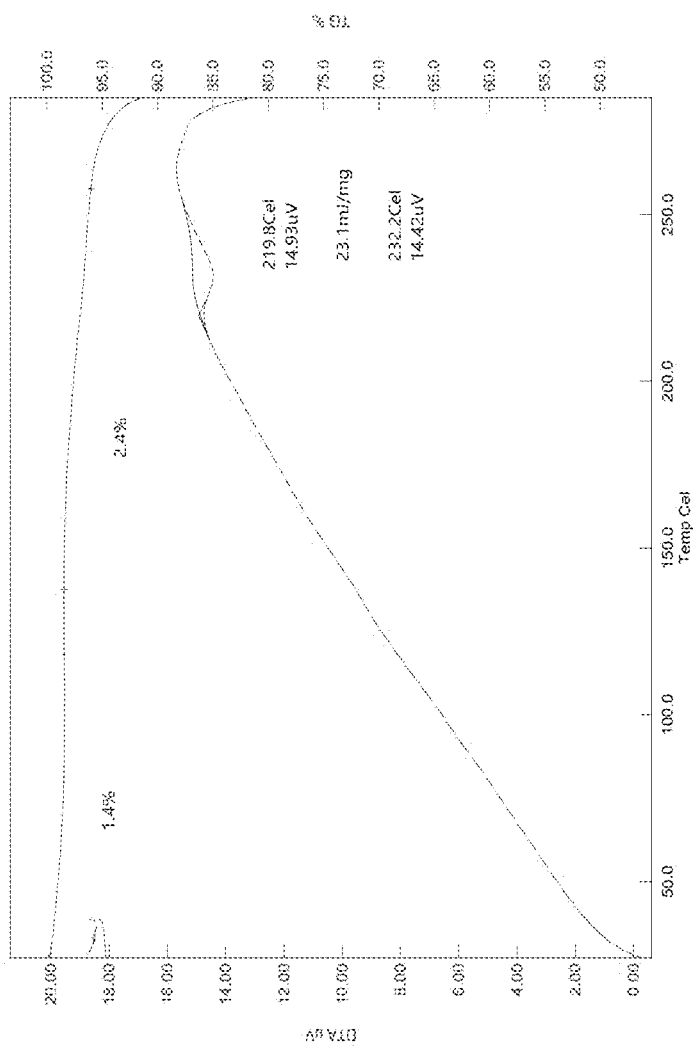
FIG. 103 sets forth a thermal analysis by TG/DTA of cyclamate Form 1.
Figure 104:
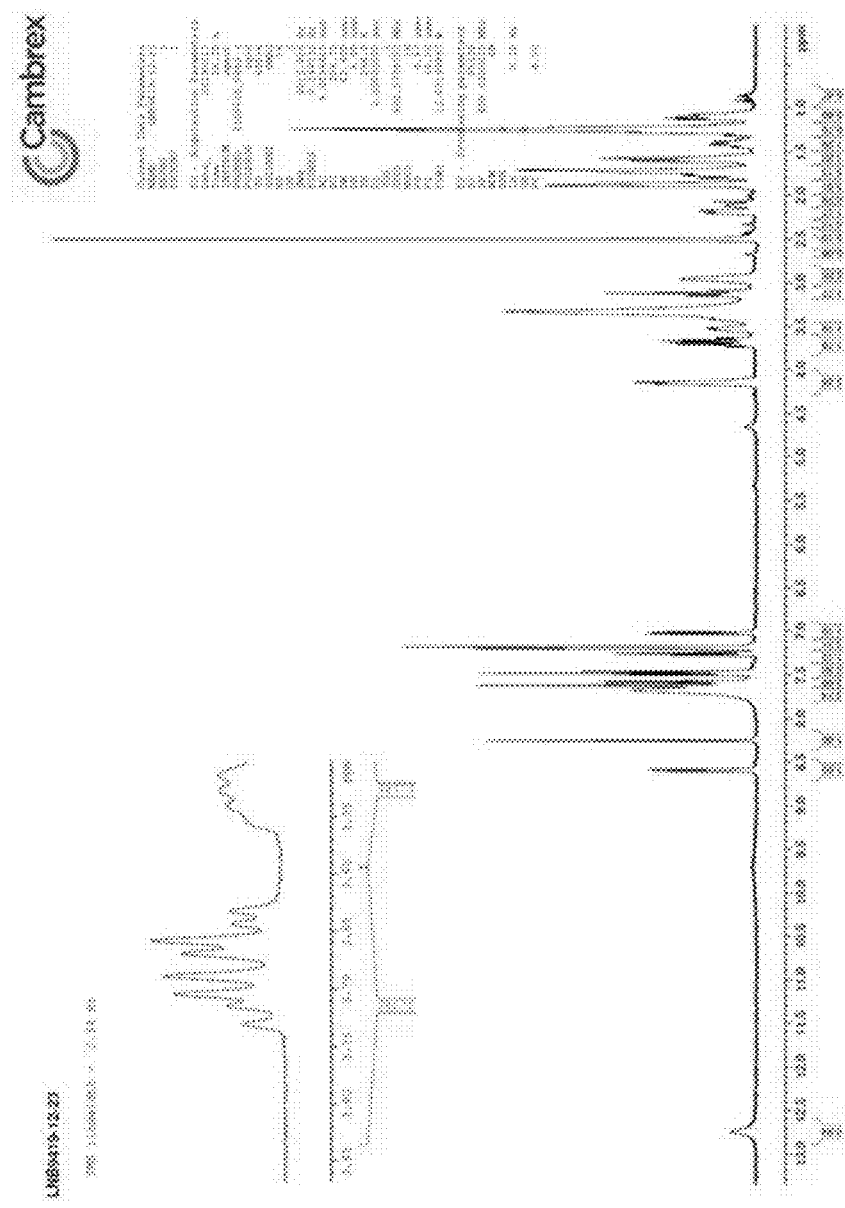
FIG. 104 sets forth a $^1$H NMR spectroscopic analysis of cyclamate Form 1.
Figure 105:
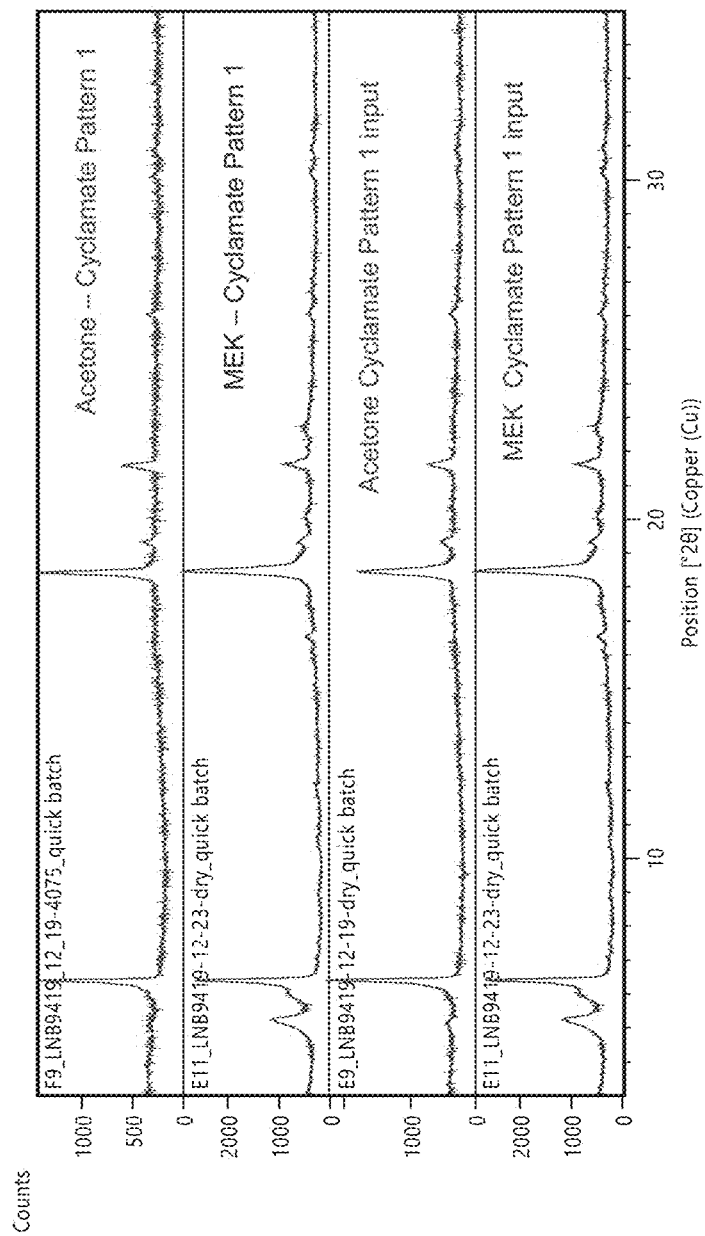
FIG. 105 sets forth comparative XRPD patterns of cyclamate Form 1 from acetone or methyl ethyl ketone after storage at 40° C./75% RH.
Figure 106:
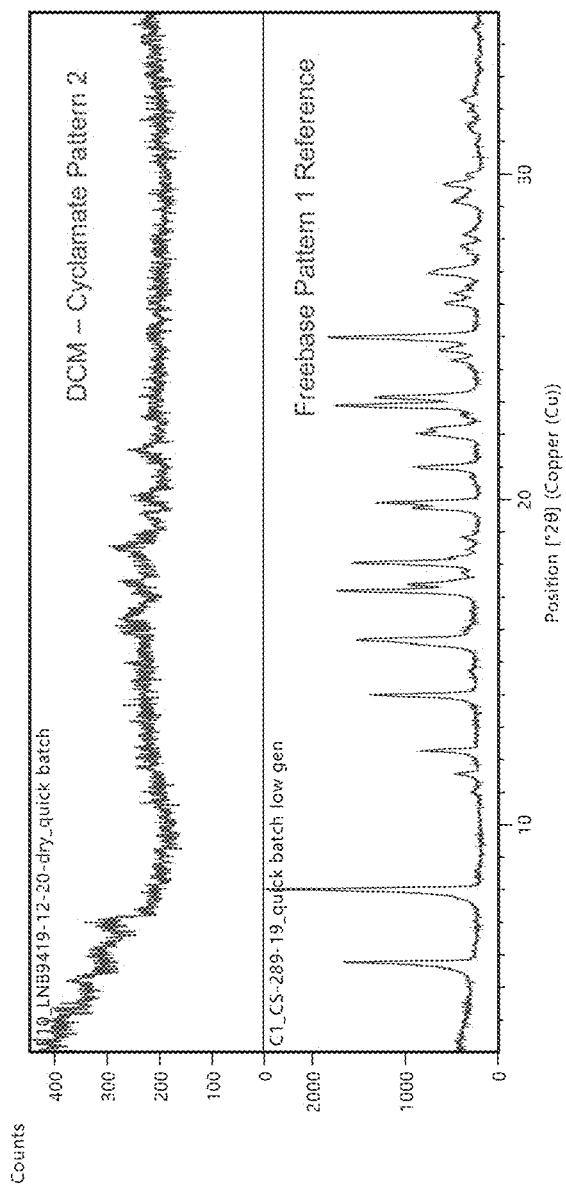
FIG. 106 sets forth comparative XRPD patterns of the freebase Form 1 and cyclamate Form 2 obtained from evaporation of dichloromethane.
Figure 108:
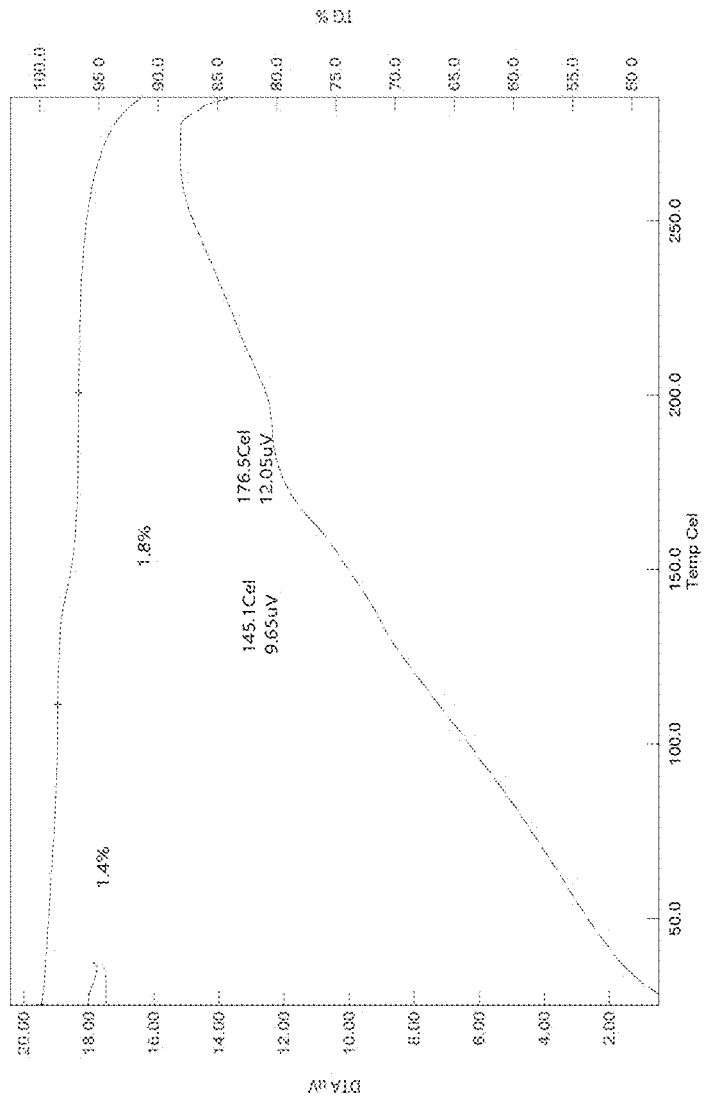
FIG. 108 sets forth a thermal analysis by TG/DTA of cyclamate Form 2.
Figure 109:
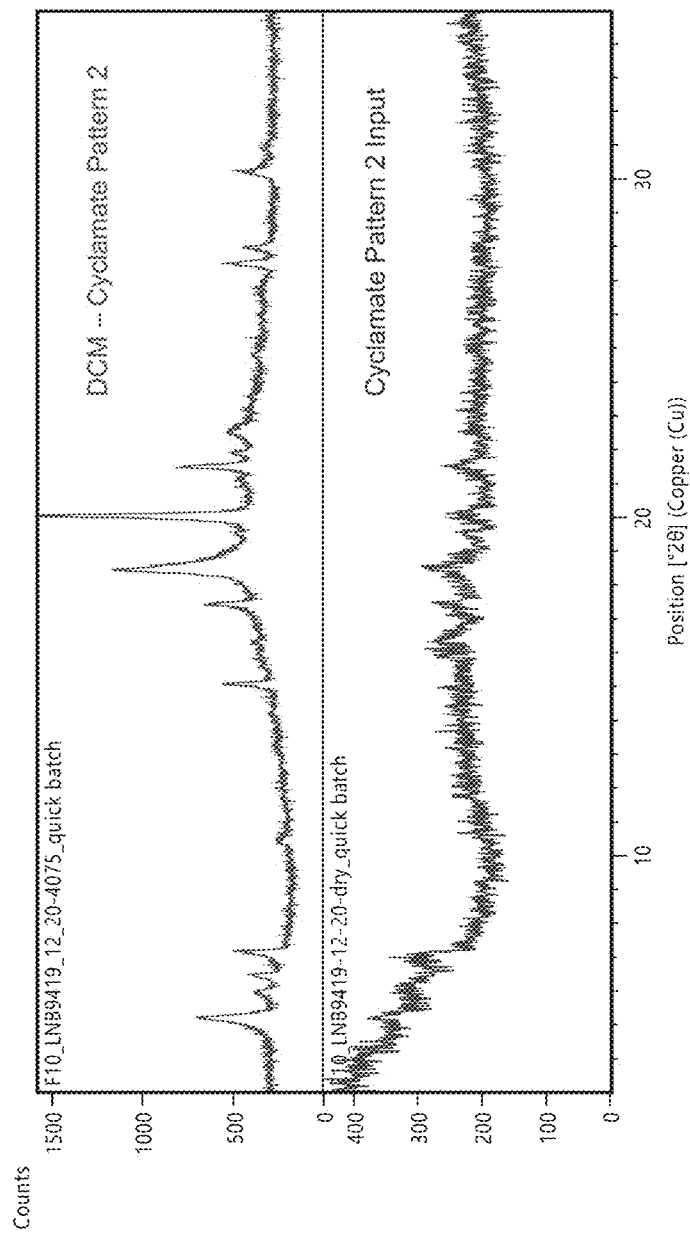
FIG. 109 sets forth comparative XRPD patterns of cyclamate Form 2 before and after storage at 40° C./75% RH.
Figure 110:
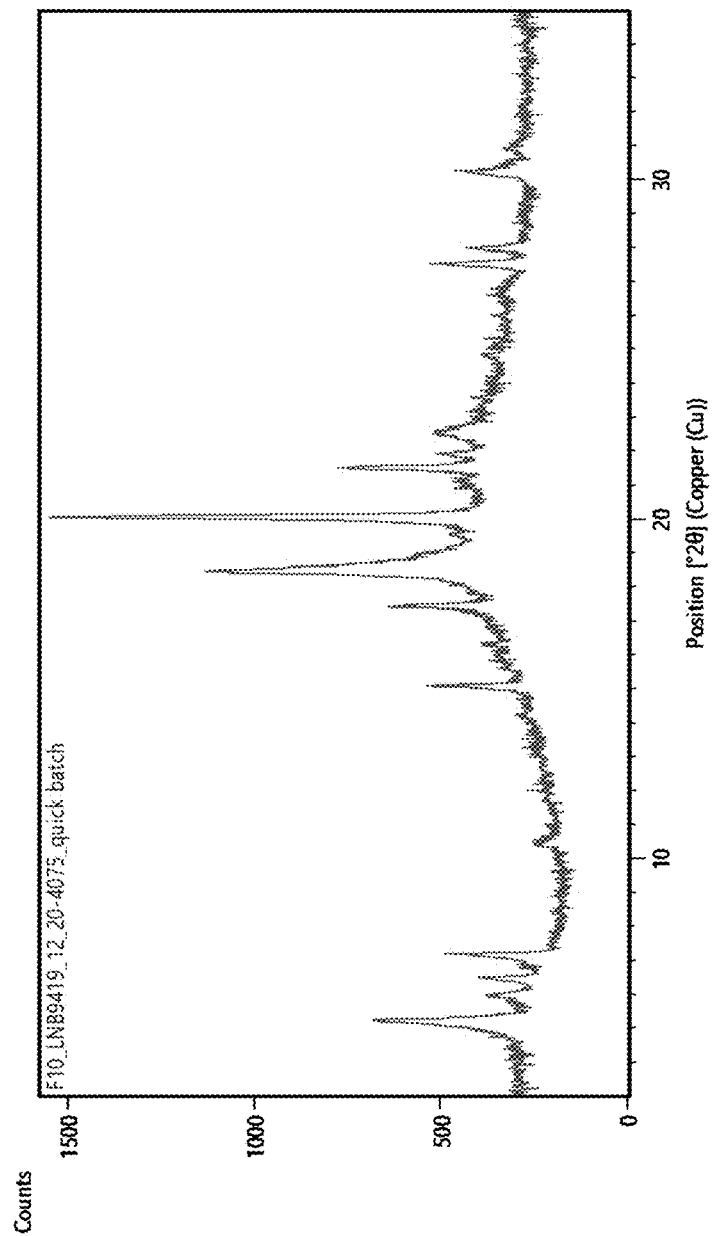
FIG. 110 sets forth XRPD pattern of cyclamate Form 2 after storage at 40° C./75% RH.
Figure 111:
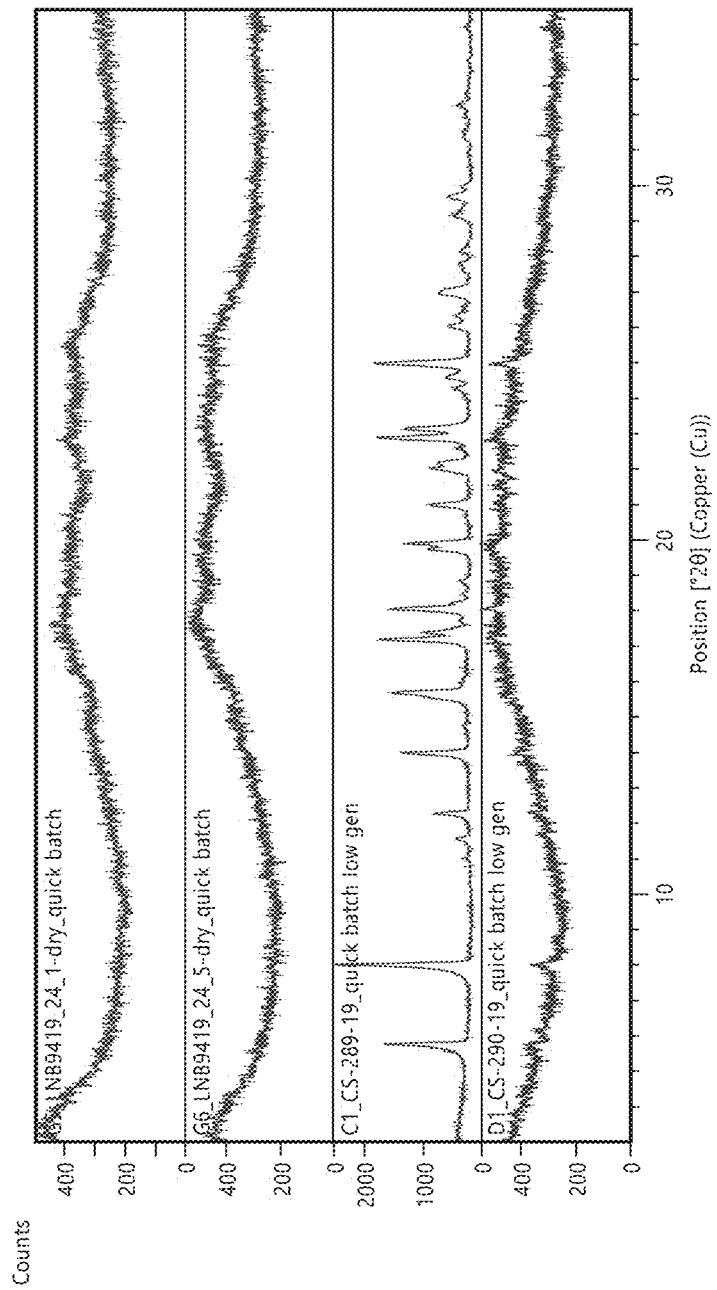
FIG. 111 sets forth comparative XRPD patterns of naphthalene-2-sulfonic acid salt obtained from acetone or methyl ethyl ketone, freebase Form 1, and amorphous form of Compound A.

TGA of the cyclamate Form 1 recovered from acetone showed a weight loss of approximately 1.4% between approximately 25° C. and approximately 120° C., and a weight loss of approximately 2.4% between approximately 140° C. and approximately 260° C. (FIG. 103). DTA (FIG. 103) showed an endothermic event with an onset at approximately 220° C. (peak at approximately 232° C.). TGA of cyclamate Form 2 recovered from dichloromethane showed a weight loss of approximately 1.4% between approximately 25° C. and approximately 110° C., and a weight loss of approximately 1.8% between approximately 110° C. and approximately 210° C. (FIG. 108). DTA (FIG. 108) showed no thermal events, with possible thermal events at 145 approximately ° C. and approximately 177° C.

TGA of naphthalene-2-sulfonic acid salt polymorph recovered from acetone showed a weight loss of approximately 4.1% between approximately 25° C. and approximately 150° C., and a weight loss of approximately 0.7% between approximately 150° C. and approximately 240° C. (FIG. 113). DTA (FIG. 113) showed endothermic events with onsets at approximately 108° C., approximately 139° C., approximately 173° C., and approximately 244° C. (peaks at approximately 109° C., approximately 150° C., approximately 174° C., and approximately 257° C.

TGA of hydrobromide Form 1 recovered from 2-methyl tetrahydrofuran showed a weight loss of approximately 3.3% between approximately 25° C. and approximately 80° C., and a weight loss of approximately 0.8% between approximately 140° C. and approximately 200° C. (FIG. 118). DTA (FIG. 118) showed endothermic events with onsets at approximately 35° C. and approximately 172° C. (peaks at approximately 47° C. and approximately 186° C.).

TGA of hydrobromide Form 1 from 2-methyl tetrahydrofuran showed a weight loss of approximately 2.6% up to 60° C., a gradual weight loss of 3.1% from about 60° C. to about 200° C. before drying. A weight loss of 0.9% was observed after drying under vacuum at 40° C. for 1 day. A weight loss of 2% below 60° C. was observed after 3 days of drying under vacuum (FIG. 238). DTA (FIG. 238) showed an endothermic event with a peak at approximately 59° C.

TGA of hydrobromide Form 2 from methyl ethyl ketone showed a weight loss of approximately 0.2% between approximately 25° C. and approximately 160° C., and a weight loss of approximately 1.6% between approximately 160° C. and approximately 220° C. (FIG. 123). DTA (FIG. 123) showed an endothermic event with an onset at approximately 202° C. (peak at approximately 211° C.).

TGA of besylate Form 1 from ethyl acetate showed a weight loss of approximately 0.8% between approximately 25° C. and approximately 180° C., and a weight gain of approximately 0.1% between approximately 180° C. and approximately 210° C. (FIG. 128). DTA (FIG. 128) showed an endothermic event with an onset at approximately 180° C. (peak at approximately 188° C.

TGA of besylate Form 1 from ethyl acetate showed a weight loss of approximately 0.4% at approximately 184° C. (FIG. 187). DTA (FIG. 187) showed an endothermic event with an onset at approximately 184° C. (peak at approximately 193° C.).

TGA of hydrochloride Form 2 from ethyl acetate showed a weight loss of approximately 9.3% at approximately 129° C. (FIG. 182). Additional weight losses of approximately 1% at approximately 60° C., 4.5% at 130° C., and 1.3% from about 130° C. to about 170° C. were observed while drying under vacuum. DTA (FIG. 182) showed an endothermic event with an onset at approximately 129° C. (peak at approximately 136° C.).

TGA of oxalate Form 1 showed a weight loss of approximately 20.8% between ambient temperature and approximately 230° C. (FIG. 192). DTA (FIG. 192) showed an endothermic event with an onset at approximately 157° C. (peak at approximately 165° C.).

TGA of oxalate Form 3 from 2-propoanol:water (90:10 v/v) showed a weight loss of approximately 17% between ambient temperature and approximately 230° C. (FIG. 195). DTA (FIG. 195) showed several endothermic events with an onset at approximately 148° C. (peak at approximately 157° C.).

TGA of oxalate Form 5 showed a weight loss of approximately 12% at approximately 159° C. (FIG. 200). DTA (FIG. 200) showed several endothermic events with an onset at approximately 159° C.

TGA of maleate Form 1 from ethyl acetate showed a weight loss of approximately 5.5% at approximately 115-125° C., approximately 4.5% at approximately 125-180° C., and approximately 5.8% at approximately 130-200° C. DTA showed an endothermic event with an onset at approximately 159° C. (peak at approximately 171° C.) or approximately 166° C. (peak at approximately 173° C.) (FIG. 205 or FIG. 206).

TGA/DTA analysis of 1,5-naphthalene disulfonate Form 1 from ethyl acetate showed no thermal events (FIG. 212).

TGA of 1,5-naphthalene disulfonic acid Form 1 and Form 3 from ethyl acetate showed a continuous weight loss from ambient temperature to decomposition (FIG. 211). DTA (FIG. 211) showed an endothermic event with an onset at approximately 111° C.

TGA of 1,5-naphthalene disulfonic acid Form 2 and Form 5 from 2-propanol:water (90:10 v/v) showed a weight loss of 13.5% below 100° C. (FIG. 217). DTA (FIG. 217) showed an endothermic event with an onset at approximately 219° C. (peak at approximately 229° C.).

TGA of 1,5-naphthalene disulfonic acid Form 4 showed a weight loss of ca. 0.6% below 100° C. (FIG. 220). DTA (FIG. 220) showed an endothermic event with an onset at approximately 215° C. (peak at approximately 231° C.).

TGA of phosphate Form 1 from acetone showed a weight loss of ca. 2.9% at approximately 60-160° C. (FIG. 225). A weight loss of 1.7% was observed below ca. 158° C. after 3 days of drying under vacuum. DTA (FIG. 225) showed an endothermic event with an onset at approximately 157-158° C. (peak at approximately 165° C.).

TGA of phosphate Form 2 from ethyl acetate showed a weight loss of ca. 5.2% below 150° C. (FIG. 232). A weight loss of 4.6% was observed below ca. 158° C. after 3 days of drying under vacuum. DTA (FIG. 232) showed an endothermic event with an onset at approximately 128° C. (peak at approximately 134° C.).

TGA of besylate Form 1 from ethyl acetate showed a weight loss of approximately 0.4% at approximately 184° C. (FIG. 187). DTA (FIG. 187) showed an endothermic event with an onset at approximately 184° C. (peak at approximately 193° C.).

TGA of hydrochloride Form 2 from ethyl acetate showed a weight loss of approximately 9.3% at approximately 129° C. (FIG. 182). Additional weight losses of approximately 1% at approximately 60° C., 4.5% at 130° C., and 1.3% from about 130° C. to about 170° C. were observed while drying under vacuum. DTA (FIG. 182) showed an endothermic event with an onset at approximately 129° C. (peak at approximately 136° C.).

TGA of oxalate Form 1 showed a weight loss of approximately 20.8% between ambient temperature and approximately 230° C. (FIG. 192). DTA (FIG. 192) showed an endothermic event with an onset at approximately 157° C. (peak at approximately 165° C.).

TGA of oxalate Form 3 from 2-propanol:water (90:10 v/v) showed a weight loss of approximately 17% between ambient temperature and approximately 230° C. (FIG. 195). DTA (FIG. 195) showed several endothermic events with an onset at approximately 148° C. (peak at approximately 157° C.).

TGA of oxalate Form 5 showed a weight loss of approximately 12% at approximately 159° C. (FIG. 200). DTA (FIG. 200) showed several endothermic events with an onset at approximately 159° C.

TGA of maleate Form 1 from ethyl acetate showed a weight loss of approximately 5.5% at approximately 115-125° C., approximately 4.5% at 125-180° C., and approximately 5.8% at approximately 130-200° C. DTA showed an endothermic event with an onset at approximately 159° C. (peak at approximately 171° C.) or approximately 166° C. (peak at approximately 173° C.) (FIG. 205 or FIG. 206).

Example 4: Additional Preparation of the Polymorphs of the Application

Preparation of Form 1, Form 4 Form 8, Form 10, Form 11, edisylate Form 1, cyclamate Form 1, besylate Form 1, hydrobromide Form 2, and phosphate Form 1 were scaled up. Form 1, Form 4, Form 8, and Form 11 were observed to be anhydrous and non-hygroscopic, with area purities ≥98.8% observed. Form 10 was observed to be slightly hygroscopic, with area purities ≥95.9% observed. Edisylate Form 1 was observed to have area % impurities ≥97.9%. Cyclamate Form 1 was observed to have area % impurities ≥42.6%. Besylate Form 1 was observed to have area % impurities ≥97.5% when prepared on 400 mg scale. Besylate Form 1 was observed to have area % impurities ≥91.1% when prepared on 500 mg scale. Hydrobromide Form 1 was observed to have area % impurities ≥77.9%. Hydrobromide Form 2 was observed to have area % impurities ≥98.1%. Phosphate Form 1 was observed to have area % impurities ≥98.1%.

Form 1 Preparation and Assessment

To ca. 300 mg of amorphous Compound A, 10 mL of 2-propanol was added. The resulting slurry was temperature cycled between 40° C. and 5° C. in 2 hour cycles for ca. 72 hours. XRPD analysis was then carried out on a portion of the material which was isolated by centrifuge filtration using a 0.22 μm nylon filter. The bulk material was then isolated by centrifuge filtration and dried under vacuum at ca. 40° C. overnight, and then re-analyzed by XRPD.

Figure 20:
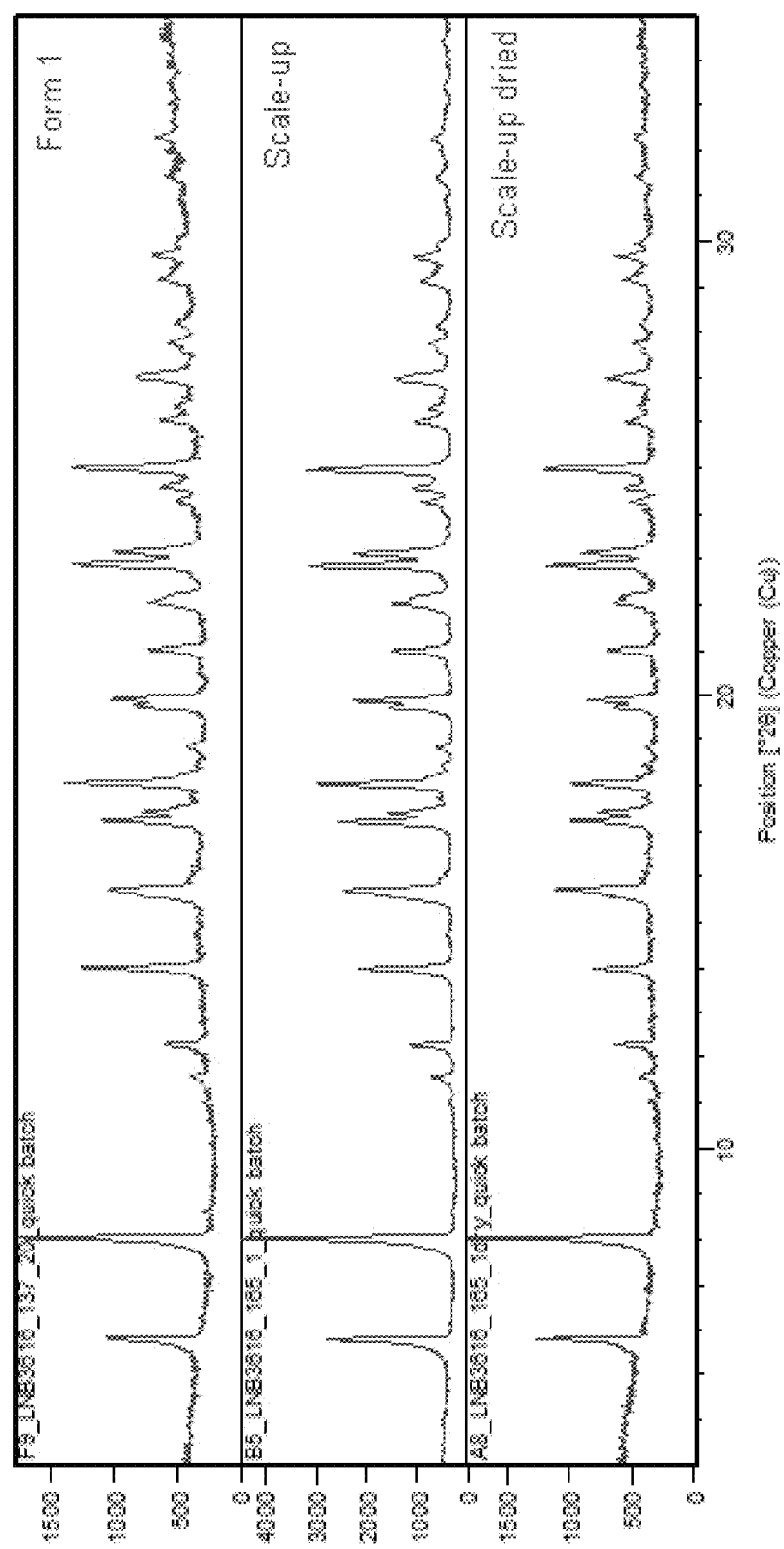
FIG. 20 sets forth XRPD patterns of Form 1 as a reference sample (top panel), and a 300 mg scale-up Form 1 sample before drying (middle panel) and after drying (bottom panel).
Figure 21B:
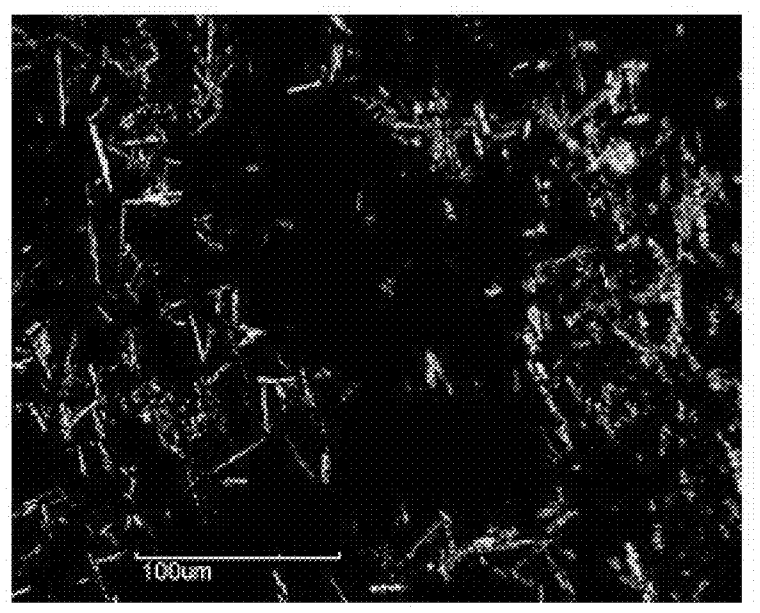
FIG. 21B sets forth a PLM image of Form 1 under polarized lenses.
Figure 21A:
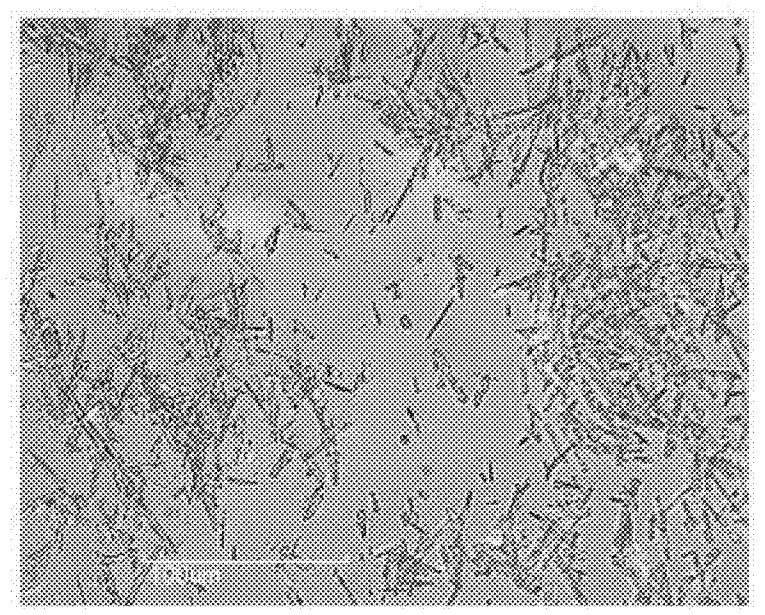
FIG. 21A sets forth a PLM image of Form 1 under non-polarized lenses.
Figure 22:
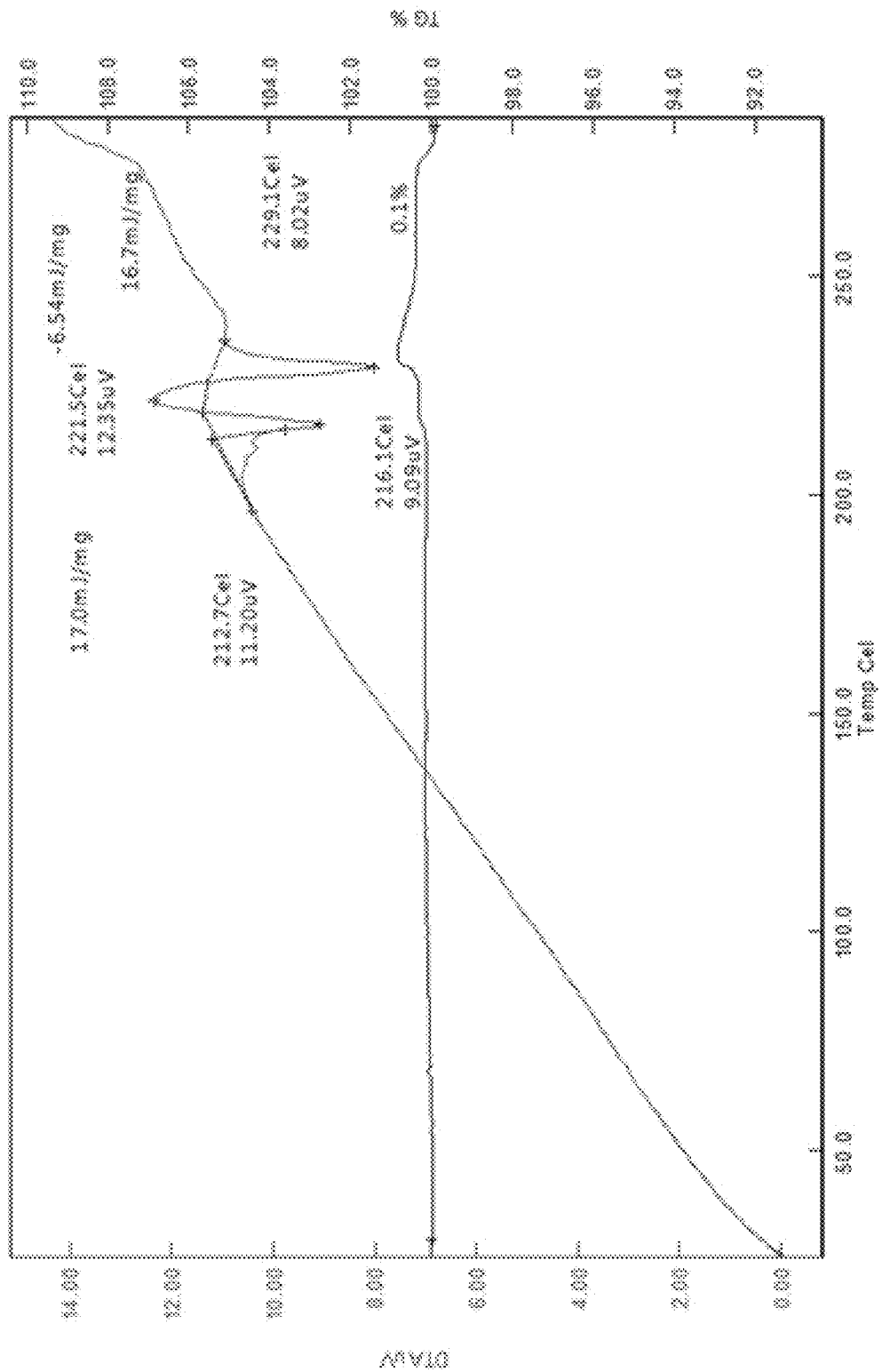
FIG. 22 sets forth a thermal analysis by TG/DTA of Form 1.
Figure 24:
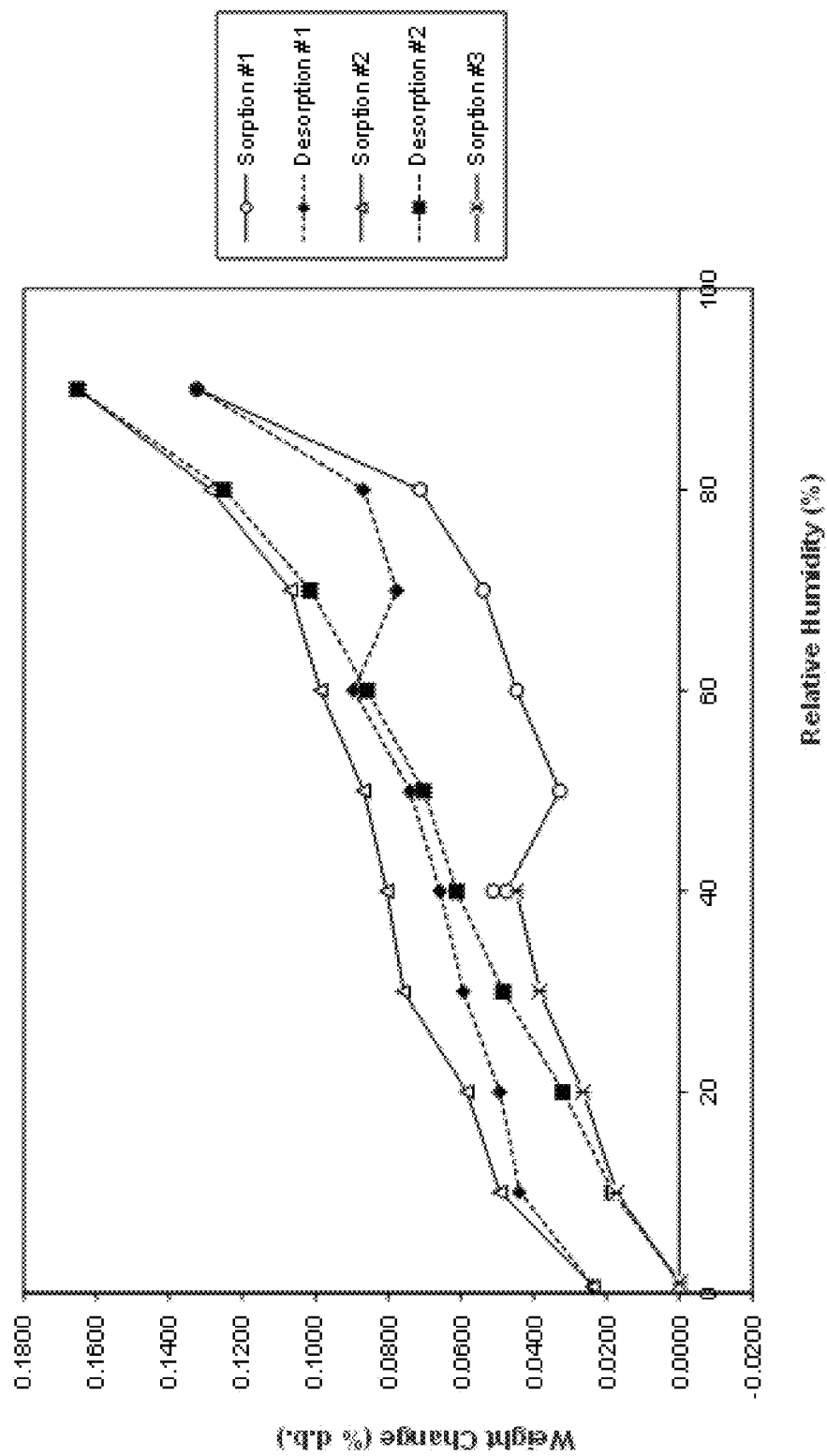
FIG. 24 sets forth a gravimetric vapor sorption (GVS) analysis of Form 1.
Figure 25:
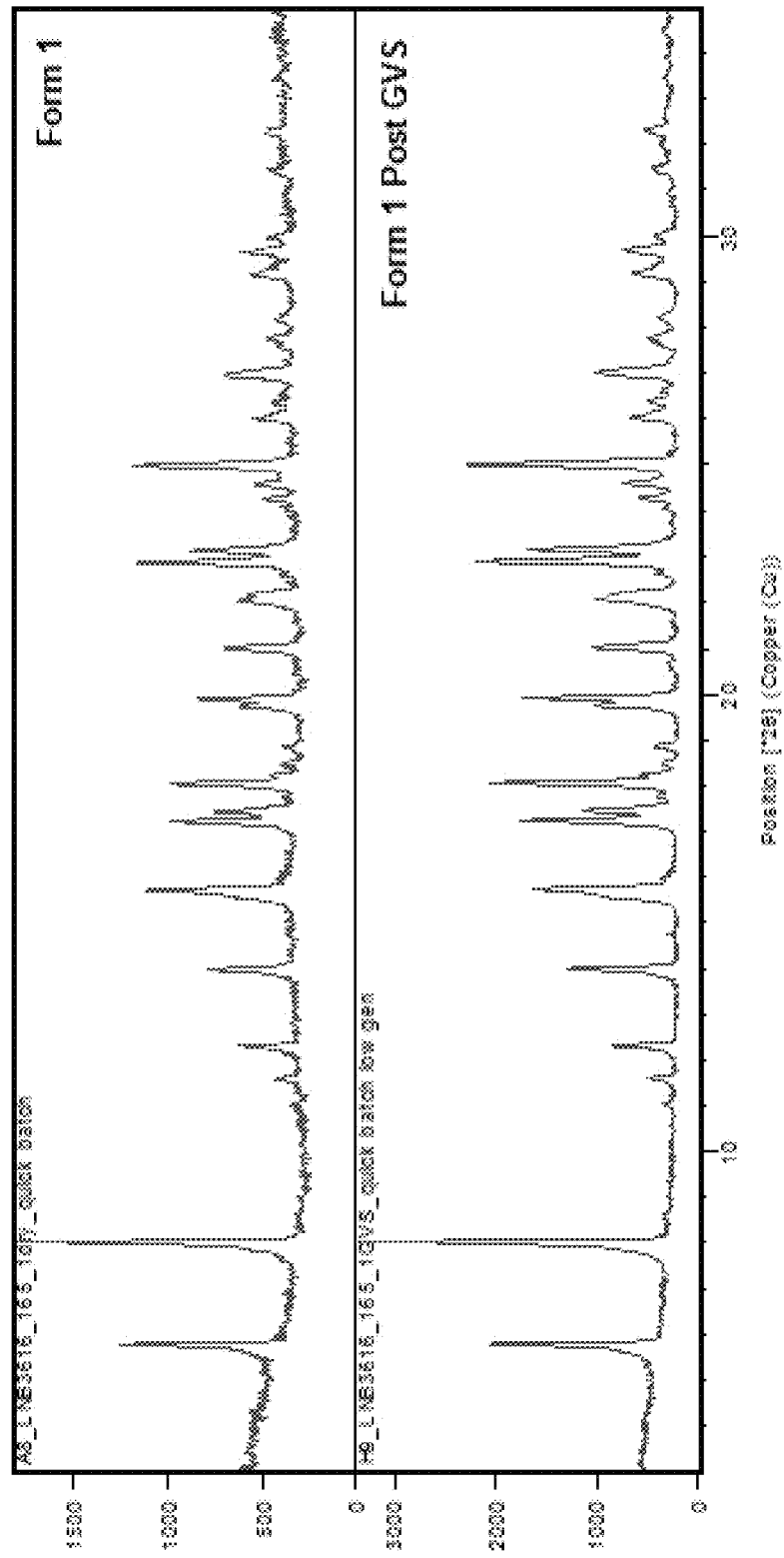
FIG. 25 sets forth XRPD patterns of Form 1 before (top panel) and after (bottom panel) GVS.
Figure 26:
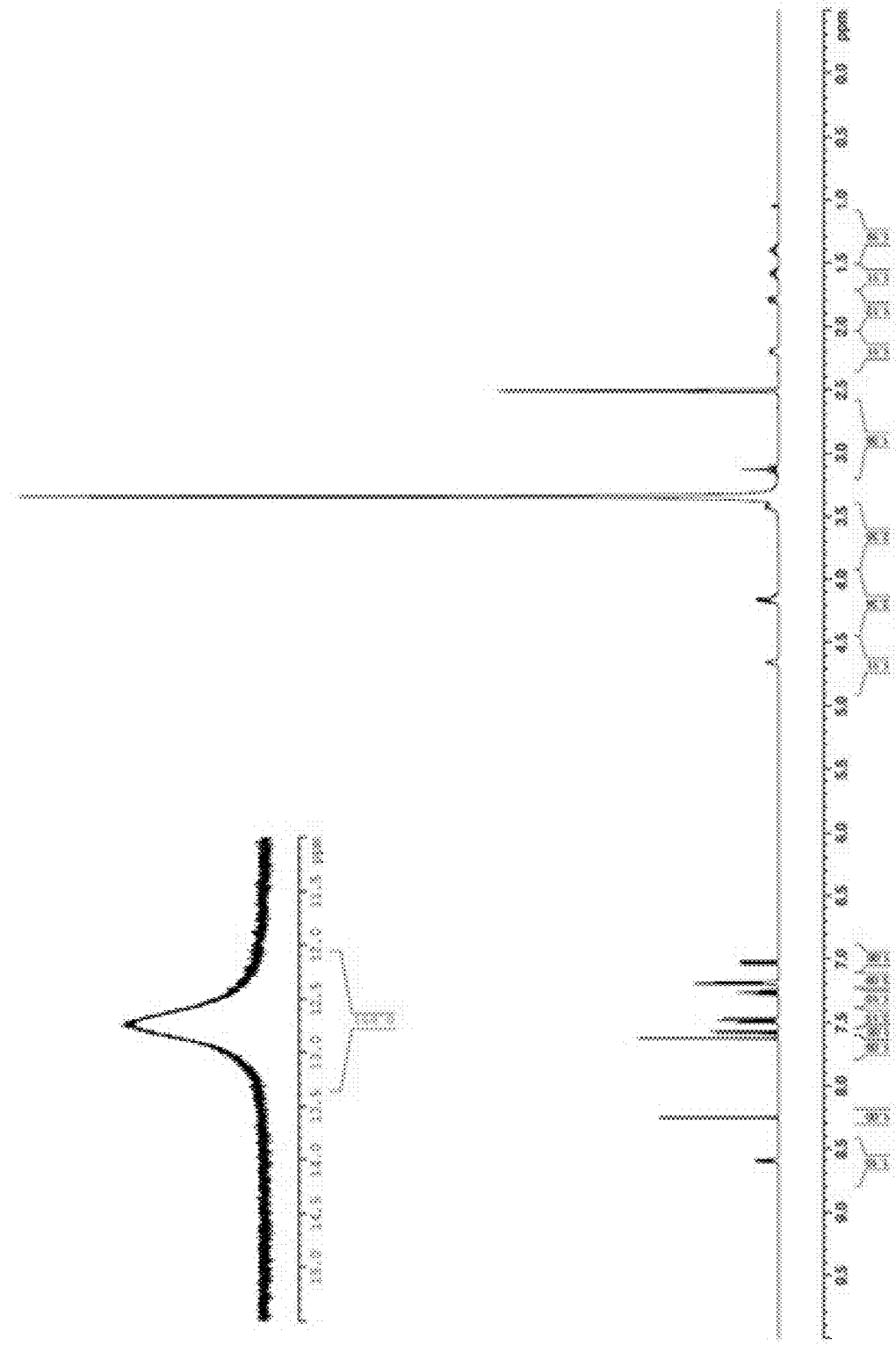
FIG. 26 sets forth a $^1$H NMR spectroscopic analysis of Form 1.
Figure 27:
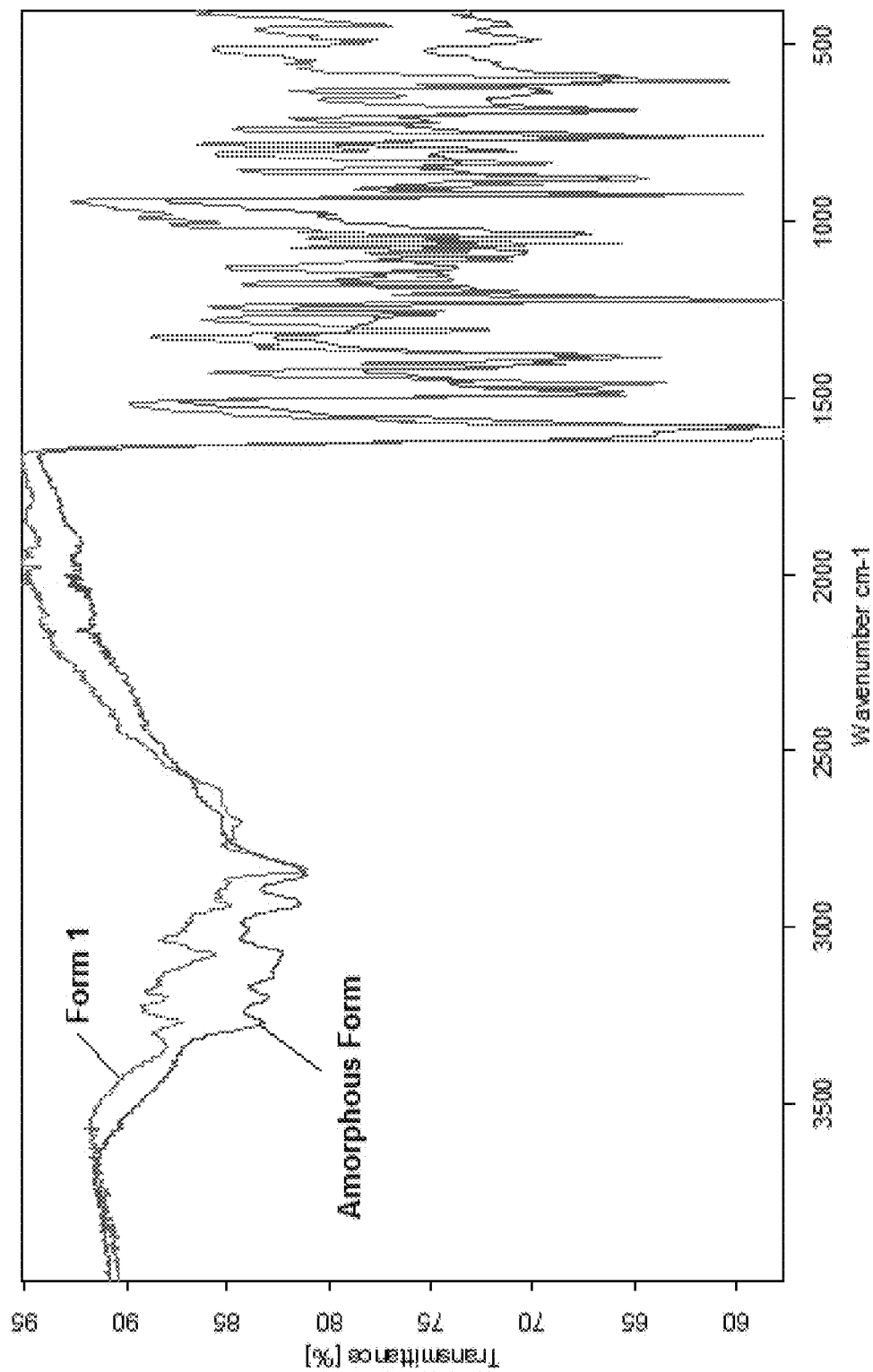
FIG. 27 sets forth comparative infrared (IR) spectra of an amorphous form of Compound A and Form 1.

The XRPD analysis of the isolated Form 1 material showed a diffractogram consistent with Form 1 both before and after drying (FIG. 20). PLM analysis showed birefringent, needle-like particles (FIG. 21A and FIG. 21B). TGA of Form 1 showed a weight loss of 0.1% between ca. 25° C. and 300° C. (FIG. 22). DTA (FIG. 22) showed 2 endotherms and an exotherm between ca. 210° C. and 230° C. The TG/DTA was largely consistent with the primary screen, but showed less weight loss. DSC analysis (FIG. 23) of Form 1 showed 3 endotherms with onsets ca. 208° C. (peak ca. 210° C.), 215° C. (peak ca. 217° C.), and 227° C. (peak ca. 228° C.), and an exotherm with onset ca. 217° C. (peak ca. 219° C.). GVS analysis showed Form 1 to be non-hygroscopic with <0.2% uptake at 90% RH (FIG. 24). Post-GVS analysis showed the material to remain Form 1 after exposure to elevated humidity conditions (FIG. 25). The $^1$H-NMR spectrum of Form 1 was found to be consistent with the chemical structure of Compound A and no 2-propanol traces were observed (FIG. 26). The HPLC area % purity was measured to be 99.3%. IR analysis showed Form 1 to correspond with Compound A material (FIG. 27). The data overall confirmed Form 1 to be an anhydrous, non-hygroscopic solid form.

Form 4 Preparation and Assessment

To ca. 300 mg of amorphous Compound A, 10 mL of diisopropyl ether was added. The slurry was temperature cycled between 40° C. and 5° C. in 2 hour cycles for ca. 72 hours. XRPD analysis was then carried out on a portion of the material which was isolated by centrifuge filtration using a 0.22 μm nylon filter. The bulk material was then isolated by centrifuge filtration and dried under vacuum at ca. 40° C. overnight, then re-analyzed by XRPD.

Figure 30:
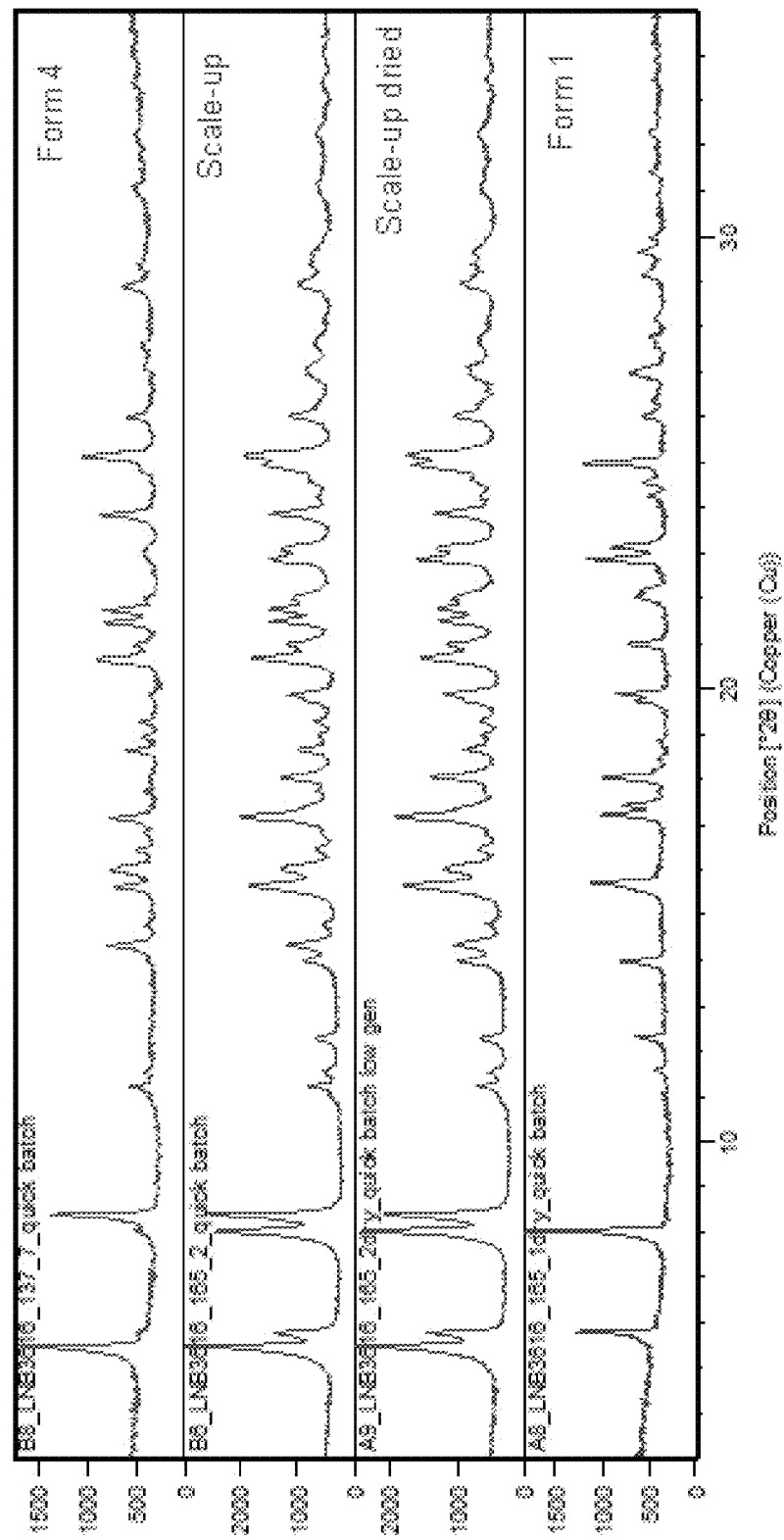
FIG. 30 sets forth XRPD patterns of Form 4 (top panel) and Form 1 (bottom panel) as reference samples, and a 300 mg scale-up Form 4 sample before drying (second row from top) and after drying (third row from top).
Figure 31B:
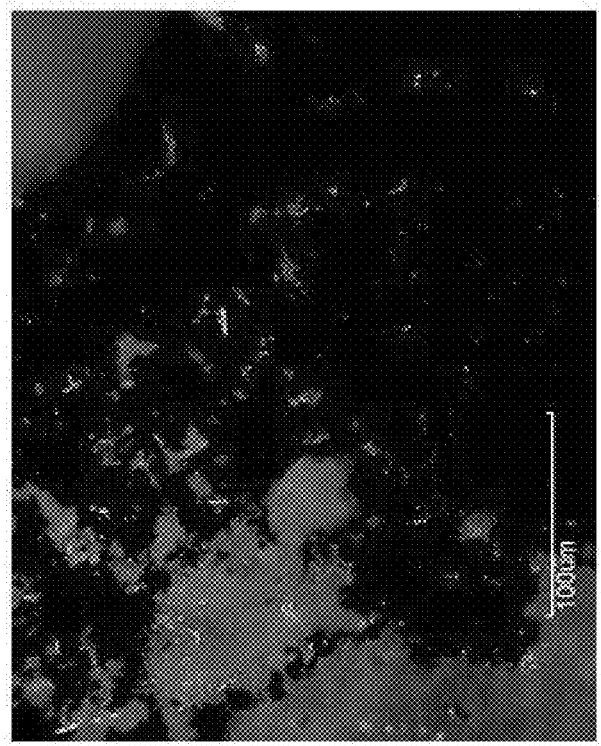
FIG. 31B sets forth a PLM image of Form 4 under polarized lenses.
Figure 31A:
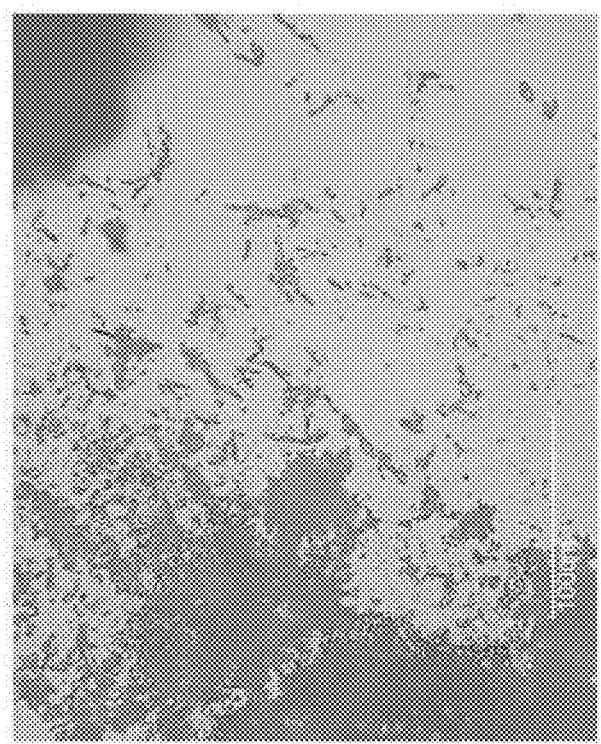
FIG. 31A sets forth a PLM image of Form 4 under non-polarized lenses.
Figure 32:
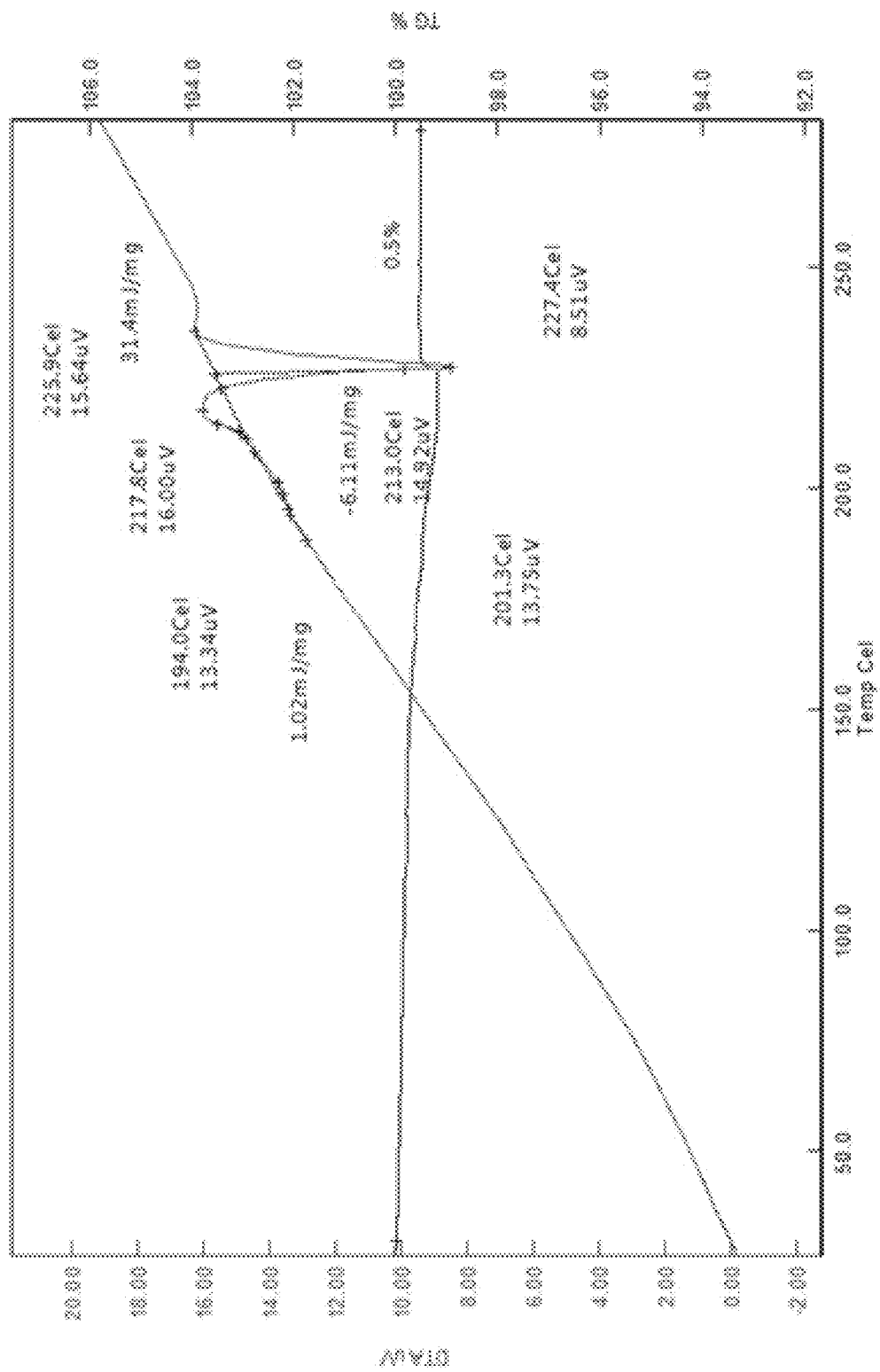
FIG. 32 sets forth a thermal analysis by TG/DTA of Form 4.
Figure 34:
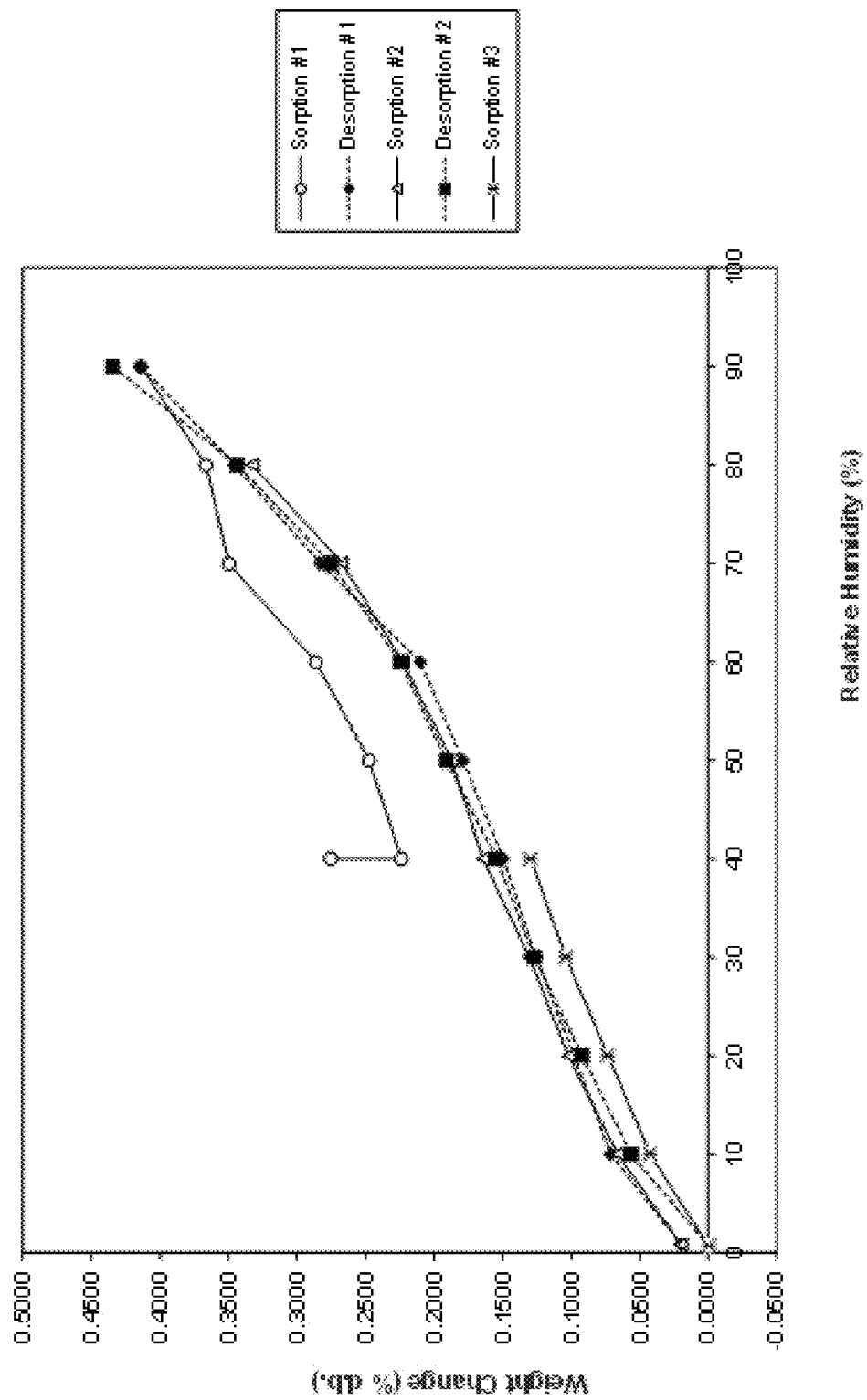
FIG. 34 sets forth a GVS analysis of Form 4.
Figure 35:
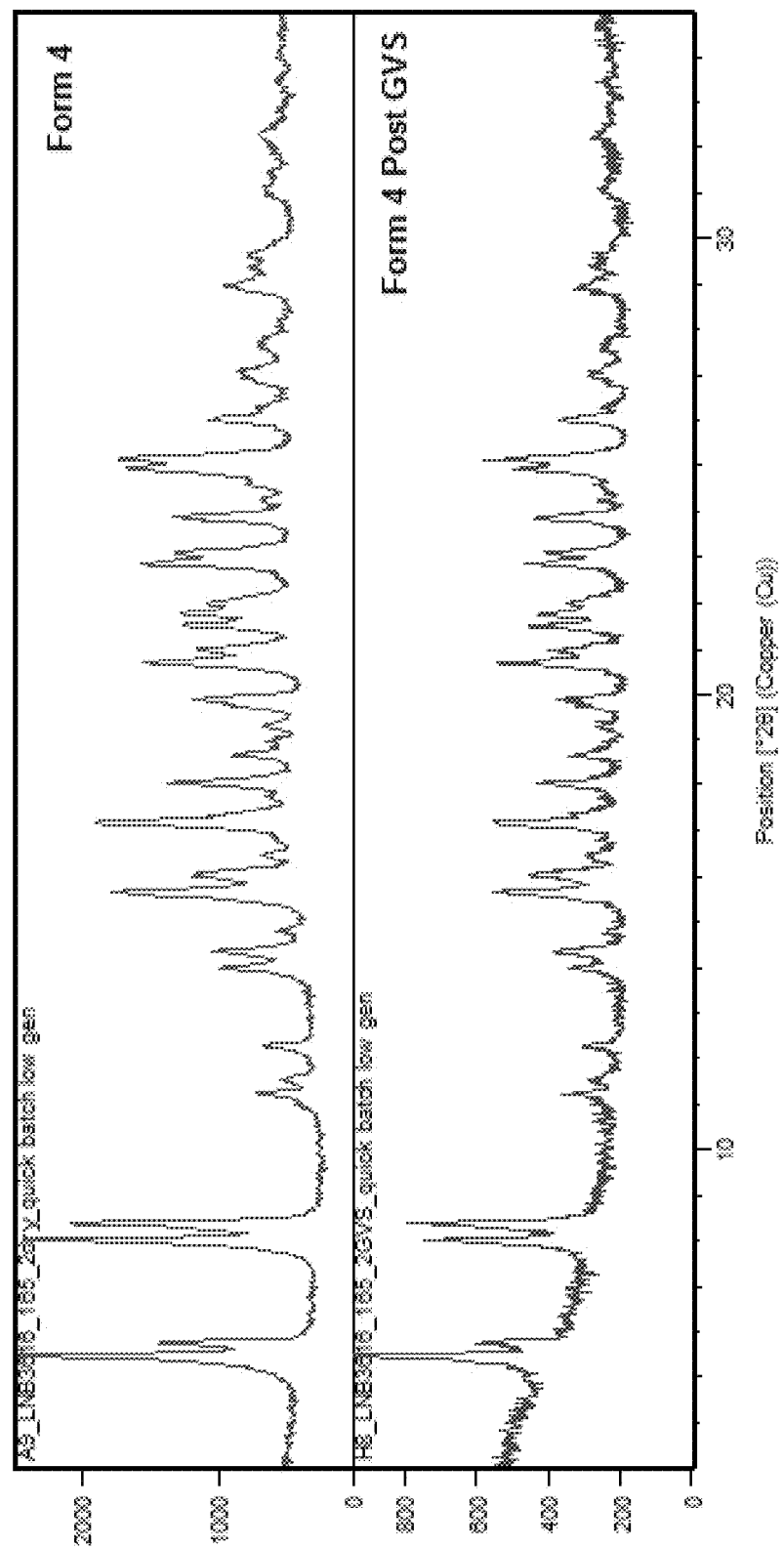
FIG. 35 sets forth XRPD patterns of Form 4 before (top panel) and after (bottom panel) GVS.
Figure 36:
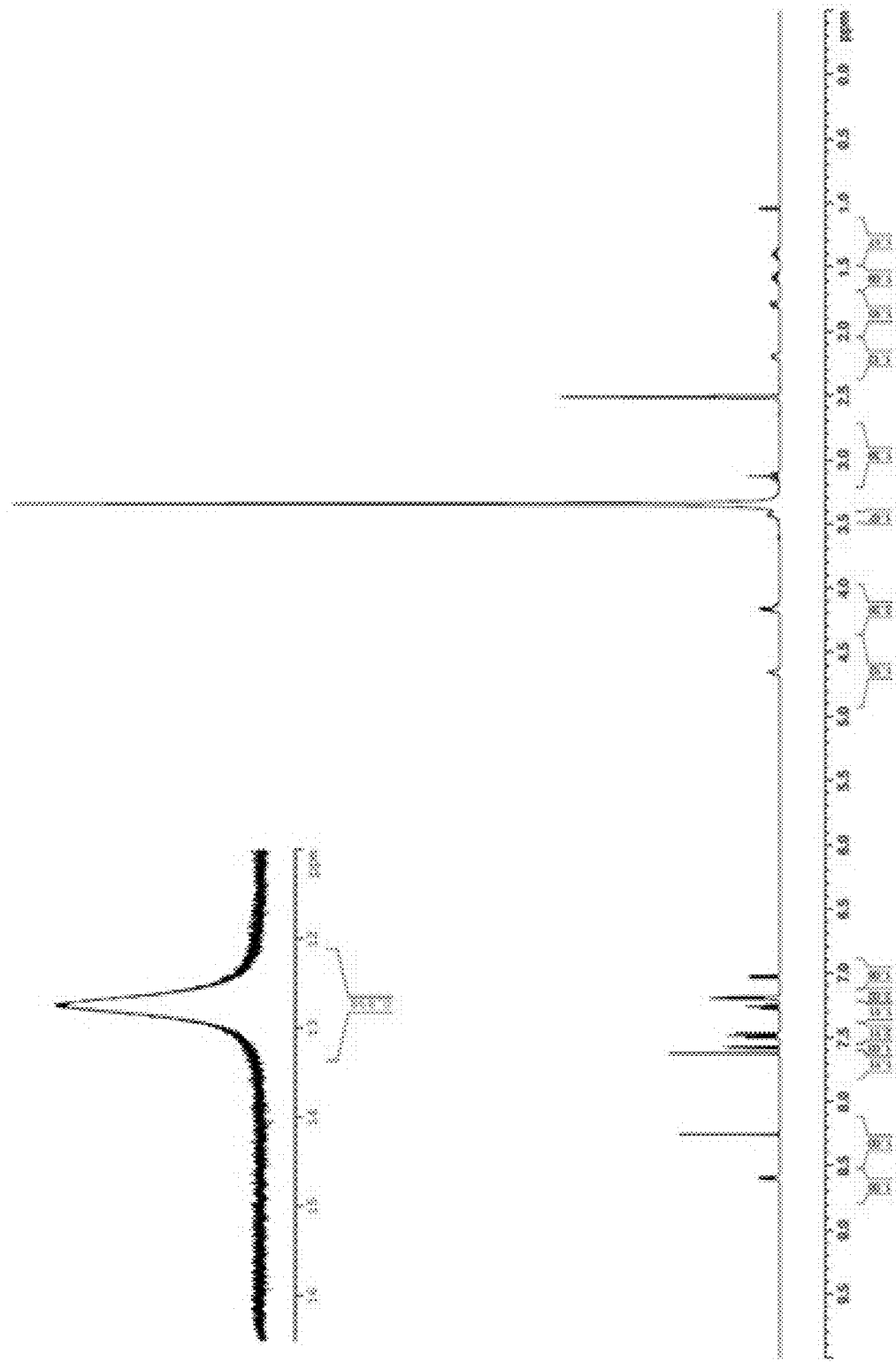
FIG. 36 sets forth a $^1$H NMR spectroscopic analysis of Form 4.
Figure 37:
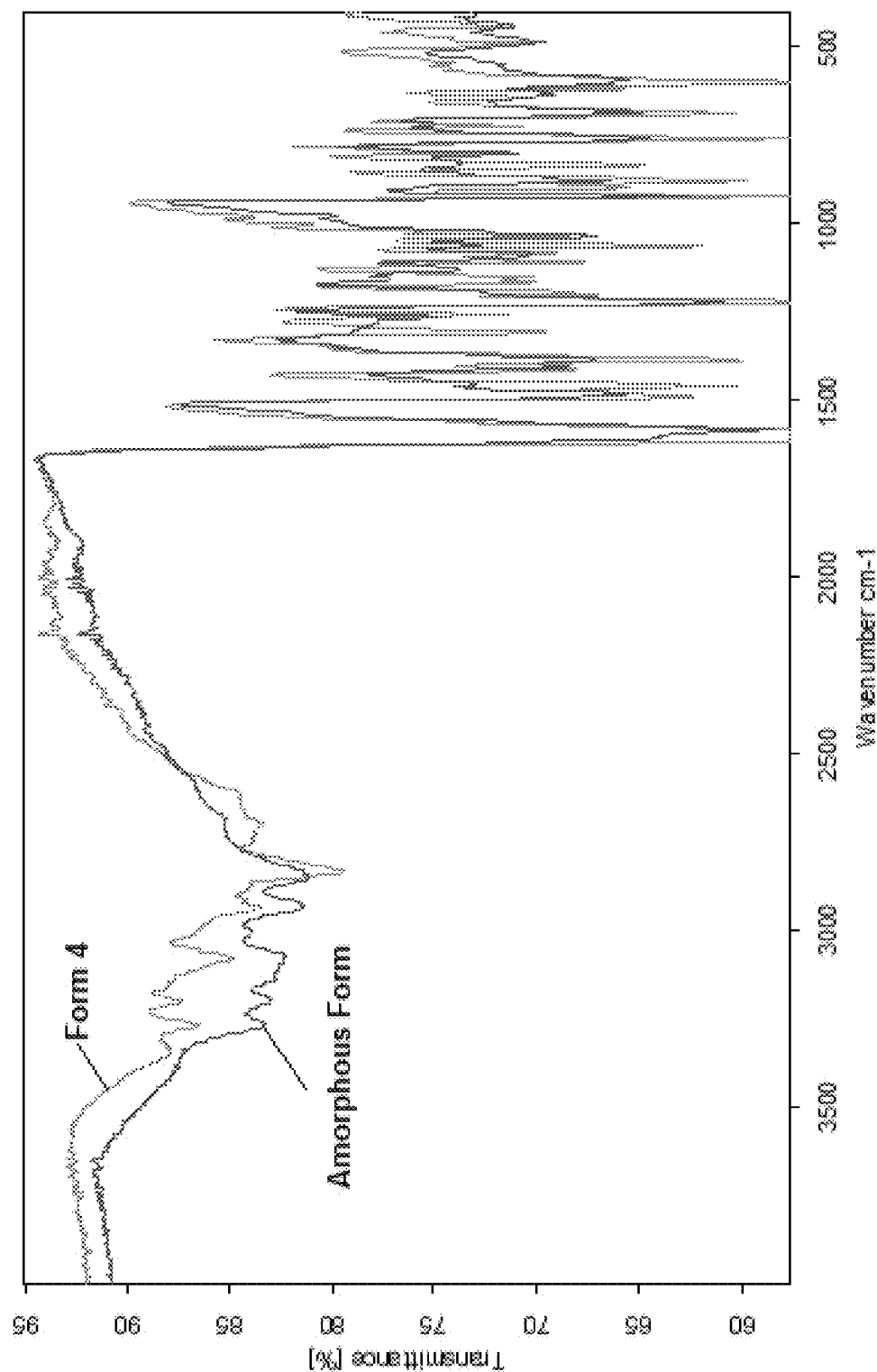
FIG. 37 sets forth comparative IR spectra of an amorphous form of Compound A and Form 4.
Figure 38:
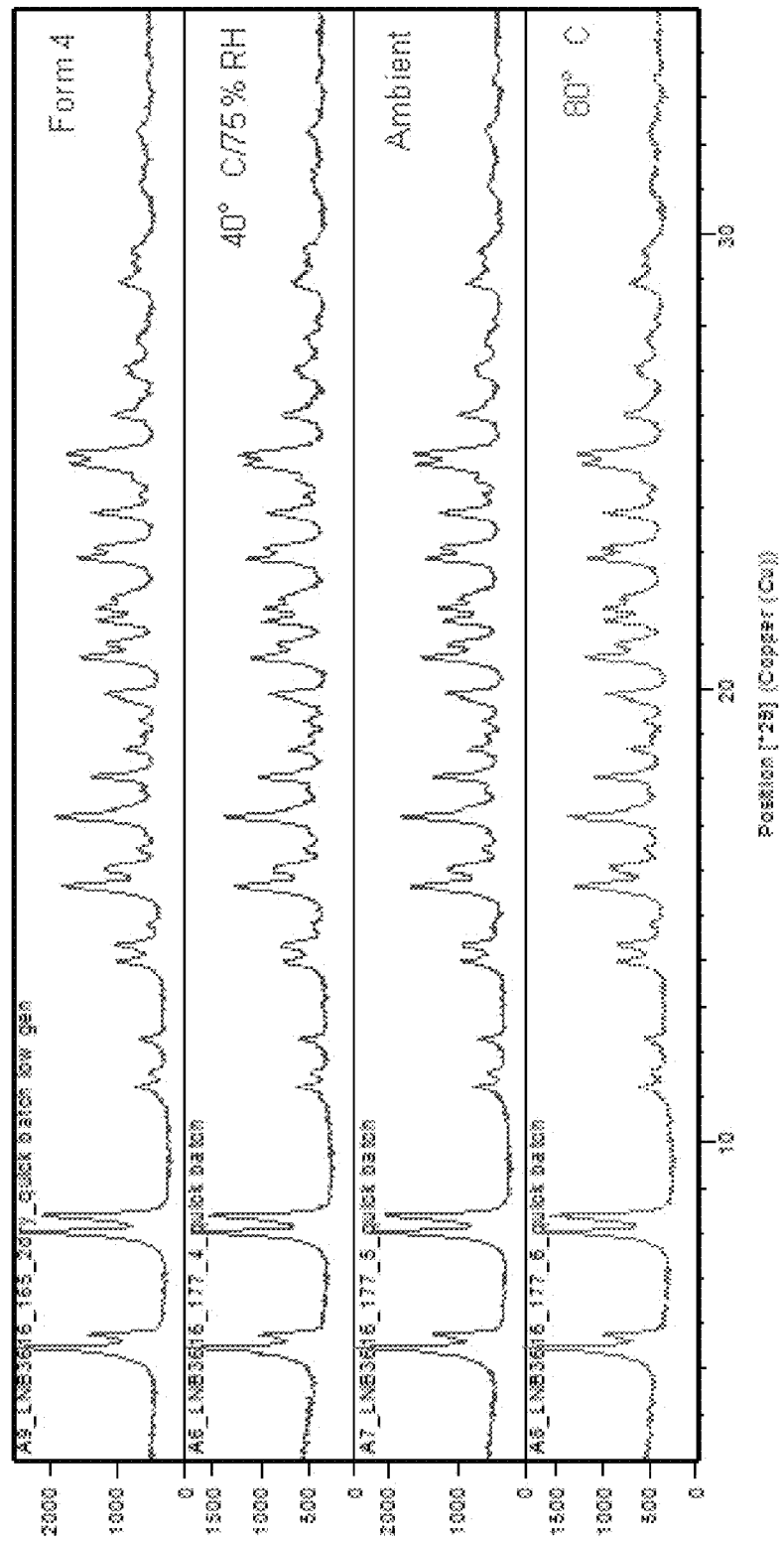
FIG. 38 sets forth XRPD patterns of Form 4 before (top panel) and after storage at: i) 40° C./75% relative humidity (RH) (second row from top), ii) ambient (approximately 25° C.) (third row from top), and iii) 80° C. (bottom panel).

The XRPD analysis of the isolated Form 4 material showed a diffractogram predominantly consistent with Form 4, both before and after drying (FIG. 30). Minimal traces of Form 1 also appeared to be present. PLM analysis showed birefringent, needle-like particles for Form 4 (FIG. 31A and FIG. 31B). TGA of Form 4 showed a weight loss of 0.5% between ca. 25° C. and 300° C. (FIG. 32). DTA (FIG. 32) showed a very small endotherm with onset ca. 194° C. (peak ca. 201° C.), an exotherm with onset ca. 213° C. (peak ca. 218° C.), and an endotherm with onset ca. 226° C. (peak ca. 227° C.). The TG/DTA was fairly consistent with the primary screen with less weight loss. DSC analysis (FIG. 33) of Form 4 showed a small endotherm with onset ca. 197° C. (peak ca. 203° C.), an exotherm with onset ca. 215° C. (peak ca. 217° C.), and an endotherm with onset ca. 226° C. (peak ca. 229° C.). GVS analysis showed Form 4 to be non-hygroscopic with a 0.4% uptake at 90% RH (FIG. 34). Post-GVS analysis showed the material to remain Form 4 after exposure to elevated humidity conditions (FIG. 35). The $^1$H-NMR spectrum of Form 4 was found to be consistent with the chemical structure of Compound A and no traces of solvent were observed to be present (FIG. 36). The HPLC area % purity was measured to be 98.8%. IR analysis showed Form 4 to correspond with Compound A material (FIG. 37). The data overall confirmed Form 4 to be an anhydrous, non-hygroscopic solid form.

Form 8 Preparation and Assessment

To ca. 300 mg of amorphous Compound A, 10 mL of ethanol was added along with a small amount of Form 8 seed. The slurry was temperature cycled between 40° C. and 5° C. in 2 hour cycles for ca. 72 hours. XRPD analysis was carried out on a portion of the material removed with a glass pipette/spatula and showed the material to be Form 1. The solvent from this attempted preparation of Form 8 was evaporated under vacuum at ca. 40° C. overnight. To this material 0.5 mL of THF was then added and the slurry was temperature cycled between 40° C. and 5° C. overnight to prepare Form 5, for later desolvation to Form 8. The Form 5 material obtained from THF temperature cycling was dried under vacuum for ca. 1 hour at 130° C. XRPD analysis showed the material to correspond predominantly with Form 8. The TG/DTA was not consistent with Form 8, therefore the material was re-slurried and temperature cycled in 0.4 mL of THF. After ca. 2 hours, a further 0.1 mL of THF was added as the sample was not stirring. After ca. 3 hours further stirring, the sample was found to be Form 5. The obtained Form 5 was dried under vacuum at ca. 150° C. for 30 minutes. The dried material was found to be Form 8 by XRPD and TG/DTA.

Figure 40:
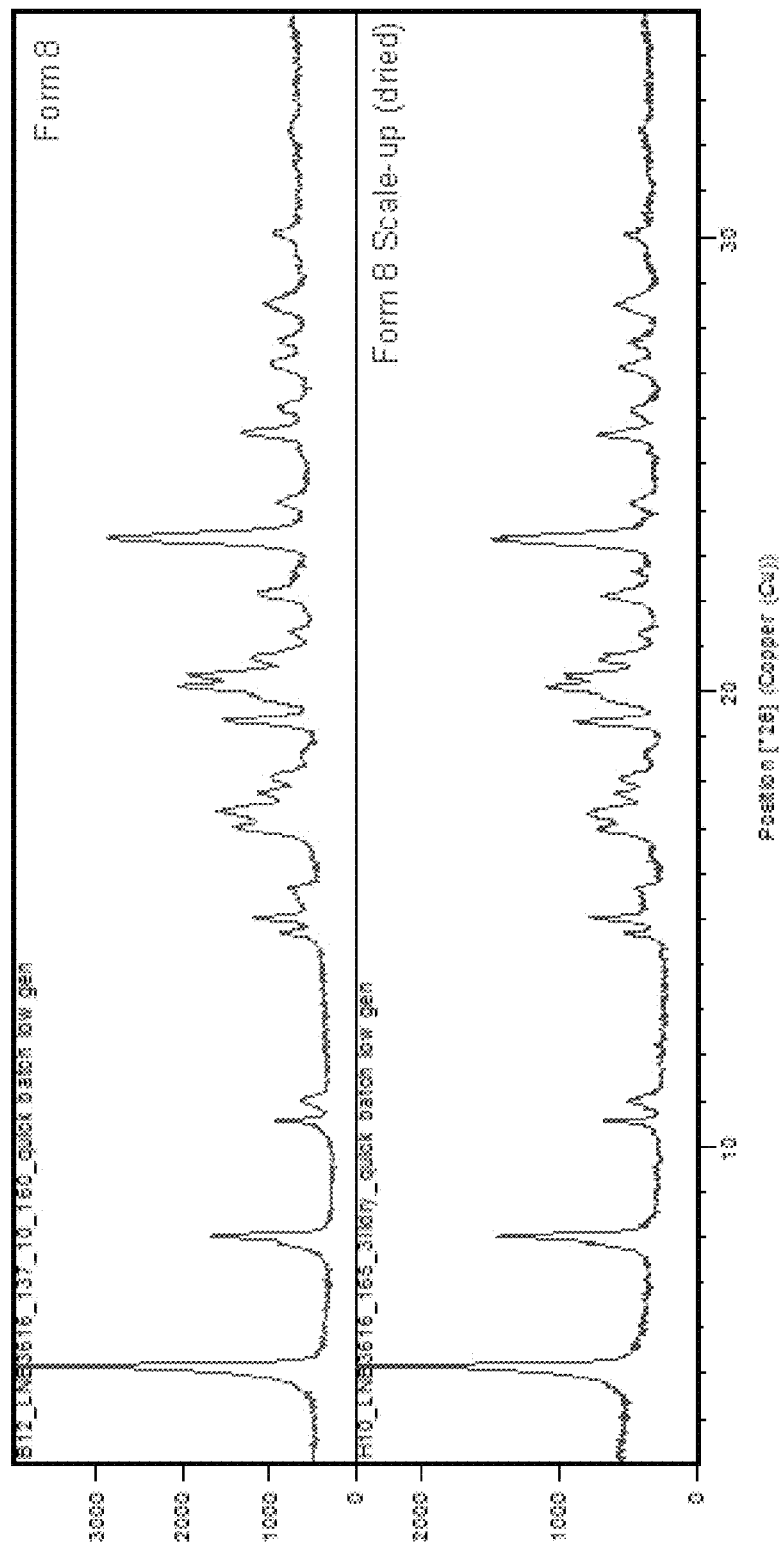
FIG. 40 sets forth XRPD patterns of Form 8 as a reference sample (top panel) and a 300 mg scale-up Form 8 sample after drying at ca. 150° C. (bottom panel).
Figure 41B:
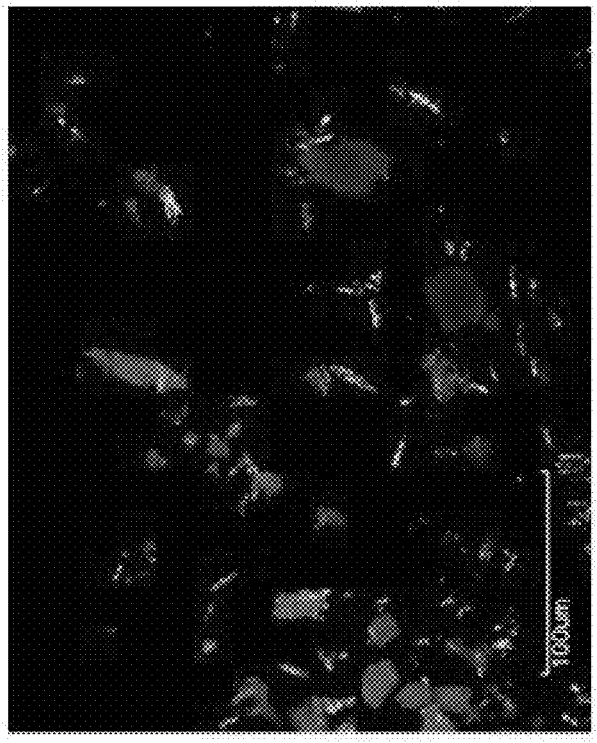
FIG. 41B sets forth a PLM image of Form 8 under polarized lenses.
Figure 41A:
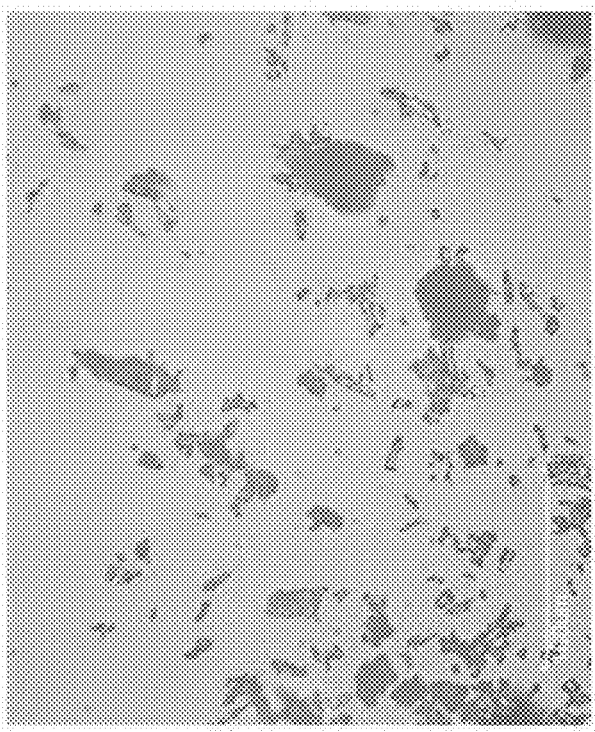
FIG. 41A sets forth a PLM image of Form 8 under non-polarized lenses.
Figure 42:
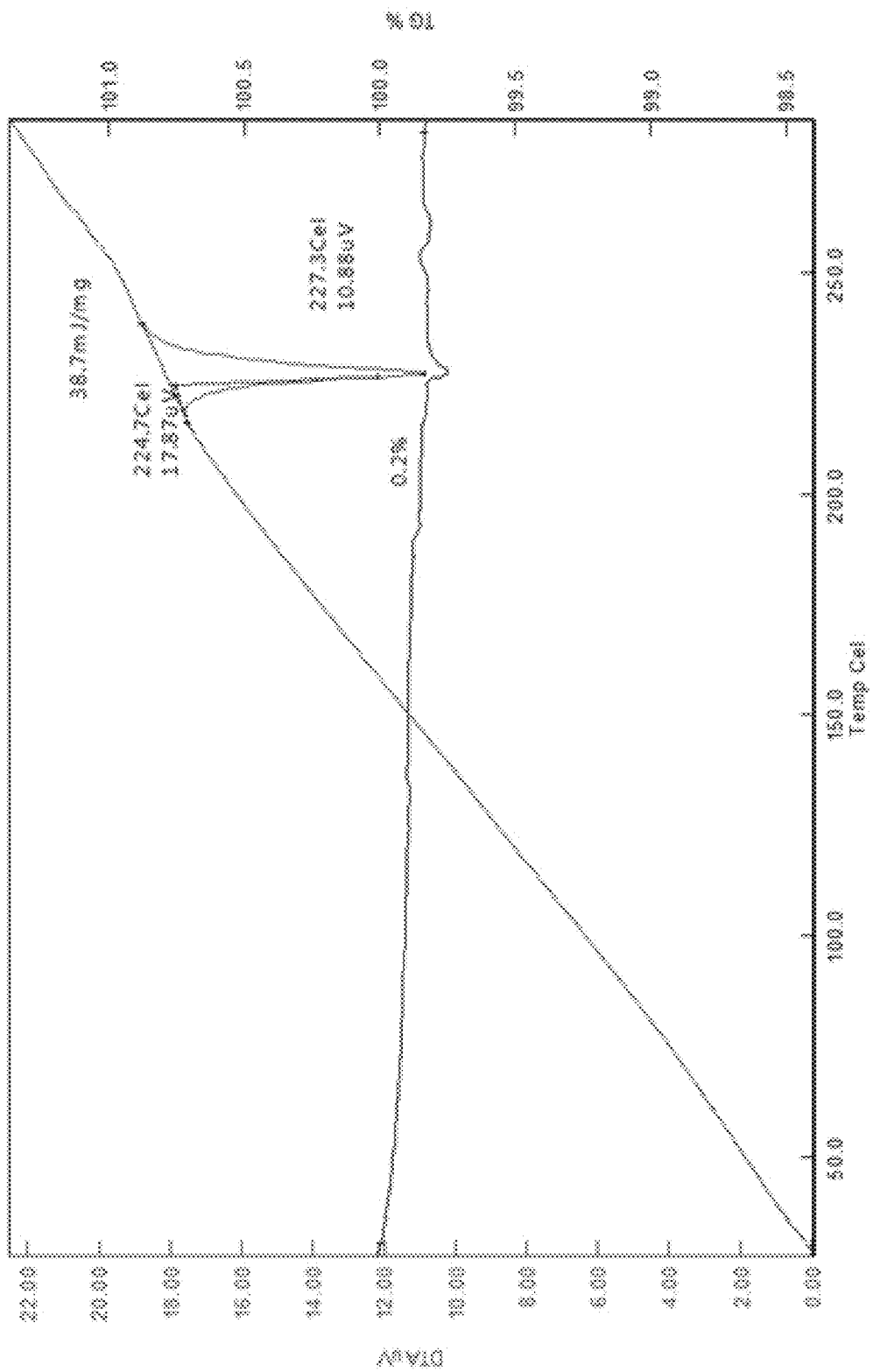
FIG. 42 sets forth a thermal analysis by TG/DTA of Form 8.
Figure 44:
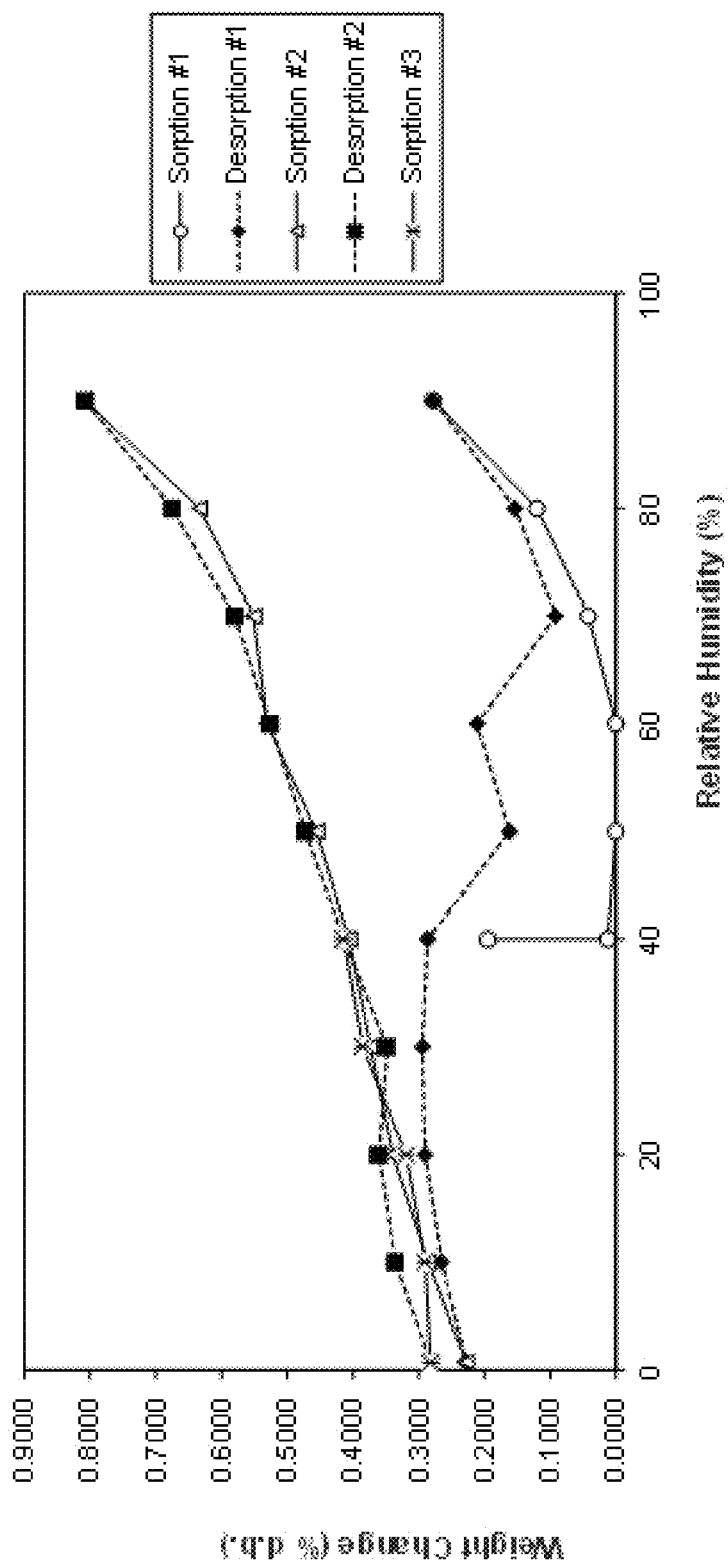
FIG. 44 sets forth a GVS analysis of Form 8.
Figure 45:
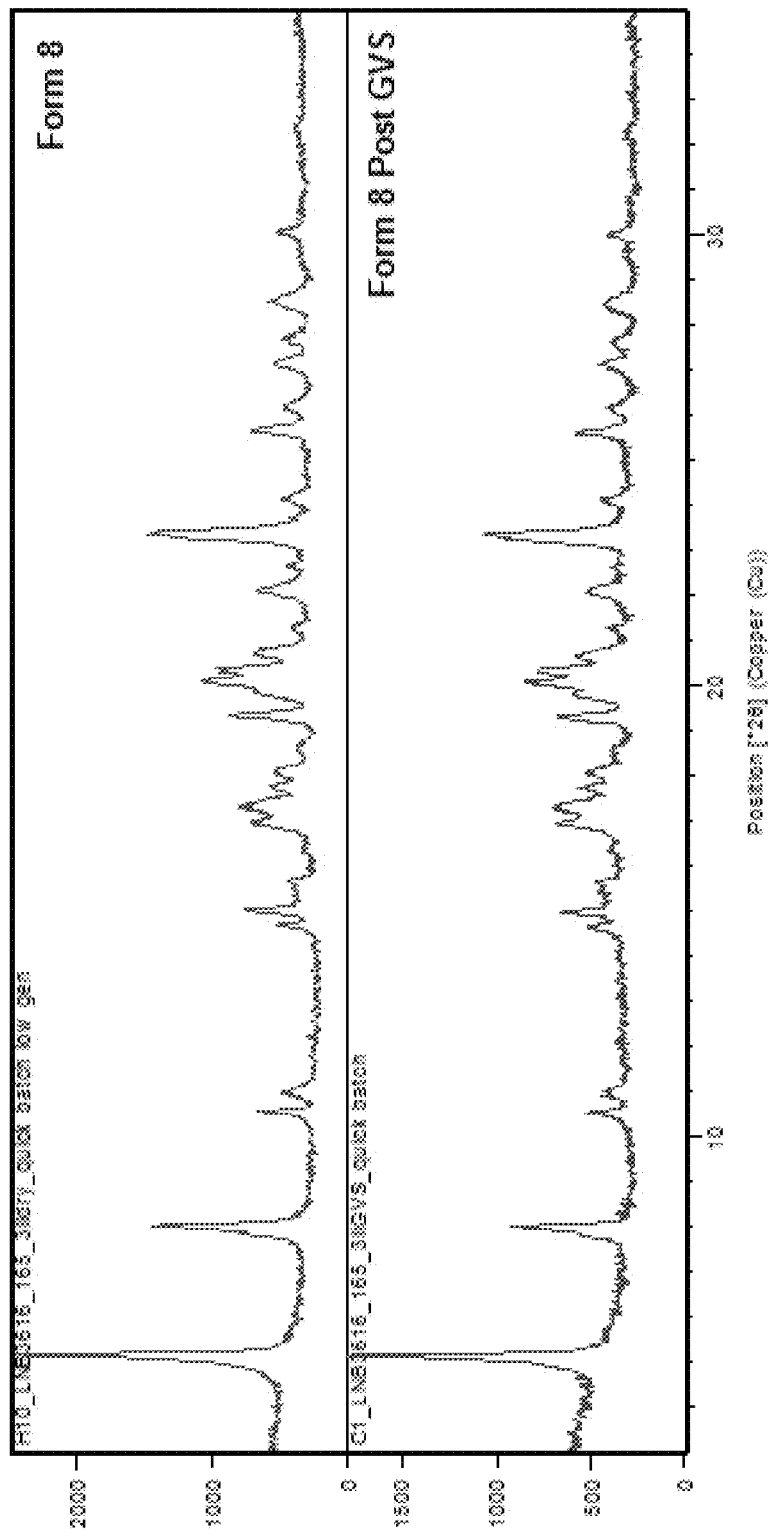
FIG. 45 sets forth XRPD patterns of Form 8 before (top panel) and after (bottom panel) GVS.
Figure 46:
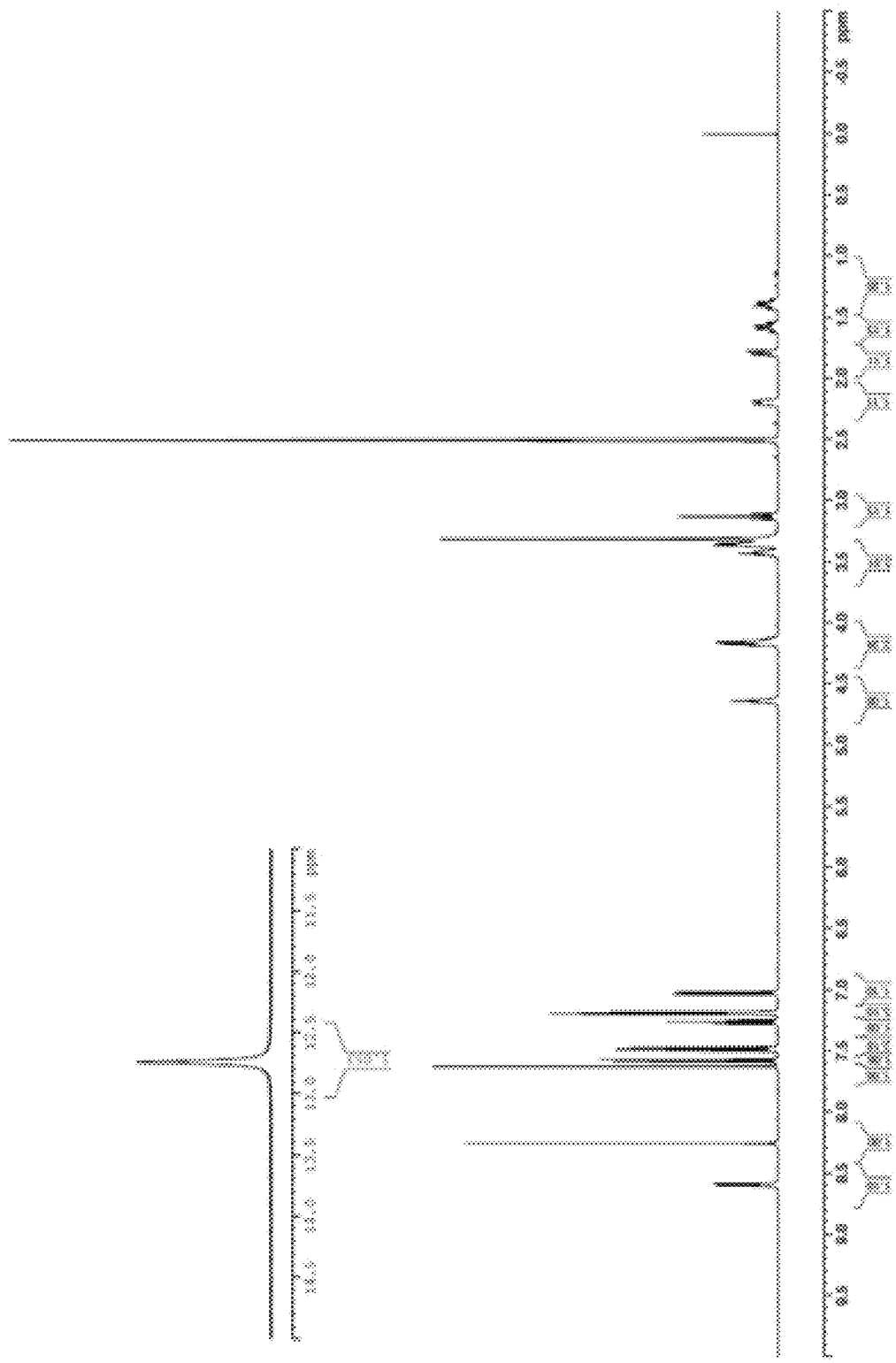
FIG. 46 sets forth a $^1$H NMR spectroscopic analysis of Form 8.
Figure 47:
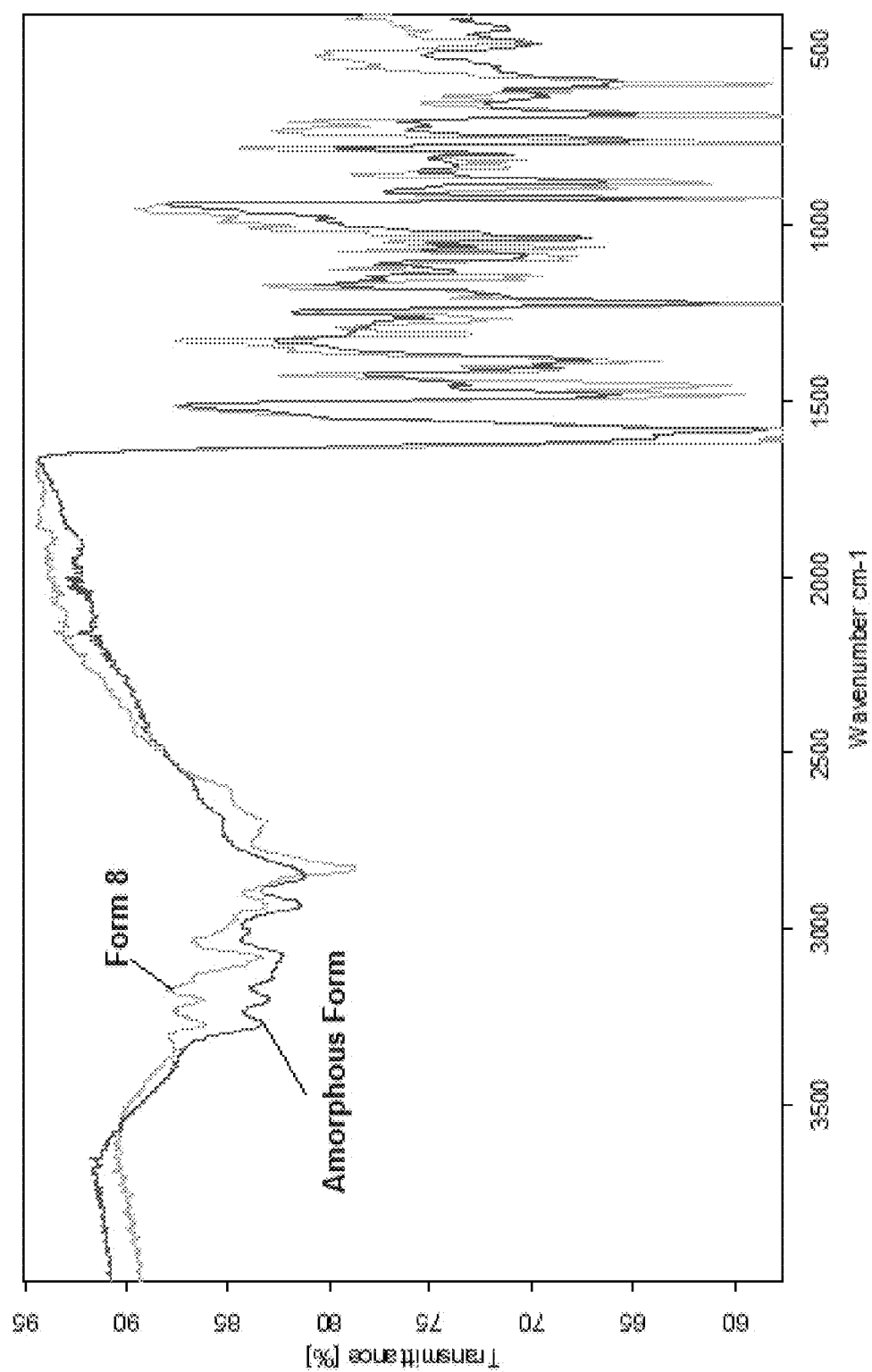
FIG. 47 sets forth comparative IR spectra of an amorphous form of Compound A and Form 8.
Figure 48:
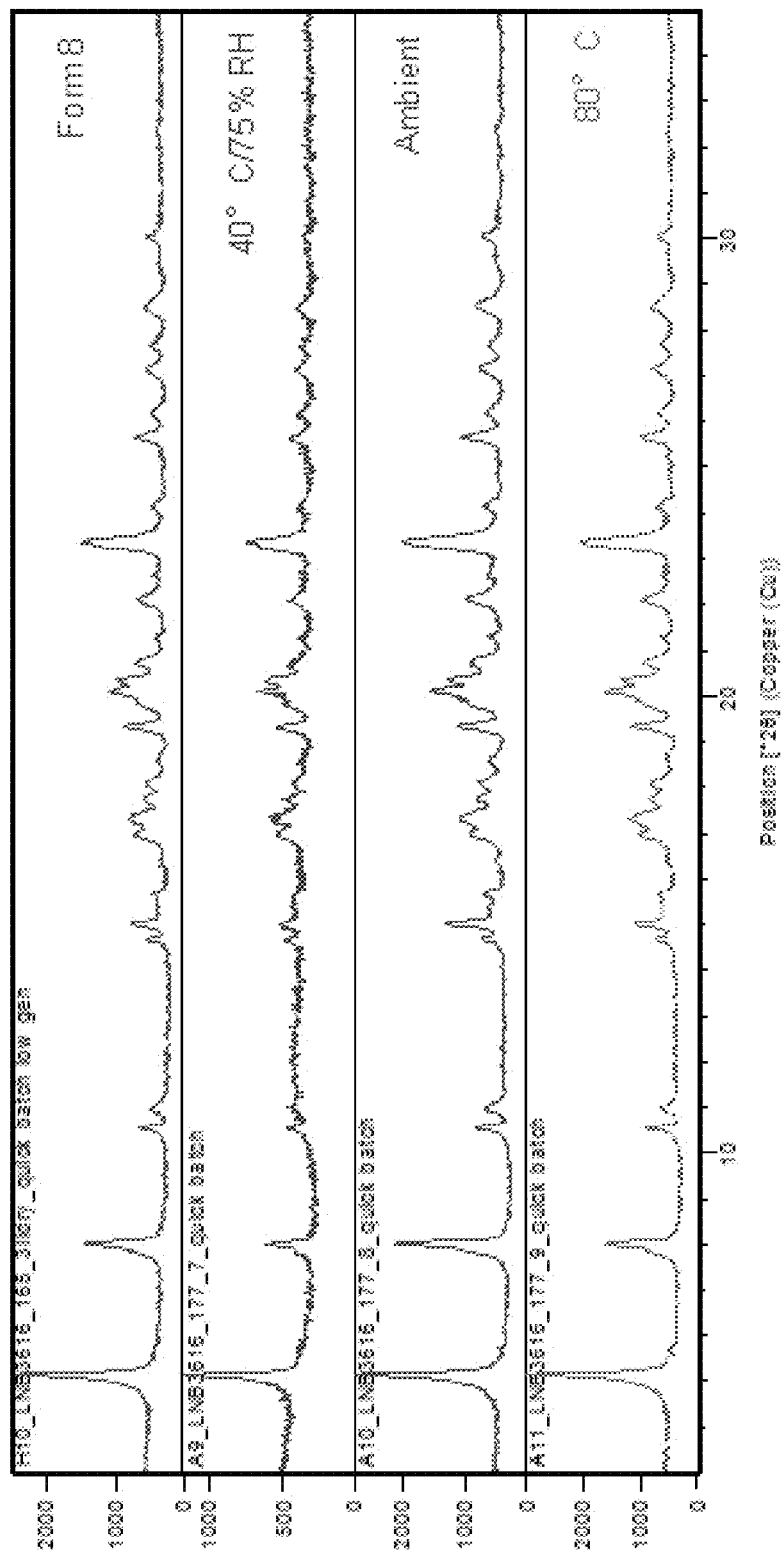
FIG. 48 sets forth XRPD patterns of Form 8 before (top panel) and after storage at: i) 40° C./75% relative humidity (RH) (second row from top), ii) ambient (approximately 25° C.) (third row from top), and iii) 80° C. (bottom panel).

The XRPD analysis of the Form 5 material from THF dried at ca. 150° C. under vacuum, showed a diffractogram consistent with Form 8 (FIG. 40). PLM analysis showed birefringent, needle-like particles for Form 8 (FIG. 41A and FIG. 41B). TGA of Form 8 showed a weight loss of 0.2% between ca. 25° C. and 300° C. (FIG. 42). DTA (FIG. 42) showed an endotherm with onset ca. 225° C. and peak ca. 227° C. This is consistent with the primary screen. DSC analysis (FIG. 43) of Form 8 showed an endotherm with onset ca. 225° C. and peak ca. 229° C. GVS analysis (FIG. 44) showed Form 8 to be non-hygroscopic with a <0.3% uptake at 90% RH for the first cycle and 0.8% uptake at 90% RH for the second cycle. Initially a mass loss was observed, with sorption at 90% RH only slightly greater than the initial mass. Only 2.4 mg of sample was analyzed due to limited materials amounts (compared with >10 mg for Form 1 and Form 4). Post-GVS analysis showed the material to remain Form 8 after exposure to elevated humidity conditions (FIG. 45). The $^1$H-NMR spectrum of Form 8 was found to be consistent with the chemical structure of Compound A (FIG. 46). The HPLC area % purity was measured to be 99.0%. IR analysis showed Form 8 to correspond with Compound A material (FIG. 47).

Form 10 Preparation and Assessment

To ca. 200 mg of Compound A, 5 mL of acetonitrile:water (95:5 v:v) was added. The slurry was temperature cycled between 40° C. and 20° C. in 4 hour cycles for ca. 72 hours. XRPD analysis was carried out on a portion of the material removed by centrifuge filtration using a 0.22 μm nylon filter. The solvent was evaporated at ambient temperature. The dried material was analyzed by XRPD, TG/DSC, HPLC, and $^1$H NMR.

Figure 69:
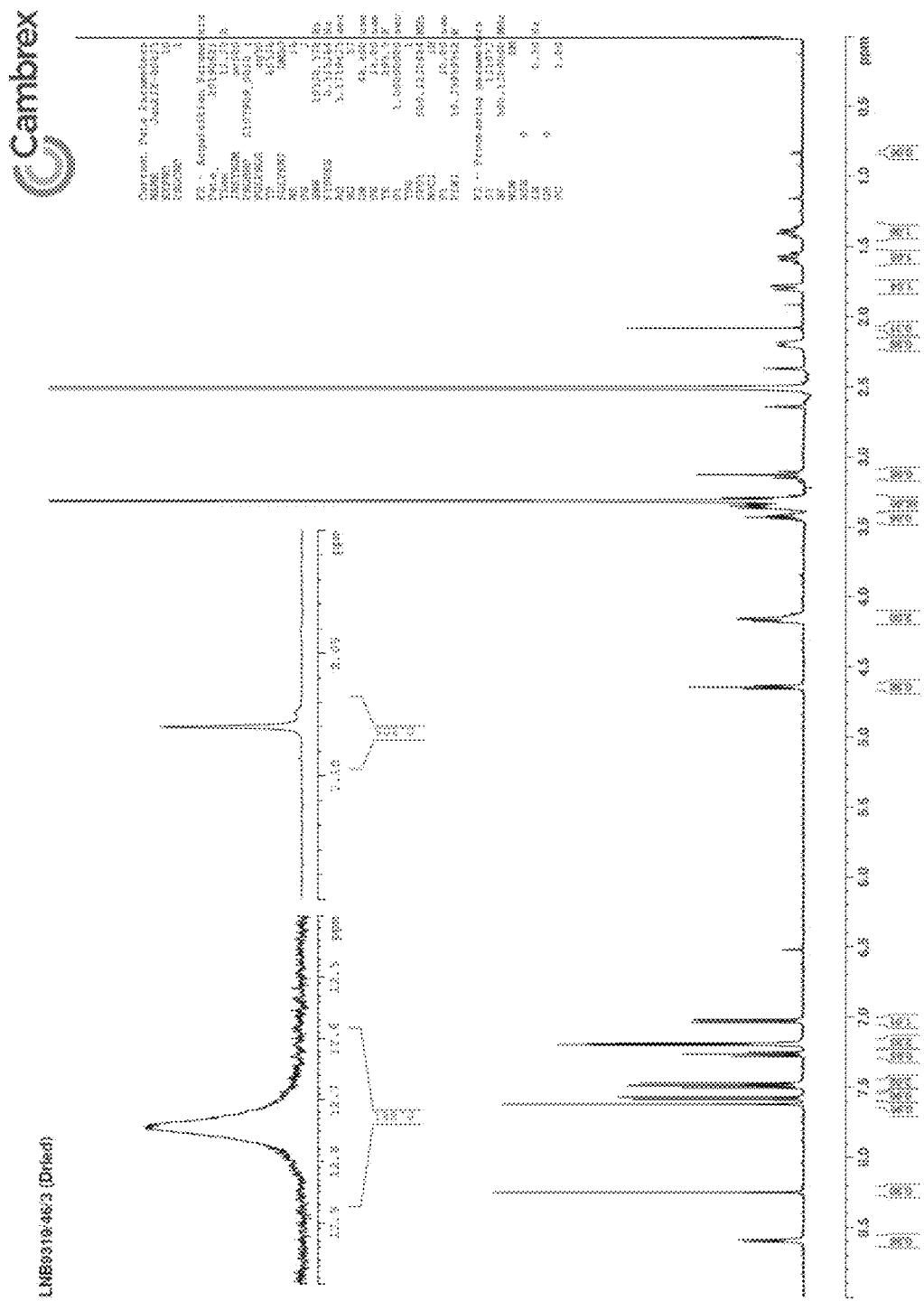
FIG. 69 sets forth a $^1$H NMR spectroscopic analysis of Form 10 obtained from 200 mg scale-up.
Figure 72:
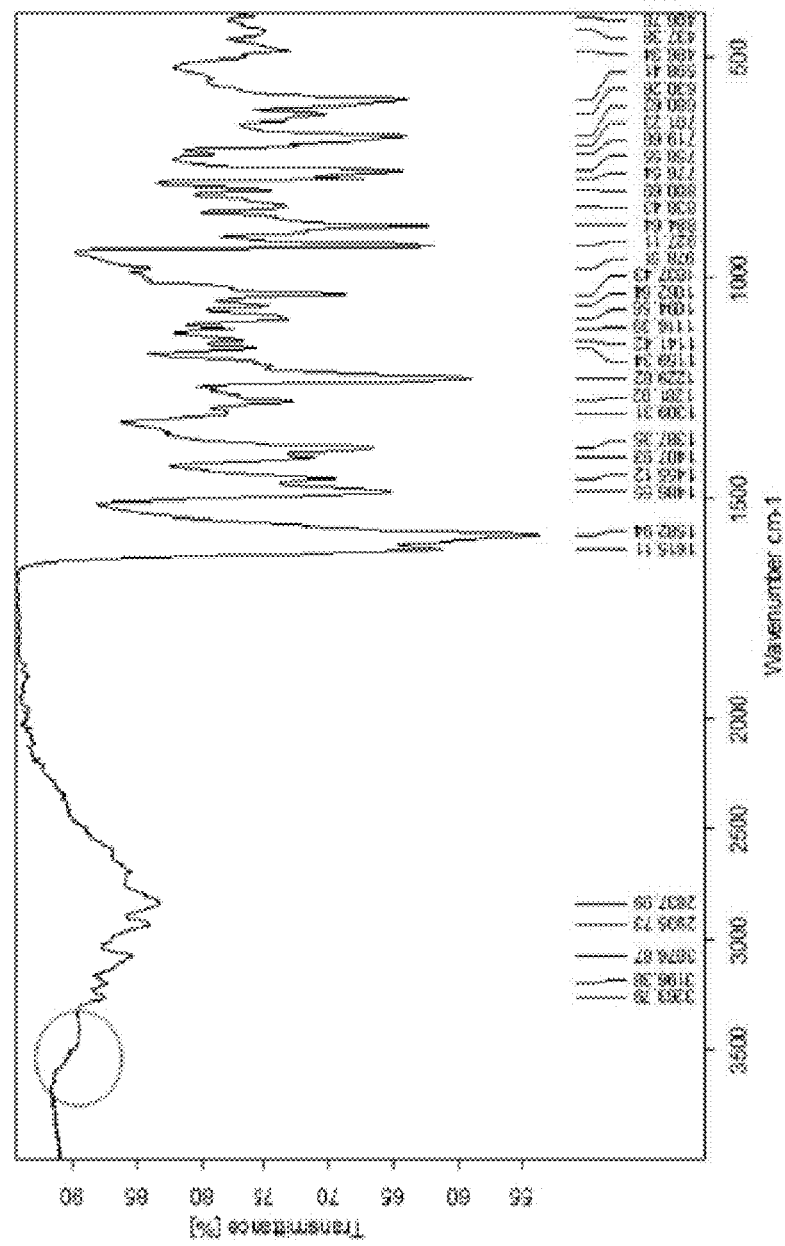
FIG. 72 sets forth an IR spectroscopic analysis of Form 10 obtained from 200 mg scale-up.
Figure 73:
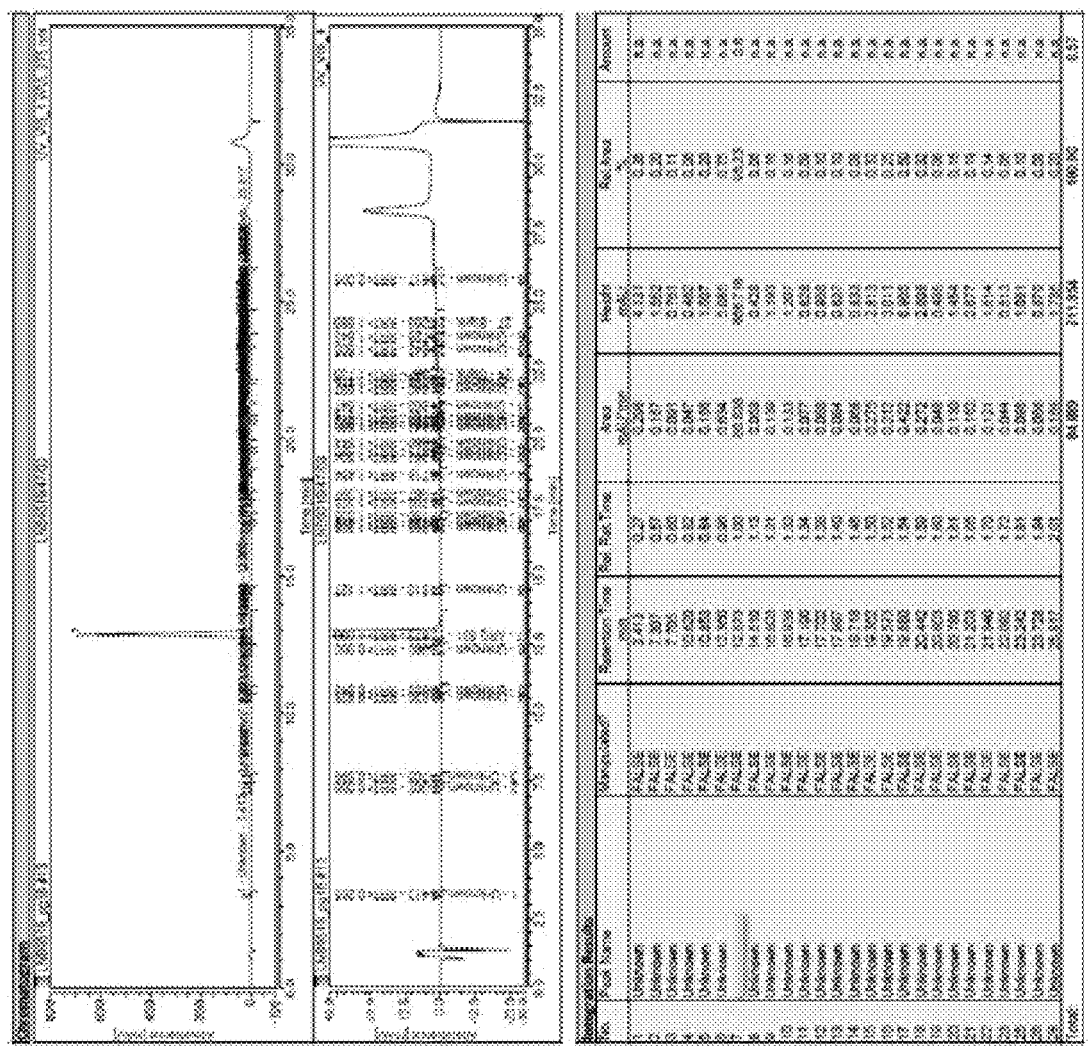
FIG. 73 sets forth an High Performance Liquid Chromatography-Ultraviolet Detection (HPLC-UV) chromatogram of Form 10 obtained from 200 mg scale-up.
Figure 74:
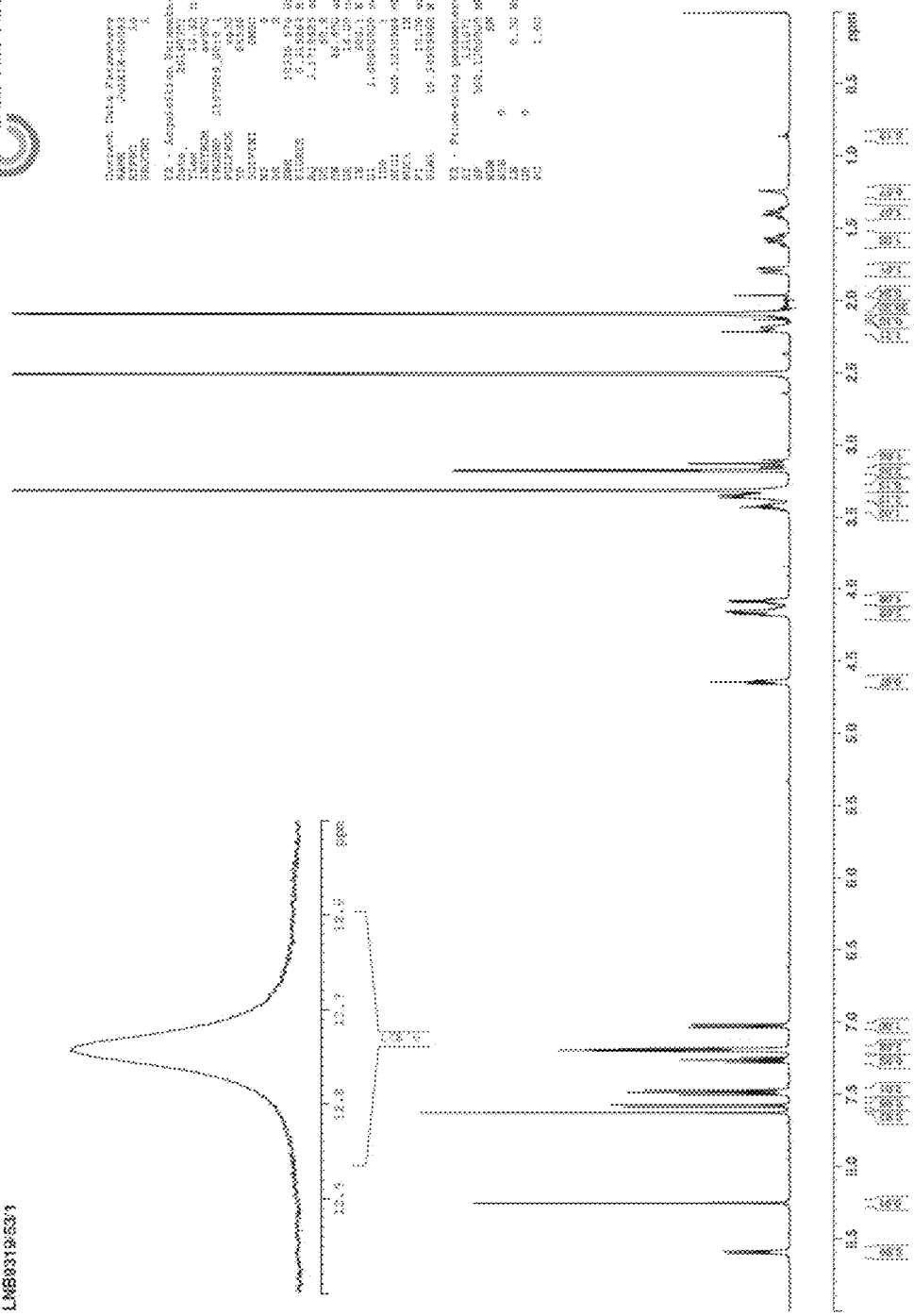
FIG. 74 sets forth a $^1$H NMR spectroscopic analysis of Form 10 obtained from 400 mg scale-up.

The XRPD analysis of the Form 10 material from acetonitrile:water (95:5 v:v) dried at ambient temperature, showed a diffractogram consistent with Form 10 (FIG. 70). TGA of Form 10 showed a weight loss of 0.9% between ca. 70° C. and 150° C. (FIG. 71). DSC (FIG. 71) showed endothermic events with onsets at approximately 62° C., approximately 205° C., and approximately 213° C. (peaks at approximately 147° C., approximately 207° C., and approximately 251° C.). The $^1$H-NMR spectrum of Form 10 was found to be consistent with the chemical structure of Compound A (FIG. 69). The HPLC area % purity was measured to be 95.2%. IR analysis showed Form 10 to correspond with Compound A material (FIG. 72).

Approximately 200 mg of amorphous Compound A and 20 mL of acetonitrile:water (95:5 v:v) were added to two 20 mL vials. The slurries were temperature cycled between 40° C. and 20° C. in 4 hour cycles for ca. 24 hours. After 24 hours, the solid had not dissolved completely. Approximately 10 mL from each vial was dispensed into a new 20 mL vial and an additional 10 mL of acetonitrile:water (95:5 v:v) was added to the four 20 mL vials. The slurries were temperature cycled between 40° C. and 20° C. in 4 hour cycles for ca. 24 hours. The resulting clear solutions were pipetted evenly into forty 2 mL glass vials. The solvent was evaporated at ambient temperature for approximately 24 hours. The dried material was analyzed by XRPD, TG/DSC, DSC, PLM, KF, FT-IR, and HPLC.

Figure 77:
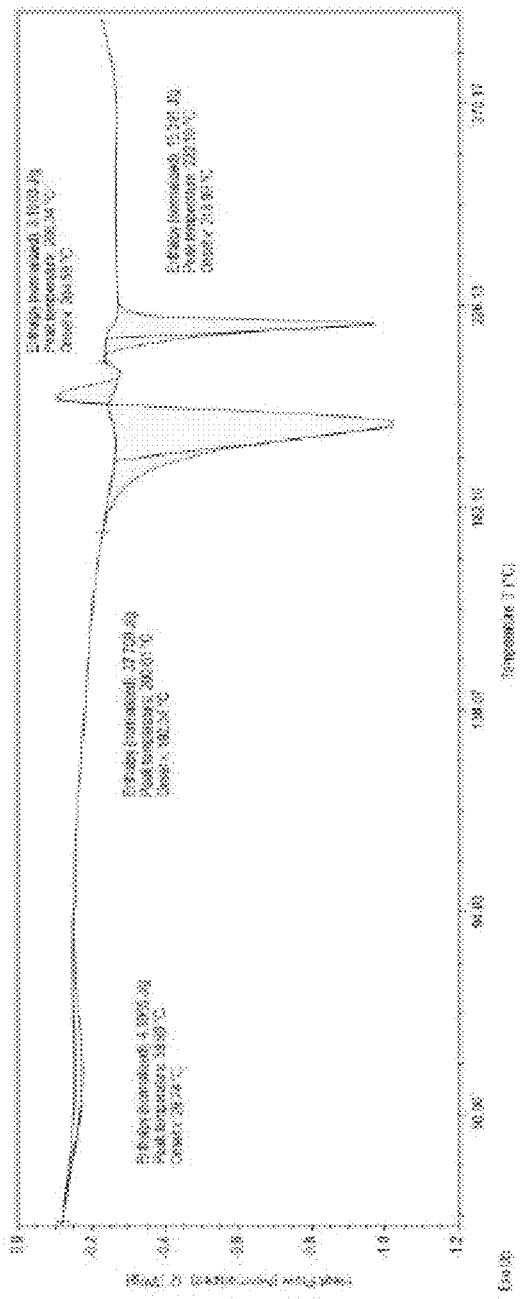
FIG. 77 sets forth a thermal analysis by a first heat DSC of Form 10 obtained from 400 mg scale-up.
Figure 78:
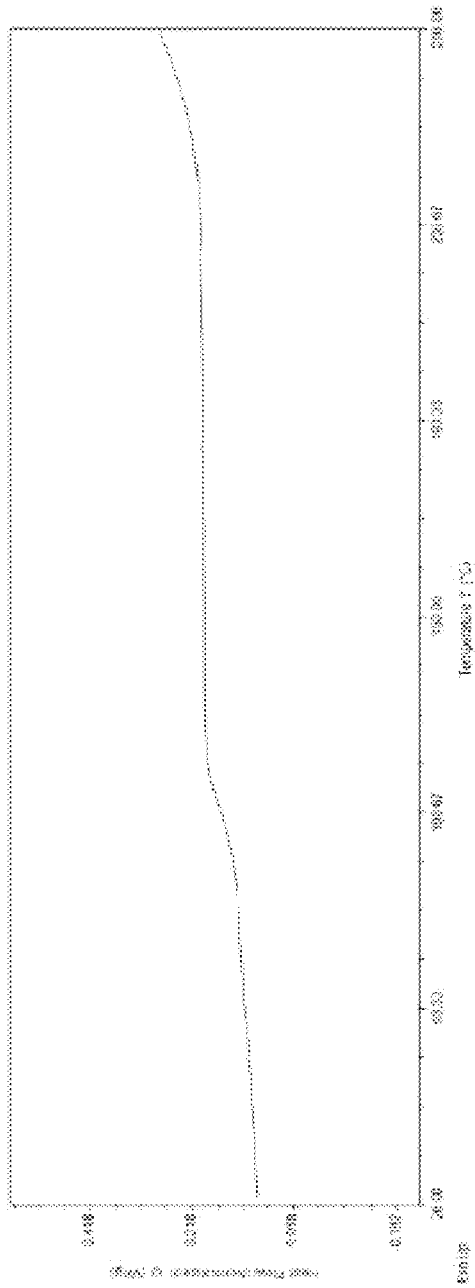
FIG. 78 sets forth a thermal analysis by a cool DSC of Form 10 obtained from 400 mg scale-up.
Figure 79:
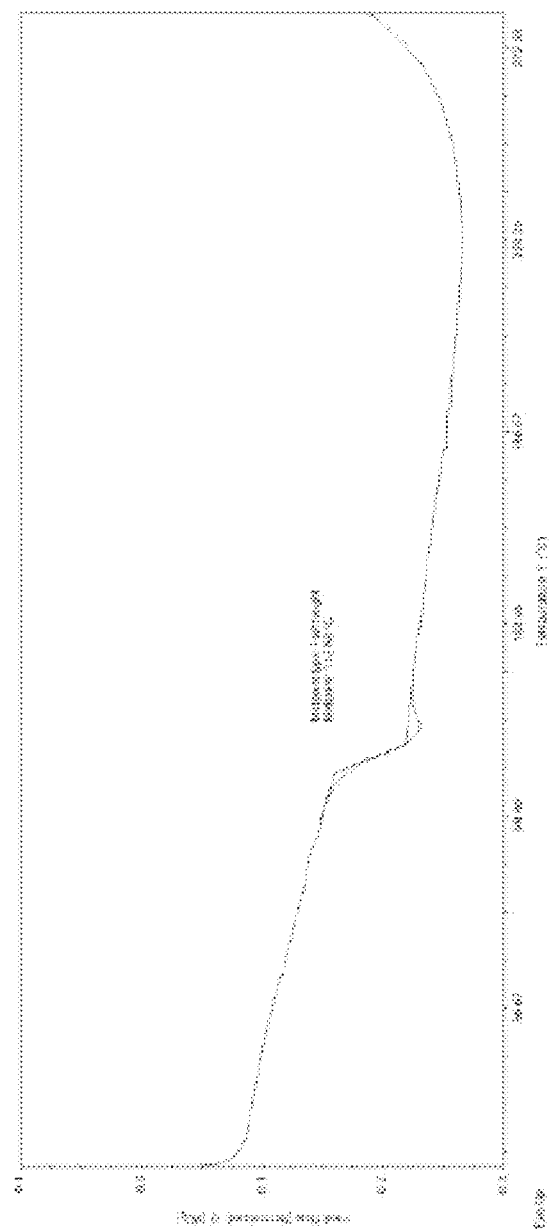
FIG. 79 sets forth a thermal analysis by a second heat DSC of Form 10 obtained from 400 mg scale-up.
Figure 80:
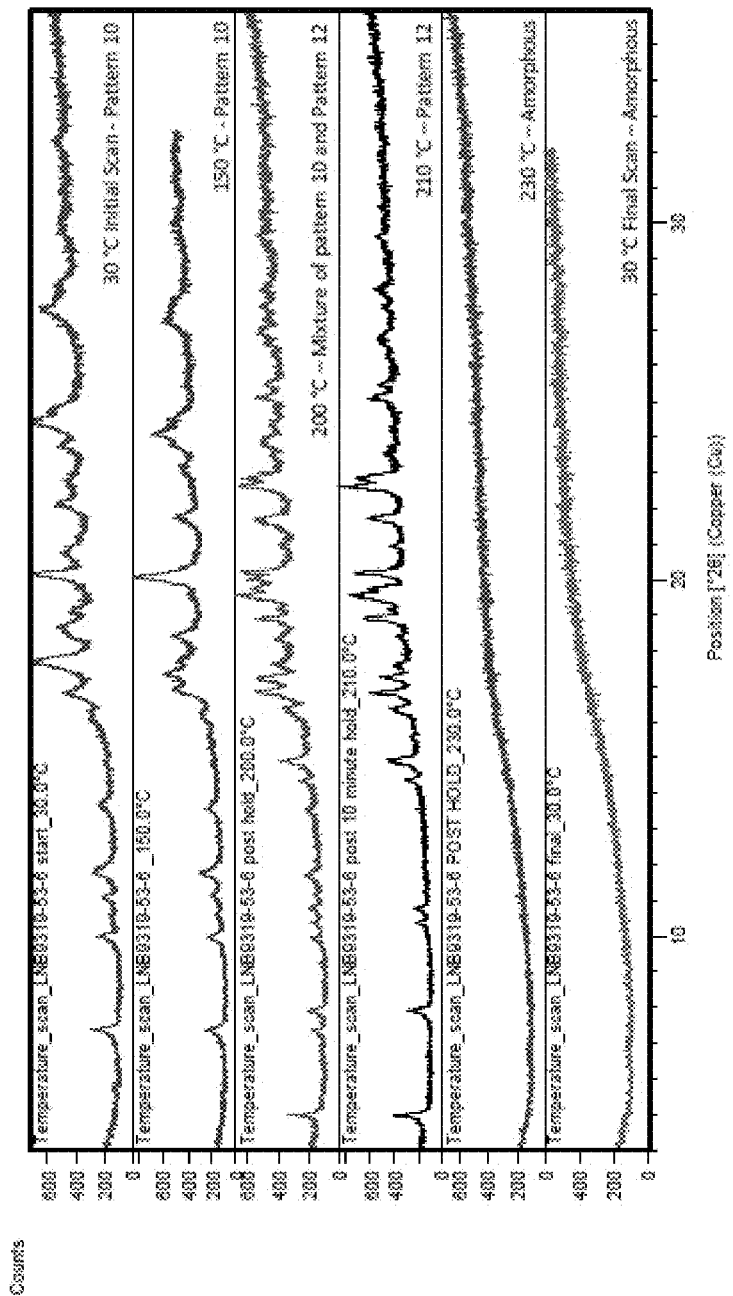
FIG. 80 sets forth variable temperature X-ray powder diffraction (VT-XRPD) patterns of Form 10 obtained at 30° C., 150° C., 200° C., 210° C., and 230° C. obtained from 400 mg scale-up.
Figure 81:
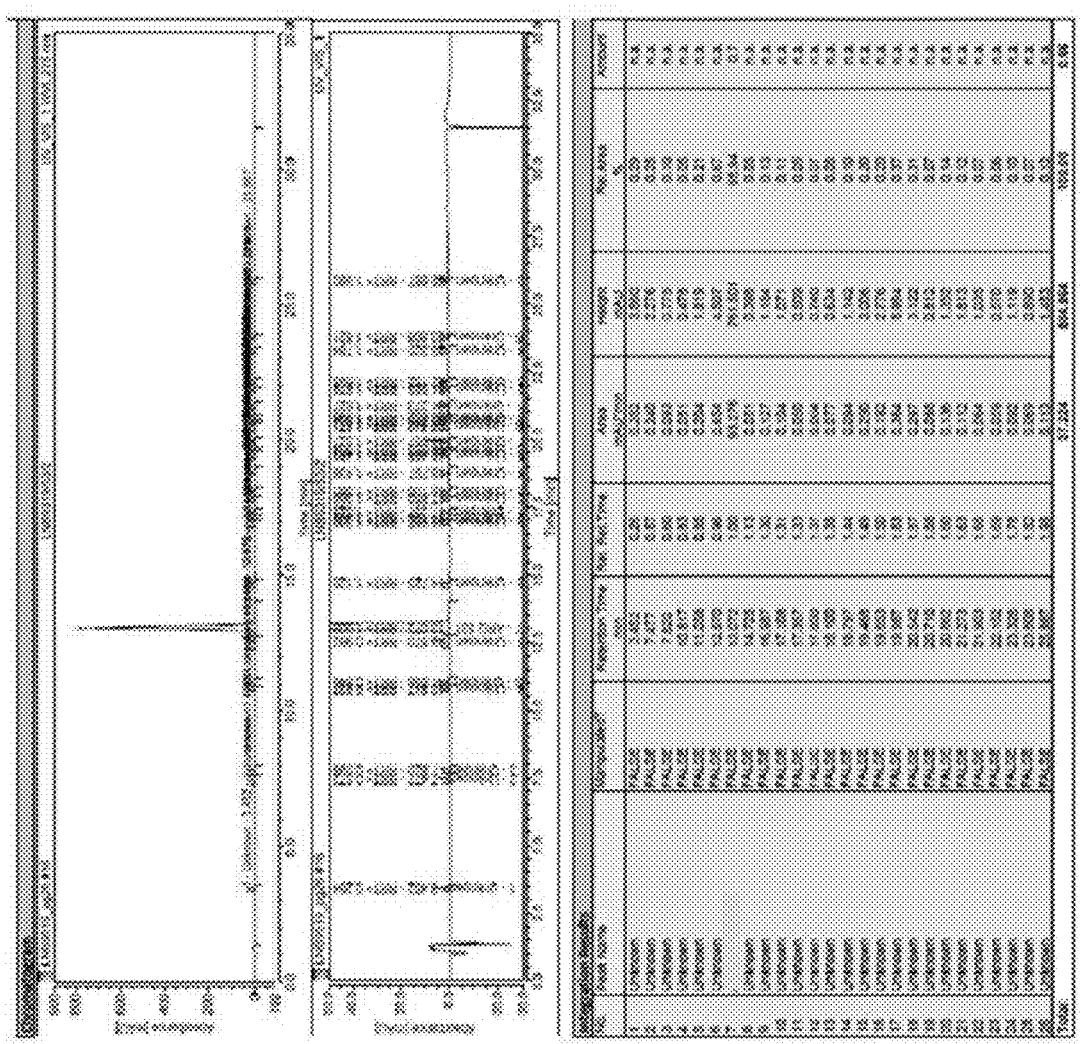
FIG. 81 sets forth an HPLC-UV chromatogram of Form 10 obtained from 400 mg scale-up.
Figure 82:
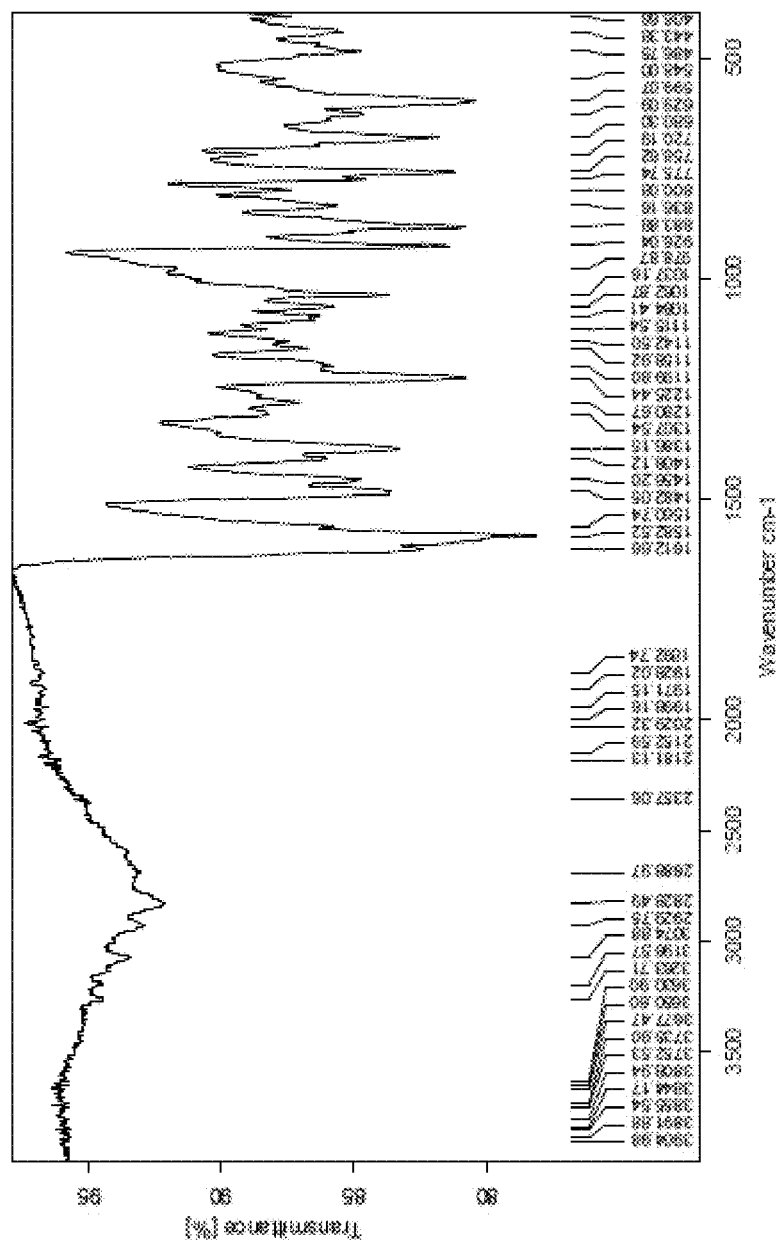
FIG. 82 sets forth an IR spectroscopic analysis of Form 10 obtained from 400 mg scale-up.
Figure 85:
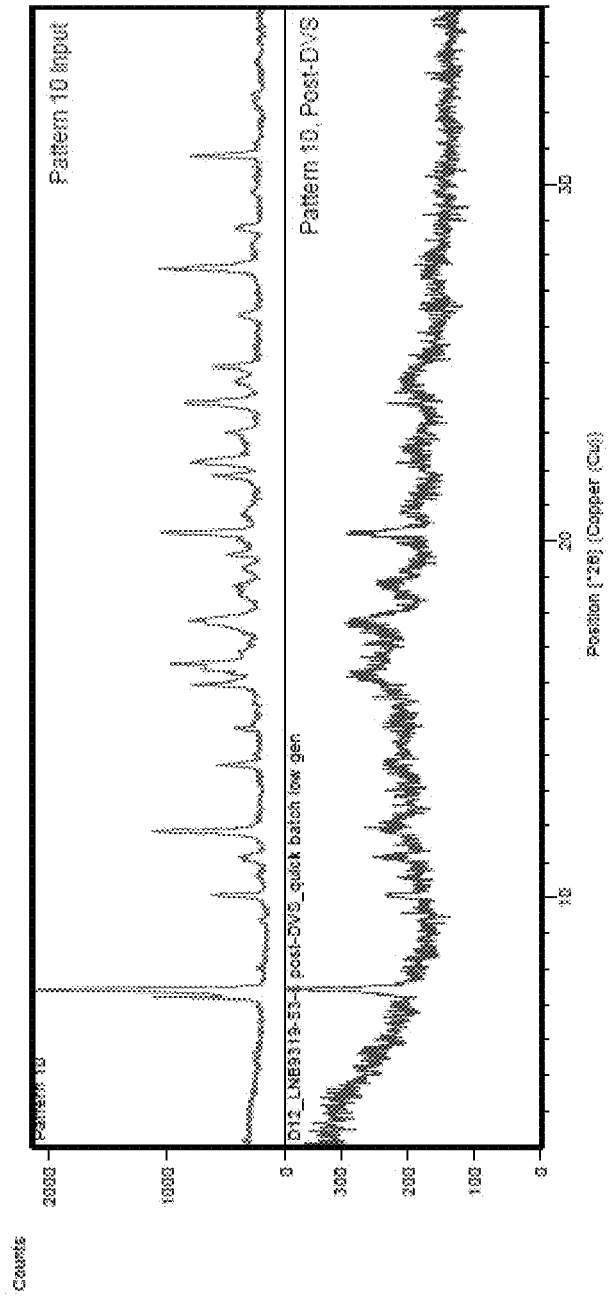
FIG. 85 sets forth comparative XRPD pattern of Form 10 with the XRPD pattern of Form 10 obtained post-DVS obtained from 400 mg scale-up.
Figure 86:
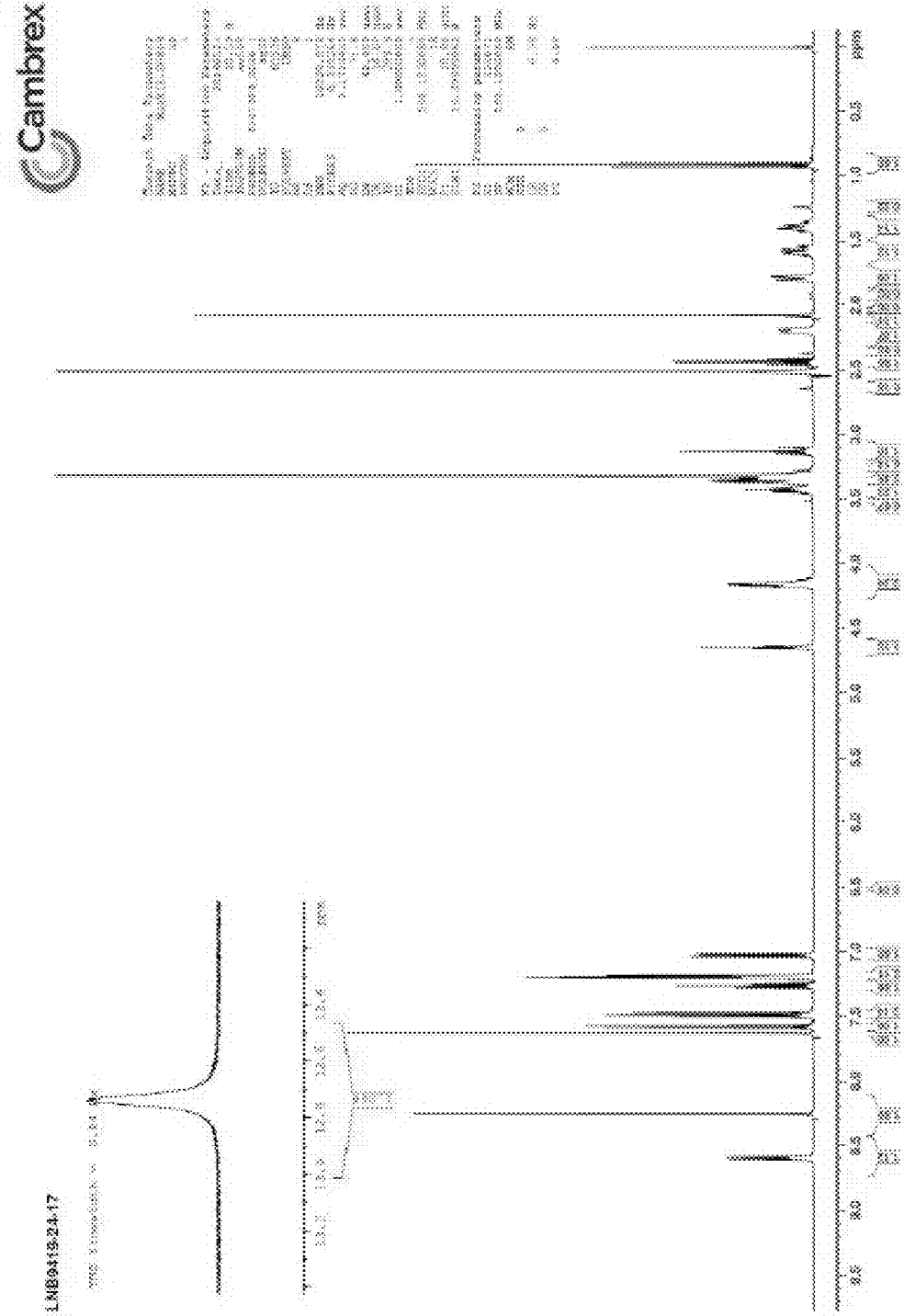
FIG. 86 sets forth a $^1$H NMR spectroscopic analysis of Form 11.
Figure 87:
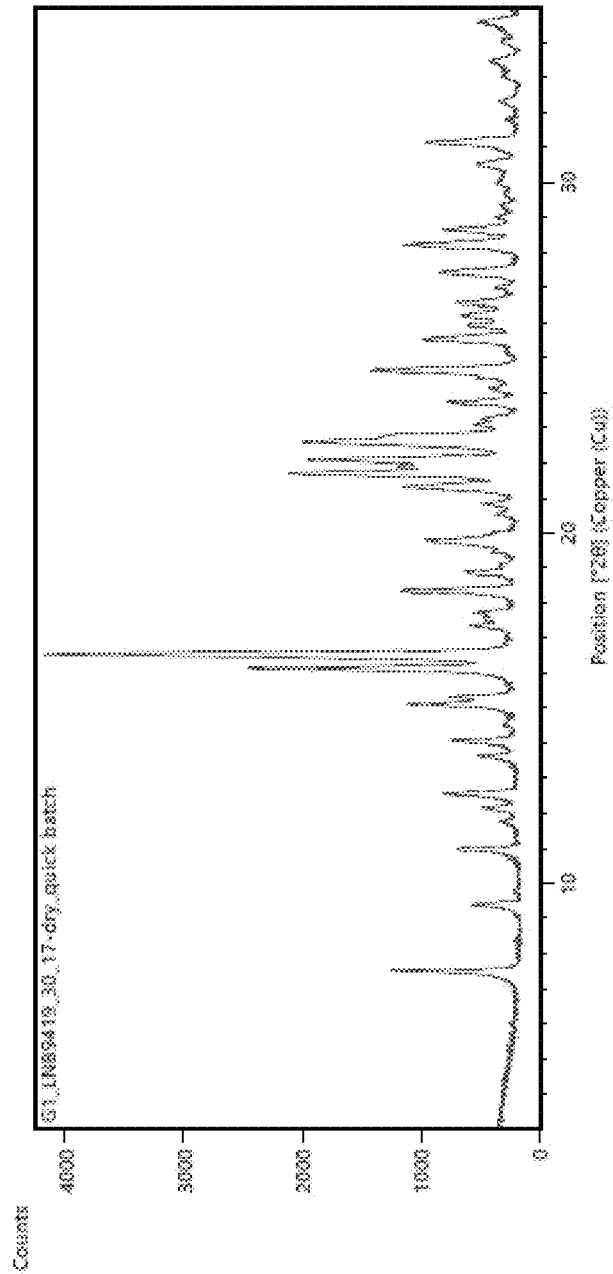
FIG. 87 sets forth an XRPD pattern of Form 11.

The XRPD analysis of the Form 10 material from acetonitrile:water (95:5 v:v) dried at ambient temperature, showed a diffractogram consistent with Form 10. PLM analysis showed birefringent particles for Form 10 (FIG. 76A and FIG. 76B). TGA of Form 10 showed weight losses of 0.5% between ca. 70° C. and 150° C., and 1.7% between ca. 150° C. and 300° C. (FIG. 75). DSC (FIG. 75) showed endothermic events with onsets at approximately 195° C. and approximately 230° C. (peaks at approximately 201° C. and approximately 231° C.). The thermogram obtained during the initial DSC heating cycle showed a broad endothermic event with an onset at 30° C. (peak at 60° C.), which was mostly likely the result of dehydration (FIG. 77). A second, sharp endothermic event was observed with an onset at 192° C. (peak at 201° C.). The sample then recrystallizes, as evidenced by the exothermic event at 205° C. (peak at 206° C.). A final endothermic event was observed at 219° C. (peak at 222° C.). The DSC cool cycle (FIG. 78) did not show any significant thermal events. The second DSC heat cycle (FIG. 79) showed a glass transition with a midpoint of 113° C. VT-XRPD (FIG. 80) showed that Form 10 persisted upon heating to 150° C. with poor crystallinity; Form 10 converted to Form 12 between ca. 200° C. and ca. 210° C.; and the sample became amorphous at 230° C. and remained amorphous upon cooling to 30° C. (Table 2). KF analysis showed a water content of 1.48% or 0.4 equivalents. This is consistent with TGA analysis where 0.45 equivalents of water were lost above 150° C. (FIG. 75). DVS analysis (FIG. 83 and FIG. 84) showed Form 10 to be slightly hygroscopic with a 0.94% uptake at 90% RH. Post-DVS XRPD analysis showed no change in form, but reduction in crystallinity (FIG. 85). The $^1$H-NMR spectrum of Form 10 was found to be consistent with the chemical structure of Compound A (FIG. 79). The HPLC area % purity was measured to be 95.9%. IR analysis showed Form 10 to correspond with Compound A material (FIG. 82).

TABLE 2

VT-XRPD Results Summary Form 10

| Run | Temp (° C.) | Identity |
|---|---|---|
| 1 | 30 | Form 10 |
| 2 | 150 | Form 10 |
| 3 | 200 | Form 10       Form 12 |
| 4 | 210 | Form 12 |
| 5 | 230 | Amorphous |
| 6 | 30 | Amorphous |

Form 11 Preparation and Assessment

To ca. 200 mg of amorphous Compound A, 2 mL of methyl ethyl ketone was added. The slurry was temperature cycled between 40° C. and 20° C. in 4 hour cycles for ca. 72 hours. XRPD analysis was carried out on a portion of the material removed by centrifuge filtration using a 0.22 μm nylon filter. The solvent was evaporated and the solid was dried at 40° C. for ca. 72 hours. The dried material was analyzed by XRPD, TG/DSC, HPLC, and $^1$H NMR.

Figure 88:
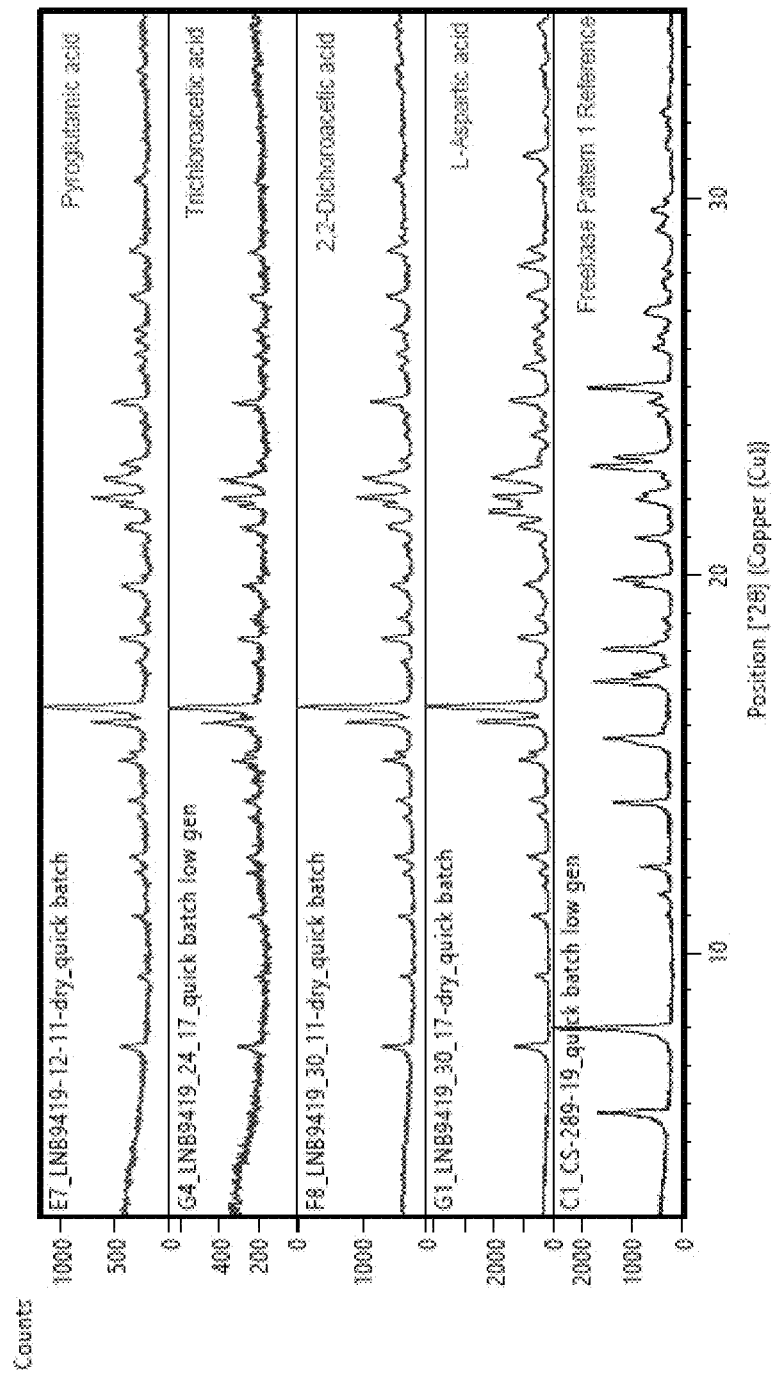
FIG. 88 sets forth comparative XRPD pattern of Form 11 with the XRPD patterns of Form 11 from pyrogluatmic acid evaporation, trichloroacetic acid evaporation, 2,2-dichloroacetic acid, and L-aspartic acid.
Figure 91:
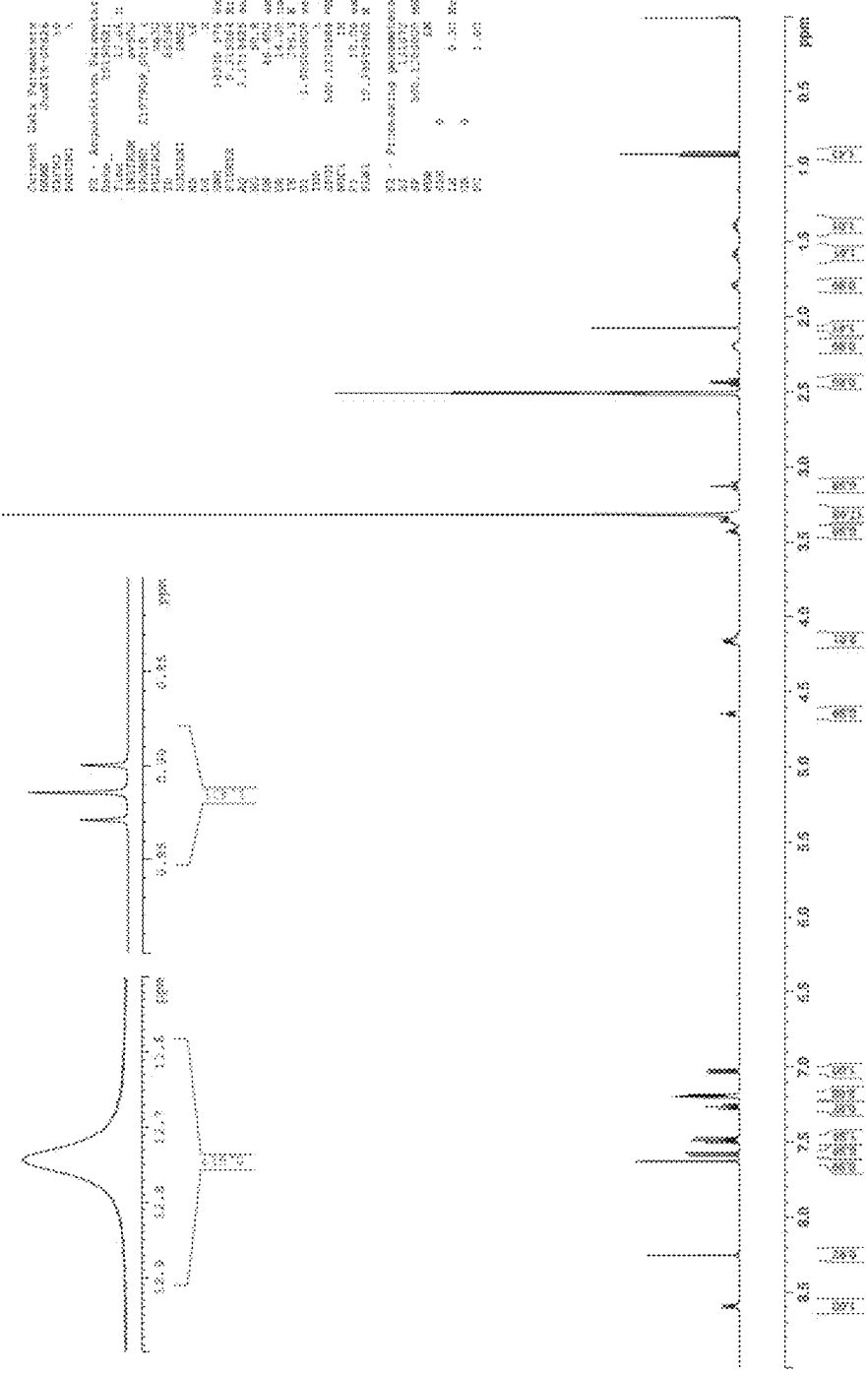
FIG. 91 sets forth a $^1$H NMR spectroscopic analysis of Form 11 obtained from 200 mg scale-up.
Figure 92:
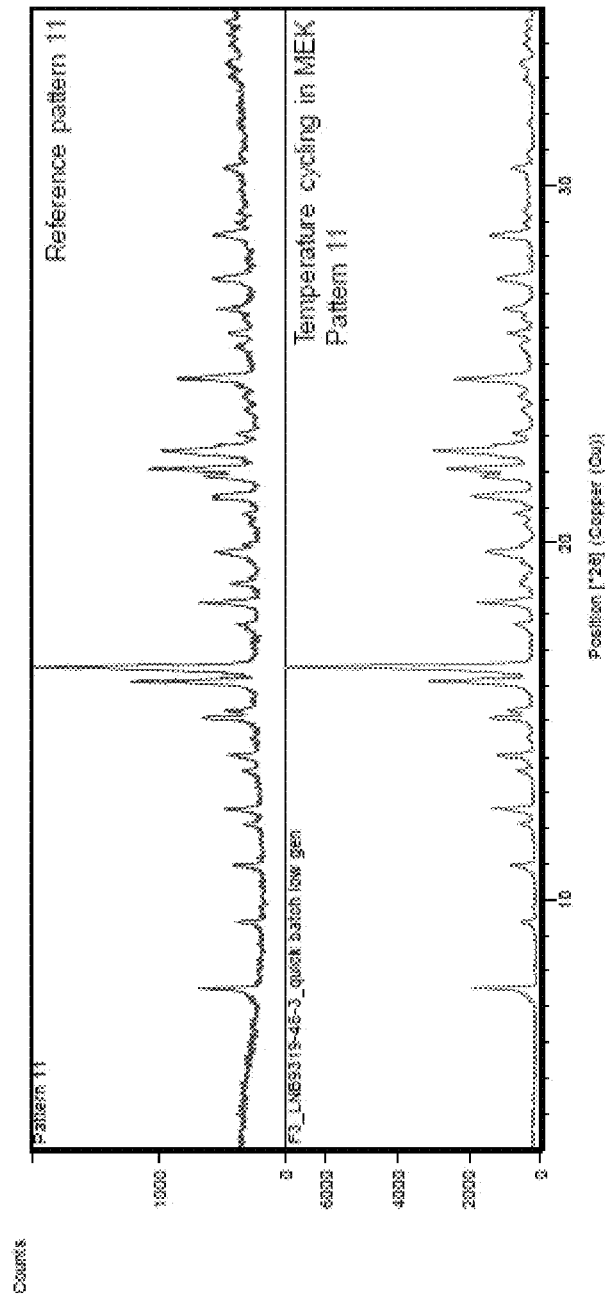
FIG. 92 sets forth comparative XRPD pattern of Form 11 with the XRPD pattern of Form 11 from 200 mg scale-up.

The XRPD analysis of the Form 11 material from methyl ethyl ketone dried at 40° C., showed a diffractogram consistent with Form 11 (FIG. 88). TGA of Form 11 showed a weight loss of approximately 7.2% between approximately 100° C. and approximately 150° C., and a weight loss of approximately 1.7% between approximately 150° C. and approximately 300° C. (FIG. 93). DSC (FIG. 93) showed endothermic events at ca. 119° C., ca. 195° C., ca. 210° C., and ca. 224° C. (peaks at ca. 128° C., ca. 202° C., ca. 213° C., and ca. 226° C.) as measured by scanning calorimetry (DSC). The $^1$H-NMR spectrum of Form 11 was found to be consistent with the chemical structure of Compound A (FIG. 91). The HPLC area % purity was measured to be 98.7%.

Edisylate Form 1 Preparation and Assessment

To ca. 400 mg Compound A, 6 mL methanol was added. A solution of 1,2-ethane disulfonic acid (1.1 equivalents based on the weight of the freebase) in methanol (6 mL) was added to Compound A at 25° C. The mixture was temperature cycled between 40° C. and 5° C. in 4 hour cycles for ca. 72 hours. XRPD analysis was carried out on a portion of the material removed by vacuum filtration. The solvent was evaporated and the solid was dried at 40° C. under vacuum for ca. 18 hours. The dried material was analyzed by XRPD, PLM, TG/DTA, DSC, DVS, FT-IR, KF, HPLC, and $^1$H NMR.

The XRPD analysis of the edisylate Form 1 material from methanol dried at 40° C. under vacuum showed a diffractogram consistent with edisylate Form 1 (FIG. 131 and FIG. 133). TGA of edisylate Form 1 showed a weight loss of 0.32% between ca. 70° C. and 210° C. followed by a weight loss of 0.35% between ca. 210° C. and 240° C. (FIG. 134). DSC (FIG. 135) showed an endothermic event with an onset at approximately 233° C. (peak at approximately 240° C.). The $^1$H-NMR spectrum of edisylate Form 1 showed 0.57 equivalents of 1,2-ethane disulfonic acid and trace amounts of methanol (FIG. 139). The HPLC area % purity was measured to be 97.9% (FIG. 140). FT-IR analysis was performed on edisylate Form 1 (FIG. 138). PLM analysis showed small particles with no clear morphology for edisylate Form 1 (FIG. 132). KF analysis showed a moisture content of 0.94%. DVS analysis (FIG. 136) of edisylate Form 1 showed a moisture uptake of ca. 4.6% at 90% RH. Post-DVS XRPD analysis showed no change in form from the input material (FIG. 137). XRPD analysis after storage at 40° C./75% RH, 80° C., and ambient temperature for 1 week showed no change in form from the input material (FIG. 141). XRPD analysis after salt disproportionation studies show no change from the input material after 48 hours slurrying edisylate Form 1 in water (FIG. 142). The measured pH for this sample was 2.32 after slurrying edisylate Form 1 in water for 48 hours. XRPD analysis after thermodynamic solubility studies show no change from the input material after slurrying edisylate Form 1 in the respective buffer at 25° C. for 48 hours (FIG. 143 and Table 7).

Cyclamate Form 1 Preparation and Assessment

To ca. 400 mg Compound A, 6 mL methyl ethyl ketone was added. A solution of cyclamic acid (1.1 equivalents based on the weight of the freebase) in methyl ethyl ketone (6 mL) was added to Compound A at 25° C. The mixture was temperature cycled between 40° C. and 5° C. in 4 hour cycles for ca. 72 hours. XRPD analysis was carried out on a portion of the material removed by vacuum filtration. The solvent was evaporated and the solid was dried at 40° C. under vacuum for ca. 18 hours. The dried material was analyzed by XRPD, PLM, TG/DTA, DSC, DVS, FT-IR, KF, HPLC, and $^1$H NMR.

The XRPD analysis of the cyclamate Form 1 material from methyl ethyl ketone dried at 40° C. under vacuum showed a diffractogram consistent with cyclamate Form 1 (FIG. 144). TGA of cyclamate Form 1 showed a weight loss of 2.9% between ca. 50° C. and 210° C. (FIG. 146). DTA (FIG. 146) showed an endothermic event with an onset at approximately 229° C. (peak at 247° C.). DSC (FIG. 147) showed a broad exothermic event with an onset at approximately 69° C. (peak at approximately 114° C.) and an endothermic event with an onset at approximately 230° C. (peak at approximately 243° C.). The $^1$H-NMR spectrum of cyclamate Form 1 showed 1.3 equivalents of cyclamic acid and ca. 1.81% (0.16 equivalents) methyl ethyl ketone present (FIG. 151). The HPLC area % purity was measured to be 42.6% (FIG. 152). FT-IR analysis was performed on cyclamate Form 1 (FIG. 150). PLM analysis showed aggregated particles with some birefringence (FIG. 145). KF analysis was carried out using direct addition method and showed a moisture content of 0.73%. DVS analysis (FIG. 148) of cyclamate Form 1 showed a moisture uptake of ca. 5.6% at 90% RH. Post-DVS XRPD analysis showed no change in form from the input material (FIG. 149). XRPD analysis after storage at 40° C./75% RH, 80° C., and ambient temperature for 1 week showed no change in form from the input material (FIG. 153). XRPD analysis after salt disproportionation studies show that the material becomes partially crystalline after 1 hour, with the material staying partially crystalline after 48 hours slurrying cyclamate Form 1 in water (FIG. 154). The measured pH for this sample was 2.19 after slurrying cyclamate Form 1 in water for 48 hours. XRPD analysis after thermodynamic solubility studies shows cyclamate Form 1 becomes poorly crystalline after slurrying in the respective buffer at 25° C. for 48 hours (FIG. 155).

Besylate Form 1 Preparation and Assessment

To ca. 400 mg of Compound A, 2 mL 2-methyl tetrahydrofuran was added. A solution of benzene sulfonic acid (1.1 equivalents based on the weight of the freebase) in 2-methyl tetrahydrofuran (2 mL) was added to Compound A at 25° C. The mixture was temperature cycled between 40° C. and 5° C. in 4 hour cycles for ca. 72 hours. XRPD analysis was carried out on a portion of the material removed by vacuum filtration. The solvent was evaporated and the solid was dried at 40° C. under vacuum for ca. 18 hours. The dried material was analyzed by XRPD, PLM, TG/DTA, DSC, DVS, FT-IR, KF, HPLC, and $^1$H NMR.

The XRPD analysis of the besylate Form 1 material from 2-methyl tetrahydrofuran dried at 40° C. under vacuum showed a diffractogram consistent with besylate Form 1 (FIG. 156 and FIG. 158). TGA of besylate Form 1 showed a weight loss of 0.6% between ca. 50° C. and 160° C. (FIG. 159). DTA (FIG. 159) showed an endothermic event with an onset at approximately 183° C. (peak at 189° C.). DSC (FIG. 160) showed an endothermic event with an onset at approximately 182° C. (peak at approximately 188° C.). The $^1$H-NMR spectrum of besylate Form 1 showed 1 equivalents of benzene sulfonic acid and ca 0.38% (0.33 equivalents) 2-methyl tetrahydrofuran present (FIG. 164). The HPLC area % purity was measured to be 97.5% (FIG. 165). FT-IR analysis was performed on besylate Form 1 (FIG. 163). PLM analysis showed small rod-like particles with agglomeration and birefringence (FIG. 157). KF analysis was carried out using direct addition method and showed a moisture content of 0.24%. DVS analysis (FIG. 161) of besylate Form 1 showed a moisture uptake of ca. 2% at 90% RH. Post-DVS XRPD analysis showed no change in form from the input material (FIG. 162). XRPD analysis after storage at 40° C./75% RH, 80° C., and ambient temperature for 1 week showed no change in form from the input material (FIG. 166). XRPD analysis after salt disproportionation studies show the material becomes a gel-like, amorphous solid after 24 hours slurrying in water, with the material staying partially crystalline after 48 hours slurrying besylate Form 1 in water (FIG. 1557. The measured pH for this sample was 1.96 after slurrying besylate Form 1 in water for 48 hours. XRPD analysis after thermodynamic solubility studies shows besylate Form 1 becomes poorly crystalline after slurrying in the respective buffer at 25° C. for 48 hours (FIG. 168).

Besylate Form 1 Preparation and Assessment

To ca. 500 mg of Compound A, 5 mL ethyl acetate was added. The suspension was stirred at ambient temperature (ca. 22° C.). Benzene sulfonic acid (ca. 176 mg) was dissolved in 0.5 mL ethyl acetate and added to the suspension of freebase at ca. 22° C. Some precipitation was observed. The suspension was transferred to an incubator shaker and shaken at ca. 50° C. for 2 hours. The slurry was temperature cycled between 40° C. and 5° C. in 2 hour cycles for ca. 6 hours. The suspension was stirred at 5° C. for an additional 24 hours. The solid was air dried for 40 minutes and then further dried under vacuum at 40° C. for ca. 96 hours. A light brown solid was obtained. The dried material was analyzed by XRPD, PLM, TG/DTA, DSC, DVS, FT-IR, KF, HPLC, and $^1$H NMR.

The XRPD analysis of the besylate Form 1 material from ethyl acetate dried at 40° C. under vacuum showed a diffractogram consistent with besylate Form 1 (FIG. 270). TGA of besylate Form 1 showed a weight loss of 0.8% between ambient temperature and 180° C. (FIG. 272). DSC (FIG. 273) showed an endothermic event with an onset at approximately 172° C. (peak at approximately 174° C.). The $^1$H-NMR spectrum of besylate Form 1 showed 0.024 equivalents of ethyl acetate and a 1:1 acid:base stoichiometry (FIG. 278). The HPLC area purity was measured to be 91.1% (FIG. 285). FT-IR analysis was performed on besylate Form 1, indicating that it was different than the freebase form (FIG. 277). PLM analysis showed very small birefringent particles with an irregular morphology (FIG. 271). KF analysis showed a moisture content of 2.0%. DVS analysis (FIG. 274 and FIG. 275) of besylate Form 1 showed a moisture uptake of ca. 2.3% at 90% RH. Post-DVS XRPD analysis showed no change in form from the input material (FIG. 276). XRPD analysis after storage at 40° C./75% RH, 80° C., and ambient temperature for 1 week showed no change in form from the input material (FIG. 279). XRPD analysis after salt disproportionation studies show no change from the input material after 48 hours slurrying besylate Form 1 in water (FIG. 280). The measured pH for this sample was 2.60 after slurrying besylate Form 1 in water for 48 hours. XRPD analysis after thermodynamic solubility studies show no change from the input material after slurrying besylate Form 1 in the respective buffer at 25° C. for 48 hours (FIG. 281). The hydration study results are summarized in Table 8. XRPD analysis after hydration are shown in FIG. 282.

Cyclamate Form 1 Preparation and Assessment

To ca. 400 mg of Compound A, 6 mL methyl ethyl ketone was added. A solution of cyclamic acid (1.1 equivalents based on the weight of the freebase) in methyl ethyl ketone (6 mL) was added to the slurry of amorphous Compound A at 25° C. The slurry was temperature cycled between 40° C. and 5° C. in 4 hour cycles for ca. 72 hours. XRPD analysis was carried out on a portion of the material removed by vacuum filtration. The solvent was evaporated and the solid was dried at 40° C. under vacuum for ca. 18 hours. The dried material was analyzed by XRPD, PLM, TG/DTA, DSC, DVS, FT-IR, KF, HPLC, and $^1$H NMR.

The XRPD analysis of the cyclamate Form 1 material from methyl ethyl ketone dried at 40° C. under vacuum showed a diffractogram consistent with cyclamate Form 1 (FIG. 144). TGA of cyclamate Form 1 showed a weight loss of 2.9% between ca. 50° C. and 210° C. (FIG. 146). DTA (FIG. 146) showed an endothermic event with an onset at approximately 229° C. (peak at 247° C.). DSC (FIG. 147) showed a broad exothermic event with an onset at approximately 69° C. (peak at approximately 114° C.) and an endothermic event with an onset at approximately 230° C.

(peak at approximately 243° C.). The ¹H-NMR spectrum of cyclamate Form 1 showed 1.3 equivalents of cyclamic acid and ca. 1.81% (0.16 equivalents) methyl ethyl ketone present (FIG. 151). The HPLC area % purity was measured to be 42.6% (FIG. 152). FT-IR analysis was performed on cyclamate Form 1 (FIG. 150). PLM analysis showed aggregated particles with some birefringence (FIG. 145). KF analysis was carried out using direct addition method and showed a moisture content of 0.73%. DVS analysis (FIG. 148) of cyclamate Form 1 showed a moisture uptake of ca. 5.6% at 90% RH. Post-DVS XRPD analysis showed no change in form from the input material (FIG. 149). XRPD analysis after storage at 40° C./75% RH, 80° C., and ambient temperature for 1 week showed no change in form from the input material (FIG. 153). XRPD analysis after salt disproportionation studies show that the material becomes partially crystalline after 1 hour, with the material staying partially crystalline after 48 hours slurrying cyclamate Form 1 in water (FIG. 154). The measured pH for this sample was 2.19 after slurrying cyclamate Form 1 in water for 48 hours. XRPD analysis after thermodynamic solubility studies shows cyclamate Form 1 becomes poorly crystalline after slurrying in the respective buffer at 25° C. for 48 hours (FIG. 155).

Hydrobromide Form 1 Preparation and Assessment

To ca. 500 mg of Compound A, 5 mL ethyl acetate was added. The suspension was stirred at ambient temperature (ca. 22° C.). Hydrobromic acid (ca. 126 µL) was slowly added to the suspension of freebase at ca. 22° C. Some precipitation was observed. The suspension was transferred to an incubator shaker and shaken at ca. 50° C. for 2 hours. The slurry was cooled to 5° C. under stirring and further stirred at ca. 5° C. for ca. 24 hours. The experiment was temperature cycled from 5° C. to 40° C. (2 hour cycles) for 6 hours. The experiment was stirred at 5° C. for ca. 24 hours. Stirring was stopped and the solid and liquid were separated by pipetting the liquid. The solid was air dried for 40 minutes and then further dried under vacuum at 40° C. for ca. 96 hours. A light brown solid was obtained. The dried material was analyzed by) XRFD, PLM, TG/DTA, DSC, DVS, FT-IR, KF, HPLC, and ¹H NMR.

The XRPD analysis of the hydrobromide Form 1 material from ethyl acetate dried at 40° C. under vacuum showed a diffractogram consistent with hydrobromide Form 1 (FIG. 257). TGA of hydrobromide Form 1 showed a weight loss of 1.3% between ambient temperature and 60° C., and a weight loss of 1.5% between about 60° C. and about 166° C. (FIG. 259). DSC (FIG. 260) showed endothermic events with onsets at approximately 63-86° C. and approximately 150° C. (peak at approximately 163° C.). The ¹H-NMR spectrum of hydrobromide Form 1 showed 0.02 equivalents of ethyl acetate (FIG. 265). The HPLC area % purity was measured to be 77.9% (FIG. 284). FT-IR analysis was performed on hydrobromide Form 1, indicating that it was different than the freebase form (FIG. 264). PLM analysis showed small birefringence with an irregular morphology (FIG. 258). KF analysis showed a moisture content of 7.39%. DVS analysis (FIG. 261 and FIG. 262) of hydrobromide Form 1 showed a moisture uptake of ca. 7.0% at 90% RH. Post-DVS XRPD analysis showed no change in form from the input material (FIG. 263). XRPD analysis after storage at 40° C./75% RH, 80° C., and ambient temperature for 1 week showed no change in form from the input material (FIG. 266). XRPD analysis after salt disproportionation studies show no change from the input material after 48 hours slurrying hydrobromide Form 1 in water (FIG. 268). The measured pH for this sample was 2.39 after slurrying hydrobromide Form 1 in water for 48 hours. XRPD analysis after thermodynamic solubility studies show no change from the input material after slurrying hydrobromide Form 1 in the respective buffer at 25° C. for 48 hours (FIG. 281). The hydration study results are summarized in Table 8. XRPD analysis after hydration are shown in FIG. 269.

Hydrobromide Form 2 Preparation and Assessment

To ca. 400 mg of Compound A, 3 mL methyl ethyl ketone was added. A solution of hydrobromic acid (1.1 equivalents based on the weight of the freebase) in methyl ethyl ketone (3 mL) was added to Compound A at 25° C. The mixture was temperature cycled between 40° C. and 5° C. in 4 hour cycles for ca. 6 days. XRPD analysis was carried out on a portion of the material removed by vacuum filtration. The solvent was evaporated and the solid was dried at 40° C. under vacuum for ca. 18 hours. The dried material was analyzed by XRPD, PLM, TG/DTA, DSC, DVS, FT-IR, KF, HPLC, and ¹H NMR.

The XRPD analysis of the hydrobromide Form 2 material methyl ethyl ketone dried at 40° C. under vacuum showed a diffractogram consistent with hydrobromide Form 2 (FIG. 169). TGA of hydrobromide Form 2 showed a weight loss of 0.4% between ca. 30° C. and 60° C., and a weight loss of 1.6% between ca. 140° C. and 210° C. (FIG. 171). DTA (FIG. 171) showed an endothermic event with an onset at approximately 202° C. (peak at 210° C.). DSC (FIG. 172) showed endothermic events with onsets at approximately 68° C., approximately 165° C., and approximately 203° C. (peaks at approximately 90° C., approximately 175° C., and approximately 211° C.). The ¹H-NMR spectrum of hydrobromide Form 2 showed that the salt had formed and ca 0.47% (0.031 equivalents) methyl ethyl ketone present (FIG. 176). The HPLC area % purity was measured to be 98.1% (FIG. 177). FT-IR analysis was performed on hydrobromide Form 2 (FIG. 175). PLM analysis showed small rod-like particles with agglomeration and birefringence (FIG. 170). KF analysis was carried out using direct addition method and showed a moisture content of 1.97%. DVS analysis (FIG. 173) of hydrobromide Form 2 showed a moisture uptake of ca. 2.4% at 90% RH. Post-DVS XRPD analysis showed no change in form from the input material (FIG. 174). XRPD analysis after storage at 40° C./75% RH, 80° C., and ambient temperature for 1 week showed no change in form from the input material (FIG. 178). XRPD analysis after salt disproportionation studies show the material becomes partially crystalline after 24 hours slurrying in water, with the material staying hydrobromide Form 2 after 48 hours slurrying (FIG. 179). The measured pH for this sample was 1.86 after slurrying hydrobromide Form 2 in water for 48 hours. XRPD analysis after thermodynamic solubility studies shows hydrobromide Form 2 becomes poorly crystalline after slurrying in water and at pH 4.5 and 6.5 at 25° C. for 48 hours, while hydrobromide Form 1 and 2 are observed after slurrying in at pH 1 at 25° C. for 48 hours (FIG. 180).

Phosphate Form 1 Preparation and Assessment

To ca. 500 mg of Compound A, 5 mL acetone was added. The suspension was stirred at ambient temperature (ca. 22° C.). Phosphoric acid (ca. 76 µL) was slowly added to the suspension of freebase at ca. 22° C. The slurry was cooled to 5° C. under stirring and further stirred at ca. 5° C. for ca. 24 hours. Crystallization of light brown solid was observed. Stirring was stopped and the solid and liquid were separated by pipetting the liquid. The solid was air dried for 40 minutes and then further dried under vacuum at 40° C. for ca. 72 hours. A light brown solid was obtained. The dried material was analyzed by XRPD, PLM, TG/DTA, DSC, DVS, FT-IR, KF, HPLC, and $^1$H NMR.

The XRPD analysis of the phosphate Form 1 material from acetone dried at 40° C. under vacuum showed a diffractogram consistent with phosphate Form 1 (FIG. 244). TGA of phosphate Form 1 showed a weight loss of 2.4% between about 130° C. and about 160° C., and a weight loss of 1.5% between about 60° C. and about 166° C. (FIG. 246). DSC (FIG. 247) showed an endothermic event with an onset at approximately 157° C. (peak at approximately 164° C.). The $^1$H-NMR spectrum of phosphate Form 1 showed 0.26 equivalents of acetone and water (FIG. 252). The HPLC area % purity was measured to be 98.4% (FIG. 283). FT-IR analysis was performed on phosphate Form 1, indicating that it was different than the freebase form (FIG. 251). PLM analysis showed crystalline, birefringent particles with a rod-like morphology as well as some glass-like particles that do not exhibit birefringence (FIG. 245). KF analysis showed a moisture content of 3.74%. DVS analysis (FIG. 248 and FIG. 249) of phosphate Form 1 showed a moisture uptake of ca. 3.2% at 90% RH. Post-DVS XRPD analysis showed no change in form from the input material (FIG. 250). XRPD analysis after storage at 40° C./75% RH, 80° C., and ambient temperature for 1 week showed no change in form from the input material (FIG. 253). XRPD analysis after salt disproportionation studies show no change from the input material after 48 hours slurrying phosphate Form 1 in water (FIG. 254). The measured pH for this sample was 2.66 after slurrying hydrobromide Form 1 in water for 48 hours. XRPD analysis after thermodynamic solubility studies show no change from the input material after slurrying phosphate Form 1 in the respective buffer at 25° C. for 48 hours (FIG. 255). The hydration study results are summarized in Table 8. XRPD analysis after hydration are shown in FIG. 256.

Example 5: Assessment of the Polymorphs of the Application

7 Day Stability Testing

Stability testing was carried out for the polymorphs of the salts, as well as amorphous Compound A in open vials at 40° C./75% RH, ambient and 80° C. for 1 week. For each of the polymorphic forms assessed (Form 1, Form 4 Form 8, and edisylate Form 1, cyclamate Form 1, and besylate Form 1), no decrease in area % purity or form changes were observed, indicating that the forms tested were stable for 1 week at ambient, 40° C./75% RH and 80° C. (FIG. 28, FIG. 38, FIG. 48, FIG. 50, FIG. 137, FIG. 149, and FIG. 162). Table 3 shows the results of stability testing. Additional stability testing results are described herein above.

TABLE 3

Stability testing results

| Form | Conditions | T = 0 purity (%) | Purity after 1 week (%) | Form |
|---|---|---|---|---|
| Form 1 | 40° C./75% RH | 99.3 | 99.4 | Form 1 |
|  | Ambient |  | 99.3 | Form 1 |
|  | 80° C. |  | 99.4 | Form 1 |
| Form 4 | 40° C./75% RH | 98.8 | 98.9 | Form 4 |
|  | Ambient |  | 98.9 | Form 4 |
|  | 80° C. |  | 98.9 | Form 4 |
| Form 8 | 40° C./75% RH | 99.0 | 99.0 | Form 8 |
|  | Ambient |  | 99.0 | Form 8 |
|  | 80° C. |  | 99.0 | Form 8 |
| Edisylate Form 1 | 40° C./75% RH | 97.9 | 98.1 | Edisylate Form 1 |
|  | 80° C. |  | 97.5 | Edisylate Form 1 |
|  | Ambient |  | 97.9 | Edisylate Form 1 |
| Cyclamate Form 1 | 40° C./75% RH | 42.2 | 41.1 | Cyclamate Form 1 |
|  | 80° C. |  | 41.3 | Cyclamate Form 1 |
|  | Ambient |  | 41.1 | Cyclamate Form 1 |
| Besylate Form 1 | 40° C./75% RH | 97.4 | 97.8 | Besylate Form 1 |
|  | 80° C. |  | 97.4 | Besylate Form 1 |
|  | Ambient |  | 97.4 | Besylate Form 1 |
| Amorphous | 40° C./75% RH | 98.7 | 98.9 | Amorphous solid |
|  | 80° C. |  | 98.9 | Amorphous solid |
|  | Ambient |  | 98.9 | Amorphous solid |

Long Term Stability Testing

Long term stability testing was carried out for Form 1 at 25° C./60% RH. For each test, no decrease in area % purity or form changes were observed, indicating that the forms tested were stable for at 25° C./60% RH. The water content was measured by KF analysis. Table 4 shows the results of the long term stability testing.

TABLE 4

Long Term Storage Stability of Form 1

| Length of Storage (months) | 0 | 1 | 3 | 6 | 9 | 12 | 18 | 24 |
|---|---|---|---|---|---|---|---|---|
| Crystallinity (XRPD) | Form 1 | Not Tested | Not Tested | Form 1 | Not Tested | Form 1 | Not Tested | Form 1 |
| Chemical Purity (% AUC) | 98.9 | 98.8 | 98.8 | 98.9 | 98.9 | 98.8 | 99.0 | 98.9 |
| Water Content (KF) (%) | 0.16 | 0.28 | 0.41 | 0.47 | 0.29 | 0.46 | 0.49 | 0.37 |

Accelerated Stability Testing

Accelerated stability testing was carried out for Form 1 at 40° C./75% RH for 6 months. At each time interval, no decrease in area % purity or form changes were observed, indicating that the forms tested were stable. The water content was measured by KF analysis. Table 5 shows the results of the long term stability testing.

TABLE 5

Accelerated Stability Storage of Form 1

| | Stability Storage 40° C./75% RH Stability Time Point (Months) | | | |
|---|---|---|---|---|
| Test | 0 | 1 | 3 | 6 |
| Crystallinity (XRPD) | Form 1 | Not Tested | Not Tested | Form 1 |
| Chemical Purity (% Area) | 98.9 | 98.8 | 98.8 | 98.9 |
| Water Content (KF) (%) | 0.16 | 0.36 | 0.53 | 0.57 |

Aqueous and Acetone Solubility

Figure 39:
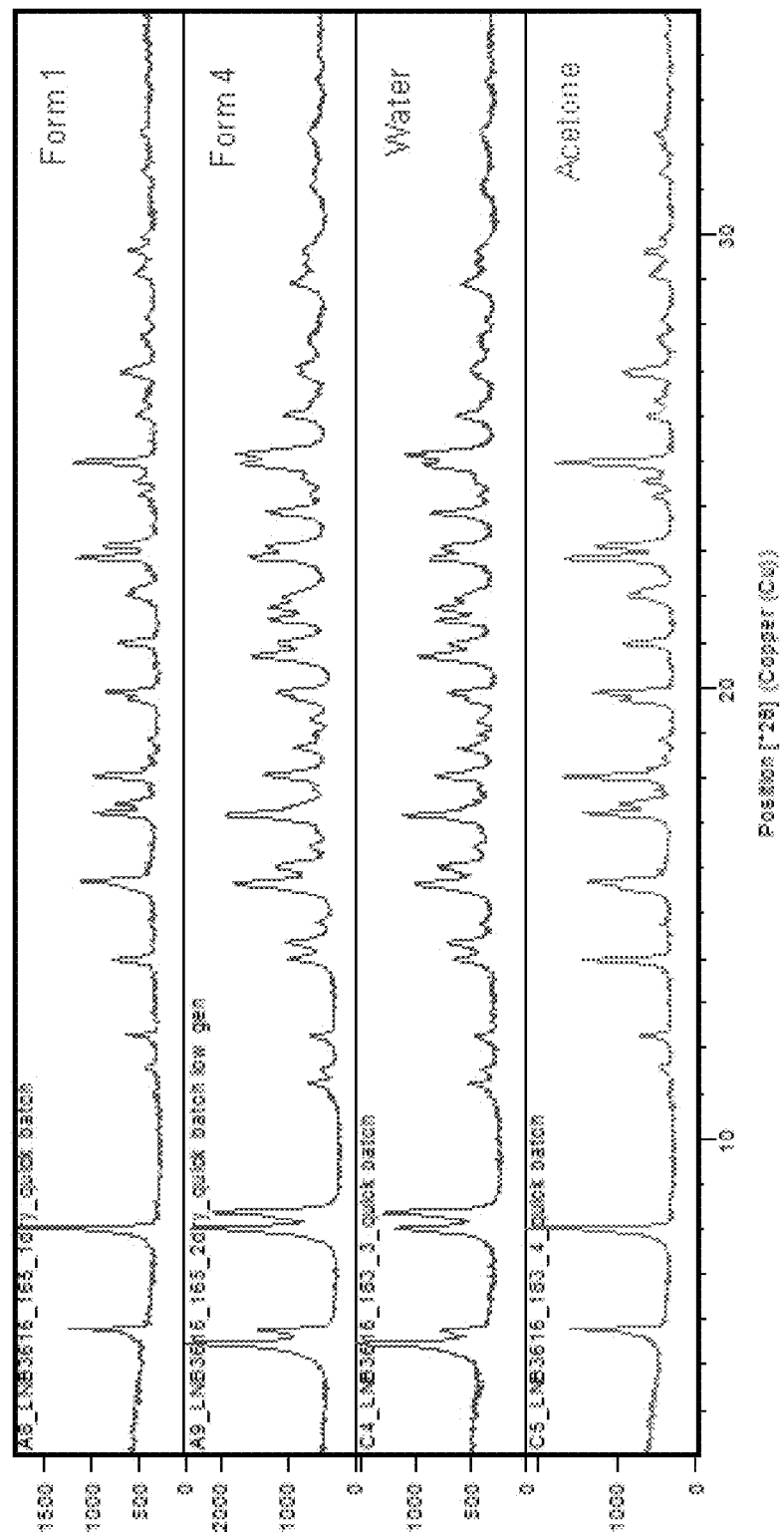
FIG. 39 sets forth XRPD patterns of Form 1 (top panel) and Form 4 (second row from top) as reference samples and Form 4 after aqueous solubility determination (third row from top) and after acetone solubility determination (bottom panel).
Figure 49:
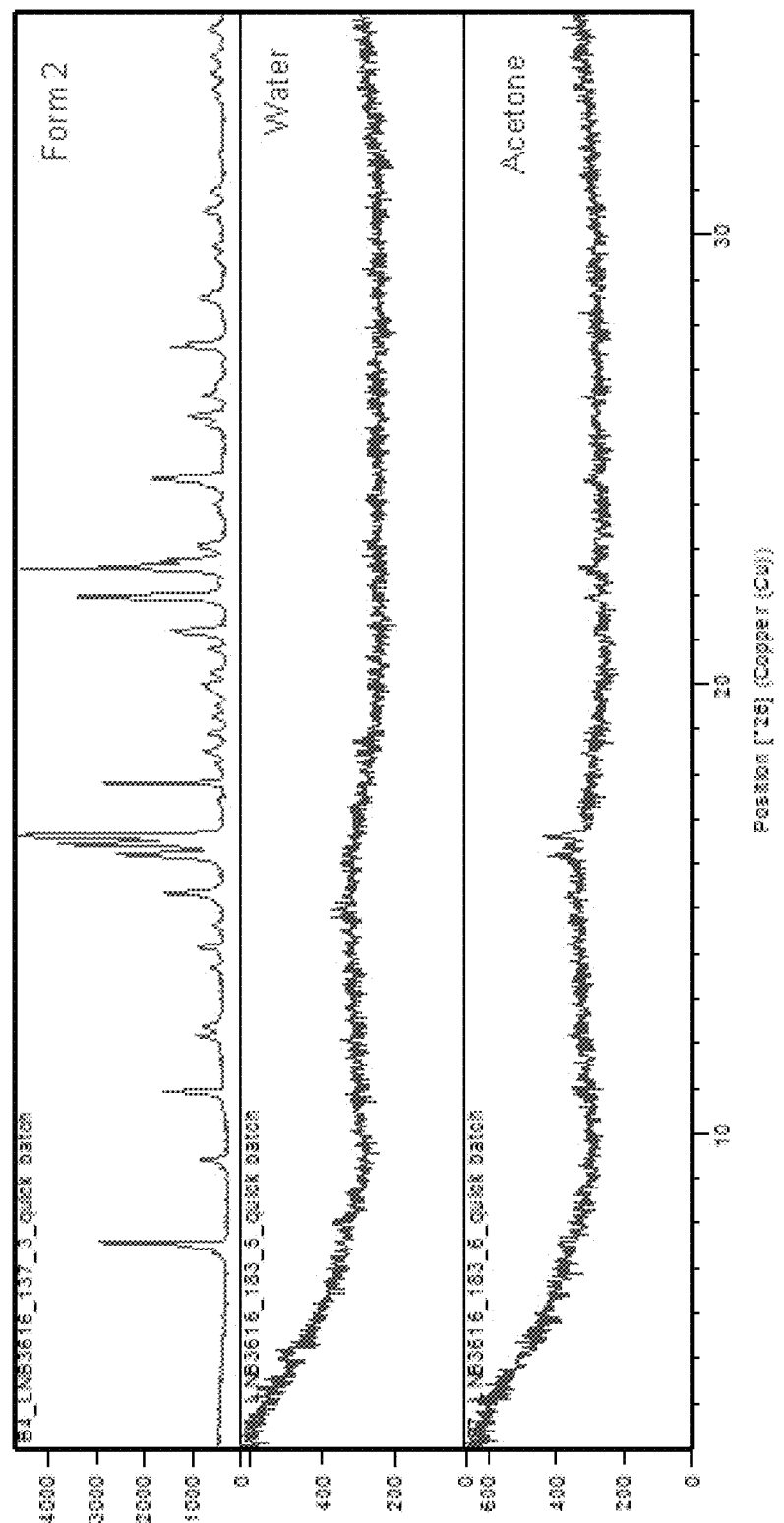
FIG. 49 sets forth XRPD patterns of Form 2 (top panel) as a reference sample and Form 8 after aqueous solubility determination (middle panel) and after acetone solubility determination (bottom panel).

Aqueous and acetone solubility was carried out using 3-10 mg of material, depending on availability, and slurrying in 150-200 μL of acetone or 300 μL of deionized water. The samples were agitated at ambient temperature then filtered by centrifugation (0.22 μm nylon filter) after ca. 24 hours and the solids analyzed by XRPD as damp solids. The filtrates were analyzed by HPLC for concentration determination. The water solubility was too low for detection using the current analytical method. When slurrying in acetone, conversion to Form 2 was observed for Form 1 and Form 8 input solids (FIG. 29, FIG. 39, and FIG. 49). Table 6 shows the results from the aqueous and acetone solubility testing.

TABLE 6

Aqueous and acetone solubility results

| Sample used | Solvent | Solubility (mg/mL) | Form |
|---|---|---|---|
| Form 1 | Water | API not detected | Form 1 |
| | Acetone | 12.3 | Form 2* |
| Form 4 | Water | API not detected | Form 4 |
| | Acetone | 15.1 | Form 1 |
| Form 8 | Water | API not detected | AXRPD |
| | Acetone | 11.5 | Form 2* |

*Small amount of material analyzed
AXRPD: Amorphous by XRPD, but limited material for analysis Disproportionation Studies Samples of salts described herein were prepared for disproportionation studies. Approximately 15 mg of the salt material was suspended in 4 mL of deionized water at ambient temperature (ca. 22° C.). The slurry of the salt was shaken at ambient temperature and analyzed after: 1 h, 24 h, and 48 h. Each sample was filtered using a centrifuge filter. The solid was analyzed by XRPD. pH measurements were performed for the solution (three pH measurements were carried out for each sample and the average pH was calculated). The solution obtained after 48 h of slurrying was submitted for HPLC analysis to determine the aqueous solubility of the salt.

Thermodynamic Solubility pH Measurements

Thermodynamic solubility pH measurements were carried out using ca. 20 mg of material and slurrying in 0.5 mL of the respective buffer at 25° C. for 48 hours. After 2 hours at 25° C., the pH of each slurry was measured and the pH was adjusted, where required. After 24 hours at 25° C., the pH of each slurry was measured and the pH was adjusted, where required. After 48 hours at 25° C., the slurries were separated by centrifugation. The solids were analyzed by XRPD, while the pH of the separated liquors were also measured. The results are summarized in Table 7. XRPD analysis after thermodynamic solubility studies shows no change from the input material after slurrying edisylate Form 1 in the respective buffer at 25° C. for 48 hours (FIG. 143). XRPD analysis after thermodynamic solubility studies shows cyclamate Form 1 became poorly crystalline after slurrying in the respective buffer at 25° C. for 48 hours (FIG. 155). XRPD analysis after thermodynamic solubility studies shows hydrobromide Form 2 becomes poorly crystalline after slurrying in water and at pH 4.5 and 6.5 at 25° C. for 48 hours, while hydrobromide Form 1 and 2 are observed after slurrying in at pH 1 at 25° C. for 48 hours (FIG. 180).

TABLE 7

Thermodynamic Solubility pH Measurements Results

| Input Material | Input Solvent | pH - 2 Hours at 25° C. | pH - 24 Hours at 25° C. | pH - 48 Hours at 25° C. | XPRD - 48 Hours at 25° C. | Solubility (mg/mL) |
|---|---|---|---|---|---|---|
| Edisylate Pattern 1 | Water | 2.32 | 2.18 | 2.37 | Edisylate Form 1 | <LOD |
| | pH 1 | 0.17 | 0.70 | 1.11 | Edisylate Form 1 | 0.7 |
| | pH 4.5 | 4.40 | 4.29 | 4.22 | Edisylate Form 1 | <LOD |
| | pH 6.5 | 6.44 | 6.03 | 5.68 | Edisylate Form 1 | <0.1 |
| Cyclamate Form 1 | Water | 2.19 | 1.96 | 2.24 | Poorly Crystalline | <0.1 |
| | pH 1 | 0.20 | 0.40 | 1.70 | Poorly Crystalline | <0.1 |
| | pH 4.5 | 3.96 | 3.88 | 4.09 | Poorly Crystalline | <LOD |
| | pH 6.5 | 2.89 | 2.75 | 3.36 | Poorly Crystalline | <LOD |

TABLE 7-continued

Thermodynamic Solubility pH Measurements Results

| Input Material | Input Solvent | pH - 2 Hours at 25° C. | pH - 24 Hours at 25° C. | pH - 48 Hours at 25° C. | XPRD - 48 Hours at 25° C. | Solubility (mg/mL) |
|---|---|---|---|---|---|---|
| Besylate Form 1 | Water | 1.96 | 1.68 | 1.84 | Poorly Crystalline | 0.2 |
| | pH 1 | 0.19 | 0.37 | 1.07 | Poorly Crystalline | 0.2 |
| | pH 4.5 | 4.20 | 3.80 | 3.82 | Poorly Crystalline | <0.1 |
| | pH 6.5 | 3.31 | 2.51 | 3.26 | Poorly Crystalline | <LOD |
| Hydrobromide Form 2 | Water | 1.86 | 1.34 | 1.86 | Poorly crystalline | 0.5 |
| | pH 1 | 0.27 | 0.40 | 0.78 | Hydrobromide Form 1 + 2 | <0.1 |
| | pH 4.5 | 3.97 | 3.62 | 3.84 | Poorly crystalline | <0.1 |
| | pH 6.5 | 3.53 | 2.61 | 3.44 | Poorly crystalline | <LOD |

Hydration Studies

Hydration experiments were performed at 25° C. and 50° C. in water/acetone mixtures with the following water content (volume %): 2%, 5%, and 20%. The samples were prepared by adding 250 µL of the water/acetone mixture to 15 mg of the salt sample. The samples were stirred at 25° C. or at 50° C. After 2 days, the samples were inspected for the presence of solid. If solid was not observed, additional salt material was added to the dissolved samples. Samples were stirred for an additional 3 days. After 5 days, samples were filtered and the solid obtained was analyzed by XRPD. The results of the hydration studies are summarized in Table 8. Besylate Form 1 was recovered from 2% and 5% water experiments at 25° C. The other besylate Form 1 experiments gave a gum. XRPD diffractograms obtained after the hydration studies for besylate Form 1 are shown in FIG. 282. Hydrobromide Form 1 was recovered from 2% and 5% water experiments at 25° C. A potentially new form was observed at 2% water at 50° C., but the crystallinity was low. The other hydrobromide Form 1 experiments gave a gum. XRPD diffractograms obtained after the hydration studies for hydrobromide Form 1 are shown in FIG. 269. Phosphate Form 1 was recovered from 2% and 5% water experiments at 25° C. A potentially new form was observed at 2% water at 50° C., but the crystallinity was low. The other phosphate Form 1 experiments gave a gum. XRPD diffractograms obtained after the hydration studies for phosphate Form 1 are shown in FIG. 256.

TABLE 8

Hydration Studies Results

| Form | Composition | 25° C. | 50° C. |
|---|---|---|---|
| Besylate Form 1 | 2% water | Form 1 | Form 1 |
| | 5% water | Gum | Gum |
| | 20% water | Gum | Gum |
| Hydrobromide Form 1 | 2% water | Form 1 | low crystallinity |
| | 5% water | Form 1 | Gum |
| | 20% water | Gum | Gum |
| Phosphate Form 1 | 2% water | Form 1 | Form 1 |
| | 5% water | Form 1 | Form 6 |
| | 20% water | Gum | Gum |

Competitive Slurrying

Approximately 5 mg of each form (Form 1 and Form 4, Form 1 and Form 8, and Form 4 and Form 8) was weighed and agitated at ambient and 50° C. in minimal acetone, ethanol, diisopropyl ether (DIPE) and acetonitrile. Approximately 8 drops of each solvent was added and the samples were then agitated for ca. 48 hours, before being analyzed by XRPD. Table 9 details the conditions.

TABLE 9

Conditions for competitive slurrying

| Input forms | Solvent | Temperature |
|---|---|---|
| 1 and 4 | Acetone Ethanol DIPE Acetonitrile | Ambient |
| | Acetone Ethanol DIPE Acetonitrile | 50° C. |
| 1 and 8 | Acetone Ethanol DIPE Acetonitrile | Ambient |
| | Acetone Ethanol DIPE Acetonitrile | 50° C. |
| 4 and 8 | Acetone Ethanol DIPE Acetonitrile | Ambient |
| | Acetone Ethanol DIPE Acetonitrile | 50° C. |

Figure 51:
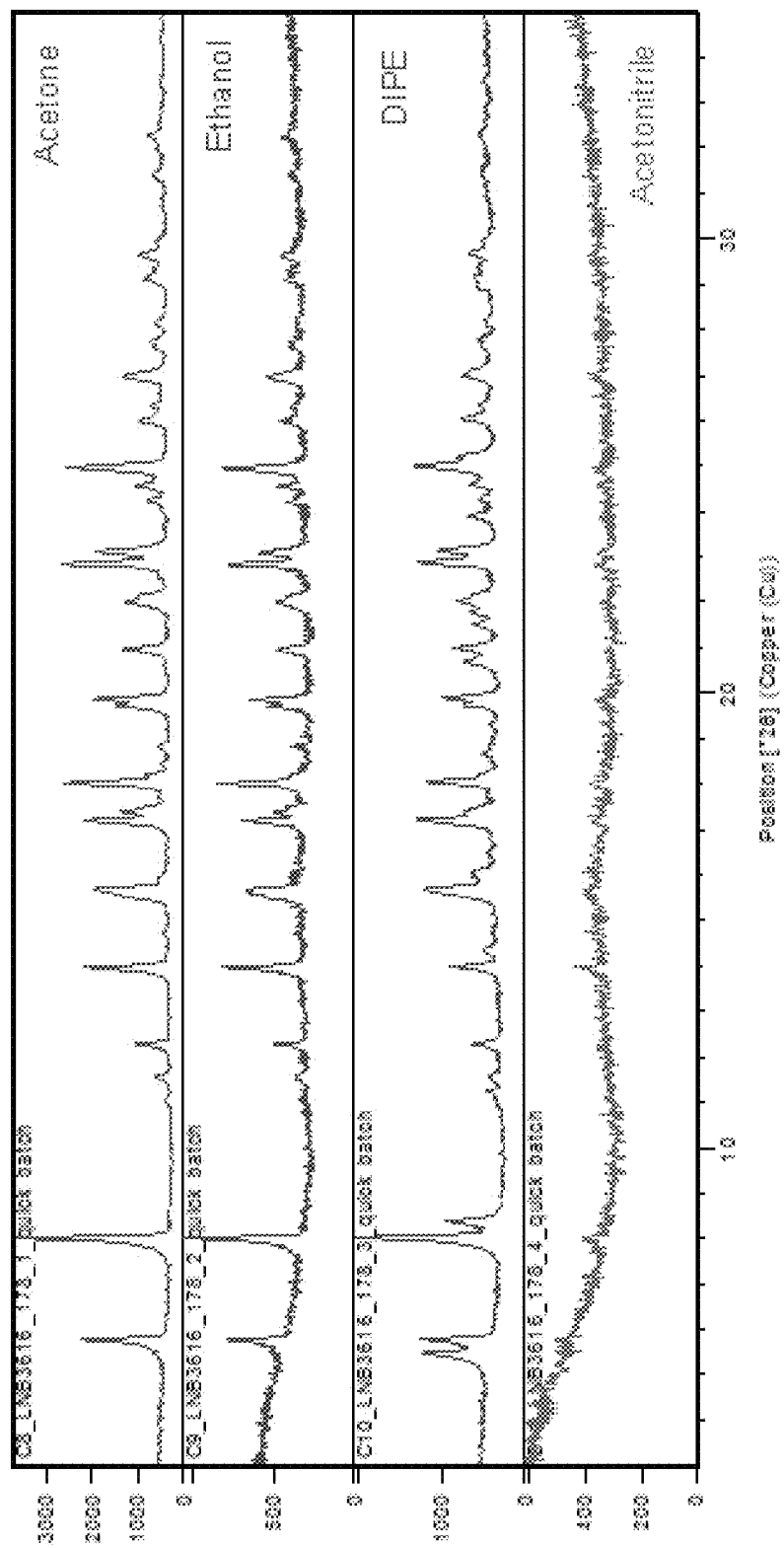
FIG. 51 sets forth XRPD patterns after competitive slurrying of Form 1 and Form 4 at ambient (approximately 25° C.) conditions in: i) acetone (top panel), ii) ethanol (second row from top), iii) diisopropyl ether (DIPE) (third row from top), and iv) acetonitrile (bottom panel).
Figure 52:
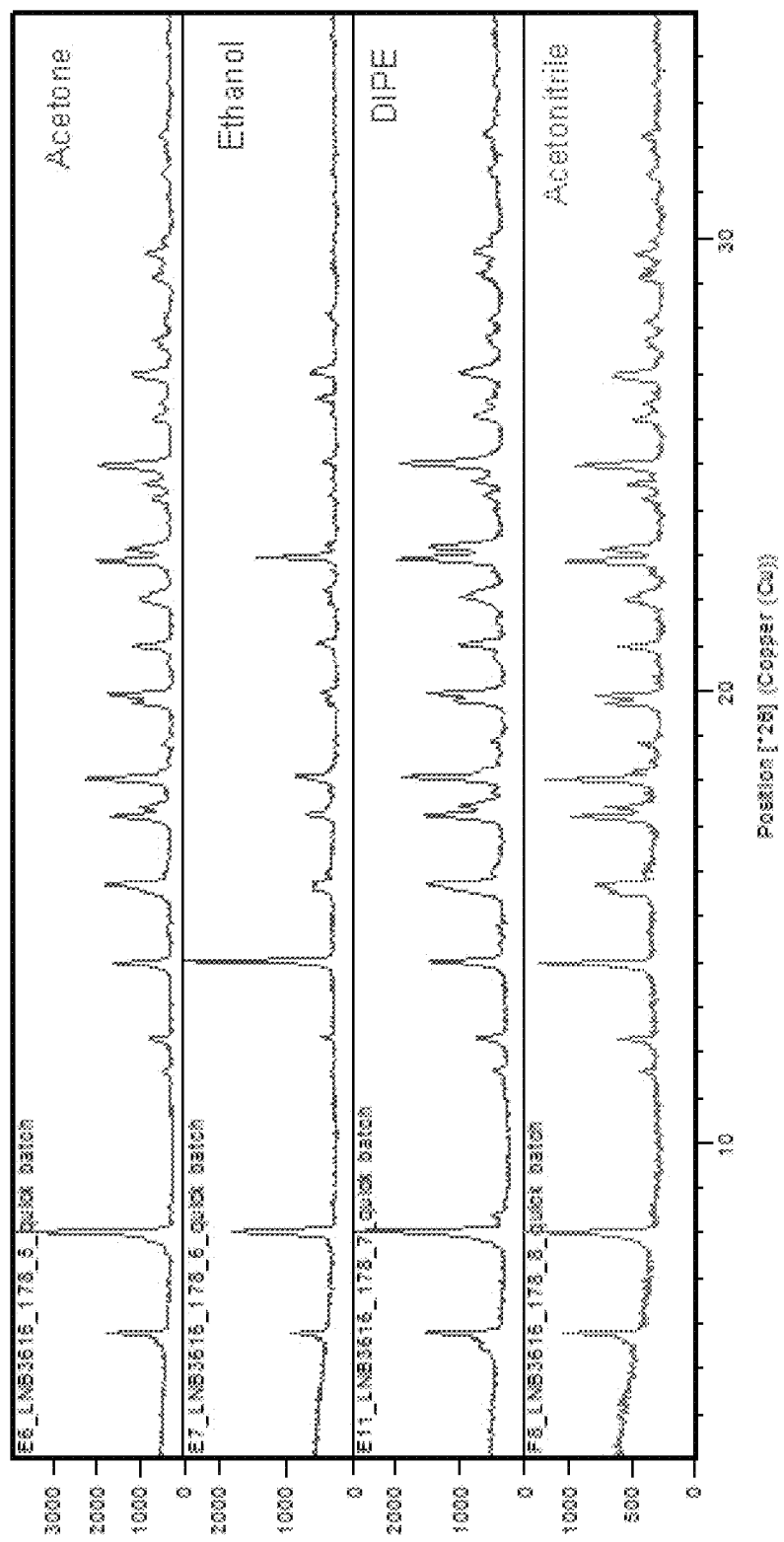
FIG. 52 sets forth XRPD patterns after competitive slurrying of Form 1 and Form 4 at 50° C. in: i) acetone (top panel), ii) ethanol (second row from top), iii) diisopropyl ether (DIPE) (third row from top), and iv) acetonitrile (bottom panel).
Figure 53:
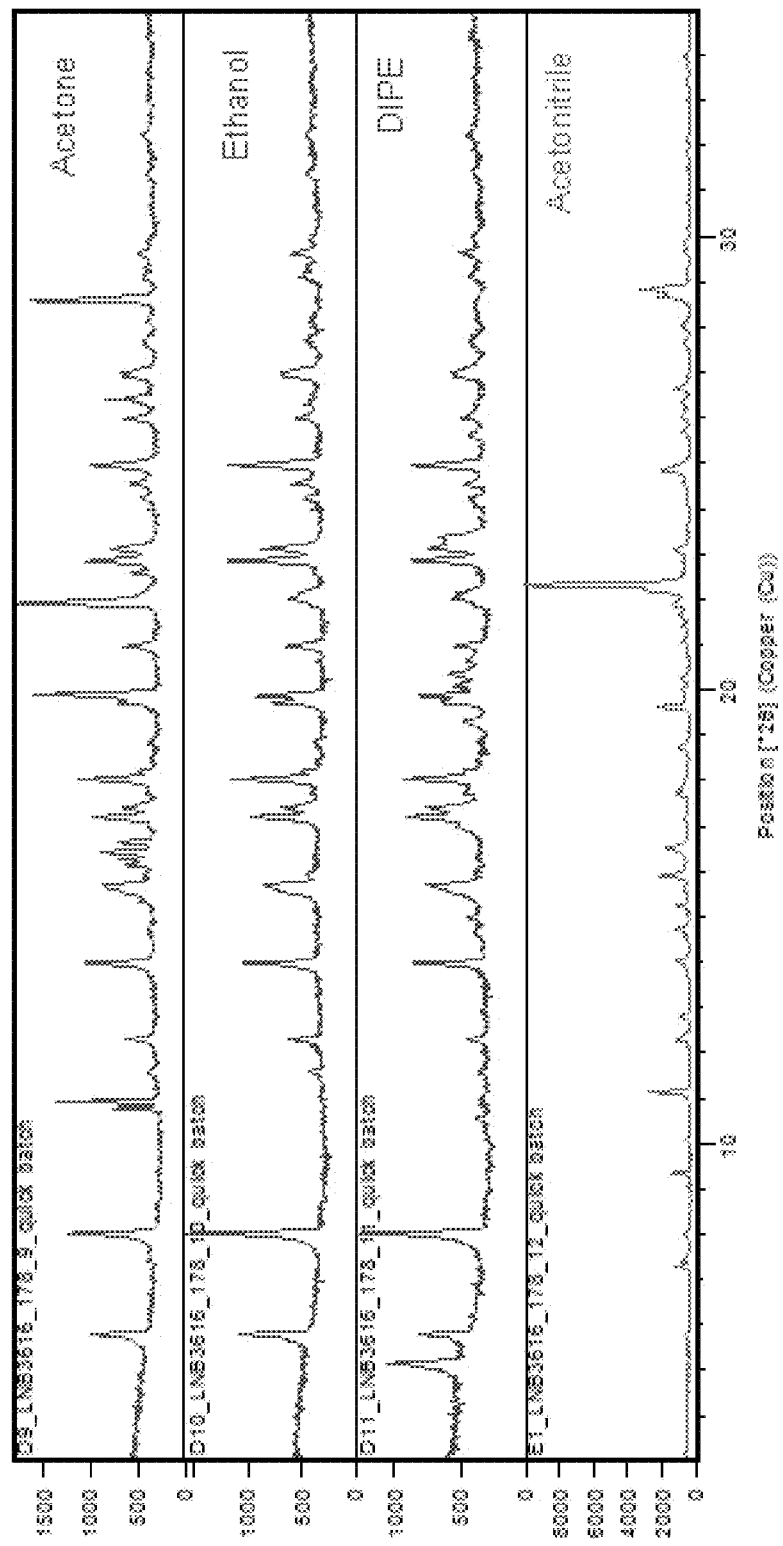
FIG. 53 sets forth XRPD patterns after competitive slurrying of Form 1 and Form 8 at ambient (approximately 25° C.) conditions in: i) acetone (top panel), ii) ethanol (second row from top), iii) diisopropyl ether (DIPE) (third row from top), and iv) acetonitrile (bottom panel).
Figure 54:
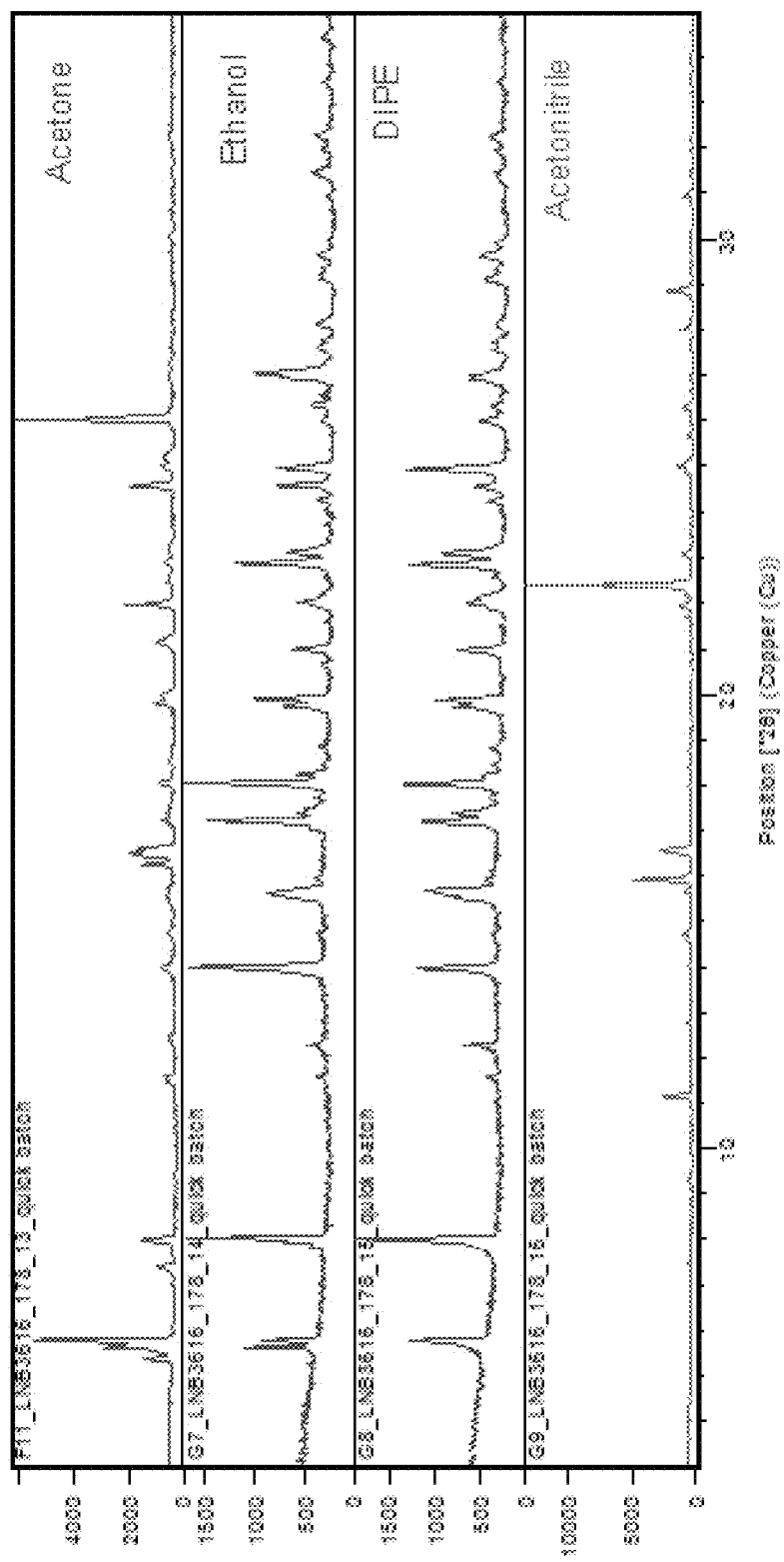
FIG. 54 sets forth XRPD patterns after competitive slurrying of Form 1 and Form 8 at 50° C. in: i) acetone (top panel), ii) ethanol (second row from top), iii) diisopropyl ether (DIPE) (third row from top), and iv) acetonitrile (bottom panel).
Figure 55:
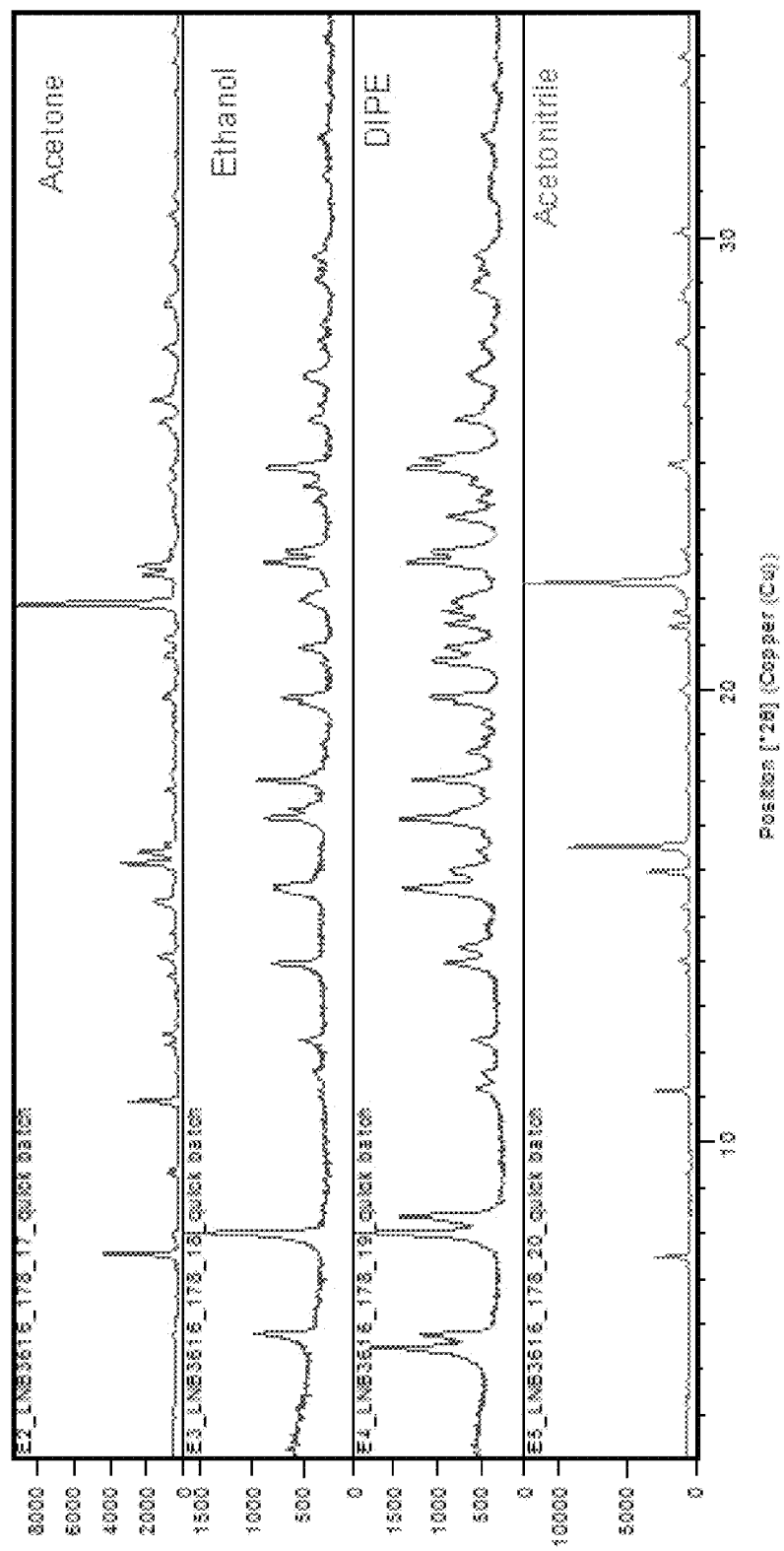
FIG. 55 sets forth XRPD patterns after competitive slurrying of Form 4 and Form 8 at ambient (approximately 25° C.) conditions in: i) acetone (top panel), ii) ethanol (second row from top), iii) diisopropyl ether (DIPE) (third row from top), and iv) acetonitrile (bottom panel).
Figure 56:
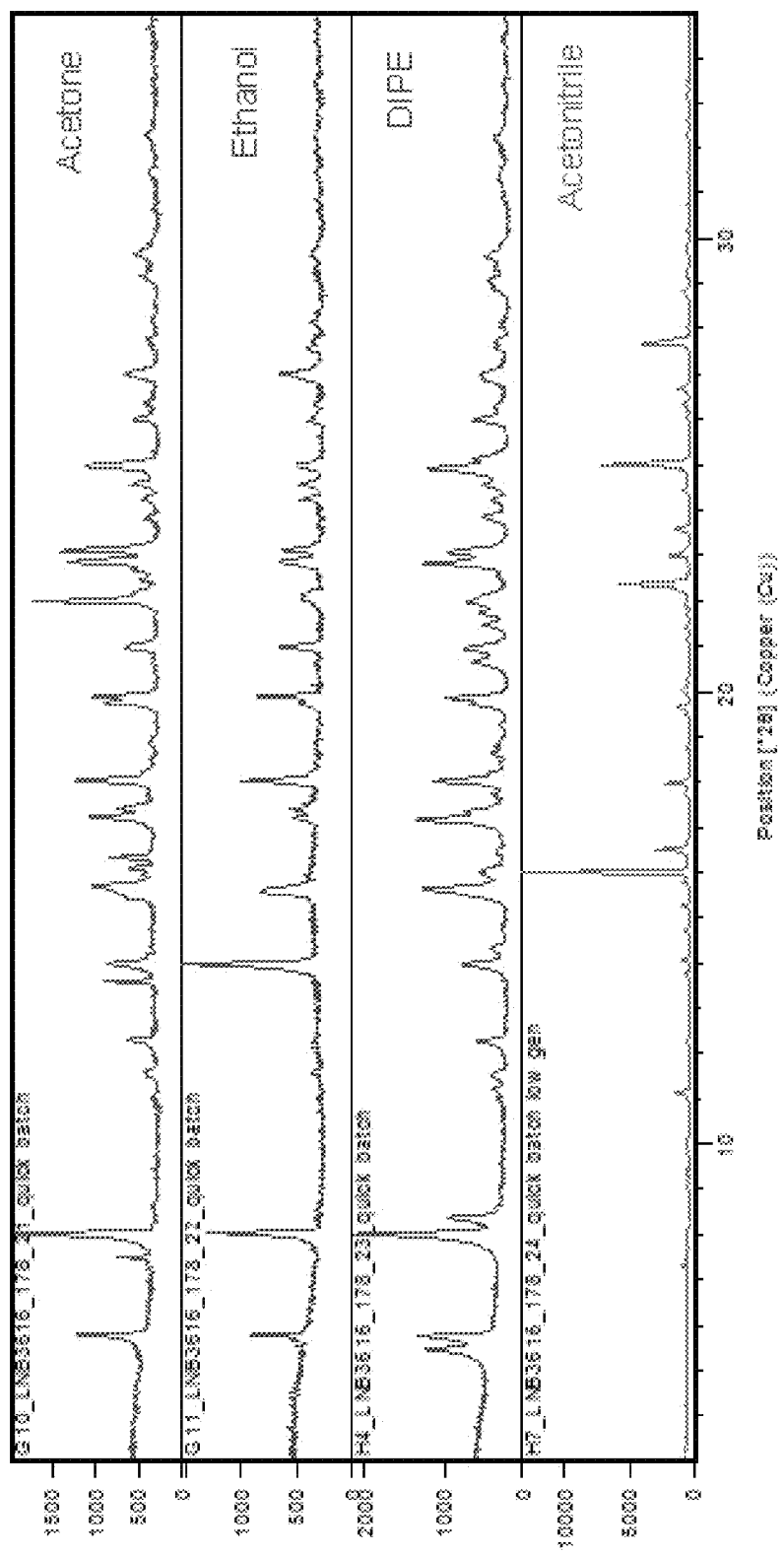
FIG. 56 sets forth XRPD patterns after competitive slurrying of Form 4 and Form 8 at 50° C. in: i) acetone (top panel), ii) ethanol (second row from top), iii) diisopropyl ether (DIPE) (third row from top), and iv) acetonitrile (bottom panel).

Predominantly Form 1 was observed, mixtures of Form 1 and Form 2 were also observed. Form 1 was the dominant form from Form 1 and Form 4 slurrying (FIG. 51 and FIG. 52). Form 1 was the dominant form from Form 1 and Form 8 slurrying although mixtures with Form 2 were observed in acetone and acetonitrile and a mixture with Form 8 from DIPE at ambient (FIG. 53 and FIG. 54). Form 4 and Form 8 produced Form 1 and Form 2 mixtures, pure Form 1, pure Form 4 and pure Form 2, results were the same at both temperatures (FIG. 55 and FIG. 56). Competitive slurrying experiments between Form 1 and Form 8, Form 1 and Form 4 and Form 4 and Form 8 at ambient and 50° C. showed predominantly Form 1. Overall, the data indicated Form 1 to be the more stable form under the conditions assessed. Form 2 was also observed in a number of slurries where acetone and acetonitrile were employed. The propensity for solvation, resulting in Form 2, was also high in acetone and acetonitrile. Table 10 shows the results from competitive slurrying.

TABLE 10

Competitive slurrying results

| Solvent | Temperature | Input forms | Form |
|---|---|---|---|
| Acetone | Ambient | 1 and 4 | Form 1 |
| Ethanol | | | Form 1 |
| DIPE | | | Form 4 |
| Acetonitrile | | | Form 1 (WD) |
| Acetone | 50° C. | | Form 1 |
| Ethanol | | | Form 1 |
| DIPE | | | Form 1 |
| Acetonitrile | | | Form 1 |
| Acetone | Ambient | 1 and 8 | Form 1/ Form 2 |
| Ethanol | | | Form 1 |
| DIPE | | | Form 1/ Form 8 |
| Acetonitrile | | | Form 1/ Form 2 |
| Acetone | 50° C. | | Form 1/ Form 2 |
| Ethanol | | | Form 1 |
| DIPE | | | Form 1 |
| Acetonitrile | | | Form 1/ Form 2 |
| Acetone | Ambient | 4 and 8 | Form 1/ Form 2 |
| Ethanol | | | Form 1 |
| DIPE | | | Form 4 |
| Acetonitrile | | | Form 2 |
| Acetone | 50° C. | | Form 1/ Form 2 |
| Ethanol | | | Form 1 |
| DIPE | | | Form 4 |
| Acetonitrile | | | Form 2 |

WD: Weak data

Figure 9:
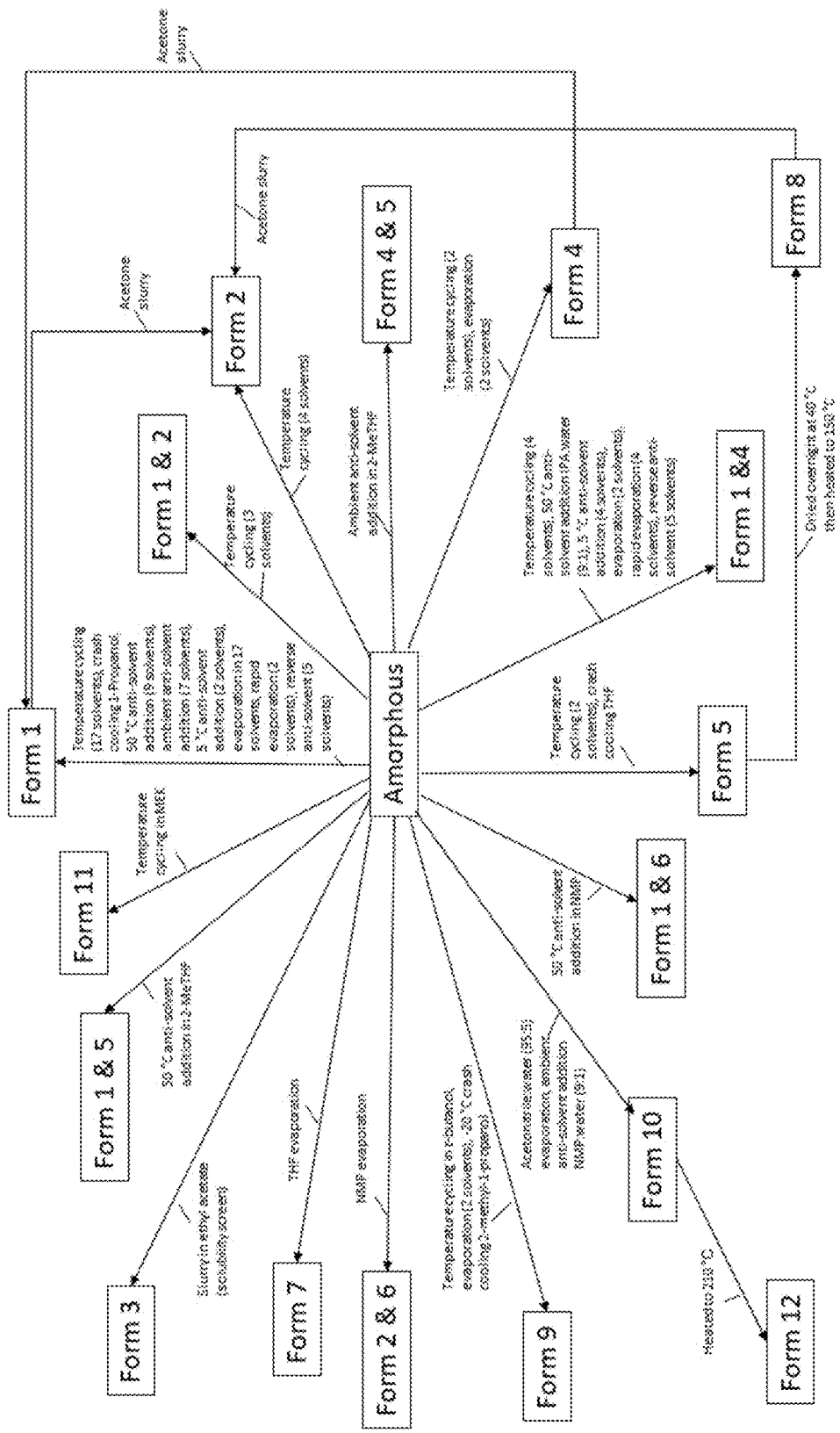
FIG. 9 sets forth a form diagram illustrating relationships between solid forms of Compound A.

Overall, a total of 12 different polymorphic forms have been observed for the Compound A free base, with Form 1 found to be the thermodynamically more stable form under the conditions assessed. FIG. 8 is an example comparison of XRPD diffractograms of Form 1, Form 2, Form 4, Form 5, Form 6, Form 7 and Form 8 (FIG. 57, FIG. 58, FIG. 59, FIG. 60, FIG. 61, FIG. 62, and FIG. 63). FIG. 9 is a form diagram illustrating the relationship between polymorphic forms. Table 11 summarizes the results associated with Form 1, Form 4 and Form 8.

TABLE 11

Summary of Form 1, Form 4, and Form 8 results

| Analysis | Amorphous Compound A | Form 1 | Form 4 | Form 8 |
|---|---|---|---|---|
| XRPD (crystallinity) | Amorphous | Good | Good | Good |
| PLM (morphology) | Glassy, no birefringence | Needles | Small needles | Needles |
| TGA (weight loss) | 1.3% 25-190° C., 0.5% 200-270° C. | 0.1% 25-300° C. | 0.5% 25-300° C. | 0.2% 25-300° C. |
| DSC (thermal events) | Exotherm onset 179° C., endotherm 226° C. | 3 endotherms onsets 208° C., 215° C. & 227° C. & exotherm 217° C. | Endotherms onsets 197° C. & 226° C. & exotherm 215° C. | Endotherm onset 225° C. |
| GVS (hygroscopicity) | 3.9% uptake | <0.2% uptake | 0.4% uptake | 0.8% uptake |
| XRPD post GVS | Remained unchanged | Remained unchanged | Remained unchanged | Remained unchanged |
| HPLC purity | 98.70% | 99.3% | 98.8% | 99.0% |
| Aqueous solubility | <10 mg/mL, solvent addition method | API not detected | API not detected | API not detected |
| XRPD post aqueous solubility | Form 1 from solubility screen | Form 1 | Form 4 | Amorphous, limited material |
| Acetone solubility | ≥16 mg/mL partial dissolution, solvent addition method (Form 2 residual solid with additional peaks) | 12.3 mg/mL (Form 2 residual solid) | 15.1 mg/mL (Form 1 residual solid) | 11.5 mg/mL (Form 2 residual solid) |
| Stability testing | No drop in purity or change in form | No drop in purity or change in form | No drop in purity or change in form | No drop in purity or change in form |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A solid form of (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone free base (Compound A), wherein the solid form is:
    a Form 1 polymorph of Compound A characterized by an X-ray powder diffraction pattern comprising peaks at approximately 5.8, 8.0, 18.0, 22.9, and 25.0° 2θ using Cu Kα radiation.

2. The Form 1 polymorph of claim 1, characterized by an X-ray powder diffraction pattern comprising peaks at approximately 5.8, 8.0, 14.0, 15.7, 17.2, 17.4, 18.0, 19.7, 19.9, 22.0, 22.9, 23.1, and 25.0° 2θ using Cu Kα radiation.

3. The Form 1 polymorph of claim 1, characterized by an X-ray powder diffraction pattern comprising peaks at approximately 5.8, 8.0, 12.3, 14.0, 15.5, 15.7, 17.2, 17.4, 18.0, 19.7, 19.9, 21.0, 22.0, 22.2, 22.9, 23.1, 24.6, 25.0, 26.0, 26.9, and 29.7° 2θ using Cu Kα radiation.

4. The Form 1 polymorph of claim 1, characterized by an X-ray powder diffraction pattern substantially similar to that set forth in FIG. 57.

5. The Form 1 polymorph of claim 1, further characterized by an endothermic event with an onset between approximately 208° C. and approximately 230° C. as measured by DTA or DSC.

6. The Form 1 polymorph of claim 5, characterized by endothermic events with onset between approximately 208° C. and approximately 210° C., between approximately 213° C. and approximately 215° C., and between approximately 227° C. and approximately 230° C. as measured by DTA or DSC.

7. The Form 1 polymorph of claim 5, characterized by a DTA thermogram substantially similar to that set forth in FIG. 11.

8. The Form 1 polymorph of claim 5, characterized by a DTA thermogram substantially similar to that set forth in FIG. 22.

9. The Form 1 polymorph of claim 5, characterized by a DSC thermogram substantially similar to that set forth in FIG. 23.

* * * * *